(12) United States Patent
Sarria-Millan et al.

(10) Patent No.: US 7,951,991 B2
(45) Date of Patent: May 31, 2011

(54) POLYNUCLEOTIDES ENCODING PLANT PRENYL PROTEASES

(75) Inventors: Rodrigo Sarria-Millan, Durham, NC (US); Stefan Henkes, Potsdam (DE); Damian Allen, Cary, NC (US); Oswaldo da Costa e Silva, Neustadt (DE); Ruoying Chen, Apex, NC (US); Jiangxin Wan, Bath (CA); Yafan Huang, Bath (CA); Delina Mary-Jane Melo, Inverary (CA); Monika Maria Kuzma, Battersea (CA); Angela Patricia Gilley Sample, Inverary (CA)

(73) Assignees: BASF Plant Science GmbH (DE); Performance Plants, Inc. (CA)

( * ) Notice: Subject to any disclaimer, the term of this patent is extended or adjusted under 35 U.S.C. 154(b) by 427 days.

(21) Appl. No.: 11/879,226

(22) Filed: Jul. 17, 2007

(65) Prior Publication Data

US 2008/0072350 A1 Mar. 20, 2008

Related U.S. Application Data

(63) Continuation-in-part of application No. 10/362,902, filed as application No. PCT/US01/26854 on Aug. 27, 2001, now abandoned, application No. 11/879,226, which is a continuation-in-part of application No. 10/210,760, filed on Aug. 1, 2002, now abandoned.

(60) Provisional application No. 60/227,794, filed on Aug. 25, 2000, provisional application No. 60/309,396, filed on Aug. 1, 2001, provisional application No. 60/337,084, filed on Dec. 4, 2001.

(51) Int. Cl.
*A01H 5/00* (2006.01)
*A01H 5/10* (2006.01)
*C12N 15/09* (2006.01)
*C12N 15/82* (2006.01)
*C12N 15/29* (2006.01)

(52) U.S. Cl. ........ 800/278; 800/298; 800/295; 800/317; 800/320; 435/468; 435/320.1; 435/69.1; 536/23.2; 536/23.6

(58) Field of Classification Search ........................ None
See application file for complete search history.

(56) References Cited

U.S. PATENT DOCUMENTS

| | | | |
|---|---|---|---|
| 5,107,065 A | 4/1992 | Shewmaker et al. | |
| 5,759,829 A | 6/1998 | Shewmaker et al. | |
| 2004/0010821 A1 | 1/2004 | McCourt et al. | |
| 2005/0172361 A1 | 8/2005 | Huang | |
| 2006/0021092 A1* | 1/2006 | McCourt et al. | 800/289 |

FOREIGN PATENT DOCUMENTS

| | | |
|---|---|---|
| EP | 1 033 405 A2 | 9/2000 |
| WO | WO-98/05786 A2 | 2/1998 |
| WO | WO-99 06580 A2 | 2/1999 |
| WO | WO-02/16625 A2 | 2/2002 |

OTHER PUBLICATIONS

International Search Report for PCT/US01/26854, Jan. 17, 2003.
European Search Report for Application EP02791519.8, May 18, 2009.
Asamizu, E., et al., DNA Research, vol. 7 (2000), pp. 175-180.
"A. thaliana putative CAAX prenyl protease (At4g1320)", GenBank, Accession No. AL161491, Mar. 10, 2000. MIPS at the Max Planck-Institut.
Arenas-Huertero, et al., "Analysis of *Arabidopsis* Glucose Insensitive Mutants, gin5 and gin6, Reveals a Central Role of the Plant Hormone ABA in the Regulation of Plant Vegetative Development by Sugar", Genes Dev., vol. 14, (2000), pp. 2085-2096.
Beaudoin, et al., "Interactions Between Abscisic Acid and Ethylene Signaling Cascades", Plant Cell, vol. 12, (2000), pp. 1103-1115.
Bonetta, et al., "Farnesylation is Involved in Meristem Organization in *Arabidopsis*", Planta, vol. 211, (2000), pp. 182-190.
Cohen, P., "Signal Integration at the Level of Protein Kinases, Protein Phosphatases and their Substrates", Trends Biochem. Sci., vol. 17, (1992), pp. 408-413.
Colon-Cariviona, et al., "Aux/IAA Proteins are Phosphorylated by Phytochrome in Vitro", Plant Physiol., vol. 124, (2000), pp. 1728-1738.
Kang, et al., Starch and Fatty Acid Synthesis in Plastids from Developing Embryos of Oilseed Rape (*Brassica napus* L.), Plant J., vol. 6, No. 6, (1994), pp. 795-805.
Kuo, et al., "Okadaic Acid, a Protein Phosphatase Inhibitor. Blocks Calcium Changes, Gene Expression, and Cell Death Induced by Gibberellin in Wheat Aleurone Cells", Plant Cell., vol. 8, (1996), pp. 259-269.
Nakamura, et al., "A Large Scale Analysis of cDNA in *Arabidopsis thaliana*", Database Accession No. AV557199, Jun. 16, 2000.
Plaxton, W.C., The Organization and Regulation of Plant Glycolysis, Annu. Rev. Plant Physiol. Plant Mol. Biol., vol. 47, (1996), pp. 185-214.
Ritchie, et al., "Calcium-Dependent Protein Phosphorylation may Mediate the Gibberellic Acid Response in Barley Alourono", Plant Physiol., vol. 116, (1998), pp. 765-776.
Roberts, et al., "Calcium-modulated Proteins: Targets of Intracellular Calcium Signals in Higher Plants", Annu. Rev. Plant Physiol. Plant Mol. Biol., vol. 43, (1992), pp. 375-414.
Scheet, et al., "The Sequence of *A. thaliana* IGOO2N01", Database Accession No. AF007269, Jun. 24, 1997.
Shoemaker, et al., "Public Soybean EST Project", Database Accession No. AI759788, Jun. 30, 1999.
Walbot, V., "Maize ESTs from Various cDNA Libraries Sequenced at Stanford University", Database Accession No. AW146879, Nov. 4, 1999.

(Continued)

*Primary Examiner* — Medina A Ibrahim
(74) *Attorney, Agent, or Firm* — Connolly Bove Lodge & Hutz LLP

(57) ABSTRACT

The invention provides polynucleotides encoding plant prenyl protease polypeptides, vectors, host cells, and transgenic plant comprising the polynucleotides. The invention also provides methods of producing transgenic plants that have altered levels of prenyl protease polynucleotides and polypeptides, and transgenic plants that have increased tolerance to an environmental stress as compared to a wild type plant.

55 Claims, 56 Drawing Sheets

OTHER PUBLICATIONS

Wickner, et al., "Function of DnaJ and DnaK as Chaperones in Origin-Specific DNA Binding by RepA", Nature, vol. 350, (1991), pp. 165-167.

Zhou, et al., "Glucose and Ethylene Signal Transduction Crosstalk Revealed by an *Arabidopsis* glucose-insensitive Mutant", Proc. Natl. Acad. Sci. USA, vol. 95, (1998), pp. 10294-10299.

Zhu, et al., "Expression of an *Atriplex nummularia* Gene Encoding a Protein Homologous to the bacterial Molecular Chaperone DnaJ," The Plant Cell, vol. 5, (1993), pp. 341-349.

Ziegelhoffr et al., "Cloning of the *Arabidopsis WIGGUM* Gene Identifies a Role for Farnesylation in Menstem Development", PNAS, vol. 97, (2000), pp. 7633-7638.

Guo et al., PNAS. USA, vol. 101, (2004), pp. 9205-9210.

Lazar, et al., Molecular Cell Biology, vol. 8, (1988), pp. 1247-1252.

Hill et al., Biochemical Biophysical Research Communications, vol. 244, (1998), pp. 573-577.

Lyznik et al., Molecular and General Genetics, vol. 230, Nos. 1-2, (1991), pp. 209-218.

Paszkowski et al., The EMBO Journal, vol. 7, No. 13, (1988), pp. 4021-4026.

Risseeuw, et al, The Plant Journal, vol. 11, No. 4, (1997), pp. 717-728.

Thykjaer et al., Plant Molecular Biology, vol. 35, No. 4, (1997), pp. 523-530.

Kaye, et al., Plant Physiology, vol. 116, No. 4, (1998), pp. 1367-1377.

Iturriaga, et al., Plant Molecular Biology, vol. 20, No. 3, (1992), pp. 555-558.

EMBO Accession No. AF353722, Apr. 27, 2001.

Pei et al., TIBS, vol. 26, No. 5, (2001), pp. 275-277.

International Search Report for PCT/IB02/03887, Jul. 28, 2003.

Sandler, S.J., et al., "Inhibition of Gene Expression in Transformed Plants by Antisense RNA", Plant Molecular Biology, vol. 11, No. 3, (1988), pp. 301-310.

Van Der Krol, A.R., et al., "Inhibition of Flower Pigmentation by Antisense CHS Genes; Promoter and Minimal Sequence Requirement for the Antisense Effect", Plant Mol. Biol., vol. 14, No. 4, (1990), pp. 457-466.

Waterhouse, et al., "Virus Resistance and Gene Silencing: Killing the Messenger", Trends Plant Sci., vol. 4, No. 11, (1999), pp. 452-457.

Temple, S.J., et al., "Down-regulation of Specific Members of the Glutamine Synthetase Gene Family in Alfalfa by Antisense RNA Technology", Plant Mol. Biol., vol. 37, No. 3, (1998), pp. 535-547.

* cited by examiner

Figure 4A

```
GmCPP        ------------------------------------------------------------
GmPrPase2    ------------------------------------------------------------
AtCPP        ------------------------------------------------------------
AtPrPase1    ------------------------------------------------------------
AtPrPase2    ------------------------------------------------------------
AFC1         ------------------------------------------------------------
AT4g01320    ------------------------------------------------------------
AF007269     ATGGCGATTCCTTTCATGGAAACCGTCGTGGGTAAGCTTCAAAACCTTTTTCTGAGACAT   60
BnCPP        ------------------------------------------------------------
ZmPrPase2    ------------------------------------------------------------
PpPrPase1    ------------------------------------------------------------

GmCPP        ------------------------------------------------------------
GmPrPase2    ------------------------------------------------------------
AtCPP        ------------------------------------------------------------
AtPrPase1    ------------------------------------------------------------
AtPrPase2    ------------------------------------------------------------
AFC1         ------------------------------------------------------------
AT4g01320    ------------------------------------------------------------
AF007269     TTTACTATCCTGTTTCACTCATCGTATTTCGTTTTTGTTTGGGTTTTGCTTTCTGTGTTG  120
BnCPP        ------------------------------------------------------------
ZmPrPase2    ------------------------------------------------------------
PpPrPase1    ------------------------------------------------------------

GmCPP        ------------------------------------------------------------
GmPrPase2    ------------------------------------------------------------
AtCPP        ------------------------------------------------------------
AtPrPase1    ------------------------------------------------------------
AtPrPase2    ------------------------------------------------------------
AFC1         ------------------------------------------------------------
AT4g01320    ------------------------------------------------------------
AF007269     TGTGTGTTGAGATTCCATGACTCGTTTGTTTCATATACCATCGTCTCTGCTTCTCGTTTC  180
BnCPP        ------------------------------------------------------------
ZmPrPase2    ------------------------------------------------------------
PpPrPase1    ------------------------------------------------------------

GmCPP        ------------------------------------------------------------
GmPrPase2    ------------------------------------------------------------
AtCPP        ------------------------------------------------------------
AtPrPase1    ------------------------------------------------------------
AtPrPase2    ------------------------------------------------------------
AFC1         ------------------------------------------------------------
AT4g01320    ------------------------------------------------------------
AF007269     TAAATTTTGTTCTTTTCTAATAGTGCGTACCTTGATCTGAGGTTTTATTACTCCTACTAG  240
BnCPP        ------------------------------------------------------------
ZmPrPase2    ------------------------------------------------------------
PpPrPase1    ------------------------------------------------------------
```

Figure 4B

```
GmCPP       ------------------------------------------------------------
GmPrPase2   ------------------------------------------------------------
AtCPP       ------------------------------------------------------------
AtPrPase1   ------------------------------------------------------------
AtPrPase2   ------------------------------------------------------------
AFC1        ------------------------------------------------------------
AT4g01320   ------------------------------------------------------------
AF007269    TTTCTTGTCTTACTCGTGCGTTTGATTTGATTTGAGCTTATGTGATTTCATCATCTCTTC 300
BnCPP       ------------------------------------------------------------
ZmPrPase2   ------------------------------------------------------------
PpPrPase1   ------------------------------------------------------------

GmCPP       ------------------------------------------------------------
GmPrPase2   ------------------------------------------------------------
AtCPP       ------------------------------------------------------------
AtPrPase1   ------------------------------------------------------------
AtPrPase2   ------------------------------------------------------------
AFC1        ------------------------------------------------------------
AT4g01320   ------------------------------------------------------------
AF007269    CTCGGTTTTAGAATGTACGGAGCTTCTCTGTTAACCAAAATCTAGGATTTGGGAAGAAAA 360
BnCPP       ------------------------------------------------------------
ZmPrPase2   ------------------------------------------------------------
PpPrPase1   ------------------------------------------------------------

GmCPP       ------------------------------------------------------------
GmPrPase2   ------------------------------------------------------------
AtCPP       ------------------------------------------------------------
AtPrPase1   ------------------------------------------------------------
AtPrPase2   ------------------------------------------------------------
AFC1        ------------------------------------------------------------
AT4g01320   ------------------------------------------------------------
AF007269    GTCGGAGTCTTTTTTTTCCTCATTCCCGATTGGAAATTGAGAATCTTGAAATTTTTCTTT 420
BnCPP       ------------------------------------------------------------
ZmPrPase2   ------------------------------------------------------------
PpPrPase1   ------------------------------------------------------------

GmCPP       ------------------------------------------------------------
GmPrPase2   ------------------------------------------------------------
AtCPP       ------------------------------------------------------------
AtPrPase1   ------------------------------------------------------------
AtPrPase2   ------------------------------------------------------------
AFC1        ------------------------------------------------------------
AT4g01320   ------------------------------------------------------------
AF007269    GTTCAAGTCATACAGCTTGAGGTTTTGGGTTTTCTTGTCAGGGTATTATTATGTTCGTGA 480
BnCPP       ------------------------------------------------------------
ZmPrPase2   ------------------------------------------------------------
PpPrPase1   ------------------------------------------------------------
```

Figure 4C

```
GmCPP        ------------------------------------------------------------
GmPrPase2    ------------------------------------------------------------
AtCPP        ------------------------------------------------------------
AtPrPase1    ------------------------------------------------------------
AtPrPase2    ------------------------------------------------------------
AFC1         ------------------------------------------------------------
AT4g01320    ------------------------------------------------------------
AF007269     CTGCAACTAGAGTTTTCTGGAGTTTTTTGAAATGGGTTTTGTGTTGTGGAACCGTATGTG 540
BnCPP        ------------------------------------------------------------
ZmPrPase2    --------------------------------------------AAATCCGAGCTC 12
PpPrPase1    ------------------------------------------------------------

GmCPP        ------------------------------------------------------------
GmPrPase2    ------------------------------------------------------------
AtCPP        ------------------------------------------------------------
AtPrPase1    ------------------------------------------------------------
AtPrPase2    ------------------------------------------------------------
AFC1         ------------------------------------------------------------
AT4g01320    ------------------------------------------------------------
AF007269     AATGTTGCATCAAAACTCTTTCAGTGCTCCAATGTTTCCATCAGTAGTCAGCACAAGAGA 600
BnCPP        ------------------------------------------------------------
ZmPrPase2    CGGAATCGAGCAAAGCACCCGAGCCTGCGCCGCGTCAAGCCGTCAAAGCTCCCCCGCTTC 72
PpPrPase1    ------------------------------------------------------------

GmCPP        ------------------------------------------------------------
GmPrPase2    -------------------------------------------------------GCGAG 5
AtCPP        ------------------------------------------------------------
AtPrPase1    ------------------------------------------------------------
AtPrPase2    ------------------------------------------------------------
AFC1         ------------------------------------------------------------
AT4g01320    ------------------------------------------------------------
AF007269     TCTTTTTATATCTGGTTGATCAAAAAAGTAGATGATGTTATTGAATTTTCAGTGATGGAG 660
BnCPP        ------------------------------------------------------------
ZmPrPase2    ATACCATTCCCTCCCCCGATCCCTCGCCTCAGCCCTCAGCTCCGCCCCTCGGTTTCCGAA 132
PpPrPase1    ------------------------------------------------------------

GmCPP        -----------------------------ATGGCGTTTCCC--TACATGGAAGCCG 25
GmPrPase2    CTCTCGTTCGGTTCATCAGCGTGTGTCTCAGCCATGGCGTTTCCC--TACATGGAAGCCG 63
AtCPP        -----------------------------ATGGCGATTCCT--TTCATGGAAACCG 25
AtPrPase1    -----------------------------ATGGCGATTCCT--TTCATGGAAACCG 25
AtPrPase2    -----------------------------ATGGCGATTCCT--TTCATGGAAACCG 25
AFC1         -----------------------------ATGGCGATTCCT--TTCATGGAAACCG 25
AT4g01320    -----------------------------ATGGCGATTCCT--TTCATGGAAACCG 25
AF007269     TATCTGTTGTTGTGGCATTTAGAGTAGATTCGTATTTCATCTTCTGTTTTATTCTTTTTC 720
BnCPP        -----------------------------ATGGCGATTCCT--TTCATGGAAACCG 25
ZmPrPase2    GCGCCACCGCCGACGTGGCCTCCCTCGGCTCCAATGGCGTTGCCC--TACCTGGAGGCCG 190
PpPrPase1    ------------------------------------------------------------
```

Figure 4D

```
GmCPP       TTGTCGGATTTATGATATTAATGTACATTTTTGAAACTTACTTGGATGTGCGACAACATA 85
GmPrPase2   TTGTCGGATTTATGATATTAATGTACATTTTTGAAACTTACTTGGATGTGCGACAACATA 123
AtCPP       TCGTGGGTTTTATGATAGTGATGTACATTTTTGAGACGTATTTGGATCTGAGGCAACTCA 85
AtPrPase1   TCGTGGGTTTTATGATAGTGATGTACATTTTTGAGACGTATTTGGATCTGAGGCAACTCA 85
AtPrPase2   TCGTGGGTTTTATGATAGTGATGTACATTTTTGAGACGTATTTGGATCTGAGGCAACTCA 85
AFC1        TCGTGGGTTTTATGATAGTGATGTACATTTTTGAGACGTATTTGGATCTGAGGCAACTCA 85
AT4g01320   TCGTGGGTTTTATGATAGTGATGTACATTTTTGAGACGTATTTGGATCTGAGGCAACTCA 85
AF007269    TTACAGGTTTTATGATAGTGATGTACATTTTTGAGACGTATTTGGATCTGAGGCAACTCA 780
BnCPP       TCGTTGGTTTTATGATAGTGATGTACGTTTTTGAGACGTATTTGGATCTGAGGCAACATA 85
ZmPrPase2   TGCTTTGCTTTATGATTTTCATGTACATATTTGAGACATATCTTGACATCCGTCAGCATA 250
PpPrPase1   ------------------------------------GGATCCCCCGGGCTGCAGGAATTCG 25
Consensus                                       NNNTNNNNNGNNNTNNNNNANNNNN GmCPP       GGGCC--CTCAAACTTCCTACTCTTCCAAAGACTTTAGAGGGTGTTATCAGCCAAGAGAA 143
GmPrPase2   GGGCC--CTCAAACTTCCTACTCTTCCAAAGACTTTAGAAGGTGTTATCAGCCAAGAGAA 181
AtCPP       CTGCT--CTCAAGCTTCCAACTCTCCCGAAAACCTTGGTTGGTGTAATTAGCCAAGAGAA 143
AtPrPase1   CTGCT--CTCAAGCTTCCAACTCTCCCGAAAACCTTGGTTGGTGTAATTAGCCAAGAGAA 143
AtPrPase2   CTGCT--CTCAAGCTTCCAACTCTCCCGAAAACCTTGGTTGGTGTAATTAGCCAAGAGAA 143
AFC1        CTGCT--CTCAAGCTTCCAACTCTCCCGAAAACCTTGGTTGGTGTAATTAGCCAAGAGAA 143
AT4g01320   CTGCT--CTCAAGCTTCCAACTCTCCCGAAAACCTTGGTTGGTGTAATTAGCCAAGAGAA 143
AF007269    CTGCT--CTCAAGCTTCCAACTCTCCCGAAAACCTTGGTTGGTGTAATTAGCCAAGAGAA 838
BnCPP       CTGCT--CTCAAGCTTCCCACTCTCCCAAAGACTTTGGTTGGAGTCATTAGCCAAGAGAA 143
ZmPrPase2   GAGCC--CTCAAGCTGCCAACTTTGCCAAAACCCCTGCTGGGAGTAATTAGTGACGAAAA 308
PpPrPase1   GCACGAGCTCAAGCTGTCCAATCTGCCAGCGCCTCTCAAGGGAATAGTTAGTCAAGAGAA 85
Consensus   NNNCN  CTCAANCTNNCNANTNTNCCNNNNNCNNTNNNNGGNNTNNTNAGNNANGANAA GmCPP       ATTTGAGAAATCTAGAGCCTATAG------------------------------------ 167
GmPrPase2   ATTTGAGAAATCTAGAGCCTATAG------------------------------------ 205
AtCPP       GTTTGAGAAATCACGAGCATACAG------------------------------------ 167
AtPrPase1   GTTTGAGAAATCACGAGCATACAG------------------------------------ 167
AtPrPase2   GTTTGAGAAATCACGAGCATACAG------------------------------------ 167
AFC1        GTTTGAGAAATCACGAGCATACAG------------------------------------ 167
AT4g01320   GTTTGAGAAATCACGAGCATACAG------------------------------------ 167
AF007269    GTTTGAGAAATCACGAGCATACAGTCTTGACAAAAGGTTTCGTCTTGATCATATTTATAT 898
BnCPP       GTTTGAGAAATCTCGAGCTTACAG------------------------------------ 167
ZmPrPase2   GTTTGAACGCTCTAGAGCTTATAG------------------------------------ 332
PpPrPase1   ATTTGAGAAAGCGCAGGCGTACAG------------------------------------ 109
Consensus   NTTTGANNNNNCNNNNGCNTANAG GmCPP       ------------------------------------------TCTTGATAAA---AGC 180
GmPrPase2   ------------------------------------------TCTTGATAAA---AGC 218
AtCPP       ------------------------------------------TCTTGACAAA---AGC 180
AtPrPase1   ------------------------------------------TCTTGACAAA---AGC 180
AtPrPase2   ------------------------------------------TCTTGACAAA---AGC 180
AFC1        ------------------------------------------TCTTGACAAA---AGC 180
AT4g01320   -------------------------GGATATCATCACTGAGAACTTTAATATATGCAGC 201
AF007269    CATTTAGTTTTTTATAATTGCCAGGGGATATCATCACTGAGAACTTTAATATATGCAGC 958
BnCPP       ------------------------------------------TCTTGACAAA---AGC 180
ZmPrPase2   ------------------------------------------CCTCGACAAA---AGC 345
PpPrPase1   ------------------------------------------CTTAGACAAG---AGC 122
Consensus                                               NNTNNANANNNNNAGC
```

Figure 4E

```
GmCPP       CACTTCCATTTTGTTCACGAGTTTGTGACAATAGTGACAGACTCTACAATTTTGTACTTT 240
GmPrPase2   CACTTCCATTTTGTTCACGAGTTTGTGACAATAGTGACAGACTCTACAATTTTGTACTTT 278
AtCPP       TATTTTCACTTTGTTCATGAGTTTGTAACTATACTTATGGACTCTGCAATTTTGTTCTTT 240
AtPrPase1   TATTTTCACTTTGTTCATGAGTTTGTAACTATACTTATGGACTCTGCAATTTTGTTCTTT 240
AtPrPase2   TATTTTCACTTTGTTCATGAGTTTGTAACTATACTTATGGACTCTGCAATTTTGTTCTTT 240
AFC1        TATTTTCACTTTGTTCATGAGTTTGTAACTATACTTATGGACTCTGCAATTTTGTTCTTT 240
AT4g01320   TATTTTCACTTTGTTCATGAGTTTGTAACTATACTTATGGACTCTGCAATTTTGTTCTTT 261
AF007269    TATTTTCACTTTGTTCATGAGTTTGTAACTATACTTATGGACTCTGCAATTTTGTTCTTT 1018
BnCPP       CATTTTCACTTTGTTCATGAGTTTGTTACTATACTTATGGACTCTGCGATTCTGTTCTTT 240
ZmPrPase2   TATTTCCATTTTGTTCATGAGGCTGTGACTATTTTAATGGATACTACAATACTATACTAT 405
PpPrPase1   CGATTCCATTTTGTGCACGCGGCTGTGAATATCGTGGAGGAATCGGCAATTCTTCTGCTG 182
Consensus   NNNTTNCANTTTGTNCANGNGNNTGTNANNATNNTNNNNGANNCNNCNATNNTNNNNNNN GmCPP       GGGGTATTGCCCTGGTTTTGGAAG------------------------------------ 264
GmPrPase2   GGGGTATTGCCCTGGTTTTGGAAG------------------------------------ 302
AtCPP       GGGATCTTGCCTTGGTTTTGGAAG------------------------------------ 264
AtPrPase1   GGGATCTTGCCTTGGTTTTGGAAG------------------------------------ 264
AtPrPase2   GGGATCTTGCCTTGGTTTTGGAAG------------------------------------ 264
AFC1        GGGATCTTGCCTTGGTTTTGGAAG------------------------------------ 264
AT4g01320   GGGATCTTGCCTTGGTTTTGGAAG------------------------------------ 285
AF007269    GGGATCTTGCCTTGGTTTTGGAAGGTACATATCTGGTTTCGGTATACAGTATCTCATTTT 1078
BnCPP       GGGATCTTGCCTTGGTTTTGGAAG------------------------------------ 264
ZmPrPase2   AGAGTTCTTCCCTGGTTTTGGAAG------------------------------------ 429
PpPrPase1   GGGTTGTTGCCGTGGGCGTGGGAT------------------------------------ 206
Consensus   NGNNTNNTNCCNTGGNNNTGGNAN GmCPP       ---------------------------------------------------AAATCAGGAG 274
GmPrPase2   ---------------------------------------------------AAATCAGGAG 312
AtCPP       ---------------------------------------------------ATGTCTGGAG 274
AtPrPase1   ---------------------------------------------------ATGTCTGGAG 274
AtPrPase2   ---------------------------------------------------ATGTCTGGAG 274
AFC1        ---------------------------------------------------ATGTCTGGAG 274
AT4g01320   ---------------------------------------------------ATGTCTGGAG 295
AF007269    GAATATAGAGTTGTTACATTACAATTGTAAAGTTTTCATTTTTACCTTAGATGTCTGGAG 1138
BnCPP       ---------------------------------------------------ATATCTGGCG 274
ZmPrPase2   ---------------------------------------------------AAATCTGGAG 439
PpPrPase1   ---------------------------------------------------AAGAGTGGAT 216
Consensus                                                      ANNNNNGGNN GmCPP       ATTTTATGACAATAGCTGGTTTCAATGCTGAGAATGAAATACTGCATACCCTTGCCTTCT 334
GmPrPase2   ATTTTATGACAATAGCTGGTTTCAATGCTGAGAATGAAATACTGCATACCCTTGCCTTCT 372
AtCPP       CTGTTTTACCGAGGTTGGGCCTTGATCCGGAGAATGAAATACTGCATACTCTTTCATTCT 334
AtPrPase1   CTGTTTTACCGAGGTTGGGCCTTGATCCAGAGAATGAAATACTGCATACTCTTTCATTCT 334
AtPrPase2   CAGTTTTACCGAGGTTGGGCCTTGATCCAGAGAATGAAATACTGCATACTCTTTCATTCT 334
AFC1        CTGTTTTACCGAGGTTGGGCCTTGATCCAGAGAATGAAATACTGCATACTCTTTCATTCT 334
AT4g01320   CTGTTTTACCGAGGTTGGGCCTTGATCCAGAGAATGAAATACTGCATACTCTTTCATTCT 355
AF007269    CTGTTTTACCGAGGTTGGGCCTTGATCCAGAGAATGAAATACTGCATACTCTTTCATTCT 1198
BnCPP       GCTTCTACCAATGGTGGGACTCGATCCAGAGAATGAAATCCTGCACACTCTTTCATTCT 334
ZmPrPase2   AGTTAGTTACCAGTGTTGGGCTGAGTGCTGAGAATGAGATAATACACACCCTTGCTTTCT 499
PpPrPase1   CGTTAGTAGGGAAGCTAGGGTTTGATGAGAAGAGCGAAATTTTGCAGACGCTTTCTTTTC 276
Consensus   NNNTNNTNNNNANNNNNGGNNTNNNTNNNNAGANNGANATNNTNCANACNCTTNCNTTNN
```

Figure 4F

```
GmCPP       TAGCAGGGCTGATGATTTGGTCACAG----------------------------------  360
GmPrPase2   TAGCAGGGCTGATGATTTGGTCACAG----------------------------------  398
AtCPP       TGGCTGGTGTTATGACATGGTCACAG----------------------------------  360
AtPrPase1   TGGCTGGTGTTATGACATGGTCACAG----------------------------------  360
AtPrPase2   TGGCTGGTGTTATGACATGGTCACAG----------------------------------  360
AFC1        TGGCTGGTGTTATGACATGGTCACAG----------------------------------  360
AT4g01320   TGGCTGGTGTTATGACATGGTCACAG----------------------------------  381
AF007269    TGGCTGGTGTTATGACATGGTCACAGGTGTTCCAAATAAACCCCTTCATATAGTCCTATA 1258
BnCPP       TGGCTGGTCTTATGACATGGTCACAG----------------------------------  360
ZmPrPase2   TAGCTGGTTCCATGGTTTGGTCGCAG----------------------------------  525
PpPrPase1   TTGCGGTGACCACGTTGTGGTCGCAG----------------------------------  302
Consensus   TNGCNGNNNNNANGNNNTGGTCNCAG GmCPP       ------------------------------------------------------------
GmPrPase2   ------------------------------------------------------------
AtCPP       ------------------------------------------------------------
AtPrPase1   ------------------------------------------------------------
AtPrPase2   ------------------------------------------------------------
AFC1        ------------------------------------------------------------
AT4g01320   ------------------------------------------------------------
AF007269    CGTTTAGCATCAAAATATCTATTTTCTTAAGATAATAATATTTCTTTTATATTCTGATGC 1318
BnCPP       ------------------------------------------------------------
ZmPrPase2   ------------------------------------------------------------
PpPrPase1   ------------------------------------------------------------

GmCPP       --ATAACAGATTTGCCCTTTTCTCTGTACTCAACTTTTGTGATTGAGGCCCGTCATGGTT  418
GmPrPase2   --ATAACAGATTTGCCCTTTTCTCTGTACTCAACTTTTGTGATTGAGGCCCGTCATGGTT  456
AtCPP       --ATCACTGATTTGCCATTTTCTTTGTACTCAACTTTCGTGATCGAGTCTCGGCATGGGT  418
AtPrPase1   --ATCACTGATTTGCCATTTTCTTTGTACTCAACTTTCGTGATCGAGTCTCGGCATGGGT  418
AtPrPase2   --ATCACTGATTTGCCATTTTCTTTGTACTCAACTTTCGTGATCGAGTCTCGGCATGGGT  418
AFC1        --ATCACTGATTTGCCATTTTCTTTGTACTCAACTTTCGTGATCGAGTCTCGGCATGGGT  418
AT4g01320   --ATCACTGATTTGCCATTTTCTTTGTACTCAACTTTCGTGATCGAGTCTCGGCATGGGT  439
AF007269    AGATCACTGATTTGCCATTTTCTTTGTACTCAACTTTCGTGATCGAGTCTCGGCATGGGT 1378
BnCPP       --ATCACTGATTTGCCATTTTCTTTGTACTCAACTTTCGTGATCGAGTCTCGGCATGGGT  418
ZmPrPase2   --ATTACAGACTTGCCGTTCTCTCTCTATTCAACTTTTGTTATAGAGGCTCGACATGGTT  583
PpPrPase1   --ATACTTGAGCTTCCATTCTCGCTCTACTCCACGTTTGTCATCGAGGCCCGCCATGGCT  360
Consensus   ATNNNNGANNTNCCNTTNTCNNTNTANTCNACNTTNGTNATNGAGNCNCGNCATGGNT GmCPP       TTAATAAG----------------------------------------------------  426
GmPrPase2   TTAATAAG----------------------------------------------------  464
AtCPP       TCAACAAA----------------------------------------------------  426
AtPrPase1   TCAACAAA----------------------------------------------------  426
AtPrPase2   TCAACAAA----------------------------------------------------  426
AFC1        TCAACAAA----------------------------------------------------  426
AT4g01320   TCAACAAA----------------------------------------------------  447
AF007269    TCAACAAAGTATGTCGTATTTCCAACACTACCTTGTGACTTACGTTTTTTTATCAGAGAT 1438
BnCPP       TCAACAAA----------------------------------------------------  426
ZmPrPase2   TTAACAAG----------------------------------------------------  591
PpPrPase1   TCAACAAG----------------------------------------------------  368
Consensus   TNAANAAN
```

Figure 4G

```
GmCPP        ---------------------------------CAAACACCATGGTTATTCTTTAGGGA 452
GmPrPase2    ---------------------------------CAAACACCATGGTTATTCTTTAGGGA 490
AtCPP        ---------------------------------CAAACAATATGGATGTTCATTAGGGA 452
AtPrPase1    ---------------------------------CAAACAATATGGATGTTCATTAGGGA 452
AtPrPase2    ---------------------------------CAAACAATATGGATGTTCATTAGGGA 452
AFC1         ---------------------------------CAAACAATATGGATGTTCATTAGGGA 452
AT4g01320    ---------------------------------CAAACAATATGGATGTTCATTAGGGA 473
AF007269     GTGGATTAAATTTGCTTCTAAATTCTGTTGACAGCAAACAATATGGATGTTCATTAGGGA 1498
BnCPP        ---------------------------------CAAACAATATGGATGTTCATTAGGGA 452
ZmPrPase2    ---------------------------------CAAACTATATGGCTCTTCATTAGGGA 617
PpPrPase1    ---------------------------------CAAACCATATGGTTGTTTTTACGGGA 394
Consensus                                     CAAACNNNATGGNTNTTNNTNNGGGA GmCPP        CATGCTTAAAGGAATTTTCCTTTCTGTAATAATTGGTCCACCTATTGTGGCTGCAATCAT 512
GmPrPase2    CATGCTTAAAGGAATTTTCCTTTCTGTAATAATTGGTCCACCTATTGTGGCTGCAATCAT 550
AtCPP        CATGATCAAAGGAACATTCCTCTCTGTCATACTAGGCCCACCCATTGTTGCTGCGATAAT 512
AtPrPase1    CATGATCAAAGGAACATTCCTCTCTGTCATACTAGGCCCACCCATTGTTGCCGCGATAAT 512
AtPrPase2    CATGATCAAAGGAACATTCCTCTCTGTCATACTAGGCCCACCCATTGTTGCTGCGATAAT 512
AFC1         CATGATCAAAGGAACATTCCTCTCTGTCATACTAGGCCCACCCATTGTTGCTGCGATAAT 512
AT4g01320    CATGATCAAAGGAACATTCCTCTCTGTCATACTAGGCCCACCCATTGTTGCTGCGATAAT 533
AF007269     CATGATCAAAGGAACATTCCTCTCTGTCATACTAGGCCCACCCATTGTTGCTGCGATAAT 1558
BnCPP        CATGATCAAAGGAATACTCCTCTCTGTCATACCTGCCCCTCCTATCGTTGCCGCAATTAT 512
ZmPrPase2    TATGATCAAAGGAATTTTACTATCCATGATATTGGGGCCACCAATCGTGGCTGCTATCAT 677
PpPrPase1    TATGATCATGGGGCTGGCTCTCATGATGGTGGTTGGCCCACCCATAGTGTCGGCAATTAT 454
Consensus    NATGNTNANNGGNNNNNNNCTNNNNNTNNTNNNNGNNCCNCCNATNGTNNCNGCNATNAT GmCPP        TGTAATAGTACAG----------------------------------------------- 525
GmPrPase2    TGTAATAGTACAG----------------------------------------------- 563
AtCPP        TTTCATAGTCCAG----------------------------------------------- 525
AtPrPase1    TTTCATAGTCCAG----------------------------------------------- 525
AtPrPase2    TTTCATAGTCCAG----------------------------------------------- 525
AFC1         TTTCATAGTCCAG----------------------------------------------- 525
AT4g01320    TTTCATAGTCCAG----------------------------------------------- 546
AF007269     TTTCATAGTCCAGGTTTGATGATTCTGGATTCATCTTATTTCTGAGTTTTTCACATGGAT 1618
BnCPP        TGTTATAGTTCAG----------------------------------------------- 525
ZmPrPase2    CTACATAGTACAG----------------------------------------------- 690
PpPrPase1    CTATATTGTGCAG----------------------------------------------- 467
Consensus    NNNNATNGTNCAG GmCPP        ------------------------------------------------------------
GmPrPase2    ------------------------------------------------------------
AtCPP        ------------------------------------------------------------
AtPrPase1    ------------------------------------------------------------
AtPrPase2    ------------------------------------------------------------
AFC1         ------------------------------------------------------------
AT4g01320    ------------------------------------------------------------
AF007269     GACTATTCTCCATTGAGTGTGAGCTTCAAAGTTTTTAGTTTTCGTGTTAAAAATTTAAAA 1678
BnCPP        ------------------------------------------------------------
ZmPrPase2    ------------------------------------------------------------
PpPrPase1    ------------------------------------------------------------
```

Figure 4H

```
GmCPP       ---------------------------------------AAAGGAGGTCCATACTTGGCCA 547
GmPrPase2   ---------------------------------------AAAGGAGGTCCATACTTGGCCA 585
AtCPP       ---------------------------------------AAAGGAGGTCCTTATCTTGCCA 547
AtPrPase1   ---------------------------------------AAAGGAGGTCCTTATCTTGCCA 547
AtPrPase2   ---------------------------------------AAAGGAGGTCCTTATCTTGCCA 547
AFC1        ---------------------------------------AAAGGAGGTCCTTATCTTGCCA 547
AT4g01320   ---------------------------------------AAAGGAGGTCCTTATCTTGCCA 568
AF007269    TTTGCTTCTCTGAGCATGAAGTTTCTATCTTTTTCCAGAAAGGAGGTCCTTATCTTGCCA 1738
BnCPP       ---------------------------------------AAAGGAGGTCCTTACCTCGCCA 547
ZmPrPase2   ----------------------------------------ATTGGAGGACCTTACCTGGCTA 712
PpPrPase1   ---------------------------------------AACGGTGGGCCATATCTTGCCC 489
Consensus                                          ANNGGNGGNCCNTANNTNGCNN GmCPP       TCTATCTTTGGGTTTTTACGTTTGGTCTTTCTATTGTGATGATGACCCTTTATCCAGTAC 607
GmPrPase2   TCTATCTTTGGGTTTTTACGTTTGGTCTTTCTATTGTGATGATGACCCTTTATCCAGTAC 645
AtCPP       TCTATCTGTGGGCATTCATGTTTATCCTGTCTCTAGTGATGATGACTATATACCCGGTCT 607
AtPrPase1   TCTATCTGTGGGCATTCATGTTTATCCTGTCTCTAGTGATGATGACTATATACCCGGTCT 607
AtPrPase2   TCTATCTGTGGGCATTCATGTTTATCCTGTCTCTAGTGATGATGACTATATACCCGGTCT 607
AFC1        TCTATCTGTGGGCATTCATGTTTATCCTGTCTCTAGTGATGATGACTATATACCCGGTCT 607
AT4g01320   TCTATCTGTGGGCATTCATGTTTATCCTGTCTCTAGTGATGATGACTATATACCCGGTCT 628
AF007269    TCTATCTGTGGGCATTCATGTTTATCCTGTCTCTAGTGATGATGACTATATACCCGGTCT 1798
BnCPP       TCTATCTGTGGGCATTCATGTTTATCCTGTCTCTAGTGATGATGACTATATACCCTGTTT 607
ZmPrPase2   TATATCTCTGGGGTTTTATGTTTGTATTAGCTCTACTGATGATGACAATATACCCCATTG 772
PpPrPase1   TCTATCTGTGGGCCTTTATGTTGCTGTTATCCCTCGTGTTGATGGCCCTATATCCCGTTC 549
Consensus   TNTATCTNTGGGNNTTNANGTTNNNNNTNNCNNTNNTGNTGATGNCNNTNTANCCNNTNN GmCPP       TAATAGCTCCACTCTTCAATAAGTTCACTCCA---------------------------- 639
GmPrPase2   TAATAGCTCCACTCTTCAATAAGTTCACTCCA---------------------------- 677
AtCPP       TGATAGCACCGCTCTTCAACAAATTCACTCCT---------------------------- 639
AtPrPase1   TGATAGCACCGCTCTTCAACAAGTTCACTCCT---------------------------- 639
AtPrPase2   TGATAGCACCGCTCTTCAACAAGTTCACTCCT---------------------------- 639
AFC1        TGATAGCACCGCTCTTCAACAAGTTCACTCCT---------------------------- 639
AT4g01320   TGATAGCACCGCTCTTCAACAAGTTCACTCCT---------------------------- 660
AF007269    TGATAGCACCGCTCTTCAACAAGTTCACTCCTGTGTGTATTTCTGTCATGGCCATTTTAC 1858
BnCPP       TGATTGCACCTCTTTTCAACAAGTTCACTCCT---------------------------- 639
ZmPrPase2   TGATAGCTCCTCTGTTCAACAAGTTCACTCCT---------------------------- 804
PpPrPase1   TCATCGCGCCTCTTTTCAACACATTCACACCC---------------------------- 581
Consensus   TNATNGCNCCNCTNTTCAANANNTTCACNCCN GmCPP       ------------------------------------------------------------
GmPrPase2   ------------------------------------------------------------
AtCPP       ------------------------------------------------------------
AtPrPase1   ------------------------------------------------------------
AtPrPase2   ------------------------------------------------------------
AFC1        ------------------------------------------------------------
AT4g01320   ------------------------------------------------------------
AF007269    AATTCACTGCTTGTTTGCATATGTTGTTACCAGACAATATAATCTCCCGCTTTTTTATGG 1918
BnCPP       ------------------------------------------------------------
ZmPrPase2   ------------------------------------------------------------
PpPrPase1   ------------------------------------------------------------
```

Figure 4I

```
GmCPP        ------CTTCCAGATGGTCAACTCAGGGAGAAAATCGAGAAACTTGCTTCCTCCCTCAAC 693
GmPrPase2    ------CTTCCAGATGGTCAACTCAGGGAGAAAATCGAGAAACTTGCTTCCTCCCTCAAC 731
AtCPP        ------CTTCCAGATGGAGACCTCCGGGAGAAGATTGAGAAACTTGCTTCTTCCCTAAAG 693
AtPrPase1    ------CTTCCAGATGGAGACCTCCGGGAGAAGATTGAGAAACTTGCTTCTTCTCTAAAG 693
AtPrPase2    ------CTTCCAGATGGAGACCTCCGGGAGAAGATTGAGAAACTTGCTTCTTCTCTAAAG 693
AFC1         ------CTTCCAGATGGAGACCTCCGGGAGAAGATTGAGAAACTTGCTTCTTCTCTAAAG 693
AT4g01320    ------CTTCCAGATGGAGACCTCCGGGAGAAGATTGAGAAACTTGCTTCTTCTCTAAAG 714
AF007269     CTATAGCTTCCAGATGGAGACCTCCGGGAGAAGATTGAGAAACTTGCTTCTTCTCTAAAG 1978
BnCPP        ------CTTCCTGATGGAGACCTCCGGGAGAAGATTGAGAAACTTGCTTCTTCTCTAAAG 693
ZmPrPase2    ------CTTCCTGAAGGAGTCCTCAGGGAAAAAATAGAGAAGCTGGCAGCTTCCCTCAAG 858
PpPrPase1    ------TTGCCAGAAGGGCAGCTTCGTGCCAAGATCGAGAAGCTGGCATCCTCCTTGGAC 635
Consensus          NTNCCNGANGGNNNNCTNNGNGNNAANATNGAGAANCTNGCNNCNTCNNTNNAN GmCPP        TATCCGTTAAAGAAACTATTTGTTGTCGATGGATCCACAAGATCAAGTCACAGCAATG-- 751
GmPrPase2    TATCCGTTAAAGAAACTATTTGTTGTCGATGGATCCACAAGATCAAGTCACAGCAATG-- 789
AtCPP        TTTCCTTTGAAGAAGCTGTTTGTTGTCGATGGATCTACAAGGTCAAGCCATAGCAATG-- 751
AtPrPase1    TTTCCTTTGAAGAAGCTGTTTGTTGTCGATGGATCTACAAGGTCAAGCCATAGCAATG-- 751
AtPrPase2    TTTCCTTTGAAGAAGCTGTTTGTTGTCGATGGATCTACAAGGTCAAGCCATAGCAATG-- 751
AFC1         TTTCCTTTGAAGAAGCTGTTTGTTGTCGATGGATCTACAAGGTCAAGCCATAGCAATG-- 751
AT4g01320    TTTCCTTTGAAGAAGCTGTTTGTTGTCGATGGATCTACAAGGTCAAGCCATAGCAATG-- 772
AF007269     TTTCCTTTGAAGAAGCTGTTTGTTGTCGATGGATCTACAAGGTCAAGCCATAGCAATGTG 2038
BnCPP        TTTCCTCTGAAGAAGCTGTTTGTTGTCGATGGATCTACAAGGTCAAGCCATAGTAATG-- 751
ZmPrPase2    TTTCCTTTGAAAAAGCTTTTCGTGGTAGATGGGTCTACCAGATCAAGCCACAGTAATG-- 916
PpPrPase1    TTCCCATTGAAGAAATTGTTTGTAATTGACGGTTCTACTCGGTCAAGCCATAGCAACG-- 693
Consensus    TNNCCNNNTNAANAANNTNTTNGTNNTNGANGGNTCNACNNGNTCAAGNCANAGNAANG GmCPP        ------------------------------------------------------------
GmPrPase2    ------------------------------------------------------------
AtCPP        ------------------------------------------------------------
AtPrPase1    ------------------------------------------------------------
AtPrPase2    ------------------------------------------------------------
AFC1         ------------------------------------------------------------
AT4g01320    ------------------------------------------------------------
AF007269     AGAAGCTTGAGATCTCTTCCTACCTACTTTACTCTAGTTTACCATTAGAAGCTTACGTAT 2098
BnCPP        ------------------------------------------------------------
ZmPrPase2    ------------------------------------------------------------
PpPrPase1    ------------------------------------------------------------

GmCPP        ------------------CCTATATGTATGGATTCTTCAAGAACAAGAGGATTGTCCCTT 793
GmPrPase2    ------------------CCTATATGTATGGATTCTTCAAGAACAAGAGGATTGTCCTTT 831
AtCPP        ------------------CTTACATGTATGGTTTCTTTAAGAACAAAAGGATTGTTCTTT 793
AtPrPase1    ------------------CTTACATGTATGGTTTCTTTAAGAACAAAAGGATTGTTCTTT 793
AtPrPase2    ------------------CTTACATGTATGGTTTCTTTAAGAACAAAAGGATTGTTCTTT 793
AFC1         ------------------CTTACATGTATGGTTTCTTTAAGAACAAAAGGATTGTTCTTT 793
AT4g01320    ------------------CTTACATGTATGGTTTCTTTAAGAACAAAAGGATTGTTCTTT 814
AF007269     CTTGTTACATCATACAGGCTTACATGTATGGTTTCTTTAAGAACAAAAGGATTGTTCTTT 2158
BnCPP        ------------------CTTACATGTATGGTTTCTTTAAGAACAAAAGGATTGTTCTTT 793
ZmPrPase2    ------------------CCTACATGTATGGTTTTTTCAAGAACAAGCGCATAGTACTCT 958
PpPrPase1    ------------------CCTACATGTATGGATTTTACAACAGCAAGCGCATCGTTCTGT 735
Consensus                      CNTANATGTATGGNTTNTNNAANANCAANNGNATNGTNCNNT
```

Figure 4J

```
GmCPP       ATGACACATTAATTCAACAG---------------------------------------- 813
GmPrPase2   ATGACACATTAATTCAACAG---------------------------------------- 851
AtCPP       ATGATACGTTGATTCAGCAG---------------------------------------- 813
AtPrPase1   ATGATACGTTGATTCAGCAG---------------------------------------- 813
AtPrPase2   ATGATACGTTGATTCAGCAG---------------------------------------- 813
AFC1        ATGATACGTTGATTCAGCAG---------------------------------------- 813
AT4g01320   ATGATACGTTGATTCAGCAG---------------------------------------- 834
AF007269    ATGATACGTTGATTCAGCAGGTACTGTGACTCTTGATGCTTCAAACGAGCTATACTCACA 2218
BnCPP       ATGACACATTGATTCAGCAG---------------------------------------- 813
ZmPrPase2   ATGACACATTGATTCAGCAG---------------------------------------- 978
PpPrPase1   ACGACACTCTAATATCGCAA---------------------------------------- 755
Consensus   ANGANACNNTNATNNNNCAN GmCPP       ---------------------------------------TGCAAAGACGATGA 827
GmPrPase2   ---------------------------------------TGCAAAGACGATGA 865
AtCPP       ---------------------------------------TGCAAGAATGAGGA 827
AtPrPase1   ---------------------------------------TGCAAGAATGAGGA 827
AtPrPase2   ---------------------------------------TGCAAGAATGAGGA 827
AFC1        ---------------------------------------TGCAAGAATGAGGA 827
AT4g01320   ---------------------------------------TGCAAGAATGAGGA 848
AF007269    TTTCTGTTTCTGGTTCTGAAACATAACATAATCTTCTATTGTGCAGTGCAAGAATGAGGA 2278
BnCPP       ---------------------------------------TGCCAGAATGAGAA 827
ZmPrPase2   ---------------------------------------TGTAGCAATGAGGA 992
PpPrPase1   ---------------------------------------TGTAAGAATGAGGA 769
Consensus                                          TGNNNNNANGANNA GmCPP       GGAAATTGTTGCTGTTATTGCCCATGAGTTGGGACACTGGAAGCTCAACCATACTGTGTA 887
GmPrPase2   GGAAATTGTTGCTGTTATTGCCCATGAGTTGGGACACTGGAAGCTCAACCATACTGTGTA 925
AtCPP       TGAAATTGTGGCGGTTATTGCACACGAGCTTGGACATTGGAAACTGAATCACACTACATA 887
AtPrPase1   TGAAATTGTGGCGGTTATTGCACACGAGCTTGGACATTGGAAACTGAATCACACTACATA 887
AtPrPase2   TGAAATTGTGGCGGTTATTGCACACGAGCTTGGACATTGGAAACTGAATCACACTACATA 887
AFC1        TGAAATTGTGGCGGTTATTGCACACGAGCTTGGACATTGGAAACTGAATCACACTACATA 887
AT4g01320   TGAAATTGTGGCGGTTATTGCACACGAGCTTGGACATTGGAAACTGAATCACACTACATA 908
AF007269    TGAAATTGTGGCGGTTATTGCACACGAGCTTGGACATTGGAAACTGAATCACACTACATA 2338
BnCPP       TGAAATTGTGGCGGTTATTGCACACGAGCTGGGACACTGGAAGCTGAATCACACTACATA 887
ZmPrPase2   TGAGATAGTTTCTGTTATAGCACATGAACTTGGACACTGGAACTCAATCATACTGTCTA 1052
PpPrPase1   AGAAGTAGTGGCAGTTATAGCTCATGAGCTTGGCCATTGGAAGCTGAGCCACACTATGTA 829
Consensus   NGANNTNGTNNCNGTTATNGCNCANGANNTNGGNCANTGGAANCTNANNCANACTNNNTA GmCPP       CACATTTGTTGCTATGCAG----------------------------------- 906
GmPrPase2   CACATTTGTTGCTATGCAG----------------------------------- 944
AtCPP       CTCGTTCATTGCAGTTCAA----------------------------------- 906
AtPrPase1   CTCGTTCATTGCAGTTCAA----------------------------------- 906
AtPrPase2   CTCGTTCATTGCAGTTCAA----------------------------------- 906
AFC1        CTCGTTCATTGCAGTTCAA----------------------------------- 906
AT4g01320   CTCGTTCATTGCAGTTCAA----------------------------------- 927
AF007269    CTCGTTCATTGCAGTTCAAGTGAGGCTCAACCGACAGTTCAAAAACTTACTCACATCTAC 2398
BnCPP       CTCGTTCATTGCTGTTCAA----------------------------------- 906
ZmPrPase2   TTCCTTTGTAGCTGTCCAG----------------------------------- 1071
PpPrPase1   CTCGTTCCTGGCCATGCAG----------------------------------- 848
Consensus   NNCNTTNNTNGCNNTNCAN
```

Figure 4K

```
GmCPP       ------------------------------------------------------ATTCTTA  913
GmPrPase2   ------------------------------------------------------ATTCTTA  951
AtCPP       ------------------------------------------------------ATCCTTG  913
AtPrPase1   ------------------------------------------------------ATCCTTG  913
AtPrPase2   ------------------------------------------------------ATCCTTG  913
AFC1        ------------------------------------------------------ATCCTTG  913
AT4g01320   ------------------------------------------------------ATCCTTG  934
AF007269    ATTTCACTTAAGAAATCATGTCTTATGACCCTCTCTCAATGTTTTGCTTGCAGATCCTTG 2458
BnCPP       ------------------------------------------------------ATCCTTG  913
ZmPrPase2   ------------------------------------------------------CTGCTTA 1078
PpPrPase1   ------------------------------------------------------GTGCTTA  855
Consensus                                                         NTNCTTN GmCPP       CACTTCTACAATTTGGAGGATATACACTAGTGCGAAATTCAGCTGATCTGTATCGAAGCT  973
GmPrPase2   CACTTCTACAATTTGGAGGATATACACTAGTGCGAAATTCAGCTGATCTGTATCGAAGCT 1011
AtCPP       CCTTCTTACAATTTGGAGGATACACTCTTCTCAGAAACTCCACTGATCTCTTCAGGAGTT  973
AtPrPase1   CCTTCTTACAATTTGGAGGATACACTCTTGTCAGAAACTCCACTGATCTCTTCAGGAGTT  973
AtPrPase2   CCTTCTTACAATTTGGAGGATACACTCTTGTCAGAAACTCCACTGATCTCTTCAGGAGTT  973
AFC1        CCTTCTTACAATTTGGAGGATACACTCTTGTCAGAAACTCCACTGATCTCTTCAGGAGTT  973
AT4g01320   CCTTCTTACAATTTGGAGGATACACTCTTGTCAGAAACTCCACTGATCTCTTCAGGAGTT  994
AF007269    CCTTCTTACAATTTGGAGGATACACTCTTGTCAGAAACTCCACTGATCTCTTCAGGAGTT 2518
BnCPP       CCTTCTTGCAATTTGGAGGATACACTCTTGTCAGAAACTCCACTGATCTCTTCAGGAGTT  973
ZmPrPase2   TGTTTCTTCAATTTGGAGGATATACTCTAGTAAGGAGCTCCAAAGATCTATTTGGAAGTT 1138
PpPrPase1   CACTGTTGCAATTCGGAGGCTATACGCTTGTTCGGAACTCTAGTGGCCTGTTTTTGAGCT  915
Consensus   NNNTNNNTCAATTNGGAGGNTANACNCTNNTNNGNANNTCNNNNGNNCTNTNNNNNAGNT GmCPP       TTGGGTTTGATACGCAGCCAGTCCTCATTGGGCTCATCATATTTCAG------------- 1020
GmPrPase2   TTGGGTTTGATACGCAGCCAGTCCTCATTGGGCTCATCATATTTCAG------------- 1058
AtCPP       TCGGATTTGATACACAGCCTGTTCTCATTGGTTTGATCATATTTCAG------------- 1020
AtPrPase1   TCGGATTTGATACACAGCCTGTTCTCATTGGTTTGATCATATTTCAG------------- 1020
AtPrPase2   TCGGATTTGATACACAGCCTGTTCTCATTGGTTTGATCATATTTCAG------------- 1020
AFC1        TCGGATTTGATACACAGCCTGTTCTCATTGGTTTGATCATATTTCAG------------- 1020
AT4g01320   TCGGATTTGATACACAGCCTGTTCTCATTGGTTTGATCATATTTCAG------------- 1041
AF007269    TCGGATTTGATACACAGCCTGTTCTCATTGGTTTGATCATATTTCAGGTTTGTTATTTTT 2578
BnCPP       TTGGTTTTGATACACAACCAGTTCTCATTGGTTTGATCATATTTCAG------------- 1020
ZmPrPase2   TTGGCTTCAAGGACCAGCCAGTAATAATTGGATTGATCATTTTCCAG------------- 1185
PpPrPase1   TCGGTTTCTCCACACAGCCAGTGCTTATCGGGCTGATCCTATTCCAG-------------  962
Consensus   TNGGNTTNNNNNNNNCANCCNGTNNTNATNGGNNTNATCNTNTTNCAG GmCPP       ------------------------------------------------------------
GmPrPase2   ------------------------------------------------------------
AtCPP       ------------------------------------------------------------
AtPrPase1   ------------------------------------------------------------
AtPrPase2   ------------------------------------------------------------
AFC1        ------------------------------------------------------------
AT4g01320   ------------------------------------------------------------
AF007269    GCCTTTTGACACTAATCTAATGAATCAAGGATGGATTAAGAAAAAAAAACTCTAAACCTT 2638
BnCPP       ------------------------------------------------------------
ZmPrPase2   ------------------------------------------------------------
PpPrPase1   ------------------------------------------------------------
```

Figure 4L

```
GmCPP       ---------------------------CATACTGTAATCCCACTTCAGCAATTGGTCA 1051
GmPrPase2   ---------------------------CATACTGTAATCCCACTTCAGCAATTGGTCA 1089
AtCPP       ---------------------------CACACTGTAATACCACTGCAACATCTAGTAA 1051
AtPrPase1   ---------------------------CACACTGTAATACCACTGCAACATCCAGTAA 1051
AtPrPase2   ---------------------------CACACTGTAATACCACTGCAACATCTAGTAA 1051
AFC1        ---------------------------CACACTGTAATACCACTGCAACATCTAGTAA 1051
AT4g01320   ---------------------------CACACTGTAATACCACTGCAACATCTAGTAA 1072
AF007269    TGGTTATATCTCCTGTCTGATTATCACAGCACACTGTAATACCACTGCAACATCTAGTAA 2698
BnCPP       ---------------------------CACACTGTAATACCACTTCAACACCTAGTAA 1051
ZmPrPase2   ---------------------------CACACCATAATACCCATCCAACACCTTCTGA 1216
PpPrPase1   ---------------------------CACACTATTATGCCCTTCCATCATCTTGTAA 993
Consensus                              CANACNNTNATNCCNNTNCANCANNNNNTNA GmCPP       GCTTTGGTCTGAACCTAGTCAGCCGATCATTTGAATTTCAGG------------------ 1093
GmPrPase2   GCTTTGGTCTGAACCTAGTCAGCCGATCATTTGAATTTCAGG------------------ 1131
AtCPP       GCTTTGGCCTGAACCTCGTTAGTCGAGCGTTTGAGTTTCAGG------------------ 1093
AtPrPase1   GCTTTGGCCTCAACCTTGTTAGTCGAGCGTTTGAGTTTCAGG------------------ 1093
AtPrPase2   GCTTTGGCCTGAACCTCGTTAGTCGAGCGTTTGAGTTTCAGG------------------ 1093
AFC1        GCTTTGGCCTGAACCTCGTTAGTCGAGCGTTTGAGTTTCAGG------------------ 1093
AT4g01320   GCTTTGGCCTGAACCTCGTTAGTCGAGCGTTTGAGTTTCAGG------------------ 1114
AF007269    GCTTTGGCCTGAACCTCGTTAGTCGAGCGTTTGAGTTTCAGGTACCATCTTACAATCCCT 2758
BnCPP       GCTTTGACCTCAACCTTGTTAGTCGAGCGTTTGAGTTTCAGG------------------ 1093
ZmPrPase2   GCTTTTGCCTGAACCTTGTCAGCAGAGCATTTGAATTTCAGG------------------ 1258
PpPrPase1   GCTTTGCTCTCAACCTGTTGAGCCGAGCCTTCGAATTTCAGG------------------ 1035
Consensus   GCTTTNNNCTNAACCTNNTNAGNNGANCNTTNGANTTTCAGG GmCPP       ------------------------------------------------------------
GmPrPase2   ------------------------------------------------------------
AtCPP       ------------------------------------------------------------
AtPrPase1   ------------------------------------------------------------
AtPrPase2   ------------------------------------------------------------
AFC1        ------------------------------------------------------------
AT4g01320   ------------------------------------------------------------
AF007269    CAAGATCCAACCATAGTTTCTTTATTGCAATGGCAGCCTCATCTACTAATCTGAGTTAAC 2818
BnCPP       ------------------------------------------------------------
ZmPrPase2   ------------------------------------------------------------
PpPrPase1   ------------------------------------------------------------

GmCPP       --------------CTGATGGCTTTGCCAAGAAGCTTGGATATGCATCTGGATTACGCGG 1139
GmPrPase2   --------------CTGATGGCTTTGCCAAGAAGCTTGGATATGCATCTGGATTACGCGG 1177
AtCPP       --------------CTGATGCTTTTGCTGTGAAGCTTGACTATGCAAAAGATCTTCGTCC 1139
AtPrPase1   --------------CTGATGCTTTTGCTGTGAAGCTTGGCTATGCAAAAGATCTTCGTCC 1139
AtPrPase2   --------------CTGATGCTTTTGCTGTGAAGCTTGGCTATGCAAAAGATCTTCGTCC 1139
AFC1        --------------CTGATGCTTTTGCCGTGAAGCTTGGCTATGCAAAAGATCTTCGTCC 1139
AT4g01320   --------------CTGATGCTTTTGCTGTGAAGCTTGGCTATGCAAAAGATCTTCGTCC 1160
AF007269    GTTCCTTTTGCAGGCTGATGCTTTTGCTGTGAAGCTTGGCTATGCAAAAGATCTTCGTCC 2878
BnCPP       --------------CTGATGCTTTTGCAGTGAATCTTGGTTATGCAAAGGATCTACGTCC 1139
ZmPrPase2   --------------CTGATGCCTTTGCCAAGAACCTTGGATATGCCCCTCAGCTCCGAGC 1304
PpPrPase1   --------------CGGATGCGTTCGCCCCGCTCATTAGGGTACAGAGAGCCATTGAGAGC 1081
Consensus                 CNGATGNNTTNGCNNNNNNNNTNGNNTANNNNNNNNNNNNTNNGNNN
```

Figure 4M

```
GmCPP        TGGTCTTGTGAAACTACAGG---------------------------------------- 1159
GmPrPase2    TGGTCTTGTGAAACTACAGG---------------------------------------- 1197
AtCPP        TGCTCTAGTGAAACTACAGG---------------------------------------- 1159
AtPrPase1    TACTCTAGTGAAACTACAGG---------------------------------------- 1159
AtPrPase2    TGCTCTAGTGAAACTACAGG---------------------------------------- 1159
AFC1         TGCTCTAGTGAAACTACAGG---------------------------------------- 1159
AT4g01320    TGCTCTAGTGAAACTACAGGTCAGAGAAGATAACAACAGAACACAAACTGTTACCTCAAT 1220
AF007269     TGCTCTAGTGAAACTACAGGTCAGAGAAGATAACAACAGAACACAAACTGTTACCTCAAT 2938
BnCPP        TGCCCTAGTGAAGCTACAGG---------------------------------------- 1159
ZmPrPase2    AGCCCTTGTTAAACTACAGG---------------------------------------- 1324
PpPrPase1    TGGCCTGATCAAGCTGCAGG---------------------------------------- 1101
Consensus    NNNNCTNNTNAANCTNCAGG GmCPP        -------------------------------------------AGGAGAATCTGTCAGC 1175
GmPrPase2    -------------------------------------------AGGAGAATCTGTCAGC 1213
AtCPP        -------------------------------------------AAGAGAACTTATCAAC 1175
AtPrPase1    -------------------------------------------AAGAGAACTTATCAGC 1175
AtPrPase2    -------------------------------------------AAGAGAACTTATCAGC 1175
AFC1         -------------------------------------------AAGAGAACTTATCAGC 1175
AT4g01320    TTGTGTCACACACTTAAATGGATTTTTTGTTGGGATTTTGCAGGAAGAGAACTTATCAGC 1280
AF007269     TTGTGTCACACACTTAAATGGATTTTTTGTTGGGATTTTGCAGGAAGAGAACTTATCAGC 2998
BnCPP        -------------------------------------------AAGAGAACTTATCAGC 1175
ZmPrPase2    -------------------------------------------AGGAGAACTTGTCTGC 1340
PpPrPase1    -------------------------------------------AGGAGAATCTGTCTGC 1117
Consensus                                                ANGAGAANNTNTCNNC GmCPP        TATGAATACAGATCCTTGGTACTCTGCTTATCACTATTCTCATCCTCCCCTTGTTGAAAG 1235
GmPrPase2    TATGAATACAGATCCTTGGTACTCTGCTTATCACTATTCTCATCCTCCCCTTGTTGAAAG 1273
AtCPP        AATGAACACTGATCCATTGTACTCAGCTTATCACTACTCACATCCTCCTCTTGTTGAAAG 1235
AtPrPase1    AATGAATACTGATCCATTGTACTCAGCTTATCACTACTCACATCCTCCTCTTGTTGAAAG 1235
AtPrPase2    AATGAACACTGATCTATTGTACTCAGCTTATCACTACTCACATCCTCCTCTTGTTGAAAG 1235
AFC1         AATGAACACTGATCCATTGCACTCAGCTTATCACTACTCACATCCTCCTCTTGTTGAAAG 1235
AT4g01320    AATGAACACTGATCCATTGTACTCAGCTTATCACTACTCACATCCTCCTCTTGTTGAAAG 1340
AF007269     AATGAACACTGATCCATTGTACTCAGCTTATCACTACTCACATCCTCCTCTTGTTGAAAG 3058
BnCPP        GATGAACACAGACCCATTGTACTCAGCTTATCACTACTCACACCCTCCTCTTGTAGAGAG 1235
ZmPrPase2    GATGAACACCGATCCTTGGTATTCGGCATATCACTACTCCCACCCACCACTCGTCGAGAG 1400
PpPrPase1    CATGAACACGGATCCGTGGTATTCAGCGTATCATCATTCACACCCCCCGCTTGTTGAGCG 1177
Consensus    NATGAANACNGANCNNTNGNANTCNGCNTATCANNANTCNCANCCNCCNCTNGTNGANNG GmCPP        ATTGGCCGCGCTGGACGAACCGGATAAGAAGGAAGACTAA-------------------- 1275
GmPrPase2    ATTGGCTGTGCTGGACGAACCGGATAAGAAGGAAGACTAAGCAAGTAACTTAAAGATGAA 1333
AtCPP        GCTTCGAGCCACTGATGGAGAAGACAAGAAGACAGATTAA-------------------- 1275
AtPrPase1    GCTTCGAGCCATTGATGGAGAAGACAAGAAGACAGATTAA-------------------- 1275
AtPrPase2    GCTTCGAGCCATTGATGGAGAAGACAAGAAGACAGATTAA-------------------- 1275
AFC1         GCTTCGAGCCATTGATGGAGAAGACAAGAAGACAGATTAA-------------------- 1275
AT4g01320    GCTTCGAGCCATTGATGGAGAAGACAAGAAGACAGATTAA-------------------- 1380
AF007269     GCTTCGAGCCATTGATGGAGAAGACAAGAAGACAGATTAA-------------------- 3098
BnCPP        GCTTCGAGCCATTGATGGAGAAGACAAGAAGACAGATTAA-------------------- 1275
ZmPrPase2    GCTGCAAGCTCTTGAAGATTCAGACAGCAAAAAGAAGATTAGTCGATCCTTGTATGAGG 1460
PpPrPase1    ATTGCAAGCTCTTGATGAAACGTCCAAGAAAACGGATTAGAACTTACCCCCT---TCGGA 1234
Consensus    NNTNNNNGNNNNNGANGNNNNNNNNANNAANNNNGANNAN
```

Figure 4N

```
GmCPP       ------------------------------------------------------------
GmPrPase2   GAGCTGCAAAAATTGGCTATACCCTAACTTGCTATGATTTAGTGCTGCAATAGCTGTAAT 1393
AtCPP       ------------------------------------------------------------
AtPrPase1   ------------------------------------------------------------
AtPrPase2   ------------------------------------------------------------
AFC1        ------------------------------------------------------------
AT4g01320   ------------------------------------------------------------
AF007269    ------------------------------------------------------------
BnCPP       ------------------------------------------------------------
ZmPrPase2   TTTACATATGGATTTTTCCCTGCCACATGCACACCGATTCAGTGCTTGGATGGTGAGG-- 1518
PpPrPase1   CCGTAGTTGAGATTTGTAGGAATATAGCTTCTTCAGGAGAAAGAAACAAAATGAGCTATG 1294

GmCPP       ------------------------------------------------------------
GmPrPase2   ATCTCCCGGGAT------------------------------------------------ 1405
AtCPP       ------------------------------------------------------------
AtPrPase1   ------------------------------------------------------------
AtPrPase2   ------------------------------------------------------------
AFC1        ------------------------------------------------------------
AT4g01320   ------------------------------------------------------------
AF007269    ------------------------------------------------------------
BnCPP       ------------------------------------------------------------
ZmPrPase2   ------------------------------------------------------------
PpPrPase1   TCCTAGCACATCCACTGTAGAATTCACTGATGAATGACGAATAGTACATGAACACTCATT 1354

GmCPP       ---------------------------------------------
GmPrPase2   ---------------------------------------------
AtCPP       ---------------------------------------------
AtPrPase1   ---------------------------------------------
AtPrPase2   ---------------------------------------------
AFC1        ---------------------------------------------
AT4g01320   ---------------------------------------------
AF007269    ---------------------------------------------
BnCPP       ---------------------------------------------
ZmPrPase2   ---------------------------------------------
PpPrPase1   CTTTAAAAAAAAAAAAAAAAAAACTCGAGGGGGGGCCCGGTACCC 1398
```

Figure 5A

```
GmCPP        ----------MAFPYMEAVVGFMILMYIFETYLDVRQHRALKLPTLPKTLEGVISQEKFE  50
GmPrPase2    ----------MAFPYMEAVVGFMILMYIFETYLDVRQHRALKLPTLPKTLEGVISQEKFE  50
AtCPP        ----------MAIPFMETVVGFMIVMYIFETYLDLRQLTALKLPTLPKTLVGVISQEKFE  50
AtPrPase1    ----------MAIPFMETVVGFMIVMYIFETYLDLRQLTALKLPTLPKTLVGVISQEKFE  50
AtPrPase2    ----------MAIPFMETVVGFMIVMYIFETYLDLRQLTALKLPTLPKTLVGVISQEKFE  50
AFC1         ----------MAIPFMETVVGFMIVMYIFETYLDLRQLTALKLPTLPKTLVGVISQEKFE  50
AT4g01320    ----------MAIPFMETVVGFMIVMYIFETYLDLRQLTALKLPTLPKTLVGVISQEKFE  50
AF007269     ----------MAIPFMETVVGFMIVMYIFETYLDLRQLTALKLPTLPKTLI---------  41
BnCPP        ----------MAIPFMETVVGFMIVMYVFETYLDLRQHTALKLPTLPKTLVGVISQEKFE  50
ZmPrPase2    ----------MALPYLEAVLCFMIFMYIFETYLDIRQHRALKLPTLPKPLLGVISDEKFE  50
PpPrPase1    ---------------------------------LKLSNLPAPLKGIVSQEKFE  20
Yeast        MFDLKTILDHPNIPWKLIISGFSIAQFSFESYLTYRQYQKLSETKLPPVLEDEIDDETFH  60
Consensus                                            LXXXXLPXXLX GmCPP        KSRAYS-------LDKSHFHFVHEFVTIVTDSTILYFGVLPWFWKKSGDFM---TIAGFN 100
GmPrPase2    KSRAYS-------LDKSHFHFVHEFVTIVTDSTILYFGVLPWFWKKSGDFM---TIAGFN 100
AtCPP        KSRAYS-------LDKSYFHFVHEFVTILMDSAILFFGILPWFWKMSGAVL---PRLGLD 100
AtPrPase1    KSRAYS-------LDKSYFHFVHEFVTILMDSAILFFGILPWFWKMSGAVL---PRLGLD 100
AtPrPase2    KSRAYS-------LDKSYFHFVHEFVTILMDSAILFFGILPWFWKMSGAVL---PRLGLD 100
AFC1         KSRAYS-------LDKSYFHFVHEFVTILMDSAILFFGILPWFWKMSGAVL---PRLGLD 100
AT4g01320    KSRAYRDIITENFNICSYFHFVHEFVTILMDSAILFFGILPWFWKMSGAVL---PRLGLD 107
AF007269     ------------------------------------------------------------
BnCPP        KSRAYS-------LDKSHFHFVHEFVTILMDSAILFFGILPWFWKISGGFL---PMVGLD 100
ZmPrPase2    RSRAYS-------LDKSYFHFVHEAVTILMDTTILYYRVLPWFWKKSGELV---TSVGLS 100
PpPrPase1    KAQAYS-------LDKSRFHFVHAAVNIVEESAILLLGLLPWAWDKSGSLV---GKLGFD  70
Yeast        KSRNYS-------RAKAKFSIFGDVYNLAQKLVFIKYDLFPKIWHMAVSLLNAVLPVRFH 113

GmCPP        AENEILHTLAFLAGLMIWSQITDLPFSLYSTFVIEARHGFNKQTPWLFFRDMLKGIFLSV 160
GmPrPase2    AENEILHTLAFLAGLMIWSQITDLPFSLYSTFVIEARHGFNKQTPWLFFRDMLKGIFLSV 160
AtCPP        PENEILHTLSFLAGVMTWSQITDLPFSLYSTFVIESRHGFNKQTIWMFIRDMIKGTFLSV 160
AtPrPase1    PENEILHTLSFLAGVMTWSQITDLPFSLYSTFVIESRHGFNKQTIWMFIRDMIKGTFLSV 160
AtPrPase2    PENEILHTLSFLAGVMTWSQITDLPFSLYSTFVIESRHGFNKQTIWMFIRDMIKGTFLSV 160
AFC1         PENEILHTLSFLAGVMTWSQITDLPFSLYSTFVIESRHGFNKQTIWMFIRDMIKGTFLSV 160
AT4g01320    PENEILHTLSFLAGVMTWSQITDLPFSLYSTFVIESRHGFNKQTIWMFIRDMIKGTFLSV 167
AF007269     --------------------TDLPFSLYSTFVIESRHGFNKQTIWMFIRDMIKGTFLSV  80
BnCPP        PENEILHTLSFLAGLMTWSQITDLPFSLYSTFVIESRHGFNKQTIWMFIRDMIKGILLSV 160
ZmPrPase2    AENEIIHTLAFLAGSMVWSQITDLPFSLYSTFVIEARHGFNKQTIWLFIRDMIKGILLSM 160
PpPrPase1    EKSEILQTLSFLAVTTLWSQILELPFSLYSTFVIEARHGFNKQTIWLFLRDMIMGLALMM 130
Yeast        MVSTVAQSLCFLGLLSSLSTLVDLPLSYYSHFVLEEKFGFNKLTVQLWITDMIKSLTLAY 173
Consensus              XXLPXSXYSXFVXEXXXGFNKXTXXXXXXXDMXXXXLXX GmCPP        IIGPPIVAAIIVIVQKGGPYLAIYLWVFTFGLSIVMMTLYPVLIAPLFNKFTPLPDGQLR 220
GmPrPase2    IIGPPIVAAIIVIVQKGGPYLAIYLWVFTFGLSIVMMTLYPVLIAPLFNKFTPLPDGQLR 220
AtCPP        ILGPPIVAAIIFIVQKGGPYLAIYLWAFMFILSLVMMTIYPVLIAPLFNKFTPLPDGDLR 220
AtPrPase1    ILGPPIVAAIIFIVQKGGPYLAIYLWAFMFILSLVMMTIYPVLIAPLFNKFTPLPDGDLR 220
AtPrPase2    ILGPPIVAAIIFIVQKGGPYLAIYLWAFMFILSLVMMTIYPVLIAPLFNKFTPLPDGDLR 220
AFC1         ILGPPIVAAIIFIVQKGGPYLAIYLWAFMFILSLVMMTIYPVLIAPLFNKFTPLPDGDLR 220
AT4g01320    ILGPPIVAAIIFIVQKGGPYLAIYLWAFMFILSLVMMTIYPVLIAPLFNKFTPLPDGDLR 227
AF007269     ILGPPIVAAIIFIVQKGGPYLAIYLWAFMFILSLVMMTIYPVLIAPLFNKFTPLPDGDLR 140
BnCPP        IPAPPIVAAIIVIVQKGGPYLAIYLWAFMFILSLVMMTIYPVLIAPLFNKFTPLPDGDLR 220
ZmPrPase2    ILGPPIVAAIIYIVQIGGPYLAIYLWGFMFVLALLMMTIYPIVIAPLFNKFTPLPEGVLR 220
PpPrPase1    VVGPPIVSAIIYIVQNGGPYLALYLWAFMLLLSLVLMALYPVLIAPLFNTFTPLPEGQLR 190
Yeast        AIGGPILYLFLKIFDKFPTDFLWYIMVFLFVVQILAMTIIPVFIMPMFNKFTPLEDGELK 233
Consensus    XXXXPIXXXXXXXIXXXXXXXXXXYXXXFXXXXXXXXMXXXPXXIXPXFNXFTPLXXGXLX
```

Figure 5B

```
GmCPP       EKIEKLASSLNYPLKKLFVVDGSTRSSHSNAYMYGFFKNKRIVPYDTLIQQCKDDEEIVA 280
GmPrPase2   EKIEKLASSLNYPLKKLFVVDGSTRSSHSNAYMYGFFKNKRIVLYDTLIQQCKDDEEIVA 280
AtCPP       EKIEKLASSLKFPLKKLFVVDGSTRSSHSNAYMYGFFKNKRIVLYDTLIQQCKNEDEIVA 280
AtPrPase1   EKIEKLASSLKFPLKKLFVVDGSTRSSHSNAYMYGFFKNKRIVLYDTLIQQCKNEDEIVA 280
AtPrPase2   EKIEKLASSLKFPLKKLFVVDGSTRSSHSNAYMYGFFKNKRIVLYDTLIQQCKNEDEIVA 280
AFC1        EKIEKLASSLKFPLKKLFVVDGSTRSSHSNAYMYGFFKNKRIVLYDTLIQQCKNEDEIVA 280
AT4g01320   EKIEKLASSLKFPLKKLFVVDGSTRSSHSNAYMYGFFKNKRIVLYDTLIQQCKNEDEIVA 287
AF007269    EKIEKLASSLKFPLKKLFVVDGSTRSSHSNAYMYGFFKNKRIVLYDTLIQQCKNEDEIVA 200
BnCPP       EKIEKLASSLKFPLKKLFVVDGSTRSSHSNAYMYGFFKNKRIVLYDTLIQQCQNENEIVA 280
ZmPrPase2   EKIEKLAASLKFPLKKLFVVDGSTRSSHSNAYMYGFFKNKRIVLYDTLIQQCSNEDEIVS 280
PpPrPase1   AKIEKLASSLDFPLKKLFVIDGSTRSSHSNAYMYGFYNSKRIVLYDTLISQCKNEEEVVA 250
Yeast       KSIESLADRVGFPLDKIFVIDGSKRSSHSNAYFTGLPFTSKRIVLFDTLVNSNSTDEITA 293
Consensus   XXIEXLAXXXXXPLXKXFVXDGSXRSSHSNAYXXGXXXXXXXXXXXXXXXXXXXXXEXXX GmCPP       VIAHELGHWKLNHTVYTFVAMQILTLLQFGGYTLVRNSADLYRSFGFDTQ---------- 330
GmPrPase2   VIAHELGHWKLNHTVYTFVAMQILTLLQFGGYTLVRNSADLYRSFGFDTQ---------- 330
AtCPP       VIAHELGHWKLNHTTYSFIAVQILAFLQFGGYTLLRNSTDLFRSFGFDTQ---------- 330
AtPrPase1   VIAHELGHWKLNHTTYSFIAVQILAFLQFGGYTLVRNSTDLFRSFGFDTQ---------- 330
AtPrPase2   VIAHELGHWKLNHTTYSFIAVQILAFLQFGGYTLVRNSTDLFRSFGFDTQ---------- 330
AFC1        VIAHELGHWKLNHTTYSFIAVQILAFLQFGGYTLVRNSTDLFRSFGFDTQ---------- 330
AT4g01320   VIAHELGHWKLNHTTYSFIAVQILAFLQFGGYTLVRNSTDLFRSFGFDTQ---------- 337
AF007269    VIAHELGHWKLNHTTYSFIAV--------------------------------------- 221
BnCPP       VIAHELGHWKLNHTTYSFIAVQILAFLQFGGYTLVRNSTDLFRSFGFDTQ---------- 330
ZmPrPase2   VIAHELGHWKLNHTVYSFVAVQLLMFLQFGGYTLVRSSKDLFGSFGFKDQ---------- 330
PpPrPase1   VIAHELGHWKLSHTMYSFLAMQVLTLLQFGGYTLVRNSSGLFLSFGFSTQ---------- 300
Yeast       VLAHEIGHWQKNHIVNMVIFSQLHTFLIFSLFTSIYRNTSFYNTFGFFLEKSTGSFVDPV 353
Consensus   VXAHEXGHWXXXHXXXXXXXX GmCPP       -----PVLIGLIIFQHTVIPLQQLVSFGLNLVSRSFEFQADGFAKKLGYASGLRGGLVKL 385
GmPrPase2   -----PVLIGLIIFQHTVIPLQQLVSFGLNLVSRSFEFQADGFAKKLGYASGLRGGLVKL 385
AtCPP       -----PVLIGLIIFQHTVIPLQHLVSFGLNLVSRAFEFQADAFAVKLDYAKDLR------ 379
AtPrPase1   -----PVLIGLIIFQHTVIPLQHPVSFGLNLVSRAFEFQADAFAVKLGYAKDLR------ 379
AtPrPase2   -----PVLIGLIIFQHTVIPLQHLVSFGLNLVSRAFEFQADAFAVKLGYAKDLR------ 379
AFC1        -----PVLIGLIIFQHTVIPLQHLVSFGLNLVSRAFEFQADAFAVKLGYAKDLR------ 379
AT4g01320   -----PVLIGLIIFQHTVIPLQHLVSFGLNLVSRAFEFQADAFAVKLGYAKDLR------ 386
AF007269    --------------QHTVIPLQHLVSFGLNLVSRAFEFQADAFAVKLGYAKDLR------ 261
BnCPP       -----PVLIGLIIFQHTVIPLQHLVSFDLNLVSRAFEFQADAFAVNLGYAKDLR------ 379
ZmPrPase2   -----PVIIGLIIFQHTIIPIQHLLSFCLNLVSRAFEFQADAFAKNLGYAPQLR------ 379
PpPrPase1   -----PVLIGLILFQHTIMPFHHLVSFALNLLSRAFEFQADAFARSLGYREPLRAG---- 351
Yeast       ITKEFPIIIGFMLFNDLLTPLECAMQFVMSLISRTHEYQADAYAKKLGYKQNLCR----- 408
Consensus        XXXXXPXXXXXXFXXXLSRXXEXQADXXAXXXLXYXXXLX GmCPP       Q------------------------------EENLSAMNTDPWYSAYHYSH 406
GmPrPase2   Q------------------------------EENLSAMNTDPWYSAYHYSH 406
AtCPP       -PALV----KLQE------------------------ENLSTMNTDPLYSAYHYSH 406
AtPrPase1   -PTLV----KLQE------------------------ENLSAMNTDPLYSAYHYSH 406
AtPrPase2   -PALV----KLQE------------------------ENLSAMNTDLLYSAYHYSH 406
AFC1        -PALV----KLQE------------------------ENLSAMNTDPLHSAYHYSH 406
AT4g01320   -PALV----KLQVREDNNRTQTVTSICVTHLNGFFVGILQEENLSAMNTDPLYSAYHYSH 441
AF007269    -PALV----KLQVREDNNRTQ-----------------TEENLSAMNTDPLYSAYHYSH 298
BnCPP       -PALVKLQE------------------------ENLSAMNTDPLYSAYHYSH 406
ZmPrPase2   --------------------------AALVKLQEENLSAMNTDPWYSAYHYSH 406
PpPrPase1   -------------------------LIKLQEENLSAMNTDPWYSAYHHSH 376
Yeast       -------------------------ALIDLQIKNLSTMNVDPLYSSYHYSH 434
Consensus                                XNLSXMNXDXXXSXYHXSH
```

Figure 5C

```
GmCPP        PPLVERLAALDEPDKKED- 424
GmPrPase2    PPLVERLAVLDEPDKKED- 424
AtCPP        PPLVERLRATDGEDKKTD- 424
AtPrPase1    PPLVERLRAIDGEDKKTD- 424
AtPrPase2    PPLVERLRAIDGEDKKTD- 424
AFC1         PPLVERLRAIDGEDKKTD- 424
AT4g01320    PPLVERLRAIDGEDKKTD- 459
AF007269     PPLVERLRAIDGEDKKTD- 316
BnCPP        PPLVERLRAIDGEDKKTD- 424
ZmPrPase2    PPLVERLQALEDSDSKKED 425
PpPrPase1    PPLVERLQALDETSKKTD- 394
Yeast        PTLAERLTALDYVSEKKKN 453
Consensus    PXLXERLXXXXXXXXKXX
```

| Identity (%) | SEQ ID NO: | GmCPP | Gm PrPase2 | AtCPP | At PrPase1 | At PrPase2 | AFC1 | At4g01320 | BnCPP | Zm PrPase2 | Pp PrPase 1 | AF007269 |
|---|---|---|---|---|---|---|---|---|---|---|---|---|
| GmCPP | 18 | X | | | | | | | | | | |
| GmPrPase2 | 16 | 90.5 | X | | | | | | | | | |
| AtCPP | 7 | 77.1 | 70.6 | X | | | | | | | | |
| AtPrPase1 | 3 | 77.0 | 70.4 | 99.0 | X | | | | | | | |
| AtPrPase2 | 5 | 77.0 | 70.5 | 99.3 | 99.4 | X | | | | | | |
| AFC1 | 25 | 77.2 | 70.6 | 99.3 | 99.4 | 99.7 | X | | | | | |
| At4g01320 | 27 | 71.2 | 65.6 | 91.6 | 91.7 | 92.0 | 92.0 | X | | | | |
| BnCPP | 11 | 77.2 | 70.6 | 92.7 | 93.3 | 93.2 | 93.2 | 85.9 | X | | | |
| ZmPrPase2 | 23 | 62.5 | 66.2 | 62.6 | 62.6 | 62.9 | 62.9 | 59.0 | 63.0 | X | | |
| PpPrPase1 | 1 | 56.2 | 59.0 | 56.8 | 56.7 | 56.8 | 56.8 | 58.1 | 57.1 | 54.6 | X | |
| AF007269 | 29 | 32.5 | 32.7 | 40.9 | 41.0 | 41.1 | 41.1 | 44.5 | 38.6 | 34.5 | 30.2 | X |

B

| Identity (%) | SEQ ID NO: | GmCPP | Gm PrPase2 | AtCPP | At PrPase1 | At PrPase2 | AFC1 | At4g01320 | BnCPP | Zm PrPase2 | Pp PrPase 1 | AF007269 |
|---|---|---|---|---|---|---|---|---|---|---|---|---|
| GmCPP | 18 | X | | | | | | | | | | |
| GmPrPase2 | 16 | 99.7 | X | | | | | | | | | |
| AtCPP | 7 | 77.1 | 77.1 | X | | | | | | | | |
| AtPrPase1 | 3 | 77.0 | 77.0 | 99.0 | X | | | | | | | |
| AtPrPase2 | 5 | 77.0 | 77.1 | 99.3 | 99.4 | X | | | | | | |
| AFC1 | 25 | 77.2 | 77.3 | 99.3 | 99.4 | 99.7 | X | | | | | |
| At4g01320 | 27 | 71.2 | 71.3 | 91.6 | 91.7 | 92.0 | 92.0 | X | | | | |
| BnCPP | 11 | 77.2 | 77.3 | 92.7 | 93.3 | 93.2 | 93.2 | 85.9 | X | | | |
| ZmPrPase2 | 23 | 74.2 | 74.2 | 74.1 | 74.1 | 74.4 | 74.4 | 69.0 | 74.5 | X | | |
| PpPrPase1 | 1 | 63.7 | 63.6 | 64.8 | 64.6 | 64.7 | 64.8 | 61.2 | 65.2 | 65.2 | X | |
| AF007269* | 29 | 32.5 | 32.5 | 40.9 | 41.0 | 41.1 | 41.1 | 44.5 | 38.6 | 31.7 | 29.2 | X |

* No adjustment made – calculation including intron regions.

Figure 7

| Identity (Similarity) | SEQ ID NO: | GmCPP | GmPrPase2 | AtCPP | AtPrPase1 | AtPrPase2 | AFC1 | At4g 01320 | AF00 7269 | BnCPP | ZmPrPase2 | Yeast (P47154) | PpPrPase1 |
|---|---|---|---|---|---|---|---|---|---|---|---|---|---|
| GmCPP | 19 | X | | | | | | | | | | | |
| GmPrPase2 | 17 | 99.5 (99.5) | X | | | | | | | | | | |
| AtCPP | 8 | 83.0 (89.4) | 83.0 (89.4) | X | | | | | | | | | |
| AtPrPase1 | 4 | 83.5 (89.9) | 83.5 (89.9) | 98.6 (98.8) | X | | | | | | | | |
| AtPrPase2 | 6 | 83.5 (89.9) | 83.5 (89.9) | 98.8 (99.1) | 99.3 (99.3) | X | | | | | | | |
| AFC1 | 26 | 83.5 (90.1) | 83.5 (90.1) | 98.8 (99.3) | 99.3 (99.5) | 99.5 (99.8) | X | | | | | | |
| At4g01320 | 28 | 76.5 (82.4) | 76.5 (82.4) | 90.7 (90.9) | 91.1 (91.1) | 91.3 (91.3) | 91.3 (91.5) | X | | | | | |
| AF007269 | 30 | 60.1 (64.3) | 60.1 (64.3) | 69.8 (69.8) | 70.0 (70.0) | 70.3 (70.3) | 70.3 (70.5) | 68.8 (68.8) | X | | | | |
| BnCPP | 12 | 83.7 (89.9) | 83.7 (89.9) | 94.8 (96.7) | 95.3 (96.9) | 95.5 (97.2) | 95.5 (97.4) | 87.6 (89.1) | 68.0 (68.7) | X | | | |
| ZmPrPase2 | 24 | 80.2 (89.9) | 80.2 (89.9) | 80.7 (89.6) | 80.9 (89.9) | 81.2 (90.1) | 81.2 (90.4) | 74.4 (82.6) | 59.5 (65.1) | 81.4 (90.4) | X | | |
| Yeast (P47154) | 31 | 39.2 (54.2) | 39.2 (54.2) | 40.6 (56.1) | 40.4 (56.1) | 40.4 (56.1) | 40.4 (56.4) | 37.2 (51.9) | 33.3 (44.9) | 39.3 (54.3) | 39.2 (55.2) | X | |
| PpPrPase1 | 2 | 67.9 (79.0) | 67.9 (79.0) | 68.2 (79.0) | 68.6 (79.5) | 68.6 (79.5) | 68.6 (79.7) | 62.1 (72.0) | 49.3 (56.2) | 68.2 (78.5) | 67.3 (79.5) | 34.8 (51.7) | X |

Figure 16A

```
GmCPP       ------------------------------------------------------------
GmPrPase2   ------------------------------------------------------------
AtCPP       ------------------------------------------------------------
AtPrPase1   ------------------------------------------------------------
AtPrPase2   ------------------------------------------------------------
AFC1        ------------------------------------------------------------
AT4g01320   ------------------------------------------------------------
AF007269    ATGGCGATTCCTTTCATGGAAACCGTCGTGGGTAAGCTTCAAAACCTTTTTCTGAGACAT  60
BnCPP       ------------------------------------------------------------

GmCPP       ------------------------------------------------------------
GmPrPase2   ------------------------------------------------------------
AtCPP       ------------------------------------------------------------
AtPrPase1   ------------------------------------------------------------
AtPrPase2   ------------------------------------------------------------
AFC1        ------------------------------------------------------------
AT4g01320   ------------------------------------------------------------
AF007269    TTTACTATCCTGTTTCACTCATCGTATTTCGTTTTTGTTTGGGTTTTGCTTTCTGTGTTG  120
BnCPP       ------------------------------------------------------------

GmCPP       ------------------------------------------------------------
GmPrPase2   ------------------------------------------------------------
AtCPP       ------------------------------------------------------------
AtPrPase1   ------------------------------------------------------------
AtPrPase2   ------------------------------------------------------------
AFC1        ------------------------------------------------------------
AT4g01320   ------------------------------------------------------------
AF007269    TGTGTGTTGAGATTCCATGACTCGTTTGTTTCATATACCATCGTCTCTGCTTCTCGTTTC  180
BnCPP       ------------------------------------------------------------

GmCPP       ------------------------------------------------------------
GmPrPase2   ------------------------------------------------------------
AtCPP       ------------------------------------------------------------
AtPrPase1   ------------------------------------------------------------
AtPrPase2   ------------------------------------------------------------
AFC1        ------------------------------------------------------------
AT4g01320   ------------------------------------------------------------
AF007269    TAAATTTTGTTCTTTTCTAATAGTGCGTACCTTGATCTGAGGTTTTATTACTCCTACTAG  240
BnCPP       ------------------------------------------------------------

GmCPP       ------------------------------------------------------------
GmPrPase2   ------------------------------------------------------------
AtCPP       ------------------------------------------------------------
AtPrPase1   ------------------------------------------------------------
AtPrPase2   ------------------------------------------------------------
AFC1        ------------------------------------------------------------
AT4g01320   ------------------------------------------------------------
AF007269    TTTCTTGTCTTACTCGTGCGTTTGATTTGATTTGAGCTTATGTGATTTCATCATCTCTTC  300
BnCPP       ------------------------------------------------------------
```

Figure 16B

```
GmCPP       ------------------------------------------------------------
GmPrPase2   ------------------------------------------------------------
AtCPP       ------------------------------------------------------------
AtPrPase1   ------------------------------------------------------------
AtPrPase2   ------------------------------------------------------------
AFC1        ------------------------------------------------------------
AT4g01320   ------------------------------------------------------------
AF007269    CTCGGTTTTAGAATGTACGGAGCTTCTCTGTTAACCAAAATCTAGGATTTGGGAAGAAAA 360
BnCPP       ------------------------------------------------------------

GmCPP       ------------------------------------------------------------
GmPrPase2   ------------------------------------------------------------
AtCPP       ------------------------------------------------------------
AtPrPase1   ------------------------------------------------------------
AtPrPase2   ------------------------------------------------------------
AFC1        ------------------------------------------------------------
AT4g01320   ------------------------------------------------------------
AF007269    GTCGGAGTCTTTTTTTTCCTCATTCCCGATTGGAAATTGAGAATCTTGAAATTTTTCTTT 420
BnCPP       ------------------------------------------------------------

GmCPP       ------------------------------------------------------------
GmPrPase2   ------------------------------------------------------------
AtCPP       ------------------------------------------------------------
AtPrPase1   ------------------------------------------------------------
AtPrPase2   ------------------------------------------------------------
AFC1        ------------------------------------------------------------
AT4g01320   ------------------------------------------------------------
AF007269    GTTCAAGTCATACAGCTTGAGGTTTTGGGTTTTCTTGTCAGGGTATTATTATGTTCGTGA 480
BnCPP       ------------------------------------------------------------

GmCPP       ------------------------------------------------------------
GmPrPase2   ------------------------------------------------------------
AtCPP       ------------------------------------------------------------
AtPrPase1   ------------------------------------------------------------
AtPrPase2   ------------------------------------------------------------
AFC1        ------------------------------------------------------------
AT4g01320   ------------------------------------------------------------
AF007269    CTGCAACTAGAGTTTTCTGGAGTTTTTTGAAATGGGTTTTGTGTTGTGGAACCGTATGTG 540
BnCPP       ------------------------------------------------------------

GmCPP       ------------------------------------------------------------
GmPrPase2   ------------------------------------------------------------
AtCPP       ------------------------------------------------------------
AtPrPase1   ------------------------------------------------------------
AtPrPase2   ------------------------------------------------------------
AFC1        ------------------------------------------------------------
AT4g01320   ------------------------------------------------------------
AF007269    AATGTTGCATCAAAACTCTTTCAGTGCTCCAATGTTTCCATCAGTAGTCAGCACAAGAGA 600
BnCPP       ------------------------------------------------------------
```

Figure 16C

```
GmCPP        ------------------------------------------------------------
GmPrPase2    -------------------------------------------------------GCGAG    5
AtCPP        ------------------------------------------------------------
AtPrPase1    ------------------------------------------------------------
AtPrPase2    ------------------------------------------------------------
AFC1         ------------------------------------------------------------
AT4g01320    ------------------------------------------------------------
AF007269     TCTTTTTATATCTGGTTGATCAAAAAAGTAGATGATGTTATTGAATTTTCAGTGATGGAG  660
BnCPP        ------------------------------------------------------------

GmCPP        ---------------------------------ATGGCGTTTCCC--TACATGGAAGCCG   25
GmPrPase2    CTCTCGTTCGGTTCATCAGCGTGTGTCTCAGCCATGGCGTTTCCC--TACATGGAAGCCG   63
AtCPP        ---------------------------------ATGGCGATTCCT--TTCATGGAAACCG   25
AtPrPase1    ---------------------------------ATGGCGATTCCT--TTCATGGAAACCG   25
AtPrPase2    ---------------------------------ATGGCGATTCCT--TTCATGGAAACCG   25
AFC1         ---------------------------------ATGGCGATTCCT--TTCATGGAAACCG   25
AT4g01320    ---------------------------------ATGGCGATTCCT--TTCATGGAAACCG   25
AF007269     TATCTGTTGTTGTGGCATTTAGAGTAGATTCGTATTTCATCTTCTGTTTTATTCTTTTTC  720
BnCPP        ---------------------------------ATGGCGATTCCT--TTCATGGAAACCG   25
Consensus                                     ATNNCNNNTNCN   TNNATNNNNNNNN GmCPP        TTGTCGGATTTATGATATTAATGTACATTTTTGAAACTTACTTGGATGTGCGACAACATA   85
GmPrPase2    TTGTCGGATTTATGATATTAATGTACATTTTTGAAACTTACTTGGATGTGCGACAACATA  123
AtCPP        TCGTGGGTTTTATGATAGTGATGTACATTTTTGAGACGTATTTGGATCTGAGGCAACTCA   85
AtPrPase1    TCGTGGGTTTTATGATAGTGATGTACATTTTTGAGACGTATTTGGATCTGAGGCAACTCA   85
AtPrPase2    TCGTGGGTTTTATGATAGTGATGTACATTTTTGAGACGTATTTGGATCTGAGGCAACTCA   85
AFC1         TCGTGGGTTTTATGATAGTGATGTACATTTTTGAGACGTATTTGGATCTGAGGCAACTCA   85
AT4g01320    TCGTGGGTTTTATGATAGTGATGTACATTTTTGAGACGTATTTGGATCTGAGGCAACTCA   85
AF007269     TTACAGGTTTTATGATAGTGATGTACATTTTTGAGACGTATTTGGATCTGAGGCAACTCA  780
BnCPP        TCGTTGGTTTTATGATAGTGATGTACGTTTTTGAGACGTATTTGGATCTGAGGCAACATA   85
Consensus    TNNNNGGNTTTATGATANTNATGTACNTTTTTGANACNTANTTGGATNTGNGNCAACNNA GmCPP        GGGCCCTCAAACTTCCTACTCTTCCAAAGACTTTAGAGGGTGTTATCAGCCAAGAGAAAT  145
GmPrPase2    GGGCCCTCAAACTTCCTACTCTTCCAAAGACTTTAGAAGGTGTTATCAGCCAAGAGAAAT  183
AtCPP        CTGCTCTCAAGCTTCCAACTCTCCCGAAAACCTTGGTTGGTGTAATTAGCCAAGAGAAGT  145
AtPrPase1    CTGCTCTCAAGCTTCCAACTCTCCCGAAAACCTTGGTTGGTGTAATTAGCCAAGAGAAGT  145
AtPrPase2    CTGCTCTCAAGCTTCCAACTCTCCCGAAAACCTTGGTTGGTGTAATTAGCCAAGAGAAGT  145
AFC1         CTGCTCTCAAGCTTCCAACTCTCCCGAAAACCTTGGTTGGTGTAATTAGCCAAGAGAAGT  145
AT4g01320    CTGCTCTCAAGCTTCCAACTCTCCCGAAAACCTTGGTTGGTGTAATTAGCCAAGAGAAGT  145
AF007269     CTGCTCTCAAGCTTCCAACTCTCCCGAAAACCTTGGTTGGTGTAATTAGCCAAGAGAAGT  840
BnCPP        CTGCTCTCAAGCTTCCCACTCTCCCAAAGACTTTGGTTGGAGTCATTAGCCAAGAGAAGT  145
Consensus    NNGCNCTCAANCTTCCNACTCTNCCNAANACNTTNGNNGGNGTNATNAGCCAAGAGAANT GmCPP        TTGAGAAATCTAGAGCCTATAG--------------------------------------  167
GmPrPase2    TTGAGAAATCTAGAGCCTATAG--------------------------------------  205
AtCPP        TTGAGAAATCACGAGCATACAG--------------------------------------  167
AtPrPase1    TTGAGAAATCACGAGCATACAG--------------------------------------  167
AtPrPase2    TTGAGAAATCACGAGCATACAG--------------------------------------  167
AFC1         TTGAGAAATCACGAGCATACAG--------------------------------------  167
AT4g01320    TTGAGAAATCACGAGCATACAG--------------------------------------  167
AF007269     TTGAGAAATCACGAGCATACAGTCTTGACAAAAGGTTTCGTCTTGATCATATTTATATCA  900
BnCPP        TTGAGAAATCTCGAGCTTACAG--------------------------------------  167
Consensus    TTGAGAAATCNNGAGCNTANAG
```

Figure 16D

```
GmCPP        ----------------------------------------TCTTGATAAA---AGCCA  182
GmPrPase2    ----------------------------------------TCTTGATAAA---AGCCA  220
AtCPP        ----------------------------------------TCTTGACAAA---AGCTA  182
AtPrPase1    ----------------------------------------TCTTGACAAA---AGCTA  182
AtPrPase2    ----------------------------------------TCTTGACAAA---AGCTA  182
AFC1         ----------------------------------------TCTTGACAAA---AGCTA  182
AT4g01320    ----------------------GGATATCATCACTGAGAACTTTAATATATGCAGCTA  203
AF007269     TTTTAGTTTTTTATAATTGCCAGGGGATATCATCACTGAGAACTTTAATATATGCAGCTA  960
BnCPP        ----------------------------------------TCTTGACAAA---AGCCA  182
Consensus                                            NNTTNANANA   AGCNA GmCPP        CTTCCATTTTGTTCACGAGTTTGTGACAATAGTGACAGACTCTACAATTTTGTACTTTGG  242
GmPrPase2    CTTCCATTTTGTTCACGAGTTTGTGACAATAGTGACAGACTCTACAATTTTGTACTTTGG  280
AtCPP        TTTTCACTTTGTTCATGAGTTTGTAACTATACTTATGGACTCTGCAATTTTGTTCTTTGG  242
AtPrPase1    TTTTCACTTTGTTCATGAGTTTGTAACTATACTTATGGACTCTGCAATTTTGTTCTTTGG  242
AtPrPase2    TTTTCACTTTGTTCATGAGTTTGTAACTATACTTATGGACTCTGCAATTTTGTTCTTTGG  242
AFC1         TTTTCACTTTGTTCATGAGTTTGTAACTATACTTATGGACTCTGCAATTTTGTTCTTTGG  242
AT4g01320    TTTTCACTTTGTTCATGAGTTTGTAACTATACTTATGGACTCTGCAATTTTGTTCTTTGG  263
AF007269     TTTTCACTTTGTTCATGAGTTTGTAACTATACTTATGGACTCTGCAATTTTGTTCTTTGG  1020
BnCPP        TTTTCACTTTGTTCATGAGTTTGTTACTATACTTATGGACTCTGCGATTCTGTTCTTTGG  242
Consensus    NTTNCANTTTGTTCANGAGTTTGTNACNATANTNANNGACTCTNCNATTNTGTNCTTTGG GmCPP        GGTATTGCCCTGGTTTTGGAAG--------------------------------------  264
GmPrPase2    GGTATTGCCCTGGTTTTGGAAG--------------------------------------  302
AtCPP        GATCTTGCCTTGGTTTTGGAAG--------------------------------------  264
AtPrPase1    GATCTTGCCTTGGTTTTGGAAG--------------------------------------  264
AtPrPase2    GATCTTGCCTTGGTTTTGGAAG--------------------------------------  264
AFC1         GATCTTGCCTTGGTTTTGGAAG--------------------------------------  264
AT4g01320    GATCTTGCCTTGGTTTTGGAAG--------------------------------------  285
AF007269     GATCTTGCCTTGGTTTTGGAAGGTACATATCTGGTTTCGGTATACAGTATCTCATTTTGA  1080
BnCPP        GATCTTGCCTTGGTTTTGGAAG--------------------------------------  264
Consensus    GNTNTTGCCNTGGTTTTGGAAG GmCPP        ---------------------------------------AAATCAGGAGAT  276
GmPrPase2    ---------------------------------------AAATCAGGAGAT  314
AtCPP        ---------------------------------------ATGTCTGGAGCT  276
AtPrPase1    ---------------------------------------ATGTCTGGAGCT  276
AtPrPase2    ---------------------------------------ATGTCTGGAGCA  276
AFC1         ---------------------------------------ATGTCTGGAGCT  276
AT4g01320    ---------------------------------------ATGTCTGGAGCT  297
AF007269     ATATAGAGTTGTTACATTACAATTGTAAAGTTTTCATTTTTACCTTAGATGTCTGGAGCT  1140
BnCPP        ---------------------------------------ATATCTGGCGGC  276
Consensus                                            ANNTCNGGNGNN GmCPP        TTTATGACAATAGCTGGTTTCAATGCTGAGAATGAAATACTGCATACCCTTGCCTTCTTA  336
GmPrPase2    TTTATGACAATAGCTGGTTTCAATGCTGAGAATGAAATACTGCATACCCTTGCCTTCTTA  374
AtCPP        GTTTTACCGAGGTTGGGCCTTGATCCGGAGAATGAAATACTGCATACTCTTTCATTCTTG  336
AtPrPase1    GTTTTACCGAGGTTGGGCCTTGATCCAGAGAATGAAATACTGCATACTCTTTCATTCTTG  336
AtPrPase2    GTTTTACCGAGGTTGGGCCTTGATCCAGAGAATGAAATACTGCATACTCTTTCATTCTTG  336
AFC1         GTTTTACCGAGGTTGGGCCTTGATCCAGAGAATGAAATACTGCATACTCTTTCATTCTTG  336
AT4g01320    GTTTTACCGAGGTTGGGCCTTGATCCAGAGAATGAAATACTGCATACTCTTTCATTCTTG  357
AF007269     GTTTTACCGAGGTTGGGCCTTGATCCAGAGAATGAAATACTGCATACTCTTTCATTCTTG  1200
BnCPP        TTTCTACCAATGGTGGGACTCGATCCAGAGAATGAAATCCTGCACACTCTTTCATTCTTG  336
Consensus    NTTNTNNCNANNNNNGGNNTNNATNCNGAGAATGAAATNCTGCANACNCTTNCNTTCTTN
```

Figure 16E

```
GmCPP       GCAGGGCTGATGATTTGGTCACAG------------------------------------ 360
GmPrPase2   GCAGGGCTGATGATTTGGTCACAG------------------------------------ 398
AtCPP       GCTGGTGTTATGACATGGTCACAG------------------------------------ 360
AtPrPase1   GCTGGTGTTATGACATGGTCACAG------------------------------------ 360
AtPrPase2   GCTGGTGTTATGACATGGTCACAG------------------------------------ 360
AFC1        GCTGGTGTTATGACATGGTCACAG------------------------------------ 360
AT4g01320   GCTGGTGTTATGACATGGTCACAG------------------------------------ 381
AF007269    GCTGGTGTTATGACATGGTCACAGGTGTTCCAAATAAACCCCTTCATATAGTCCTATACG 1260
BnCPP       GCTGGTCTTATGACATGGTCACAG------------------------------------ 360
Consensus   GCNGGNNTNATGANNTGGTCACAG GmCPP       ------------------------------------------------------------
GmPrPase2   ------------------------------------------------------------
AtCPP       ------------------------------------------------------------
AtPrPase1   ------------------------------------------------------------
AtPrPase2   ------------------------------------------------------------
AFC1        ------------------------------------------------------------
AT4g01320   ------------------------------------------------------------
AF007269    TTTAGCATCAAAATATCTATTTTCTTAAGATAATAATATTTCTTTTATATTCTGATGCAG 1320
BnCPP       ------------------------------------------------------------

GmCPP       ATAACAGATTTGCCCTTTTCTCTGTACTCAACTTTTGTGATTGAGGCCCGTCATGGTTTT 420
GmPrPase2   ATAACAGATTTGCCCTTTTCTCTGTACTCAACTTTTGTGATTGAGGCCCGTCATGGTTTT 458
AtCPP       ATCACTGATTTGCCATTTTCTTTGTACTCAACTTTCGTGATCGAGTCTCGGCATGGGTTC 420
AtPrPase1   ATCACTGATTTGCCATTTTCTTTGTACTCAACTTTCGTGATCGAGTCTCGGCATGGGTTC 420
AtPrPase2   ATCACTGATTTGCCATTTTCTTTGTACTCAACTTTCGTGATCGAGTCTCGGCATGGGTTC 420
AFC1        ATCACTGATTTGCCATTTTCTTTGTACTCAACTTTCGTGATCGAGTCTCGGCATGGGTTC 420
AT4g01320   ATCACTGATTTGCCATTTTCTTTGTACTCAACTTTCGTGATCGAGTCTCGGCATGGGTTC 441
AF007269    ATCACTGATTTGCCATTTTCTTTGTACTCAACTTTCGTGATCGAGTCTCGGCATGGGTTC 1380
BnCPP       ATCACTGATTTGCCATTTTCTTTGTACTCAACTTTCGTGATCGAGTCTCGGCATGGGTTC 420
Consensus   ATNACNGATTTGCCNTTTTCTNTGTACTCAACTTTNGTGATNGAGNCNCGNCATGGNTTN GmCPP       AATAAG------------------------------------------------------ 426
GmPrPase2   AATAAG------------------------------------------------------ 464
AtCPP       AACAAA------------------------------------------------------ 426
AtPrPase1   AACAAA------------------------------------------------------ 426
AtPrPase2   AACAAA------------------------------------------------------ 426
AFC1        AACAAA------------------------------------------------------ 426
AT4g01320   AACAAA------------------------------------------------------ 447
AF007269    AACAAAGTATGTCGTATTTCCAACACTACCTTGTGACTTACGTTTTTTTATCAGAGATGT 1440
BnCPP       AACAAA------------------------------------------------------ 426
Consensus   AANAAN GmCPP       -------------------------------CAAACACCATGGTTATTCTTTAGGGACA 454
GmPrPase2   -------------------------------CAAACACCATGGTTATTCTTTAGGGACA 492
AtCPP       -------------------------------CAAACAATATGGATGTTCATTAGGGACA 454
AtPrPase1   -------------------------------CAAACAATATGGATGTTCATTAGGGACA 454
AtPrPase2   -------------------------------CAAACAATATGGATGTTCATTAGGGACA 454
AFC1        -------------------------------CAAACAATATGGATGTTCATTAGGGACA 454
AT4g01320   -------------------------------CAAACAATATGGATGTTCATTAGGGACA 475
AF007269    GGATTAAATTTGCTTCTAAATTCTGTTGACAGCAAACAATATGGATGTTCATTAGGGACA 1500
BnCPP       -------------------------------CAAACAATATGGATGTTCATTAGGGACA 454
Consensus                                  CAAACANNATGGNTNTTCNTTAGGGACA
```

Figure 16F

```
GmCPP       TGCTTAAAGGAATTTTCCTTTCTGTAATAATTGGTCCACCTATTGTGGCTGCAATCATTG 514
GmPrPase2   TGCTTAAAGGAATTTTCCTTTCTGTAATAATTGGTCCACCTATTGTGGCTGCAATCATTG 552
AtCPP       TGATCAAAGGAACATTCCTCTCTGTCATACTAGGCCCACCCATTGTTGCTGCGATAATTT 514
AtPrPase1   TGATCAAAGGAACATTCCTCTCTGTCATACTAGGCCCACCCATTGTTGCCGCGATAATTT 514
AtPrPase2   TGATCAAAGGAACATTCCTCTCTGTCATACTAGGCCCACCCATTGTTGCTGCGATAATTT 514
AFC1        TGATCAAAGGAACATTCCTCTCTGTCATACTAGGCCCACCCATTGTTGCTGCGATAATTT 514
AT4g01320   TGATCAAAGGAACATTCCTCTCTGTCATACTAGGCCCACCCATTGTTGCTGCGATAATTT 535
AF007269    TGATCAAAGGAACATTCCTCTCTGTCATACTAGGCCCACCCATTGTTGCTGCGATAATTT 1560
BnCPP       TGATCAAAGGAATACTCCTCTCTGTCATACCTGCCCCTCCTATCGTTGCCGCAATTATTG 514
Consensus   TGNTNAAAGGAANNNTCCTNTCTGTNATANNNGNNCCNCCNATNGTNGCNGCNATNATTN GmCPP       TAATAGTACAG------------------------------------------------- 525
GmPrPase2   TAATAGTACAG------------------------------------------------- 563
AtCPP       TCATAGTCCAG------------------------------------------------- 525
AtPrPase1   TCATAGTCCAG------------------------------------------------- 525
AtPrPase2   TCATAGTCCAG------------------------------------------------- 525
AFC1        TCATAGTCCAG------------------------------------------------- 525
AT4g01320   TCATAGTCCAG------------------------------------------------- 546
AF007269    TCATAGTCCAGGTTTGATGATTCTGGATTCATCTTATTTCTGAGTTTTTCACATGGATGA 1620
BnCPP       TTATAGTTCAG------------------------------------------------- 525
Consensus   TNATAGTNCAG GmCPP       ------------------------------------------------------------
GmPrPase2   ------------------------------------------------------------
AtCPP       ------------------------------------------------------------
AtPrPase1   ------------------------------------------------------------
AtPrPase2   ------------------------------------------------------------
AFC1        ------------------------------------------------------------
AT4g01320   ------------------------------------------------------------
AF007269    CTATTCTCCATTGAGTGTGAGCTTCAAAGTTTTTAGTTTTCGTGTTAAAAATTTAAAATT 1680
BnCPP       ------------------------------------------------------------

GmCPP       ---------------------------------------AAAGGAGGTCCATACTTGGCCATC 549
GmPrPase2   ---------------------------------------AAAGGAGGTCCATACTTGGCCATC 587
AtCPP       ---------------------------------------AAAGGAGGTCCTTATCTTGCCATC 549
AtPrPase1   ---------------------------------------AAAGGAGGTCCTTATCTTGCCATC 549
AtPrPase2   ---------------------------------------AAAGGAGGTCCTTATCTTGCCATC 549
AFC1        ---------------------------------------AAAGGAGGTCCTTATCTTGCCATC 549
AT4g01320   ---------------------------------------AAAGGAGGTCCTTATCTTGCCATC 570
AF007269    TGCTTCTCTGAGCATGAAGTTTCTATCTTTTTCCAGAAAGGAGGTCCTTATCTTGCCATC 1740
BnCPP       ---------------------------------------AAAGGAGGTCCTTACCTCGCCATC 549
Consensus                                           AAAGGAGGTCCNTANNTNGCCATC GmCPP       TATCTTTGGGTTTTTACGTTGGTCTTTCTATTGTGATGATGACCCTTTATCCAGTACTA 609
GmPrPase2   TATCTTTGGGTTTTTACGTTGGTCTTTCTATTGTGATGATGACCCTTTATCCAGTACTA 647
AtCPP       TATCTGTGGGCATTCATGTTTATCCTGTCTCTAGTGATGATGACTATATACCCGGTCTTG 609
AtPrPase1   TATCTGTGGGCATTCATGTTTATCCTGTCTCTAGTGATGATGACTATATACCCGGTCTTG 609
AtPrPase2   TATCTGTGGGCATTCATGTTTATCCTGTCTCTAGTGATGATGACTATATACCCGGTCTTG 609
AFC1        TATCTGTGGGCATTCATGTTTATCCTGTCTCTAGTGATGATGACTATATACCCGGTCTTG 609
AT4g01320   TATCTGTGGGCATTCATGTTTATCCTGTCTCTAGTGATGATGACTATATACCCGGTCTTG 630
AF007269    TATCTGTGGGCATTCATGTTTATCCTGTCTCTAGTGATGATGACTATATACCCGGTCTTG 1800
BnCPP       TATCTGTGGGCATTCATGTTTATCCTGTCTCTAGTGATGATGACTATATACCCTGTTTTG 609
Consensus   TATCTNTGGGNNTTNANGTTTNNNCTNTCTNTGTGATGATGACNNTNTANCCNGTNNTN
```

Figure 16G

```
GmCPP       ATAGCTCCACTCTTCAATAAGTTCACTCCA------------------------------ 639
GmPrPase2   ATAGCTCCACTCTTCAATAAGTTCACTCCA------------------------------ 677
AtCPP       ATAGCACCGCTCTTCAACAAATTCACTCCT------------------------------ 639
AtPrPase1   ATAGCACCGCTCTTCAACAAGTTCACTCCT------------------------------ 639
AtPrPase2   ATAGCACCGCTCTTCAACAAGTTCACTCCT------------------------------ 639
AFC1        ATAGCACCGCTCTTCAACAAGTTCACTCCT------------------------------ 639
AT4g01320   ATAGCACCGCTCTTCAACAAGTTCACTCCT------------------------------ 660
AF007269    ATAGCACCGCTCTTCAACAAGTTCACTCCTGTGTGTATTTCTGTCATGGCCATTTTACAA 1860
BnCPP       ATTGCACCTCTTTTCAACAAGTTCACTCCT------------------------------ 639
Consensus   ATNGCNCCNCTNTTCAANAANTTCACTCCN GmCPP       ------------------------------------------------------------
GmPrPase2   ------------------------------------------------------------
AtCPP       ------------------------------------------------------------
AtPrPase1   ------------------------------------------------------------
AtPrPase2   ------------------------------------------------------------
AFC1        ------------------------------------------------------------
AT4g01320   ------------------------------------------------------------
AF007269    TTCACTGCTTGTTTGCATATGTTGTTACCAGACAATATAATCTCCCGCTTTTTTATGGCT 1920
BnCPP       ------------------------------------------------------------

GmCPP       ----CTTCCAGATGGTCAACTCAGGGAGAAAATCGAGAAACTTGCTTCCTCCCTCAACTA 695
GmPrPase2   ----CTTCCAGATGGTCAACTCAGGGAGAAAATCGAGAAACTTGCTTCCTCCCTCAACTA 733
AtCPP       ----CTTCCAGATGGAGACCTCCGGGAGAAGATTGAGAAACTTGCTTCTTCCCTAAAGTT 695
AtPrPase1   ----CTTCCAGATGGAGACCTCCGGGAGAAGATTGAGAAACTTGCTTCTTCTCTAAAGTT 695
AtPrPase2   ----CTTCCAGATGGAGACCTCCGGGAGAAGATTGAGAAACTTGCTTCTTCTCTAAAGTT 695
AFC1        ----CTTCCAGATGGAGACCTCCGGGAGAAGATTGAGAAACTTGCTTCTTCTCTAAAGTT 695
AT4g01320   ----CTTCCAGATGGAGACCTCCGGGAGAAGATTGAGAAACTTGCTTCTTCTCTAAAGTT 716
AF007269    ATAGCTTCCAGATGGAGACCTCCGGGAGAAGATTGAGAAACTTGCTTCTTCTCTAAAGTT 1980
BnCPP       ----CTTCCTGATGGAGACCTCCGGGAGAAGATTGAGAAACTTGCTTCTTCTCTAAAGTT 695
Consensus       CTTCCNGATGGNNANCTCNGGGAGAANATNGAGAAACTTGCTTCNTCNCTNAANTN GmCPP       TCCGTTAAAGAAACTATTTGTTGTCGATGGATCCACAAGATCAAGTCACAGCAATG---- 751
GmPrPase2   TCCGTTAAAGAAACTATTTGTTGTCGATGGATCCACAAGATCAAGTCACAGCAATG---- 789
AtCPP       TCCTTTGAAGAAGCTGTTTGTTGTCGATGGATCTACAAGGTCAAGCCATAGCAATG---- 751
AtPrPase1   TCCTTTGAAGAAGCTGTTTGTTGTCGATGGATCTACAAGGTCAAGCCATAGCAATG---- 751
AtPrPase2   TCCTTTGAAGAAGCTGTTTGTTGTCGATGGATCTACAAGGTCAAGCCATAGCAATG---- 751
AFC1        TCCTTTGAAGAAGCTGTTTGTTGTCGATGGATCTACAAGGTCAAGCCATAGCAATG---- 751
AT4g01320   TCCTTTGAAGAAGCTGTTTGTTGTCGATGGATCTACAAGGTCAAGCCATAGCAATG---- 772
AF007269    TCCTTTGAAGAAGCTGTTTGTTGTCGATGGATCTACAAGGTCAAGCCATAGCAATGTGAG 2040
BnCPP       TCCTCTGAAGAAGCTGTTTGTTGTCGATGGATCTACAAGGTCAAGCCATAGTAATG---- 751
Consensus   TCCNNTNAAGAANCTNTTTGTTGTCGATGGATCNACAAGNTCAAGNCANAGNAATG GmCPP       ------------------------------------------------------------
GmPrPase2   ------------------------------------------------------------
AtCPP       ------------------------------------------------------------
AtPrPase1   ------------------------------------------------------------
AtPrPase2   ------------------------------------------------------------
AFC1        ------------------------------------------------------------
AT4g01320   ------------------------------------------------------------
AF007269    AAGCTTGAGATCTCTTCCTACCTACTTTACTCTAGTTTACCATTAGAAGCTTACGTATCT 2100
BnCPP       ------------------------------------------------------------
```

Figure 16H

```
GmCPP         ----------------CCTATATGTATGGATTCTTCAAGAACAAGAGGATTGTCCCTTAT 795
GmPrPase2     ----------------CCTATATGTATGGATTCTTCAAGAACAAGAGGATTGTCCTTTAT 833
AtCPP         ----------------CTTACATGTATGGTTTCTTTAAGAACAAAAGGATTGTTCTTTAT 795
AtPrPase1     ----------------CTTACATGTATGGTTTCTTTAAGAACAAAAGGATTGTTCTTTAT 795
AtPrPase2     ----------------CTTACATGTATGGTTTCTTTAAGAACAAAAGGATTGTTCTTTAT 795
AFC1          ----------------CTTACATGTATGGTTTCTTTAAGAACAAAAGGATTGTTCTTTAT 795
AT4g01320     ----------------CTTACATGTATGGTTTCTTTAAGAACAAAAGGATTGTTCTTTAT 816
AF007269      TGTTACATCATACAGGCTTACATGTATGGTTTCTTTAAGAACAAAAGGATTGTTCTTTAT 2160
BnCPP         ----------------CTTACATGTATGGTTTCTTCAAGAACAAAAGGATTGTTCTTTAT 795
Consensus                     CNTANATGTATGGNTTCTTNAAGAACAANAGGATTGTNCNTTAT GmCPP         GACACATTAATTCAACAG------------------------------------------ 813
GmPrPase2     GACACATTAATTCAACAG------------------------------------------ 851
AtCPP         GATACGTTGATTCAGCAG------------------------------------------ 813
AtPrPase1     GATACGTTGATTCAGCAG------------------------------------------ 813
AtPrPase2     GATACGTTGATTCAGCAG------------------------------------------ 813
AFC1          GATACGTTGATTCAGCAG------------------------------------------ 813
AT4g01320     GATACGTTGATTCAGCAG------------------------------------------ 834
AF007269      GATACGTTGATTCAGCAGGTACTGTGACTCTTGATGCTTCAAACGAGCTATACTCACATT 2220
BnCPP         GACACATTGATTCAGCAG------------------------------------------ 813
Consensus     GANACNTTNATTCANCAG GmCPP         ---------------------------------------TGCAAAGACGATGAGG 829
GmPrPase2     ---------------------------------------TGCAAAGACGATGAGG 867
AtCPP         ---------------------------------------TGCAAGAATGAGGATG 829
AtPrPase1     ---------------------------------------TGCAAGAATGAGGATG 829
AtPrPase2     ---------------------------------------TGCAAGAATGAGGATG 829
AFC1          ---------------------------------------TGCAAGAATGAGGATG 829
AT4g01320     ---------------------------------------TGCAAGAATGAGGATG 850
AF007269      TCTGTTTCTGGTTCTGAAACATAACATAATCTTCTATTGTGCAGTGCAAGAATGAGGATG 2280
BnCPP         ---------------------------------------TGCCAGAATGAGAATG 829
Consensus                                             TGCNANNANGANNANG GmCPP         AAATTGTTGCTGTTATTGCCCATGAGTTGGGACACTGGAAGCTCAACCATACTGTGTACA 889
GmPrPase2     AAATTGTTGCTGTTATTGCCCATGAGTTGGGACACTGGAAGCTCAACCATACTGTGTACA 927
AtCPP         AAATTGTGGCGGTTATTGCACACGAGCTTGGACATTGGAAACTGAATCACACTACATACT 889
AtPrPase1     AAATTGTGGCGGTTATTGCACACGAGCTTGGACATTGGAAACTGAATCACACTACATACT 889
AtPrPase2     AAATTGTGGCGGTTATTGCACACGAGCTTGGACATTGGAAACTGAATCACACTACATACT 889
AFC1          AAATTGTGGCGGTTATTGCACACGAGCTTGGACATTGGAAACTGAATCACACTACATACT 889
AT4g01320     AAATTGTGGCGGTTATTGCACACGAGCTTGGACATTGGAAACTGAATCACACTACATACT 910
AF007269      AAATTGTGGCGGTTATTGCACACGAGCTTGGACATTGGAAACTGAATCACACTACATACT 2340
BnCPP         AAATTGTGGCGGTTATTGCACACGAGCTGGGACACTGGAAGCTGAATCACACTACATACT 889
Consensus     AAATTGTNGCNGTTATTGCNCANGAGNTNGGACANTGGAANCTNAANCANACTNNNTACN GmCPP         CATTTGTTGCTATGCAG------------------------------------------- 906
GmPrPase2     CATTTGTTGCTATGCAG------------------------------------------- 944
AtCPP         CGTTCATTGCAGTTCAA------------------------------------------- 906
AtPrPase1     CGTTCATTGCAGTTCAA------------------------------------------- 906
AtPrPase2     CGTTCATTGCAGTTCAA------------------------------------------- 906
AFC1          CGTTCATTGCAGTTCAA------------------------------------------- 906
AT4g01320     CGTTCATTGCAGTTCAA------------------------------------------- 927
AF007269      CGTTCATTGCAGTTCAAGTGAGGCTCAACCGACAGTTCAAAAACTTACTCACATCTACAT 2400
BnCPP         CGTTCATTGCTGTTCAA------------------------------------------- 906
Consensus     CNTTNNTTGCNNTNCAN
```

Figure 16I

```
GmCPP       ------------------------------------------------------ATTCTTACA 915
GmPrPase2   ------------------------------------------------------ATTCTTACA 953
AtCPP       ------------------------------------------------------ATCCTTGCC 915
AtPrPase1   ------------------------------------------------------ATCCTTGCC 915
AtPrPase2   ------------------------------------------------------ATCCTTGCC 915
AFC1        ------------------------------------------------------ATCCTTGCC 915
AT4g01320   ------------------------------------------------------ATCCTTGCC 936
AF007269    TTCACTTAAGAAATCATGTCTTATGACCCTCTCTCAATGTTTTGCTTGCAGATCCTTGCC 2460
BnCPP       ------------------------------------------------------ATCCTTGCC 915
Consensus                                                         ATNCTTNCN GmCPP       CTTCTACAATTTGGAGGATATACACTAGTGCGAAATTCAGCTGATCTGTATCGAAGCTTT 975
GmPrPase2   CTTCTACAATTTGGAGGATATACACTAGTGCGAAATTCAGCTGATCTGTATCGAAGCTTT 1013
AtCPP       TTCTTACAATTTGGAGGATACACTCTTCTCAGAAACTCCACTGATCTCTTCAGGAGTTTC 975
AtPrPase1   TTCTTACAATTTGGAGGATACACTCTTGTCAGAAACTCCACTGATCTCTTCAGGAGTTTC 975
AtPrPase2   TTCTTACAATTTGGAGGATACACTCTTGTCAGAAACTCCACTGATCTCTTCAGGAGTTTC 975
AFC1        TTCTTACAATTTGGAGGATACACTCTTGTCAGAAACTCCACTGATCTCTTCAGGAGTTTC 975
AT4g01320   TTCTTACAATTTGGAGGATACACTCTTGTCAGAAACTCCACTGATCTCTTCAGGAGTTTC 996
AF007269    TTCTTACAATTTGGAGGATACACTCTTGTCAGAAACTCCACTGATCTCTTCAGGAGTTTC 2520
BnCPP       TTCTTGCAATTTGGAGGATACACTCTTGTCAGAAACTCCACTGATCTCTTCAGGAGTTTT 975
Consensus   NTNNTNCAATTTGGAGGATANACNCTNNTNNGAAANTCNNCTGATCTNTNNNGNAGNTTN GmCPP       GGGTTTGATACGCAGCCAGTCCTCATTGGGCTCATCATATTTCAG--------------- 1020
GmPrPase2   GGGTTTGATACGCAGCCAGTCCTCATTGGGCTCATCATATTTCAG--------------- 1058
AtCPP       GGATTTGATACACAGCCTGTTCTCATTGGTTTGATCATATTTCAG--------------- 1020
AtPrPase1   GGATTTGATACACAGCCTGTTCTCATTGGTTTGATCATATTTCAG--------------- 1020
AtPrPase2   GGATTTGATACACAGCCTGTTCTCATTGGTTTGATCATATTTCAG--------------- 1020
AFC1        GGATTTGATACACAGCCTGTTCTCATTGGTTTGATCATATTTCAG--------------- 1020
AT4g01320   GGATTTGATACACAGCCTGTTCTCATTGGTTTGATCATATTTCAG--------------- 1041
AF007269    GGATTTGATACACAGCCTGTTCTCATTGGTTTGATCATATTTCAGGTTTGTTATTTTTGC 2580
BnCPP       GGTTTTGATACACAACCAGTTCTCATTGGTTTGATCATATTTCAG--------------- 1020
Consensus   GGNTTTGATACNCANCCNGTNCTCATTGGNNTNATCATATTTCAG GmCPP       ------------------------------------------------------------
GmPrPase2   ------------------------------------------------------------
AtCPP       ------------------------------------------------------------
AtPrPase1   ------------------------------------------------------------
AtPrPase2   ------------------------------------------------------------
AFC1        ------------------------------------------------------------
AT4g01320   ------------------------------------------------------------
AF007269    CTTTTGACACTAATCTAATGAATCAAGGATGGATTAAGAAAAAAAAACTCTAAACCTTTG 2640
BnCPP       ------------------------------------------------------------

GmCPP       ---------------------------CATACTGTAATCCCACTTCAGCAATTGGTCAGC 1053
GmPrPase2   ---------------------------CATACTGTAATCCCACTTCAGCAATTGGTCAGC 1091
AtCPP       ---------------------------CACACTGTAATACCACTGCAACATCTAGTAAGC 1053
AtPrPase1   ---------------------------CACACTGTAATACCACTGCAACATCCAGTAAGC 1053
AtPrPase2   ---------------------------CACACTGTAATACCACTGCAACATCTAGTAAGC 1053
AFC1        ---------------------------CACACTGTAATACCACTGCAACATCTAGTAAGC 1053
AT4g01320   ---------------------------CACACTGTAATACCACTGCAACATCTAGTAAGC 1074
AF007269    GTTATATCTCCTGTCTGATTATCACAGCACACTGTAATACCACTGCAACATCTAGTAAGC 2700
BnCPP       ---------------------------CACACTGTAATACCACTTCAACACCTAGTAAGC 1053
Consensus                              CANACTGTAATNCCACTNCANCANNNNGTNAGC
```

Figure 16J

```
GmCPP       TTTGGTCTGAACCTAGTCAGCCGATCATTTGAATTTCAGG-------------------- 1093
GmPrPase2   TTTGGTCTGAACCTAGTCAGCCGATCATTTGAATTTCAGG-------------------- 1131
AtCPP       TTTGGCCTGAACCTCGTTAGTCGAGCGTTTGAGTTTCAGG-------------------- 1093
AtPrPase1   TTTGGCCTCAACCTTGTTAGTCGAGCGTTTGAGTTTCAGG-------------------- 1093
AtPrPase2   TTTGGCCTGAACCTCGTTAGTCGAGCGTTTGAGTTTCAGG-------------------- 1093
AFC1        TTTGGCCTGAACCTCGTTAGTCGAGCGTTTGAGTTTCAGG-------------------- 1093
AT4g01320   TTTGGCCTGAACCTCGTTAGTCGAGCGTTTGAGTTTCAGG-------------------- 1114
AF007269    TTTGGCCTGAACCTCGTTAGTCGAGCGTTTGAGTTTCAGGTACCATCTTACAATCCCTCA 2760
BnCPP       TTTGACCTCAACCTTGTTAGTCGAGCGTTTGAGTTTCAGG-------------------- 1093
Consensus   TTTGNNCTNAACCTNGTNAGNCGANCNTTTGANTTTCAGG GmCPP       ------------------------------------------------------------
GmPrPase2   ------------------------------------------------------------
AtCPP       ------------------------------------------------------------
AtPrPase1   ------------------------------------------------------------
AtPrPase2   ------------------------------------------------------------
AFC1        ------------------------------------------------------------
AT4g01320   ------------------------------------------------------------
AF007269    AGATCCAACCATAGTTTCTTTATTGCAATGGCAGCCTCATCTACTAATCTGAGTTAACGT 2820
BnCPP       ------------------------------------------------------------

GmCPP       -----------CTGATGGCTTTGCCAAGAAGCTTGGATATGCATCTGGATTACGCGGTG 1141
GmPrPase2   -----------CTGATGGCTTTGCCAAGAAGCTTGGATATGCATCTGGATTACGCGGTG 1179
AtCPP       -----------CTGATGCTTTTGCTGTGAAGCTTGACTATGCAAAAGATCTTCGTCCTG 1141
AtPrPase1   -----------CTGATGCTTTTGCTGTGAAGCTTGGCTATGCAAAAGATCTTCGTCCTA 1141
AtPrPase2   -----------CTGATGCTTTTGCTGTGAAGCTTGGCTATGCAAAAGATCTTCGTCCTG 1141
AFC1        -----------CTGATGCTTTTGCCGTGAAGCTTGGCTATGCAAAAGATCTTCGTCCTG 1141
AT4g01320   -----------CTGATGCTTTTGCTGTGAAGCTTGGCTATGCAAAAGATCTTCGTCCTG 1162
AF007269    TCCTTTTGCAGGCTGATGCTTTTGCTGTGAAGCTTGGCTATGCAAAAGATCTTCGTCCTG 2880
BnCPP       -----------CTGATGCTTTTGCAGTGAATCTTGGTTATGCAAAGGATCTACGTCCTG 1141
Consensus               CTGATGNNTTTGCNNNGAANCTTGNNTATGCANNNGNNNTNCGNNNTN GmCPP       GTCTTGTGAAACTACAGG------------------------------------------ 1159
GmPrPase2   GTCTTGTGAAACTACAGG------------------------------------------ 1197
AtCPP       CTCTAGTGAAACTACAGG------------------------------------------ 1159
AtPrPase1   CTCTAGTGAAACTACAGG------------------------------------------ 1159
AtPrPase2   CTCTAGTGAAACTACAGG------------------------------------------ 1159
AFC1        CTCTAGTGAAACTACAGG------------------------------------------ 1159
AT4g01320   CTCTAGTGAAACTACAGGTCAGAGAAGATAACAACAGAACACAAACTGTTACCTCAATTT 1222
AF007269    CTCTAGTGAAACTACAGGTCAGAGAAGATAACAACAGAACACAAACTGTTACCTCAATTT 2940
BnCPP       CCCTAGTGAAGCTACAGG------------------------------------------ 1159
Consensus   NNCTNGTGAANCTACAGG GmCPP       ------------------------------------AGGAGAATCTGTCAGCTA 1177
GmPrPase2   ------------------------------------AGGAGAATCTGTCAGCTA 1215
AtCPP       ------------------------------------AAGAGAACTTATCAACAA 1177
AtPrPase1   ------------------------------------AAGAGAACTTATCAGCAA 1177
AtPrPase2   ------------------------------------AAGAGAACTTATCAGCAA 1177
AFC1        ------------------------------------AAGAGAACTTATCAGCAA 1177
AT4g01320   GTGTCACACACTTAAATGGATTTTTTGTTGGGATTTTGCAGGAAGAGAACTTATCAGCAA 1282
AF007269    GTGTCACACACTTAAATGGATTTTTTGTTGGGATTTTGCAGGAAGAGAACTTATCAGCAA 3000
BnCPP       ------------------------------------AAGAGAACTTATCAGCGA 1177
Consensus                                       ANGAGAANNTNTCANCNA
```

Figure 16K

```
GmCPP       TGAATACAGATCCTTGGTACTCTGCTTATCACTATTCTCATCCTCCCCTTGTTGAAAGAT 1237
GmPrPase2   TGAATACAGATCCTTGGTACTCTGCTTATCACTATTCTCATCCTCCCCTTGTTGAAAGAT 1275
AtCPP       TGAACACTGATCCATTGTACTCAGCTTATCACTACTCACATCCTCCTCTTGTTGAAAGGC 1237
AtPrPase1   TGAATACTGATCCATTGTACTCAGCTTATCACTACTCACATCCTCCTCTTGTTGAAAGGC 1237
AtPrPase2   TGAACACTGATCTATTGTACTCAGCTTATCACTACTCACATCCTCCTCTTGTTGAAAGGC 1237
AFC1        TGAACACTGATCCATTGCACTCAGCTTATCACTACTCACATCCTCCTCTTGTTGAAAGGC 1237
AT4g01320   TGAACACTGATCCATTGTACTCAGCTTATCACTACTCACATCCTCCTCTTGTTGAAAGGC 1342
AF007269    TGAACACTGATCCATTGTACTCAGCTTATCACTACTCACATCCTCCTCTTGTTGAAAGGC 3060
BnCPP       TGAACACAGACCCATTGTACTCAGCTTATCACTACTCACACCCTCCTCTTGTAGAGAGGC 1237
Consensus   TGAANACNGANCNNTNGNACTCNGCTTATCACTANTCNCANCCTCCNCTTGTNGANAGNN GmCPP       TGGCCGCGCTGGACGAACCGGATAAGAAGGAAGACTAA--------------------- 1275
GmPrPase2   TGGCTGTGCTGGACGAACCGGATAAGAAGGAAGACTAAGCAAGTAACTTAAAGATGAAGA 1335
AtCPP       TTCGAGCCACTGATGGAGAAGACAAGAAGACAGATTAA--------------------- 1275
AtPrPase1   TTCGAGCCATTGATGGAGAAGACAAGAAGACAGATTAA--------------------- 1275
AtPrPase2   TTCGAGCCATTGATGGAGAAGACAAGAAGACAGATTAA--------------------- 1275
AFC1        TTCGAGCCATTGATGGAGAAGACAAGAAGACAGATTAA--------------------- 1275
AT4g01320   TTCGAGCCATTGATGGAGAAGACAAGAAGACAGATTAA--------------------- 1380
AF007269    TTCGAGCCATTGATGGAGAAGACAAGAAGACAGATTAA--------------------- 3098
BnCPP       TTCGAGCCATTGATGGAGAAGACAAGAAGACAGATTAA--------------------- 1275
Consensus   TNNNNGNNNNNGANGNANNNGANAAGAAGNNAGANTAA GmCPP       ------------------------------------------------------------
GmPrPase2   GCTGCAAAAATTGGCTATACCCTAACTTGCTATGATTTAGTGCTGCAATAGCTGTAATAT 1395
AtCPP       ------------------------------------------------------------
AtPrPase1   ------------------------------------------------------------
AtPrPase2   ------------------------------------------------------------
AFC1        ------------------------------------------------------------
AT4g01320   ------------------------------------------------------------
AF007269    ------------------------------------------------------------
BnCPP       ------------------------------------------------------------

GmCPP       ----------
GmPrPase2   CTCCCGGGAT 1405
AtCPP       ----------
AtPrPase1   ----------
AtPrPase2   ----------
AFC1        ----------
AT4g01320   ----------
AF007269    ----------
BnCPP       ----------
```

Figure 17A

```
GmCPP        MAFPYMEAVVGFMILMYIFETYLDVRQHRALKLPTLPKTLEGVISQEKFEKSRAYS----  56
GmPrPase2    MAFPYMEAVVGFMILMYIFETYLDVRQHRALKLPTLPKTLEGVISQEKFEKSRAYS----  56
AtCPP        MAIPFMETVVGFMIVMYIFETYLDLRQLTALKLPTLPKTLVGVISQEKFEKSRAYS----  56
AtPrPase1    MAIPFMETVVGFMIVMYIFETYLDLRQLTALKLPTLPKTLVGVISQEKFEKSRAYS----  56
AtPrPase2    MAIPFMETVVGFMIVMYIFETYLDLRQLTALKLPTLPKTLVGVISQEKFEKSRAYS----  56
AFC1         MAIPFMETVVGFMIVMYIFETYLDLRQLTALKLPTLPKTLVGVISQEKFEKSRAYS----  56
AT4g01320    MAIPFMETVVGFMIVMYIFETYLDLRQLTALKLPTLPKTLVGVISQEKFEKSRAYRDIIT  60
AF007269     MAIPFMETVVGFMIVMYIFETYLDLRQLTALKLPTLPKTLI-------------------  41
BnCPP        MAIPFMETVVGFMIVMYVFETYLDLRQHTALKLPTLPKTLVGVISQEKFEKSRAYS----  56
Consensus    MAXPXMEXVVGFMIXMYXFETYLDXRQXXALKLPTLPKTLX GmCPP        ---LDKSHFHFVHEFVTIVTDSTILYFGVLPWFWKKSGDFMTIAGFNAENEILHTLAFLA  113
GmPrPase2    ---LDKSHFHFVHEFVTIVTDSTILYFGVLPWFWKKSGDFMTIAGFNAENEILHTLAFLA  113
AtCPP        ---LDKSYFHFVHEFVTILMDSAILFFGILPWFWKMSGAVLPRLGLDPENEILHTLSFLA  113
AtPrPase1    ---LDKSYFHFVHEFVTILMDSAILFFGILPWFWKMSGAVLPRLGLDPENEILHTLSFLA  113
AtPrPase2    ---LDKSYFHFVHEFVTILMDSAILFFGILPWFWKMSGAVLPRLGLDPENEILHTLSFLA  113
AFC1         ---LDKSYFHFVHEFVTILMDSAILFFGILPWFWKMSGAVLPRLGLDPENEILHTLSFLA  113
AT4g01320    ENFNICSYFHFVHEFVTILMDSAILFFGILPWFWKMSGAVLPRLGLDPENEILHTLSFLA  120
AF007269     ------------------------------------------------------------
BnCPP        ---LDKSHFHFVHEFVTILMDSAILFFGILPWFWKISGGFLPMVGLDPENEILHTLSFLA  113

GmCPP        GLMIWSQITDLPFSLYSTFVIEARHGFNKQTPWLFFRDMLKGIFLSVIIGPPIVAAIIVI  173
GmPrPase2    GLMIWSQITDLPFSLYSTFVIEARHGFNKQTPWLFFRDMLKGIFLSVIIGPPIVAAIIVI  173
AtCPP        GVMTWSQITDLPFSLYSTFVIESRHGFNKQTIWMFIRDMIKGTFLSVILGPPIVAAIIFI  173
AtPrPase1    GVMTWSQITDLPFSLYSTFVIESRHGFNKQTIWMFIRDMIKGTFLSVILGPPIVAAIIFI  173
AtPrPase2    GVMTWSQITDLPFSLYSTFVIESRHGFNKQTIWMFIRDMIKGTFLSVILGPPIVAAIIFI  173
AFC1         GVMTWSQITDLPFSLYSTFVIESRHGFNKQTIWMFIRDMIKGTFLSVILGPPIVAAIIFI  173
AT4g01320    GVMTWSQITDLPFSLYSTFVIESRHGFNKQTIWMFIRDMIKGTFLSVILGPPIVAAIIFI  180
AF007269     --------TDLPFSLYSTFVIESRHGFNKQTIWMFIRDMIKGTFLSVILGPPIVAAIIFI  93
BnCPP        GLMTWSQITDLPFSLYSTFVIESRHGFNKQTIWMFIRDMIKGILLSVIPAPPIVAAIIVI  173
Consensus            TDLPFSLYSTFVIEXRHGFNKQTXWXFXRDMXKGXXLSVIXXPPIVAAIIXI GmCPP        VQKGGPYLAIYLWVFTFGLSIVMMTLYPVLIAPLFNKFTPLPDGQLREKIEKLASSLNYP  233
GmPrPase2    VQKGGPYLAIYLWVFTFGLSIVMMTLYPVLIAPLFNKFTPLPDGQLREKIEKLASSLNYP  233
AtCPP        VQKGGPYLAIYLWAFMFILSLVMMTIYPVLIAPLFNKFTPLPDGDLREKIEKLASSLKFP  233
AtPrPase1    VQKGGPYLAIYLWAFMFILSLVMMTIYPVLIAPLFNKFTPLPDGDLREKIEKLASSLKFP  233
AtPrPase2    VQKGGPYLAIYLWAFMFILSLVMMTIYPVLIAPLFNKFTPLPDGDLREKIEKLASSLKFP  233
AFC1         VQKGGPYLAIYLWAFMFILSLVMMTIYPVLIAPLFNKFTPLPDGDLREKIEKLASSLKFP  233
AT4g01320    VQKGGPYLAIYLWAFMFILSLVMMTIYPVLIAPLFNKFTPLPDGDLREKIEKLASSLKFP  240
AF007269     VQKGGPYLAIYLWAFMFILSLVMMTIYPVLIAPLFNKFTPLPDGDLREKIEKLASSLKFP  153
BnCPP        VQKGGPYLAIYLWAFMFILSLVMMTIYPVLIAPLFNKFTPLPDGDLREKIEKLASSLKFP  233
Consensus    VQKGGPYLAIYLWXFXFXLSXVMMTXYPVLIAPLFNKFTPLPDGXLREKIEKLASSLXXP GmCPP        LKKLFVVDGSTRSSHSNAYMYGFFKNKRIVPYDTLIQQCKDDEEIVAVIAHELGHWKLNH  293
GmPrPase2    LKKLFVVDGSTRSSHSNAYMYGFFKNKRIVLYDTLIQQCKDDEEIVAVIAHELGHWKLNH  293
AtCPP        LKKLFVVDGSTRSSHSNAYMYGFFKNKRIVLYDTLIQQCKNEDEIVAVIAHELGHWKLNH  293
AtPrPase1    LKKLFVVDGSTRSSHSNAYMYGFFKNKRIVLYDTLIQQCKNEDEIVAVIAHELGHWKLNH  293
AtPrPase2    LKKLFVVDGSTRSSHSNAYMYGFFKNKRIVLYDTLIQQCKNEDEIVAVIAHELGHWKLNH  293
AFC1         LKKLFVVDGSTRSSHSNAYMYGFFKNKRIVLYDTLIQQCKNEDEIVAVIAHELGHWKLNH  293
AT4g01320    LKKLFVVDGSTRSSHSNAYMYGFFKNKRIVLYDTLIQQCKNEDEIVAVIAHELGHWKLNH  300
AF007269     LKKLFVVDGSTRSSHSNAYMYGFFKNKRIVLYDTLIQQCKNEDEIVAVIAHELGHWKLNH  213
BnCPP        LKKLFVVDGSTRSSHSNAYMYGFFKNKRIVLYDTLIQQCQNENEIVAVIAHELGHWKLNH  293
Consensus    LKKLFVVDGSTRSSHSNAYMYGFFKNKRIVXYDTLIQQCXXXXEIVAVIAHELGHWKLNH
```

Figure 17B

```
GmCPP       TVYTFVAMQILTLLQFGGYTLVRNSADLYRSFGFDTQPVLIGLIIFQHTVIPLQQLVSFG 353
GmPrPase2   TVYTFVAMQILTLLQFGGYTLVRNSADLYRSFGFDTQPVLIGLIIFQHTVIPLQQLVSFG 353
AtCPP       TTYSFIAVQILAFLQFGGYTLLRNSTDLFRSFGFDTQPVLIGLIIFQHTVIPLQHLVSFG 353
AtPrPase1   TTYSFIAVQILAFLQFGGYTLVRNSTDLFRSFGFDTQPVLIGLIIFQHTVIPLQHPVSFG 353
AtPrPase2   TTYSFIAVQILAFLQFGGYTLVRNSTDLFRSFGFDTQPVLIGLIIFQHTVIPLQHLVSFG 353
AFC1        TTYSFIAVQILAFLQFGGYTLVRNSTDLFRSFGFDTQPVLIGLIIFQHTVIPLQHLVSFG 353
AT4g01320   TTYSFIAVQILAFLQFGGYTLVRNSTDLFRSFGFDTQPVLIGLIIFQHTVIPLQHLVSFG 360
AF007269    TTYSFIAV-----------------------------QHTVIPLQHLVSFG 235
BnCPP       TTYSFIAVQILAFLQFGGYTLVRNSTDLFRSFGFDTQPVLIGLIIFQHTVIPLQHLVSFD 353
Consensus   TXYXFXAX                              QHTVIPLQXXVSFX GmCPP       LNLVSRSFEFQADGFAKKLGYASGLRGGLVKLQ-------------------------- 386
GmPrPase2   LNLVSRSFEFQADGFAKKLGYASGLRGGLVKLQ-------------------------- 386
AtCPP       LNLVSRAFEFQADAFAVKLDYAKDLR-------PALV----KLQE-------------- 387
AtPrPase1   LNLVSRAFEFQADAFAVKLGYAKDLR-------PTLV----KLQE-------------- 387
AtPrPase2   LNLVSRAFEFQADAFAVKLGYAKDLR-------PALV----KLQE-------------- 387
AFC1        LNLVSRAFEFQADAFAVKLGYAKDLR-------PALV----KLQE-------------- 387
AT4g01320   LNLVSRAFEFQADAFAVKLGYAKDLR-------PALV----KLQVREDNNRTQTVTSICV 409
AF007269    LNLVSRAFEFQADAFAVKLGYAKDLR-------PALV----KLQVREDNNRTQ------- 277
BnCPP       LNLVSRAFEFQADAFAVNLGYAKDLR-------PALVKLQE------------------ 387
Consensus   LNLVSRXFEFQADXFAXXLXYAXXLR GmCPP       -----------EENLSAMNTDPWYSAYHYSHPPLVERLAALDEPDKKED 424
GmPrPase2   -----------EENLSAMNTDPWYSAYHYSHPPLVERLAVLDEPDKKED 424
AtCPP       -----------ENLSTMNTDPLYSAYHYSHPPLVERLRATDGEDKKTD 424
AtPrPase1   -----------ENLSAMNTDPLYSAYHYSHPPLVERLRAIDGEDKKTD 424
AtPrPase2   -----------ENLSAMNTDLLYSAYHYSHPPLVERLRAIDGEDKKTD 424
AFC1        -----------ENLSAMNTDPLHSAYHYSHPPLVERLRAIDGEDKKTD 424
AT4g01320   THLNGFFVGILQEENLSAMNTDPLYSAYHYSHPPLVERLRAIDGEDKKTD 459
AF007269    ----------TEENLSAMNTDPLYSAYHYSHPPLVERLRAIDGEDKKTD 316
BnCPP       -----------ENLSAMNTDPLYSAYHYSHPPLVERLRAIDGEDKKTD 424
Consensus              ENLSXMNTDXXXSAYHYSHPPLVERLXXXDXXDKKXD
```

Figure 18A

| | |
|---|---|
| AtCPP | ------------------------------------------------------------ |
| AtPrPase1 | ------------------------------------------------------------ |
| AtPrPase2 | ------------------------------------------------------------ |
| AFC1 | ------------------------------------------------------------ |
| AT4g01320 | ------------------------------------------------------------ |
| AF007269 | ATGGCGATTCCTTTCATGGAAACCGTCGTGGGTAAGCTTCAAAACCTTTTTCTGAGACAT 60 |
| | |
| AtCPP | ------------------------------------------------------------ |
| AtPrPase1 | ------------------------------------------------------------ |
| AtPrPase2 | ------------------------------------------------------------ |
| AFC1 | ------------------------------------------------------------ |
| AT4g01320 | ------------------------------------------------------------ |
| AF007269 | TTTACTATCCTGTTTCACTCATCGTATTTCGTTTTTGTTTGGGTTTTGCTTTCTGTGTTG 120 |
| | |
| AtCPP | ------------------------------------------------------------ |
| AtPrPase1 | ------------------------------------------------------------ |
| AtPrPase2 | ------------------------------------------------------------ |
| AFC1 | ------------------------------------------------------------ |
| AT4g01320 | ------------------------------------------------------------ |
| AF007269 | TGTGTGTTGAGATTCCATGACTCGTTTGTTTCATATACCATCGTCTCTGCTTCTCGTTTC 180 |
| | |
| AtCPP | ------------------------------------------------------------ |
| AtPrPase1 | ------------------------------------------------------------ |
| AtPrPase2 | ------------------------------------------------------------ |
| AFC1 | ------------------------------------------------------------ |
| AT4g01320 | ------------------------------------------------------------ |
| AF007269 | TAAATTTTGTTCTTTTCTAATAGTGCGTACCTTGATCTGAGGTTTTATTACTCCTACTAG 240 |
| | |
| AtCPP | ------------------------------------------------------------ |
| AtPrPase1 | ------------------------------------------------------------ |
| AtPrPase2 | ------------------------------------------------------------ |
| AFC1 | ------------------------------------------------------------ |
| AT4g01320 | ------------------------------------------------------------ |
| AF007269 | TTTCTTGTCTTACTCGTGCGTTTGATTTGATTTGAGCTTATGTGATTTCATCATCTCTTC 300 |
| | |
| AtCPP | ------------------------------------------------------------ |
| AtPrPase1 | ------------------------------------------------------------ |
| AtPrPase2 | ------------------------------------------------------------ |
| AFC1 | ------------------------------------------------------------ |
| AT4g01320 | ------------------------------------------------------------ |
| AF007269 | CTCGGTTTTAGAATGTACGGAGCTTCTCTGTTAACCAAAATCTAGGATTTGGGAAGAAAA 360 |
| | |
| AtCPP | ------------------------------------------------------------ |
| AtPrPase1 | ------------------------------------------------------------ |
| AtPrPase2 | ------------------------------------------------------------ |
| AFC1 | ------------------------------------------------------------ |
| AT4g01320 | ------------------------------------------------------------ |
| AF007269 | GTCGGAGTCTTTTTTTTCCTCATTCCCGATTGGAAATTGAGAATCTTGAAATTTTTCTTT 420 |

Figure 18B

```
AtCPP       ------------------------------------------------------------
AtPrPase1   ------------------------------------------------------------
AtPrPase2   ------------------------------------------------------------
AFC1        ------------------------------------------------------------
AT4g01320   ------------------------------------------------------------
AF007269    GTTCAAGTCATACAGCTTGAGGTTTTGGGTTTTCTTGTCAGGGTATTATTATGTTCGTGA 480

AtCPP       ------------------------------------------------------------
AtPrPase1   ------------------------------------------------------------
AtPrPase2   ------------------------------------------------------------
AFC1        ------------------------------------------------------------
AT4g01320   ------------------------------------------------------------
AF007269    CTGCAACTAGAGTTTTCTGGAGTTTTTTGAAATGGGTTTTGTGTTGTGGAACCGTATGTG 540

AtCPP       ------------------------------------------------------------
AtPrPase1   ------------------------------------------------------------
AtPrPase2   ------------------------------------------------------------
AFC1        ------------------------------------------------------------
AT4g01320   ------------------------------------------------------------
AF007269    AATGTTGCATCAAAACTCTTTCAGTGCTCCAATGTTTCCATCAGTAGTCAGCACAAGAGA 600

AtCPP       ------------------------------------------------------------
AtPrPase1   ------------------------------------------------------------
AtPrPase2   ------------------------------------------------------------
AFC1        ------------------------------------------------------------
AT4g01320   ------------------------------------------------------------
AF007269    TCTTTTTATATCTGGTTGATCAAAAAAGTAGATGATGTTATTGAATTTTCAGTGATGGAG 660

AtCPP       ---------------------------------------ATGGCGATTCCT--TTCATGGAAACCG 25
AtPrPase1   ---------------------------------------ATGGCGATTCCT--TTCATGGAAACCG 25
AtPrPase2   ---------------------------------------ATGGCGATTCCT--TTCATGGAAACCG 25
AFC1        ---------------------------------------ATGGCGATTCCT--TTCATGGAAACCG 25
AT4g01320   ---------------------------------------ATGGCGATTCCT--TTCATGGAAACCG 25
AF007269    TATCTGTTGTTGTGGCATTTAGAGTAGATTCGTATTTCATCTTCTGTTTTATTCTTTTTC 720
Consensus                                          ATNNCNNNTNCT    TTNATNNNNNNNN AtCPP       TCGTGGGTTTTATGATAGTGATGTACATTTTTGAGACGTATTTGGATCTGAGGCAACTCA 85
AtPrPase1   TCGTGGGTTTTATGATAGTGATGTACATTTTTGAGACGTATTTGGATCTGAGGCAACTCA 85
AtPrPase2   TCGTGGGTTTTATGATAGTGATGTACATTTTTGAGACGTATTTGGATCTGAGGCAACTCA 85
AFC1        TCGTGGGTTTTATGATAGTGATGTACATTTTTGAGACGTATTTGGATCTGAGGCAACTCA 85
AT4g01320   TCGTGGGTTTTATGATAGTGATGTACATTTTTGAGACGTATTTGGATCTGAGGCAACTCA 85
AF007269    TTACAGGTTTTATGATAGTGATGTACATTTTTGAGACGTATTTGGATCTGAGGCAACTCA 780
Consensus   TNNNNGGTTTTATGATAGTGATGTACATTTTTGAGACGTATTTGGATCTGAGGCAACTCA AtCPP       CTGCTCTCAAGCTTCCAACTCTCCCGAAAACCTTGGTTGGTGTAATTAGCCAAGAGAAGT 145
AtPrPase1   CTGCTCTCAAGCTTCCAACTCTCCCGAAAACCTTGGTTGGTGTAATTAGCCAAGAGAAGT 145
AtPrPase2   CTGCTCTCAAGCTTCCAACTCTCCCGAAAACCTTGGTTGGTGTAATTAGCCAAGAGAAGT 145
AFC1        CTGCTCTCAAGCTTCCAACTCTCCCGAAAACCTTGGTTGGTGTAATTAGCCAAGAGAAGT 145
AT4g01320   CTGCTCTCAAGCTTCCAACTCTCCCGAAAACCTTGGTTGGTGTAATTAGCCAAGAGAAGT 145
AF007269    CTGCTCTCAAGCTTCCAACTCTCCCGAAAACCTTGGTTGGTGTAATTAGCCAAGAGAAGT 840
Consensus   CTGCTCTCAAGCTTCCAACTCTCCCGAAAACCTTGGTTGGTGTAATTAGCCAAGAGAAGT
```

Figure 18C

```
AtCPP       TTGAGAAATCACGAGCATACAG--------------------------------------- 167
AtPrPase1   TTGAGAAATCACGAGCATACAG--------------------------------------- 167
AtPrPase2   TTGAGAAATCACGAGCATACAG--------------------------------------- 167
AFC1        TTGAGAAATCACGAGCATACAG--------------------------------------- 167
AT4g01320   TTGAGAAATCACGAGCATACAGG-------------------------------------- 168
AF007269    TTGAGAAATCACGAGCATACAGTCTTGACAAAAGGTTTCGTCTTGATCATATTTATATCA 900
Consensus   TTGAGAAATCACGAGCATACAG AtCPP       ---------------------------------------TCTTGACAAA---AGCTA 182
AtPrPase1   ---------------------------------------TCTTGACAAA---AGCTA 182
AtPrPase2   ---------------------------------------TCTTGACAAA---AGCTA 182
AFC1        ---------------------------------------TCTTGACAAA---AGCTA 182
AT4g01320   ----------------------GATATCATCACTGAGAACTTTAATATATGCAGCTA 203
AF007269    TTTTAGTTTTTTATAATTGCCAGGGGATATCATCACTGAGAACTTTAATATATGCAGCTA 960
Consensus                                             NNTTNANANA   AGCTA AtCPP       TTTTCACTTTGTTCATGAGTTTGTAACTATACTTATGGACTCTGCAATTTTGTTCTTTGG 242
AtPrPase1   TTTTCACTTTGTTCATGAGTTTGTAACTATACTTATGGACTCTGCAATTTTGTTCTTTGG 242
AtPrPase2   TTTTCACTTTGTTCATGAGTTTGTAACTATACTTATGGACTCTGCAATTTTGTTCTTTGG 242
AFC1        TTTTCACTTTGTTCATGAGTTTGTAACTATACTTATGGACTCTGCAATTTTGTTCTTTGG 242
AT4g01320   TTTTCACTTTGTTCATGAGTTTGTAACTATACTTATGGACTCTGCAATTTTGTTCTTTGG 263
AF007269    TTTTCACTTTGTTCATGAGTTTGTAACTATACTTATGGACTCTGCAATTTTGTTCTTTGG 1020
Consensus   TTTTCACTTTGTTCATGAGTTTGTAACTATACTTATGGACTCTGCAATTTTGTTCTTTGG AtCPP       GATCTTGCCTTGGTTTTGGAAG--------------------------------- 264
AtPrPase1   GATCTTGCCTTGGTTTTGGAAG--------------------------------- 264
AtPrPase2   GATCTTGCCTTGGTTTTGGAAG--------------------------------- 264
AFC1        GATCTTGCCTTGGTTTTGGAAG--------------------------------- 264
AT4g01320   GATCTTGCCTTGGTTTTGGAAG--------------------------------- 285
AF007269    GATCTTGCCTTGGTTTTGGAAGGTACATATCTGGTTTCGGTATACAGTATCTCATTTTGA 1080
Consensus   GATCTTGCCTTGGTTTTGGAAG AtCPP       ------------------------------------------ATGTCTGGAGCT 276
AtPrPase1   ------------------------------------------ATGTCTGGAGCT 276
AtPrPase2   ------------------------------------------ATGTCTGGAGCA 276
AFC1        ------------------------------------------ATGTCTGGAGCT 276
AT4g01320   ------------------------------------------ATGTCTGGAGCT 297
AF007269    ATATAGAGTTGTTACATTACAATTGTAAAGTTTTCATTTTTACCTTAGATGTCTGGAGCT 1140
Consensus                                              ATGTCTGGAGCN AtCPP       GTTTTACCGAGGTTGGGCCTTGATCCGGAGAATGAAATACTGCATACTCTTTCATTCTTG 336
AtPrPase1   GTTTTACCGAGGTTGGGCCTTGATCCAGAGAATGAAATACTGCATACTCTTTCATTCTTG 336
AtPrPase2   GTTTTACCGAGGTTGGGCCTTGATCCAGAGAATGAAATACTGCATACTCTTTCATTCTTG 336
AFC1        GTTTTACCGAGGTTGGGCCTTGATCCAGAGAATGAAATACTGCATACTCTTTCATTCTTG 336
AT4g01320   GTTTTACCGAGGTTGGGCCTTGATCCAGAGAATGAAATACTGCATACTCTTTCATTCTTG 357
AF007269    GTTTTACCGAGGTTGGGCCTTGATCCAGAGAATGAAATACTGCATACTCTTTCATTCTTG 1200
Consensus   GTTTTACCGAGGTTGGGCCTTGATCCNGAGAATGAAATACTGCATACTCTTTCATTCTTG AtCPP       GCTGGTGTTATGACATGGTCACAG-------------------------------- 360
AtPrPase1   GCTGGTGTTATGACATGGTCACAG-------------------------------- 360
AtPrPase2   GCTGGTGTTATGACATGGTCACAG-------------------------------- 360
AFC1        GCTGGTGTTATGACATGGTCACAG-------------------------------- 360
AT4g01320   GCTGGTGTTATGACATGGTCACAG-------------------------------- 381
AF007269    GCTGGTGTTATGACATGGTCACAGGTGTTCCAAATAAACCCCTTCATATAGTCCTATACG 1260
Consensus   GCTGGTGTTATGACATGGTCACAG
```

Figure 18D

```
AtCPP       ------------------------------------------------------------
AtPrPase1   ------------------------------------------------------------
AtPrPase2   ------------------------------------------------------------
AFC1        ------------------------------------------------------------
AT4g01320   ------------------------------------------------------------
AF007269    TTTAGCATCAAAATATCTATTTTCTTAAGATAATAATATTTCTTTTATATTCTGATGCAG 1320

AtCPP       ATCACTGATTTGCCATTTTCTTTGTACTCAACTTTCGTGATCGAGTCTCGGCATGGGTTC 420
AtPrPase1   ATCACTGATTTGCCATTTTCTTTGTACTCAACTTTCGTGATCGAGTCTCGGCATGGGTTC 420
AtPrPase2   ATCACTGATTTGCCATTTTCTTTGTACTCAACTTTCGTGATCGAGTCTCGGCATGGGTTC 420
AFC1        ATCACTGATTTGCCATTTTCTTTGTACTCAACTTTCGTGATCGAGTCTCGGCATGGGTTC 420
AT4g01320   ATCACTGATTTGCCATTTTCTTTGTACTCAACTTTCGTGATCGAGTCTCGGCATGGGTTC 441
AF007269    ATCACTGATTTGCCATTTTCTTTGTACTCAACTTTCGTGATCGAGTCTCGGCATGGGTTC 1380
Consensus   ATCACTGATTTGCCATTTTCTTTGTACTCAACTTTCGTGATCGAGTCTCGGCATGGGTTC AtCPP       AACAAA------------------------------------------------------ 426
AtPrPase1   AACAAA------------------------------------------------------ 426
AtPrPase2   AACAAA------------------------------------------------------ 426
AFC1        AACAAA------------------------------------------------------ 426
AT4g01320   AACAAA------------------------------------------------------ 447
AF007269    AACAAAGTATGTCGTATTTCCAACACTACCTTGTGACTTACGTTTTTTTATCAGAGATGT 1440
Consensus   AACAAA AtCPP       ------------------------------CAAACAATATGGATGTTCATTAGGGACA 454
AtPrPase1   ------------------------------CAAACAATATGGATGTTCATTAGGGACA 454
AtPrPase2   ------------------------------CAAACAATATGGATGTTCATTAGGGACA 454
AFC1        ------------------------------CAAACAATATGGATGTTCATTAGGGACA 454
AT4g01320   ------------------------------CAAACAATATGGATGTTCATTAGGGACA 475
AF007269    GGATTAAATTTGCTTCTAAATTCTGTTGACAGCAAACAATATGGATGTTCATTAGGGACA 1500
Consensus                                 CAAACAATATGGATGTTCATTAGGGACA AtCPP       TGATCAAAGGAACATTCCTCTCTGTCATACTAGGCCCACCCATTGTTGCTGCGATAATTT 514
AtPrPase1   TGATCAAAGGAACATTCCTCTCTGTCATACTAGGCCCACCCATTGTTGCCGCGATAATTT 514
AtPrPase2   TGATCAAAGGAACATTCCTCTCTGTCATACTAGGCCCACCCATTGTTGCTGCGATAATTT 514
AFC1        TGATCAAAGGAACATTCCTCTCTGTCATACTAGGCCCACCCATTGTTGCTGCGATAATTT 514
AT4g01320   TGATCAAAGGAACATTCCTCTCTGTCATACTAGGCCCACCCATTGTTGCTGCGATAATTT 535
AF007269    TGATCAAAGGAACATTCCTCTCTGTCATACTAGGCCCACCCATTGTTGCTGCGATAATTT 1560
Consensus   TGATCAAAGGAACATTCCTCTCTGTCATACTAGGCCCACCCATTGTTGCNGCGATAATTT AtCPP       TCATAGTCCAG------------------------------------------------- 525
AtPrPase1   TCATAGTCCAG------------------------------------------------- 525
AtPrPase2   TCATAGTCCAG------------------------------------------------- 525
AFC1        TCATAGTCCAG------------------------------------------------- 525
AT4g01320   TCATAGTCCAG------------------------------------------------- 546
AF007269    TCATAGTCCAGGTTTGATGATTCTGGATTCATCTTATTTCTGAGTTTTTCACATGGATGA 1620
Consensus   TCATAGTCCAG AtCPP       ------------------------------------------------------------
AtPrPase1   ------------------------------------------------------------
AtPrPase2   ------------------------------------------------------------
AFC1        ------------------------------------------------------------
AT4g01320   ------------------------------------------------------------
AF007269    CTATTCTCCATTGAGTGTGAGCTTCAAAGTTTTAGTTTTCGTGTTAAAAATTTAAAATT 1680
```

Figure 18E

```
AtCPP       ------------------------------------AAAGGAGGTCCTTATCTTGCCATC 549
AtPrPase1   ------------------------------------AAAGGAGGTCCTTATCTTGCCATC 549
AtPrPase2   ------------------------------------AAAGGAGGTCCTTATCTTGCCATC 549
AFC1        ------------------------------------AAAGGAGGTCCTTATCTTGCCATC 549
AT4g01320   ------------------------------------AAAGGAGGTCCTTATCTTGCCATC 570
AF007269    TGCTTCTCTGAGCATGAAGTTTCTATCTTTTTCCAGAAAGGAGGTCCTTATCTTGCCATC 1740
Consensus                                       AAAGGAGGTCCTTATCTTGCCATC AtCPP       TATCTGTGGGCATTCATGTTTATCCTGTCTCTAGTGATGATGACTATATACCCGGTCTTG 609
AtPrPase1   TATCTGTGGGCATTCATGTTTATCCTGTCTCTAGTGATGATGACTATATACCCGGTCTTG 609
AtPrPase2   TATCTGTGGGCATTCATGTTTATCCTGTCTCTAGTGATGATGACTATATACCCGGTCTTG 609
AFC1        TATCTGTGGGCATTCATGTTTATCCTGTCTCTAGTGATGATGACTATATACCCGGTCTTG 609
AT4g01320   TATCTGTGGGCATTCATGTTTATCCTGTCTCTAGTGATGATGACTATATACCCGGTCTTG 630
AF007269    TATCTGTGGGCATTCATGTTTATCCTGTCTCTAGTGATGATGACTATATACCCGGTCTTG 1800
Consensus   TATCTGTGGGCATTCATGTTTATCCTGTCTCTAGTGATGATGACTATATACCCGGTCTTG AtCPP       ATAGCACCGCTCTTCAACAAATTCACTCCT------------------------------ 639
AtPrPase1   ATAGCACCGCTCTTCAACAAGTTCACTCCT------------------------------ 639
AtPrPase2   ATAGCACCGCTCTTCAACAAGTTCACTCCT------------------------------ 639
AFC1        ATAGCACCGCTCTTCAACAAGTTCACTCCT------------------------------ 639
AT4g01320   ATAGCACCGCTCTTCAACAAGTTCACTCCT------------------------------ 660
AF007269    ATAGCACCGCTCTTCAACAAGTTCACTCCTGTGTGTATTTCTGTCATGGCCATTTTACAA 1860
Consensus   ATAGCACCGCTCTTCAACAANTTCACTCCT AtCPP       ------------------------------------------------------------
AtPrPase1   ------------------------------------------------------------
AtPrPase2   ------------------------------------------------------------
AFC1        ------------------------------------------------------------
AT4g01320   ------------------------------------------------------------
AF007269    TTCACTGCTTGTTTGCATATGTTGTTACCAGACAATATAATCTCCCGCTTTTTTATGGCT 1920

AtCPP       ----CTTCCAGATGGAGACCTCCGGGAGAAGATTGAGAAACTTGCTTCTTCCCTAAAGTT 695
AtPrPase1   ----CTTCCAGATGGAGACCTCCGGGAGAAGATTGAGAAACTTGCTTCTTCTCTAAAGTT 695
AtPrPase2   ----CTTCCAGATGGAGACCTCCGGGAGAAGATTGAGAAACTTGCTTCTTCTCTAAAGTT 695
AFC1        ----CTTCCAGATGGAGACCTCCGGGAGAAGATTGAGAAACTTGCTTCTTCTCTAAAGTT 695
AT4g01320   ----CTTCCAGATGGAGACCTCCGGGAGAAGATTGAGAAACTTGCTTCTTCTCTAAAGTT 716
AF007269    ATAGCTTCCAGATGGAGACCTCCGGGAGAAGATTGAGAAACTTGCTTCTTCTCTAAAGTT 1980
Consensus       CTTCCAGATGGAGACCTCCGGGAGAAGATTGAGAAACTTGCTTCTTCNCTAAAGTT AtCPP       TCCTTTGAAGAAGCTGTTTGTTGTCGATGGATCTACAAGGTCAAGCCATAGCAATG---- 751
AtPrPase1   TCCTTTGAAGAAGCTGTTTGTTGTCGATGGATCTACAAGGTCAAGCCATAGCAATG---- 751
AtPrPase2   TCCTTTGAAGAAGCTGTTTGTTGTCGATGGATCTACAAGGTCAAGCCATAGCAATG---- 751
AFC1        TCCTTTGAAGAAGCTGTTTGTTGTCGATGGATCTACAAGGTCAAGCCATAGCAATG---- 751
AT4g01320   TCCTTTGAAGAAGCTGTTTGTTGTCGATGGATCTACAAGGTCAAGCCATAGCAATG---- 772
AF007269    TCCTTTGAAGAAGCTGTTTGTTGTCGATGGATCTACAAGGTCAAGCCATAGCAATGTGAG 2040
Consensus   TCCTTTGAAGAAGCTGTTTGTTGTCGATGGATCTACAAGGTCAAGCCATAGCAATG AtCPP       ------------------------------------------------------------
AtPrPase1   ------------------------------------------------------------
AtPrPase2   ------------------------------------------------------------
AFC1        ------------------------------------------------------------
AT4g01320   ------------------------------------------------------------
AF007269    AAGCTTGAGATCTCTTCCTACCTACTTTACTCTAGTTTACCATTAGAAGCTTACGTATCT 2100
```

Figure 18F

```
AtCPP       ----------------CTTACATGTATGGTTTCTTTAAGAACAAAAGGATTGTTCTTTAT 795
AtPrPase1   ----------------CTTACATGTATGGTTTCTTTAAGAACAAAAGGATTGTTCTTTAT 795
AtPrPase2   ----------------CTTACATGTATGGTTTCTTTAAGAACAAAAGGATTGTTCTTTAT 795
AFC1        ----------------CTTACATGTATGGTTTCTTTAAGAACAAAAGGATTGTTCTTTAT 795
AT4g01320   ----------------CTTACATGTATGGTTTCTTTAAGAACAAAAGGATTGTTCTTTAT 816
AF007269    TGTTACATCATACAGGCTTACATGTATGGTTTCTTTAAGAACAAAAGGATTGTTCTTTAT 2160
Consensus                   CTTACATGTATGGTTTCTTTAAGAACAAAAGGATTGTTCTTTAT AtCPP       GATACGTTGATTCAGCAG------------------------------------------ 813
AtPrPase1   GATACGTTGATTCAGCAG------------------------------------------ 813
AtPrPase2   GATACGTTGATTCAGCAG------------------------------------------ 813
AFC1        GATACGTTGATTCAGCAG------------------------------------------ 813
AT4g01320   GATACGTTGATTCAGCAG------------------------------------------ 834
AF007269    GATACGTTGATTCAGCAGGTACTGTGACTCTTGATGCTTCAAACGAGCTATACTCACATT 2220
Consensus   GATACGTTGATTCAGCAG AtCPP       ---------------------------------------------TGCAAGAATGAGGATG 829
AtPrPase1   ---------------------------------------------TGCAAGAATGAGGATG 829
AtPrPase2   ---------------------------------------------TGCAAGAATGAGGATG 829
AFC1        ---------------------------------------------TGCAAGAATGAGGATG 829
AT4g01320   ---------------------------------------------TGCAAGAATGAGGATG 850
AF007269    TCTGTTTCTGGTTCTGAAACATAACATAATCTTCTATTGTGCAGTGCAAGAATGAGGATG 2280
Consensus                                                TGCAAGAATGAGGATG AtCPP       AAATTGTGGCGGTTATTGCACACGAGCTTGGACATTGGAAACTGAATCACACTACATACT 889
AtPrPase1   AAATTGTGGCGGTTATTGCACACGAGCTTGGACATTGGAAACTGAATCACACTACATACT 889
AtPrPase2   AAATTGTGGCGGTTATTGCACACGAGCTTGGACATTGGAAACTGAATCACACTACATACT 889
AFC1        AAATTGTGGCGGTTATTGCACACGAGCTTGGACATTGGAAACTGAATCACACTACATACT 889
AT4g01320   AAATTGTGGCGGTTATTGCACACGAGCTTGGACATTGGAAACTGAATCACACTACATACT 910
AF007269    AAATTGTGGCGGTTATTGCACACGAGCTTGGACATTGGAAACTGAATCACACTACATACT 2340
Consensus   AAATTGTGGCGGTTATTGCACACGAGCTTGGACATTGGAAACTGAATCACACTACATACT AtCPP       CGTTCATTGCAGTTCAA------------------------------------------- 906
AtPrPase1   CGTTCATTGCAGTTCAA------------------------------------------- 906
AtPrPase2   CGTTCATTGCAGTTCAA------------------------------------------- 906
AFC1        CGTTCATTGCAGTTCAA------------------------------------------- 906
AT4g01320   CGTTCATTGCAGTTCAA------------------------------------------- 927
AF007269    CGTTCATTGCAGTTCAAGTGAGGCTCAACCGACAGTTCAAAAACTTACTCACATCTACAT 2400
Consensus   CGTTCATTGCAGTTCAA AtCPP       -----------------------------------------------------ATCCTTGCC 915
AtPrPase1   -----------------------------------------------------ATCCTTGCC 915
AtPrPase2   -----------------------------------------------------ATCCTTGCC 915
AFC1        -----------------------------------------------------ATCCTTGCC 915
AT4g01320   -----------------------------------------------------ATCCTTGCC 936
AF007269    TTCACTTAAGAAATCATGTCTTATGACCCTCTCTCAATGTTTTGCTTGCAGATCCTTGCC 2460
Consensus                                                        ATCCTTGCC AtCPP       TTCTTACAATTTGGAGGATACACTCTTCTCAGAAACTCCACTGATCTCTTCAGGAGTTTC 975
AtPrPase1   TTCTTACAATTTGGAGGATACACTCTTGTCAGAAACTCCACTGATCTCTTCAGGAGTTTC 975
AtPrPase2   TTCTTACAATTTGGAGGATACACTCTTGTCAGAAACTCCACTGATCTCTTCAGGAGTTTC 975
AFC1        TTCTTACAATTTGGAGGATACACTCTTGTCAGAAACTCCACTGATCTCTTCAGGAGTTTC 975
AT4g01320   TTCTTACAATTTGGAGGATACACTCTTGTCAGAAACTCCACTGATCTCTTCAGGAGTTTC 996
AF007269    TTCTTACAATTTGGAGGATACACTCTTGTCAGAAACTCCACTGATCTCTTCAGGAGTTTC 2520
Consensus   TTCTTACAATTTGGAGGATACACTCTTNTCAGAAACTCCACTGATCTCTTCAGGAGTTTC
```

Figure 18G

```
AtCPP       GGATTTGATACACAGCCTGTTCTCATTGGTTTGATCATATTTCAG--------------- 1020
AtPrPase1   GGATTTGATACACAGCCTGTTCTCATTGGTTTGATCATATTTCAG--------------- 1020
AtPrPase2   GGATTTGATACACAGCCTGTTCTCATTGGTTTGATCATATTTCAG--------------- 1020
AFC1        GGATTTGATACACAGCCTGTTCTCATTGGTTTGATCATATTTCAG--------------- 1020
AT4g01320   GGATTTGATACACAGCCTGTTCTCATTGGTTTGATCATATTTCAG--------------- 1041
AF007269    GGATTTGATACACAGCCTGTTCTCATTGGTTTGATCATATTTCAGGTTTGTTATTTTTGC 2580
Consensus   GGATTTGATACACAGCCTGTTCTCATTGGTTTGATCATATTTCAG AtCPP       ------------------------------------------------------------
AtPrPase1   ------------------------------------------------------------
AtPrPase2   ------------------------------------------------------------
AFC1        ------------------------------------------------------------
AT4g01320   ------------------------------------------------------------
AF007269    CTTTTGACACTAATCTAATGAATCAAGGATGGATTAAGAAAAAAAAACTCTAAACCTTTG 2640

AtCPP       --------------------------CACACTGTAATACCACTGCAACATCTAGTAAGC 1053
AtPrPase1   --------------------------CACACTGTAATACCACTGCAACATCCAGTAAGC 1053
AtPrPase2   --------------------------CACACTGTAATACCACTGCAACATCTAGTAAGC 1053
AFC1        --------------------------CACACTGTAATACCACTGCAACATCTAGTAAGC 1053
AT4g01320   --------------------------CACACTGTAATACCACTGCAACATCTAGTAAGC 1074
AF007269    GTTATATCTCCTGTCTGATTATCACAGCACACTGTAATACCACTGCAACATCTAGTAAGC 2700
Consensus                             CACACTGTAATACCACTGCAACATCNAGTAAGC AtCPP       TTTGGCCTGAACCTCGTTAGTCGAGCGTTTGAGTTTCAGG-------------------- 1093
AtPrPase1   TTTGGCCTCAACCTTGTTAGTCGAGCGTTTGAGTTTCAGG-------------------- 1093
AtPrPase2   TTTGGCCTGAACCTCGTTAGTCGAGCGTTTGAGTTTCAGG-------------------- 1093
AFC1        TTTGGCCTGAACCTCGTTAGTCGAGCGTTTGAGTTTCAGG-------------------- 1093
AT4g01320   TTTGGCCTGAACCTCGTTAGTCGAGCGTTTGAGTTTCAGG-------------------- 1114
AF007269    TTTGGCCTGAACCTCGTTAGTCGAGCGTTTGAGTTTCAGGTACCATCTTACAATCCCTCA 2760
Consensus   TTTGGCCTNAACCTNGTTAGTCGAGCGTTTGAGTTTCAGG AtCPP       ------------------------------------------------------------
AtPrPase1   ------------------------------------------------------------
AtPrPase2   ------------------------------------------------------------
AFC1        ------------------------------------------------------------
AT4g01320   ------------------------------------------------------------
AF007269    AGATCCAACCATAGTTTCTTTATTGCAATGGCAGCCTCATCTACTAATCTGAGTTAACGT 2820

AtCPP       ------------CTGATGCTTTTGCTGTGAAGCTTGACTATGCAAAGATCTTCGTCCTG 1141
AtPrPase1   ------------CTGATGCTTTTGCTGTGAAGCTTGGCTATGCAAAGATCTTCGTCCTA 1141
AtPrPase2   ------------CTGATGCTTTTGCTGTGAAGCTTGGCTATGCAAAGATCTTCGTCCTG 1141
AFC1        ------------CTGATGCTTTTGCCGTGAAGCTTGGCTATGCAAAGATCTTCGTCCTG 1141
AT4g01320   ------------CTGATGCTTTTGCTGTGAAGCTTGGCTATGCAAAGATCTTCGTCCTG 1162
AF007269    TCCTTTTGCAGGCTGATGCTTTTGCTGTGAAGCTTGGCTATGCAAAGATCTTCGTCCTG 2880
Consensus               CTGATGCTTTTGCNGTGAAGCTTGNCTATGCAAAGATCTTCGTCCTN AtCPP       CTCTAGTGAAACTACAGG------------------------------------------ 1159
AtPrPase1   CTCTAGTGAAACTACAGG------------------------------------------ 1159
AtPrPase2   CTCTAGTGAAACTACAGG------------------------------------------ 1159
AFC1        CTCTAGTGAAACTACAGG------------------------------------------ 1159
AT4g01320   CTCTAGTGAAACTACAGGTCAGAGAAGATAACAACAGAACACAAACTGTTACCTCAATTT 1222
AF007269    CTCTAGTGAAACTACAGGTCAGAGAAGATAACAACAGAACACAAACTGTTACCTCAATTT 2940
Consensus   CTCTAGTGAAACTACAGG
```

Figure 18H

```
AtCPP        ---------------------------------------AAGAGAACTTATCAACAA 1177
AtPrPase1    ---------------------------------------AAGAGAACTTATCAGCAA 1177
AtPrPase2    ---------------------------------------AAGAGAACTTATCAGCAA 1177
AFC1         ---------------------------------------AAGAGAACTTATCAGCAA 1177
AT4g01320    GTGTCACACACTTAAATGGATTTTTTGTTGGGATTTTGCAGGAAGAGAACTTATCAGCAA 1282
AF007269     GTGTCACACACTTAAATGGATTTTTTGTTGGGATTTTGCAGGAAGAGAACTTATCAGCAA 3000
Consensus                                                   AAGAGAACTTATCANCAA AtCPP        TGAACACTGATCCATTGTACTCAGCTTATCACTACTCACATCCTCCTCTTGTTGAAAGGC 1237
AtPrPase1    TGAATACTGATCCATTGTACTCAGCTTATCACTACTCACATCCTCCTCTTGTTGAAAGGC 1237
AtPrPase2    TGAACACTGATCTATTGTACTCAGCTTATCACTACTCACATCCTCCTCTTGTTGAAAGGC 1237
AFC1         TGAACACTGATCCATTGCACTCAGCTTATCACTACTCACATCCTCCTCTTGTTGAAAGGC 1237
AT4g01320    TGAACACTGATCCATTGTACTCAGCTTATCACTACTCACATCCTCCTCTTGTTGAAAGGC 1342
AF007269     TGAACACTGATCCATTGTACTCAGCTTATCACTACTCACATCCTCCTCTTGTTGAAAGGC 3060
Consensus    TGAANACTGATCNATTGNACTCAGCTTATCACTACTCACATCCTCCTCTTGTTGAAAGGC AtCPP        TTCGAGCCACTGATGGAGAAGACAAGAAGACAGATTAA 1275
AtPrPase1    TTCGAGCCATTGATGGAGAAGACAAGAAGACAGATTAA 1275
AtPrPase2    TTCGAGCCATTGATGGAGAAGACAAGAAGACAGATTAA 1275
AFC1         TTCGAGCCATTGATGGAGAAGACAAGAAGACAGATTAA 1275
AT4g01320    TTCGAGCCATTGATGGAGAAGACAAGAAGACAGATTAA 1380
AF007269     TTCGAGCCATTGATGGAGAAGACAAGAAGACAGATTAA 3098
Consensus    TTCGAGCCANTGATGGAGAAGACAAGAAGACAGATTAA
```

Figure 19A

```
AtCPP       MAIPFMETVVGFMIVMYIFETYLDLRQLTALKLPTLPKTLVGVISQEKFEKSRAYSLDKS 60
AtPrPase1   MAIPFMETVVGFMIVMYIFETYLDLRQLTALKLPTLPKTLVGVISQEKFEKSRAYSLDKS 60
AtPrPase2   MAIPFMETVVGFMIVMYIFETYLDLRQLTALKLPTLPKTLVGVISQEKFEKSRAYSLDKS 60
AFC1        MAIPFMETVVGFMIVMYIFETYLDLRQLTALKLPTLPKTLVGVISQEKFEKSRAYSLDKS 60
AT4g01320   MAIPFMETVVGFMIVMYIFETYLDLRQLTALKLPTLPKTLVGVISQEKFEKSRAYRDIIT 60
AF007269    MAIPFMETVVGFMIVMYIFETYLDLRQLTALKLPTLPKTLI------------------ 41
Consensus   MAIPFMETVVGFMIVMYIFETYLDLRQLTALKLPTLPKTLX AtCPP       YFHFVHEFVTILMDSAILFFGILPWFWKMSGAVLPRLGLDPENEILHTLSFLAG------ 114
AtPrPase1   YFHFVHEFVTILMDSAILFFGILPWFWKMSGAVLPRLGLDPENEILHTLSFLAG------ 114
AtPrPase2   YFHFVHEFVTILMDSAILFFGILPWFWKMSGAVLPRLGLDPENEILHTLSFLAG------ 114
AFC1        YFHFVHEFVTILMDSAILFFGILPWFWKMSGAVLPRLGLDPENEILHTLSFLAG------ 114
AT4g01320   ENFNICSYFHFVHEFVTILMDSAILFFGILPWFWKMSGAVLPRLGLDPENEILHTLSFLA 120
AF007269    ------------------------------------------------------------

AtCPP       -VMTWSQITDLPFSLYSTFVIESRHGFNKQTIWMFIRDMIKGTFLSVILGPPIVAAIIFI 173
AtPrPase1   -VMTWSQITDLPFSLYSTFVIESRHGFNKQTIWMFIRDMIKGTFLSVILGPPIVAAIIFI 173
AtPrPase2   -VMTWSQITDLPFSLYSTFVIESRHGFNKQTIWMFIRDMIKGTFLSVILGPPIVAAIIFI 173
AFC1        -VMTWSQITDLPFSLYSTFVIESRHGFNKQTIWMFIRDMIKGTFLSVILGPPIVAAIIFI 173
AT4g01320   GVMTWSQITDLPFSLYSTFVIESRHGFNKQTIWMFIRDMIKGTFLSVILGPPIVAAIIFI 180
AF007269    --------TDLPFSLYSTFVIESRHGFNKQTIWMFIRDMIKGTFLSVILGPPIVAAIIFI 93
Consensus           TDLPFSLYSTFVIESRHGFNKQTIWMFIRDMIKGTFLSVILGPPIVAAIIFI AtCPP       VQKGGPYLAIYLWAFMFILSLVMMTIYPVLIAPLFNKFTPLPDGDLREKIEKLASSLKFP 233
AtPrPase1   VQKGGPYLAIYLWAFMFILSLVMMTIYPVLIAPLFNKFTPLPDGDLREKIEKLASSLKFP 233
AtPrPase2   VQKGGPYLAIYLWAFMFILSLVMMTIYPVLIAPLFNKFTPLPDGDLREKIEKLASSLKFP 233
AFC1        VQKGGPYLAIYLWAFMFILSLVMMTIYPVLIAPLFNKFTPLPDGDLREKIEKLASSLKFP 233
AT4g01320   VQKGGPYLAIYLWAFMFILSLVMMTIYPVLIAPLFNKFTPLPDGDLREKIEKLASSLKFP 240
AF007269    VQKGGPYLAIYLWAFMFILSLVMMTIYPVLIAPLFNKFTPLPDGDLREKIEKLASSLKFP 153
Consensus   VQKGGPYLAIYLWAFMFILSLVMMTIYPVLIAPLFNKFTPLPDGDLREKIEKLASSLKFP AtCPP       LKKLFVVDGSTRSSHSNAYMYGFFKNKRIVLYDTLIQQCKNEDEIVAVIAHELGHWKLNH 293
AtPrPase1   LKKLFVVDGSTRSSHSNAYMYGFFKNKRIVLYDTLIQQCKNEDEIVAVIAHELGHWKLNH 293
AtPrPase2   LKKLFVVDGSTRSSHSNAYMYGFFKNKRIVLYDTLIQQCKNEDEIVAVIAHELGHWKLNH 293
AFC1        LKKLFVVDGSTRSSHSNAYMYGFFKNKRIVLYDTLIQQCKNEDEIVAVIAHELGHWKLNH 293
AT4g01320   LKKLFVVDGSTRSSHSNAYMYGFFKNKRIVLYDTLIQQCKNEDEIVAVIAHELGHWKLNH 300
AF007269    LKKLFVVDGSTRSSHSNAYMYGFFKNKRIVLYDTLIQQCKNEDEIVAVIAHELGHWKLNH 213
Consensus   LKKLFVVDGSTRSSHSNAYMYGFFKNKRIVLYDTLIQQCKNEDEIVAVIAHELGHWKLNH AtCPP       TTYSFIAVQILAFLQFGGYTLLRNSTDLFRSFGFDTQPVLIGLIIFQHTVIPLQHLVSFG 353
AtPrPase1   TTYSFIAVQILAFLQFGGYTLVRNSTDLFRSFGFDTQPVLIGLIIFQHTVIPLQHPVSFG 353
AtPrPase2   TTYSFIAVQILAFLQFGGYTLVRNSTDLFRSFGFDTQPVLIGLIIFQHTVIPLQHLVSFG 353
AFC1        TTYSFIAVQILAFLQFGGYTLVRNSTDLFRSFGFDTQPVLIGLIIFQHTVIPLQHLVSFG 353
AT4g01320   TTYSFIAVQILAFLQFGGYTLVRNSTDLFRSFGFDTQPVLIGLIIFQHTVIPLQHLVSFG 360
AF007269    TTYSFIAV--------------------------------QHTVIPLQHLVSFG 235
Consensus   TTYSFIAV                                QHTVIPLQHXVSFG
```

Figure 19B

```
AtCPP       LNLVSRAFEFQADAFAVKLDYAKDLRPALVKLQE------------------------ 387
AtPrPase1   LNLVSRAFEFQADAFAVKLGYAKDLRPTLVKLQE------------------------ 387
AtPrPase2   LNLVSRAFEFQADAFAVKLGYAKDLRPALVKLQE------------------------ 387
AFC1        LNLVSRAFEFQADAFAVKLGYAKDLRPALVKLQE------------------------ 387
AT4g01320   LNLVSRAFEFQADAFAVKLGYAKDLRPALVKLQVREDNNRTQTVTSICVTHLNGFFVGIL 420
AF007269    LNLVSRAFEFQADAFAVKLGYAKDLRPALVKLQVREDNNRTQ----------------- 277
Consensus   LNLVSRAFEFQADAFAVKLXYAKDLRPXLVKLQX AtCPP       --ENLSTMNTDPLYSAYHYSHPPLVERLRATDGEDKKTD 424
AtPrPase1   --ENLSAMNTDPLYSAYHYSHPPLVERLRAIDGEDKKTD 424
AtPrPase2   --ENLSAMNTDLLYSAYHYSHPPLVERLRAIDGEDKKTD 424
AFC1        --ENLSAMNTDPLHSAYHYSHPPLVERLRAIDGEDKKTD 424
AT4g01320   QEENLSAMNTDPLYSAYHYSHPPLVERLRAIDGEDKKTD 459
AF007269    TEENLSAMNTDPLYSAYHYSHPPLVERLRAIDGEDKKTD 316
Consensus     ENLSXMNTDXLXSAYHYSHPPLVERLRAXDGEDKKTD
```

Figure 20A

| | | |
|---|---|---|
| GmCPP | ---------------------------------------ATGGCGTTTCCCTACATGGAAG | 22 |
| GmPrPase2 | GCGAGCTCTCGTTCGGTTCATCAGCGTGTGTCTCAGCCATGGCGTTTCCCTACATGGAAG | 60 |
| Consensus | ATGGCGTTTCCCTACATGGAAG | |

| | | |
|---|---|---|
| GmCPP | CCGTTGTCGGATTTATGATATTAATGTACATTTTTGAAACTTACTTGGATGTGCGACAAC | 82 |
| GmPrPase2 | CCGTTGTCGGATTTATGATATTAATGTACATTTTTGAAACTTACTTGGATGTGCGACAAC | 120 |
| Consensus | CCGTTGTCGGATTTATGATATTAATGTACATTTTTGAAACTTACTTGGATGTGCGACAAC | |

| | | |
|---|---|---|
| GmCPP | ATAGGGCCCTCAAACTTCCTACTCTTCCAAAGACTTTAGAGGGTGTTATCAGCCAAGAGA | 142 |
| GmPrPase2 | ATAGGGCCCTCAAACTTCCTACTCTTCCAAAGACTTTAGAAGGTGTTATCAGCCAAGAGA | 180 |
| Consensus | ATAGGGCCCTCAAACTTCCTACTCTTCCAAAGACTTTAGANGGTGTTATCAGCCAAGAGA | |

| | | |
|---|---|---|
| GmCPP | AATTTGAGAAATCTAGAGCCTATAGTCTTGATAAAAGCCACTTCCATTTTGTTCACGAGT | 202 |
| GmPrPase2 | AATTTGAGAAATCTAGAGCCTATAGTCTTGATAAAAGCCACTTCCATTTTGTTCACGAGT | 240 |
| Consensus | AATTTGAGAAATCTAGAGCCTATAGTCTTGATAAAAGCCACTTCCATTTTGTTCACGAGT | |

| | | |
|---|---|---|
| GmCPP | TTGTGACAATAGTGACAGACTCTACAATTTTGTACTTTGGGGTATTGCCCTGGTTTTGGA | 262 |
| GmPrPase2 | TTGTGACAATAGTGACAGACTCTACAATTTTGTACTTTGGGGTATTGCCCTGGTTTTGGA | 300 |
| Consensus | TTGTGACAATAGTGACAGACTCTACAATTTTGTACTTTGGGGTATTGCCCTGGTTTTGGA | |

| | | |
|---|---|---|
| GmCPP | AGAAATCAGGAGATTTTATGACAATAGCTGGTTTCAATGCTGAGAATGAAATACTGCATA | 322 |
| GmPrPase2 | AGAAATCAGGAGATTTTATGACAATAGCTGGTTTCAATGCTGAGAATGAAATACTGCATA | 360 |
| Consensus | AGAAATCAGGAGATTTTATGACAATAGCTGGTTTCAATGCTGAGAATGAAATACTGCATA | |

| | | |
|---|---|---|
| GmCPP | CCCTTGCCTTCTTAGCAGGGCTGATGATTTGGTCACAGATAACAGATTTGCCCTTTTCTC | 382 |
| GmPrPase2 | CCCTTGCCTTCTTAGCAGGGCTGATGATTTGGTCACAGATAACAGATTTGCCCTTTTCTC | 420 |
| Consensus | CCCTTGCCTTCTTAGCAGGGCTGATGATTTGGTCACAGATAACAGATTTGCCCTTTTCTC | |

| | | |
|---|---|---|
| GmCPP | TGTACTCAACTTTTGTGATTGAGGCCCGTCATGGTTTTAATAAGCAAACACCATGGTTAT | 442 |
| GmPrPase2 | TGTACTCAACTTTTGTGATTGAGGCCCGTCATGGTTTTAATAAGCAAACACCATGGTTAT | 480 |
| Consensus | TGTACTCAACTTTTGTGATTGAGGCCCGTCATGGTTTTAATAAGCAAACACCATGGTTAT | |

| | | |
|---|---|---|
| GmCPP | TCTTTAGGGACATGCTTAAAGGAATTTTCCTTTCTGTAATAATTGGTCCACCTATTGTGG | 502 |
| GmPrPase2 | TCTTTAGGGACATGCTTAAAGGAATTTTCCTTTCTGTAATAATTGGTCCACCTATTGTGG | 540 |
| Consensus | TCTTTAGGGACATGCTTAAAGGAATTTTCCTTTCTGTAATAATTGGTCCACCTATTGTGG | |

| | | |
|---|---|---|
| GmCPP | CTGCAATCATTGTAATAGTACAGAAAGGAGGTCCATACTTGGCCATCTATCTTTGGGTTT | 562 |
| GmPrPase2 | CTGCAATCATTGTAATAGTACAGAAAGGAGGTCCATACTTGGCCATCTATCTTTGGGTTT | 600 |
| Consensus | CTGCAATCATTGTAATAGTACAGAAAGGAGGTCCATACTTGGCCATCTATCTTTGGGTTT | |

| | | |
|---|---|---|
| GmCPP | TTACGTTTGGTCTTTCTATTGTGATGATGACCCTTTATCCAGTACTAATAGCTCCACTCT | 622 |
| GmPrPase2 | TTACGTTTGGTCTTTCTATTGTGATGATGACCCTTTATCCAGTACTAATAGCTCCACTCT | 660 |
| Consensus | TTACGTTTGGTCTTTCTATTGTGATGATGACCCTTTATCCAGTACTAATAGCTCCACTCT | |

| | | |
|---|---|---|
| GmCPP | TCAATAAGTTCACTCCACTTCCAGATGGTCAACTCAGGGAGAAAATCGAGAAACTTGCTT | 682 |
| GmPrPase2 | TCAATAAGTTCACTCCACTTCCAGATGGTCAACTCAGGGAGAAAATCGAGAAACTTGCTT | 720 |
| Consensus | TCAATAAGTTCACTCCACTTCCAGATGGTCAACTCAGGGAGAAAATCGAGAAACTTGCTT | |

| | | |
|---|---|---|
| GmCPP | CCTCCCTCAACTATCCGTTAAAGAAACTATTTGTTGTCGATGGATCCACAAGATCAAGTC | 742 |
| GmPrPase2 | CCTCCCTCAACTATCCGTTAAAGAAACTATTTGTTGTCGATGGATCCACAAGATCAAGTC | 780 |
| Consensus | CCTCCCTCAACTATCCGTTAAAGAAACTATTTGTTGTCGATGGATCCACAAGATCAAGTC | |

Figure 20B

```
GmCPP       ACAGCAATGCCTATATGTATGGATTCTTCAAGAACAAGAGGATTGTCCCTTATGACACAT 802
GmPrPase2   ACAGCAATGCCTATATGTATGGATTCTTCAAGAACAAGAGGATTGTCCTTTATGACACAT 840
Consensus   ACAGCAATGCCTATATGTATGGATTCTTCAAGAACAAGAGGATTGTCCNTTATGACACAT GmCPP       TAATTCAACAGTGCAAAGACGATGAGGAAATTGTTGCTGTTATTGCCCATGAGTTGGGAC 862
GmPrPase2   TAATTCAACAGTGCAAAGACGATGAGGAAATTGTTGCTGTTATTGCCCATGAGTTGGGAC 900
Consensus   TAATTCAACAGTGCAAAGACGATGAGGAAATTGTTGCTGTTATTGCCCATGAGTTGGGAC GmCPP       ACTGGAAGCTCAACCATACTGTGTACACATTTGTTGCTATGCAGATTCTTACACTTCTAC 922
GmPrPase2   ACTGGAAGCTCAACCATACTGTGTACACATTTGTTGCTATGCAGATTCTTACACTTCTAC 960
Consensus   ACTGGAAGCTCAACCATACTGTGTACACATTTGTTGCTATGCAGATTCTTACACTTCTAC GmCPP       AATTTGGAGGATATACACTAGTGCGAAATTCAGCTGATCTGTATCGAAGCTTTGGGTTTG 982
GmPrPase2   AATTTGGAGGATATACACTAGTGCGAAATTCAGCTGATCTGTATCGAAGCTTTGGGTTTG 1020
Consensus   AATTTGGAGGATATACACTAGTGCGAAATTCAGCTGATCTGTATCGAAGCTTTGGGTTTG GmCPP       ATACGCAGCCAGTCCTCATTGGGCTCATCATATTTCAGCATACTGTAATCCCACTTCAGC 1042
GmPrPase2   ATACGCAGCCAGTCCTCATTGGGCTCATCATATTTCAGCATACTGTAATCCCACTTCAGC 1080
Consensus   ATACGCAGCCAGTCCTCATTGGGCTCATCATATTTCAGCATACTGTAATCCCACTTCAGC GmCPP       AATTGGTCAGCTTTGGTCTGAACCTAGTCAGCCGATCATTTGAATTTCAGGCTGATGGCT 1102
GmPrPase2   AATTGGTCAGCTTTGGTCTGAACCTAGTCAGCCGATCATTTGAATTTCAGGCTGATGGCT 1140
Consensus   AATTGGTCAGCTTTGGTCTGAACCTAGTCAGCCGATCATTTGAATTTCAGGCTGATGGCT GmCPP       TTGCCAAGAAGCTTGGATATGCATCTGGATTACGCGGTGGTCTTGTGAAACTACAGGAGG 1162
GmPrPase2   TTGCCAAGAAGCTTGGATATGCATCTGGATTACGCGGTGGTCTTGTGAAACTACAGGAGG 1200
Consensus   TTGCCAAGAAGCTTGGATATGCATCTGGATTACGCGGTGGTCTTGTGAAACTACAGGAGG GmCPP       AGAATCTGTCAGCTATGAATACAGATCCTTGGTACTCTGCTTATCACTATTCTCATCCTC 1222
GmPrPase2   AGAATCTGTCAGCTATGAATACAGATCCTTGGTACTCTGCTTATCACTATTCTCATCCTC 1260
Consensus   AGAATCTGTCAGCTATGAATACAGATCCTTGGTACTCTGCTTATCACTATTCTCATCCTC GmCPP       CCCTTGTTGAAAGATTGGCCGCGCTGGACGAACCGGATAAGAAGGAAGACTAA------- 1275
GmPrPase2   CCCTTGTTGAAAGATTGGCTGTGCTGGACGAACCGGATAAGAAGGAAGACTAAGCAAGTA 1320
Consensus   CCCTTGTTGAAAGATTGGCNGNGCTGGACGAACCGGATAAGAAGGAAGACTAA GmCPP       ------------------------------------------------------------
GmPrPase2   ACTTAAAGATGAAGAGCTGCAAAAATTGGCTATACCCTAACTTGCTATGATTTAGTGCTG 1380

GmCPP       -----------------------
GmPrPase2   CAATAGCTGTAATATCTCCCGGGAT 1405
```

Figure 21

```
GmCPP       MAFPYMEAVVGFMILMYIFETYLDVRQHRALKLPTLPKTLEGVISQEKFEKSRAYSLDKS  60
GmPrPase2   MAFPYMEAVVGFMILMYIFETYLDVRQHRALKLPTLPKTLEGVISQEKFEKSRAYSLDKS  60
Consensus   MAFPYMEAVVGFMILMYIFETYLDVRQHRALKLPTLPKTLEGVISQEKFEKSRAYSLDKS GmCPP       HFHFVHEFVTIVTDSTILYFGVLPWFWKKSGDFMTIAGFNAENEILHTLAFLAGLMIWSQ  120
GmPrPase2   HFHFVHEFVTIVTDSTILYFGVLPWFWKKSGDFMTIAGFNAENEILHTLAFLAGLMIWSQ  120
Consensus   HFHFVHEFVTIVTDSTILYFGVLPWFWKKSGDFMTIAGFNAENEILHTLAFLAGLMIWSQ GmCPP       ITDLPFSLYSTFVIEARHGFNKQTPWLFFRDMLKGIFLSVIIGPPIVAAIIVIVQKGGPY  180
GmPrPase2   ITDLPFSLYSTFVIEARHGFNKQTPWLFFRDMLKGIFLSVIIGPPIVAAIIVIVQKGGPY  180
Consensus   ITDLPFSLYSTFVIEARHGFNKQTPWLFFRDMLKGIFLSVIIGPPIVAAIIVIVQKGGPY GmCPP       LAIYLWVFTFGLSIVMMTLYPVLIAPLFNKFTPLPDGQLREKIEKLASSLNYPLKKLFVV  240
GmPrPase2   LAIYLWVFTFGLSIVMMTLYPVLIAPLFNKFTPLPDGQLREKIEKLASSLNYPLKKLFVV  240
Consensus   LAIYLWVFTFGLSIVMMTLYPVLIAPLFNKFTPLPDGQLREKIEKLASSLNYPLKKLFVV GmCPP       DGSTRSSHSNAYMYGFFKNKRIVPYDTLIQQCKDDEEIVAVIAHELGHWKLNHTVYTFVA  300
GmPrPase2   DGSTRSSHSNAYMYGFFKNKRIVLYDTLIQQCKDDEEIVAVIAHELGHWKLNHTVYTFVA  300
Consensus   DGSTRSSHSNAYMYGFFKNKRIVXYDTLIQQCKDDEEIVAVIAHELGHWKLNHTVYTFVA GmCPP       MQILTLLQFGGYTLVRNSADLYRSFGFDTQPVLIGLIIFQHTVIPLQQLVSFGLNLVSRS  360
GmPrPase2   MQILTLLQFGGYTLVRNSADLYRSFGFDTQPVLIGLIIFQHTVIPLQQLVSFGLNLVSRS  360
Consensus   MQILTLLQFGGYTLVRNSADLYRSFGFDTQPVLIGLIIFQHTVIPLQQLVSFGLNLVSRS GmCPP       FEFQADGFAKKLGYASGLRGGLVKLQEENLSAMNTDPWYSAYHYSHPPLVERLAALDEPD  420
GmPrPase2   FEFQADGFAKKLGYASGLRGGLVKLQEENLSAMNTDPWYSAYHYSHPPLVERLAVLDEPD  420
Consensus   FEFQADGFAKKLGYASGLRGGLVKLQEENLSAMNTDPWYSAYHYSHPPLVERLAXLDEPD GmCPP       KKED  424
GmPrPase2   KKED  424
Consensus   KKED
```

POLYNUCLEOTIDES ENCODING PLANT PRENYL PROTEASES

RELATED APPLICATIONS

This application is a continuation-in-part of U.S. application Ser. No. 10/362,902 and a continuation-in-part of U.S. application Ser. No. 10/210,760. U.S. application Ser. No. 10/362,902 is a national stage application (under 37 U.S.C. 371) of PCT/US01/26854 filed Aug. 27, 2001, which claims benefit of U.S. provisional application 60/227,794, filed Aug. 25, 2000. U.S. application Ser. No. 10/210,760, filed Aug. 1, 2002, claims benefit of U.S. provisional application 60/309,396, filed Aug. 1, 2001, and U.S. provisional application 60/337,084, filed Dec. 4, 2001. The disclosure of each of the above-mentioned applications is incorporated herein by reference in its entirety.

SUBMISSION ON COMPACT DISC

The contents of the following submission on compact discs is incorporated herein by reference in its entirety: two copies of the Sequence Listing (COPY 1 and COPY 2) and a computer readable form copy of the Sequence Listing (CRF COPY), all on compact disc, each containing: file name: Final Sequence Listing-15342-00001; date recorded: Jul. 16, 2007; size: 316 KB.

FIELD OF THE INVENTION

The present invention provides novel polynucleotides encoding plant prenyl protease polypeptides, and fragments and homologs thereof. Also provided are vectors, host cells, and recombinant methods for producing said polypeptides. Also included are transgenic plants expressing the novel polynucleotides. The present invention also includes transgenic plant cells, tissues and plants having novel phenotypes resulting from the expression of these polynucleotides in either the sense or antisense orientation. The invention further relates to methods of applying these novel plant polypeptides to the identification, prevention, and/or conferment of resistance, including resistance to various plant diseases and/or disorders, particularly drought resistance.

BACKGROUND OF THE INVENTION

Drought is one of the most limiting factors in plant growth and productivity. Crop and yield losses due to drought spells in crops such as soybeans, corn, rice and cotton represent a significant economic problem. Moreover, drought is also responsible for food shortages in many countries worldwide. Developing crops tolerant to drought is a strategy that has potential to alleviate some of these adverse situations.

Traditional plant breeding strategies to develop new lines of plants that exhibit tolerance to drought are relatively slow and require specific tolerant lines for crossing with the desired commercial lines. Limited germplasm resources for drought tolerance and incompatibility in crosses between distantly related plant species therefore represent significant problems encountered in conventional breeding. In contrast, plant genetic transformation and availability of useful genes subjected to specific expression patterns allow one to generate drought-tolerant plants using transgenic approaches.

Plants are exposed during their entire life cycle to conditions of reduced environmental water content. Most plants have evolved strategies to protect themselves against these conditions of desiccation. However, if the severity and duration of the drought conditions are extensive, the effects on plant development, growth and yield of most crop plants are profound.

The physiology of a drought-stressed plant is dramatically altered as compared with a plant grown under normal conditions. Most of the changes and their causes remain uncharacterized. Abscisic acid (ABA) plays a central role in mediating the processes between desiccation perception and cellular changes. ABA increases readily upon the onset of cell desiccation and exogenously applied ABA mimics many of the responses induced by water-stress. An increase in ABA causes the closure of stomata, thereby decreasing water loss through transpiration.

The identification of genes that transduce ABA into a cellular response opens the possibility of exploiting these regulators to enhance desiccation tolerance in crop species. In principle, these ABA signaling genes can be coupled with the appropriate controlling elements to allow optimal plant growth, development and productivity. Thus, not only would these genes allow the genetic tailoring of crops to withstand transitory environmental stresses, but they should also broaden the environments where traditional crops can be grown.

The regulation of protein phosphorylation by kinases and phosphatases is accepted as a universal mechanism of cellular control (Cohen 1992, Trends Biochem. Sci. 17: 408-413), and $Ca^{2+}$ and calmodulin signals are frequently transduced via $Ca^{2+}$ and calmodulin-dependent kinases and phosphatases (Roberts & Harmon 1992, Annu. Rev. Plant Physiol. Plant Mol. Biol. 43: 375-414). Okadaic acid, a protein phosphatase inhibitor, has been found to affect both gibberellic (GA) and absisic acid (ABA) pathways (Kuo et al. 1996, Plant Cell. 8: 259-269). Although the molecular basis of GA and ABA signal transduction remains poorly understood, it seems well established that the two phytohormones are involved in overall regulatory processes in seed development (e.g. Ritchie & Gilroy 1998, Plant Physiol. 116: 765-776; Arenas-Huertero et al. 2000, Genes Dev. 14: 2085-2096). Likewise, the plant hormones ethylene (e.g. Zhou et al. 1998, Proc. Natl. Acad. Sci. USA 95: 10294-10299; Beaudoin et al. 2000, Plant Cell 2000: 1103-1115) and auxin (e.g. Colon-Carmona et al. 2000, Plant Physiol. 124:1728-1738) are involved in controlling plant development as well.

Protein farnesylation, the addition of a C-terminal, 15-carbon chain to proteins and subsequent processing, has been identified as being crucial for the mediating role of ABA in the desiccation-signal transduction chain. In short, protein farnesylation is required for ABA-induced stomata closure, thus for control of water loss.

Protein farnesylation is a three-step enzymatic reaction as shown in FIG. 1. Potentially, each of these steps could represent a target for genetic manipulation of the prenylation process to generate a desired phenotype such as stress tolerance.

The drought-tolerant phenotype of the era1 *Arabidopsis* mutant is due to a null mutation in the β-subunit of the enzyme farnesyl transferase (FTase), the first enzyme in the protein farnesylation pathway. Farnesyl transferase is a heterodimeric enzyme that provides the specific addition of a farnesyl pyrophosphate moiety onto the substrate target sequence. The target sequence is defined as a sequence of four amino acids which are present at the carboxy terminus of the protein and is referred to as a CaaX motif in which the "C" is cysteine, "a" is any aliphatic amino acid and "X" is any amino acid. The α subunit is common with a second prenylation enzyme, geranylgeranyl transferase, that has a different β subunit and adds a geranylgeranyl isoprenyl pyrophosphate moiety to the target sequence.

In plants, prenylation has been linked to cell cycle control, meristem development, and phytohormone signal transduction, however, few details of the role of prenylation, the substrate proteins or the extent to which the plant system will be analogous to the mammalian and yeast systems are known. The most characterized substrates for CaaX modification are the Ras and a-factor proteins of yeast. Although there are three steps to complete protein maturation, abolition or modification of any one step does not necessarily result in cessation of target biological activities. Ras function is attenuated if the –aaX tripeptide is not cleaved but not abolished and some proteins retain the –aaX tripeptide after farnesylation.

In *Arabidopsis*, more than 600 proteins contain a CaaX motif, suggesting a role for the post-translational modification by prenylation in numerous cellular processes. In *Arabidopsis*, it has been demonstrated that the loss-of-function of the β-subunit of farnesyl transferase will result in an ABA-hypersensitive phenotype. Although it is still not clear why plants lacking the functional β-subunit of farnesyl transferase become more sensitive to ABA, it clearly suggests that protein prenylation is involved in regulation of the homeostasis of ABA sensitivity. The balance of ABA cellular responses, whether more sensitive or less sensitive to ABA, is possibly regulated by the relative activities of prenylated proteins. The changes in *Arabidopsis* prenyl protease expression and gene activity may affect the activity of two pools of genes, one pool acting as positive regulators (pool A) and the second pool (pool B) as negative regulators, which require prenylation in order to function properly. Pool A may contain genes that can promote ABA sensitivity, and pool B genes that may reduce ABA sensitivity. The homeostasis of ABA sensitivity may therefore be governed by the ratio of activity of pool A to pool B. For example, in the case of up-regulation of *Arabidopsis* prenyl protease in *Arabidopsis*, the activity ratio of pool A over pool B may be increased due to differences in substrate affinity of pool A proteins toward *Arabidopsis* prenyl protease, thus the homeostasis of ABA sensitivity is changed, and the *Arabidopsis* prenyl protease over-expression plants are more sensitive to ABA.

There is a need in the art to identify new plant genes encoding these protein farnesylation enzymes as another opportunity to generate plants tolerant to environmental stress, such as drought.

BRIEF SUMMARY OF THE INVENTION

The present invention provides novel polynucleotides encoding prenyl protease polypeptides or active fragments thereof from *Physcomitrella patens, Arabidopsis thaliana*, rapeseed (*Brassica napus*), soybeans (*Glycine max*), and corn (*Zea mays*).

The present invention fulfills a need in the art, in part, by providing the isolated polynucleotide and polypeptide sequences of plant-derived PrPases from five species, namely, the PrPase sequences from moss (*Physcomitrella patens*; PpPrPase1), three PrPase sequences from *Arabidopsis thaliana* (AtPrPase1, AtPrPase2, and AtCPP), two PrPase from soybeans (*Glycine max*; GmPrPase2 and GmCPP), one PrPase from corn (*Zea mays*; ZmPrPase2), and one from rapeseed (*Brassica napus*; BnCPP). The invention also provides partial PrPase sequences from soybean (GmPrPase1) and corn (ZmPrPase1).

In a first embodiment, an isolated or recombinant polynucleotide is provided which encodes a plant prenyl protease having the amino acid sequence of SEQ ID NO: 4 or a homolog of SEQ ID NO: 4 having prenyl protease activity and having at least 70% identity at the amino acid level to SEQ ID NO: 4, with the proviso that the polynucleotide as set forth in SEQ ID NO: 27 and the polynucleotide as set forth in SEQ ID NO: 29 are excluded.

In a further embodiment, the invention provides an isolated or recombinant polynucleotide wherein the polynucleotide comprises a nucleotide sequence selected from the group consisting of a polynucleotide as set forth in SEQ ID NO: 1, 3, 5, 7, 11, 14, 16, 18, 21, or 23; a polynucleotide encoding the polypeptide as set forth in SEQ ID NO: 2, 4, 6, 8, 12, 15, 17, 19, 22, or 24; a polynucleotide encoding a polypeptide having at least 95% identity at the amino acid level to SEQ ID NO: 2, 4, 6, 15, 17, 22, or 24; a polynucleotide encoding a polypeptide having at least 99% identity at the amino acid level to SEQ ID NO: 8; a polynucleotide encoding a polypeptide having at least 96% identity at the amino acid level to SEQ ID NO: 12; a polynucleotide encoding a polypeptide having at least 85% identity at the amino acid level to SEQ ID NO: 19; and a polynucleotide complementary to any of these sequences.

The nucleic acid can be, for example, a genomic DNA fragment, a cDNA molecule, or is naturally occurring. In one aspect, the invention provides a nucleic acid that includes the sequence of SEQ ID NO: 84, 86, 88 or 90. The invention also provides a nucleic acid sequence that is complementary to the nucleic acid sequence of SEQ ID NO: 7, SEQ ID NO: 11, or SEQ ID NO: 18, for example, SEQ ID NO: 9, 13, or 20.

A further embodiment is an isolated polypeptide molecule that comprises the sequence of SEQ ID NO: 85, 87, 89, or 91.

Further described are transformation vectors useful to transform plants, such as *Physcomitrella, Arabidopsis*, rapeseed, soybeans, and corn plants. Such vectors comprise one or more of the nucleic acid molecules described herein. The invention provides for plants and host cells transformed with a PrPase nucleic acid or a vector comprising a PrPase nucleic acid. For example, a vector may comprise at least one of the nucleic acid sequences of SEQ ID NO: 41, 42, or 52-69.

In further embodiments, the invention provides methods of using the polynucleotides and polypeptides of the invention to create transgenic plants with one or more desirable traits, which include, but are not limited to, enhanced plant defense, increased tolerance to stress, drought tolerance, salt tolerance, ultraviolet (uv) tolerance, enhanced flower development, delayed senescence, increased ABA sensitivity, terpene synthesis, increased formation of seed storage compounds (like oil, sugars and proteins), increased yield, increased productivity and increased biomass compared to a wild type plant, and the identification, prevention, and/or conferment of resistance to various plant diseases and/or disorders by introducing into one or more cells of a plant a compound that alters (e.g., increases or decreases) PrPase expression or activity in the plant. In one aspect, the compound is a PrPase nucleic acid or polypeptide. In one embodiment, the nucleic acid is an inhibitor of farnesylation. Alternatively, the compound is a PrPase double stranded RNA-inhibition hair-pin nucleic acid or PrPase antisense nucleic acid.

The present invention further provides a general method for engineering drought-tolerant plants, said method being generally applicable to all plants.

Moreover, the present invention provides the first results suggesting that modulation of PrPase gene expression in a plant directly correlates with increased drought tolerance as compared to untransformed control plants. The present invention also describes methods of engineering drought-tolerant rapeseed, soybeans, and corn plants strains generated through modulation of PrPase expression.

In a preferred embodiment, the invention provides a method of producing a transgenic plant comprising an isolated or recombinant nucleic acid encoding a prenyl protease wherein the plant has increased tolerance to an environmental stress as compared to a wild type variety of the plant, comprising transforming a plant cell with an expression vector comprising a polynucleotide sequence encoding a prenyl protease and generating from the plant cell the transgenic plant with increased tolerance to stress, wherein the polynucleotide encodes the amino acid sequence of SEQ ID NO: 4 or a homolog of SEQ ID NO: 4 having prenyl protease activity and having at least 70% identity at the amino acid level to SEQ ID NO: 4.

In another preferred embodiment, the transgenic plant produced by the above method has increased tolerance to an environmental stress selected from the group consisting of drought, high temperature, and low temperature.

Further provided is the promoter of the *Arabidopsis* USP gene. This promoter is expressed most strongly during seed developmental stages, i.e. it is a seed-specific promoter.

Further provided is the promoter of the *Arabidopsis* FTase gene. This promoter is expressed most strongly in guard-cells, i.e. it is a guard-cell specific promoter. In another aspect of this invention, the promoter of an *Arabidopsis* PrPase is described. This promoter is guard-cell specific and can be used to engineer traits such as drought tolerance and regulation of gas exchange in the plant.

Moreover, the present invention provides novel polynucleotides encoding plant PrPase polypeptides, including a substantially purified PrPase polypeptide, and fragments and homologs thereof. Also provided are vectors, host cells, and recombinant methods for producing said polypeptides.

The invention further provides a method for producing a PrPase polypeptide by providing a cell containing a PrPase nucleic acid, e.g., a vector that includes a PrPase nucleic acid, and culturing the cell under conditions sufficient to express the PrPase polypeptide encoded by the nucleic acid. The expressed PrPase polypeptide can then be recovered from the cell. Preferably, the cell produces little or no endogenous PrPase polypeptide. The cell can be, e.g., a prokaryotic cell or eukaryotic cell.

Another aspect of this invention provides yeast expression vectors used to produce large quantities of the *Arabidopsis* PrPase in yeast.

The invention also provides methods for more particularly refining the function of the polynucleotides and/or polypeptides of the present invention.

The invention is also directed to plants transformed with the polynucleotides of the invention, to seed and progeny thereof, and to methods of producing these transgenic plants.

BRIEF DESCRIPTION OF THE FIGURES/DRAWINGS

FIG. 1—Schematic representation of the protein farnesylation pathway. This figure identifies the known enzymes involved in the protein farnesylation pathway, in addition to their functional relationship. For illustration purposes, a prospective target protein is represented by a dotted line; while the solid line represents the 15-carbon atom chain added to the C-terminus of the target protein at the "CaaX" site. "C" is Cysteine, "a" is any aliphatic amino acid, and "X" is any amino acid. The 15-carbon chain is added to a conserved Cysteine (C) by the enzyme farnesyl transferase (Ftase). The last three amino acid residues (aaX) are cleaved by the enzyme prenyl protease (PrPase). Lastly, the modified Cysteine is methylated by a methylase to create the final active product of the protein farnesylation pathway.

FIG. 2 is a schematic representation of the vector constructs, A) pBI121-AtCPP, B) pBI121-antisense-AtCPP, and C) pBI121-HP-AtCPP.

FIG. 3—Comparison of the Exon/Intron structure of the computer-predicted ORF of the *Arabidopsis* PrPase from genomic sequence of GenBank Accession No. AF007269 (SEQ ID NO: 30; labeled as Predicted Ara PrPase; predicted from Genefinder (P. Green and L. Hillier, National Center for Biotechnology Information ("NCBI") website)) and experimentally demonstrated ORFs of the *Arabidopsis* PrPases (SEQ ID NO: 4 and 6; labeled as Ara PrPase1-2). The exons are numbered sequentially in both clones. Corresponding exons are placed below each other. The lines connecting the introns have no biological significance. Breaks were introduced in the sequences to make this figure.

FIG. 4A-N—Nucleic acid multiple sequence alignment (ClustalW algorithm, blosum scoring matrix, default parameters for ClustalW 1.82) of GmCPP (SEQ ID NO: 18), GmPrPase2 (SEQ ID NO: 16), AtCPP (SEQ ID NO: 7), AtPrPase1 (SEQ ID NO: 3), AtPrPase2 (SEQ ID NO: 5), BnCPP (SEQ ID NO: 11), ZmPrPase2 (SEQ ID NO: 23), PpPrPase1 (SEQ ID NO: 1), and three other disclosed *Arabidopsis* PrPases sequences: AT4g01320 (SEQ ID NO: 27; GenBank Accession NO: AL161491), AF007269 (SEQ ID NO: 29), and AFC1 (SEQ ID NO: 25; GenBank Accession NO: AF353722). The consensus sequence (bottom line) is shown in SEQ ID NO: 84.

FIG. 5A-C—Amino acid multiple sequence alignment (ClustalW algorithm, blosum scoring matrix, using default parameters) of GmCPP (SEQ ID NO: 19), GmPrPase2 (SEQ ID NO: 17), AtCPP (SEQ ID NO: 8), AtPrPase1 (SEQ ID NO: 4), AtPrPase2 (SEQ ID NO: 6), BnCPP (SEQ ID NO: 12), ZmPrPase2 (SEQ ID NO: 24), PpPrPase1 (SEQ ID NO: 2), three other disclosed *Arabidopsis* PrPases sequences: AT4g01320 (SEQ ID NO: 28; GenBank Accession NO: AL161491), AF007269 (SEQ ID NO: 30), and AFC1 (SEQ ID NO: 26; GenBank Accession NO: AF353722), and the sequence of the *Saccharomyces cerevisiae* PrPase (Swiss-Prot Accession No. P47154; SEQ ID NO: 31). The boxed area is the zinc metalloprotease motif (HEXXH). The consensus sequence (bottom line) is shown in SEQ ID NO: 85.

FIG. 6 is a comparison of nucleic acid sequence identities between the sequences of the invention (SEQ ID NOs: 1, 3, 5, 7, 11, 16, 18, 23), and three other disclosed *Arabidopsis* PrPases sequences (GenBank Accession NOs: AL161491 (AT4g01320; SEQ ID NO: 27), AF007269 (SEQ ID NO: 29), and AF353722 (AFC1; SEQ ID NO: 25)) as determined by EMBOSS Pairwise Alignment algorithms (Parameters: Blosum 62 matrix, 10.0 gap penalty, 0.1 extend penalty). FIG. 6A shows the comparison using the full-length sequences (including the 5'- and 3'-end non-coding sequences). FIG. 6B shows the comparison using the coding region of the sequences (excluding the 5'- and 3'-end non-coding sequences).

FIG. 7—Amino acid sequence comparison as determined by EMBOSS Pairwise Alignment algorithms (Parameters: Blosum 62 matrix, 10.0 gap penalty, 0.1 extend penalty) of the PrPase polypeptides of the present invention (SEQ ID NOS: 2, 4, 6, 8, 12, 17, 19, 24), other disclosed *Arabidopsis* PrPases sequences (GenBank Accession NOs: AL161491 (AT4g01320; SEQ ID NO: 28), AF007269 (SEQ ID NO: 30), and AF353722 (AFC1; SEQ ID NO: 26)), and sequence of the *Saccharomyces cerevisiae* PrPase (Swiss-Prot Accession No. P47154; SEQ ID NO: 31). The percent identity is shown with the percent similarity values in parenthesis.

FIG. 8 is an illustration showing the relative expression of AtCPP mRNA transcript (solid bars) and AtCPP protein levels (stippled bars) in several pBI121-AtCPP transgenic lines.

FIG. 9 is a histogram showing the percentage of lines which were categorized as ABA sensitive, moderately ABA sensitive or ABA insensitive. Seedlings were assessed on agar plates containing 1 µM ABA and scored at 21 days growth. Thirty-six lines of the pBI121-AtCPP over-expression construct were assessed at 21 days by leaf and seedling development. Thirty-two lines of the 35S-HP-AtCPP down-regulation construct were assessed at 21 days for leaf and seedling development. Each line was assessed by plating approximately 100 seeds per plate and the seedlings scored and recorded as the percent insensitive seedlings per plate. Each line was then expressed as a percent of wild type (Wt). Lines were categorized as sensitive (less than 1% of Wt) solid bars, intermediate (1-50% of Wt) diagonally lined or insensitive (greater than 50% of Wt) stippled, based on their relationship to Wt and the percentage of each category plotted as a histogram.

FIG. 10 is a photograph showing the response of wild type and a pRD29A-HP-AtCPP transgenic line to various concentrations of ABA in two week old seedlings.

FIG. 11 is a histogram showing the analysis of transgenic plants containing the pBI121-AtCPP over-expression construct (SEQ ID NO: 41). Water loss is shown per gram of shoot dry weight after four days of water stress treatment. Lines that are marked with a star are those which were strongly ABA sensitive. Lines marked with a triangle are moderately ABA sensitive. Bars represent means of eight replicates. Lines marked with a filled dot above the bar represents lines which were significantly different from control at a p=0.05 value.

Figure 1:
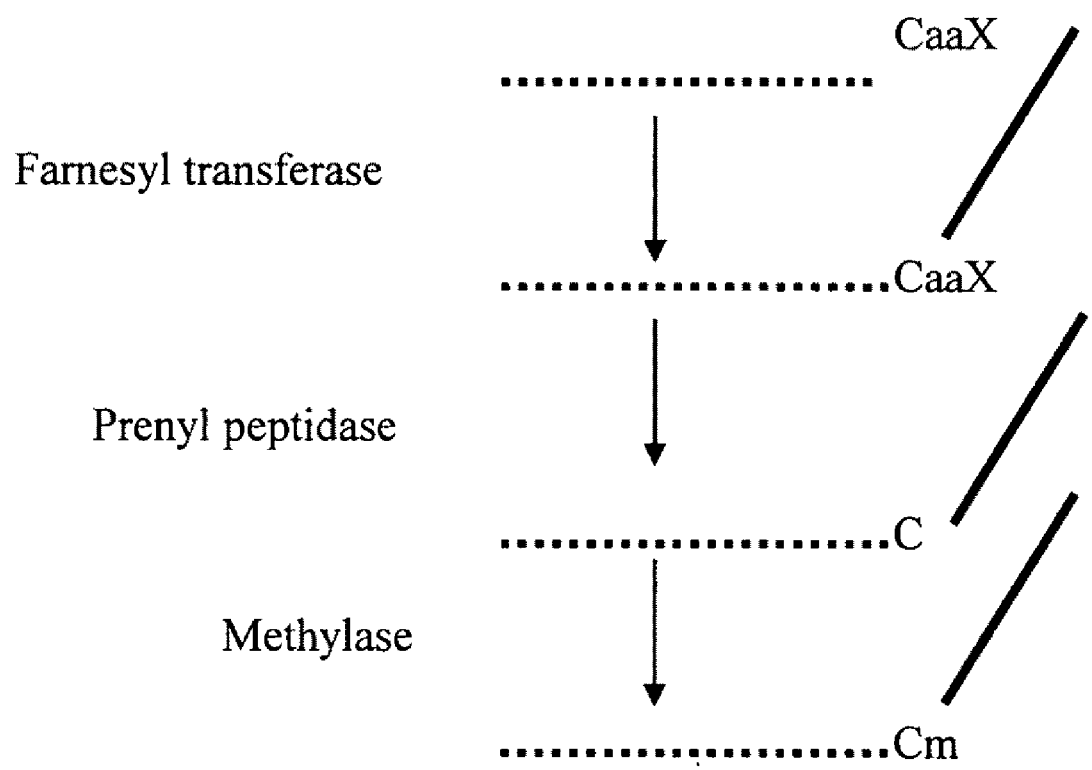

FIG. 16A-K—Nucleic acid multiple sequence alignment (ClustalW algorithm, blosum scoring matrix, using default parameters) of the PrPase sequences of the invention from dicot plants: GmCPP (SEQ ID NO: 18), GmPrPase2 (SEQ ID NO: 16), AtCPP (SEQ ID NO: 7), AtPrPase1 (SEQ ID NO: 3), AtPrPase2 (SEQ ID NO: 5), BnCPP (SEQ ID NO: 11); and three other disclosed dicot PrPases sequences: GenBank Accession NOs: AL161491 (AT4g01320; SEQ ID NO: 27), AF007269 (SEQ ID NO: 29), and AF353722 (AFC1; SEQ ID NO: 25). The consensus sequence (bottom line) is shown in SEQ ID NO: 86.

FIG. 17A-B—Amino acid multiple sequence alignment (ClustalW algorithm, blosum scoring matrix, using default parameters) of the PrPase sequences of the invention from dicot plants: GmCPP (SEQ ID NO: 19), GmPrPase2 (SEQ ID NO: 17), AtCPP (SEQ ID NO: 8), AtPrPase1 (SEQ ID NO: 4), AtPrPase2 (SEQ ID NO: 6), BnCPP (SEQ ID NO: 12); and three other disclosed dicot PrPases sequences: GenBank Accession NOs: AL161491 (AT4g01320; SEQ ID NO: 28), AF007269 (SEQ ID NO: 30), and AF353722 (AFC1; SEQ ID NO: 26). The consensus sequence (bottom line) is shown in SEQ ID NO: 87.

FIG. 18A-H—Nucleic acid multiple sequence alignment (ClustalW algorithm, blosum scoring matrix, using default parameters) of the *Arabidopsis* PrPase sequences of the invention: AtCPP (SEQ ID NO: 7), AtPrPase1 (SEQ ID NO: 3), AtPrPase2 (SEQ ID NO: 5); and three other disclosed *Arabidopsis* PrPases sequences: GenBank Accession NOs: AL161491 (AT4g01320; SEQ ID NO: 27), AF007269 (SEQ ID NO: 29), and AF353722 (AFC1; SEQ ID NO: 25). The consensus sequence (bottom line) is shown as SEQ ID NO: 88.

FIG. 19A-B—Amino acid multiple sequence alignment (ClustalW algorithm, blosum scoring matrix, using default parameters) of the *Arabidopsis* PrPase sequences of the invention: AtCPP (SEQ ID NO: 8), AtPrPase1 (SEQ ID NO: 4), AtPrPase2 (SEQ ID NO: 6); and other disclosed *Arabidopsis* PrPases sequences: GenBank Accession NOs: AL161491 (AT4g01320; SEQ ID NO: 28), AF007269 (SEQ ID NO: 30), and AF353722 (AFC1; SEQ ID NO: 26). The consensus sequence (bottom line) is shown in SEQ ID NO: 89.

FIG. 20A-B—Nucleic acid multiple sequence alignment (ClustalW algorithm, blosum scoring matrix, using default parameters) of the soybean PrPase sequences of the invention: GmCPP (SEQ ID NO: 18) and GmPrPase2 (SEQ ID NO: 16). The consensus sequence (bottom line) is shown in SEQ ID NO: 90.

FIG. 21—Amino acid multiple sequence alignment (ClustalW algorithm, blosum scoring matrix, using default parameters) of the soybean PrPase sequences of the invention: GmCPP (SEQ ID NO: 19) and GmPrPase2 (SEQ ID NO: 17). The consensus sequence (bottom line) is shown in SEQ ID NO: 91.

DETAILED DESCRIPTION OF THE INVENTION

The present invention may be understood more readily by reference to the following detailed description of the preferred embodiments of the invention and the Examples included herein.

One aspect of this invention pertains to isolated nucleic acid molecules that encode PrPase polypeptides from *Physcomitrella patens, Arabidopsis thaliana*, soybeans, rapeseed, and corn. Moreover, this invention pertains to nucleic acid fragments originated from the clones mentioned above, as well as to other nucleic acid fragments from other organisms that can be isolated using the described nucleic acid fragments as probes in hybridization experiments.

As explained above, introduction of a PrPase into plants can improve tolerance to environmental stress. This invention also describes modulation of PrPase gene activity in a plant. The only condition necessary to realize either of these embodiments is the isolation of the corresponding PrPase genes from the target plants. The use of the described clones to isolate corresponding PrPase genes from other plants is something appreciated by someone skilled in the art.

Modulation of PrPase gene activity can be accomplished by reduction in PrPase, for example by: (a) antisense gene-expression repression, (b) targeted antibodies to PrPase, and (c) targeted, engineered promoter repression with for example zinc-finger derived transcription factors.

The present invention can make a significant contribution to the art by providing new strategies to engineer drought-tolerance in crop plants, especially the use of the previously unknown PrPase clones from plant origin. The polynucleotides and polypeptides of the present invention have uses which include conferring resistance to or modulating susceptibility to biotic and/or abiotic stresses such as heat, drought, and salt stress in plants.

In one embodiment, over-expression of a PrPase polypeptide of the present invention within a plant using a constitutive promoter (e.g., 35S, or other promoters disclosed herein), preferably not in the guard-cell, improves drought and salt tolerance in a plant.

In another embodiment, overexpression of a PrPase polypeptide of the present invention within a plant using a seed-specific promoter (e.g., unknown seed protein, USP, promoter) increases the amount of seed storage compounds.

Constitutive over-expression in plants of the farnesylation pathway, namely of a prenyl protease, may result in increased cell proliferation and increased plant growth. The polynucleotides and polypeptides of the present invention, including fragments thereof, have uses that include modulating plant growth, and potentially plant yield, preferably increasing plant growth.

The polynucleotides can also be used to express recombinant proteins for analysis, characterization and agronomic use, to express recombinant proteins to raise antibodies directed against polypeptides of the present invention, as markers for tissues in which the corresponding protein is expressed (e.g., preferentially, or non-preferentially), as hybridization markers on Southern gels, as genetic markers for breeding assistance, as RFLP markers, as markers for genotyping (varieties, etc), and the encoded protein, can, at the very least, be used as a molecular weight marker.

The polynucleotides of the present invention are also useful as chromosome markers or tags (when labeled) to identify chromosomes, to map related gene positions within a chromosome, or as a comparative reference to endogenous DNA sequences of mutant plants to identify allelic variants, and/or spontaneous or biotic mutations.

The polynucleotides of the present invention are also useful for genetic fingerprinting, for selecting and making oligomers for attachment to a "gene chip" or other support, including for examination of expression patterns for particular genes, to differentiate intron and/or exon boundaries, to identify splice and/or allelic variants, and as diagnostic tools for identification of developmental stages, disease states, and/or nutrient levels.

The present invention encompasses polynucleotides that hybridize to the polynucleotides of the present invention under either stringent or non-stringent conditions and their uses as described herein. Such hybridization may be used to identify orthologs, homologs, allelic variants, variants, and/or mutants of the polynucleotides of the present invention. Additionally, the polynucleotides of the present invention may be used to clone orthologs, homologs, alleleic variants, variants, and/or mutants of the polynucleotides of the present by using oligonucleotides directed to polynucleotide sequences of the present invention, and performing PCR on plant cell or tissue samples.

The present invention encompasses the identification of proteins, nucleic acids, or other molecules, that bind to polypeptides and polynucleotides of the present invention (for example, in a receptor-ligand interaction). The polynucleotides of the present invention can also be used in interaction trap assays (such as, for example, that described by Ozenberger and Young (Mol. Endocrinol., 9(10):1321-9, (1995); and Ann. NY Acad. Sci., 7; 766:279-81, (1995)).

Potential uses of polynucleotides and polypeptides of the present invention include nutrition (e.g., as an amino acid supplement), as a carbon source, as nitrogen source, as a carbohydrate source, modulating plant defense activity, modulating signal transduction, modulating metabolite transport (e.g., carbon, nitrogen fluxes, etc.), conferring abiotic stress tolerance and/or resistance (water, drought, cold, salt, etc.), conferring xenobiotic stress tolerance and/or resistance, and development control (for example, yield, flowering time, etc.).

The polynucleotide and polypeptides of the present invention are useful as probes for the identification and isolation of full-length cDNAs and/or genomic DNA which correspond to the polynucleotides of the present invention, as probes to hybridize and discover novel, related DNA sequences, as probes for positional cloning of these or related sequences, as probes to "subtract-out" known sequences in the process of discovering other novel polynucleotides, as probes to quantify gene expression, and as probes for microarrays.

In addition, polynucleotides and polypeptides of the present invention may comprise one, two, three, four, five, six, seven, eight, or more membrane domains.

Also, in preferred embodiments the present invention provides methods for further refining the biological function of the polynucleotides and/or polypeptides of the present invention.

Specifically, the invention provides methods for using the polynucleotides and polypeptides of the invention to identify orthologs, homologs, variants, and/or allelic variants of the invention. Also provided are methods of using the polynucleotides and polypeptides of the invention to identify the entire coding region of the molecules of the invention, non-coding regions of the molecules of the invention, regulatory sequences associated with the molecules of the invention, and secreted, mature, pro-, prepro- and other forms of the molecules of the invention.

In further preferred embodiments, methods are provided for evolving the polynucleotides and polypeptides of the present invention using molecular evolution to create and identify novel variants with desired structural, functional, and/or physical characteristics.

The present invention in further preferred embodiments provides for other experimental methods and procedures currently available to derive functional assignments. These procedures include but are not limited to spotting of clones on arrays, micro-array technology, PCR based methods and other procedures that could use sequence information from our clones to build a primer or a hybrid partner.

As used herein, the term "environmental stress" refers to any sub-optimal growing condition and includes, but is not limited to, sub-optimal conditions associated with salinity, drought, temperature, metal, chemical, pathogenic and oxidative stresses, or combinations thereof. In preferred embodiments, the environmental stress can be salinity, drought, or temperature, or combinations thereof, and in particular, can be high salinity, low water content or low temperature. It is also to be understood that as used in the specification and in the claims, "a" or "an" can mean one or more, depending upon the context in which it is used. Thus, for example, reference to "a cell" can mean that at least one cell can be utilized.

As also used herein, the term "nucleic acid" and "polynucleotide" refer to RNA or DNA that is linear or branched, single or double stranded, or a hybrid thereof. The term also encompasses RNA/DNA hybrids. The term "nucleic acid molecule" is intended to also include DNA molecules (e.g., cDNA or genomic DNA), RNA molecules (e.g., mRNA), analogs of the DNA or RNA generated using nucleotide analogs, and derivatives, fragments and homologs thereof. These terms also encompass untranslated sequences located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine and others can also be used for antisense, dsRNA and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR and in vitro or in vivo transcription.

An "isolated" nucleic acid molecule is one that is substantially separated from other nucleic acid molecules which are present in the natural source of the nucleic acid (e.g., sequences encoding other polypeptides). Preferably, an "isolated" nucleic acid is free of some of the sequences which naturally flank the nucleic acid (i.e., sequences located at the 5' and 3' ends of the nucleic acid) in its naturally occurring replicon. For example, a cloned nucleic acid is considered isolated. In various embodiments, the isolated nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. In further embodiments, the isolated PrPase nucleic acid molecule can contain less than about 5 mb, 1 mb, 0.5 mb, 0.1 mb, 50 kb, 25 kb, 20 kb, 10 kb, 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. A nucleic acid is also considered isolated if it has been altered by human intervention, or placed in a locus or location that is not its natural site, or if it is introduced into a cell by agroinfection or other means of transformation. Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

Specifically excluded from the definition of "isolated nucleic acids" are: naturally-occurring chromosomes (such as chromosome spreads), artificial chromosome libraries, genomic libraries, and cDNA libraries that exist either as an in vitro nucleic acid preparation or as a transfected/transformed host cell preparation, wherein the host cells are either an in vitro heterogeneous preparation or plated as a heterogeneous population of single colonies. Also specifically excluded are the above libraries wherein a specified nucleic acid makes up less than 5% of the number of nucleic acid inserts in the vector molecules. Further specifically excluded are whole cell genomic DNA or whole cell RNA preparations (including whole cell preparations that are mechanically sheared or enzymatically digested). Even further specifically excluded are the whole cell preparations found as either an in vitro preparation or as a heterogeneous mixture separated by electrophoresis wherein the nucleic acid of the invention has not further been separated from the heterologous nucleic acids in the electrophoresis medium (e.g., further separating by excising a single band from a heterogeneous band population in an agarose gel or nylon blot).

One aspect of the invention pertains to isolated PrPase proteins, and biologically active portions thereof, or derivatives, fragments, analogs or homologs thereof. In one embodiment, native PrPase proteins can be isolated from cells or tissue sources by an appropriate purification scheme using standard protein purification techniques. In another embodiment, PrPase proteins are produced by recombinant DNA techniques. Alternative to recombinant expression, a PrPase protein or polypeptide can be synthesized chemically using standard peptide synthesis techniques.

An "isolated" or "purified" protein or biologically active portion thereof is substantially free of cellular material or other contaminating proteins from the cell or tissue source from which the PrPase protein is derived, or substantially free from chemical precursors or other chemicals when chemically synthesized. The language "substantially free of cellular material" includes preparations of PrPase protein in which the protein is separated from cellular components of the cells from which it is isolated or recombinantly produced. In one embodiment, the language "substantially free of cellular material" includes preparations of PrPase protein having less than about 30% (by dry weight) of non-PrPase protein (also referred to herein as a "contaminating protein"), more preferably less than about 20% of non-PrPase protein, still more preferably less than about 10% of non-PrPase protein, and most preferably less than about 5% non-PrPase protein. When the PrPase protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of PrPase protein in which the protein is separated from chemical precursors or other chemicals that are involved in the synthesis of the protein. In one embodiment, the language "substantially free of chemical precursors or other chemicals" includes preparations of PrPase protein having less than about 30% (by dry weight) of chemical precursors or non-PrPase chemicals, more preferably less than about 20% chemical precursors or non-PrPase chemicals, still more preferably less than about 10% chemical precursors or non-PrPase chemicals, and most preferably less than about 5% chemical precursors or non-PrPase chemicals.

Polynucleotides and Polypeptides of the Invention

The present invention provides novel polynucleotide and polypeptide sequences of plant-derived prenyl protease (PrPase) from five species namely, the nucleic acid PrPase sequences and the encoded polypeptides from the moss *Physcomitrella patens* (PpPrPase1, SEQ ID NOS: 1, 2), three from *Arabidopsis thaliana* (AtPrPase1, SEQ ID NOS: 3, 4; AtPrPase2, SEQ ID NOS: 5, 6; and AtCPP, SEQ ID NOS: 7, 8), two from soybeans *Glycine max* (GmPrPase2, SEQ ID NOS: 16, 17; and GmCPP, SEQ ID NOS: 18, 19), one from corn *Zea mays* (ZmPrPase2, SEQ ID NOS: 23, 24), and one from rapeseed *Brassica napus* (BnCPP, SEQ ID NOS: 11, 12). The invention also provides partial PrPase sequences from soybean (GmPrPase1, SEQ ID NOS: 14, 15) and corn (ZmPrPase1, SEQ ID NOS: 21, 22).

The sequences are collectively referred to as "PrPase nucleic acids", "PrPase polynucleotides" or "PrPase antisense nucleic acids" and the corresponding encoded polypeptide is referred to as a "PrPase polypeptide" or "PrPase protein". Unless indicated otherwise, "PrPase" is meant to refer to any of the novel sequences disclosed herein.

The prenyl proteases of the invention have recognizable homology at the nucleotide and amino acid level to both human and yeast prenyl proteases. Additionally, in a BLAST search of public sequence databases, it was found, for example, that the AtCPP nucleic acid sequence has 99.3% identity to an *Arabidopsis thaliana* CaaX processing zinc-metallo endoprotease (AFC1) mRNA (Genbank Accession No.: AF353722). FIG. 6A. The full amino acid sequence of the AtCPP protein of the invention was found to be 98.8% identical to *Arabidopsis thaliana* CaaX processing zinc-metallo endoprotease (AFC1) polypeptide (Genbank Accession No.: AAK39514). FIG. 7. A multiple alignment of the eight polypeptides of the invention (SEQ ID NO: 2, 4, 6, 8, 12, 17, 19, and 24), of yeast, and of three other published *Arabidopsis* PrPases is illustrated in FIG. 5 with the consensus sequence shown in SEQ ID NO: 85. Similarly, a multiple alignment of the polynucleotides of the invention (SEQ ID NO: 1, 3, 5, 7, 11, 16, 18, and 23) and of three other published *Arabidopsis* PrPase sequences is illustrated in FIG. 4 with the consensus sequence shown in SEQ ID NO: 84.

The percent identity between the various sequences of FIGS. 4 and 5 are tabulated in FIGS. 6 and 7. A multiple alignment of the PrPase sequences for dicot plants of the invention and three published PrPase are provided in FIGS. 16 and 17 with the consensus sequences shown in SEQ ID NOs: 86-87. A multiple alignment of the PrPase sequences for *Arabidopsis* are provided in FIGS. 18 and 19 with the consensus sequences shown in SEQ ID NOs: 88-89. A multiple alignment of the PrPase sequences of the invention for soybean plants are provided in FIGS. 20 and 21 with the consensus sequences shown in SEQ ID NOs: 90-91.

Figure 3:
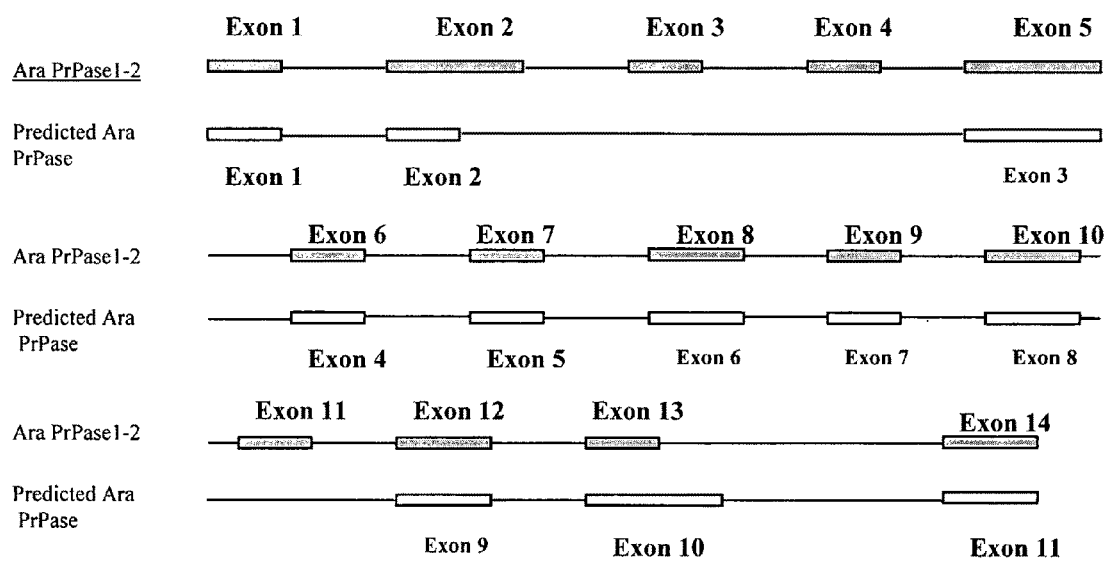

The previously described genomic sequence encoding the *Arabidopsis* PrPase (GenBank accession number AF007269, gene="A_IG002N01.21) was predicted by the computer program (Genefinder (P. Green and L. Hillier, National Center for Biotechnology Information (NCBI) website)) to contain an ORF at positions 24979 to 28076. That predicted ORF does not reflect the real ORF for this gene as shown in FIG. 3.

Based on their structural and functional relatedness to known CaaX prenyl protease proteins, the PrPase proteins of the invention are novel members of the CaaX prenyl protease family of proteins. PrPase nucleic acids, and their encoded polypeptides, according to the invention are useful in a variety of applications and contexts. For example, the nucleic acids (i.e., sense or antisense PrPase nucleic acids) can be used to produce transgenic plants that have an increased resistance to biotic and abiotic stresses, e.g., chilling stress, salt stress, water stress (e.g., drought), wound healing, pathogen challenge, grazing pests, or herbicides. Additionally, the transgenic plants have an increased productivity during both optimal and suboptimal growth conditions, increased yield, increased biomass, or delayed senescence. Alternatively, the transgenic plants have an increased sensitivity to the phytohormone abscisic acid (ABA). By resistant is meant the plant grows under stress conditions (e.g., high salt, decreased water, low temperatures) or under conditions that normally inhibit, to some degree, the growth of an untransformed plant.

Although it is believed the encoded polypeptides may share at least some biological activities with prenyl proteases, a number of methods of determining the exact biological function of these clones are either known in the art or are described elsewhere herein. Briefly, the function of these clones may be determined, for example, by applying microarray methodology. The clones of the present invention may be arrayed on microchips for expression profiling. Depending on which polynucleotide probe is used to hybridize to the slides, a change in expression of a specific gene may provide additional insight into the function of this gene based upon the conditions being studied. For example, an observed increase or decrease in expression levels when the polynucleotide probe used comes from tissue that has been cold treated might indicate a function in modulating cold tolerance. Tissue deprived of water or stressed by other biotic or abiotic stresses (heat, drought, high light, high salt, etc.) should be used to extract RNA to prepare the probe. Moreover, different stages of seed development (early, middle, late) could be used to extract RNA to prepare the probe.

In addition, the function of the proteins may be assessed by applying quantitative PCR methodology, for example. Real time quantitative PCR would provide the capability of following the expression of specific genes throughout the plant development cycle, for example. Quantitative PCR methodology requires only a nominal amount of tissue from each developmentally important step (3 days germinated seedlings; 1 week old seedlings and their roots, shoots, and stems; roots, leaves and stems before the onset of flowering, flowers and their different parts; and/or developing embryos) is usually used to perform such experiments. Therefore, the application of quantitative PCR methodology to refining the biological function of these polypeptides is encompassed by the present invention. Also encompassed by the present invention are PCR probes corresponding to the polynucleotide sequences provided or portions thereof.

The function of the proteins may also be assessed through complementation assays in yeast. For example, transforming yeast deficient in prenyl protease activity and assessing their ability to grow would provide convincing evidence that the clones of the invention have prenyl protease activity. Additional assay conditions and methods that may be used in assessing the function of the polynucleotides and polypeptides of the present invention are known in the art.

Alternatively, the biological function of the encoded polypeptides may be determined by disrupting a homologue of the polypeptides in *Synechosystis*. Cyanobacteria (blue-green algae) is considered a precursor to the plant chloroplast. It possesses both photosynthetic systems and many other metabolic processes similar to those of plants. These processes are often targets for many commercial herbicides, and this organism has been widely used in the study of the mode of action of many classes of herbicides. *Synechocystis* is one of the best-studied cyanobacteria. In addition to most of the features common to cyanobacteria, it offers many other advantages. *Synechocystis* has a naturally occurring genetic transformation system, thus entailing vigorous and sophisticated genetic and molecular manipulation (e.g. targeted-gene disruption, gene replacement, etc.) applicable to some of the well-characterized systems (*S. cerevisiae, E. coli*). Most importantly, the availability of the complete genomic sequence information of the *Synechocystis* affords an avenue for the rapid identification and cloning of gene(s) of interest, and elucidation of gene function through genetic and molecular means.

Moreover, the biological function of polypeptides may be determined by the application of antisense and/or sense methodology and the resulting generation of transgenic plants. Expressing a particular gene in either sense or antisense orientation in a transgenic plant can lead to respectively higher or lower expression levels of that particular gene. Altering the endogenous expression levels of a gene can lead to the observation of a particular phenotype that can then be used to derive indications on the function of the gene. The gene can be either over-expressed or under expressed in every cell of the plant at all times using a strong ubiquitous promoter, or it can be expressed in one or more discrete parts of the plant using a well characterized tissue-specific promoter (i.e., a root promoter or a flower specific promoter or a seed-specific promoter), or it can be expressed at a specified time of development using an inducible and/or a developmentally regulated promoter.

In the case of the transgenic plants of the invention, if no phenotype is apparent in normal growth conditions, observing the plants under stress conditions (deprivation of water, presence of high salt, or other biotic or abiotic stresses, such as cold, heat, drought, high light, etc.) may lead to understanding the function of the genes. Therefore, the application of antisense and/or sense methodology to the creation of transgenic plants to refine the biological function of the polypeptides is encompassed by the present invention.

Many polynucleotide sequences, such as EST sequences, are publicly available and accessible through sequence databases. Some of these sequences are related to the sequences of the invention and may have been publicly available prior to conception of the present invention. Such related polynucleotides are specifically excluded from the scope of the present invention.

PpPrPase1

The polynucleotide sequence of the partial PrPase from *Physcomitrella patens* (Clone ID No: PpPrPase1) of the present invention is provided as SEQ ID NO: 1. The polynucleotide sequence contains a sequence of 1398 nucleotides. The deduced amino acid sequence of SEQ ID NO: 1 is provided as SEQ ID NO: 2 and contains 394 amino acids.

In further embodiments, deletion mutants of PpPrPase1 are encompassed by the present invention, the following N-terminal deletion mutants: L1-D394, K2-D394, L3-D394, S4-D394, N5-D394, L6-D394, P7-D394, A8-D394, P9-D394, L10-D394, K11-D394, G12-D394, I13-D394, V14-D394, S15-D394, Q16-D394, E17-D394, K18-D394, F19-D394, E20-D394, K21-D394, A22-D394, Q23-D394, A24-D394, Y25-D394, S26-D394, L27-D394, D28-D394, K29-D394, S30-D394, R31-D394, F32-D394, H33-D394, F34-D394, V35-D394, H36-D394, A37-D394, A38-D394, V39-D394, N40-D394, I41-D394, V42-D394, E43-D394, E44-D394, S45-D394, A46-D394, I47-D394, L48-D394, L49-D394, L50-D394, G51-D394, L52-D394, L53-D394, P54-D394, W55-D394, A56-D394, W57-D394, D58-D394, K59-D394, S60-D394, G61-D394, S62-D394, L63-D394, V64-D394, G65-D394, K66-D394, L67-D394, G68-D394, F69-D394, D70-D394, E71-D394, K72-D394, S73-D394, E74-D394, I75-D394, L76-D394, Q77-D394, T78-D394, L79-D394, S80-D394, F81-D394, L82-D394, A83-D394, V84-D394, T85-D394, T86-D394, L87-D394, W88-D394, S89-D394, Q90-D394, I91-D394, L92-D394, E93-D394, L94-D394, P95-D394, F96-D394, S97-D394, L98-D394, Y99-D394, S100-D394, T101-D394, F102-D394, V103-D394, I104-D394, E105-D394, A106-D394, R107-D394, H108-D394, G109-D394, F110-D394, N111-D394, K112-D394, Q113-D394, T114-D394, I115-D394, W116-D394, L117-D394, F118-D394, L119-D394, R120-D394, D121-D394, M122-D394, I123-D394, M124-D394, G125-D394, L126-D394, A127-D394, L128-D394, M129-D394, M130-D394, V131-D394, V132-D394, G133-D394, P134-D394, P135-D394, I136-D394, V137-D394, S138-D394, A139-D394, I140-D394, I141-D394, Y142-D394, I143-D394, V144-D394, Q145-D394, N146-D394, G147-D394, G148-D394, P149-D394, Y150-D394, L151-D394, A152-D394, L153-D394, Y154-D394, L155-D394, W156-D394, A157-D394, F158-D394, M159-D394, L160-D394, L161-D394, L162-D394, S163-D394, L164-D394, V165-D394, L166-D394, M167-D394, A168-D394, L169-D394, Y170-D394, P171-D394, V172-D394, L173-D394, I174-D394, A175-D394, P176-D394, L177-D394, F178-D394, N179-D394, T180-D394, F181-D394, T182-D394, P183-D394, L184-D394, P185-D394, E186-D394, G187-D394, Q188-D394, L189-D394, R190-D394, A191-D394, K192-D394, I193-D394, E194-D394, K195-D394, L196-D394, A197-D394, S198-D394, S199-D394, L200-D394, D201-D394, F202-D394, P203-D394, L204-D394, K205-D394, K206-D394, L207-D394, F208-D394, V209-D394, I210-D394, D211-D394, G212-D394, S213-D394, T214-D394, R215-D394, S216-D394, S217-D394, H218-D394, S219-D394, N220-D394, A221-D394, Y222-D394, M223-D394, Y224-D394, G225-D394, F226-D394, Y227-D394, N228-D394, S229-D394, K230-D394, R231-D394, I232-D394, V233-D394, L234-D394, Y235-D394, D236-D394, T237-D394, L238-D394, I239-D394, S240-D394, Q241-D394, C242-D394, K243-D394, N244-D394, E245-D394, E246-D394, E247-D394, V248-D394, V249-D394, A250-D394, V251-D394, I252-D394, A253-D394, H254-D394, E255-D394, L256-D394, G257-D394, H258-D394, W259-D394, K260-D394, L261-D394, S262-D394, H263-D394, T264-D394, M265-D394, Y266-D394, S267-D394, F268-D394, L269-D394, A270-D394, M271-D394, Q272-D394, V273-D394, L274-D394, T275-D394, L276-D394, L277-D394, Q278-D394, F279-D394, G280-D394, G281-D394, Y282-D394, T283-D394, L284-D394, V285-D394, R286-D394, N287-D394, S288-D394, S289-D394, G290-D394, L291-D394, F292-D394, L293-D394, S294-D394, F295-D394, G296-D394, F297-D394, S298-D394, T299-D394, Q300-D394, P301-D394, V302-D394, L303-D394, I304-D394, G305-D394, L306-D394, I307-D394, L308-D394, F309-D394, Q310-D394, H311-D394, T312-D394, I313-D394, M314-D394, P315-D394, F316-D394, H317-D394, H318-D394, L319-D394, V320-D394, S321-D394, F322-D394, A323-D394, L324-D394, N325-D394, L326-D394, L327-D394, S328-D394, R329-D394, A330-D394, F331-D394, E332-D394, F333-D394, Q334-D394, A335-D394, D336-D394, A337-D394, F338-D394, A339-D394, R340-D394, S341-D394, L342-D394, G343-D394, Y344-D394, R345-D394, E346-D394, P347-D394, L348-D394, R349-D394, A350-D394, G351-D394, L352-D394, I353-D394, K354-D394, L355-D394, Q356-D394, E357-D394, E358-D394, N359-D394, L360-D394, S361-D394, A362-D394, M363-D394, N364-D394, T365-D394, D366-D394, P367-D394, W368-D394, Y369-D394, S370-D394, A371-D394, Y372-D394, H373-D394, H374-D394, S375-D394, H376-D394, P377-D394, P378-D394, L379-D394, V380-D394, E381-D394, R382-D394, L383-D394, Q384-D394, A385-D394, L386-D394, D387-D394, E388-D394, of SEQ ID NO: 2. The invention includes the polynucleotide sequences encoding these mutant polypeptides.

In further embodiments, deletion mutants of PpPrPase1 are encompassed by the present invention, including the following C-terminal deletion mutants: L1-D394, L1-T393, L1-K392, L1-K391, L1-S390, L1-T389, L1-E388, L1-D387, L1-L386, L1-A385, L1-Q384, L1-L383, L1-R382, L1-E381, L1-V380, L1-L379, L1-P378, L1-P377, L1-H376, L1-S375, L1-H374, L1-H373, L1-Y372, L1-A371, L1-S370, L1-Y369, L1-W368, L1-P367, L1-D366, L1-T365, L1-N364, L1-M363, L1-A362, L1-S361, L1-L360, L1-N359, L1-E358, L1-E357, L1-Q356, L1-L355, L1-K354, L1-I353, L1-L352, L1-G351, L1-A350, L1-R349, L1-L348, L1-P347, L1-E346, L1-R345, L1-Y344, L1-G343, L1-L342, L1-S341, L1-R340, L1-A339, L1-F338, L1-A337, L1-D336, L1-A335, L1-Q334, L1-F333, L1-E332, L1-F331, L1-A330, L1-R329, L1-S328, L1-L327, L1-L326, L1-N325, L1-L324, L1-A323, L1-F322, L1-S321, L1-V320, L1-L319, L1-H318, L1-H317, L1-F316, L1-P315, L1-M314, L1-I313, L1-T312, L1-H311, L1-Q310, L1-F309, L1-L308, L1-I307, L1-L306, L1-G305, L1-I304, L1-L303, L1-V302, L1-P301, L1-Q300, L1-T299, L1-S298, L1-F297, L1-G296, L1-F295, L1-S294, L1-L293, L1-F292, L1-L291, L1-G290, L1-S289, L1-S288, L1-N287, L1-R286, L1-V285, L1-L284, L1-T283, L1-Y282, L1-G281, L1-G280, L1-F279, L1-Q278, L1-L277, L1-L276, L1-T275, L1-L274, L1-V273, L1-Q272, L1-M271, L1-A270, L1-L269, L1-F268, L1-S267, L1-Y266, L1-M265, L1-T264, L1-H263, L1-S262, L1-L261, L1-K260, L1-W259, L1-H258, L1-G257, L1-L256, L1-E255, L1-H254, L1-A253, L1-I252, L1-V251, L1-A250, L1-V249, L1-V248, L1-E247, L1-E246, L1-E245, L1-N244, L1-K243, L1-C242, L1-Q241, L1-S240, L1-I239, L1-L238, L1-T237, L1-D236, L1-Y235, L1-L234, L1-V233, L1-I232, L1-R231, L1-K230, L1-S229, L1-N228, L1-Y227, L1-F226, L1-G225, L1-Y224, L1-M223, L1-Y222, L1-A221, L1-N220, L1-S219, L1-H218, L1-S217, L1-S216, L1-R215, L1-T214, L1-S213, L1-G212, L1-D211, L1-I210, L1-V209, L1-F208, L1-L207, L1-K206, L1-K205, L1-L204, L1-P203, L1-F202, L1-D201, L1-L200, L1-S199, L1-S198, L1-A197, L1-L196, L1-K195, L1-E194, L1-I193, L1-K192, L1-A191, L1-R190, L1-L189, L1-Q188, L1-G187, L1-E186, L1-P185, L1-L184, L1-P183, L1-T182, L1-F181, L1-T180, L1-N179, L1-F178, L1-L177, L1-P176, L1-A175, L1-I174, L1-L173, L1-V172, L1-P171, L1-Y170, L1-L169, L1-A168, L1-M167, L1-L166, L1-V165, L1-L164, L1-S163, L1-L162, L1-L161, L1-L160, L1-M159, L1-F158, L1-A157, L1-W156, L1-L155, L1-Y154, L1-L153, L1-A152, L1-L151, L1-Y150, L1-P149, L1-G148, L1-G147, L1-N146, L1-Q145, L1-V144, L1-I143, L1-Y142, L1-I141, L1-I140, L1-A139, L1-S138, L1-V137, L1-I136, L1-P135, L1-P134, L1-G133, L1-V132, L1-V131, L1-M130, L1-M129, L1-L128, L1-A127, L1-L126, L1-G125, L1-M124, L1-I123, L1-M122, L1-D121, L1-R120, L1-L119, L1-F118, L1-L117, L1-W116, L1-I115, L1-T114, L1-Q113, L1-K112, L1-N111, L1-F110, L1-G109, L1-H108, L1-R107, L1-A106, L1-E105, L1-I104, L1-V103, L1-F102, L1-T101, L1-S100, L1-Y99, L1-L98, L1-S97, L1-F96, L1-P95, L1-L94, L1-E93, L1-L92, L1-I91, L1-Q90, L1-S89, L1-W88, L1-L87, L1-T86, L1-T85, L1-V84, L1-A83, L1-L82, L1-F81, L1-S80, L1-L79, L1-T78, L1-Q77, L1-L76, L1-I75, L1-E74, L1-S73, L1-K72, L1-E71, L1-D70, L1-F69, L1-G68, L1-L67, L1-K66, L1-G65, L1-V64, L1-L63, L1-S62, L1-G61, L1-S60, L1-K59, L1-D58, L1-W57, L1-A56, L1-W55, L1-P54, L1-L53, L1-L52, L1-G51, L1-L50, L1-L49, L1-L48, L1-I47, L1-A46, L1-S45, L1-E44, L1-E43, L1-V42, L1-I41, L1-N40, L1-V39, L1-A38, L1-A37, L1-H36, L1-V35, L1-F34, L1-H33, L1-F32, L1-R31, L1-S30, L1-K29, L1-D28, L1-L27, L1-S26, L1-Y25, L1-A24, L1-Q23, L1-A22, L1-K21, L1-E20, L1-F19, L1-K18, L1-E17, L1-Q16, L1-S15, L1-V14, L1-I13, L1-G12, L1-K11, L1-L10, L1-P9, L1-A8, L1-P7, of SEQ ID NO: 2. The invention includes the polynucleotide sequences encoding these mutant polypeptides.

AtPrPase1

The nucleotide sequence of the full-length PrPase (AtPrPase1) from *Arabidopsis thaliana* (Clone ID No: AtPrPase1) of the present invention is provided as SEQ ID NO: 3. The polynucleotide sequence contains a sequence of 1275 nucleotides. The deduced amino acid sequence of SEQ ID NO: 3 is provided as SEQ ID NO: 4 and contains 424 amino acids.

In a further embodiment, the invention also encompasses the promoter of the AtPrPase1 gene (SEQ ID NO: 10). The promoter has uses including, but not limited to, directing expression of a gene of interest in plant guard-cells. The gene of interest may be any gene endogenous to a plant, a non-plant derived gene (e.g., viral, mammalian, human, synthetic, molecularly evolved, bacterial, fungal, etc.), a reporter gene, a marker gene, a desired input trait, a desired output trait, a gene capable of conferring a specific phenotype in a plant, one or more genes of the present invention, antibody genes, antibody genes directed against the polypeptides of the present invention, antisense genes, in addition to other genes known in the art and/or disclosed herein.

In further embodiments, deletion mutants of AtPrPase1 are encompassed by the present invention, including the following N-terminal deletion mutants: M1-D424, A2-D424, I3-D424, P4-D424, F5-D424, M6-D424, E7-D424, T8-D424, V9-D424, V10-D424, G11-D424, F12-D424, M13-D424, I14-D424, V15-D424, M16-D424, Y17-D424, I18-D424, F19-D424, E20-D424, T21-D424, Y22-D424, L23-D424, D24-D424, L25-D424, R26-D424, Q27-D424, L28-D424, T29-D424, A30-D424, L31-D424, K32-D424, L33-D424, P34-D424, T35-D424, L36-D424, P37-D424, K38-D424, T39-D424, L40-D424, V41-D424, G42-D424, V43-D424, I44-D424, S45-D424, Q46-D424, E47-D424, K48-D424, F49-D424, E50-D424, K51-D424, S52-D424, R53-D424, A54-D424, Y55-D424, S56-D424, L57-D424, D58-D424, K59-D424, S60-D424, Y61-D424, F62-D424, H63-D424, F64-D424, V65-D424, H66-D424, E67-D424, F68-D424, V69-D424, T70-D424, I71-D424, L72-D424, M73-D424, D74-D424, S75-D424, A76-D424, I77-D424, L78-D424, F79-D424, F80-D424, G81-D424, I82-D424, L83-D424, P84-D424, W85-D424, F86-D424, W87-D424, K88-D424, M89-D424, S90-D424, G91-D424, A92-D424, V93-D424, L94-D424, P95-D424, R96-D424, L97-D424, G98-D424, L99-D424, D100-D424, P101-D424, E102-D424, N103-D424, E104-D424, I105-D424, L106-D424, H107-D424, T108-D424, L109-D424, S110-D424, F111-D424, L112-D424, A113-D424, G114-D424, V115-D424, M116-D424, T117-D424, W118-D424, S119-D424, Q120-D424, I121-D424, T122-D424, D123-D424, L124-D424, P125-D424, F126-D424, S127-D424, L128-D424, Y129-D424, S130-D424, T131-D424, F132-D424, V133-D424, I134-D424, E135-D424, S136-D424, R137-D424, H138-D424, G139-D424, F140-D424, N141-D424, K142-D424, Q143-D424, T144-D424, I145-D424, W146-D424, M147-D424, F148-D424, I149-D424, R150-D424, D151-D424, M152-D424, I153-D424, K154-D424, G155-D424, T156-D424, F157-D424, L158-D424, S159-D424, V160-D424, I161-D424, L162-D424, G163-D424, P164-D424, P165-D424, I166-D424, V167-D424, A168-D424, A169-D424, I170-D424, I171-D424, F172-D424, I173-D424, V174-D424, Q175-D424, K176-D424, G177-D424, G178-D424, P179-D424, Y180-D424, L181-D424, A182-D424, I183-D424, Y184-D424, L185-D424, W186-D424, A187-D424, F188-D424, M189-D424, F190-D424, I191-D424, L192-D424, S193-D424, L194-D424, V195-D424, M196-D424, M197-D424, T198-D424, I199-D424, Y200-D424, P201-D424, V202-D424, L203-D424, I204-D424, A205-D424, P206-D424, L207-D424, F208-D424, N209-D424, K210-D424, F211-D424, T212-D424, P213-D424, L214-D424, P215-D424, D216-D424, G217-D424, D218-D424, L219-D424, R220-D424, E221-D424, K222-D424, I223-D424, E224-D424, K225-D424, L226-D424, A227-D424, S228-D424, S229-D424, L230-D424, K231-D424, F232-D424, P233-D424, L234-D424, K235-D424, K236-D424, L237-D424, F238-D424, V239-D424, V240-D424, D241-D424, G242-D424, S243-D424, T244-D424, R245-D424, S246-D424, S247-D424, H248-D424, S249-D424, N250-D424, A251-D424, Y252-D424, M253-D424, Y254-D424, G255-D424, F256-D424, F257-D424, K258-D424, N259-D424, K260-D424, R261-D424, I262-D424, V263-D424, L264-D424, Y265-D424, D266-D424, T267-D424, L268-D424, I269-D424, Q270-D424, Q271-D424, C272-D424, K273-D424, N274-D424, E275-D424, D276-D424, E277-D424, I278-D424, V279-D424, A280-D424, V281-D424, I282-D424, A283-D424, H284-D424, E285-D424, L286-D424, G287-D424, H288-D424, W289-D424, K290-D424, L291-D424, N292-D424, H293-D424, T294-D424, T295-D424, Y296-D424, S297-D424, F298-D424, I299-D424, A300-D424, V301-D424, Q302-D424, I303-D424, L304-D424, A305-D424, F306-D424, L307-D424, Q308-D424, F309-D424, G310-D424, G311-D424, Y312-D424, T313-D424, L314-D424, V315-D424, R316-D424, N317-D424, S318-D424, T319-D424, D320-D424, L321-D424, F322-D424, R323-D424, S324-D424, F325-D424, G326-D424, F327-D424, D328-D424, T329-D424, Q330-D424, P331-D424, V332-D424, L333-D424, I334-D424, G335-D424, L336-D424, I337-D424, I338-D424, F339-D424, Q340-D424, H341-D424, T342-D424, V343-D424, I344-D424, P345-D424, L346-D424, Q347-D424, H348-D424, P349-D424, V350-D424, S351-D424, F352-D424, G353-D424, L354-D424, N355-D424, L356-D424, V357-D424, S358-D424, R359-D424, A360-D424, F361-D424, E362-D424, F363-D424, Q364-D424, A365-D424, D366-D424, A367-D424, F368-D424, A369-D424, V370-D424, K371-D424, L372-D424, G373-D424, Y374-D424, A375-D424, K376-D424, D377-D424, L378-D424, R379-D424, P380-D424, T381-D424, L382-D424, V383-D424, K384-D424, L385-D424, Q386-D424, E387-D424, E388-D424, N389-D424, L390-D424, S391-D424, A392-D424, M393-D424, N394-D424, T395-D424, D396-D424, P397-D424, L398-D424, Y399-D424, S400-D424, A401-D424, Y402-D424, H403-D424, Y404-D424, S405-D424, H406-D424, P407-D424, P408-D424, L409-D424, V410-D424, E411-D424, R412-D424, L413-D424, R414-D424, A415-D424, I416-D424, D417-D424, G418-D424, of SEQ ID NO: 4. The invention includes the polynucleotide sequences encoding these mutant polypeptides.

In further embodiments, deletion mutants of AtPrPase1 are encompassed by the present invention, including the following C-terminal deletion mutants: M1-D424, M1-T423, M1-K422, M1-K421, M1-D420, M1-E419, M1-G418, M1-D417, M1-I416, M1-A415, M1-R414, M1-L413, M1-R412, M1-E411, M1-V410, M1-L409, M1-P408, M1-P407, M1-H406, M1-S405, M1-Y404, M1-H403, M1-Y402, M1-A401, M1-S400, M1-Y399, M1-L398, M1-P397, M1-D396, M1-T395, M1-N394, M1-M393, M1-A392, M1-S391, M1-L390, M1-N389, M1-E388, M1-E387, M1-Q386, M1-L385, M1-K384, M1-V383, M1-L382, M1-T381, M1-P380, M1-R379, M1-L378, M1-D377, M1-K376, M1-A375, M1-Y374, M1-G373, M1-L372, M1-K371, M1-V370, M1-A369, M1-F368, M1-A367, M1-D366, M1-A365, M1-Q364, M1-F363, M1-E362, M1-F361, M1-A360, M1-R359, M1-S358, M1-V357, M1-L356, M1-N355, M1-L354, M1-G353, M1-F352, M1-S351, M1-V350, M1-P349, M1-H348, M1-Q347, M1-L346, M1-P345, M1-I344, M1-V343, M1-T342, M1-H341, M1-Q340, M1-F339, M1-I338, M1-I337, M1-L336, M1-G335, M1-I334, M1-L333, M1-V332, M1-P331, M1-Q330, M1-T329, M1-D328, M1-F327, M1-G326, M1-F325, M1-S324, M1-R323, M1-F322, M1-L321, M1-D320, M1-T319, M1-S318, M1-N317, M1-R316, M1-V315, M1-L314, M1-T313, M1-Y312, M1-G311, M1-G310, M1-F309, M1-Q308, M1-L307, M1-F306, M1-A305, M1-L304, M1-I303, M1-Q302, M1-V301, M1-A300, M1-I299, M1-F298, M1-S297, M1-Y296, M1-T295, M1-T294, M1-H293, M1-N292, M1-L291, M1-K290, M1-W289, M1-H288, M1-G287, M1-L286, M1-E285, M1-H284, M1-A283, M1-I282, M1-V281, M1-A280, M1-V279, M1-I278, M1-E277, M1-D276, M1-E275, M1-N274, M1-K273, M1-C272, M1-Q271, M1-Q270, M1-I269, M1-L268, M1-T267, M1-D266, M1-Y265, M1-L264, M1-V263, M1-I262, M1-R261, M1-K260, M1-N259, M1-K258, M1-F257, M1-F256, M1-G255, M1-Y254, M1-M253, M1-Y252, M1-A251, M1-N250, M1-S249, M1-H248, M1-S247, M1-S246, M1-R245, M1-T244, M1-S243, M1-G242, M1-D241, M1-V240, M1-V239, M1-F238, M1-L237, M1-K236, M1-K235, M1-L234, M1-P233, M1-F232, M1-K231, M1-L230, M1-S229, M1-S228, M1-A227, M1-L226, M1-K225, M1-E224, M1-I223, M1-K222, M1-E221, M1-R220, M1-L219, M1-D218, M1-G217, M1-D216, M1-P215, M1-L214, M1-P213, M1-T212, M1-F211, M1-K210, M1-N209, M1-F208, M1-L207, M1-P206, M1-A205, M1-I204, M1-L203, M1-V202, M1-P201, M1-Y200, M1-I199, M1-T198, M1-M197, M1-M196, M1-V195, M1-L194, M1-S193, M1-L192, M1-I191, M1-F190, M1-M189, M1-F188, M1-A187, M1-W186, M1-L185, M1-Y184, M1-I183, M1-A182, M1-L181, M1-Y180, M1-P179, M1-G178, M1-G177, M1-K176, M1-Q175, M1-V174, M1-I173, M1-F172, M1-I171, M1-I170, M1-A169, M1-A168, M1-V167, M1-I166, M1-P165, M1-P164, M1-G163, M1-L162, M1-I161, M1-V160, M1-S159, M1-L158, M1-F157, M1-T156, M1-G155, M1-K154, M1-I153, M1-M152, M1-D151, M1-R150, M1-I149, M1-F148, M1-M147, M1-W146, M1-I145, M1-T144, M1-Q143, M1-K142, M1-N141, M1-F140, M1-G139, M1-H138, M1-R137, M1-S136, M1-E135, M1-I134, M1-V133, M1-F132, M1-T131, M1-S130, M1-Y129, M1-L128, M1-S127, M1-F126, M1-P125, M1-L124, M1-D123, M1-T122, M1-I121, M1-Q120, M1-S119, M1-W118, M1-T117, M1-M116, M1-V115, M1-G114, M1-A113, M1-L112, M1-F111, M1-S110, M1-L109, M1-T108, M1-H107, M1-L106, M1-I105, M1-E104, M1-N103, M1-E102, M1-P100, M1-D100, M1-L99, M1-G98, M1-L97, M1-R96, M1-P95, M1-L94, M1-V93, M1-A92, M1-G91, M1-S90, M1-M89, M1-K88, M1-W87, M1-F86, M1-W85, M1-P84, M1-L83, M1-I82, M1-G81, M1-F80, M1-F79, M1-L78, M1-F77, M1-A76, M1-S75, M1-D74, M1-M73, M1-L72, M1-I71, M1-T70, M1-V69, M1-F68, M1-E67, M1-H66, M1-V65, M1-F64, M1-H63, M1-F62, M1-Y61, M1-S60, M1-K59, M1-D58, M1-L57, M1-S56, M1-Y55, M1-A54, M1-R53, M1-S52, M1-K51, M1-E50, M1-F49, M1-K48, M1-E47, M1-Q46, M1-S45, M1-I44, M1-V43, M1-G42, M1-V41, M1-L40, M1-T39, M1-K38, M1-P37, M1-L36, M1-T35, M1-P34, M1-L33, M1-K32, M1-L31, M1-A30, M1-T29, M1-L28, M1-Q27, M1-R26, M1-L25, M1-D24, M1-L23, M1-Y22, M1-T21, M1-E20, M1-F19, M1-I18, M1-Y17, M1-M16, M1-V15, M1-I14, M1-M13, M1-F12, M1-G11, M1-V10, M1-V9, M1-T8, M1-E7, of SEQ ID NO: 4. The invention includes the polynucleotide sequences encoding these mutant polypeptides.

AtPrPase2

The nucleotide sequence of a full-length PrPase (AtPrPase2) from *Arabidopsis thaliana* (Clone ID No: AtPrPase2) of the present invention is provided as SEQ ID NO: 5. The polynucleotide sequence contains a sequence of 1275 nucleotides. SEQ ID NO: 3 and SEQ ID NO: 5 are full-length *Arabidopsis* AtPrPases with 8 nucleotide differences at nucleotide positions: 276, 504, 1046, 1062, 1068, 1141, 1182, and 1190, which are alternative embodiments of this sequence of the invention. The deduced amino acid sequence of SEQ ID NO: 5 is provided as SEQ ID NO: 6 and contains 424 amino acids. SEQ ID NO: 4 and SEQ ID NO: 6 are full-length *Arabidopsis* AtPrPases with 3 amino acid differences at amino acid positions: 349, 381, and 397.

In preferred embodiments, deletion mutants of AtPrPase2 are encompassed by the present invention, including the following N-terminal deletion mutants: M1-D424, A2-D424, I3-D424, P4-D424, F5-D424, M6-D424, E7-D424, T8-D424, V9-D424, V10-D424, G11-D424, F12-D424, M13-D424, I14-D424, V15-D424, M16-D424, Y17-D424, I18-D424, F19-D424, E20-D424, T21-D424, Y22-D424, L23-D424, D24-D424, L25-D424, R26-D424, Q27-D424, L28-D424, T29-D424, A30-D424, L31-D424, K32-D424, L33-D424, P34-D424, T35-D424, L36-D424, P37-D424, K38-D424, T39-D424, L40-D424, V41-D424, G42-D424, V43-D424, I44-D424, S45-D424, Q46-D424, E47-D424, K48-D424, F49-D424, E50-D424, K51-D424, S52-D424, R53-D424, A54-D424, Y55-D424, S56-D424, L57-D424, D58-D424, K59-D424, S60-D424, Y61-D424, F62-D424, H63-D424, F64-D424, V65-D424, H66-D424, E67-D424, F68-D424, V69-D424, T70-D424, I71-D424, L72-D424, M73-D424, D74-D424, S75-D424, A76-D424, I77-D424, L78-D424, F79-D424, F80-D424, G81-D424, I82-D424, L83-D424, P84-D424, W85-D424, F86-D424, W87-D424, K88-D424, M89-D424, S90-D424, G91-D424, A92-D424, V93-D424, L94-D424, P95-D424, R96-D424, L97-D424, G98-D424, L99-D424, D100-D424, P101-D424, E102-D424, N103-D424, E104-D424, I105-D424, L106-D424, H107-D424, T108-D424, L109-D424, S110-D424, F111-D424, L112-D424, A113-D424, G114-D424, V115-D424, M116-D424, T117-D424, W118-D424, S119-D424, Q120-D424, I121-D424, T122-D424, D123-D424, L124-D424, P125-D424, F126-D424, S127-D424, L128-D424, Y129-D424, S130-D424, T131-D424, F132-D424, V133-D424, I134-D424, E135-D424, S136-D424, R137-D424, H138-D424, G139-D424, F140-D424, N141-D424, K142-D424, Q143-D424, T144-D424, I145-D424, W146-D424, M147-D424, F148-D424, I149-D424, R150-D424, D151-D424, M152-D424, I153-D424, K154-D424, G155-D424, T156-D424, F157-D424, L158-D424, S159-D424, V160-D424, I161-D424, L162-D424, G163-D424, P164-D424, P165-D424, I166-D424, V167-D424, A168-D424, A169-D424, I170-D424, I171-D424, F172-D424, I173-D424, V174-D424, Q175-D424, K176-D424, G177-D424, G178-D424, P179-D424, Y180-D424, L181-D424, A182-D424, I183-D424, Y184-D424, L185-D424, W186-D424, A187-D424, F188-D424, M189-D424, F190-D424, I191-D424, L192-D424, S193-D424, L194-D424, V195-D424, M196-D424, M197-D424, T198-D424, I199-D424, Y200-D424, P201-D424, V202-D424, L203-D424, I204-D424, A205-D424, P206-D424, L207-D424, F208-D424, N209-D424, K210-D424, F211-D424, T212-D424, P213-D424, L214-D424, P215-D424, D216-D424, G217-D424, D218-D424, L219-D424, R220-D424, E221-D424, K222-D424, I223-D424, E224-D424, K225-D424, L226-D424, A227-D424, S228-D424, S229-D424, L230-D424, K231-D424, F232-D424, P233-D424, L234-D424, K235-D424, K236-D424, L237-D424, F238-D424, V239-D424, V240-D424, D241-D424, G242-D424, S243-D424, T244-D424, R245-D424, S246-D424, S247-D424, H248-D424, S249-D424, N250-D424, A251-D424, Y252-D424, M253-D424, Y254-D424, G255-D424, F256-D424, F257-D424, K258-D424, N259-D424, K260-D424, R261-D424, I262-D424, V263-D424, L264-D424, Y265-D424, D266-D424, T267-D424, L268-D424, I269-D424, Q270-D424, Q271-D424, C272-D424, K273-D424, N274-D424, E275-D424, D276-D424, E277-D424, I278-D424, V279-D424, A280-D424, V281-D424, I282-D424, A283-D424, H284-D424, E285-D424, L286-D424, G287-D424, H288-D424, W289-D424, K290-D424, L291-D424, N292-D424, H293-D424, T294-D424, T295-D424, Y296-D424, S297-D424, F298-D424, I299-D424, A300-D424, V301-D424, Q302-D424, I303-D424, L304-D424, A305-D424, F306-D424, L307-D424, Q308-D424, F309-D424, G310-D424, G311-D424, Y312-D424, T313-D424, L314-D424, V315-D424, R316-D424, N317-D424, S318-D424, T319-D424, D320-D424, L321-D424, F322-D424, R323-D424, S324-D424, F325-D424, G326-D424, F327-D424, D328-D424, T329-D424, Q330-D424, P331-D424, V332-D424, L333-D424, I334-D424, G335-D424, L336-D424, I337-D424, I338-D424, F339-D424, Q340-D424, H341-D424, T342-D424, V343-D424, I344-D424, P345-D424, L346-D424, Q347-D424, H348-D424, L349-D424, V350-D424, S351-D424, F352-D424, G353-D424, L354-D424, N355-D424, L356-D424, V357-D424, S358-D424, R359-D424, A360-D424, F361-D424, E362-D424, F363-D424, Q364-D424, A365-D424, D366-D424, A367-D424, F368-D424, A369-D424, V370-D424, K371-D424, L372-D424, G373-D424, Y374-D424, A375-D424, K376-D424, D377-D424, L378-D424, R379-D424, P380-D424, A381-D424, L382-D424, V383-D424, K384-D424, L385-D424, Q386-D424, E387-D424, E388-D424, N389-D424, L390-D424, S391-D424, A392-D424, M393-D424, N394-D424, T395-D424, D396-D424, L397-D424, L398-D424, Y399-D424, S400-D424, A401-D424, Y402-D424, H403-D424, Y404-D424, S405-D424, H406-D424, P407-D424, P408-D424, L409-D424, V410-D424, E411-D424, R412-D424, L413-D424, R414-D424, A415-D424, I416-D424, D417-D424, G418-D424, of SEQ ID NO: 6. The invention includes the polynucleotide sequences encoding these mutant polypeptides.

In further embodiments, deletion mutants of AtPrPase2 are encompassed by the present invention, including the following C-terminal deletion mutants: M1-D424, M1-T423, M1-K422, M1-K421, M1-D420, M1-E419, M1-G418, M1-D417, M1-I416, M1-A415, M1-R414, M1-L413, M1-R412, M1-E411, M1-V410, M1-L409, M1-P408, M1-P407, M1-H406, M1-S405, M1-Y404, M1-H403, M1-Y402, M1-A401, M1-S400, M1-Y399, M1-L398, M1-L397, M1-D396, M1-T395, M1-N394, M1-M393, M1-A392, M1-S391, M1-L390, M1-N389, M1-E388, M1-E387, M1-Q386, M1-L385, M1-K384, M1-V383, M1-L382, M1-A381, M1-P380, M1-R379, M1-L378, M1-D377, M1-K376, M1-A375, M1-Y374, M1-G373, M1-L372, M1-K371, M1-V370, M1-A369, M1-F368, M1-A367, M1-D366, M1-A365, M1-Q364, M1-F363, M1-E362, M1-F361, M1-A360, M1-R359, M1-S358, M1-V357, M1-L356, M1-N355, M1-L354, M1-G353, M1-F352, M1-S351, M1-V350, M1-L349, M1-H348, M1-Q347, M1-L346, M1-P345, M1-I344, M1-V343, M1-T342, M1-H341, M1-Q340, M1-F339, M1-I338, M1-I337, M1-L336, M1-G335, M1-I334, M1-L333, M1-V332, M1-P331, M1-Q330, M1-T329, M1-D328, M1-F327, M1-G326, M1-F325, M1-S324, M1-R323, M1-F322, M1-L321, M1-D320, M1-T319, M1-S318, M1-N317, M1-R316, M1-V315, M1-L314, M1-T313, M1-Y312, M1-G311, M1-G310, M1-F309, M1-Q308, M1-L307, M1-F306, M1-A305, M1-L304, M1-I303, M1-Q302, M1-V301, M1-A300, M1-I299, M1-F298, M1-S297, M1-Y296, M1-T295, M1-T294, M1-H293, M1-N292, M1-L291, M1-K290, M1-W289, M1-H288, M1-G287, M1-L286, M1-E285, M1-H284, M1-A283, M1-I282, M1-V281, M1-A280, M1-V279, M1-I278, M1-E277, M1-D276, M1-E275, M1-N274, M1-K273, M1-C272, M1-Q271, M1-Q270, M1-I269, M1-L268, M1-T267, M1-D266, M1-Y265, M1-L264, M1-V263, M1-I262, M1-R261, M1-K260, M1-N259, M1-K258, M1-F257, M1-F256, M1-G255, M1-Y254, M1-M253, M1-Y252, M1-A251, M1-N250, M1-S249, M1-H248, M1-S247, M1-S246, M1-R245, M1-T244, M1-S243, M1-G242, M1-D241, M1-V240, M1-V239, M1-F238, M1-L237, M1-K236, M1-K235, M1-L234, M1-P233, M1-F232, M1-K231, M1-L230, M1-S229, M1-S228, M1-A227, M1-L226, M1-K225, M1-E224, M1-I223, M1-K222, M1-E221, M1-R220, M1-L219, M1-D218, M1-G217, M1-D216, M1-P215, M1-L214, M1-P213, M1-T212, M1-F211, M1-K210, M1-N209, M1-F208, M1-L207, M1-P206, M1-A205, M1-I204, M1-L203, M1-V202, M1-P201, M1-Y200, M1-I199, M1-T198, M1-M197, M1-M196, M1-V195, M1-L194, M1-S193, M1-L192, M1-I191, M1-F190, M1-M189, M1-F188, M1-A187, M1-W186, M1-L185, M1-Y184, M1-I183, M1-A182, M1-L181, M1-Y180, M1-P179, M1-G178, M1-G177, M1-K176, M1-Q175, M1-V174, M1-I173, M1-F172, M1-I171, M1-I170, M1-A169, M1-A168, M1-V167, M1-I166, M1-P165, M1-P164, M1-G163, M1-L162, M1-I161, M1-V160, M1-S159, M1-L158, M1-F157, M1-T156, M1-G155, M1-K154, M1-I153, M1-M152, M1-D151, M1-R150, M1-I149, M1-F148, M1-W147, M1-W146, M1-I145, M1-T144, M1-Q143, M1-K142, M1-N141, M1-F140, M1-G139, M1-H138, M1-R137, M1-S136, M1-E135, M1-I134, M1-V133, M1-F132, M1-T131, M1-S130, M1-Y129, M1-L128, M1-S127, M1-F126, M1-P125, M1-L124, M1-D123, M1-T122, M1-I121, M1-Q120, M1-S119, M1-W118, M1-T117, M1-M116, M1-V115, M1-G114, M1-A113, M1-L112, M1-F111, M1-S110, M1-L109, M1-T108, M1-H107, M1-L106, M1-I105, M1-E104, M1-N103, M1-E102, M1-P101, M1-D100, M1-L99, M1-G98, M1-L97, M1-R96, M1-P95, M1-L94, M1-V93, M1-A92, M1-G91, M1-S90, M1-M89, M1-K88, M1-W87, M1-F86, M1-W85, M1-P84, M1-L83, M1-I82, M1-G81, M1-F80, M1-F79, M1-L78, M1-I77, M1-A76, M1-S75, M1-D74, M1-M73, M1-L72, M1-I71, M1-T70, M1-V69, M1-F68, M1-E67, M1-H66, M1-V65, M1-F64, M1-H63, M1-F62, M1-Y61, M1-S60, M1-K59, M1-D58, M1-L57, M1-S56, M1-Y55, M1-A54, M1-R53, M1-S52, M1-K51, M1-E50, M1-F49, M1-K48, M1-E47, M1-Q46, M1-S45, M1-I44, M1-V43, M1-G42, M1-V41, M1-L40, M1-T39, M1-K38, M1-P37, M1-L36, M1-T35, M1-P34, M1-L33, M1-K32, M1-L31, M1-A30, M1-T29, M1-L28, M1-Q27, M1-R26, M1-L25, M1-D24, M1-L23, M1-Y22, M1-T21, M1-E20, M1-F19, M1-I18, M1-Y17, M1-M16, M1-V15, M1-I14, M1-M13, M1-F12, M1-G11, M1-V10, M1-V9, M1-T8, M1-E7, of SEQ ID NO: 6. The invention includes the polynucleotide sequences encoding these mutant polypeptides.

GmPrPase

The nucleotide sequence of the full-length PrPase from soybeans (*Glycine max*) (Clone ID No: GmPrPase2) of the present invention is provided as SEQ ID NO: 16. The deduced amino acid sequence of SEQ ID NO: 16 is provided as SEQ ID NO: 17. A partial PrPase nucleotide sequence from soybean (Clone ID No: GmPrPase1) is provided as SEQ ID NO: 14 with the deduced amino acid sequence as SEQ ID NO: 15.

In further embodiments, deletion mutants of GmPrPase are encompassed by the present invention, including the following N-terminal deletion mutants: M1-C400, A2-C400, F3-C400, P4-C400, Y5-C400, M6-C400, E7-C400, A8-C400, V9-C400, V10-C400, G11-C400, F12-C400, M13-C400, I14-C400, L15-C400, M16-C400, Y17-C400, I18-C400, F19-C400, E20-C400, T21-C400, Y22-C400, L23-C400, D24-C400, V25-C400, R26-C400, Q27-C400, H28-C400, R29-C400, A30-C400, L31-C400, K32-C400, L33-C400, P34-C400, T35-C400, L36-C400, P37-C400, K38-C400, T39-C400, L40-C400, E41-C400, G42-C400, V43-C400, I44-C400, S45-C400, Q46-C400, E47-C400, K48-C400, F49-C400, E50-C400, K51-C400, S52-C400, R53-C400, A54-C400, Y55-C400, S56-C400, L57-C400, D58-C400, K59-C400, S60-C400, H61-C400, F62-C400, H63-C400, F64-C400, V65-C400, H66-C400, E67-C400, F68-C400, V69-C400, T70-C400, I71-C400, V72-C400, T73-C400, D74-C400, S75-C400, T76-C400, I77-C400, L78-C400, Y79-C400, F80-C400, G81-C400, V82-C400, L83-C400, P84-C400, W85-C400, F86-C400, W87-C400, K88-C400, K89-C400, S90-C400, G91-C400, D92-C400, F93-C400, M94-C400, T95-C400, I96-C400, A97-C400, G98-C400, F99-C400, N100-C400, A101-C400, E102-C400, N103-C400, E104-C400, I105-C400, L106-C400, H107-C400, T108-C400, L109-C400, A110-C400, F111-C400, L112-C400, A113-C400, G114-C400, L115-C400, M116-C400, I117-C400, W118-C400, S119-C400, Q120-C400, I121-C400, T122-C400, D123-C400, L124-C400, P125-C400, F126-C400, S127-C400, L128-C400, Y129-C400, S130-C400, T131-C400, F132-C400, V133-C400, I134-C400, E135-C400, A136-C400, R137-C400, H138-C400, G139-C400, F140-C400, N141-C400, K142-C400, Q143-C400, T144-C400, P145-C400, W146-C400, L147-C400, F148-C400, F149-C400, R150-C400, D151-C400, M152-C400, L153-C400, K154-C400, G155-C400, I156-C400, F157-C400, L158-C400, S159-C400, V160-C400, I161-C400, I162-C400, G163-C400, P164-C400, P165-C400, I166-C400, V167-C400, A168-C400, A169-C400, I170-C400, I171-C400, V172-C400, I173-C400, V174-C400, Q175-C400, K176-C400, G177-C400, G178-C400, P179-C400, Y180-C400, L181-C400, A182-C400, I183-C400, Y184-C400, L185-C400, W186-C400, V187-C400, F188-C400, T189-C400, F190-C400, G191-C400, L192-C400, S193-C400, I194-C400, V195-C400, M196-C400, M197-C400, T198-C400, L199-C400, Y200-C400, P201-C400, V202-C400, L203-C400, I204-C400, A205-C400, P206-C400, L207-C400, F208-C400, N209-C400, K210-C400, F211-C400, T212-C400, P213-C400, L214-C400, P215-C400, D216-C400, G217-C400, Q218-C400, L219-C400, R220-C400, E221-C400, K222-C400, I223-C400, E224-C400, K225-C400, L226-C400, A227-C400, S228-C400, S229-C400, L230-C400, N231-C400, Y232-C400, P233-C400, L234-C400, K235-C400, L236-C400, L237-C400, F238-C400, V239-C400, V240-C400, D241-C400, G242-C400, S243-C400, T244-C400, R245-C400, S246-C400, S247-C400, H248-C400, S249-C400, N250-C400, A251-C400, Y252-C400, M253-C400, Y254-C400, G255-C400, F256-C400, F257-C400, K258-C400, N259-C400, K260-C400, R261-C400, I262-C400, V263-C400, L264-C400, Y265-C400, D266-C400, T267-C400, L268-C400, I269-C400, Q270-C400, Q271-C400, C272-C400, K273-C400, D274-C400, D275-C400, E276-C400, E277-C400, I278-C400, V279-C400, A280-C400, V281-C400, I282-C400, A283-C400, H284-C400, E285-C400, L286-C400, G287-C400, H288-C400, W289-C400, K290-C400, L291-C400, N292-C400, H293-C400, T294-C400, V295-C400, Y296-C400, T297-C400, F298-C400, V299-C400, A300-C400, M301-C400, Q302-C400, I303-C400, L304-C400, T305-C400, L306-C400, L307-C400, Q308-C400, F309-C400, G310-C400, G311-C400, Y312-C400, T313-C400, L314-C400, V315-C400, R316-C400, N317-C400, S318-C400, A319-C400, D320-C400, L321-C400, Y322-C400, R323-C400, S324-C400, F325-C400, G326-C400, F327-C400, D328-C400, T329-C400, Q330-C400, P331-C400, V332-C400, L333-C400, I334-C400, G335-C400, L336-C400, I337-C400, I338-C400, F339-C400, Q340-C400, H341-C400, T342-C400, V343-C400, I344-C400, P345-C400, L346-C400, Q347-C400, Q348-C400, L349-C400, V350-C400, S351-C400, F352-C400, G353-C400, L354-C400, N355-C400, L356-C400, V357-C400, S358-C400, R359-C400, S360-C400, F361-C400, E362-C400, F363-C400, Q364-C400, A365-C400, D366-C400, G367-C400, F368-C400, A369-C400, K370-C400, K371-C400, L372-C400, G373-C400, Y374-C400, A375-C400, S376-C400, G377-C400, L378-C400, R379-C400, G380-C400, G381-C400, L382-C400, V383-C400, K384-C400, L385-C400, Q386-C400, E387-C400, E388-C400, N389-C400, L390-C400, S391-C400, A392-C400, M393-C400, N394-C400, of SEQ ID NO: 15 or 17. The invention includes the polynucleotide sequences encoding these mutant polypeptides.

In further embodiments, deletion mutants of GmPrPase are encompassed by the present invention, including the following C-terminal deletion mutants: M1-C400, M1-S399, M1-C398, M1-P397, M1-D396, M1-T395, M1-N394, M1-M393, M1-A392, M1-S391, M1-L390, M1-N389, M1-E388, M1-E387, M1-Q386, M1-L385, M1-K384, M1-V383, M1-L382, M1-G381, M1-G380, M1-R379, M1-L378, M1-G377, M1-S376, M1-A375, M1-Y374, M1-G373, M1-L372, M1-K371, M1-K370, M1-A369, M1-F368, M1-G367, M1-D366, M1-A365, M1-Q364, M1-F363, M1-E362, M1-F361, M1-S360, M1-R359, M1-S358, M1-V357, M1-L356, M1-N355, M1-L354, M1-G353, M1-F352, M1-S351, M1-V350, M1-L349, M1-Q348, M1-Q347, M1-L346, M1-P345, M1-I344, M1-V343, M1-T342, M1-H341, M1-Q340, M1-F339, M1-I338, M1-I337, M1-L336, M1-G335, M1-I334, M1-L333, M1-V332, M1-P331, M1-Q330, M1-T329, M1-D328, M1-F327, M1-G326, M1-F325, M1-S324, M1-R323, M1-Y322, M1-L321, M1-D320, M1-A319, M1-S318, M1-N317, M1-R316, M1-V315, M1-L314, M1-T313, M1-Y312, M1-G311, M1-G310, M1-F309, M1-Q308, M1-L307, M1-L306, M1-T305, M1-L304, M1-I303, M1-Q302, M1-M301, M1-A300, M1-V299, M1-F298, M1-T297, M1-Y296, M1-V295, M1-T294, M1-H293, M1-N292, M1-L291, M1-K290, M1-W289, M1-H288, M1-G287, M1-L286, M1-E285, M1-H284, M1-A283, M1-I282, M1-V281, M1-A280, M1-V279, M1-I278, M1-E277, M1-E276, M1-D275, M1-D274, M1-K273, M1-C272, M1-Q271, M1-Q270, M1-I269, M1-L268, M1-T267, M1-D266, M1-Y265, M1-L264, M1-V263, M1-I262, M1-R261, M1-K260, M1-N259, M1-K258, M1-F257, M1-F256, M1-G255, M1-Y254, M1-M253, M1-Y252, M1-A251, M1-N250, M1-S249, M1-H248, M1-S247, M1-S246, M1-R245, M1-T244, M1-S243, M1-G242, M1-D241, M1-V240, M1-V239, M1-F238, M1-L237, M1-K236, M1-K235, M1-L234, M1-P233, M1-Y232, M1-N231, M1-L230, M1-S229, M1-S228, M1-A227, M1-L226, M1-K225, M1-E224, M1-I223, M1-K222, M1-E221, M1-R220, M1-L219, M1-Q218, M1-G217, M1-D216, M1-P215, M1-L214, M1-P213, M1-T212, M1-F211, M1-K210, M1-N209, M1-F208, M1-L207, M1-P206, M1-A205, M1-I204, M1-L203, M1-V202, M1-P201, M1-Y200, M1-L199, M1-T198, M1-M197, M1-M196, M1-V195, M1-I194, M1-S193, M1-L192, M1-G191, M1-F190, M1-T189, M1-F188, M1-V187, M1-W186, M1-L185, M1-Y184, M1-I183, M1-A182, M1-L181, M1-Y180, M1-P179, M1-G178, M1-G177, M1-K176, M1-Q175, M1-V174, M1-I173, M1-V172, M1-I171, M1-I170, M1-A169, M1-A168, M1-V167, M1-I166, M1-P165, M1-P164, M1-G163, M1-I162, M1-I161, M1-V160, M1-S159, M1-L158, M1-F157, M1-I156, M1-G155, M1-K154, M1-L153, M1-M152, M1-D151, M1-R150, M1-F149, M1-F148, M1-L147, M1-W146, M1-P145, M1-T144, M1-Q143, M1-K142, M1-N141, M1-F140, M1-G139, M1-H138, M1-R137, M1-A136, M1-E135, M1-I134, M1-V133, M1-F132, M1-T131, M1-S130, M1-Y129, M1-L128, M1-S127, M1-F126, M1-P125, M1-L124, M1-D123, M1-T122, M1-I121, M1-Q120, M1-S119, M1-W118, M1-I117, M1-M116, M1-L115, M1-G114, M1-A113, M1-L112, M1-F111, M1-A110, M1-L109, M1-T108, M1-H107, M1-L106, M1-I105, M1-E104, M1-N103, M1-E102, M1-A101, M1-N100, M1-F99, M1-G98, M1-A97, M1-I96, M1-T95, M1-M94, M1-F93, M1-D92, M1-G91, M1-S90, M1-K89, M1-K88, M1-W87, M1-F86, M1-W85, M1-P84, M1-L83, M1-V82, M1-G81, M1-F80, M1-Y79, M1-L78, M1-I77, M1-T76, M1-S75, M1-D74, M1-T73, M1-V72, M1-I71, M1-T70, M1-V69, M1-F68, M1-E67, M1-H66, M1-V65, M1-F64, M1-H63, M1-F62, M1-H61, M1-S60, M1-K59, M1-D58, M1-L57, M1-S56, M1-Y55, M1-A54, M1-R53, M1-S52, M1-K51, M1-E50, M1-F49, M1-K48, M1-E47, M1-Q46, M1-S45, M1-I44, M1-V43, M1-G42, M1-E41, M1-L40, M1-T39, M1-K38, M1-P37, M1-L36, M1-T35, M1-P34, M1-L33, M1-K32, M1-L31, M1-A30, M1-R29, M1-H28, M1-Q27, M1-R26, M1-V25, M1-D24, M1-L23, M1-Y22, M1-T21, M1-E20, M1-F19, M1-L18, M1-Y17, M1-M16, M1-L15, M1-I14, M1-M13, M1-F12, M1-G11, M1-V10, M1-V9, M1-A8, M1-E7, of SEQ ID NO: 15 or 17. The invention includes the polynucleotide sequences encoding these mutant polypeptides.

ZmPrPase

The nucleotide sequence of the full-length PrPase from corn (*Zea mays*) (Clone ID No: ZmPrPase2) of the present invention is provided as SEQ ID NO: 23. The deduced amino acid sequence of SEQ ID NO: 23 is provided as SEQ ID NO: 24. A partial PrPase nucleotide sequence from corn (Clone ID No: ZmPrPase1) is provided as SEQ ID NO: 21 with the deduced amino acid sequence as SEQ ID NO: 22.

In further embodiments, deletion mutants of ZmPrPase are encompassed by the present invention, including the following N-terminal deletion mutants: T1-D329, R2-D329, L3-D329, S4-D329, A5-D329, E6-D329, N7-D329, E8-D329, I9-D329, I10-D329, H11-D329, T12-D329, L13-D329, A14-D329, F15-D329, L16-D329, A17-D329, G18-D329, S19-D329, M20-D329, V21-D329, W22-D329, S23-D329, Q24-D329, I25-D329, T26-D329, D27-D329, L28-D329, P29-D329, F30-D329, S31-D329, L32-D329, Y33-D329, S34-D329, T35-D329, F36-D329, V37-D329, I38-D329, E39-D329, A40-D329, R41-D329, H42-D329, G43-D329, F44-D329, N45-D329, K46-D329, Q47-D329, T48-D329, I49-D329, W50-D329, L51-D329, F52-D329, I53-D329, R54-D329, D55-D329, M56-D329, I57-D329, K58-D329, G59-D329, I60-D329, L61-D329, L62-D329, S63-D329, M64-D329, I65-D329, L66-D329, G67-D329, P68-D329, P69-D329, I70-D329, V71-D329, A72-D329, A73-D329, I74-D329, I75-D329, Y76-D329, I77-D329, V78-D329, Q79-D329, I80-D329, G81-D329, G82-D329, P83-D329, Y84-D329, L85-D329, A86-D329, I87-D329, Y88-D329, L89-D329, W90-D329, G91-D329, F92-D329, M93-D329, F94-D329, V95-D329, L96-D329, A97-D329, L98-D329, L99-D329, M100-D329, M101-D329, T102-D329, I103-D329, Y104-D329, P105-D329, I106-D329, V107-D329, I108-D329, A109-D329, P110-D329, L111-D329, F112-D329, N113-D329, K114-D329, F115-D329, T116-D329, P117-D329, L118-D329, P119-D329, E120-D329, G121-D329, V122-D329, L123-D329, R124-D329, E125-D329, K126-D329, I127-D329, E128-D329, K129-D329, L130-D329, A131-D329, A132-D329, S133-D329, L134-D329, K135-D329, F136-D329, P137-D329, L138-D329, K139-D329, K140-D329, L141-D329, F142-D329, V143-D329, V144-D329, D145-D329, G146-D329, S147-D329, T148-D329, R149-D329, S150-D329, S151-D329, H152-D329, S153-D329, N154-D329, A155-D329, Y156-D329, M157-D329, Y158-D329, G159-D329, F160-D329, F161-D329, K162-D329, N163-D329, K164-D329, R165-D329, I166-D329, V167-D329, L168-D329, Y169-D329, D170-D329, T171-D329, L172-D329, I173-D329, Q174-D329, Q175-D329, C176-D329, S177-D329, N178-D329, E179-D329, D180-D329, E181-D329, I182-D329, V183-D329, S184-D329, V185-D329, I186-D329, A187-D329, H188-D329, E189-D329, L190-D329, G191-D329, H192-D329, W193-D329, K194-D329, L195-D329, N196-D329, H197-D329, T198-D329, V199-D329, Y200-D329, S201-D329, F202-D329, V203-D329, A204-D329, V205-D329, Q206-D329, L207-D329, L208-D329, M209-D329, F210-D329, L211-D329, Q212-D329, F213-D329, G214-D329, G215-D329, Y216-D329, T217-D329, L218-D329, V219-D329, R220-D329, S221-D329, S222-D329, K223-D329, D224-D329, L225-D329, F226-D329, G227-D329, S228-D329, F229-D329, G230-D329, F231-D329, K232-D329, D233-D329, Q234-D329, P235-D329, V236-D329, I237-D329, I238-D329, G239-D329, L240-D329, I241-D329, I242-D329, F243-D329, P244-D329, H245-D329, T246-D329, I247-D329, I248-D329, P249-D329, I250-D329, Q251-D329, H252-D329, L253-D329, L254-D329, S255-D329, F256-D329, R257-D329, L258-D329, N259-D329, L260-D329, V261-D329, S262-D329, R263-D329, A264-D329, F265-D329, E266-D329, F267-D329, Q268-D329, A269-D329, D270-D329, A271-D329, F272-D329, A273-D329, K274-D329, N275-D329, L276-D329, G277-D329, Y278-D329, A279-D329, P280-D329, Q281-D329, L282-D329, R283-D329, A284-D329, A285-D329, L286-D329, V287-D329, K288-D329, L289-D329, Q290-D329, E291-D329, E292-D329, N293-D329, L294-D329, S295-D329, A296-D329, M297-D329, N298-D329, T299-D329, D300-D329, P301-D329, W302-D329, Y303-D329, S304-D329, A305-D329, Y306-D329, H307-D329, Y308-D329, S309-D329, H310-D329, P311-D329, P312-D329, L313-D329, V314-D329, E315-D329, R316-D329, L317-D329, Q318-D329, A319-D329, L320-D329, E321-D329, D322-D329, S323-D329, of SEQ ID NO: 22 or 24. The invention includes the polynucleotide sequences encoding these mutant polypeptides.

In further embodiments, deletion mutants of ZmPrPase are encompassed by the present invention, including the following C-terminal deletion mutants: T1-D329, T1-E328, T1-K327, T1-K326, T1-D325, T1-D324, T1-S323, T1-D322, T1-E321, T1-L320, T1-A319, T1-Q318, T1-L317, T1-R316, T1-E315, T1-V314, T1-L313, T1-P312, T1-P311, T1-H310, T1-S309, T1-Y308, T1-H307, T1-Y306, T1-A305, T1-S304, T1-Y303, T1-W302, T1-P301, T1-D300, T1-T299, T1-N298, T1-M297, T1-A296, T1-S295, T1-L294, T1-N293, T1-E292, T1-E291, T1-Q290, T1-L289, T1-K288, T1-V287, T1-L286, T1-A285, T1-A284, T1-R283, T1-L282, T1-Q281, T1-P280, T1-A279, T1-Y278, T1-G277, T1-L276, T1-N275, T1-K274, T1-A273, T1-F272, T1-A271, T1-D270, T1-A269, T1-Q268, T1-F267, T1-E266, T1-F265, T1-A264, T1-R263, T1-S262, T1-V261, T1-L260, T1-N259, T1-L258, T1-R257, T1-F256, T1-S255, T1-L254, T1-L253, T1-H252, T1-Q251, T1-I250, T1-P249, T1-I248, T1-I247, T1-T246, T1-H245, T1-P244, T1-F243, T1-I242, T1-I241, T1-L240, T1-G239, T1-I238, T1-I237, T1-V236, T1-P235, T1-Q234, T1-D233, T1-K232, T1-F231, T1-G230, T1-F229, T1-S228, T1-G227, T1-F226, T1-L225, T1-D224, T1-K223, T1-S222, T1-S221, T1-R220, T1-V219, T1-L218, T1-T217, T1-Y216, T1-G215, T1-G214, T1-F213, T1-Q212, T1-L211, T1-F210, T1-M209, T1-L208, T1-L207, T1-Q206, T1-V205, T1-A204, T1-V203, T1-F202, T1-S201, T1-Y200, T1-V199, T1-T198, T1-H197, T1-N196, T1-L195, T1-K194, T1-W193, T1-H192, T1-G191, T1-L190, T1-E189, T1-H188, T1-A187, T1-I186, T1-V185, T1-S184, T1-V183, T1-I182, T1-E181, T1-D180, T1-E179, T1-N178, T1-S177, T1-C176, T1-Q175, T1-Q174, T1-I173, T1-L172, T1-T171, T1-D170, T1-Y169, T1-L168, T1-V167, T1-I166, T1-R165, T1-K164, T1-N163, T1-K162, T1-F161, T1-F160, T1-G159, T1-Y158, T1-M157, T1-Y156, T1-A155, T1-N154, T1-S153, T1-H152, T1-S151, T1-S150, T1-R149, T1-T148, T1-S147, T1-G146, T1-D145, T1-V144, T1-V143, T1-F142, T1-L141, T1-K140, T1-K139, T1-L138, T1-P137, T1-F136, T1-K135, T1-L134, T1-S133, T1-A132, T1-A131, T1-L130, T1-K129, T1-E128, T1-I127, T1-K126, T1-R124, T1-L123, T1-V122, T1-G121, T1-E120, T1-P119, T1-L118, T1-P117, T1-T116, T1-F115, T1-K114, T1-N113, T1-F112, T1-L111, T1-P110, T1-A109, T1-I108, T1-V107, T1-I106, T1-P105, T1-Y104, T1-I103, T1-T102, T1-M101, T1-M100, T1-L99, T1-L98, T1-A97, T1-L96, T1-V95, T1-F94, T1-M93, T1-F92, T1-G91, T1-W90, T1-L89, T1-Y88, T1-I87, T1-A86, T1-L85, T1-Y84, T1-P83, T1-G82, T1-G81, T1-I80, T1-Q79, T1-I78, T1-I77, T1-Y76, T1-I75, T1-I74, T1-A73, T1-A72, T1-V71, T1-I70, T1-P69, T1-P68, T1-G67, T1-L66, T1-I65, T1-M64, T1-S63, T1-L62, T1-L61, T1-I60, T1-G59, T1-K58, T1-I57, T1-M56, T1-D55, T1-R54, T1-I53, T1-F52, T1-L51, T1-W50, T1-I49, T1-T48, T1-Q47, T1-K46, T1-N45, T1-F44, T1-G43, T1-H42, T1-R41, T1-A40, T1-E39, T1-I38, T1-V37, T1-F36, T1-T35, T1-S34, T1-Y33, T1-L32, T1-S31, T1-F30, T1-P29, T1-L28, T1-D27, T1-T26, T1-I25, T1-Q24, T1-S23, T1-W22, T1-V21, T1-M20, T1-S19, T1-G18, T1-A17, T1-L16, T1-F15, T1-A14, T1-L13, T1-T12, T1-H11, T1-I10, T1-I9, T1-E8, T1-N7, of SEQ ID NO: 22 or 24. The invention includes the polynucleotide sequences encoding these mutant polypeptides.

TABLE 1

| cDNA Clone ID | Vector | NT SEQ ID NO: X | Total NT Seq. of Clone | 5' NT of Start Codon of ORF | 3' NT of ORF | AA SEQ ID NO: Y | Total AA of ORF |
|---|---|---|---|---|---|---|---|
| PpPrPase1 | pCR2.1 | 1 | 1398 | 33 | 1214 | 2 | 394 |
| AtPrPase1 | pCR2.1 | 3 | 1275 | 1 | 1272 | 4 | 424 |
| AtPrPase2 | pCR2.1 | 5 | 1275 | 1 | 1272 | 6 | 424 |
| AtCPP |  | 7 | 1275 | 1 | 1275 | 8 | 424 |
| BnCPP |  | 11 | 1275 | 1 | 1275 | 12 | 424 |
| GmPrPase1 | pCR2.1 | 14 | 1434 | 233 | 1432 | 15 | 400 |
| GmPrPase2 |  | 16 | 1405 | 39 | 1313 | 17 | 424 |
| GmCPP |  | 18 | 1275 | 1 | 1275 | 19 | 424 |
| ZmPrPase1 | pCR2.1 | 21 | 1301 | 1 | 987 | 22 | 329 |
| ZmPrPase2 |  | 23 | 1518 | 166 | 1443 | 24 | 424 |

Table 1 summarizes the information corresponding to each "cDNA Clone ID." The nucleotide sequences identified as NT SEQ ID NO: 1, 3, 5, 14, and 21 were assembled from partially homologous ("overlapping") sequences obtained from the corresponding "cDNA clone ID" identified in Table 1 and, in some cases, from additional related DNA clones. The overlapping sequences were assembled into a single contiguous sequence of high redundancy (usually several overlapping sequences at each nucleotide position), resulting in a final sequence identified under "NT SEQ ID NO:X."

"Vector" in Table 1 refers to the type of vector contained in the cDNA Clone ID. pCR2.1 was obtained from Invitrogen, Inc.

"Total NT Seq. Of Clone" in Table 1 refers to the total number of nucleotides in the clone identified by "cDNA Clone ID." The nucleotide position of a sequence under NT SEQ ID NO:X of the putative start codon (methionine) is identified as "5' NT of Start Codon of ORF."

The translated amino acid sequence, beginning with the methionine, is identified in Table 1 as "AA SEQ ID NO:Y," although other reading frames can also be easily translated using known molecular biology techniques. The polypeptides produced by these alternative open reading frames are specifically contemplated by the present invention.

The total number of amino acids within the open reading frame of a sequence under AA SEQ ID NO:Y is identified in Table 1 as "Total AA of ORF".

DNA sequences generated by sequencing reactions can contain sequencing errors. The errors exist as misidentified nucleotides, or as insertions or deletions of nucleotides in the generated DNA sequence. The erroneously inserted or deleted nucleotides may cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

For those applications requiring precision in the nucleotide sequence or the amino acid sequence, the present invention provides the nucleotide sequence identified as SEQ ID NOs: 1, 3, 5, 7, 11, 14, 16, 18, 21, and 23 and the predicted translated amino acid sequence identified as SEQ ID NOs: 2, 4, 6, 8, 12, 15, 17, 19, 22, and 24. Moreover, the amino acid sequence of the protein encoded by a particular clone can also be directly determined by peptide sequencing or by expressing the protein in a suitable host cell containing the cDNA, collecting the protein, and determining its sequence. Thus, minor errors in the nucleotide sequence can be recognized by persons skilled in the art.

The present invention also relates to the genes corresponding to SEQ ID NOs: 1, 3, 5, 7, 11, 14, 16, 18, 21, and 23, or SEQ ID NOs: 2, 4, 6, 8, 12, 15, 17, 19, 22, and 24. The corresponding gene can be isolated in accordance with known methods using the sequence information disclosed herein. Such methods include preparing probes or primers from the disclosed sequence and identifying or amplifying the corresponding gene from appropriate sources of genomic material.

Also provided in the present invention are species homologs, allelic variants, and/or orthologs. The skilled artisan could, using procedures well-known in the art, obtain the polynucleotide sequence corresponding to full-length genes (including, but not limited to the full-length coding region), allelic variants, splice variants, orthologs, and/or species homologs of genes corresponding to SEQ ID NOs: 1, 3, 5, 7, 11, 14, 16, 18, 21, and 23, or SEQ ID NOs: 2, 4, 6, 8, 12, 15, 17, 19, 22, and 24, relying on the sequences disclosed herein. For example, allelic variants and/or species homologs may be isolated and identified by making suitable probes or primers which correspond to the 5', 3', or internal regions of the sequences provided herein and screening a suitable nucleic acid source for allelic variants and/or the desired homologue.

The polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The polypeptides may be in the form of the protein, or may be a part of a larger protein, such as a fusion protein. It is often advantageous to include an additional amino acid sequence which contains secretory or leader sequences, pro-sequences, sequences which aid in purification, such as multiple histidine residues, or an additional sequence to confer stability during recombinant production.

The polypeptides of the present invention are preferably provided in an isolated form, and preferably are substantially purified. A recombinantly produced version of a polypeptide can be substantially purified using techniques known in the art, such as, for example, by the one-step method described in Smith and Johnson, Gene 67:31-40 (1988). Polypeptides of the invention also can be purified from natural, synthetic or recombinant sources using protocols known in the art.

The present invention provides a polynucleotide comprising, or alternatively consisting of, the sequence identified as SEQ ID NOs: 1, 3, 5, 7, 11, 14, 16, 18, 21, or 23. The present invention also provides a polypeptide comprising, or alternatively consisting of, the sequence identified as SEQ ID NOs: 2, 4, 6, 8, 12, 15, 17, 19, 22, or 24. The present invention also provides polynucleotides encoding a polypeptide comprising, or alternatively consisting of the polypeptide sequence of SEQ ID NOs: 2, 4, 6, 8, 12, 15, 17, 19, 22, or 24.

The present invention encompasses polynucleotides which are complementary to the PrPase polynucleotides disclosed herein. Such sequences may be complementary to the sequence disclosed as SEQ ID NOs: 1, 3, 5, 7, 11, 14, 16, 18, 21, or 23, and/or the nucleic acid sequence encoding the sequence disclosed as SEQ ID NOs: 2, 4, 6, 8, 12, 15, 17, 19, 22, or 24. In another embodiment, an isolated nucleic acid molecule of the invention comprises a nucleic acid molecule that is a complement of the nucleotide sequence shown in SEQ ID NO: 1, 3, 5, 7, 11, 14, 16, 18, 21, or 23, or a portion of these nucleotide sequence. A nucleic acid molecule that is complementary to the nucleotide sequence shown in SEQ ID NO:1, 4, 17, 76, 78, 80, 82, or 84 is one that is sufficiently complementary to the nucleotide sequence shown in SEQ ID NO: 1, 3, 5, 7, 11, 14, 16, 18, 21, or 23 that it can hydrogen bond with few or no mismatches to the nucleotide sequence shown in SEQ ID NO: 1, 3, 5, 7, 11, 14, 16, 18, 21, or 23, thereby forming a stable duplex. Exemplary complement nucleic acid sequences include the sequences of SEQ ID NO: 9, 13, and 20.

As used herein, the term "complementary" refers to Watson-Crick or Hoogsteen base pairing between nucleotide units of a nucleic acid molecule, and the term "binding" means the physical or chemical interaction between two polypeptides or compounds or associated polypeptides or compounds or combinations thereof. Binding includes ionic, non-ionic, Von der Waals, hydrophobic interactions, etc. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates.

Hybridization

The present invention also encompasses polynucleotides capable of hybridizing, preferably under reduced stringency conditions, more preferably under stringent conditions, and most preferably under highly stringent conditions, to polynucleotides described herein. Nucleic acid hybridization techniques are well known in the art. Examples of stringency conditions are shown in Table 2 below: highly stringent conditions are those that are at least as stringent as, for example, conditions A-F; stringent conditions are at least as stringent as, for example, conditions G-L; and reduced stringency conditions are at least as stringent as, for example, conditions M-R.

TABLE 2

| Stringency Condition | Polynucleotide Hybrid†† | Hybrid Length (bp)‡ | Hyridization Temperature and Buffer† | Wash Temperature and Buffer† |
|---|---|---|---|---|
| A | DNA:DNA | > or equal to 50 | 65° C.; 1xSSC -or- 42° C.; 1xSSC, 50% formamide | 65° C.; 0.3xSSC |
| B | DNA:DNA | <50 | Tb*; 1xSSC | Tb*; 1xSSC |
| C | DNA:RNA | > or equal to 50 | 67° C.; 1xSSC -or- 45° C.; 1xSSC, 50% formamide | 67° C.; 0.3xSSC |
| D | DNA:RNA | <50 | Td*; 1xSSC | Td*; 1xSSC |
| E | RNA:RNA | > or equal to 50 | 70° C.; 1xSSC -or- 50° C.; 1xSSC, 50% formamide | 70° C.; 0.3xSSC |
| F | RNA:RNA | <50 | Tf*; 1xSSC | Tf*; 1xSSC |
| G | DNA:DNA | > or equal to 50 | 65° C.; 4xSSC -or- 45° C.; 4xSSC, 50% formamide | 65° C.; 1xSSC |
| H | DNA:DNA | <50 | Th*; 4xSSC | Th*; 4xSSC |
| I | DNA:RNA | > or equal to 50 | 67° C.; 4xSSC -or- 45° C.; 4xSSC, 50% formamide | 67° C.; 1xSSC |
| J | DNA:RNA | <50 | Tj*; 4xSSC | Tj*; 4xSSC |
| K | RNA:RNA | > or equal to 50 | 70° C.; 4xSSC -or- 40° C.; 6xSSC, 50% formamide | 67° C.; 1xSSC |
| L | RNA:RNA | <50 | Tl*; 2xSSC | Tl*; 2xSSC |
| M | DNA:DNA | > or equal to 50 | 50° C.; 4xSSC -or- 40° C. 6xSSC, 50% formamide | 50° C.; 2xSSC |
| N | DNA:DNA | <50 | Tn*; 6xSSC | Tn*; 6xSSC |
| O | DNA:RNA | > or equal to 50 | 55° C.; 4xSSC -or- 42° C.; 6xSSC, 50% formamide | 55° C.; 2xSSC |
| P | DNA:RNA | <50 | Tp*; 6xSSC | Tp*; 6xSSC |
| Q | RNA:RNA | > or equal to 50 | 60° C.; 4xSSC -or- 45° C.; 6xSSC, 50% formamide | 60° C.; 2xSSC |
| R | RNA:RNA | <50 | Tr*; 4xSSC | Tr*; 4xSSC |

‡The "hybrid length" in Table 2 is the anticipated length for the hybridized region(s) of the hybridizing polynucleotides. When hybridizing a polynucletotide of unknown sequence, the hybrid is assumed to be that of the hybridizing polynucleotide of the present invention. When polynucleotides of known sequence are hybridized, the hybrid length can be determined by aligning the sequences of the polynucleotides and identifying the region or regions of optimal sequence complementarity. Methods of aligning two or more polynucleotide sequences and/or determining the percent identity between two polynucleotide sequences are well known in the art (e.g., MegAlign program of the DNA*Star suite of programs, etc).
†SSPE in Table 2 (1xSSPE is 0.15M NaCl, 10 mM NaH2PO4, and 1.25 mM EDTA, pH 7.4) can be substituted for SSC (1xSSC is 0.15M NaCl anmd 15 mM sodium citrate) in the hybridization and wash buffers; washes are performed for 15 minutes after hybridization is complete. The hybridizations and washes may additionally include 5X Denhardt's reagent, .5-1.0% SDS, 100 ug/ml denatured, fragmented salmon sperm DNA, 0.5% sodium pyrophosphate, and up to 50% formamide.
*Tb-Tr in Table 2. The hybridization temperature for hybrids anticipated to be less than 50 base pairs in length should be 5-10° C. less than the melting temperature Tm of the hybrids there Tm is determined according to the following equations. For hybrids less than 18 base pairs in length, Tm(° C.) = 2(# of A + T bases) + 4(# of G + C bases). For hybrids between 18 and 49 base pairs in length, Tm(° C.) = 81.5 + 16.6($\log_{10}$[Na+]) + 0.41(% G + C) − (600/N), where N is the number of bases in the hybrid, and [Na+] is the concentration of sodium ions in the hybridization buffer ([NA+] for 1xSSC = .165 M).
††The present invention encompasses the substitution of any one, or more DNA or RNA hybrid partners with either a peptide nucleic acid ("PNA"), or a modified polynucleotide. Such modified polynucleotides are known in the art.

Additional examples of stringency conditions for polynucleotide hybridization are known to those skilled in the art and are provided, for example, in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M., Ausubel et al., eds, John Wiley and Sons, Inc., sections 2.10 and 6.3-6.4, which are hereby incorporated by reference herein.

Preferably, such hybridizing polynucleotides have at least 70% sequence identity (more preferably, at least 80% identity; and most preferably at least 90% or 95% identity) with the polynucleotide of the present invention to which they hybridize, where sequence identity is determined by comparing the sequences of the hybridizing polynucleotides when aligned so as to maximize overlap and identity while minimizing sequence gaps. The determination of identity is well known in the art.

In another embodiment, an isolated nucleic acid molecule of the invention is at least 6 nucleotides in length and hybridizes under stringent conditions to the nucleic acid molecule comprising the nucleotide sequence of SEQ ID NO: 1, 3, 5, 7, 11, 14, 16, 18, 21, or 23. In another embodiment, the nucleic acid is at least 10, 25, 50, 100, 250, 500 or 750 nucleotides in length. In another embodiment, an isolated nucleic acid molecule of the invention hybridizes to the coding region. As used herein, the term "hybridizes under stringent conditions" is intended to describe conditions for hybridization and washing under which nucleotide sequences at least 60% homologous to each other typically remain hybridized to each other.

Homologs (i.e., nucleic acids encoding PrPase proteins derived from species other than *Arabidopsis thaliana, Physcomitrella patens, Brassica napus, Zea mays,* or *Glycine max*) or other related sequences (e.g., paralogs) can be obtained by low, moderate or high stringency hybridization with all or a portion of the particular sequence as a probe using methods well known in the art for nucleic acid hybridization and cloning.

Alternatively, the phrase "stringent hybridization conditions" can refer to conditions under which a probe, primer or oligonucleotide will hybridize to its target sequence, but to no other sequences. Stringent conditions are sequence-dependent and will be different depending upon circumstances. Longer sequences hybridize specifically at higher temperatures than shorter sequences. Generally, stringent conditions are selected to be about 5° C. lower than the thermal melting point ($T_m$) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 nt to 50 nt) and at least about 60° C. for longer probes, primers and oligonucleotides. Stringent conditions may also be achieved with the addition of destabilizing agents, such as formamide.

Preferably, the conditions are such that sequences at least about 65%, 70%, 75%, 85%, 90%, 95%, 98%, or 99% homologous to each other typically remain hybridized to each other. A non-limiting example of stringent hybridization conditions is hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C. This hybridization is followed by one or more washes in 0.2×SSC, 0.01% BSA at 50° C. An isolated nucleic acid molecule of the invention that hybridizes under stringent conditions to the nucleic acid sequences of the invention can correspond to a naturally occurring nucleic acid molecule. As used herein, a "naturally-occurring" nucleic acid molecule refers to an RNA or DNA molecule having a nucleotide sequence that occurs in nature (e.g., encodes a natural protein).

In another embodiment, a nucleic acid sequence that is hybridizable to the nucleic acid molecule comprising the nucleotide sequence of SEQ ID NO: 1, 3, 5, 7, 11, 14, 16, 18, 21, or 23, or fragments, analogs or derivatives thereof, under conditions of moderate stringency is provided. A non-limiting example of moderate stringency hybridization conditions are hybridization in 6×SSC, 5×Denhardt's solution, 0.5% SDS and 100 mg/ml denatured salmon sperm DNA at 55° C., followed by one or more washes in 1×SSC, 0.1% SDS at 37° C. Other conditions of moderate stringency that may be used are well known in the art. See, e.g., Ausubel et al. (eds.), 1993, CURRENT PROTOCOLS IN MOLECULAR BIOLOGY, John Wiley & Sons, NY, and Kriegler, 1990, GENE TRANSFER AND EXPRESSION, A LABORATORY MANUAL, Stockton Press, NY.

In yet another embodiment, a nucleic acid that is hybridizable to the nucleic acid molecule comprising the nucleotide sequence of SEQ ID NO: 1, 3, 5, 7, 11, 14, 16, 18, 21, or 23, or fragments, analogs or derivatives thereof, under conditions of low stringency, is provided. A non-limiting example of low stringency hybridization conditions are hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2×SSC, 25 mM Tris-HCl (pH 7.4), 5 mM EDTA, and 0.1% SDS at 50° C. Other conditions of low stringency that may be used are well known in the art (e.g., as employed for cross-species hybridizations). See, e.g., Ausubel et al. (eds.), 1993, CURRENT PROTOCOLS IN MOLECULAR BIOLOGY, John Wiley & Sons, NY, and Kriegler, 1990, GENE TRANSFER AND EXPRESSION, A LABORATORY MANUAL, Stockton Press, NY; Shilo and Weinberg, 1981, *Proc Natl Acad Sci USA* 78: 6789-6792.

The invention encompasses the application of PCR methodology to the polynucleotide sequences of the present invention and/or the cDNA encoding the polypeptides of the present invention. PCR techniques for the amplification of nucleic acids are described in U.S. Pat. No. 4,683,195 and Saiki et al., Science, 239:487-491 (1988). PCR, for example, may include the following steps, of denaturation of template nucleic acid (if double-stranded), annealing of primer to target, and polymerization. The nucleic acid probed or used as a template in the amplification reaction may be genomic DNA, cDNA, RNA, or a PNA. PCR may be used to amplify specific sequences from genomic DNA, specific RNA sequence, and/or cDNA transcribed from mRNA. References for the general use of PCR techniques, including specific method parameters, include Mullis et al., Cold Spring Harbor Symp. Quant. Biol., 51:263, (1987), Ehrlich (ed), PCR Technology, Stockton Press, NY, 1989; Ehrlich et al., Science, 252:1643-1650, (1991); and "PCR Protocols, A Guide to Methods and Applications", Eds., Innis et al., Academic Press, New York, (1990).

The present invention includes mature forms of the polypeptide of SEQ ID NO: 2, 4, 6, 8, 12, 15, 17, 19, 22, or 24, and the polynucleotides which encode them. As used herein, a "mature" form of a polypeptide or protein described herein relates to the product of a naturally occurring polypeptide or precursor form or proprotein or any precursor or proprotein which is or can be processed to mature form. Alternatively, it may be defined as the polypeptide, precursor or proprotein encoded by an open reading frame.

Polynucleotide and Polypeptide Variants

The present invention also encompasses variants (e.g., allelic variants, orthologs, etc.) of the polynucleotide sequence disclosed herein in SEQ ID NO: 1, 3, 5, 7, 11, 14, 16, 18, 21, and 23, and/or the complementary strand thereto.

The present invention also encompasses variants of the polypeptide sequence, and/or fragments thereof, disclosed in SEQ ID NO: 2, 4, 6, 8, 12, 15, 17, 19, 22, or 24.

The invention further encompasses nucleic acid molecules that differ from the nucleotide sequences shown in SEQ ID NO: 1, 3, 5, 7, 11, 14, 16, 18, 21, or 23 due to the degeneracy of the genetic code. These nucleic acids thus encode the same PrPase protein as that encoded by the nucleotide sequence shown in SEQ ID NO: 1, 3, 5, 7, 11, 14, 16, 18, 21, or 23, e.g., the polypeptide of SEQ ID NO: 2, 4, 6, 8, 12, 15, 17, 19, 22, or 24. In another embodiment, an isolated nucleic acid molecule of the invention has a nucleotide sequence encoding a protein having an amino acid sequence shown in SEQ ID NO: 2, 4, 6, 8, 12, 15, 17, 19, 22, or 24.

"Variant" refers to a polynucleotide or polypeptide differing from the polynucleotide or polypeptide of the present invention, but retaining essential properties thereof. Generally, variants are overall closely similar, and, in many regions, identical to the polynucleotide or polypeptide of the present invention.

The present invention is also directed to polynucleotide sequences which comprise, or alternatively consist of, a polynucleotide sequence which is at least 70%, 80%, 85%, 90%, 91%, 92%, 93%, 94%, 95%, 96%, 97%, 98%, or 99% identical to, the following non-limiting examples, the polynucleotide sequence of the coding region of the sequence in SEQ ID NO: 1, 3, 5, 7, 11, 14, 16, 18, 21, or 23, the complementary strand of said coding region, a polynucleotide sequence encoding the polypeptide identified as SEQ ID NO: 2, 4, 6, 8, 12, 15, 17, 19, 22, or 24. The invention also encompasses polynucleotide fragments of any of the polynucleotide sequences provided herein.

The present invention encompasses polypeptide sequences which comprise, or alternatively consist of, an amino acid sequence which is at least 70%, 75%, 80%, 85%, 90%, 91%, 92%, 93%, 94%, 95%, 96%, 97%, 98%, or 99% identical to, the following non-limited examples, the polypeptide sequence identified as SEQ ID NO: 2, 4, 6, 8, 12, 15, 17, 19, 22, or 24, and/or polypeptide fragments of any of the polypeptides provided herein.

Preferably, the present invention is directed to an isolated or recombinant polynucleotide wherein the polynucleotide comprises a nucleotide sequence selected from the group consisting of a polynucleotide as set forth in SEQ ID NO: 1, 3, 5, 7, 11, 14, 16, 18, 21, or 23; or a polynucleotide encoding the polypeptide as set forth in SEQ ID NO: 2, 4, 6, 8, 12, 15, 17, 19, 22, or 24.

The term "sequence identity" refers to the degree to which two polynucleotide or polypeptide sequences are identical on a nucleotide-by-nucleotide or residue-by-residue basis over a particular region of comparison. The term "percentage of sequence identity" is calculated by comparing two optimally aligned sequences over that region of comparison (e.g., gaps can be introduced in either of the sequences being compared for optimal alignment between the sequences). The amino acid residues or nucleotides at corresponding amino acid positions or nucleotide positions are then compared. The number of positions at which the identical nucleic acid base (e.g., A, T, C, G, U, or I, in the case of nucleic acids) or amino acid residue occurs in both sequences is determined to yield the number of matched positions, dividing the number of matched positions by the total number of positions in the region of comparison (i.e., the window size), and multiplying the result by 100 to yield the percentage of sequence identity. As used herein amino acid or nucleic acid "homology" is equivalent to amino acid or nucleic acid "identity."

As a practical matter, whether any particular nucleic acid molecule or polypeptide is at least 70%, 75%, 80%, 85%, 90%, 91%, 92%, 93%, 94%, 95%, 96%, 97%, 98%, or 99% identical to a nucleotide sequence or amino acid sequence of the present invention can be determined conventionally using known computer programs. Homology or identity determination using computer programs is well known in the art. The skilled artisan will further appreciate that results may vary depending on the parameters and computer program used.

A preferred method for determining the best overall match between a query sequence (a sequence of the present invention) and a subject sequence, also referred to as a global sequence alignment, can be determined using the EMBOSS Pairwise Alignment Algorithms program (publicly available online at EMBL-EBI (European Bioinformatics Institute)). This program uses the Needleman-Wunsch global alignment algorithm to find the optimum alignment (including gaps) of two sequences when considering their entire length (Needleman, S. B. and Wunsch, C. D. (1970) J. Mol. Biol. 48, 443-453). Preferred parameters used in an EMBOSS Pairwise Alignment of DNA or protein sequences to calculate percent identity are: Matrix=BLOSUM62, Gap Open Penalty=10.0, Gap Extension Penalty=0.1.

The CLUSTALW computer program (Thompson, J. D., et al., Nucleic Acids Research, 2(22):4673-4680, (1994)), which is based on the algorithm of Higgins, D. G., et al., Computer Applications in the Biosciences (CABIOS), 8(2): 189-191, (1992), can also be used. In a sequence alignment the query and subject sequences are both DNA sequences. An RNA sequence can be compared by converting U's to T's. The result of said global sequence alignment is in percent identity. Preferred parameters used in a CLUSTALW alignment of DNA or protein sequences to calculate percent identity are: Matrix=BLOSUM, k-tuple=1, Number of Top Diagonals=5, Gap Penalty=3, Gap Open Penalty 10, Gap Extension Penalty=0, Scoring Method=Percent, Window Size=5 or the length of the subject sequence, whichever is shorter.

If the subject sequence is shorter than the query sequence because of 5' or 3' deletions, not because of internal deletions, a manual correction must be made to the results. This is because the CLUSTALW program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the CLUSTALW sequence alignment. This percentage is then subtracted from the percent identity, calculated by the above CLUSTALW program using the specified parameters, to arrive at a final percent identity score. This corrected score is what may be used for the purposes of the present invention. Only bases outside the 5' and 3' bases of the subject sequence, as displayed by the CLUSTALW alignment, which are not matched/aligned with the query sequence, are calculated for the purposes of manually adjusting the percent identity score.

For example, by a nucleic acid having a nucleotide sequence at least 95% "identical" to a reference nucleotide sequence of the present invention, it is intended that the nucleotide sequence of the nucleic acid is identical to the reference sequence except that the nucleotide sequence may include up to five point mutations per each 100 nucleotides of the reference nucleotide sequence encoding the polypeptide. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence of one of the sequences of the invention, the ORF (open reading frame), or any fragment specified as described herein.

As another example, by a polypeptide having an amino acid sequence at least, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

In another embodiment, derivatives and analogs may be full length or other than full length, if the derivative or analog contains a modified nucleic acid or amino acid. Derivatives or analogs of the nucleic acids or proteins of the invention include, but are not limited to, molecules comprising regions that are substantially homologous to the nucleic acids or proteins of the invention, in various embodiments, by at least about 70%, 80%, 85%, 90%, 95%, 98%, or even 99% identity (with a preferred identity of 80-99%) over a nucleic acid or amino acid sequence of identical size or when compared to an aligned sequence in which the alignment is done by a computer homology program known in the art, or whose encoding nucleic acid is capable of hybridizing to the complement of a sequence encoding the aforementioned proteins under stringent, moderately stringent, or low stringent conditions. See e.g. Ausubel, et al., CURRENT PROTOCOLS IN MOLECULAR BIOLOGY, John Wiley & Sons, New York, N.Y., 1993, and below. An exemplary program is the Gap program (Wisconsin Sequence Analysis Package, Version 8 for UNIX, Genetics Computer Group, University Research Park, Madison, Wis.) using the default settings, which uses the algorithm of Smith and Waterman (Adv. Appl. Math., 1981, 2: 482-489, which is incorporated herein by reference in its entirety).

A "homologous nucleic acid sequence" or "homologous amino acid sequence," or variations thereof, refer to sequences characterized by a homology at the nucleotide level or amino acid level as discussed above. Homologous nucleotide sequences encode those sequences coding for isoforms of a PrPase polypeptide. Isoforms can be expressed in different tissues of the same organism as a result of, for example, alternative splicing of RNA. Alternatively, isoforms can be encoded by different genes. Homologous nucleotide sequences also include, but are not limited to, naturally occurring allelic variations and mutations of the nucleotide sequences set forth herein. Exemplary homologous nucleic acid sequences include the nucleic acid sequences of SEQ ID NO: 84, 86, 88, and 90. Homologous nucleic acid sequences include those nucleic acid sequences that encode conservative amino acid substitutions in sequences of the invention, as well as a polypeptide having PrPase activity, e.g. substrate binding.

The variants may contain alterations in the coding regions, non-coding regions, or both. Especially preferred are polynucleotide variants containing alterations which produce silent substitutions, additions, or deletions, but do not alter substantially the properties or activities of the encoded polypeptide. Nucleotide variants produced by silent substitutions due to the degeneracy of the genetic code are preferred. Moreover, variants in which 5-10, 1-5, or 1-2 amino acids are substituted, deleted, or added in any combination are also preferred. Polynucleotide variants can be produced for a variety of reasons, e.g., to optimize codon expression for a particular host (change codons in the mRNA to those preferred by a bacterial host such as *E. coli*).

Naturally occurring variants are called "allelic variants," and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level and are included in the present invention. Alternatively, non-naturally occurring variants may be produced by mutagenesis techniques or by direct synthesis.

In addition to the *Arabidopsis thaliana, Physcomitrella patens, Brassica napus, Zea mays*, or *Glycine max* PrPase nucleotide sequence shown in SEQ ID NO: 1, 3, 5, 7, 11, 14, 16, 18, 21, or 23, it will be appreciated by those skilled in the art that DNA sequence polymorphisms that lead to changes in the amino acid sequences of PrPase may exist within a population (e.g., of the plant). Such genetic polymorphism in the PrPase gene may exist among individuals within a population due to natural allelic variation. As used herein, the terms "gene" and "recombinant gene" refer to nucleic acid molecules comprising an open reading frame encoding a PrPase protein, preferably a plant PrPase protein. Such natural allelic variations can typically result in 1-5% variance in the nucleotide sequence of the PrPase gene. Any and all such nucleotide variations and resulting amino acid polymorphisms in PrPase that are the result of natural allelic variation and that do not alter the functional activity of PrPase are intended to be within the scope of the invention.

Moreover, nucleic acid molecules encoding PrPase proteins from other species, and thus that have a nucleotide sequence that differs from the sequences of the invention are intended to be within the scope of the invention. Nucleic acid molecules corresponding to natural allelic variants and homologues of the PrPase polynucleotides of the invention can be isolated based on their homology to the *Arabidopsis thaliana, Physcomitrella patens, Brassica napus, Zea mays*, or *Glycine max* PrPase nucleic acids disclosed herein using the cDNAs, or a portion thereof, as a hybridization probe according to standard hybridization techniques under stringent hybridization conditions.

In addition to naturally-occurring allelic variants of the PrPase sequence that may exist, the skilled artisan will further appreciate that changes can be introduced by mutation into the nucleotide sequences of the invention, thereby leading to changes in the amino acid sequence of the encoded PrPase protein, without significantly altering the function of the PrPase protein. For example, nucleotide substitutions leading to amino acid substitutions at "non-essential" amino acid residues can be made in the sequence of SEQ ID NO: 1, 3, 5, 7, 11, 14, 16, 18, 21, or 23. A "non-essential" amino acid residue is a residue that can be altered from the wild-type sequence of PrPase without substantially altering the biological activity, whereas an "essential" amino acid residue is required for biological activity. For example, amino acid residues that are conserved among the PrPase proteins of the present invention are predicted to be less amenable to alteration.

In general, a PrPase-like variant that preserves PrPase-like function includes any variant in which residues at a particular position in the sequence have been substituted by other amino acids, and further include the possibility of inserting an additional residue or residues between two residues of the parent protein as well as the possibility of deleting one or more residues from the parent sequence. Any amino acid substitution, insertion, or deletion is encompassed by the invention. In favorable circumstances, the substitution is a conservative substitution as explained above.

Mutations can be introduced into the nucleotide sequence of SEQ ID NO: 1, 3, 5, 7, 11, 14, 16, 18, 21, or 23 by standard techniques, such as site-directed mutagenesis and PCR-mediated mutagenesis. Following mutagenesis of SEQ ID NO: 1, 3, 5, 7, 11, 14, 16, 18, 21, or 23, the encoded protein can be expressed by any recombinant technology known in the art and the activity of the protein can be determined. For example, a mutant PrPase protein can be assayed for (1) the ability to form protein:protein interactions with other PrPase proteins, other cell-surface proteins, or biologically active portions thereof, (2) complex formation between a mutant PrPase protein and a PrPase receptor; (3) the ability of a mutant PrPase protein to bind to an intracellular target protein or biologically active portion thereof; (e.g., avidin proteins); (4) the ability to bind PrPase protein; or (5) the ability to specifically bind an anti-PrPase protein antibody.

Besides conservative amino acid substitution, variants of the present invention include, but are not limited to, the following: (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as, for example, an IgG Fc fusion region peptide, or leader or secretory sequence, or a sequence facilitating purification. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331-340 (1967); Robbins et al., Diabetes 36: 838-845 (1987); Cleland et al., Crit. Rev. Therapeutic Drug Carrier Systems 10:307-377 (1993).)

Moreover, the invention further includes polypeptide variants created through the application of molecular evolution ("DNA Shuffling") methodology to the polynucleotide disclosed as SEQ ID NO:X, and/or the cDNA encoding the polypeptide disclosed as SEQ ID NO:Y. Such DNA Shuffling technology is known in the art (e.g., WPC, Stemmer, PNAS, 91:10747, (1994)).

A further embodiment of the invention relates to a polypeptide which comprises the amino acid sequence of the present invention having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a peptide or polypeptide to have an amino acid sequence which comprises the amino acid sequence of the present invention, which contains at least one, but not more than 10, 9, 8, 7, 6, 5, 4, 3, 2 or 1 amino acid substitutions. In specific embodiments, the number of additions, substitutions, and/or deletions in the amino acid sequence of the present invention or fragments thereof (e.g., the mature form and/or other fragments described herein), is 1-5, 5-10, 5-25, 5-50, 10-50 or 50-150, conservative amino acid substitutions are preferable.

Polynucleotide and Polypeptide Fragments

The present invention is directed to polynucleotide fragments of the polynucleotides of the invention, in addition to polypeptides encoded therein by said polynucleotides and/or fragments.

In the present invention, a "polynucleotide fragment" refers to a short polynucleotide having a nucleic acid sequence which is a portion of that shown in SEQ ID NO:X (wherein X is any polynucleotide of the invention) or the complementary strand thereto, or is a portion of a polynucleotide sequence encoding the polypeptide of SEQ ID NO:Y (wherein Y is any polypeptide of the invention). The nucleotide fragments of the invention are preferably at least about 15 nt, and more preferably at least about 20 nt, still more preferably at least about 30 nt, and even more preferably, at least about 40 nt, at least about 50 nt, at least about 75 nt, or at least about 150 nt in length. A fragment "at least 20 nt in length," for example, is intended to include 20 or more contiguous bases from the nucleotide sequence shown in SEQ ID NO:X. In this context "about" includes the particularly recited value, a value larger or smaller by several (5, 4, 3, 2, or 1) nucleotides, at either terminus, or at both termini. These nucleotide fragments have uses that include, but are not limited to, as diagnostic probes and primers. Of course, larger fragments (e.g., 50, 150, 500, 600, 2000 nucleotides) are preferred.

Moreover, representative examples of polynucleotide fragments of the invention, include, for example, fragments comprising, or alternatively consisting of, a sequence from about nucleotide number 1-50, 51-100, 101-150, 151-200, 201-250, 251-300, 301-350, 351-400, 401-450, 451-500, 501-550, 551-600, 651-700, 701-750, 751-800, 800-850, 851-900, 901-950, 951-1000, 1001-1050, 1051-1100, 1101-1150, 1151-1200, 1201-1250, 1251-1300, 1301-1350, 1351-1400, 1401-1450, 1451-1500, 1501-1550, 1551-1600, 1601-1650, 1651-1700, 1701-1750, 1751-1800, 1801-1850, 1851-1900, 1901-1950, 1951-2000, or 2001 to the end of SEQ ID NO:X, or the complementary strand thereto. In this context "about" includes the particularly recited ranges, and ranges larger or smaller by several (5, 4, 3, 2, or 1) nucleotides, at either terminus or at both termini. Preferably, these fragments encode a polypeptide which has biological activity. More preferably, these polynucleotides can be used as probes or primers. Also encompassed by the present invention are polynucleotides which hybridize to these nucleic acid molecules under stringent hybridization conditions or lower stringency conditions, as are the polypeptides encoded by these polynucleotides.

In the present invention, a "polypeptide fragment" refers to an amino acid sequence which is a portion of that contained in SEQ ID NO:Y. Protein (polypeptide) fragments may be "free-standing," or comprised within a larger polypeptide of which the fragment forms a part or region, most preferably as a single continuous region. Representative examples of polypeptide fragments of the invention, include, for example, fragments comprising, or alternatively consisting of, from about amino acid number 1-20, 21-40, 41-60, 61-80, 81-100, 102-120, 121-140, 141-160, or 161 to the end of the coding region. Moreover, polypeptide fragments can be about 20, 30, 40, 50, 60, 70, 80, 90, 100, 110, 120, 130, 140, or 150 amino acids in length. In this context "about" includes the particularly recited ranges or values, and ranges or values larger or smaller by several (5, 4, 3, 2, or 1) amino acids, at either extreme or at both extremes. Polynucleotides encoding these polypeptides are also encompassed by the invention.

Preferred polypeptide fragments include the full-length protein. Further preferred polypeptide fragments include the full-length protein having a continuous series of deleted residues from the amino or the carboxy terminus, or both. For example, any number of amino acids, ranging from 1-60, can be deleted from the amino terminus of the full-length polypeptide. Similarly, any number of amino acids, ranging from 1-30, can be deleted from the carboxy terminus of the full-length protein. Furthermore, any combination of the above amino and carboxy terminus deletions are preferred. Similarly, polynucleotides encoding these polypeptide fragments are also preferred.

Alternatively, the nucleic acid molecule of the invention can comprise only a portion of the nucleic acid sequence of SEQ ID NO: 1, 3, 5, 7, 11, 14, 16, 18, 21, or 23, e.g., a fragment that can be used as a probe or primer, or a fragment encoding a biologically active portion of PrPase. Fragments provided herein can also be defined as sequences of at least 6 (contiguous) nucleic acids or at least 4 (contiguous) amino acids, a length sufficient to allow for specific hybridization in the case of nucleic acids or for specific recognition of an epitope in the case of amino acids, respectively, and are at most some portion less than a full length sequence. Fragments may be derived from any contiguous portion of a nucleic acid or amino acid sequence of choice. Derivatives are nucleic acid sequences or amino acid sequences formed from the native compounds either directly or by modification or partial substitution. Analogs are nucleic acid sequences or amino acid sequences that have a structure similar to, but not identical to, the native compound but differs from it in respect to certain components or side chains. Analogs may be synthetic or from a different evolutionary origin and may have a similar or opposite metabolic activity compared to wild type.

Also preferred are polypeptide and polynucleotide fragments characterized by structural or functional domains, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Polypeptide fragments of SEQ ID NO:Y falling within conserved domains are specifically contemplated by the present invention. Moreover, polynucleotides encoding these domains are also contemplated.

Other preferred polypeptide fragments are biologically active fragments. Biologically active fragments are those exhibiting activity similar, but not necessarily identical, to an activity of the polypeptide of the present invention, which can include mature forms, as measured in a particular biological assay, with or without dose dependency. The biological activity of the fragments may include an improved desired activity, or a decreased undesirable activity. Polynucleotides encoding these polypeptide fragments are also encompassed by the invention. A nucleic acid fragment encoding a "biologically active portion of PrPase" can be prepared by isolating a portion of SEQ ID NO: 1, 3, 5, 7, 11, 14, 16, 18, 21, or 23 that encodes a polypeptide having a PrPase biological activity, expressing the encoded portion of PrPase protein (e.g., by recombinant expression in vitro) and assessing the activity of the encoded portion of PrPase. In another embodiment, a nucleic acid fragment encoding a biologically active portion of PrPase includes one or more regions.

In a preferred embodiment, the functional activity displayed by a polypeptide encoded by a polynucleotide fragment of the invention may be one or more biological activities typically associated with the full-length polypeptide of the invention. Illustrative of these biological activities includes the fragments ability to interact with at lease one of the same proteins which bind to the full-length, the fragments ability to bind to at least one of the same polynucleotides as the full-length protein, the fragments ability to bind to a receptor of the full-length protein, the fragments ability to bind to a ligand of the full-length protein, and the fragments ability to multimerize with the full-length protein. However, the skilled artisan would appreciate that some fragments may have biological activities which are desirable and directly inapposite to the biological activity of the full-length protein. The functional activity of polypeptides of the invention, including fragments, variants, derivatives, and analogs thereof can be determined by numerous methods available to the skilled artisan.

Biologically active portions of a PrPase protein include peptides comprising amino acid sequences sufficiently homologous to or derived from the amino acid sequence of the PrPase protein, e.g., the amino acid sequence shown in SEQ ID NO: 8 that include fewer amino acids than the full length PrPase proteins, and exhibit at least one activity of a PrPase protein, e.g. substrate binding. Typically, biologically active portions comprise a domain or motif with at least one activity of the PrPase protein. A biologically active portion of a PrPase protein can be a polypeptide which is, for example, 10, 25, 50, 100 or more amino acids in length.

A biologically active portion of a PrPase protein of the present invention may contain at least one of the above-identified domains conserved between the PrPase proteins. Moreover, other biologically active portions, in which other regions of the protein are deleted, can be prepared by recombinant techniques and evaluated for one or more of the functional activities of a native PrPase protein.

A biologically active portion or a PrPase protein can be the N-terminal domain of the PrPase polypeptide. Alternatively, a biologically active portion or a PrPase protein can be the C-terminal domain of the PrPase polypeptide. Preferably, the biologically active portion comprises at least 75 amino acids of the C-terminal domain. More preferably, the biologically active portion comprises at least 25 amino acids of the C-terminal domain. Most preferably, the biologically active portion comprises at least 10 amino acids of the C-terminal.

In an embodiment, the PrPase protein has an amino acid sequence shown in SEQ ID NO: 2, 4, 6, 8, 12, 15, 17, 19, 22, or 24. In other embodiments, the PrPase protein is substantially homologous to SEQ ID NO: 2, 4, 6, 8, 12, 15, 17, 19, 22, or 24 and retains the functional activity of the protein of SEQ ID NO: 2, 4, 6, 8, 12, 15, 17, 19, 22, or 24, yet differs in amino acid sequence due to natural allelic variation or mutagenesis. Accordingly, in another embodiment, the PrPase protein is a protein that comprises an amino acid sequence at least about 45% homologous to the amino acid sequence of SEQ ID NO: 2, 4, 6, 8, 12, 15, 17, 19, 22, or 24 and retains the functional activity of the PrPase proteins of SEQ ID NO: 2, 4, 6, 8, 12, 15, 17, 19, 22, or 24.

Exemplary homologous PrPase polypeptides include for example the polypeptide sequences of SEQ ID NO: 85, 87, 89, and 91.

Fusion Proteins

The invention also provides PrPase chimeric or fusion proteins, i.e. a PrPase polypeptide (all or portion) fused-in-frame to be linked to a non-PrPase polypeptide. The non-PrPase polypeptide can be fused to the N-terminus or C-terminus of the PrPase polypeptide. A PrPase chimeric or fusion protein of the invention can be produced by standard recombinant DNA techniques. Any polypeptide of the present invention can be used to generate fusion proteins. Moreover, fusion proteins may also be engineered to improve characteristics of the polypeptide of the present invention. The polypeptides of the present invention can also be fused to marker sequences (also referred to as "tags").

Polypeptides of the present invention, including fragments and/or variants thereof, may be fused to any of a number of known, and yet to be determined, toxins, such as ricin, saporin (Mashiba H, et al., Ann NY Acad. Sci. 1999; 886:233-5), HC toxin (Tonukari N J, et al., Plant Cell. 2000 February; 12(2): 237-248), BT endotoxin, or pseudomonas endotoxin. Such fusions could be used to deliver the toxins to desired tissues for which a ligand or a protein capable of binding to the polypeptides of the invention exists.

Polypeptide Libraries

In a further embodiment, libraries of fragments of the PrPase protein coding sequence can be used to generate a variegated population of PrPase fragments for screening and subsequent selection of variants of a PrPase protein. In one embodiment, a library of coding sequence fragments can be generated by treating a double stranded PCR fragment of a PrPase coding sequence with a nuclease under conditions wherein nicking occurs only about once per molecule, denaturing the double stranded DNA, renaturing the DNA to form double stranded DNA that can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the PrPase protein.

Variants of the PrPase protein that function as either PrPase agonists (mimetics) or as PrPase antagonists can be identified by screening combinatorial libraries of mutants, e.g., truncation mutants, of the PrPase protein for PrPase protein agonist or antagonist activity. In one embodiment, a variegated library of PrPase variants is generated by combinatorial mutagenesis at the nucleic acid level and is encoded by a variegated gene library. A variegated library of PrPase variants can be produced by, for example, enzymatically ligating a mixture of synthetic oligonucleotides into gene sequences such that a degenerate set of potential PrPase sequences is expressible as individual polypeptides, or alternatively, as a set of larger fusion proteins (e.g., for phage display) containing the set of PrPase sequences therein. There are a variety of methods which can be used to produce libraries of potential PrPase variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential PrPase sequences. Methods for synthesizing degenerate oligonucleotides are known in the art (see, e.g., Narang (1983) *Tetrahedron* 39:3; Itakura et al. (1984) *Annu Rev Biochem* 53:323; Itakura et al. (1984) *Science* 198:1056; Ike et al. (1983) *Nucl Acid Res* 11:477.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of PrPase proteins and can be amenable to high throughput analysis.

Vectors, Host Cells, and Protein Production

The present invention also relates to vectors containing the polynucleotide of the present invention, host cells, and the production of polypeptides by recombinant techniques. The vector may be, for example, a phage, plasmid, viral, or retroviral vector. Retroviral vectors may be replication competent or replication defective. In the latter case, viral propagation generally will occur only in complementing host cells. As used herein, the term "vector" refers to a nucleic acid molecule capable of transporting another nucleic acid to which it has been linked.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The vectors of the invention can be recombinant expression vectors which comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to includes promoters, enhancers and other expression control elements (e.g., polyadenylation signals). Such regulatory sequences are described, for example, in Goeddel, GENE EXPRESSION TECHNOLOGY: METHODS IN ENZYMOLOGY 185, Academic Press, San Diego, Calif. (1990).

The polynucleotide insert of the present invention should be operatively linked to an appropriate promoter, such as the 35S promoter, the 34S promoter, CMV promoter, phage lambda PL promoter, the *E. coli* lac, trp, phoA and tac promoters, the SV40 early and late promoters, promoters of retroviral LTRs, constitutive promoters, and ABA inducible promoters to name a few. In addition, it may be desirable, or required, in some instances to direct expression of the nucleotide sequence only in certain host cells by having tissue-specific or cell type-specific promoters operably linked to a polynucleotide of the present invention. Examples of suitable plant-expressible promoters selectively expressed in particular tissues or cell types are well known in the art and include, but are not limited to, guard cell specific promoters, seed specific promoters (e.g., WO 89/03887), organ-primordia specific promoters (An et al., Plant Cell, 8:15-30, (1996)), stem-specific promoters (Keller et al., EMBO J., 7:3625-

3633, (1988)), leaf specific promoters (Hudspeth et al., Plant. Mol. Biol., 12:579-589, (1989)), mesophyl-specific promoters (such as the light inducible Rubisco promoters), root-specific promoters (Keller et al., Genes Devel., 3:1639-1646, (1989)), tuber-specific promoters (Keil et al., EMBO J., 8:1323-1330, (1989)), vascular tissue specific promoters (Peleman et al., Gene, 84:359-369, (1989)), meristem specific promoters (such as the promoter of the SHOOTMERISTEMLESS (STM) gene, Long, et al., Nature, 379:66-69, (1996)), primodia specific promoter (such as the Antirrhinum CycD3a gene promoter, Doonan et al., in "Plant Cell Division" (Francis, Duditz, and Inze, Eds), Portland Press, London, (1998)), another specific promoters (WO 89/10396, WO 92/13956, and WO 92/13957), stigma-specific promoters (WO 91/02068), degiscence-zone specific promoters (WO 97/13865), seed-specific promoters (WO 89/03887), etc. Organ-specific promoters are also well known. For example, the patatin class I promoter is transcriptionally activated only in the potato tuber and can be used to target gene expression in the tuber (Bevan, M., 1986, *Nucleic Acids Research* 14:4625-4636). Another potato-specific promoter is the granule-bound starch synthase (GBSS) promoter (Visser, R. G. R, et al., 1991, *Plant Molecular Biology* 17:691-699). Other organ-specific promoters appropriate for a desired target organ can be isolated using known procedures. These control sequences are generally associated with genes uniquely expressed in the desired organ. In a typical higher plant, each organ has thousands of mRNAs that are absent from other organ systems (reviewed in Goldberg, P., 1986, *Trans. R. Soc. London B*314:343).

Further examples of suitable promoters include promoters from genes such as rice actin (McElroy, et al., Plant Cell, 163-171 (1990)); ubiquitin (Christensen, et al., Plant Mol. Biol., 12: 619-632 (1992); and Christensen, et al., Plant Mol. Biol., 18: 675-689 (1992)); pEMU (Last, et al., Theor. Appl. Genet., 81: 581-588 (1991)); MAS (Velten, et al., EMBO J., 3: 2723-2730 (1984)); maize H3 histone (Lepetit, et al., Mol. Gen. Genet., 231: 276-285 (1992); and Atanassvoa, et al., Plant Journal, 2(3): 291-300 (1992)), the Smas promoter, the cinnamyl alcohol dehydrogenase promoter (U.S. Pat. No. 5,683,439), the rubisco promoter, the GRP1-8 promoter, ALS promoter, (WO 96/30530), a synthetic promoter, such as, Rsyn7, SCP and UCP promoters, ribulose-1,3-diphosphate carboxylase, fruit-specific promoters, heat shock promoters. Additional promoters that may be operably linked to a polynucleotide of the present invention may be found in McElroy and Brettel, Tibtech, Vol. 12, February, 1994. Moreover, a number of promoters are currently being used for transformation of dicotyledonous plants. These promoters come from a variety of different sources. One group of commonly used promoters were isolated from *Agrobacterium tumefaciens*, where they function to drive the expression of opine synthase genes carried on the T-DNA segment that is integrated into the plant genome during infection. These promoters include the octopine synthase (ocs) promoter (L. Comai et al., 1985; C. Waldron et al., 1985), the mannopine synthase (mas) promoter (L. Comai et al., 1985; K. E. McBride and K. R. Summerfelt, 1990) and the nopaline synthase (nos) promoter (M. W. Bevan et al., 1983; L. Herrera-Estrella et al., 1983, R. T. Fraley et al., 1983, M. De Block et al., 1984; R. Hain et al., 1985). These promoters are active in a wide variety of plant tissue.

In addition, the promoters disclosed in the following publications may also be operably linked to a polynucleotide of the present invention: U.S. Pat. Nos. 5,623,067; 5,683,439; 5,712,112; 5,723,751; 5,723,754; 5,723,757; 5,744,334; 5,750,385; 5,750,399; 5,767,363; 5,783,393; 5,789,214; 5,792,922; 5,792,933; 5,801,027; 5,804,694; 5,814,618; 5,824,857; 5,824,863; 5,824,865; 5,824,866; 5,824,872; and 5,929,302; and International Publication Nos. WO 96/30530, WO 97/49727, WO 98/00533, WO 98/03655, WO 98/07846, WO 98/08961, WO 98/08962, WO 98/10734, WO 98/16634, WO 98/22593, WO 98/38295, and WO 98/44097; and European Patent Application No. EP 0 846 770.

Several viral promoters are also used to, drive heterologous gene expression in dicots (J. C. Kridl and R. M. Goodman, 1986) and may be operably linked to a polynucleotide of the present invention. The Cauliflower Mosaic Virus 35S promoter is one of the promoters used most often for dicot transformation because it confers high levels of gene expression in almost all tissues (J. Odell et al., 1985; D. W. Ow et al., 1986; D. M. Shah et al., 1986). Modifications of this promoter are also used, including a configuration with two tandem 35S promoters (R. Kay et al., 1987) and the mas-35S promoter (L. Comai et al., 1990), which consists of the mannopine synthase promoter in tandem with the 35S promoter. Both of these promoters drive even higher levels of gene expression than a single copy of the 35S promoter. Other viral promoters that have been used include the Cauliflower Mosaic Virus 19S promoter (J. Paszkowski et al., 1984; E. Balazs et al.; Mogen, et al., 1990, Plant Cell, 2: 1261-1272) and the 34S promoter from the figwort mosaic virus (M. Sanger et al., 1990).

Alternatively, the polynucleotide insert of the present invention could be operatively linked to any of a number of inducible promoters known in the art, which include, but are not limited to: tetracycline inducible promoters, small-molecule inducible promoters, light inducible promoters, chemical compounds (e.g., safeners, herbicides, glucocorticoids, etc.), abiotic stress inducible promoters (e.g., wounding, heavy metals, cold-sensitive promoters, heat-sensitive promoters, salt sensitive promoters, drought sensitive promoters, hypoxia inducible (such as those disclosed in EP 1012317), etc.), biotic stress promoters (e.g., pathogen or pest infection including infection by fungi, viruses, bacteria, insects, nematodes, mycoplasms, and mycoplasma-like organisms, etc.). Examples of plant-expressible inducible promoters suitable for the invention are: nematode inducible promoters (such as those disclosed in WO 92/21757 and/or EP1007709), fungus inducible promoters (WO 93/19188, WO 96/28561), chemically inducible *Arabidopsis* PR-1 promoter (WO 98/03536), the inducible promoters disclosed in WO 98/45445, the inducible promoters disclosed in U.S. Pat. No. 5,804,693, the tomato soft fruit inducible promoter disclosed in U.S. Pat. No. 5,821,398, promoters inducible after application of glucocorticoids such as dexamethasone, or promoters repressed or activated after application of tetracyclin (Gatz et al., PNAS USA, 85:1394-1397, (1988)). Other suitable inducible promoters will be known to the skilled artisan.

Exemplary expression vector constructs include for example the constructs of SEQ ID NO: 41, 42, 52, 53, 55, 56, 57, 58, 60, 61, 63, 64, 66, 67, and 69. Additional exemplary expression vector constructs include constructs comprising PrPase anti-sense nucleic acid such as SEQ ID NO: 51, 54, 59, 62, 65, and 68.

In addition, the polynucleotide insert of the present invention could be operatively linked to "artificial" or chimeric promoters and transcription factors. Specifically, the artificial promoter could comprise, or alternatively consist, of any combination of cis-acting DNA sequence elements that are recognized by trans-acting transcription factors. Preferably, the cis acting DNA sequence elements and trans-acting transcription factors are operable in plants. Further, the trans-acting transcription factors of such "artificial" promoters could also be "artificial" or chimeric in design themselves and could act as activators or repressors to said "artificial" promoter. For example, a chimeric promoter of the invention could comprise one or more, upstream activating sequences from the Octopine Synthase gene (OCS), matrix attachment regions (MAR), etc.

One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication). Other vectors are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors or plant transformation vectors, binary or otherwise, which serve equivalent functions.

The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

The expression constructs may additionally comprise 5' leader sequences in the expression constructs. Such leader sequences can act to enhance translation. Translation leaders are known in the art and include: picornavirus leaders, for example, EMCV leader (Encephalomyocarditis 5' noncoding region) (Elroy-Stein, O., Fuerst, T. R., and Moss, B. (1989) PNAS USA, 86:6126-6130); polyvirus leaders, for example, TEV leader (Tobacco Etch Virus) (Allison et al. (1986)); MDMV leader (Maize Dwarf Mosaic Virus) (Virology, 154: 9-20); and human immunoglobulin heavy-chain binding protein (BiP), (Macejak, D. G., and Sarnow, P. (1991) Nature, 353:90-94); untranslated leader from the coat protein mRNA of alfalfa mosaic virus (AMV RNA 4), (Jobling, S. A., and Gehrke, L., (1987) Nature, 325:622-625); tobacco mosaic virus leader (TW), (Gallie, D. R. et al. (1989) Molecular Biology of RNA, pages 237-256); and maize chlorotic mottle virus leader (MCNW) (Lommel, S. A. et al. (1991) Virology, 81:382-385). See also, Della-Cioppa et al. (1987) Plant Physiology., 84:965-968. Other methods known to enhance translation can also be utilized, for example, introns, and the like.

Additional regulatory elements that may be connected to a PrPase encoding nucleic acid sequence for expression in plant cells include terminators, polyadenylation sequences, and nucleic acid sequences encoding signal peptides that permit localization within a plant cell or secretion of the protein from the cell. Such regulatory elements and methods for adding or exchanging these elements with the regulatory elements PrPase gene are known, and include, but are not limited to, 3' termination and/or polyadenylation regions such as those of the *Agrobacterium tumefaciens* nopaline synthase (nos) gene (Bevan, et al., Nucl. Acids Res., 12: 369-385 (1983)); the potato proteinase inhibitor II (PINII) gene (Keil, et al., Nucl. Acids Res., 14: 5641-5650 (1986) and hereby incorporated by reference); and An, et al., Plant Cell, 1: 115-122 (1989)); and the CaMV 19S gene (Mogen, et al., Plant Cell, 2: 1261-1272 (1990)).

As indicated, the expression vectors will preferably include at least one selectable marker. Such markers include, but are not limited to, dihydrofolate reductase, G418 or neomycin resistance, kanamycin resistance, hygromycin resistance, bialaphos resistance, sulfonoamide resistance, stretomycin resistance, spectinomycin resistance, chlorosulfuron resistance, glyphosphate resistance, and methotrexate resistance, for eukaryotic cell culture and tetracycline, kanamycin or ampicillin resistance genes for culturing in *E. coli* and other bacteria. Markers may also include resistance to bleomycin and gentamicin. For Example, after transforming plant cells, those cells having the vector will be identified by their ability to grow on a medium containing the particular antibiotic/marker. Replication sequences, of bacterial or viral origin, are generally also included to allow the vector to be cloned in a bacterial or phage host, preferably a broad host range prokaryotic origin of replication is included. A selectable marker for bacteria should also be included to allow selection of bacterial cells bearing the desired construct.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

Representative examples of appropriate hosts include, but are not limited to, bacterial cells, such as *E. coli, Streptomyces, Bacillus subtilis*, and *Salmonella typhimurium* cells (or any bacterial strain capable of expressing heterologous polypeptides); fungal cells, such as yeast cells (e.g., *Saccharomyces cerevisiae, Pichia pastoris* (ATCC Accession No. 201178), *Schizosaccharomyces pombe, Kluyveromyces strains, Candida*, or any yeast strain capable of expressing heterologous proteins); insect cells such as *Drosophila* S2 and *Spodoptera* Sf9 cells; plant cells, and specifically plant cells and/or tissues derived from any of the plants listed in Table 3. Plant host cells include, for example, plant cells that could function as suitable hosts for the expression of a polynucleotide of the invention include epidermal cells, mesophyll and other ground tissues, and vascular tissues in leaves, stems, floral organs, and roots. Appropriate culture mediums and conditions for the above-described host cells are known in the art.

The polynucleotides and polypeptides of the present invention can be targeted to the chloroplast or amyloplast for expression. In this manner, the expression construct will additionally contain a polynucleotide sequence encoding a transit peptide operably linked to a polynucleotide of the present invention to direct the polynucleotide of the present invention to the chloroplasts. Such transit peptides are known in the art. See, for example, Von Heijne et al. (1991) Plant Mol. Biol. Rep. 9:104-126; Clark et al. (1989) J. Biol. Chem. 264: 17544-17550; Della-Cioppa et al. (1987) Plant Physiol. 84:965-968; Romer et al. (1993) Biochem. Biophys. Res Commun. 196:1414-1421; and Shah et al. (1986) Science 233:478-481.

The expression construct may also comprise any other necessary regulators such as nuclear localization signals (Kalderon et al. (1984) Cell 39:499-509; and Lassner et al. (1991) Plant Molecular Biology 17:229-234); plant translational consensus sequences (Joshi, C. P. (1987) Nucleic Acids Research 15:6643 6653), introns (Luehrsen and Walbot (1991) Mol. Gen. Genet. 225:81-93) and the like, operably linked to a polynucleotide of the present invention.

Plant signal sequences, including, but not limited to, signal-peptide encoding DNA/RNA sequences which target proteins to the extracellular matrix of the plant cell (Dratewka-Kos, et al., J. Biol. Chem., 264: 4896-4900 (1989)) and the *Nicotiana plumbaginifolia* extension gene (DeLoose, et al., Gene, 99: 95-100 (1991)), or signal peptides which target proteins to the vacuole like the sweet potato sporamin gene (Matsuka, et al., Proc. Nat'l Acad. Sci. (USA), 88: 834 (1991)) and the barley lectin gene (Wilkins, et al., Plant Cell, 2: 301-313 (1990)), or signals which cause proteins to be secreted such as that of PRIb (Lind, et al., Plant Mol. Biol., 18: 47-53 (1992)), or those which target proteins to the plastids such as that of rapeseed enoyl-ACP reductase (Verwaert, et al., Plant Mol. Biol., 26: 189-202 (1994)) are useful in the invention.

It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., PrPase proteins, mutant forms of PrPase proteins, fusion proteins, etc.).

The recombinant expression vectors of the invention can be designed for expression of PrPase proteins in prokaryotic or eukaryotic cells. For example, PrPase proteins can be expressed in bacterial cells such as *Escherichia coli*, insect cells (using baculovirus expression vectors) yeast cells, plant cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

The polynucleotide sequences encoding the proteins or polypeptides of the present invention may be particularly useful in the genetic manipulation of plants. In this manner, the polynucleotides of the invention are provided in expression cassettes for expression in the plant of interest. Where appropriate, the gene(s) may be optimized for increased expression in the transformed plant. That is, the polynucleotides can be synthesized using plant preferred codons for improved expression specific to a particular species. Methods are available in the art for synthesizing plant preferred genes. See, for example, U.S. Pat. Nos. 5,380,831, 5,436,391, and Murray et al. (1989) Nucleic Acids Res. 17:477-498, herein incorporated by reference.

Depending upon the species in which the DNA sequence of interest is to be expressed, it may be desirable to synthesize the sequence with plant preferred codons, or alternatively with chloroplast preferred codons. The plant preferred codons may be determined from the codons of highest frequency in the proteins expressed in the largest amount in the particular plant species of interest. See, EPA 0359472; EPA 0385962; WO 91/16432; Perlak et al. (1991) Proc. Natl. Acad. Sci. USA 88:3324-3328; and Murray et al. (1989) Nucleic Acids Research. In this manner, the polynucleotide sequences can be optimized for expression in any plant. It is recognized that all or any part of the gene sequence may be optimized or synthetic. That is, synthetic or partially optimized sequences may also be used.

Additionally, it may be desirable to selectively express a polypeptide of the present invention in a specific target cell or tissue of a plant by synthesizing the encoding polynucleotide sequence to contain codons optimized for high translational efficiency within the particular target cell or tissue. Such methods are known in the art and are specifically provided in PCT International Publication No. WO 00/42190 (which is hereby incorporated herein by reference).

Additional sequence modifications are known to enhance gene expression in a cellular host. These include elimination of sequences encoding spurious polyadenylation signals, exon-intron splice site signals, transposon like repeats, and other such well-characterized sequences that may be deleterious to gene expression. The G-C content of the sequence may be adjusted to levels average for a given cellular host, as calculated by reference to known genes expressed in the host cell. When possible, the sequence may be modified to avoid predicted hairpin secondary mRNA structures.

For in situ production of the antisense mRNA of GST, those regions of the glutathione S-transferase ("GST") gene which are transcribed into GST mRNA, including the untranslated regions thereof, are inserted into the expression vector under control of the promoter system in a reverse orientation. The resulting transcribed mRNA is then complementary to that normally produced by the plant.

Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988. *Gene* 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) *Gene* 69:301-315) and pET 11d (Studier et al., GENE EXPRESSION TECHNOLOGY: METHODS IN ENZYMOLOGY 185, Academic Press, San Diego, Calif. (1990) 60-89).

One strategy to maximize recombinant protein expression in *E. coli* is to express the protein in a host bacteria with an impaired capacity to proteolytically cleave the recombinant protein. See, e.g., Gottesman, GENE EXPRESSION TECHNOLOGY: METHODS IN ENZYMOLOGY 185, Academic Press, San Diego, Calif. (1990) 119-128. Another strategy is to alter the nucleic acid sequence of the nucleic acid to be inserted into an expression vector so that the individual codons for each amino acid are those preferentially utilized in *E. coli* (see, e.g., Wada, et al., 1992. *Nucl. Acids Res.* 20: 2111-2118). Such alteration of nucleic acid sequences of the invention can be carried out by standard DNA synthesis techniques.

Among vectors preferred for use in bacteria include pQE70, pQE60 and pQE-9, available from QIAGEN, Inc.; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Preferred expression vectors for use in yeast systems include, but are not limited to pYES2, pYD1, pTEF1/Zeo, pYES2/GS, pPICZ, pGAPZ, pGAPZalph, pPIC9, pPIC3.5, pHIL-D2, pHIL-S1, pPIC3.5K, pPIC9K, and PAO815 (all available from Invitrogen, Carlbad, Calif.).

In another embodiment, the PrPase expression vector is a yeast expression vector. Examples of vectors for expression in yeast *Saccharomyces cerivisiae* include pYepSec1 (Baldari, et al., 1987. *EMBO J.* 6: 229-234), pMFa (Kurjan and Herskowitz, 1982. *Cell* 30: 933-943), pJRY88 (Schultz et al., 1987. *Gene* 54: 113-123), pYES2 (Invitrogen Corporation, San Diego, Calif.), and picZ (InVitrogen Corp, San Diego, Calif.).

Alternatively, PrPase can be expressed in insect cells using baculovirus expression vectors.

In a preferred embodiment, a nucleic acid of the invention is expressed in plants cells using a plant expression vector. Examples of plant expression vectors systems include tumor inducing (Ti) plasmid or portion thereof found in *Agrobacterium*, cauliflower mosaic virus (CAMV) DNA and vectors such as pBI121. Preferred expression vectors in plant systems include, but are not limited to, Bin 19 (ATCC Deposit No: 37327), GA437 (ATCC Deposit No: 37350), pAK1003 (ATCC Deposit No: 37425), pAS2022 (ATCC Deposit No: 37426), pAS2023 (ATCC Deposit No: 37427), pAP2034 (ATCC Deposit No: 37428), pC22 (ATCC Deposit No: 37493), pHS24 (ATCC Deposit No: 37841), pHS85 (ATCC Deposit No: 37842), pPM1 (ATCC Deposit No: 40172), pGV3111SE (ATCC Deposit No: 53213), pCGN978 (ATCC Deposit No: 67064), pFL61 (ATCC Deposit No: 77215), pGPTV-KAN (ATCC Deposit No: 77388), pGPTV-HPT (ATCC Deposit No: 77389), pGPTV-DHFR (ATCC Deposit No: 77390), pGPTV-BAR (ATCC Deposit No: 77391), pGPTV-BLEO (ATCC Deposit No: 77392), and/or pPE1000 (ATCC Deposit No: 87573). The skilled artisan would appreciate that any of the above vectors could easily be modified to either include or delete specific elements as may be required for operability. Other suitable vectors will be readily apparent to the skilled artisan.

For expression in plants, the recombinant expression cassette will contain in addition to the PrPase nucleic acids, a plant promoter region, a transcription initiation site (if the coding sequence to transcribed lacks one), and a transcription termination/polyadenylation sequence. The termination/polyadenylation region may be obtained from the same gene as the promoter sequence or may be obtained from different genes. Unique restriction enzyme sites at the 5' and 3' ends of the cassette are typically included to allow for easy insertion into a pre-existing vector.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell.

Introduction of the construct into the host cell can be effected by biolistic transformation (Klein et al., Nature, 327: 70-73 (1987)), PEG-mediated transfection (Paskowski, et al., EMBO J., 3:2717, (1984)), calcium phosphate transfection, DEAE-dextran mediated transfection, cationic lipid-mediated transfection, electroporation (Fromm, et al., PNAS, USA, 82:5824 (1985)), transduction, infection, *Agrobacterium tumefaciens*-directed infection, or other methods. Such methods are described in many standard laboratory manuals, such as Davis et al., Basic Methods in Molecular Biology (1986).

A polypeptide of this invention can be recovered and purified from recombinant cell cultures by well-known methods.

Alternatively, a polypeptide or protein may also be expressed in a form which will facilitate purification. Polypeptides of the present invention, can also be recovered from: products purified from natural sources, including tissues and cells, whether directly isolated or cultured; products of chemical synthetic procedures; and products produced by recombinant techniques from a prokaryotic or eukaryotic host, including, for example, bacterial, yeast, and higher plant cells.

The present invention encompasses polynucleotides of the present invention that are chemically synthesized, or reproduced as peptide nucleic acids (PNA), or according to other methods known in the art. The use of PNAs would serve as the preferred form if the polynucleotides are incorporated onto a solid support, or gene chip. For the purposes of the present invention, a peptide nucleic acid (PNA) is a polyamide type of DNA analog and the monomeric units for adenine, guanine, thymine and cytosine are available commercially (Perceptive Biosystems). Certain components of DNA, such as phosphorus, phosphorus oxides, or deoxyribose derivatives, are not present in PNAs. As disclosed by P. E. Nielsen, M. Egholm, R. H. Berg and O. Buchardt, Science 254, I497 (1991); and M. Egholm, O. Buchardt, L. Christensen, C. Behrens, S. M. Freier, D. A. Driver, R. H. Berg, S. K. Kim, B. Norden, and P. E. Nielsen, Nature 365, 666 (1993), PNAs bind specifically and tightly to complementary DNA strands and are not degraded by nucleases. In fact, PNA binds more strongly to DNA than DNA itself does. This is probably because there is no electrostatic repulsion between the two strands, and also the polyamide backbone is more flexible. Because of this, PNA/DNA duplexes bind under a wider range of stringency conditions than DNA/DNA duplexes, making it easier to perform multiplex hybridization. Smaller probes can be used than with DNA due to the stronger binding characteristics of PNA:DNA hybrids. In addition, it is more likely that single base mismatches can be determined with PNA/DNA hybridization because a single mismatch in a PNA/DNA 15-mer lowers the melting point ($T_m$) by 8°-20° C., vs. 4°-16° C. for the DNA/DNA 15-mer duplex. Also, the absence of charge groups in PNA means that hybridization can be done at low ionic strengths and reduce possible interference by salt during the analysis.

In addition, polypeptides, analogs, derivatives, and/or fragments of the invention can be chemically synthesized.

Each of the polynucleotides identified herein can be used in numerous ways as reagents, including for chromosome identification and mapping, as a diagnostic or prognostic marker, for control of gene expression through triple helix formation or antisense DNA or RNA, for producing a new trait in the host cell, for identifying organisms from minute biological samples, as polymorphic markers, for identifying the source of a particular tissue.

In preferred embodiments, the polynucleotides are used for modulating, inhibiting, increasing, decreasing, or introducing traits in a plant including one or more of drought tolerance, UV tolerance, flower development, terpene synthesis, abiotic stressed tolerance, heat stress tolerance, cold stress tolerance, nutritional stress tolerance, xenobiotic stress tolerance, protein storage capability, oil storage capability, amino acid content, amino acid composition, carbohydrate storage capability, oil content, oil composition, carbohydrate content, carbohydrate composition, fiber content, fiber composition, metabolite content, metaboliter composition, vitamin content, and/or vitamin composition. The polynucleotides of the invention, are useful in modulating plant yield, plant development, plant differentiation, root growth, root morphology, plant color, plant aroma, plant flavor, palatability of plant tissue, plant organoleptic properties, may be useful in phytoremediation, and/or plant defense. Moreover, the polypeptides of the invention may also be useful in modulating the plants ability to serve as a plant neutriceutical, pharmaceutical, or phytoceutical. Alternatively, polypeptides of the invention may also be useful in modulating the plants ability to produce plant neutriceuticals, pharmaceuticals, or phytoceuticals of either endogenous or exogenous origin (e.g., from another plant species, a human, a mammal, an animal, or other organism). In these contexts, the term "plant" may be applied to mean any plant cell, plant tissue, plant fluid, or plant feature, and includes plant infection structures, which may include, but are not limited to an appressorium, a gall, a canker, and/or nodules. In these contexts, the term "modulate" may be applied to mean the qualitative or quantitative increase, decrease, introduction of, inhibition of, complete loss of, or over-expression of a specific trait or characteristic.

Each of the polypeptides identified herein can be used in numerous ways appreciated by those skilled in the art, including assaying protein levels in a biological sample using antibody-based techniques and in vivo imaging.

The PrPase proteins can be used to screen compounds that modulate the PrPase protein activity or expression. In addition, anti-PrPase antibodies can be made and used to detect and isolate PrPase proteins and modulate PrPase activity.

Another aspect of the present invention relates to methods for the introduction of nucleic acid (DNA, RNA, and antisense DNA or RNA) sequences into an organism, preferably a plant, to achieve expression of a polypeptide of the present invention. This method requires a polynucleotide which codes for a polypeptide of the invention operatively linked to a promoter and other genetic elements necessary for the expression of the polypeptide by the organism or a target tissue. Such transgenic and delivery techniques are known in the art, see, for example, WO90/11092, which is herein incorporated by reference.

The polynucleotide constructs can be delivered by any method that delivers materials to the cells of an organism, such as, biolistic injection into the plant tissues (apical meristem, root, flower, stem, and the like). The polynucleotide constructs may be delivered in an acceptable liquid or aqueous carrier.

In one embodiment, the polynucleotide of the invention is delivered as a naked polynucleotide. The term "naked" polynucleotide, DNA or RNA refers to sequences that are free from any delivery vehicle that acts to assist, promote or facilitate entry into the cell, including viral sequences, viral particles, liposome formulations, lipofectin or precipitating agents and the like. However, the polynucleotides of the invention can also be delivered in liposome formulations and lipofectin formulations and the like can be prepared by methods well known to those skilled in the art. Such methods are described, for example, in U.S. Pat. Nos. 5,593,972, 5,589,466, and 5,580,859, which are herein incorporated by reference.

The polynucleotide vector constructs of the invention may integrate into the host genome and may replicate. Appropriate vectors include pWLNEO, pSV2CAT, pOG44, pXT1 and pSG available from Stratagene; pSVK3, pBPV, pMSG and pSVL available from Pharmacia; and pEF1/V5, pcDNA3.1, and pRc/CMV2 available from Invitrogen. Other suitable vectors will be readily apparent to the skilled artisan.

Any strong promoter known to those skilled in the art can be used for driving the expression of polynucleotide sequence of the invention. Suitable promoters include the 35S, 34S, and actin promoters, in addition to any other promoter known in the art and/or described elsewhere herein. The promoter also may be the native promoter for the polynucleotides of the invention.

The naked polynucleotides are delivered by any method known in the art, including, but not limited to, direct injection, direct needle injection at the delivery site, topical administration, and so-called "gene guns". These delivery methods are known in the art.

The constructs may also be delivered with delivery vehicles such as viral sequences, viral particles, liposome formulations, lipofectin, precipitating agents, etc. Such methods of delivery are known in the art.

In certain embodiments, cells are engineered, ex vivo or in vivo, using a retroviral particle containing RNA that comprises a sequence encoding polypeptides of the invention. Retroviral integration has been detected to occur in plants based upon the identification of a pararetrovirus sequences within the tobacco genome. Since such integration was determined to occur at very limited integration sites, such a pararetrovirus may represent a desirable genetic transformation vehicle for the polynucleotides of the present invention (Jakowitsch, J., et al., PNAS 96(23):13241-6 (1999).

The present invention also encompasses the application of retrotransposons to the genetic transformation of plants. The retrotransposons would preferably represent retrotransposons with known plant host range and would comprise polynucleotides encoding polypeptides of the present invention. Many retrotransposons are known in the art, some of which are described by Bennetzen J L, Trends Microbiol., 4(9):347-53 (1996) which is hereby incorporated herein by reference.

Polynucleotide constructs are made using standard techniques known in the art.

Preferably, the polynucleotide encoding a polypeptide of the invention contains a secretory signal sequence that facilitates secretion of the protein. Typically, the signal sequence is positioned in the coding region of the polynucleotide to be expressed towards or at the 5' end of the coding region. The signal sequence may be homologous or heterologous to the polynucleotide of interest and may be homologous or heterologous to the cells to be transformed. Additionally, the signal sequence may be chemically synthesized using methods known in the art.

Plant Transformation

The invention includes protoplast, plants cells, plant tissue and plants (e.g., monocots and dicots) transformed with a PrPase nucleic acid, a vector containing a PrPase nucleic acid or an expression vector containing a PrPase nucleic acid (i.e., sense or antisense). As used herein, "plant" is meant to include not only a whole plant but also a portion thereof (i.e., cells, and tissues, including for example, leaves, stems, shoots, roots, flowers, fruits and seeds and the progeny derived therefrom).

The plant can be any plant type including, for example, species from the genera *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocal-*

*lis, Nemesis, Pelargonium, Panieum, Pennisetum, Ranunculus, Senecio, Salpiglossis, Cucumis, Browaalia, Glycine, Pisum, Phaseolus, Lolium, Oryza, Zea, Avena, Hordeum, Secale, Triticum, Sorghum, Gossypium, Picea, Caco,* and *Populus.*

Preferred plants, may include the following non-limiting examples, including barley, oats, rye, sorghum, pea, sunflower, tobacco, cotton, petunia, tomato, broccoli, lettuce, apple, plum, orange, and lemon, and more preferably rice, maize, conola, wheat, sugarbeet, sugarcane, and soybean, in addition to other plants known in the art and referenced more particularly elsewhere herein (e.g., Table 3).

Non-limiting examples of suitable recipient plants for introducing polynucleotides of the invention, polynucleotides encoding the polypeptides of the invention, and/or fragments, and variants therein, are listed in Table 3 below:

TABLE 3

RECIPIENT PLANTS

| COMMON NAME | FAMILY | LATIN NAME |
|---|---|---|
| Maize | Gramineae | *Zea mays* |
| Maize, Dent | Gramineae | *Zea mays dentiformis* |
| Maize, Flint | Gramineae | *Zea mays vulgaris* |
| Maize, Pop | Gramineae | *Zea mays microsperma* |
| Maize, Soft | Gramineae | *Zea mays amylacea* |
| Maize, Sweet | Gramineae | *Zea mays amyleasaccharata* |
| Maize, Sweet | Gramineae | *Zea mays saccharate* |
| Maize, Waxy | Gramineae | *Zea mays ceratina* |
| Wheat, Dinkel | Pooideae | *Triticum spelta* |
| Wheat, Durum | Pooideae | *Triticum durum* |
| Wheat, English | Pooideae | *Triticum turgidum* |
| Wheat, Large Spelt | Pooideae | *Triticum spelta* |
| Wheat, Polish | Pooideae | *Triticum polonium* |
| Wheat, Poulard | Pooideae | *Triticum turgidum* |
| Wheat, Singlegrained | Pooideae | *Triticum monococcum* |
| Wheat, Small Spelt | Pooideae | *Triticum monococcum* |
| Wheat, Soft | Pooideae | *Triticum aestivum* |
| Rice | Gramineae | *Oryza sativa* |
| Rice, American Wild | Gramineae | *Zizania aquatica* |
| Rice, Australian | Gramineae | *Oryza australiensis* |
| Rice, Indian | Gramineae | *Zizania aquatica* |
| Rice, Red | Gramineae | *Oryza glaberrima* |
| Rice, Tuscarora | Gramineae | *Zizania aquatica* |
| Rice, West African | Gramineae | *Oryza glaberrima* |
| Barley | Pooideae | *Hordeum vulgare* |
| Barley, Abyssinian Intermediate, also Irregular | Pooideae | *Hordeum irregulare* |
| Barley, Ancestral Tworow | Pooideae | *Hordeum spontaneum* |
| Barley. Beardless | Pooideae | *Hordeum trifurcatum* |
| Barley, Egyptian | Pooideae | *Hordeum trifurcatum* |
| Barley, fourrowed | Pooideae | *Hordeum vulgare polystichon* |
| Barley, sixrowed | Pooideae | *Hordeum vulgare hexastichon* |
| Barley, Tworowed | Pooideae | *Hordeum distichon* |
| Cotton, Abroma | Dicotyledoneae | *Abroma augusta* |
| Cotton, American Upland | Malvaceae | *Gossypium hirsutum* |
| Cotton, Asiatic Tree, also Indian Tree | Malvaceae | *Gossypium arboreum* |
| Cotton, Brazilian, also, Kidney, and, Pernambuco | Malvaceae | *Gossypium barbadense brasiliense* |
| Cotton, Levant | Malvaceae | *Gossypium herbaceum* |
| Cotton, Long Silk, also Long Staple, Sea Island | Malvaceae | *Gossypium barbadense* |
| Cotton, Mexican, also Short Staple | Malvaceae | *Gossypium hirsutum* |
| Soybean, Soya | Leguminosae | *Glycine max* |
| Sugar beet | Chenopodiaceae | *Beta vulgaris altissima* |
| Sugar cane | Woody-plant | *Arenga pinnata* |
| Tomato | Solanaceae | *Lycopersicon esculentum* |

TABLE 3-continued

RECIPIENT PLANTS

| COMMON NAME | FAMILY | LATIN NAME |
|---|---|---|
| Tomato, Cherry | Solanaceae | *Lycopersicon esculentum cerasiforme* |
| Tomato, Common | Solanaceae | *Lycopersicon esculentum commune* |
| Tomato, Currant | Solanaceae | *Lycopersicon pimpinellifolium* |
| Tomato, Husk | Solanaceae | *Physalis ixocarpa* |
| Tomato, Hyenas | Solanaceae | *Solanum incanum* |
| Tomato, Pear | Solanaceae | *Lycopersicon esculentum pyriforme* |
| Tomato, Tree | Solanaceae | *Cyphomandra betacea* |
| Potato | Solanaceae | *Solanum tuberosum* |
| Potato, Spanish, Sweet potato | Convolvulaceae | *Ipomoea batatas* |
| Rye, Common | Pooideae | *Secale cereale* |
| Rye, Mountain | Pooideae | *Secale montanum* |
| Pepper, Bell | Solanaceae | *Capsicum annuum grossum* |
| Pepper, Bird, also Cayenne, Guinea | Solanaceae | *Capsicum annuum minimum* |
| Pepper, Bonnet | Solanaceae | *Capsicum sinense* |
| Pepper, Bullnose, also Sweet | Solanaceae | *Capsicum annuum grossum* |
| Pepper, Cherry | Solanaceae | *Capsicum annuum cerasiforme* |
| Pepper, Cluster, also Red Cluster | Solanaceae | *Capsicum annuum fasciculatum* |
| Pepper, Cone | Solanaceae | *Capsicum annuum conoides* |
| Pepper, Goat, also Spur | Solanaceae | *Capsicum frutescens* |
| Pepper, Long | Solanaceae | *Capsicum frutescens longum* |
| Pepper, Oranamental Red, also Wrinkled | Solanaceae | *Capsicum annuum abbreviatum* |
| Pepper, Tabasco Red | Solanaceae | *Capsicum annuum conoides* |
| Lettuce, Garden | Compositae | *Lactuca sativa* |
| Lettuce, Asparagus, also Celery | Compositae | *Lactuca sativa asparagina* |
| Lettuce, Blue | Compositae | *Lactuca perennis* |
| Lettuce, Blue, also Chicory | Compositae | *Lactuca pulchella* |
| Lettuce, Cabbage, also Head | Compositae | *Lactuca sativa capitata* |
| Lettuce, Cos, also Longleaf, Romaine | Compositae | *Lactuca sativa longifolia* |
| Lettuce, Crinkle, also Curled, Cutting, Leaf | Compositae | *Lactuca sativa crispa* |
| Celery | Umbelliferae | *Apium graveolens dulce* |
| Celery, Blanching, also Garden | Umbelliferae | *Apium graveolens dulce* |
| Celery, Root, also Turniprooted | Umbelliferae | *Apium graveolens rapaceum* |
| Eggplant, Garden | Solanaceae | *Solanum melongena* |
| Sorghum | Sorghum | All crop species |
| Alfalfa | Leguminosae | *Medicago sativum* |
| Carrot | Umbelliferae | *Daucus carota sativa* |
| Bean, Climbing | Leguminosae | *Phaseolus vulgaris vulgaris* |
| Bean, Sprouts | Leguminosae | *Phaseolus aureus* |
| Bean, Brazilian Broad | Leguminosae | *Canavalia ensiformis* |
| Bean, Broad | Leguminosae | *Vicia faba* |
| Bean, Common, also French, White, Kidney | Leguminosae | *Phaseolus vulgaris* |
| Bean, Egyptian | Leguminosae | *Dolichos lablab* |
| Bean, Long, also Yardlong | Leguminosae | *Vigna sesquipedalis* |
| Bean, Winged | Leguminosae | *Psophocarpus tetragonolobus* |
| Oat, also Common, Side, Tree | Avena | *Avena sativa* |
| Oat, Black, also Bristle, Lopsided | Avena | *Avena strigosa* |
| Oat, Bristle | Avena | |
| Pea, also Garden, Green, Shelling | Leguminosae | *Pisum, sativum sativum* |
| Pea, Blackeyed | Leguminosae | *Vigna sinensis* |
| Pea, Edible Podded | Leguminosae | *Pisum sativum axiphium* |
| Pea, Grey | Leguminosae | *Pisum sativum speciosum* |
| Pea, Winged | Leguminosae | *Tetragonolobus purpureus* |

TABLE 3-continued

RECIPIENT PLANTS

| COMMON NAME | FAMILY | LATIN NAME |
|---|---|---|
| Pea, Wrinkled | Leguminosae | *Pisum sativum medullare* |
| Sunflower | Compositae | *Helianthus annuus* |
| Squash, Autumn, Winter | Dicotyledoneae | *Cucurbita maxima* |
| Squash, Bush, also Summer | Dicotyledoneae | *Cucurbita pepo melopepo* |
| Squash, Turban | Dicotyledoneae | *Cucurbita maxima turbaniformis* |
| Cucumber | Dicotyledoneae | *Cucumis sativus* |
| Cucumber, African, also Bitter | | *Momordica charantia* |
| Cucumber, Squirting, also Wild | | *Ecballium elaterium* |
| Cucumber, Wild | | *Cucumis anguria* |
| Poplar, California | Woody-Plant | *Populus trichocarpa* |
| Poplar, European Black | | *Populus nigra* |
| Poplar, Gray | | *Populus canescens* |
| Poplar, Lombardy | | *Populus italica* |
| Poplar, Silverleaf, also White | | *Populus alba* |
| Poplar, Western Balsam | | *Populus trichocarpa* |
| Tobacco | Solanaceae | *Nicotiana* |
| *Arabidopsis thaliana* | Cruciferae | *Arabidopsis thaliana* |
| Turfgrass | Lolium | |
| Turfgrass | Agrostis | |
| | Other families of turfgrass | |
| Clover | Leguminosae | |

Numerous methods for introducing foreign genes into plants are known and can be used to insert a gene into a plant host, including biological and physical plant transformation protocols. See, for example, Miki et al., (1993) "Procedure for Introducing Foreign DNA into Plants", In: Methods in Plant Molecular Biology and Biotechnology, Glick and Thompson, eds., CRC Press, Inc., Boca Raton, pages 67-88 and Andrew Bent in, Clough S J and Bent A F, 1998. Floral dipping: a simplified method for *Agrobacterium*-mediated transformation of *Arabidopsis thaliana*. The methods chosen vary with the host plant, and include chemical transfection methods such as calcium phosphate, polyethylene glycol (PEG) transformation, microorganism-mediated gene transfer such as *Agrobacterium* (Horsch, et al., Science, 227: 1229-31 (1985)), electroporation, protoplast transformation, micro-injection, flower dipping and biolistic bombardment.

Also included in the invention are methods of producing a transgenic plant. The method includes introducing into one or more plant cells a compound that alters PrPase expression or activity in the plant to generate a transgenic plant cell and regenerating a transgenic plant from the transgenic cell. In some aspects the compound increases alters PrPase expression or activity. Alternatively, the compound decrease alters PrPase expression or activity. The compound can be, e.g., (i) a PrPase polypeptide; (ii) a nucleic acid encoding a PrPase polypeptide; (iii) a nucleic acid that increases expression of a nucleic acid that encodes a PrPase polypeptide; (iv) a nucleic acid that decreases the expression of a nucleic acid that encodes a PrPase polypeptide; (v) a PrPase antisense nucleic acid and derivatives, fragments, analogs and homologs thereof. A nucleic acid that increases expression of a nucleic acid that encodes a PrPase polypeptide includes, e.g., promoters, enhancers. The nucleic acid can be either endogenous or exogenous. Preferably, the "compound" is a nucleic acid encoding a PrPase polypeptide of the invention. For example, the compound comprises the nucleic acid sequence of SEQ ID NO: 1, 3, 5, 7, 11, 14, 16, 18, 21, or 23, or a fragment thereof. Alternatively, the compound is a PrPase antisense nucleic acid. For example, the compound comprises the nucleic acid sequence of SEQ ID NO: 9, 13, or 20.

In various aspects the transgenic plant has an altered phenotype as compared to a wild type plant (i.e., untransformed). By altered phenotype is meant that the plant has a one or more characteristic that is different from the wild type plant. For example, the transgenic plant has an increased resistance to stress. An "increased" stress means that the transgenic plant can grow under stress conditions (e.g., high salt, decreased water, low temperatures, high temperatures) or under conditions that normally inhibit the growth of an untransformed plant. Stresses include, for example, chilling stress, heat stress, heat shock, salt stress, water stress (i.e., drought), nutritional stress, disease, grazing pests, wound healing, pathogens such as for example fungi, bacteria, nematodes, viruses or parasitic weed and herbicides. Alternatively, the transformed plant has an increased (i.e., enhanced) ABA sensitivity. The enhanced ABA sensitivity is at the seedling growth stage. Alternatively, the enhanced ABA sensitivity is at the mature plant stage. Additional altered phenotypes include for example, enhanced vegetative growth (e.g., increased leaf number, thickness and overall biomass), delayed reproductive growth (e.g., flowering later); enhanced seedling vigor (e.g., increased root biomass and length), enhanced lateral root formation and therefore soil penetration more extensive vascular system resulting in an enhanced transport system. In preferred embodiments, the growth and/or yield of transgenic plants is improved relative to a wild-type under a stress condition.

The polynucleotides of the invention are introduced into plant cells using, for example, *Agrobacterium*-mediated transformation, microprojectile-mediated transformation, sonication of target cells, liposome or spheroplast fusion, direct uptake into protoplasts by $CaCl_2$ precipitation, electroporation of protoplasts and whole cells and tissues, wounding by particle bombardment followed by use of *Agrobacterium* for DNA delivery, intact meristem transformation, split meristem method.

Once a single transformed plant has been obtained, conventional plant breeding methods can be used to transfer the gene and associated regulatory sequences via crossing and backcrossing.

Methodologies to determine plant growth or response to stress include for example, height measurements, weight measurements, leaf area, ability to flower, water use, transpiration rates and yield.

Infectious Agents and Pests

A polynucleotide or polypeptide of the present invention can be used to detect, prevent, and/or confer resistance to infectious agents and/or pests which may, for example, inhibit the plants ability to control cellular division, differentiation, and development; absorption of water and minerals from the soil and the translocation of these substances throughout the plant; photosynthesis and translocation of the photosynthetic products to areas of use or storage; metabolism of synthesized compounds; reproduction; and storage of plant food-stuffs for overwintering or reproduction. For example, infection of the root (e.g., root rot), interferes with absorption of water and nutrients from the soil; infection of the xylem vessels (e.g., vascular wilts, cankers, etc.) interferes with translocation of water and minerals to the crown of the plant; infection of the foliage (e.g., leaf spots, blights, mosaics, etc.) interferes with photosynthesis; infection of the cortex (e.g., cortical canker, viral and mycoplasmal infections of phloem, etc.) interferes with the downward translocation of photosynthetic products; flower infections (e.g., bacterial and fungal blights, viral, mycoplasmal, and fungal infections of flowers, etc.) interfere with reproduction; and infections of fruit (e.g., fruit rot, etc.) interfere with reproduction or storage of reserve food stuffs for the new plant.

Infectious agents and pests include, but are not limited to, viruses, bacteria, fungi, parasitic agents (i.e. parasitic weeds), herbaceous species, nematodes, and insects.

Defense Mechanisms and Plant Hormones

A polypeptide or polynucleotide and/or agonist or antagonist of the present invention can be used to increase a plants defense mechanisms against either environmental or pathogenic stresses (e.g., viral, fungal, mycoplasma, bacterial, nematode, herbicidal, insecticidal, acid rain, drought, chemical, etc.). Such defense mechanisms may be a combination of structural characteristics (i.e., to serve as a physical barrier to inhibit a pathogen, for example, from entering or spreading throughout the plant), and biochemical reactions either on the scale of the whole plant or of individual cells (e.g., producing substances that are either toxic to the pathogen, or create an environment that is non-permissive for pathogen survival, etc.).

A polynucleotide or polypeptide and/or agonist or antagonist of the present invention can be used to modulate the hormone levels within a plant (including any of its cells, tissues, and/or organs, etc.). Examples of hormones that may be modulated by the present invention, either directly or indirectly, generally include, but are not limited to, auxins, indoleacetic acid, gibberellins, cytokinins, ethylene, abscisic acid, polyamines, jasmonates, salicylic acid, and brassinolides (see, for example, Davies, P. J., in "Plant Hormones: Physiology, Biochemistry, and Molecular Biology", Kluwer Academic Publishers, Boston, 1995; which is hereby incorporated by reference in its entirety herein).

Regeneration

The development or regeneration of plants from either single plant protoplasts or various explants is well known in the art (Weissbach and Weissbach, 1988, Plant Molecular Biology, Methods in Enzymology, Vol. 118, Academic Press, Orlando, Fla.). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing a foreign, exogenous gene that encodes a polypeptide of interest introduced by *Agrobacterium* from leaf explants can be achieved by methods well known in the art such as described (Horsch et al., 1985). In this procedure, transformants are cultured in the presence of a selection agent and in a medium that induces the regeneration of shoots in the plant strain being transformed as described (Fraley et al., 1983). In particular, U.S. Pat. No. 5,349,124 (specification incorporated herein by reference) details the creation of genetically transformed lettuce cells and plants resulting therefrom which express hybrid crystal proteins conferring insecticidal activity against Lepidopteran larvae to such plants.

This procedure typically produces shoots within two to four months and those shoots are then transferred to an appropriate root-inducing medium containing the selective agent and an antibiotic to prevent bacterial growth. Shoots that rooted in the presence of the selective agent to form plantlets are then transplanted to soil or other media to allow the production of roots. These procedures vary depending upon the particular plant strain employed, such variations being well known in the art.

Preferably, the regenerated plants are self-pollinated to provide homozygous transgenic plants, or pollen obtained from the regenerated plants is crossed to seed-grown plants of agronomically important, preferably inbred lines. Conversely, pollen from plants of those important lines is used to pollinate regenerated plants. A transgenic plant of the present invention containing a desired polypeptide is cultivated using methods well known to one skilled in the art.

A preferred transgenic plant is an independent segregant and can transmit the PrPase gene and its activity to its progeny. A more preferred transgenic plant is homozygous for the gene, and transmits that gene to all of its offspring on sexual mating. Seed from a transgenic plant may be grown in the field or greenhouse, and resulting sexually mature transgenic plants are self-pollinated to generate true breeding plants. The progeny from these plants become true breeding lines that are evaluated for increased expression of the PrPase transgene.

A polynucleotide or polypeptide of the present invention can be used to modulate a plants nutritional status.

A polynucleotide or polypeptide of the present invention may increase the plants ability, either directly or indirectly, to initiate and/or maintain biotic associations with other organisms. Such associations may be symbiotic, nonsymbiotic, endosymbiotic, macrosymbiotic, and/or microsymbiotic in nature.

In another embodiment, a polynucleotide or polypeptide and/or agonist or antagonist of the present invention may increase the plants ability to synthesize and/or release a pheromone.

A polynucleotide or polypeptide and/or agonist or antagonist of the present invention may have chemotaxis activity.

A polypeptide of the present invention may be used to screen for molecules that bind to the polypeptide or for molecules to which the polypeptide binds. The binding of the polypeptide and the molecule may activate (agonist), increase, inhibit (antagonist), or decrease activity of the polypeptide or the molecule bound. Examples of such molecules include antibodies, oligonucleotides, proteins (e.g., receptors), or small molecules.

Antisense, Ribozymes, PNA Moieties

In further embodiments, the invention encompasses antagonists which correspond to the polynucleotide sequences of the invention, and in particular, the complementary strand of the PrPase polynucleotides.

Another aspect of the invention pertains to isolated antisense nucleic acid molecules that are hybridizable to or complementary to the nucleic acid molecule comprising the nucleotide sequence of SEQ ID NO: 1, 3, 5, 7, 11, 14, 16, 18, 21, or 23, or fragments, analogs or derivatives thereof. An "antisense" nucleic acid comprises a nucleotide sequence that is complementary to a "sense" nucleic acid encoding a protein, e.g., complementary to the coding strand of a double-stranded cDNA molecule or complementary to an mRNA sequence. In specific aspects, antisense nucleic acid molecules are provided that comprise a sequence complementary to at least about 10, 25, 50, 100, 250 or 500 nucleotides or an entire PrPase coding strand, or to only a portion thereof. Nucleic acid molecules encoding fragments, homologs, derivatives and analogs of a PrPase protein of SEQ ID NO: 2, 4, 6, 8, 12, 15, 17, 19, 22, or 24, or antisense nucleic acids complementary to a PrPase nucleic acid sequence of SEQ ID NO: 1, 3, 5, 7, 11, 14, 16, 18, 21, or 23 are additionally provided. Exemplary PrPase anti-sense nucleic acid include the nucleic acid sequences of SEQ ID NO: 9, 13, and 20.

The antisense nucleic acids may be transiently generated within the organism (e.g., sequence contained within an inducible or constitutively expressed vector introduced into the cells of an organism), stably generated within the organism (e.g., sequence contained within an inducible or constitutively expressed vector introduced into the cells of an organism using transgenic methods, including viral integration, etc.) or may be exogenously administered. For a nucleic acid to serve an antisense role, it is only necessary that it has sequence homology to the sense RNA product of the gene of interest. A number of methods of administering antisense nucleic acids, their compositions, and designs are known in the art and encompassed by the invention (see for example, Agrawal S, et al., Mol Med. Today. 2000 February; 6(2):72-81; Yacyshyn B R, et al, Can J Gastroenterol. 1999 November; 13(9):745-51; Mrsny R J., J Drug Target. 1999; 7(1):1-10; Toulme J J, et al, Nucleic Acids Symp Ser. 1997; (36):39-41), Okano, Neurochem., 56:560 (1991); Oligodeoxynucleotides as Antisense Inhibitors of Gene Expression, CRC Press, Boca Raton, Fla. (1988); and Cooper S R, et al., Pharmacol Ther. 1999 May-June; 82(2-3):427-35). Likewise, a number of methods have been developed regarding the application of triple helix antisense technology to modulating gene expression (see, for example, Gowers D M, et al, Nucleic Acids Res. 1999 Apr. 1; 27(7):1569-77; and Chan P P, et al., J Mol. Med. 1997 April; 75(4):267-82).

Antisense technology has wide-ranging applications in plants. For example, antisense RNA has been shown to effectively downregulate a variety of plant genes as described by Shimada, et al., Theor. Appl. Genet., 86:665-672, (1993); Kull, et al., J. Genet. Breed., 49:67-76, (1995)., Slabas and Elborough, WO 97/07222; Knutzon et al., Proc. Natl. Acad. Sci. USA, 89:2624-2628, (1992), and Baulcombe D C., Plant Mol. Biol. 1996 October; 32(1-2):79-88).

The antisense nucleic acids of the invention comprise a sequence complementary to at least a portion of an RNA transcript of a gene of interest. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded antisense nucleic acids of the invention, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a RNA sequence of the invention it may contain and still form a stable duplex (or triplex as the case may be). One skilled in the art can ascertain a tolerable degree of mismatch by use of standard procedures to determine the melting point of the hybridized complex.

Antisense oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., Nature, 372:333-335 (1994). Thus, oligonucleotides complementary to either the 5'- or 3'-non-translated, non-coding regions of a polynucleotide sequence of the invention could be used in an antisense approach to inhibit translation of endogenous mRNA. Oligonucleotides complementary to the 5' untranslated region of the mRNA should include the complement of the AUG start codon.

Antisense oligonucleotides complementary to mRNA coding regions are less efficient inhibitors of translation but could be used in accordance with the invention. The term "coding region" refers to the region of the nucleotide sequence comprising codons which are translated into amino acid residues (e.g., the protein coding region of Physcomitrella patens, Arabidopsis thaliana, Brassica napus, Zea mays, or Glycine max PrPase corresponds to SEQ ID NO: 2, 4, 6, 8, 12, 15, 17, 19, 22, or 24). The antisense nucleic acid molecule can be complementary to the entire coding region of PrPase mRNA, but more preferably is an oligonucleotide that is antisense to only a portion of the coding or noncoding region of PrPase mRNA. Whether designed to hybridize to the 5'-, 3'- or coding region of mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides. In another specific aspect, an antisense oligonucleotide can be, for example, about 5, 10, 15, 20, 25, 30, 35, 40, 45 or 50 nucleotides in length.

The antisense oligonucleotide may be modified at the base moiety, sugar moiety, or phosphate backbone. The oligonucleotide may include other appending groups such as peptides, or agents facilitating transport across the cell membrane (see, e.g., Letsinger et al., 1989, Proc. Natl. Acad. Sci. USA 86:6553-6556; Lemaitre et al., 1987, Proc. Natl. Acad. Sci. 84:648-652; PCT Publication No. WO 88/09810, published Dec. 15, 1988) or blood-brain barrier (see, e.g., PCT Publication No. WO 89/10134, published Apr. 25, 1988), hybridization-triggered cleavage agents (see, e.g., Krol et al., 1988, BioTechniques 6:958-976) or intercalating agents (see, e.g., Zon, 1988, Pharm. Res. 5:539-549).

The oligonucleotide can also be a peptido-nucleic acid ("PNA") based on a linked N-(2-aminoethyl)glycine backbone to which normal DNA bases have been attached (Egholm et al., 1993, Nature 365:566-67). This PNA obeys specific Watson-Crick base pairing, but with greater free energy of binding and correspondingly higher melting temperatures. Suitable oligomers may be constructed entirely from PNAs or from mixed PNA and DNA and/or RNA oligomers. In fact, PNA:DNA chimeras have increased solubility characteristics, as compared to DNA:DNA or DNA:RNA chimeras of the same sequence. Most notably, PNAs have the unique ability to displace one strand of a DNA double-helix thus making them highly suitable in antisense applications (Uhlmann E., Biol. Chem. 1998 August-September; 379(8-9): 1045-52).

In various embodiments, the nucleic acids of PrPase can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) Bioorg Med Chem 4: 5-23). As used herein, the terms "peptide nucleic acids" or "PNAs" can also refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) above; Perry-O'Keefe et al. (1996) PNAS 93: 14670-675.

PNAs of PrPase can be used in therapeutic and diagnostic applications. For example, PNAs can be used as antisense or antigene agents for sequence-specific modulation of gene expression by, e.g., inducing transcription or translation arrest or inhibiting replication. PNAs of PrPase can also be used, e.g., in the analysis of single base pair mutations in a gene by, e.g., PNA directed PCR clamping; as artificial restriction enzymes when used in combination with other enzymes, e.g., S1 nucleases (Hyrup B. (1996) above); or as probes or primers for DNA sequence and hybridization (Hyrup et al. (1996), above; Perry-O'Keefe (1996), above).

In another embodiment, PNAs of PrPase can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of PrPase can be generated that may combine the advantageous properties of PNA and DNA. Such chimeras allow DNA recognition enzymes, e.g., RNase H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996) above). The synthesis of PNA-DNA chimeras can be performed as described in Hyrup (1996) above and Finn et al. (1996) *Nucl Acids Res* 24: 3357-63. For example, a DNA chain can be synthesized on a solid support using standard phosphoramidite coupling chemistry, and modified nucleoside analogs, e.g., 5'-(4-methoxytrityl)amino-5'-deoxy-thymidine phosphoramidite, can be used between the PNA and the 5' end of DNA (Mag et al. (1989) *Nucl Acid Res* 17: 5973-88). PNA monomers are then coupled in a stepwise manner to produce a chimeric molecule with a 5' PNA segment and a 3' DNA segment (Finn et al. (1996) above). Alternatively, chimeric molecules can be synthesized with a 5' DNA segment and a 3' PNA segment. See, Petersen et al. (1975) *Bioorg Med Chem Lett* 5: 1119-11124.

In a further embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In another embodiment, the anti-sense oligonucleotide of the invention may comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine.

In another embodiment, the anti-sense oligonucleotide comprises at least one modified sugar moiety selected from the group including, but not limited to, arabinose, 2-fluoroarabinose, xylulose, and hexose.

In yet another embodiment, the anti-sense oligonucleotide may be conjugated to another molecule, e.g., a peptide, hybridization triggered cross-linking agent, transport agent, hybridization-triggered cleavage agent, etc.

The anti-sense oligonucleotides of the invention may be synthesized by standard methods known in the art, e.g., by use of an automated DNA synthesizer (such as are commercially available from Biosearch, Applied Biosystems, etc.). As examples, phosphorothioate oligos may be synthesized by the method of Stein et al. (1988, Nucl. Acids Res. 16:3209), methylphosphonate oligos can be prepared by use of controlled pore glass polymer supports (Sarin et al., 1988, Proc. Natl. Acad. Sci. USA 85:7448-7451), etc.

An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used.

Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are generated in situ such that they hybridize with or bind to cellular mRNA and/or genomic DNA encoding a PrPase protein to thereby inhibit expression of the protein, e.g., by inhibiting transcription and/or translation. The hybridization can be by conventional nucleotide complementarity to form a stable duplex, or, for example, in the case of an antisense nucleic acid molecule that binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of antisense molecules, vector constructs in which the antisense nucleic acid molecule is placed under the control of a strong pol II or pol III promoter are preferred.

In a specific embodiment, the oligonucleotide comprises catalytic RNA, or a ribozyme (see, e.g., PCT International Publication WO 90/11364, published Oct. 4, 1990; Sarver et al., 1990, Science 247:1222-1225; Hasselhoff, et al., Nature 342:76-79 (1988)). Ribozymes have been used to downregulate gene expression, and more recently in the downregulation of plant proteins (seem e.g., PCT International Publication WO 97/10328).

In still another embodiment, an antisense nucleic acid of the invention is a ribozyme. Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585-591)) can be used to catalytically cleave PrPase mRNA transcripts to thereby inhibit translation of PrPase mRNA. A ribozyme having specificity for a PrPase-encoding nucleic acid can be designed based upon the nucleotide sequence of a PrPase DNA disclosed herein (i.e., SEQ ID NO: 7, SEQ ID NO: 11, or SEQ ID NO:

18). For example, a derivative of a Tetrahymena L-19 IVS RNA can be constructed in which the nucleotide sequence of the active site is complementary to the nucleotide sequence to be cleaved in a PrPase-encoding mRNA. See, e.g., Cech et al. U.S. Pat. No. 4,987,071; and Cech et al. U.S. Pat. No. 5,116, 742. Alternatively, PrPase mRNA can be used to select a catalytic RNA having a specific ribonuclease activity from a pool of RNA molecules. See, e.g., Bartel et al., (1993) *Science* 261:1411-1418.

Alternatively, PrPase gene expression can be inhibited by targeting nucleotide sequences complementary to the regulatory region of the PrPase (e.g., the PrPase promoter and/or enhancers) to form triple helical structures that prevent transcription of the PrPase gene in target cells. See generally, Helene. (1991) *Anticancer Drug Des.* 6: 569-84; Helene. et al. (1992) *Ann. N.Y. Acad. Sci.* 660:27-36; and Maher (1992) *Bioassays* 14: 807-15.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res* 15: 6625-6641). In another embodiment, the oligonucleotide is a 2'-O-methylribonucleotide (Inoue et al., 1987, Nucl. Acids Res. 15:6131-6148), or a chimeric RNA-DNA analogue (Inoue et al., 1987, FEBS Lett. 215:327-330).

Such modifications include, by way of nonlimiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in applications.

Double Stranded RNA Inhibition (RNAi) by Hairpin Nucleic Acids

Another aspect of the invention pertains to the use of post transcriptional gene silencing (PTGS) to repress gene expression, including use of the sequences disclosed herein to produce small interfering RNAs. Double stranded RNA can initiate the sequence specific repression of gene expression in plants and animals. Double stranded RNA is processed to short duplex oligomers of 21-23 nucleotides in length. These small interfering RNAs suppress the expression of endogenous and heterologous genes in a sequence specific manner (Fire et al. Nature 391:806-811, Carthew, Curr. Opin. in Cell Biol., 13:244-248, Elbashir et al., Nature 411:494-498). An RNAi suppressing construct can be designed in a number of ways, for example, transcription of a inverted repeat which can form a long hair pin molecule, inverted repeats separated by a spacer sequence that could be an unrelated sequence such as GUS or an intron sequence. Transcription of sense and antisense strands by opposing promoters or cotranscription of sense and antisense genes.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control.

Having generally described the invention, the same will be more readily understood by reference to the following examples, which are provided by way of illustration and are not intended as limiting.

EXAMPLES

Example 1

Growth of *Physcomitrella patens* Cultures

For this study, plants of the species *Physcomitrella patens* (Hedw.) B.S.G. from the collection of the genetic studies section of the University of Hamburg were used. They originated from the strain 16/14 collected by H.L.K. Whitehouse in Gransden Wood, Huntingdonshire (England), which was subcultured from a spore by Engel (1968, Am J Bot 55, 438-446). Proliferation of the plants was carried out by means of spores and by means of regeneration of the gametophytes. The protonema developed from the haploid spore as a chloroplast-rich chloronema and chloroplast-low caulonema, on which buds formed after approximately 12 days. These grew to give gametophores bearing antheridia and archegonia. After fertilization, the diploid sporophyte with a short seta and the spore capsule resulted, in which the meiospores mature.

Culturing was carried out in a climatic chamber at an air temperature of 25° C. and light intensity of 55 micromol s$^{-1}$ m$^{-2}$ (white light; Philips TL 65W/25 fluorescent tube) and a light/dark change of 16/8 hours. The moss was either modified in liquid culture using Knop medium according to Reski and Abel (1985, Planta 165, 354-358) or cultured on Knop solid medium using 1% oxoid agar (Unipath, Basingstoke, England).

The protonemas used for RNA and DNA isolation were cultured in aerated liquid cultures. The protonemas were comminuted every 9 days and transferred to fresh culture medium.

Example 2

Isolation of Total RNA and Poly-(A)+ RNA and cDNA Library Construction from *Physcomitrella patens*

For the investigation of transcripts, both total RNA and poly-(A)+ RNA were isolated. The total RNA was obtained from wild-type 9 d old protonemata following the GTC-method (Reski et al. 1994, Mol. Gen. Genet., 244:352-359).

The Poly(A)+ RNA was isolated using Dyna Beads$^R$ (Dynal, Oslo, Norway) following the instructions of the manufacturer's protocol. After determination of the concentration of the RNA or of the poly(A)+ RNA, the RNA was precipitated by addition of 1/10 volumes of 3 M sodium acetate pH 4.6 and 2 volumes of ethanol and stored at −70 degree C.

RNA Preparation from *Arabidopsis* Seeds—"Hot" Extraction:
1. Buffers, Enzymes and Solutions
   2M KCl
   Proteinase K
   Phenol (for RNA)
   Chloroform:Isoamylalcohol
   (Phenol:choloroform 1:1; pH adjusted for RNA)
   4 M LiCl, DEPC-treated
   DEPC-treated water
   3M NaOAc, pH 5, DEPC-treated
   Isopropanol
   70% ethanol (made up with DEPC-treated water)
   Resuspension buffer: 0.5% SDS, 10 mM Tris pH 7.5, 1 mM EDTA made up with DEPC-treated water as this solution can not be DEPC-treated Extraction Buffer:
0.2M Na Borate
30 mM EDTA
30 mM EGTA
1% SDS*(250 µl of 10% SDS-solution for 2.5 ml buffer)
1% Deoxycholate (25 mg for 2.5 ml buffer)
2% PVPP (unsoluable—50 mg for 2.5 ml buffer)
2% PVP 40K (50 mg for 2.5 ml buffer)
10 mM DTT*
100 mM-Mercaptoethanol*(fresh, handle under fume hood—use 35 µl of 14.3M solution for 5 ml buffer)

2. Extraction

Heat extraction buffer up to 80° C. Grind tissue in liquid nitrogen-cooled mortar, transfer tissue powder to 1.5 ml tube. Tissue should kept frozen until buffer is added so transfer the sample with precooled spatula and keep the tube in liquid nitrogen all time. Add 350 µl preheated extraction buffer (here for 100 mg tissue. Buffer volume can be as much as 500 µl for bigger samples) to tube, vortex and heat tube to 80° C. for ~1 min. Keep then on ice. Vortex sample, grind additionally with electric mortar.

3. Digestion

Add Proteinase K (0.15 mg/100 mg tissue), vortex and keep at 37° C. for one hour.

4. First Purification

Add 27 µl 2M KCl. Chill on ice for 10 min. Centrifuge at 12.000 rpm for 10 minutes at room temperature. Transfer supernatant to fresh, RNAase-free tube and do one phenol extraction, followed by a choloroform:isoamylalcohol extraction. Add 1 vol. isopropanol to supernatant and chill on ice for 10 min. Pellet RNA by centrifugation (7000 rpm for 10 min at RT). Resolve pellet in 1 ml 4M LiCl by 10 to 15 min vortexing. Pellet RNA by 5 min centrifugation.

5. Second Purification

Resuspend pellet in 500 µl Resuspension buffer. Add 500 µl phenol and vortex. Add 250 µl chloroform:isoamylalcohol and vortex. Spin for 5 min. and transfer supernatant to fresh tube. Repeat choloroform:isoamylalcohol extraction until interface is clear. Transfer supernatant to fresh tube and add ⅒ vol 3M NaOAc, pH 5 and 600 µl isopropanol. Keep at −20 for 20 min or longer. Pellet RNA by 10 min centrifugation. Wash pellet once with 70% ethanol. Remove all remaining alcohol before resolving pellet with 15 to 20 µl DEPC-water. Determine quantity and quality by measuring the absorbance of a 1:200 dilution at 260 and 280 nm. 40 µg RNA/ml=1OD260

For cDNA library construction first strand synthesis was achieved using Murine Leukemia Virus reverse transcriptase (Roche, Mannheim, Germany) and oligo-d(T)-primers, second strand synthesis by incubation with DNA polymerase I, Klenow enzyme and RNAseH digestion at 12 degree C. (2 h), 16 degree C. (1 h) and 22 degree C. (1 h). The reaction was stopped by incubation at 65 degree C. (10 min) and subsequently transferred to ice. Double stranded DNA molecules were blunted by T4-DNA-polymerase (Roche, Mannheim) at 37 degree C. (30 min). Nucleotides were removed by phenol/chloroform extraction and Sephadex G50 spin columns. EcoRI adapters (Pharmacia, Freiburg, Germany) were ligated to the cDNA ends by T4-DNA-ligase (Roche, 12 degree C., overnight) and phosphorylated by incubation with polynucleotide kinase (Roche, 37 degree C., 30 min). This mixture was subjected to separation on a low melting agarose gel. DNA molecules larger than 300 basepairs were eluted from the gel, phenol extracted, concentrated on Elutip-D-columns (Schleicher and Schuell, Dassel, Germany) and were ligated to vector arms and packed into lambda ZAPII phages or lambda ZAP-Express phages using the Gigapack Gold Kit (Stratagene, Amsterdam, Netherlands) using material and following the instructions of the manufacturer.

Example 3

Sequencing and Function Annotation of *Physcomitrella patens* ESTs cDNA libraries as described in Example 2 were used for DNA sequencing according to standard methods, in particular by the chain termination method using the ABI PRISM Big Dye Terminator Cycle Sequencing Ready Reaction Kit (Perkin-Elmer, Weiterstadt, Germany). Random Sequencing was carried out subsequent to preparative plasmid recovery from cDNA libraries via in vivo mass excision, retransformation, and subsequent plating of DH10B on agar plates (material and protocol details from Stratagene, Amsterdam, Netherlands. Plasmid DNA was prepared from overnight grown *E. coli* cultures grown in Luria-Broth medium containing ampicillin (see Sambrook et al. (1989) (Cold Spring Harbor Laboratory Press: ISBN 0-87969-309-6)) on a Qiagene DNA preparation robot (Qiagen, Hilden) according to the manufacturers protocols. Sequencing primers with the following nucleotide sequences were used:

```
Qiagen1: 5'-CAGGAAACAGCTATGACC-3'    (SEQ ID NO: 32)

Qiagen2: 5'-CTAAAGGGAACAAAAGCTG-3'   (SEQ ID NO: 33)

Qiagen3: 5'-TGTAAAACGACGGCCAGT-3'    (SEQ ID NO: 34)
```

Sequences were processed and annotated using the software package EST-MAX commercially provided by Bio-Max (Munich, Germany). The program incorporates practically all bioinformatics methods important for functional and structural characterization of protein sequences.

The most important algorithms incorporated in EST-MAX are:

FASTA: Very sensitive sequence database searches with estimates of statistical significance; Pearson W. R. (1990) Rapid and sensitive sequence comparison with FASTP and FASTA. Methods Enzymol. 183:63-98.

BLAST: Very sensitive sequence database searches with estimates of statistical significance. Altschul S. F., Gish W., Miller W., Myers E. W., and Lipman D. J. Basic local alignment search tool. Journal of Molecular Biology 215:403-10.

PREDATOR: High-accuracy secondary structure prediction from single and multiple sequences. Frishman, D. and Argos, P. (1997) 75% accuracy in protein secondary structure prediction. Proteins, 27:329-335.

CLUSTALW: Multiple sequence alignment. Thompson, J. D., Higgins, D. G. and Gibson, T. J. (1994) CLUSTAL W: improving the sensitivity of progressive multiple sequence alignment through sequence weighting, positions-specific gap penalties and weight matrix choice. Nucleic Acids Research, 22:4673-4680.

TMAP: Transmembrane region prediction from multiply aligned sequences. Persson, B. and Argos, P. (1994) Prediction of transmembrane segments in proteins utilising multiple sequence alignments. J. Mol. Biol. 237:182-192.

ALOM2: Transmembrane region prediction from single sequences. Klein, P., Kanehisa, M., and DeLisi, C. Prediction of protein function from sequence properties: A discriminant analysis of a database. Biochim. Biophys. Acta 787:221-226 (1984). Version 2 by Dr. K. Nakai.

PROSEARCH: Detection of PROSITE protein sequence patterns. Kolakowski L. F. Jr., Leunissen J. A. M., Smith J. E. (1992) ProSearch: fast searching of protein sequences with regular expression patterns related to protein structure and function. Biotechniques 13, 919-921.

BLIMPS: Similarity searches against a database of ungapped blocks. J. C. Wallace and Henikoff S., (1992)

PATMAT: A searching and extraction program for sequence, pattern and block queries and databases, CABIOS 8:249-254. Written by Bill Alford.

Example 4

Identification of *Arabidopsis*, Soybean and Corn ORFs Corresponding to PrPase

The *Physcomitrella patens*, PpPrPase (SEQ ID NO: 1), was identified in EST-MAX through BLAST analysis. The top hit of the BLAST is an *Arabidopsis* unknown ORF. The second and the third hits are human and yeast caax prenyl protease. Further analysis of the unknown *Arabidopsis* ORF revealed that it is a predicted ORF from computer analysis, using the program Genefinder (P. Green and L. Hillier, National Center for Biotechnology Information). The ORF is located on the complementary strand of the BAC clone AF007269 (GenBank accession number, gene="A_IG002N01.21) from 24979 to 28076.

Using this computer predicted *Arabidopsis* AtPrPase cDNA as a query, BLAST search in various maize and soybean databases has identified one corn ZmPrPase EST (SEQ ID NO: 21) and one soybean GmPrPase EST (SEQ ID NO: 14).

Example 5

Cloning of *Arabidopsis* cDNAs Encoding for PrPase

Total RNA Isolation from *Arabidopsis thaliana*

The total RNA was obtained from wild-type 14 day old *Arabidopsis thaliana* following the Van Slogteren (1983 Plant Mol. Biol. 2: 321-333) method with slight modifications. Tissue (200 mg) was frozen with liquid nitrogen and ground to a fine powder with a mortar and pestle. The powder was placed in a microfuge tube and the RNA was extracted with 500 ul of extraction buffer (phenyl: 0.1 M LiCl, 100 mM Tris-HCl [pH8.0], 10 mM EDTA, 1% SDS (w/v) [1:1]) preheated to 90° C. The mixture was heated further for 1 min at 90° C. and then vortexed for 5 mins. Proteins were extracted by adding 250 ul of chloroform: isoamyl:alcohol (24:1) and the mixture was vortexed for 5 mins and centrifuged for 15 mins at 13,000 rpm in an Eppendorf centrifuge 5414 at 4° C. The aqueous layer was removed and the protein extraction was repeated twice more. One volume of 4 mM LiCl was added and the RNA was allowed to precipitate overnight at 4° C. To collect the RNA, the mixture was centrifuged for 15 min at 4° C. at 13,000 rpm in an Eppendorf centrifuge 5414. The pellet was resuspended in 250 ul sterile, deionized water. To precipitate the RNA, 0.1 vols of 3M sodium acetate (pH5.2) and 2 vols 100% ethanol were added. An aliquote was taken and centrifuged for 20 mins at 4° C. at 13,000 rpm in an Eppendorf centrifuge 5414. The pellet was washed with 70% ethanol to remove salts from the pellet and dried using a speed vac. The pellet was resuspended in 25 ul DEPC H$_2$O and analyzed for integrity via electrophoresis. The RNA was stored at −70° C.

RT-PCR and Cloning of *Arabidopsis* AtPrPase

The synthetic oligonucleotide primers (MWG-Biotech) were designed based on the BAC clone sequence (GenBank accession number AF007269, gene="A_IG002N01.21", complement 24979 . . . 28076).

```
APP forward:
                                    (SEQ ID NO: 35)
5' CCGTTAACAGCCATGGCGATTCCTTTCATGGAA 3'

APP reverse:
                                    (SEQ ID NO: 36)
5' GTCCCGGGACTTAATCTGTCTTCTTGTCTT 3'
```

The primers designed contained a HpaI site in the 5' region and an XmaI site in the 3' region for cloning purpose.

The synthesis of the first strand cDNA was achieved using AMV Reverse Transcriptase (Roche, Mannheim, Germany). The resulting single-stranded cDNA was amplified via Polymerase Chain Reaction (PCR) utilizing the two gene specific primers. The conditions for the reaction were standard conditions with Expand High Fidelity PCR system (Roche). The parameters for the reaction were: five minutes at 94° C. followed by five cycles of 40 seconds at 94° C., 40 seconds at 50° C. and 1.5 minutes at 72° C. This was followed by thirty cycles of 40 seconds at 94° C., 40 seconds at 65° C. and 1.5 minutes at 72° C. The fragment generated under these RT-PCR conditions was 1.3 kilobase long.

The fragment was extracted from agarose gel with a QIAquick Gel Extraction Kit (Qiagen) and ligated into the TOPO pCR 2.1 vector (Invitrogen) following manufacture's instructions. Recombinant vectors were transformed into Top10 cells (Invitrogen) using standard conditions. Transformed cells were selected for on LB agar containing 100 µg/ml carbenicillin, 0.8 mg X-gal (5-bromo-4-chloro-3-indolyl-β-D-galactoside) and 0.8 mg IPTG (isopropylthio-β-D-galactoside) grown overnight at 37° C. White colonies were selected and used to inoculate 3 ml of liquid LB containing 100 µg/ml ampicillin and grown overnight at 37° C. Plasmid DNA was extracted using the QIAprep Spin Miniprep Kit (Qiagen) following manufacture's instructions.

The RT-PCR cloned *Arabidopsis* AtPrPase1 and AtPrPase2 were sequenced to obtain their complete cDNA sequences (SEQ ID NO: 3 and SEQ ID NO: 5).

Example 6

In Vivo Complementation of the SM3614 Yeast (PrPase) Mutant

The fragment containing the *Arabidopsis* AtPrPase1 cDNA was excised from the recombinant PCR2.1 TOPO vector by digestion with EcoRI (Roche) according to manufacture's instructions. The subsequent fragment was excised from agarose gel with a QIAquick Gel Extraction Kit (QIAgen) according to manufacture's instructions and ligated into the yeast expression vector pYES2 (Invitrogen), also cleaved with EcoRI and dephosphorylated prior to ligation.

The recombinant expression pYES2 vector containing the *Arabidopsis* AtPrPase1 cDNA in the sense orientation under the yeast GAL1 promoter was transformed into the yeast mutant SM3614 (MATa rcel Δ::TRP1 step24D::LEU2) (Tam et al. 1998) following Invitrogen's protocol. The transformed cells were selected for on Complete Supplement Mixture (CSM) minus Uracil 0.8% agar (Bio 101, Inc.) grown at 30° C. for two days. The transformed colonies were selected to make master plates containing patches of the transformed SM3614 on CSM plates minus Uracil supplemented with 2% galactose for induction of the expression of the *Arabidopsis*

AtPrPase1. The plates were grown at 30° C. for two days. The master plates were replica plated onto a lawn of wild type yeast SM 1068 (MATα lys1) (Tam et al. 1998, The Journal of Cell Biology, 142, 635-649) on SD plates supplemented with 2% galactose under various mating conditions and incubated at 30° C. for two days.

Example 7

Cloning of Soybean and Corn cDNAs Encoding for PrPase

Construction of cDNA Libraries of Soybean and Corn

To isolate the clones encoding PrPase from soybean and corn the cDNA libraries were created with SMART RACE cDNA Amplification kit (Clontech Laboratories) following manufacture's instructions. Total RNA created as described in Example 5 was used as the template. Three-week old corn leaves and stems and soybean leaves were used for total RNA preparation respectively.

Cloning of Soybean and Corn cDNAs Encoding for PrPase

The EST sequences for ZmPrPase and GmPrPase identified from the database search as described in Example 4 were used to design oligos for RACE. The extended partial sequences for ZmPrPase and GmPrPase were obtained by performing Rapid Amplification of cDNA Ends polymerase chain reaction (RACE PCR) using the Advantage 2 PCR kit (Clontech Laboratories) and the SMART RACE cDNA amplification kit (Clontech Laboratories) using a Biometra T3 Thermocycler following the manufacture's instructions. The gene specific synthetic oligonucleotide primer (MWG-Biotech) used were:

For ZmPrPase:

```
                                        (SEQ ID NO: 37)
5' RACE oligo:    5' AGCAGCCACGATTGGTGGCCCCAAT 3'

(SEQ ID NO: 38)
3' RACE oligo:    5' GGGCCACCAATCGTGGCTGCTATCA 3'
```

For GmPrPase:

```
                                        (SEQ ID NO: 39)
5' RACE oligo:    5' CGCAGCCAGTCCTCATTGGGCTCATC 3'

(SEQ ID NO: 40)
3' RACE oligo:    5' CGGATAGTTGAGGGAGGAAGCAAG 3'
```

The sequences obtained from the RACE reactions were compiled to give the nucleotide sequences for the partial GmPrPase (SEQ ID NO: 14) and the partial ZmPrPase (SEQ ID NO: 21).

Having the partial sequences for soybean and corn, full-length sequences were obtained. The nucleotide sequence of the full-length PrPase from soybean (*Glycine max*) (Clone ID No: GmPrPase2) is provided as SEQ ID NO: 16 with the deduced amino acid sequence as SEQ ID NO: 17. The nucleotide sequence of the full-length PrPase from corn (*Zea mays*) (Clone ID No: ZmPrPase2) is provided as SEQ ID NO: 23 with the deduced amino acid sequence as SEQ ID NO: 24.

Example 8

Engineering Drought-Tolerant *Arabidopsis* Plants

Binary Vector Construction: pGMSG and pGMGG

The pLMNC53 vector (Mankin, 2000, PHD thesis) was digested with HindIII (Roche) and blunt-end filled with Klenow enzyme and 0.1 mM dNTPs (Roche) according to manufacture's instructions. This fragment was extracted from agarose gel with a QIAquick Gel Extraction Kit (Qiagen) according to manufacture's instructions. The purified fragment was then digested with EcoRI (Roche) according to manufacture's instructions. This fragment was extracted from agarose gel with a QIAquick Gel Extraction Kit (Qiagen) according to manufacture's instructions. The resulting 1.4 kilobase fragment, the gentamycin cassette, included the nos promoter (Becker et al., 1992 Plant Molecular Biology 20: 1195-7), aacCI gene (Hajdukiewicz et al., 1994 Plant Molecular Biology 25: 989-94), and the g7 terminator (Becker et al., 1992).

The vector pBlueScript was digested with EcoRI and SmaI (Roche) according to manufacture's instructions. The resulting fragment was extracted from agarose gel with a QIAquick Gel Extraction Kit (Qiagen) according to manufacture's instructions. The digested pBlueScript vector and the gentamycin cassette fragments were ligated with T4 DNA Ligase (Roche) according to manufacture's instructions, joining the two respective EcoRI sites and joining the blunt-ended HindIII site with the SmaI site.

The recombinant vector (pGMBS) was transformed into Top10 cells (Invitrogen) using standard conditions. Transformed cells were selected for on LB agar containing 100 g/ml carbenicillin, 0.8 mg X-gal (5-bromo-4-chloro-3-indolyl-β-D-galactoside) and 0.8 mg IPTG (isopropylthio-β-D-galactoside), grown overnight at 37° C. White colonies were selected and used to inoculate 3 ml of liquid LB containing 100 µg/ml ampicillin and grown overnight at 37° C. Plasmid DNA was extracted using the QIAprep Spin Miniprep Kit (Qiagen) following manufacture's instructions. Analyses of subsequent clones and restriction mapping were performed according to standard molecular biology techniques (Sambrook et al. 1989).

Both the pGMBS vector and plbxSuperGUS vector were digested with XbaI and KpnI (Roche) according to manufacture's instructions, excising the gentamycin cassette from pGMBS and producing the backbone from the plbxSuperGUS vector. The resulting fragments were extracted from agarose gel with a QIAquick Gel Extraction Kit (Qiagen) according to manufacture's instructions. These two fragments were ligated with T4 DNA ligase (Roche) according to manufacture's instructions.

The resulting recombinant vector (pGMSG) was transformed into Top10 cells (Invitrogen) using standard conditions. Transformed cells were selected for on LB agar containing 100 µg/ml carbenicillin, 0.8 mg X-gal (5-bromo-4-chloro-3-indolyl-β-D-galactoside) and 0.8 mg IPTG (isopropylthio-β-D-galactoside), grown overnight at 37° C. White colonies were selected and used to inoculate 3 ml of liquid LB containing 100 µg/ml ampicillin and grown overnight at 37° C. Plasmid DNA was extracted using the QIAprep Spin Miniprep Kit (Qiagen) following manufacture's instructions. Analyses of subsequent clones and restriction mapping were performed according to standard molecular biology techniques (Sambrook et al. 1989).

Another example for a plant binary vector is the pGMGG vector, where both the pBinK vector containing the guard cell-specific promoter KST1 (Bernd Muller-Rober, 1999) and pGMSG vector were digested with XbaI and SmaI according to manufacture's instructions, excising KST1 from pBinK and producing the backbone from the pGMSG vector. The resulting fragments were extracted from agarose gel with QIAquick Gel Extraction Kit (Qiagen) according to manufacture's instructions. These two fragments were ligated with T4 DNA ligase (Roche) according to manufacture's instructions.

The resulting recombinant vector (pGMGG) was transformed into Top10 cells (Invitrogen) using standard conditions. Transformed cells were selected for on LB agar containing 100 μg/ml carbenicillin, 0.8 mg X-gal (5-bromo-4-chloro-3-indolyl-β-D-galactoside) and 0.8 mg IPTG (isopropylthio-β-D-galactoside), grown overnight at 37° C. White colonies were selected and used to inoculate 3 ml of liquid LB containing 100 μg/ml ampicillin and grown overnight at 37° C. Plasmid DNA was extracted using the QIAprep Spin Miniprep Kit (Qiagen) following manufacture's instructions. Analyses of subsequent clones and restriction mapping were performed according to standard molecular biology techniques (Sambrook et al. 1989).

Subcloning of Arabidopsis AtPrPases into the Binary Vectors

The fragment containing the Arabidopsis PrPase cDNA was excised from the recombinant PCR2.1 TOPO vector by digestion with HpaI and XmaI (Roche) according to manufacture's instructions. The subsequent fragment was excised from agarose gel with a QIAquick Gel Extraction Kit (QIAgen) according to manufacture's instructions and ligated into the binary vectors pGMSG, cleaved with XmaI and Ecl136II and dephosphorylated prior to ligation.

The clones AtPrPase1 (SEQ ID NO: 3) and AtPrPase2 (SEQ ID NO: 5) were cloned into pGMSG vectors in sense orientation. The resulting recombinant pGMSG vectors contained the Arabidopsis prenyl protease under the control of the constitutive super promoter.

Agrobacterium Transformation

The recombinant vectors were transformed into Agrobacterium tumefaciens C58C1 and PMP90 according to standard conditions (Hoefgen and Willmitzer, 1990).

Plant Transformation

Arabidopsis thaliana ecotypes C24 and Col-2 were grown and transformed according to standard conditions (Bechtold 1993, Acad. Sci. Paris. 316:1194-1199, Bent et al. 1994, Science 265:1856-1860).

Screening of Transformed Plants

Seeds were sterilized according to standard protocols (Xiong et al. 1999, Plant Molecular Biology Reporter 17: 159-170). Seeds were plated on ½ MS 0.6% agar supplemented with 1-3% sucrose and 50-150 μg/ml gentamycin. Seeds on plates were vernalized for two days at 4° C. The seeds were germinated in a climatic chamber at an air temperature of 22° C. and light intensity of 55 micromols$^{-1}$ m$^{-2}$ (white light; Philips TL 65W/25 fluorescent tube) and 24 hour light. Transformed seedlings were selected after 7-14 and transferred to ½ MS 0.6% agar plates supplemented with 1% sucrose and allowed to recover for 1-5 days.

Drought Tolerance Screening

The transgenic plants were screened for their improved drought tolerance. Seedlings were transferred to dry, sterile filter paper and allowed to desiccate for 4 hours. Seedlings were then removed and placed on ½ MS 0.6% agar plates and scored after two days.

Salt Tolerance Screening

The transgenic plants are screened for the improved salt tolerance. Seedlings are transferred to ½ MS liquid supplemented with 600 mM NaCl and allowed to incubate for 2-4 hours. Seedlings are then removed and placed on ½ MS 0.6% agar plates and scored for surviving seedlings after two days.

Example 9

Engineering Drought-Tolerant Soybean Plants

The GmPrPase clones (SEQ ID NO: 14 and 16) are cloned into pGMSG vectors in sense orientation. These constructs are used to transform soybean as described below.

Seeds of soybean are surface sterilized with 70% ethanol for 4 minutes at room temperature with continuous shaking, followed by 20% (v/v) Clorox supplemented with 0.05% (v/v) Tween for 20 minutes with continuous shaking. Then, the seeds are rinsed 4 times with distilled water and placed on moistened sterile filter paper in a Petri dish at room temperature for 6 to 39 hours. The seed coats are peeled off, and cotyledons are detached from the embryo axis. The embryo axis is examined to make sure that the meristematic region is not damaged. The excised embryo axes are collected in a half-open sterile Petri dish and air dried to a moisture content less than 20% (fresh weight) in a sealed Petri dish until further use.

Agrobacterium tumefaciens culture is prepared from a single colony in LB solid medium plus appropriate antibiotics (e.g. 100 mg/l streptomycin, 50 mg/l kanamycin) followed by growth of the single colony in liquid LB medium to an optical density at 600 nm of 0.8. Then, the bacteria culture is pelleted at 7000 rpm for 7 minutes at RT, and resuspended in MS (Murashige and Skoog, 1962) medium supplemented with 100 μM acetosyringone. Bacteria cultures are incubated in this pre-induction medium for 2 hours at RT before use. The axis of soybean zygotic seed embryos at approximately 15% moisture content are imbibed for 2 hours at RT with the pre-induced Agrobacterium suspension culture. The embryos are removed from the imbibition culture and are transferred to Petri dishes containing solid MS medium supplemented with 2% sucrose and incubated for 2 days, in the dark at RT. Alternatively, the embryos are placed on top of moistened (liquid MS medium) sterile filter paper in a Petri dish and incubated under the same conditions described above. After this period, the embryos are transferred to either solid or liquid MS medium supplemented with 500 mg/L carbenicillin or 300 mg/L cefotaxime to kill the agrobacteria. The liquid medium is used to moisten the sterile filter paper. The embryos are incubated during 4 weeks at 25° C., under 150 μmol m$^{-2}$ sec$^{-1}$ and 12 hours photoperiod. Once the seedlings have produced roots, they are transferred to sterile metromix soil. The medium of the in vitro plants is washed off before transferring the plants to soil. The plants are kept under a plastic cover for 1 week to favor the acclimatization process. Then the plants are transferred to a growth room where they are incubated at 25° C., under 150 μmol m$^{-2}$ sec$^{-1}$ light intensity and 12 hours photoperiod for about 80 days.

The transgenic plants are screened for their improved drought tolerance according to the screening method described in Example 8 to demonstrate that transgene expression confers drought tolerance.

Example 10

Engineering Drought-Tolerant Rapeseed Plants with the AtPrPase Clones

The AtPrPase constructs of Example 8 are used to transform rapeseed as described below.

The method of plant transformation described in Example 8 is also applicable to Brassica and other crops. Seeds of canola are surface sterilized with 70% ethanol for 4 minutes at room temperature with continuous shaking, followed by 20% (v/v) Clorox supplemented with 0.05% (v/v) Tween for 20 minutes, at RT with continuous shaking. Then, the seeds are rinsed 4 times with distilled water and placed on moistened sterile filter paper in a Petri dish at room temperature for 18 hours. Then the seed coats are removed and the seeds are air dried overnight in a half-open sterile Petri dish. During this period the seeds lose approx. 85% of its water content. The seeds are then stored at room temperature in a sealed Petri dish until further use. DNA constructs and embryo imbibitions are as described in Example 8. Samples of the primary transgenic plants (T0) are analyzed by PCR to confirm the presence of T-DNA. These results are confirmed by Southern hybridization in which DNA is electrophoresed on a 1% agarose gel and transferred to a positively charged nylon membrane (Roche Diagnostics). The PCR DIG Probe Synthesis Kit (Roche Diagnostics) is used to prepare a digoxigenin-labelled probe by PCR, and used as recommended by the manufacturer.

The transgenic plants are screened for their improved drought tolerance according to the screening method described in Example 8 to demonstrate that transgene expression confers drought tolerance.

Example 11

Engineering Drought-Tolerant Corn Plants

The ZmPrPase clones (SEQ ID NO: 21 and 23) are cloned into pGMSG vectors in sense orientation. These constructs are used to transform corn.

The imbibition of dry embryos with a culture of *Agrobacterium* is also applicable to maize embryo axes. The experimental protocol is the same as described in Example 8 but using maize seeds as the source of embryos.

The transgenic plants are screened for their improved drought tolerance according to the screening method described in Example 8 to demonstrate that transgene expression confers drought tolerance.

Example 12

Guard-Cell Specific Expression of the AtPrPase1 Promoter

The promoter region of AtPrPase (SEQ ID NO: 10) is cloned into pGMSG in place of the superpromoter, driving the reporter gene GUS (Jefferson et al., 1987). The resulting construct is transformed into *Arabidopsis* plants as described in Example 8.

The transgenic plants are screened for their guard-cell specific staining to demonstrate that the transgene expression confers guard-cell specific promoter activity.

Example 13

Over-Expression of PrPase in Plants Leads to Increased Stress Tolerance and Plant Growth The AtPrPase clones (SEQ ID NO: 3 and 5) used to transform *Arabidopsis*, as described in Example 8 are used to transform soybean, rapeseed, and corn as described in Examples 9, 10, and 11, respectively.

The transgenic plants are screened for their improved stress tolerance according to the screening method described in Example 8 to demonstrate that transgene expression confers stress tolerance.

The transgenic plants are further screened for their growth rate to demonstrate that transgene expression confers increased growth rates.

Specifically, transgenic *Arabidopsis* plants transformed with AtPrPase1 (SEQ ID NO: 3 encoding SEQ ID NO: 4) were assessed for stress tolerance and plant growth. The transgenic *Arabidopsis* plants were grown for three weeks in a growth chamber at a temperature of 22° C., 55% relative humidity and light intensity of 40 micromols$^{-1}$ m$^{-2}$ (white light; Philips TL 65W/25 fluorescent tube) and 16 hours light and 8 hours dark day length cycle. Soil moisture was maintained throughout this time at approximately 50% of the maximum water-holding capacity of soil. After 3 weeks, the entire above-group plant biomass was collected, dried at 65° C. for 2 days and weighed.

Three independent experiments were conducted with data shown in Table 4. In each experiment, 10 transgenic events were selected, 10-12 transgenic plants were assayed for each event (including the control event). Different control plants were used for comparison in each experiment. The dry weight was calculated by averaging plants of the same transformation event (given in grams in Table 4). The analysis was run using a Least Square Mean (LSMEAN).

The first experiment used *Arabidopsis* ecotype C24 as control. The vector control plants were generated by transforming into the wild type C24 plants the T-DNA of a binary vector containing between the left and right borders a selectable marker cassette (Promoter-selectable marker-Terminator) and a cassette with no gene of interest (promoter-terminator).

The second experiment used both MTXC24 and BPSC24 as controls, where MTXC24 and BPSC24 were single seed descent variants of the *Arabidopsis* C24 ecotype.

The third experiment used *Arabidopsis* ecotype Col-0 as control.

In all three experiments, AtPrPase1 (SEQ ID NO: 3 encoding SEQ ID NO: 4) transgenic plants in each of the corresponding control background, under limited water condition, accumulated more dry weight than the corresponding control plants as shown in Table 4.

TABLE 4

| Experiment | Control used | Control Dry Weight | | AtPrPase1 Dry Weight | |
|---|---|---|---|---|---|
| | | LSMean | Std. Error | LSMean | Std. Error |
| 1 | SC24 | 0.098269 | 0.0045776 | 0.141823 | 0.0043416 |
| 2 | MTX C24 | 0.0547 | 0.0035 | 0.1047 | 0.0028 |
| | BPS C24 | 0.0581 | 0.0035 | | |
| 3 | Col-0 | 0.189 | 0.009 | 0.213 | 0.003 |

Example 14

Transformation of Dicotyledons

The polynucleotides of the present invention, including the polynucleotides encoding the polypeptides of the present invention, may be used to transform dicotyledons in an effort to confer specific traits into the plant. Such polynucleotides may be either the full-length polynucleotide, fragments, the complementary strand, or variants thereof, and may be either by themselves or operably fused to heterologous polynucleotides.

Transformation techniques for dicotyledons are well known in the art and include *Agrobacterium*-based techniques and techniques which do not require *Agrobacterium*.

Non-*Agrobacterium* techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., EMBO J. 3: 2717-2722 (1984), Potrykus et al., Mol. Gen. Genet. 199: 169-177 (1985), Reich et al., Biotechnology 4: 1001-1004 (1986), and Klein et al., Nature 327: 70-73 (1987). In each case the transformed cells are regenerated to whole plants using standard techniques known in the art.

*Agrobacterium*-mediated transformation is a preferred technique for transformation of dicotyledons because of its high efficiency of transformation and its broad utility with many different species. The many crop species which are routinely transformable by *Agrobacterium* include tobacco, tomato, sunflower, cotton, oilseed rape, potato, soybean, alfalfa and poplar (EP 0 317 511 (cotton), EP 0 249 432 (tomato, to Calgene), WO 87/07299 (Brassica, to Calgene), U.S. Pat. No. 4,795,855 (poplar)). *Agrobacterium* transformation typically involves the transfer of the binary vector carrying the foreign DNA of interest (e.g. pCIB200 or pCIB2001) to an appropriate *Agrobacterium* strain which may depend of the complement of vir genes carried by the host *Agrobacterium* strain either on a co-resident Ti plasmid or chromosomally (e.g. strain CIB542 for pCIB200 and pCIB2001 (Uknes et al. Plant Cell 5: 159-169 (1993)). The transfer of the recombinant binary vector to *Agrobacterium* is accomplished by a triparental mating procedure using *E. coli* carrying the recombinant binary vector, a helper *E. coli* strain which carries a plasmid such as pRK2013 and which is able to mobilize the recombinant binary vector to the target *Agrobacterium* strain. Alternatively, the recombinant binary vector can be transferred to *Agrobacterium* by DNA transformation (Hofgen & Willmitzer, Nucl. Acids Res. 16: 9877 (1988)).

Transformation of the target plant species by recombinant *Agrobacterium* usually involves co-cultivation of the *Agrobacterium* with explants from the plant and follows protocols well known in the art. Transformed tissue is regenerated on selectable medium carrying the antibiotic or herbicide resistance marker present between the binary plasmid T-DNA borders.

Other methods for the transformation of dicotyledons are known in the art. Thus, this example should be not construed as limiting the scope of the invention to only those examples illustrated above or elsewhere herein.

Example 15

Transformation of Monocotyledons

The polynucleotides of the present invention, including the polynucleotides encoding the polypeptides of the present invention, may be used to transform monocotyledons in an effort to confer specific traits into the plant. Such polynucleotides may be either the full-length polynucleotide, fragments, the complementary strand, or variants thereof, and may be either by themselves or operably fused to heterologous polynucleotides as described in more detail elsewhere herein.

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e. co-transformation) and both these techniques are suitable for use with this invention. Co-transformation may have the advantage of avoiding complex vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. Biotechnology 4: 1093-1096 (1986)).

Patent Applications EP 0 292 435 (to Ciba-Geigy), EP 0 392 225 (to Ciba-Geigy) and WO 93/07278 (to Ciba-Geigy) describe techniques for the preparation of callus and protoplasts from an elite inbred line of maize, transformation of protoplasts using PEG or electroporation, and the regeneration of maize plants from transformed protoplasts. Gordon-Kamm et al., Plant Cell 2: 603-618 (1990) and Fromm et al., Biotechnology 8: 833-839 (1990) have published techniques for transformation of A188-derived maize line using particle bombardment. Furthermore, application WO 93/07278 (to Ciba-Geigy) and Koziel et al., Biotechnology 11: 194-200 (1993) describe techniques for the transformation of elite inbred lines of maize by particle bombardment. This technique utilizes immature maize embryos of 1.5-2.5 mm length excised from a maize ear 14-15 days after pollination and a PDS-1000He Biolistics device for bombardment.

Transformation of rice can also be undertaken by direct gene transfer techniques utilizing protoplasts or particle bombardment. Protoplast-mediated transformation has been described for Japonica-types and Indica-types (Zhang et al., Plant Cell Rep 7: 379-384 (1988); Shimamoto et al. Nature 338: 274-277 (1989); Datta et al. Biotechnology 8: 736-740 (1990)). Both types are also routinely transformable using particle bombardment (Christou et al. Biotechnology 9: 957-962 (1991)).

Patent Application EP 0 332 581 (to Ciba-Geigy) describes techniques for the generation, transformation and regeneration of Pooideae protoplasts. These techniques allow the transformation of *Dactylis* and wheat. Furthermore, wheat transformation was been described by Vasil et al., Biotechnology 10: 667-674 (1992) using particle bombardment into cells of type C long-term regenerable callus, and also by Vasil et al., Biotechnology 11: 1553-1558 (1993) and Weeks et al., Plant Physiol. 102: 1077-1084 (1993) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75-1 mm in length) are plated onto MS medium with 3% sucrose (Murashige & Skoog, Physiologia Plantarum 15: 473-497 (1962)) and 3 mg/l 2,4-D for induction of somatic embryos which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2-3 h and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the DuPont Biolistics, helium device using a burst pressure of about 1000 psi using a standard 80 mesh screen. After bombardment, the embryos are placed back into the dark to recover for about 24 h (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contained half-strength MS, 2% sucrose, and the same concentration of selection agent.

An additional method of transforming monocots is found in International Publication No. WO 00/12734, and describes the application of the Ac-Ds transposon system to the insertion of transgenes into plants.

Other methods for the transformation of monocotyledons are known in the art. Thus, this example should be not construed as limiting the scope of the invention to only those examples illustrated above or elsewhere herein.

Example 16

Method of Transforming Plants Using Vacuum Infiltration

Transformation of plants may serve as a vital tool in assessing the biological function of a particular polynucleotide or polypeptide. For example, a plant may be transformed with a vector capable of downregulating a particular gene via anti-sense regulation (i.e., the vector may express a transcript of the gene of interest in the anti-sense direction), or the vector may simply be capable of overexpressing a particular polypeptide, for example. By observing the resulting phenotypes of the transformant, one may derive protein function using techniques known in the art and described elsewhere herein.

The following method of transforming plant material may be applicable to any plant species, though is particularly suited for use in *Arabidopsis*.

*Arabidopsis* is grown at 20° C., 8 hr light, 18° C. 16 dark until needed for transformation and is fertilized once a week from below. Plants are thinned to ~1 per square inch and are used immediately upon bolting. Short days allow stronger vegetative plant growth and increase seed yield.

Plants are transferred to 20° C., 16 hr light, 18° C. 8 hr dark. The plants should bolt quickly, and they are ready to infiltrate when the primary inflorescences are 10-15 cm tall and the secondary inflorescences are appearing at the rosette.

In the meantime, constructs are transformed into *Agrobacterium tumefaciens* strain EHA105 (Hood et al., Transgenic Research 2:208-218 (1993)) (see Direct *Agrobacterium* Transformation:Freeze-Thaw Method below). When the plants are ready to transform, 1 ml of an overnight culture is used to innoculate a 500 ml culture of YEB medium (2 L flask) containing the appropriate antibiotic for the construct and 50 ug/mL rifampicin (C58 Agro and or 25 mg/mL gentamycin (pMP90)). Cultures are grown for 2 days at 28° C., ~275 rmp. YEB media is described below.

When $OD_{600}$ is greater than 2.0, the culture is centrifuged for 30 min, at 3500 rpm and resuspended in 0.5-1.0 ml of infiltration medium described below.

The resuspended culture is placed in a container with a large bell jar, and pots containing plants to be infiltrated are inverted into the infiltration medium so that the entire plant is covered (including the rosette, but not too much soil). Any large air bubbles under the plants are removed. A vacuum (~700 Hg) is drawn, the suction is closed, and the plants are allowed to sit under vacuum for 5 min. The vacuum pressure is quickly released and the pots are briefly drained.

Infiltrated plants are grown as before at 20° C., 16 hr light, and 18° C. 8 hr dark. Plants are staked as the bolts grow. When the plants are finished flowering, the $T_0$ seeds are harvested.

Seeds are sterilized and screened for transformants on the selective medium described below. Dark green (resistant) plants are transferred to secondary selection plate a week after germination, then to soil after 6-10 days. New transplants are kept covered for several days.

| Plant media: | | |
|---|---|---|
| For 1 L | Vacuum Infiltration Medium | Selection Medium |
| MS Salts | 2.2 g | 4.3 g |
| B5Vitamins, 1000X | 1.0 mL | 1.0 mL |
| Sucrose | 50 g | 10 g |
| MES, 200 mg/mL pH 5.7 with KOH | 2.5 mL | 2.5 mL |
| Benzylamonipurine (BAP, 1 mg/mL) | 44 µL | — |
| Silweet L-77 | 200 µL | — |
| Phytagar | — | 8 g |
| Pursuit (1 mM) | — | 100 µL |

| Bacterial Media | YEP |
|---|---|
| Yeast extract | 1.0 g |
| Beef Extract | 5.0 g |
| Peptone | 5.0 g |
| Sucrose | 5.0 g |
| $MgSO_4$ | 0.5 g |

The skilled artisan would appreciate that the above transformation method could be modified to apply to other species of plants. Such modification may include the addition of new steps, the deletion of any of the steps described, and/or substitution of reagents.

Direct *Agrobacterium* Transformation:Freeze-Thaw Method.

An *Agrobacterium* strain containing the appropriate helper Ti plasmid is grown in 5 mL of YEP medium overnight at 28° C. 2 ml of the overnight culture is added to 50 ml YEP medium in a 259 mL flask and shaken vigorously (250 rpm) at 28° C. until the culture grows to an $OD_{600}$ of 0.5 to 1.0. The culture is chilled on ice. The cell suspension is centrifuged at 3000 g for 5 min at 4° C.

The supernatant solution is discarded. The cells are resuspend in 1 mL of 20 mM $CaCl_2$ solution (ice-cold). 0.1 mL aliquots are dispensed into prechilled Eppendorf tubes. About 1 ug of plasmid DNA is added to the cells.

The cells are frozen in liquid nitrogen. The cells are thawed by incubating the test tube in a 37° C. water bath for 5 min. 1 mL of YEP medium is added to the tube and the tube incubated at 28° C. for 2-4 hr with gentle rocking. This period allows the bacteria to express the antibiotic resistance genes. The tubes are centrifuged for 30 s in an Eppendorf centrifuge. The supernatant solution is discarded and the cells resuspended in 0.1 mL YEP medium The cells are spread onto a YEP agar plate containing 3-5 ug/mL tetracycline and 10-25 ug/mL kanamycin. The plate is incubated at 28° C. Transformed colonies should appear in 2-3 days.

The skilled artisan would appreciate that the above transformation method could be modified. Such modification may include the addition of new steps, the deletion of any of the steps described, and/or substitution of reagents.

Example 17

Functional Determination of Proteins Using Metabolite Profiling

The present invention encompasses the application of metabolite profiling to the identification of gene function for the polypeptides of the present invention. In one example, transgenic plants could be produced which are either incapable of expressing a protein of the present invention, or that have decreased expression levels of a protein of the present invention. Such transgenic plants could be produced by creating knockout constructs to inactivate or delete the endogenous gene, for example, using methods known in the art. Alternatively, the transgenic plants could be produced by inserting into the plant a construct that expresses antagonists of a protein of the present invention (e.g., antisense oligonucleotides, antisense genes, antibodies, etc.). Other examples of methods of producing transgenic plants, including specific strategies, are known in the art, some of which are described elsewhere herein.

Once a protein of the present invention is inactivated, or its expression inhibited, the resulting metabolite profile of the plant can be ascertained, and the function of the protein assigned. Some of the anticipated metabolic profiles of inhibiting or inactivating the expression of a protein of the present invention in a plant may resemble known nutritional deficiencies, pathogenic diseases, biotic stresses, or abiotic stresses, for example, many of which are disclosed elsewhere herein. In addition, the metabolic profile of a transgenic plant of the present invention may be useful in identifying the specific pathways the polypeptide of the present invention is a member of, in addition, to identifying the potential downstream and/or upstream effectors or affectors, respectively. In addition, it may be possible to identify the mode of action of a polypeptide of the present invention.

A number of methods are known in the art for identifying the metabolic profile of a plant. A non-limiting example is provided by Sauter, H., et al., in "Metabolic Profiling of Plants: A New Diagnostic Technique", Synthesis and Chemistry of Agrochemicals II, Baker, D. R., Fenyes, J. G., and Moberg, W. K., eds, ACS Symposium Series, 433, Chapter 24, pp. 288-299, (1991). Briefly, transgenic plants of the invention, or plants in which the expression of a polypeptide of the present invention is inhibited or inactivated, are grown in growth chambers. The shoots are harvested and immediately deep frozen until further treatment. The frozen plant samples are weighed and a threefold amount (W:W) of ethanol is added. The mixture is then macerated in a mixer and the resulting suspension is left for 2 hours for extraction. The next steps are filtration, evaporation, and silylation with N-Methyl-N-(trimethylsilyl)trifluoroacetamide (MSTFA). Internal standard alkanes are also added, thus allowing for the calculation of retention coefficients, as well as, quantification. The crude mixture is then subjected to gas chromotography on a methyl silicon gum fused silica capillary column (30 m DB-1. Injection temperature 230° C. Oven temperature 100°-320° C., 4° C./min; 15 min 320° C.). Retention coefficients are then calculated relative to internal standards (n-C10H22=1000, n-C28H58=2800).

The above protocol can be applied to numerous test plants, in addition, to controls. The data from the resulting profiles are then grouped together (i.e., one group for the test plants, another group for the controls) to arrive at an average profile for each group. In the latter step, the corresponding peaks (i.e., those peaks with equal retention coefficients) are grouped together and the peak heights are subjected to statistical analysis.

The differences in metabolic profiles between the test and control plants are determined by calculating the "difference profile" between the two groups. The difference profile is calculated by dividing the peal heights. This difference profile provides a semiquantitative estimate of the change in magnitude of one metabolic with respect to the other.

Once the above is completed, the peaks are then associated with particular metabolites (i.e., the metabolite identify of each peak is determined). By comparing the metabolite profile of proteins known to modulate specific pathways in a plant, to those of the present invention, clues for and/or identification of the function of a polypeptide of the present invention may be determined. Other methods are known in the art, and any one or more steps, may be equally substituted with such methods.

Example 18

RT-PCR Amplification and Cloning of CaaX Prenyl Proteases

Total RNA was isolated from leaf tissue of *Arabidopsis thaliana*, *Brassica napus* and *Glycine max*, using the Qiagen RNeasy kit and used as template to amplify the CaaX prenyl proteases (CPP) genes by RT-PCR. Reaction conditions were as follows; 1× reaction buffer (10 mM Tris-HCl pH 8.8, 1.5 mM $MgCl_2$, 50 mM KCl), dNTP's at 200 μM, 1 pM AtCPP BamFW and AtCPP SmaRV primers, 2.5 U. Pfu DNA polymerase, and template plus water to a final volume of 100 μL. Reactions were run at 1 minute 94° C., 1 minute 60° C., 1 minute 72° C., for 30 cycles. Primers used to PCR amplify *Arabidopsis* and *Brassica* sequences were those identified by SEQ ID NO: 43 and SEQ ID NO: 44. Primers used to PCR amplify the Glycine sequence were those identified by SEQ ID NO: 70 and SEQ ID NO: 71. PCR products were separated from the RT-PCR reaction mixture using the Qiagen PCR column spin kit and ligated into the prepared cloning vector, pBluescript KS+. The vector had been prepared by digestion with EcoRV and treated with Taq polymerase in the presence of dTTP to produce a 3' overhand suitable for ligation with the PCR products. The ligation products were transformed into *E. coli* DH5α cells, positive colonies selected and the resulting inserts sequenced. The above methodology is applicable to obtain homologous sequences and may require alternative primers.

```
AtCPP BamFW:
                                       (SEQ ID NO: 43)
5'-AAAGGATCCATGGCGATTCCTTTCATGG-3'

AtCPP SmaRV:
                                       (SEQ ID NO: 44)
5'-AAACCCGGGTTAATCTGTCTTCTTGTCTTCTCCA-3'

GmCPP SmaFW:
                                       (SEQ ID NO: 70)
5'-AAACCCGGGATGGCGTTTCCCTACATGGAAGCC-3'

GmCPP SacRV:
                                       (SEQ ID NO: 71)
5'-AAAGAGCTCTTAGTCTTCCTTCTTATCCGGTTCG-3'
```

Example 19

Vector Construction

Figure 2:
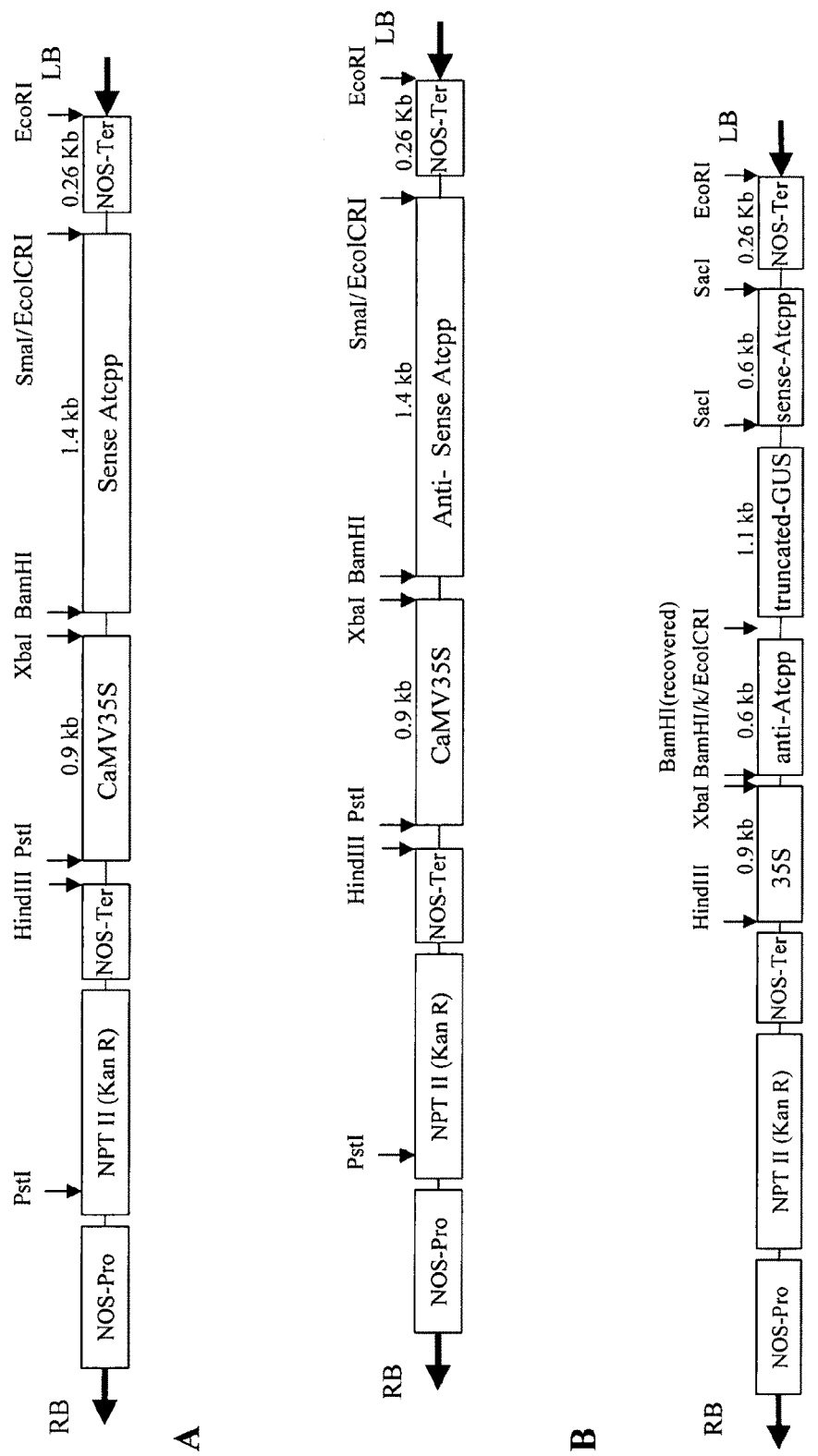

Construction of the pBI121-AtCPP construct (SEQ ID NO: 41) was prepared as follows. The pBI121 vector was digested with BamHI and SmaI. The AtCPP, 1.4 kb DNA fragment from RT-PCR (SEQ ID NO: 7) was digested with BamHI and SmaI and ligated into the pBI121 vector. The GUS sequence was then removed by digestion with SmaI and EcoICRI and the vector ligated after purification of the vector from the GUS insert to produce the pBI121-AtCPP vector (FIG. 2A). This construct was used to further generate constructs expressing the CPP gene from *Brassica* and *Glycine*. To produce the pBI121-BnCPP construct (SEQ ID NO: 63) primer pairs identified by SEQ ID NO: 43 and SEQ ID NO: 44 are used to PCR amplify the appropriate fragment which is ligated into the prepared parent vector. To produce the pBI121-GmCPP construct (SEQ ID NO: 57) primer pairs identified by SEQ ID NO: 70 and SEQ ID NO: 71 are used to PCR amplify the appropriate fragment which is ligated into the prepared parent vector.

Construction of the pBI121-antisense-AtCPP construct (SEQ ID NO: 51). The antisense fragment was produced using PCR amplification with SEQ ID NO: 7 as template and primers identified as SEQ ID NO: 48 and SEQ ID NO: 49, listed in Table 5. This fragment was digested with BamHI and SmaI and used to replace the sense fragment of the pBI121-AtCPP construct (SEQ ID NO: 41), to yield SEQ ID NO: 51 (FIG. 2B). This construct, SEQ ID NO: 51, was used to further generate constructs expressing the antisense CPP gene from *Brassica* and *Glycine*. To produce the pBI121-antisense-BnCPP construct (SEQ ID NO: 65) primer pairs identified by SEQ ID NO: 72 and SEQ ID NO: 73 are used to PCR amplify the appropriate fragment which is ligated into the prepared parent vector. To produce the pBI121-antisense-GmCPP construct (SEQ ID NO: 59) primer pairs identified by SEQ ID NO: 74 and SEQ ID NO: 75 are used to PCR amplify the appropriate fragment which is ligated into the prepared parent vector.

Construction of the pBI121-HP-AtCPP construct (SEQ ID NO: 42). The cloning strategy involved truncating the GUS gene of pBI121 and flanking the GUS sequence with a AtCPP fragment in the antisense orientation upstream of the GUS and in the sense orientation on the downstream side of GUS. The pBI121 vector was digested with SmaI and SacI, the GUS sequence and the vector fragments were purified from one another. The isolated GUS fragment was digested using EcoRV and the 1079 bp. blunt ended EcoRV/SacI fragment isolated. This was ligated back into the digested parent vector at the SmaI/SacI sites. This intermediate vector was used in the subsequent production of the hair-pin vectors. The AtCPP fragment to be used as the gene specific hair-pin sequence was isolated by PCR. Primers identified as SEQ ID NO: 45 and SEQ ID NO: 46, listed in Table 5, were used to generate a 596 bp fragment. Cloning of the sense orientation fragment was achieved by digesting the PCR AtCPP fragment with SacI and ligation into the SacI site at the 3' end of GUS. To insert the same fragment upstream of GUS, the BamHI site was opened and the ends blunted with Klenow. The PCR amplified AtCPP fragment was digested with EcoICRI, which is an isoschizomer of SacI but leaves blunt ends, and ligated into the blunted BamHI site of the vector to yield the final construct (FIG. 2C). The intermediate construct used to produce SEQ ID NO: 42 above contained only the truncated GUS gene and no CPP sequences this intermediate vector was used to further generate constructs expressing hair-pin CPP gene constructs from *Brassica* and *Glycine*. To produce the pBI121-HP-BnCPP construct (SEQ ID NO: 64) primer pairs identified by SEQ ID NO: 74 and SEQ ID NO: 75 are used to PCR amplify the sense fragment and primer pairs identified by SEQ ID NO: 76 and SEQ ID NO: 77 are used to PCR amplify the antisense fragment. These fragments are cloned into the prepared intermediate vector described above. To produce the pBI121-HP-GmCPP construct (SEQ ID NO: 58) primer pairs identified by SEQ ID NO: 78 and SEQ ID NO: 79 are used to PCR amplify the sense fragment and primer pairs identified by SEQ ID NO: 80 and SEQ ID NO: 81 are used to PCR amplify the antisense fragment. These fragments are cloned into the prepared intermediate vector described above.

The above vector constructs were modified to place the genes under the control of alternative promoters, such as, but not limited to, the RD29A or MuA. This was accomplished by excising the 35S promoter sequence and replacing it with an appropriate promoter sequence. In this way SEQ ID NOs: 55 and 56 were generated and SEQ ID NOs: 54, 57-69 can be constructed.

TABLE 5

| | | |
|---|---|---|
| AtCPP-HP-SacFW | 5'-CTGGAGCTCTTTTACCGAGGTTGGGCCTTGATCC-3' | (SEQ ID NO: 45) |
| AtCPP-HP-SacRV | 5'-ATTGAGCTCCCAATGTCCAAGCTCGTGTGCAATA-3' | (SEQ ID NO: 46) |
| AtCPP-anti-SmaFW | 5'-AAACCCGGGATGGCGATTCCTTTCATGG-3' | (SEQ ID NO: 48) |
| AtCPP-anti-BamRV | 5'-AAAGGATCCTTAATCTGTCTTCTTGTCTTCTCCA-3' | (SEQ ID NO: 49) |
| BnCPP-anti-SmaFW | 5'-AAACCCGGGATGGCGATTCCTTTCATGG-3' | (SEQ ID NO: 72) |
| BnCPP-anti-BamRV | 5'-AAAGGATCCTTAATCTGTCTTCTTGTCTTCTCC-3' | (SEQ ID NO: 73) |
| BnCPP-HP-Sac-FW | 5'-AAAGAGCTCTTCTACCAATGGTGGGACTCG-3' | (SEQ ID NO: 74) |
| BnCPP-HP-Sac-RV | 5'-AAAGAGCTCCCAGTGTCCCAGCTCGTGTG-3' | (SEQ ID NO: 75) |
| BnCPP-HP-BamFW | 5'-AAAGGATCCTTCTACCAATGGTGGGACTCG-3' | (SEQ ID NO: 76) |
| BnCPP-HP-XbaRV | 5'-AAATCTAGACCAGTGTCCCAGCTCGTGTG-3' | (SEQ ID NO: 77) |
| GmCPP-HP-Sac-FW | 5'-GATGAGCTCACAAGATCAAGTCACAGCAATGCCT-3' | (SEQ ID NO: 78) |

TABLE 5-continued

| | | |
|---|---|---|
| GmCPP-HP-Sac-RV | 5'-AAAGAGCTCCCGGTTCGTCCAGCGCGGCC-3' | (SEQ ID NO: 79) |
| GmCPP-HP-BamFW | 5'-GATGGATCCACAAGATCAAGTCACAGCAATGCCT-3' | (SEQ ID NO: 80) |
| GmCPP-HP-XbaRV | 5'-CCTTCTAGACCGGTTCGTCCAGCGCGGCC-3' | (SEQ ID NO: 81) |

Example 20

Sequence Analysis

*Arabidopsis thaliana* PrPase (AtCPP)

A disclosed nucleic acid of 1275 nucleotides referred to as AtCPP is shown in SEQ ID NO: 7.

A disclosed PrPase polypeptide encoded by SEQ ID NO: 7 has 424 amino acid residues and is presented as SEQ ID NO: 8.

The present invention also includes a nucleic acid sequence complementary to the *Arabidopsis thaliana* CaaX prenyl protease of SEQ ID NO: 7. The disclosed complementary sequence is shown as SEQ ID NO: 9.

Due to the nature of the cloning strategy the sequence presented is not full length but is missing the 5' and 3' non-translated regions. The percent identities of the *Arabidopsis thaliana* nucleotide sequence and its encoded amino acid sequence to that of other PrPase sequences as determined by EMBOSS Pairwise Alignment analysis are shown in FIGS. 6 and 7.

Using the sequences disclosed herein as hybridization probes, one is able to screen and isolate full length sequences from cDNA or genomic libraries or use the rapid amplification of cDNA ends (RACE) technology or other such PCR techniques.

*Brassica napus* PrPase (BnCPP)

A disclosed nucleic acid of 1275 nucleotides referred to as BnCPP is shown in SEQ ID NO: 11. A disclosed PrPase polypeptide encoded by SEQ ID NO: 11 has 424 amino acid residues and is presented in SEQ ID NO: 12.

The present invention also includes a nucleic acid sequence complementary to the *Brassica napus* CaaX prenyl protease of SEQ ID NO: 11. The disclosed complementary sequence is shown as SEQ ID NO: 13.

Due to the nature of the cloning strategy the sequence presented is not full length but is missing the 5' and 3' non-translated regions. The percent identities of the *Brassica napus* nucleotide sequence and its encoded amino acid sequence to that of other PrPase sequences as determined by EMBOSS Pairwise Alignment analysis are shown in FIGS. 6 and 7.

Using the sequences disclosed herein as hybridization probes, one is able to screen and isolate full length sequences from cDNA or genomic libraries or use the rapid amplification of cDNA ends (RACE) technology or other such PCR techniques.

*Glycine max* PrPase (GmCPP)

A disclosed nucleic acid of 1275 nucleotides referred to as GmCPP is shown in SEQ ID NO: 18.

A disclosed PrPase polypeptide encoded by SEQ ID NO: 18 has 424 amino acid residues and is presented in SEQ ID NO: 19.

The present invention also includes a nucleic acid sequence complementary to the *Glycine max* CaaX prenyl protease of SEQ ID NO: 18. The disclosed complementary sequence is shown as SEQ ID NO: 20.

Due to the nature of the cloning strategy the sequence presented is not full length but is missing the 5' and 3' non-translated regions. The percent identities of the *Glycine max* nucleotide sequence and its encoded amino acid sequence to that of other PrPase sequences as determined by EMBOSS Pairwise Alignment analysis are shown in FIGS. 6 and 7.

Using the sequences disclosed herein as hybridization probes, one is able to screen and isolate full length sequences from cDNA or genomic libraries or use the rapid amplification of cDNA ends (RACE) technology or other such PCR techniques.

The PrPase nucleic acids and amino acids disclosed above have homology to other disclosed PrPase sequences (GenBank ID NOs: AL161491 (AT4g01320), AF007269 and AF353722; WO 02/16625 A2). The nucleic acid and amino acid homology between these and other sequences is shown in the EMBOSS Pairwise Alignment analysis shown in FIGS. 4 and 5.

Example 21

Plant Transformation

*Arabidopsis* transgenic plants were made by the method of dipping flowering plants into an *Agrobacterium* culture, based on the method of Andrew Bent in, Clough S J and Bent A F, 1998. Floral dipping: a simplified method for *Agrobacterium*-mediated transformation of *Arabidopsis thaliana*. Wild type plants were grown under standard conditions until the plant has both developing flowers and open flowers. The plant was inverted for 2 minutes into a solution of *Agrobacterium* culture carrying the appropriate gene construct. Plants were then left horizontal in a tray and kept covered for two days to maintain humidity and then righted and bagged to continue growth and seed development. Mature seed was bulk harvested.

Transformed T1 plants were selected by germination and growth on MS plates containing 50 µg/ml kanamycin. Green, kanamycin resistant (Kan$^R$) seedlings were identified after 2 weeks growth and transplanted to soil. Plants were bagged to ensure self fertilization and the T2 seed of each plant harvested separately. During growth of T1 plants leaf samples were harvested, DNA extracted and Southern blot and PCR analysis performed.

T2 seeds were analysed for Kan$^R$ segregation. From those lines that showed a 3:1 resistant phenotype, surviving T2 plants were grown, bagged during seed set, and T3 seed harvested from each line. T3 seed was again used for Kan$^R$ segregation analysis and those lines showing 100% Kan$^R$ phenotype were selected as homozygous lines. Further molecular and physiological analysis was done using T3 seedlings.

Transgenic *Brassica napus*, *Glycine max* and *Zea mays* plants were produced using *Agrobacterium* mediated transformation of cotyledon petiole tissue. Seeds were sterilized as follows. Seeds were wetted with 95% ethanol for a short period of time such as 15 seconds. Approximately 30 ml of sterilizing solution I was added (70% Javex, 100 µl Tween20)

and left for approximately 15 minutes. Solution I was removed and replaced with 30 ml of solution II (0.25% mecuric chloride, 100 µl Tween20) and incubated for about 10 minutes. Seeds were rinsed with at least 500 ml double distilled sterile water and stored in a sterile dish. Seeds were germinated on plates of ½ MS medium, pH 5.8, supplemented with 1% sucrose and 0.7% agar. Fully expanded cotyledons were harvested and placed on Medium I (Murashige minimal organics (MMO), 3% sucrose, 4.5 mg/L benzyl adenine (BA), 0.7% phytoagar, pH5.8). An *Agrobacterium* culture containing the nucleic acid construct of interest was grown for 2 days in AB Minimal media. The cotyledon explants were dipped such that only the cut portion of the petiole is contacted by the *Agrobacterium* solution. The explants were then embedded in Medium I and maintained for 5 days at 24° C., with 16, 8 hr light dark cycles.

Explants were transferred to Medium II (Medium 1,300 mg/L timentin) for a further 7 days and then to Medium III (Medium II, 20 mg/L kanamycin). Any root or shoot tissue which had developed at this time was dissected away. Transfer explants to fresh plates of Medium III after 14-21 days. When regenerated shoot tissue developed the regenerated tissue was transferred to Medium IV (MMO, 3% sucrose, 1.0% phytoagar, 300 mg/L timentin, 20 mg/L 20 mg/L kanamycin). Once healthy shoot tissue developed shoot tissue dissected from any callus tissue was dipped in 10×IBA and transferred to Medium V (Murashige and Skooge (MS), 3% sucrose, 0.2 mg/L indole butyric acid (IBA), 0.7% agar, 300 mg/L timentin, 20 mg/L 20 mg/L kanamycin) for rooting. Healthy plantlets were transferred to soil. The above method, with or without modifications, is suitable for the transformation of numerous plant species including *Glycine max, Zea mays* and cotton.

Transgenic *Glycine max, Zea mays* and cotton can be produced using *Agrobacterium*-based methods which are known to one of skill in the art. Alternatively one can use a particle or non-particle biolistic bombardment transformation method. An example of non-particle biolistic transformation is given in U.S. Patent Application 20010026941. This method has been used to produce transgenic *Glycine max* and *Zea mays* plants. Viable plants are propagated and homozygous lines are generated. Plants are tested for the presence of drought tolerance, physiological and biochemical phenotypes as described elsewhere.

The following table identifies the constructs and the species which they have been transformed.

TABLE 6

Transformation List

| SEQ ID NO: | Construct | Species Transformed |
| --- | --- | --- |
| 41 | pBII121-AtCPP | *A. thaliana, B. napus* |
| 42 | pBII121-HP-AtCPP | *A. thaliana* |
| 52 | pRD29A-AtCPP | *A. thaliana, B. napus* |
| 53 | pRD29A-HP-AtCPP | *A. thaliana* |
| 55 | MuA-AtCPP | *Glycine max, Zea mays* |

Non-limiting examples of vector constructs suitable for plant transformation are given in SEQ ID NOs: 41, 42, 51-69. The right and left border repeats correspond to the first 24 nucleotide positions and the last 25 nucleotide positions of each construct.

SEQ ID NO: 41 is the nucleic acid sequence of pBI121-AtCPP. The 35S promoter is at positions 2515-3318 and the AtCPP sense sequence is at positions 3334-4608 of SEQ ID NO: 41.

SEQ ID NO: 42 is the nucleic acid sequence of pBI121-HP-AtCPP. The 35S promoter is at positions 2515-3318, the AtCPP anti-sense sequence at positions 3336-3925, the truncated GUS fragment at positions 3936-4958; and the AtCPP sense sequence at positions 4959-5548 of SEQ ID NO: 42.

SEQ ID NO: 51 is the nucleic acid sequence of pBI121-antisense-AtCPP. The 35S promoter is at positions 2515-3318 and the AtCPP anti-sense sequence at positions 3334-4608 of SEQ ID NO: 51.

SEQ ID NO: 52 is the nucleic acid sequence of RD29A-AtCPP. The RD29A promoter is at positions 2515-2865 and the AtCPP sense sequence at positions 3458-4732 of SEQ ID NO: 52.

SEQ ID NO: 53 is the nucleic acid sequence of RD29A-HP-AtCPP. The RD29A promoter is at positions 2515-3442, the AtCPP anti-sense sequence at positions 3460-4069, the truncated GUS fragment at positions 4060-5082, and the *A. thaliana* CaaX prenyl protease sense fragment at positions 5083-5675 of SEQ ID NO: 53.

SEQ ID NO: 54 is the nucleic acid sequence of RD29A-antisense-AtCPP. The RD29A promoter is at positions 2515-3442 and the AtCPP anti-sense sequence is at positions 3458-4732 of SEQ ID NO: 54.

SEQ ID NO: 55 is the nucleic acid sequence of MuA-AtCPP. The MuA promoter is at positions 2502-2863 and the *A. thaliana* CaaX prenyl protease sense sequence at positions 2864-4138 of SEQ ID NO: 55.

SEQ ID NO: 56 is the nucleic acid sequence of MuA-GmCPP. The MuA promoter is at positions 2502-2865 and the *G. max* CaaX prenyl protease sense sequence at positions 2866-4140 of SEQ ID NO: 56.

SEQ ID NO: 57 is the nucleic acid sequence of pBI121-GmCPP. The 35S promoter is at positions 2515-3318 and the *G. max* CaaX prenyl protease sense sequence at positions 3339-4613 of SEQ ID NO: 57.

SEQ ID NO: 58 is the nucleic acid sequence of pBI121-HP-GmCPP. The 35S promoter is at positions 2515-3318, the antisense prenyl protease fragment of *G. max* at positions 3328-3856, the *G. max* sense prenyl protease fragment is at positions 4888-5416, and the truncated GUS fragment at positions 3865-4827 of SEQ ID NO: 58.

SEQ ID NO: 59 is the nucleic acid sequence of pBI121-antisense-GmCPP. The 35S promoter is at positions 2515-3318 is the GmCPP anti-sense sequence at positions 3339-4613 of SEQ ID NO: 59.

SEQ ID NO: 60 is the nucleic acid sequence of pRD29A-GmCPP. The RD29A promoter is at positions 2515-3442 and the GmCPP sense sequence at positions 3463-4737 of SEQ ID NO: 60.

SEQ ID NO: 61 is the nucleic acid sequence of pRD29A-HP-GmCPP. The RD29A promoter is at positions 2515-3442, the GmCPP antisense sequence at positions 3452-3980, and the GmCPP sense sequence at positions 5012-5540 of SEQ ID NO: 61.

SEQ ID NO: 62 is the nucleic acid sequence of pRD29A-antisense-GmCPP. The RD29A promoter is at positions 2515-3442 and the GmCPP antisense sequence at positions 3463-4737 of SEQ ID NO: 62.

SEQ ID NO: 63 is the nucleic acid sequence of pBI121-BnCPP. The 35S promoter is at positions 2515-3318 and the BnCPP antisense sequence at positions 3334-4608 of SEQ ID NO: 63.

SEQ ID NO: 64 is the nucleic acid sequence of pBI121-HP-BnCPP. The 35S promoter is at positions 2515-3318, the BnCPP antisense sequence at positions 3328-3917, the BnCPP sense fragment at positions 4949-5538, and the truncated GUS fragment at positions 3926-4888 of SEQ ID NO: 64.

SEQ ID NO: 65 is the nucleic acid sequence of pBI121-antisense-BnCPP. The 35S promoter is at positions 2515-3318 and the BnCPP antisense sequence at positions 3334-4608 of SEQ ID NO: 65.

SEQ ID NO: 66 is the nucleic acid sequence of pRD29A-BnCPP. The RD29A promoter is at positions 2515-3420 and the BnCPP sense sequence at positions 3458-4732 of SEQ ID NO: 66.

SEQ ID NO: 67 is the nucleic acid sequence of pRD29A-HP-BnCPP. The RD29A promoter is at positions 2515-3442, the BnCPP antisense sequence at positions 3452-4041, the BnCPP sense fragment at positions 5073-5640, and the truncated GUS fragment at positions 4050-5072 of SEQ ID NO: 67.

SEQ ID NO: 68 is the nucleic acid sequence of pRD29A-antisense-BnCPP. The RD29A promoter is at positions 2515-3420 and the BnCPP antisense sequence at positions 3458-4732 of SEQ ID NO: 68.

SEQ ID NO: 69 is the nucleic acid sequence of MuA-BnCPP. The MuA promoter is at positions 2502-2820 and the BnCPP sense sequence at positions 2863-4138 of SEQ ID NO: 69.

Example 22

Southern Analysis

Genomic Southern blot analysis of transgenic *Arabidopsis* was performed using standard techniques known to one skilled in the art. Typically, 10 µg of DNA was electrophoresed in a 0.8% agarose gel and transferred to an appropriate membrane such as Hybond N+ (Amersham Pharmacia Biotech). Pre-hybridization and hybridization conditions were as suggested by the membrane manufacturer, typically at 65° C. The final stringency wash was typically at 1×SSC and 0.1% SDS at 65° C. The NPTII coding region was typically used as the radiolabeled probe in Southern blot analysis.

Thirty-seven *Arabidopsis* lines were selected as homozygous pBI121-AtCPP over-expression lines for further examination. The Southern blot depicted a representative blot confirming the presence of the pBI121-AtCPP transgene. Lines were confirmed to be transgenic by PCR analysis using transgene specific primers in the PCR assays.

Thirty-three *Arabidopsis* lines were selected as homozygous pBI121-HP-AtCPP hair-pin down-regulation lines for further examination. The Southern blot depicted a representative blot confirming the presence of the pBI121-HP-AtCPP hair-pin construct. All lines were confirmed to be transgenic by PCR analysis using transgene specific primers in the PCR assays.

*Arabidopsis* lines were selected as homozygous pRD29A-AtCPP over-expression lines for further examination. The Southern blot depicted a representative blot confirming the presence of the pRD29A-AtCPP transgene. Lines were confirmed to be transgenic by PCR analysis using transgene specific primers in the PCR assays.

*Arabidopsis* lines were selected as homozygous pRD29A-HP-AtCPP lines for further examination. The Southern blot depicted a representative blot confirming the presence of the pRD29A-HP-AtCPP transgene. Lines were confirmed to be transgenic by PCR analysis using transgene specific primers in the PCR assays.

Example 23

PCR Analysis of Transgenic Plants

PCR was used as a method to confirm the presence of the transgene in all transgenic lines and every construct. Typical PCR mixtures contained: 1× reaction buffer (10 mM Tris-HCl pH 8.8, 1.5 mM $MgCl_2$, 50 mM KCl), dNTP's at 200 µM, 1 pM forward and reverse primer, 2.5 U. Taq DNA polymerase, and template plus water to a final volume of 50 µL. Reactions were run at 1 minute 94° C., 1 minute 60° C., 1 minute 72° C., for 30 cycles. Primers used in the analysis of pBI121-AtCPP and pBI121-HP-AtCPP transgenic plants were as shown in Table 7. Primers used in the analysis of pRD29A-AtCPP were RD29AP1 (SEQ ID NO: 82) and SEQ ID NO: 44. Primers used in the analysis of pRD29A-HP-AtCPP transgenic plants were those identified as RD29AP1 (SEQ ID NO: 82), SEQ ID NO: 44 and SEQ ID NO: 45, Nosterm-RV (SEQ ID NO: 83).

TABLE 7

| | | |
|---|---|---|
| pBI121-AtCPP BamFW: | 5'-GCCGACAGTGGTCCCAAAGATGG-3' | (SEQ ID NO: 47) |
| p35S-AtCPP SmaRV: | 5'-AAACCCGGGTTAATCTGTCTTCTTGTCTTCTCCA-3' | (SEQ ID NO: 44) |
| p35S-HP-AtCPP BamFW: | 5'-CTGGAGCTCTTTTACCGAGGTTGGGCCTTGATCC-3' | (SEQ ID NO: 45) |
| p35S-HP-AtCPP SmaRV: | 5'-GCAAGACCGGCAACAGGA-3' | (SEQ ID NO: 50) |
| pRD29AP1: | 5'-TTTAAGCTTGGAGCCATAGATGCAATTCAA-3' | (SEQ ID NO: 82) |
| Nosterm-RV: | 5'-GCAAGACCGGCAACAGGA-3' | (SEQ ID NO: 83) |

Example 24

Northern Analysis of Transgenic Plants

Figure 8:
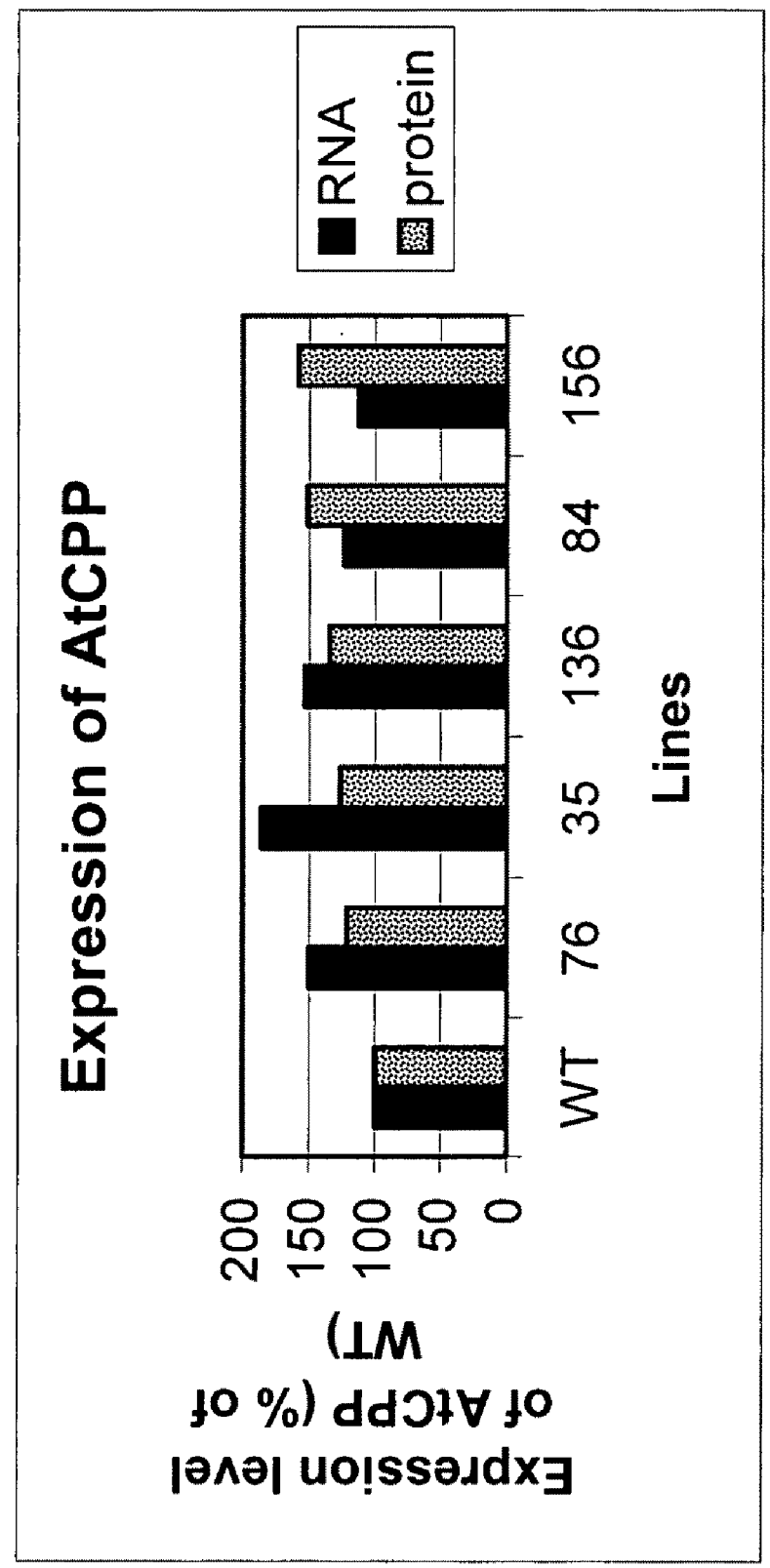

Total RNA was isolated from developing leaf tissue of 27 35S-AtCPP *Arabidopsis* lines (T3 plants). Approximately 10 µg of total RNA was loaded into each lane. The Northern blot was first probed with $P^{32}$ labeled, single-stranded antisense transcript of AtCPP which detects sense transcript, then stripped and re-probed with cDNA of β-tubulin that was used as a reference. The hybridizing bands of AtCPP and β-tubulin were scanned and quantified using the UN-Scan-It programme (Silk Scientific, Utah, USA), and the ratio of the two hybridizing bands for each sample was obtained. The ratio of the wild type plants was set to 100%, and was compared with those of the transgenic lines. Twenty-one out of twenty-seven lines showed higher expression of AtCPP transcript as compared to the wild type. Values ranged from 104% to 282% of wild type. The results of five lines (35, 84, 76, 136, and 156) of the 21 over-expressing lines is shown in FIG. 8.

Example 25

Production of Polyclonal Antibodies Against AtCPP

Anti-AtCPP antibodies were generated using AtCPP fusion protein over-expressed in *E. coli*. The over-expression vector, pMAL-p2, contains 1175 bp malE gene that is located upstream of AtCPP and encodes a 43 KDa maltose-binding protein (MBP). The 1275 bp BamHI/SmaI DNA fragment of AtCPP was inserted into pMAL-p2 at BamHI and SalI sites. The SalI site was converted into blunt end using Klenow fragment. The resulting fusion protein MBP-AtCPP was then over-expressed in DH5α, and purified by one-step affinity for MBP as described by the manufacturer (New England Biolab). The soluble fraction of the crude bacterial extract containing the MBP-AtCPP fusion protein was loaded to a amylose column (1.5 cm×10.0 cm), and the proteins were eluted with 10 mM maltose in column buffer (50 mM Tris-HCl, pH 7.5, 1 mM EDTA, and 200 mM NaCl). Fractions containing purified MBP-AtCPP fusion protein were pooled, and concentrated with a Centriprep-30 concentrator (Amicon). All purification steps were carried out at 4° C. To generate an antibody, the purified fusion protein was further separated by SDS-PAGE and the Coomassie stained band corresponding to the fusion protein was excised. The identity of the fusion protein was confirmed by Western analysis using anti-MBP antibodies (purchased from New England Biolab). The protein was eluted from the gel slice by electroelution and then emulsified in Ribi adjuvant (Ribi Immunochem) to a final volume of 1 ml. MBP-AtCPP protein was injected into a 3 kg New Zealand rabbit on day 1 and booster injections were given on day 21 and day 35 with 175 µg of the protein each time. High-titer antisera were obtained one week after the final injection.

Example 26

Western Blot Analysis of 35S-AtCPP Transgenic Lines Using Anti-AtCPP Antibodies Western analysis was performed to examine expression level of AtCPP in the transgenic lines compared with that of wild type plants. Anti-Bip antibody, an ER lumenal protein (Stressgen, Victoria, BC, Canada) was used as a reference. Total proteins were extracted from developing leaf tissue of five $ABA^S$ lines and a wild type control. The antigenic protein bands of AtCPP and Bip were scanned and quantified using the UN-Scan-It programme (Silk Scientific, Utah, USA) and the ratio of the two protein bands for each sample was obtained. The ratio of the wild type plants was set to 100%, and was compared with those of the transgenic lines. Data is presented in FIG. 8 indicating that the AtCPP protein level was increased in the transgenic lines compared to the wild type plants.

Example 27

ABA Sensitivity of Transgenic Seedlings

Approximately 100 seeds were assessed per line per 9 cm plate. Seeds were plated on minimal medium (½ MS) supplemented with no ABA or 1.0 µM ABA. Plates were chilled for 3 days at 4° C. in the dark, and incubated for up to 21 days at 22° C. with 24 hour continuous light. Plates were assessed for germination, cotyledon expansion, true leaf development and seedling vigor. Seedlings were assessed for ABA sensitivity over 21 days of growth at which time sensitive seedlings were arrested at the cotyledon stage, lacked true leaves, and showed inhibition of root growth. Wild type control Columbia plants had two to three pairs of true leaves and a well developed root system. Lines were categorized as ABA sensitive ($ABA^S$) if less than 1% of plants looked like control, moderately ABA sensitive ($ABA^{MS}$) if more than 1% but less than 50% of looked like control, or ABA insensitive ($ABA^{Wt}$) if greater than 50% looked like control.

For example, if a plate had 20 healthy seedlings and the control plate had 60 healthy seedlings, the line would be 33% of control and categorized as moderately ABA sensitive.

Figure 9:
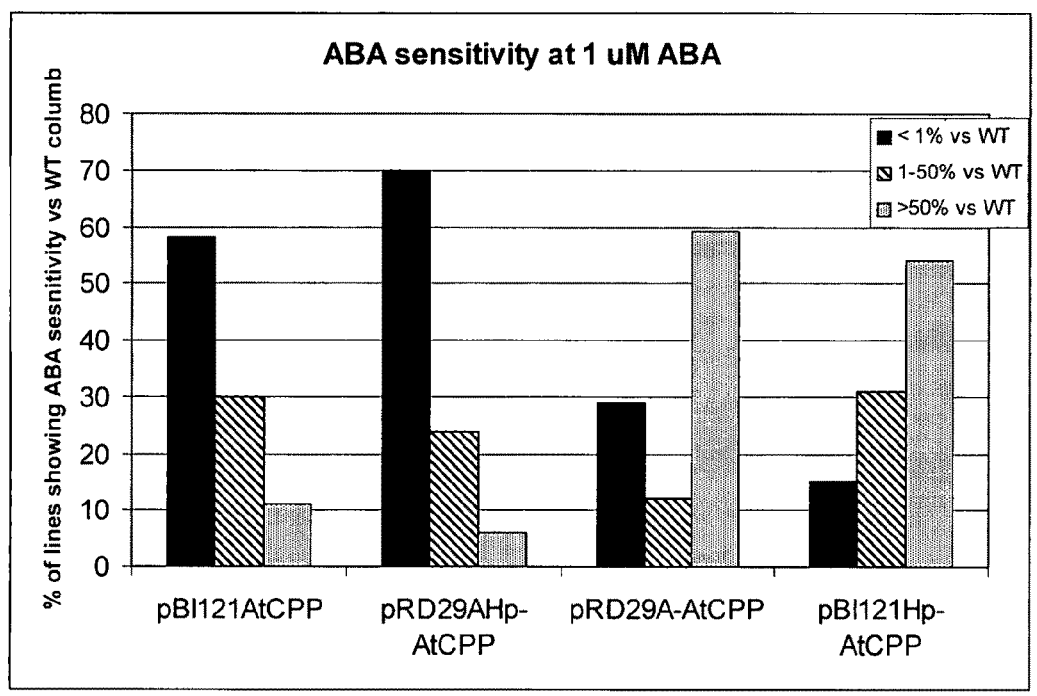
Figure 10:
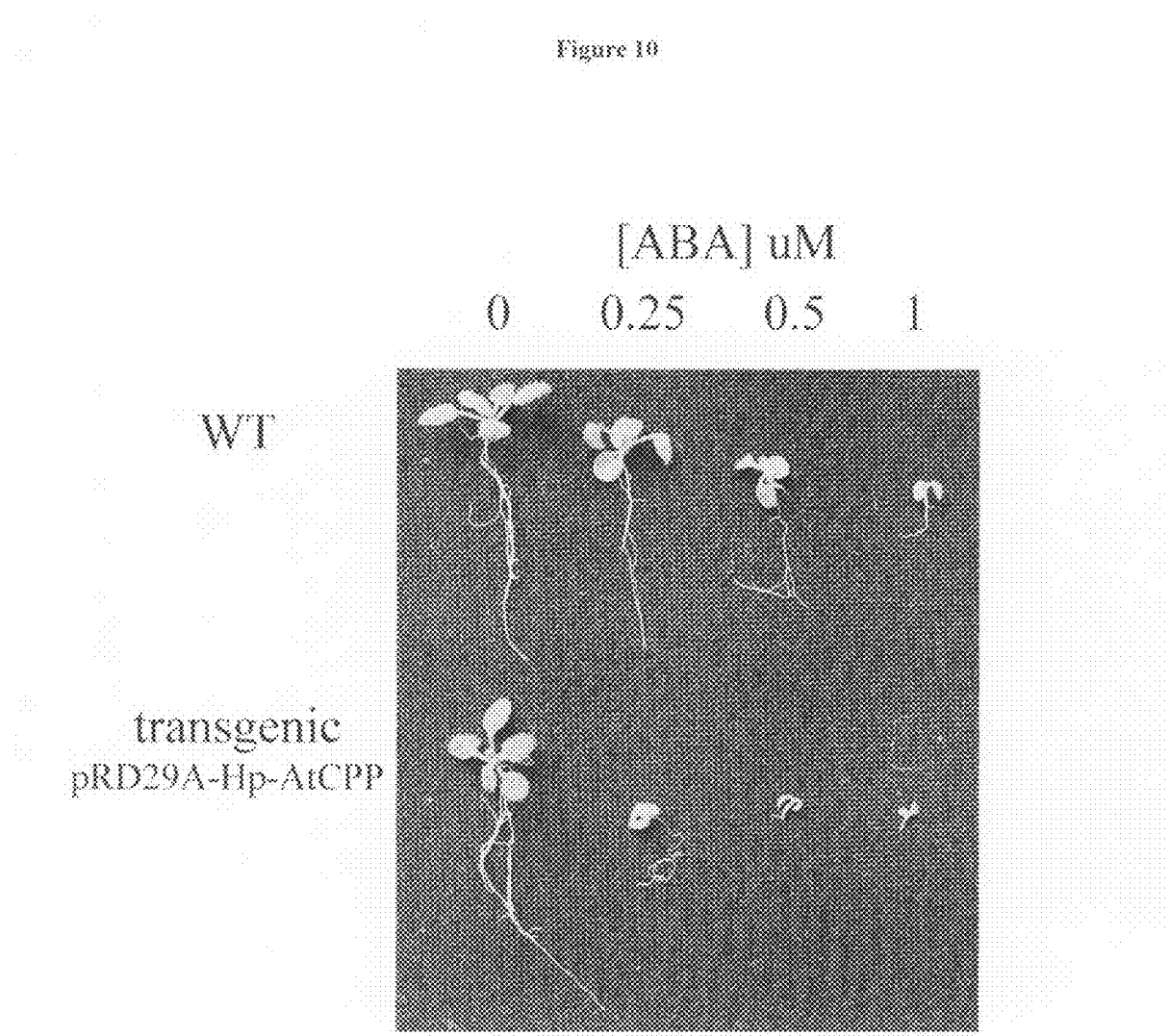

All four vector constructs (pBI121-AtCPP, pBI121Hp-AtCPP, pRD29AHp-AtCPP, pRD29A-ATCPP) have resulted in transgenic lines of *Arabidopsis* which have increased sensitivity to ABA which is indicative of stress tolerance. The data for all 4 constructs is shown in FIG. 9. Of the lines transformed with the pBI121-AtCPP construct to over-express the AtCPP gene, 58% (21 out of 36) were classified as sensitive and an added 30% (11 out of 36) were classified as moderately sensitive. These lines were tested again in T4 and T5 generations and their ABA sensitivity was still present indicating that ABA sensitivity is an inheritable trait. Of the lines transformed with the pBI121-HP-AtCPP construct to down-regulate the AtCPP gene by double stranded RNA-inhibition, 15% (7 out of 45) were classified as sensitive and 31% (14 out of 45) were classified as moderately sensitive. To illustrate the increased sensitivity of transgenic lines to ABA, FIG. 10 shows the results of germination and seedling development over a range of ABA concentrations. Wild type and pRD29A-HP-AtCPP are compared. Of the lines transformed with pRD29AHp-AtCPP 70% (12 out of 17) showed high sensitivity and 24% (4 out of 17) showed moderate sensitivity to ABA. Of the lines transformed with pRD29A-AtCPP 29% (5 out of 17) showed high sensitivity and 12% (2 out of 17) moderate sensitivity to ABA. Clearly all 4 transgene constructs are altering ABA sensitivity and ABA signal transduction.

Example 28

Drought Experiments

*Arabidopsis* plants were grown five plants per 4" or 3" pot, in a replicated water-stress experiment. All pots were filled with equal amounts of homogeneous premixed and wetted soil. Plants were grown under 16 hour daylight (150-200 µmol/m$^2$/s) at 22° C. and 70% relative humidity. On the day that the first flower opened drought treatment was initiated. First soil water content in each pot was equalized on a weight basis and any further watering of plants was stopped. Daily measurements of soil water content were taken by recording total pot weight. At the end of the drought treatment (6 to 9 days for experiments in 4" pots and 4-5 days for experiments in 3" pots) plants were harvested and shoot dry weights determined. Differences in plant growth were factored into the analysis by expressing water loss on a per gram shoot dry weight basis.

Figure 11:
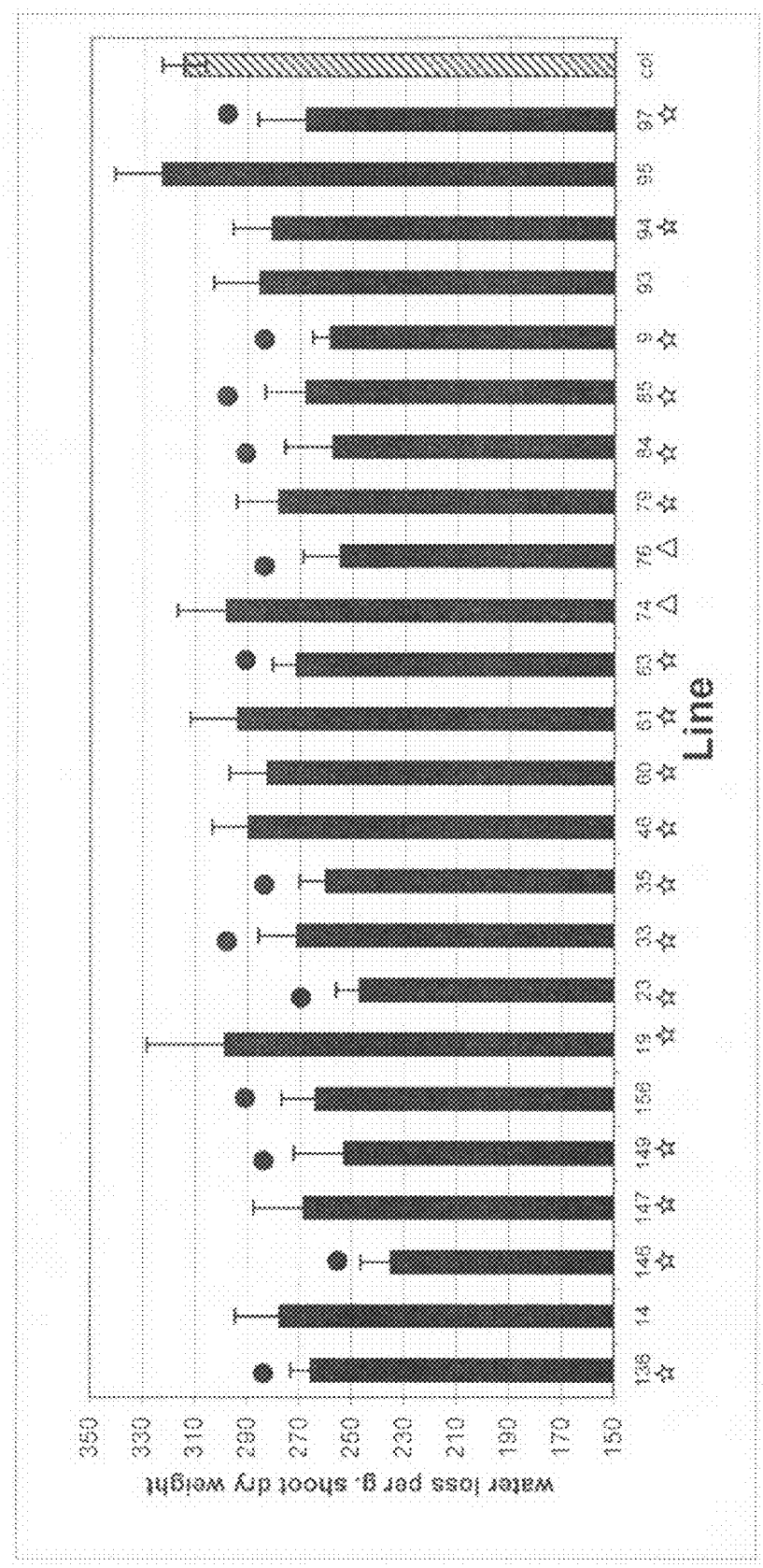

28a) pBI121-AtCPP, Drought Stress Screen:

Analysis of pBI121-AtCPP transgenic lines during water-stress treatment experiments of up to an eight day period, shows a strong trend towards increased soil water content and reduced water loss per gram of shoot biomass. After three days of water-stress treatment most lines had increased soil water content relative to the wild type control with four out of twenty-four lines, 146, 149, 156 and 97, showing a statistically significant difference. The amount of water lost per gram of shoot biomass was lower for all lines except one (95), and thirteen of these lines were significantly different from the wild type Columbia control (FIG. 11). All of the lines showing a statistically significant lower water loss per gram shoot biomass also showed an increased ABA sensitivity. There is also a strong trend, for all but one line (95), which is $ABA^{Wt}$, towards greater shoot biomass at the end of the drought stress treatment. Seven of those lines 136, 146, 23, 46, 76, 84 and 9, were statistically significant from control at a p=0.05 value.

28b) pBI121-AtCPP, Water Loss Per Gram Shoot Biomass During Water Stress Treatment:

Lines 35, 76, 95 and a wild type control were grown and placed under a water-stress treatment as above. Plants were harvested at 2 days, 4 days and 6 days of drought treatment. The $ABA^S$ lines, 35 and 76, showed a statistically significant reduction in water-loss relative to shoot dry weight at all three time points (Table 8). Additionally, the two $ABA^S$ transgenic lines had increased shoot biomass, due to increased leaf biomass, and maintained higher soil water contents during drought treatment.

TABLE 8

Water loss (g) per Shoot dry weight (g) after 2, 4 and 6 days of drought-stress treatment. Values in bold indicate statistically significant differences from Columbia.

| Line | 2 days Mean | Std. Error | 4 days Mean | Std. Error | 6 days Mean | Std. Error |
|---|---|---|---|---|---|---|
| 35 | 212.5 | 3.5 | 308.0 | 9.9 | 297.7 | 11.2 |
| 76 | 227.2 | 5.8 | 321.2 | 8.5 | 293.8 | 5.0 |
| 95 | 287.0 | 5.1 | 377.3 | 14.8 | 348.5 | 25.5 |
| Columbia Wild type | 265.3 | 11.8 | 408.2 | 7.7 | 345.9 | 6.7 |

28c) pBI121-AtCPP, Drought Stress and Shoot Recovery:

Water-stress tolerance and determination of post drought-treatment recovery ability was assessed using 20 of the 24 pBI121-AtCPP transgenic lines. Drought treatment was imposed for 6 days after which the plants were watered and allowed to grow for 6 days. Recovered shoot fresh biomass was then determined. Soil water content of these plants was measured daily during the drought treatment and the results confirm previously seen trends. All ABA sensitive ($ABA^S$) lines that showed a statistically significantly reduction of water loss on a per gram dry weight basis in experiment 34a, continued to show a significant greater soil water content than control plants in this experiment (Table 9). Additionally, Table 9 shows that the recovered shoot fresh biomass after 6 days of drought treatment was significantly greater in all the ABAs lines than Columbia.

TABLE 9

Soil water content on day 3 of drought treatment and recovered shoot fresh weight after 6 days of drought treatment (values in bold were significantly different from Columbia at p = 0.05)

| Line | ABA status ABA | soil water content day 3 Mean (% initial) | Std Error | recovered shoot biomass Mean (g) | Std Error |
|---|---|---|---|---|---|
| 136 | $ABA^S$ | 46.6 | 1.9 | 4.5 | 0.16 |
| 14 | $ABA^S$ | 50.25 | 0.7 | 4.1 | 0.12 |
| 146 | $ABA^S$ | 45.9 | 2.5 | 4.0 | 0.11 |

TABLE 9-continued

Soil water content on day 3 of drought treatment and recovered shoot fresh weight after 6 days of drought treatment (values in bold were significantly different from Columbia at p = 0.05)

| Line | ABA status ABA | soil water content day 3 Mean (% initial) | Std Error | recovered shoot biomass Mean (g) | Std Error |
|---|---|---|---|---|---|
| 147 | $ABA^S$ | 45.1 | 1.7 | 4.0 | 0.15 |
| 149 | $ABA^S$ | 45.3 | 1.8 | 3.8 | 0.17 |
| 156 | $ABA^S$ | 47.1 | 1.9 | 4.0 | 0.134 |
| 23 | $ABA^S$ | 49 | 1.4 | 4.0 | 0.17 |
| 33 | $ABA^S$ | 46.9 | 1.6 | 4.3 | 0.14 |
| 35 | $ABA^S$ | 41.7 | 1.7 | 4.0 | 0.11 |
| 46 | $ABA^S$ | 44.8 | 1.7 | 3.8 | 0.09 |
| 63 | $ABA^S$ | 46.3 | 1.4 | 4.0 | 0.19 |
| 76 | $ABA^S$ | 47.8 | 1.0 | 3.9 | 0.17 |
| 79 | $ABA^S$ | 45.4 | 1.1 | 4.1 | 0.09 |
| 84 | $ABA^S$ | 46.8 | 1.9 | 4.1 | 0.16 |
| 85 | $ABA^S$ | 45.3 | 1.9 | 4.0 | 0.12 |
| 9 | $ABA^S$ | 45.2 | 2.1 | 3.9 | 0.12 |
| 93 | $ABA^{wt}$ | 43.5 | 1.2 | 2.8 | 0.07 |
| 94 | $ABA^S$ | 46.9 | 1.5 | 3.9 | 0.13 |
| 97 | $ABA^S$ | 53 | 1.2 | 3.8 | 0.16 |
| 95 | $ABA^{Wt}$ | 41.9 | 1.2 | 2.7 | 0.06 |
| Columbia | $ABA^{Wt}$ | 41.3 | 1.0 | 2.7 | 0.04 |

28d) pBI121-AtCPP, Seed Yield After Drought Stress Treatment:

Seed yield after drought stress during flowering was examined using ten pBI121-AtCPP transgenic lines, eight of which were $ABA^S$. Plants were grown one per 4" pot and were exposed to 9 days of drought treatment as described above. A second group of plants was grown and maintained under well watered conditions as the optimal group. After 9 days of drought treatment plants were re-watered and allowed to continue growth and seed set to maturity. After drought-treatment conditions all eight $ABA^S$ lines had increased yields relative to controls, which ranged from 109% to 126% of the Columbia (Table 10). Drought-treatment resulted in a reduction of yield in all lines, including controls, relative to plants grown under optimal conditions. Expression of the seed yields obtained from drought-treated group relative to the same line under optimal conditions shows that the transgenics preserve a larger percentage of optimal seed yield than do wild type lines.

TABLE 10

Seed Yield following 9 days drought-treatment

| Line | ABA status ABA | Seed Yield (g per plant) Mean (g) | Std Error | % Columbia | % Optimal |
|---|---|---|---|---|---|
| 156 | $ABA^S$ | 0.735 | 0.044 | 126.2 | 83.7 |
| 63 | $ABA^S$ | 0.675 | 0.061 | 116.0 | 71.0 |
| 146 | $ABA^S$ | 0.666 | 0.053 | 114.4 | 72.9 |
| 94 | $ABA^S$ | 0.644 | 0.052 | 110.6 | 68.8 |
| 84 | $ABA^S$ | 0.642 | 0.049 | 110.4 | 61.8 |
| 76 | $ABA^S$ | 0.631 | 0.055 | 108.5 | 66.6 |
| 136 | $ABA^S$ | 0.630 | 0.051 | 108.3 | 74.1 |
| 35 | $ABA^S$ | 0.614 | 0.054 | 105.6 | 74.2 |
| 93 | $ABA^{Wt}$ | 0.567 | 0.041 | 97.5 | 60.0 |
| 95 | $ABA^{Wt}$ | 0.388 | 0.088 | 66.7 | 43.4 |
| Columbia | $ABA^{Wt}$ | 0.582 | 0.060 | 100 | 53.8 |

Figure 12:
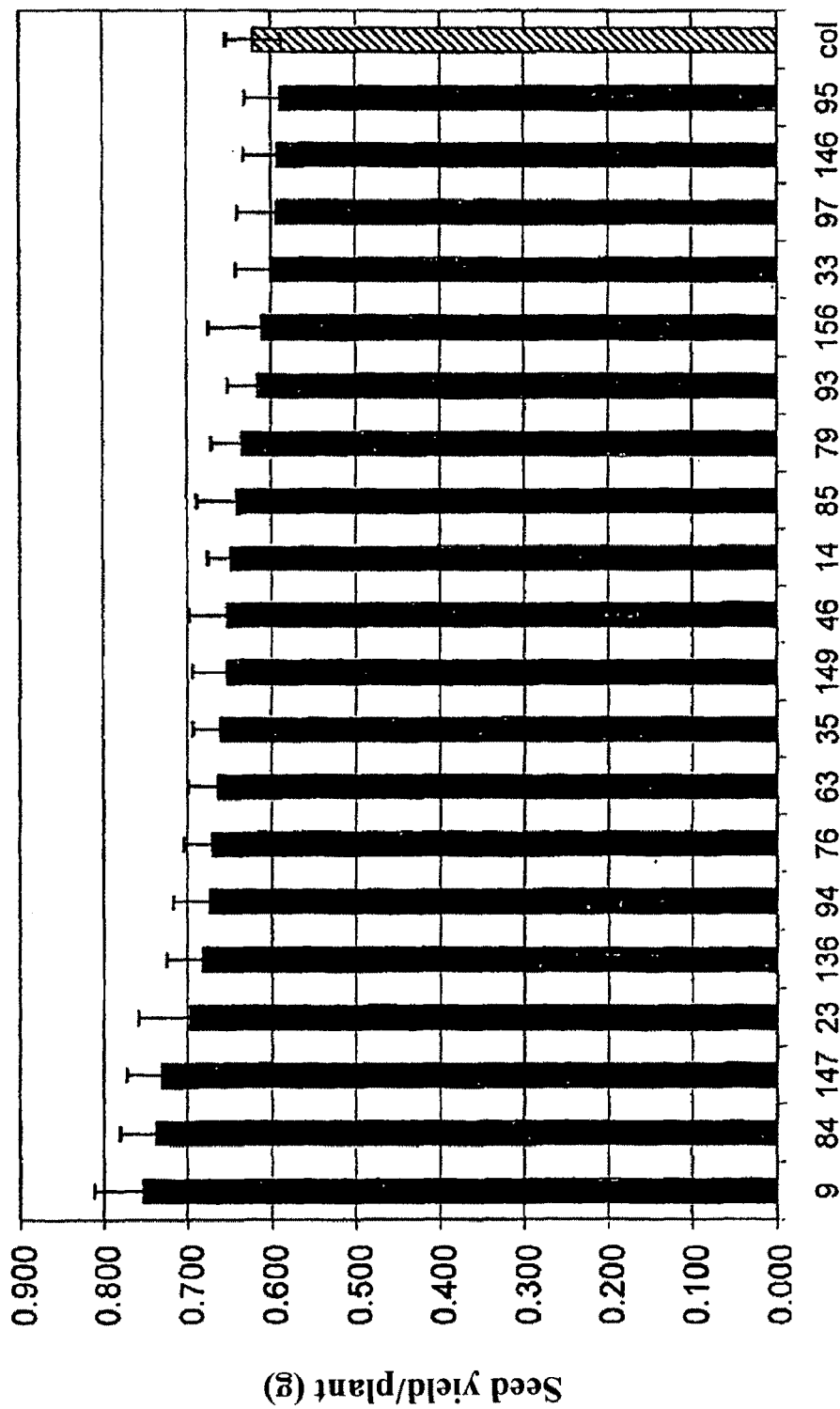
FIG. 12 is a histogram showing seed yield in grams of transgenic *Arabidopsis* lines of pBI121-AtCPP grown under optimal water conditions.

28e) pBI121-AtCPP Seed Yield and Growth Under Optimal Water Conditions:

The lines evaluated above and a number of additional lines were examined in a growth and yield experiment under optimal, well-watered conditions. Results indicated that the $ABA^S$ lines were shorter at the stage of first open flower, had more rosette leaves, however, by maturity there were no differences in plant height of transgenics and Columbia. Moreover, the $ABA^S$ transgenics showed similar or higher seed yields ranging from 95% to 121% of the wild type control (FIG. 12).

28f) pRD29A-HP-AtCPP Screen for Drought Tolerant Phenotype:

Analysis of 17 transgenic lines identified 7 candidate drought tolerant lines (12, 22, 23, 47, 82, 83, 90) on the basis of higher soil water content and lower water loss per g of shoot dry weight (Table 11). All 7 drought tolerant candidate lines showed strong ABA sensitivity and lines that did not show drought tolerance did not show ABA sensitivity.

TABLE 11

Soil water content after 3 days of drought treatment and water lost per g shoot dry weight. Values in bold are statistically different from those of Columbia wild type (p = 0.05)

| Line | ABA status ABA | soil water content day 2 | | water lost in 2 days/g shootDW | |
|---|---|---|---|---|---|
| | | Mean (% initial) | Std Error | Mean (g/g) | Std Error |
| 10 | $ABA^S$ | 33.4 | 1.6 | 199.1 | 4.5 |
| 11 | $ABA^S$ | 34.6 | 3.3 | 173.1 | 1.6 |
| 12 | $ABA^S$ | 36.2 | 2.0 | 179.5 | 5.0 |
| 126 | $ABA^{MS}$ | 32.5 | 2.6 | 199.1 | 4.1 |
| 127 | $ABA^{MS}$ | 33.5 | 2.0 | 195.6 | 10.6 |
| 14 | $ABA^S$ | 32.7 | 1.2 | 203 | 4.9 |
| 17 | $ABA^S$ | 29.9 | 1.8 | 200.7 | 7.3 |
| 22 | $ABA^S$ | 39.3 | 2.1 | 170.0 | 3.0 |
| 23 | $ABA^S$ | 35.7 | 1.4 | 174.9 | 2.6 |
| 42 | $ABA^{MS}$ | 28 | 0.7 | 185.4 | 5.8 |
| 47 | $ABA^S$ | 35.9 | 2.2 | 181.2 | 7.7 |
| 7 | $ABA^{Wt}$ | 35 | 1.3 | 201.8 | 5.1 |
| 82 | $ABA^S$ | 36.7 | 2.2 | 178.3 | 4.0 |
| 83 | $ABA^S$ | 40 | 1.4 | 180.7 | 6.9 |
| 9 | $ABA^S$ | 31.4 | 1.4 | 173.8 | 8.7 |
| 90 | $ABA^S$ | 38.2 | 1.3 | 177.6 | 6.2 |
| 93 | $ABA^{Wt}$ | 30.7 | 1.8 | 175.3 | 4.6 |
| Columbia | $ABA^{Wt}$ | 32.1 | 1.2 | 196.9 | 6.2 |

Example 29

Growth Analysis

The growth analysis of most promising constructs has been set up at 3 stages. Eight plants per line were grown in 3" pots with one plant per pot at 22 C, 16 hr light (150-200 μmol/m²/s) and 70% RH. Plants were harvested at vegetative growth stage (2 week old seedlings), bolting growth stage (at first open flower) and mid-flowering growth stage (5 to 7 days from first open flower). Also, in some growth experiments additional group of plants was grown in 4" pots (one per pot and 10 plants per line) to maturity for seed yield determinations.

29a) pBI121-AtCPP Growth Under Optimal and Biotic Stress Conditions

The growth and productivity of pBI121-AtCPP transgenic Arabidopsis lines was examined at several stages of development under optimal growth conditions. Although optimal growth conditions were maintained, plants were assessed to be under a degree of stress that was later determined to be a result of the soil properties. Soil analysis found a fungal contaminant that was believed to be responsible for the biotic stress. This stress could be negated by sterilization of the soil prior to use. Eight $ABA^S$ lines, two with normal ABA sensitivity ($ABA^{Wt}$) and a wild type Columbia control were analyzed.

Figure 13:
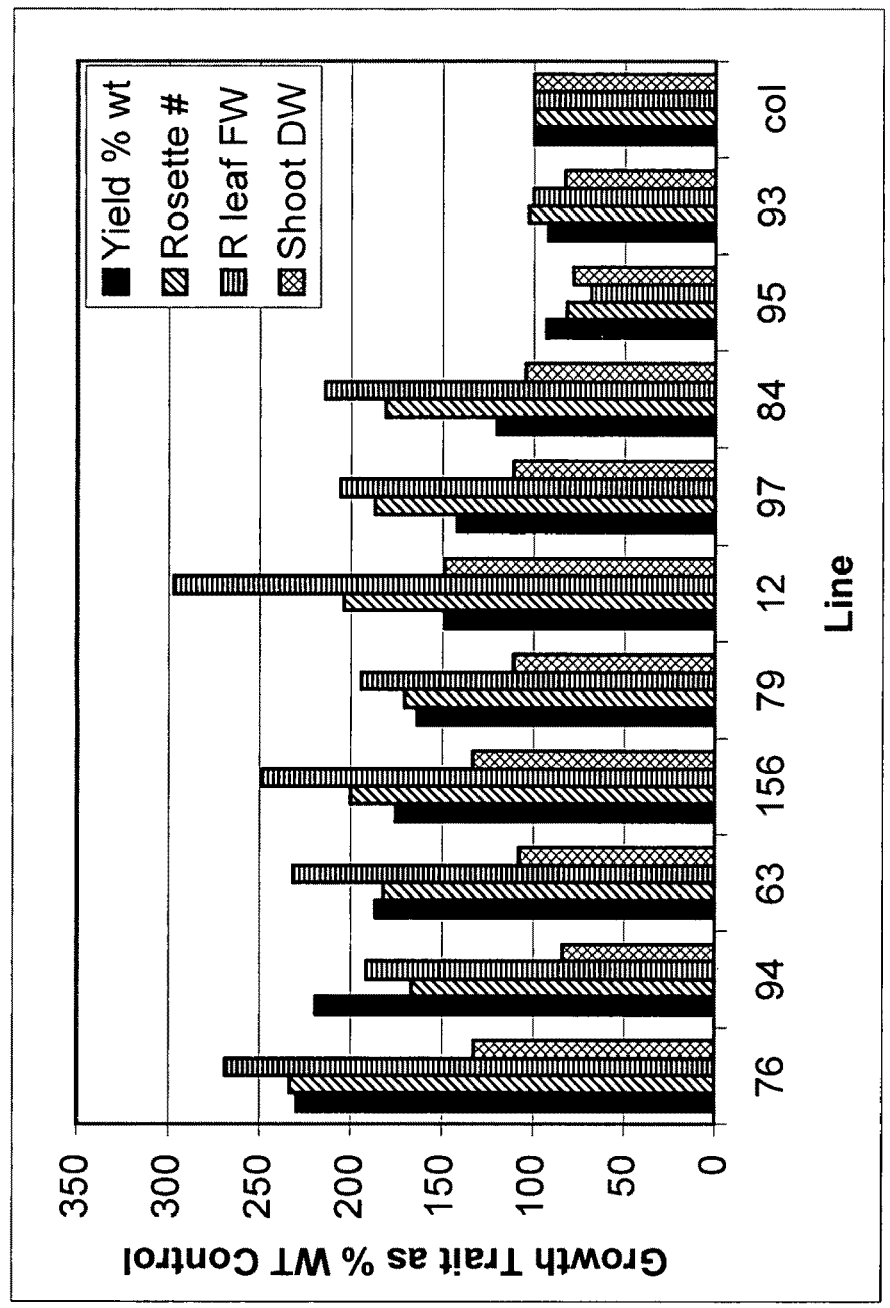
FIG. 13 is a bar chart showing growth and yield of transgenic *Arabidopsis* lines of pBI121-AtCPP grown under optimal watering conditions plus a biotic stress condition. Yields as a % of wild type, rosette leaf number, rosette leaf fresh weight and shoot dry weight are plotted.

FIG. 13 presents the results of various growth (from mid-flowering stage) and yield parameters and each trait is expressed as a percentage of the Columbia control. The results strongly support an enhanced growth phenotype. This enhanced growth phenotype is present at all growth stages. At the vegetative stage, all $ABA^S$ transgenic plants showed an increase in leaf number relative to that of the wild type with four of the eight lines showing a statistically significant difference. The two $ABA^{Wt}$ lines showed the same or fewer leaves relative to wild type.

At the bolting stage $ABA^S$ transgenics showed an increase in leaf number but plants were shorter at this stage (first open flower) than controls. The shoot fresh weight of transgenics was significantly increased relative to that of controls, ranging from 80% to 342% of the wild type. The $ABA^S$ transgenics displayed a delay in flowering from one to three days. The $ABA^{Wt}$ transgenics did not show delayed flowering, increased shoot fresh weight or increased height.

At the flowering stage of development the enhanced growth phenotype is maintained (greater leaf number and fresh weight), however, there were no observable differences in plant height indicating that transgenics bolt shorter but reach same final plant height.

Of particular significance is the observation, that under these conditions (biotic stress due to presence of fungi in the soil) yields of the $ABA^S$ transgenics were significantly higher, ranging from 120% to 229% of the wild type control. The $ABA^{Wt}$ lines showed similar or slightly reduced yields relative to the Columbia control. This finding indicates that $ABA^S$ transgenic lines are affected less by the biotic stress. This observation has been confirmed, where 5 of the drought tolerant lines were grown in contaminated soil to maturity. The seed yields of transgenic lines, even though greatly reduced relative to optimal conditions, were 2.5 to 4.5 fold higher than those of Columbia wild type (Table 12).

TABLE 12

Seed yield of pBI121-AtCPP lines grown in contaminated soil. Values in bold indicate statistical differences at p = 0.05

| Line | ABA sensitivity | Seed Yield per plant (g) | % of Columbia |
|---|---|---|---|
| 156 | $ABA^S$ | 0.33 ± 0.04 | 316% |
| 23 | $ABA^S$ | 0.35 ± 0.05 | 336% |
| 76 | $ABA^S$ | 0.31 ± 0.04 | 296% |
| 84 | $ABA^S$ | 0.25 ± 0.33 | 237% |
| 9 | $ABA^S$ | 0.48 ± 0.05 | 455% |
| Columbia | $ABA^{Wt}$ | 0.11 ± 0.03 | |

Figure 14:
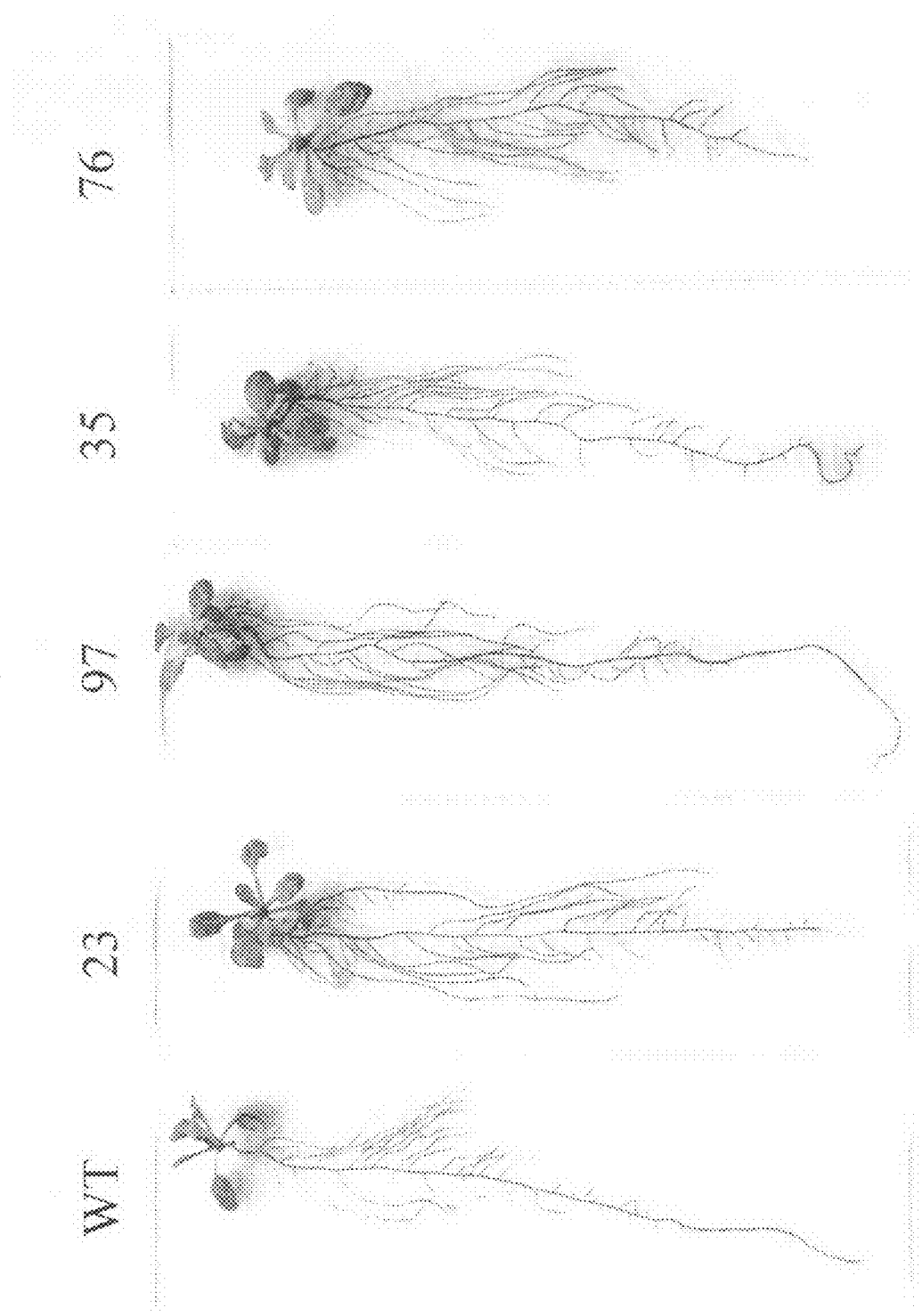
FIG. 14 are photographs showing 12 day old seedling growth of transgenic *Arabidopsis* lines of pBI121-AtCPP (35S AtCPP) grown on agar plates. Changes to root growth visible (toluidin blue).

29b) pBI121-AtCPP Early Seedling Growth:

Four $ABA^S$ and one $ABA^{Wt}$ line plus Columbia were examined for early seedling growth on agar plates. Twenty seeds were plated in a line on agar plates containing 50% MS with 1% sucrose and vitamins and 6 plates per line were used. Plates were placed on slants, which allowed roots to grow downwards. Root length was measured on 7-day old seedlings and shoot and root biomass determined on 11-day old seedlings. Two of the $ABA^S$ transgenic lines had significantly longer roots and all 4 $ABA^S$ lines had shoot dry weights 114% to 123% of controls and root dry weights of 116% to 151% of controls. As a result, the shoot biomass to rootbiomass ratios were slightly reduced in transgenics. These results indicate that enhanced growth of these transgenics is evident in the early growth stage, shortly after germination, and the root growth is more enhanced relative to shoot growth. In a different experiment seedlings were pulled out of agar and roots were stained with toluidine blue to show their structure. FIG. 14 shows that transgenic lines had more extensive lateral root system, which would account for greater root biomass.

29c) pRD29A-HP-AtCPP Optimal Growth Characteristics

Figure 15:
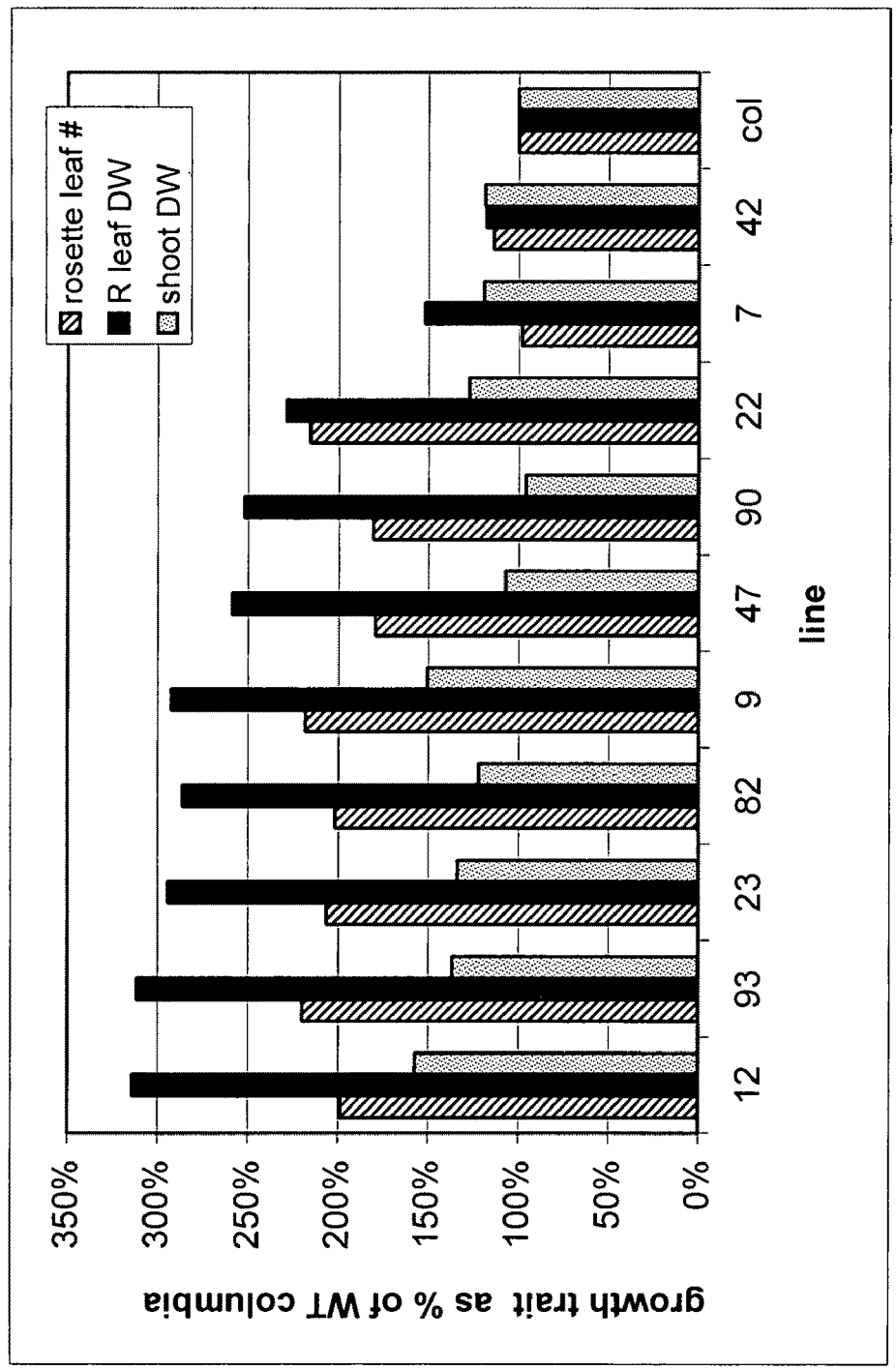
FIG. 15 is a bar chart showing growth of transgenic *Arabidopsis* lines of pRD29A-HP-AtCPP grown under optimal watering conditions. Rosette leaf number, rosette leaf dry weight and shoot dry weight are plotted.

An optimal growth study has been conducted with 10 lines as described before. Vegetative growth data showed that two of the lines (12 and 9) had significantly more leaves and seven of the lines (12, 22, 23, 47, 82, 9) had significantly greater shoot biomass. Bolting data showed that eight of the lines (12, 22, 23, 47, 82, 9, 90, 93) were significantly delayed in flowering by one to two days, and seven of the lines were significantly shorter than Columbia at first open flower. All of the lines except 42 and 7 had significantly greater number of rosette leaves and shoot FW and this trend is maintained into the mid-flowering harvest (FIG. 15). The plant height, however, by mid-flowering harvest was not significantly different between the transgenic lines and control. All the lines that showed this enhanced growth also showed drought tolerance and ABA sensitivity.

Example 30

Ultrastructure pBI121-AtCPP

Two of the drought tolerant and $ABA^S$ lines (35 and 76) plus Wt Columbia were used to examine stem and root cross-sections for any differences in ultrastructure. Free hand sections of mature stems (plants flowering for 10 days) were obtained from above the first node, stained with toluidine blue and preserved with glycerol. The stems of transgenic plants appeared to have more dense cellular structure and contain one or two more vascular bundles than those of Columbia Wt indicating more enhanced water and nutrient transport system.

Leaf disks were taken and fresh weights determined. Transgenic leaf disks were significantly heavier, 20-24% greater than corresponding wild type controls. This increase is believed to be as a result of a thicker leaf.

Example 31

Cold Stress Experiment pBI121-AtCPP

Four drought tolerant, $ABA^S$ lines (156, 23, 35, 76) and one $ABA^{Wt}$ (95) line plus wild type Columbia were included in a cold stress study. Plants were grown in 3" pots one per pot) with 10 replicate pots per line at 22 C for 10 days (7 days on agar plates and 4 in soil). The cold stress group was moved into 7° C. for 5 days while the optimal group was left at 22 C. After 5 days in the cold both cold stress group and the optimal group were harvested for shoot biomass determination. $ABA^S$ and drought tolerant lines had significantly greater shoot biomass than Columbia in both optimal (25 to 39% greater shoot fresh weight) and cold stress groups (18 to 44% greater shoot DW) (Table 13). Results of an eight-day cold stress showed that differences between the transgenic lines and Columbia were even more pronounced (53 to 61% greater shoot fresh weight). This result indicates greater plant vigor and better ability of transgenics to cope with cold stress.

TABLE 13

Shoot fresh weight of optimal and cold stressed (5 C. for 5 d) pBI121-AtCPP. Values in bold indicate statistical difference at p = 0.05

| Line | ABA sensitivity | Optimal shoot FW | | Cold stress shoot FW | |
| --- | --- | --- | --- | --- | --- |
| | | mg | % of Columbia | mg | % of Columbia |
| 156 | $ABA^S$ | 95.4 ± 3.7 | 137% | 23.1 0.7 | 118% |
| 23 | $ABA^S$ | 96.3 ± 3.9 | 139% | 28.3 1.5 | 144% |
| 35 | $ABA^S$ | 87.0 ± 1.7 | 125% | 25.3 1.4 | 130% |
| 76 | $ABA^S$ | 94.7 ± 2.2 | 136% | 27.3 1.5 | 140% |
| 95 | ABAWt | 67 ± 2.4 | 96% | 21.4 1.0 | 109% |
| Columbia | ABAWt | 69 ± 1.9 | | 19.6 1.1 | |

Example 32

Drought Stress Under High Temperature pBI121-AtCPP

A drought stress experiment was conducted as described above except that day temperature of 32° C. (16 hr) and night temperature of 22° C. (8 hr) was maintained. These temperatures were achieved daily over a 2 hr ramping period. Four $ABA^S$ and one $ABA^{Wt}$ line plus Columbia were included. Plants were monitored daily for water loss and soil water content and after 5 days of drought treatment half of the plants were harvested and the other half was re- and watered and allowed to recover for four days. Shoots were harvested and shoot fresh weight determined. The results (Table 14) of this experiment showed that previously identified drought tolerant lines maintained their drought tolerant phenotype at high temperature and were able to recover well from the drought stress at high temperature

TABLE 14

Soil water content on day 2 and water lost in 2 days/final shoot dry weight plus recovery shoot FW after 5 days of drought stress at 32 C. day and 22 C. night temperatures. Values in bold indicate significant differences from the Columbia control.

| line | ABA sensitivity | soil water content day 2 | water lost in 2 d/shoot DW | recovered shoot FW (g) |
| --- | --- | --- | --- | --- |
| 136 | $ABA^S$ | 50.4 ± 1.1 | 485.7 ± 18.5 | 1.30 ± 0.04 |
| 146 | $ABA^S$ | 52.1 ± 1.0 | 504.5 ± 7.9 | 1.15 ± 0.04 |
| 35 | $ABA^S$ | 52.2 ± 0.8 | 502.8 ± 15.8 | 1.19 ± 0.02 |
| 76 | $ABA^S$ | 52.1 ± 0.6 | 435.6 ± 10.5 | 1.11 ± 0.03 |
| 95 | ABAWt | 50.0 ± 0.9 | 518.2 ± 13.0 | 0.86 ± 0.03 |
| Columbia | ABAWt | 48.6 ± 0.6 | 559.7 ± 19.0 | 0.84 ± 0.03 |

Example 33

Heat Stress and Seed Yield pBI121-AtCPP

Two $ABA^S$ lines and one $ABA^{Wt}$ line plus Columbia were examined for the effect of heat stress during flowering on the final seed yield. Plants were grown in 4 inch pots (one/pot) as described above and 9 days from first open flower the temperature was ramped from 22 C to 43 C over 2 hours and plants were kept at 43 C for 2 hr. Temperature was then ramped back to 22 C over 2 hours and plants were grown under optimal conditions until maturity. The seed yields from this experiment are shown in Table 15. One of the drought-tolerant lines (35) had significantly greater yield than Columbia.

TABLE 15

Seed yield of pBI121-AtCPP lines after two hour 43 C. heat stress 9 days from first open flower. Values in bold are statistically significant from Columbia.

| line | ABA sensitivity | seed yield (g/plant) | seed yield (% of col.) |
|---|---|---|---|
| 35 | ABA$^S$ | 0.55 ± 0.05 | 347% |
| 76 | ABA$^S$ | 0.24 ± 0.03 | 148% |
| 95 | ABAWt | 0.11 ± 0.02 | 69% |
| Columbia | ABAWt | 0.16 ± 0.03 | |

The effect of heat shock on lines of pBI121-AtCPP at the early flowering stage was assessed. Three ABA$^S$ lines (76, 136, 97) a ABA$^{Wt}$ line (95) and a Columbia wild type control were seeded in 128 cell flats, one flat per line. At the early flowering stage flats were exposed to a temperature of 46.8° C. for 50 minutes and then returned to normal growth conditions. Lack of continued growth from main meristems was defined as main meristem death and scored for each line. Data is shown in Table 16.

TABLE 16

Meristem death due to heat shock

| Line | Wt | 95 | 76 | 136 | 97 |
|---|---|---|---|---|---|
| % Death | 91 | 97 | 79 | 59 | 18 |

Example 34

Stomata Density Determinations pBI121AtCPP

Two ABA$^S$ lines (76 and 35) plus Columbia were examined for stomata density on the upper and lower leaf surface. Nail polish imprints of the upper and lower epidermis were obtained from a fully expanded leaf #5. These imprints were analyzed under the microscope and the number of stomata per $8.7 \times 10^{-8}$ m$^2$ were counted. There were no significant differences found between transgenics and Columbia in the stomata of the upper or lower epidermis (Table 17). The increases seen in drought tolerance and reduced water loss is not attributable to a reduced number of leaf stomata.

TABLE 17

Stomata numbers per $8.7 \times 10^{-8}$ m$^2$ of abaxial and adaxial epidermis of fully expanded leaf #5 in pBI121AtCPP.

| line | ABA sensitivity | stomata on upper epidermis | stomata on lower epidermis |
|---|---|---|---|
| 35 | ABA$^S$ | 68 ± 5 | 103 ± 7 |
| 76 | ABA$^S$ | 58 ± 6 | 120 ± 16 |
| Columbia | ABAWt | 57 ± 6 | 116 ± 11 |

Example 35

PrPase Consensus Sequences

Also included in the invention are the PrPase consensus sequences. The consensus sequences were generated by alignment of the PrPase polypeptide and nucleic acid sequences.

The consensus sequence for the nucleic acid sequence alignment of GmCPP (SEQ ID NO: 18), GmPrPase2 (SEQ ID NO: 16), AtCPP (SEQ ID NO: 7), AtPrPase1 (SEQ ID NO: 3), AtPrPase2 (SEQ ID NO: 5), BnCPP (SEQ ID NO: 11), ZmPrPase2 (SEQ ID NO: 23), PpPrPase1 (SEQ ID NO: 1), and three other disclosed *Arabidopsis* PrPases sequences (AT4g01320 (SEQ ID NO: 27); AF007269 (SEQ ID NO: 29), and AFC1 (SEQ ID NO: 25)) as shown in FIG. 4 is provided in SEQ ID NO: 84. The consensus sequence for the corresponding amino acid sequence alignment shown in FIG. 5 is provided in SEQ ID NO: 85.

The consensus sequence for the nucleic acid alignment of the PrPase sequences of the invention from dicot plants (GmCPP (SEQ ID NO: 18), GmPrPase2 (SEQ ID NO: 16), AtCPP (SEQ ID NO: 7), AtPrPase1 (SEQ ID NO: 3), AtPrPase2 (SEQ ID NO: 5), BnCPP (SEQ ID NO: 11)) and three other disclosed dicot PrPases sequences (AT4g01320 (SEQ ID NO: 27), AF007269 (SEQ ID NO: 29), and AFC1 (SEQ ID NO: 25)) as shown in FIG. 16 is provided in SEQ ID NO: 86. The consensus sequence for the corresponding amino acid sequence alignment shown in FIG. 17 is provided in SEQ ID NO: 87.

The consensus sequence for the nucleic acid alignment of the *Arabidopsis* PrPase sequences of the invention (AtCPP (SEQ ID NO: 7), AtPrPase1 (SEQ ID NO: 3), AtPrPase2 (SEQ ID NO: 5)) and three other disclosed *Arabidopsis* PrPases sequences (AT4g01320 (SEQ ID NO: 27), AF007269 (SEQ ID NO: 29), and AFC1 (SEQ ID NO: 25)) as shown in FIG. 18 is provided in SEQ ID NO: 88. The consensus sequence for the corresponding amino acid sequence alignment shown in FIG. 19 is provided in SEQ ID NO: 89.

The consensus sequence for the nucleic acid alignment of the soybean PrPase sequences of the invention: GmCPP (SEQ ID NO: 18) and GmPrPase2 (SEQ ID NO: 16) as shown in FIG. 20 is provided in SEQ ID NO: 90. The consensus sequence for the corresponding amino acid sequence alignment shown in FIG. 21 is provided in SEQ ID NO: 91.

The "X" in the consensus sequence represents any amino acid and the "N" represents any nucleotide. Preferably "X" is a conservative amino acid substitution and the "N" a conservative nucleotide substitution. More preferably, "X" is the amino acid and "N" the nucleotide most prevalent at a given position.

We claim:

1. An isolated or recombinant polynucleotide encoding a plant prenyl protease having an amino acid sequence comprising amino acids 1 to 424 of SEQ ID NO: 4 or a full-length homolog of the plant prenyl protease of SEQ ID NO: 4 wherein the homolog has prenyl protease activity and at least 92% identity at the amino acid level to amino acids 1 to 424 of SEQ ID NO: 4.

2. The isolated or recombinant polynucleotide of claim 1, wherein the polynucleotide comprises a nucleotide sequence selected from the group consisting of:
   a) a polynucleotide comprising nucleotides 1 to 1275 of SEQ ID NO: 3;
   b) a polynucleotide comprising nucleotides 1 to 1275 of SEQ ID NO: 5;
   c) a polynucleotide encoding a polypeptide comprising amino acids 1 to 424 of SEQ ID NO: 6;
   d) a polynucleotide encoding a polypeptide having at least 95% identity at the amino acid level to amino acids 1 to 424 of SEQ ID NO: 4;
   e) a polynucleotide encoding a polypeptide having at least 95% identity at the amino acid level to amino acids 1 to 424 of SEQ ID NO: 6;
   f) a polynucleotide complementary to the polynucleotide of any of a) through e).

3. An isolated or recombinant polynucleotide encoding a plant prenyl protease, wherein the polynucleotide comprises a nucleotide sequence selected from the group consisting of:
   a) a polynucleotide comprising nucleotides 1 to 1405 of SEQ ID NO: 16;
   b) a polynucleotide encoding a polypeptide comprising amino acids 1 to 424 of SEQ ID NO: 17;
   c) a polynucleotide encoding a polypeptide having at least 95% identity at the amino acid level to amino acids 1 to 424 of SEQ ID NO: 17;
   d) a polynucleotide complementary to the polynucleotide of any of a) through c).

4. The polynucleotide of claim 1, wherein the polynucleotide is in a plant expression vector.

5. The polynucleotide of claim 4, wherein the expression vector comprises a promoter that directs expression of the polynucleotide.

6. The polynucleotide of claim 5, wherein the promoter is selected from the group consisting of a constitutive promoter, an ABA inducible promoter, a tissue-specific promoter, a guard cell-specific promoter, and a developmentally regulated promoter.

7. The polynucleotide of claim 4, wherein the expression vector is in a plant cell.

8. The polynucleotide of claim 4, wherein the expression vector is in a plant.

9. An isolated or recombinant polynucleotide encoding a plant prenyl protease, wherein the polynucleotide comprises a nucleotide sequence selected from the group consisting of:
   a) a polynucleotide comprising nucleotides 1 to 1275 of SEQ ID NO: 7;
   b) a polynucleotide comprising nucleotides 1 to 1275 of SEQ ID NO: 11;
   c) a polynucleotide comprising nucleotides 1 to 1275 of SEQ ID NO: 18;
   d) a polynucleotide encoding a polypeptide comprising amino acids 1 to 424 of SEQ ID NO: 8;
   e) a polynucleotide encoding a polypeptide comprising amino acids 1 to 424 of SEQ ID NO: 12;
   f) a polynucleotide encoding a polypeptide comprising amino acids 1 to 424 of SEQ ID NO: 19;
   g) a polynucleotide encoding a polypeptide having at least 99% identity at the amino acid level to amino acids 1 to 424 of SEQ ID NO: 8;
   h) a polynucleotide encoding a polypeptide having at least 96% identity at the amino acid level to amino acids 1 to 424 of SEQ ID NO: 12;
   i) a polynucleotide encoding a polypeptide having at least 85% identity at the amino acid level to amino acids 1 to 424 of SEQ ID NO: 19; and
   j) a polynucleotide complementary to the polynucleotide of any of a) through i).

10. The polynucleotide of claim 9, wherein the polynucleotide is in a plant expression vector.

11. The polynucleotide of claim 10, wherein the expression vector comprises a promoter that directs expression of the polynucleotide.

12. The polynucleotide of claim 11, wherein the promoter is selected from the group consisting of a constitutive promoter, an ABA inducible promoter, a tissue-specific promoter, a guard cell-specific promoter, and a developmentally regulated promoter.

13. The polynucleotide of claim 10, wherein the expression vector is in a plant cell.

14. The polynucleotide of claim 10, wherein the expression vector is in a plant.

15. A transgenic plant cell which comprises an expression cassette which expresses a plant prenyl protease having an amino acid sequence comprising amino acids 1 to 424 of SEQ ID NO: 4 or a full-length homolog of the plant prenyl protease of SEQ ID NO: 4 wherein the homolog has prenyl protease activity and at least 80% identity at the amino acid level to amino acids 1 to 424 of SEQ ID NO: 4.

16. The transgenic plant cell of claim 15, wherein the homolog has an amino acid sequence selected from the group consisting of
   a) a polypeptide comprising amino acids 1 to 424 of SEQ ID NO: 6;
   b) a polypeptide having at least 95% identity at the amino acid level to amino acids 1 to 424 of SEQ ID NO: 4; and
   c) a polypeptide having at least 95% identity at the amino acid level to amino acids 1 to 424 of SEQ ID NO: 6.

17. The transgenic plant cell of claim 15, wherein the homolog has an amino acid sequence selected from the group consisting of
   a) a polypeptide comprising amino acids 1 to 424 of SEQ ID NO: 17; and
   b) a polypeptide having at least 95% identity at the amino acid level to amino acids 1 to 424 of SEQ ID NO: 17.

18. The transgenic plant cell of claim 15, wherein the homolog has an amino acid sequence selected from the group consisting of
   a) a polypeptide comprising amino acids 1 to 424 of SEQ ID NO: 8;
   b) a polypeptide comprising amino acids 1 to 424 of SEQ ID NO: 12;
   c) a polypeptide comprising amino acids 1 to 424 of SEQ ID NO: 19;
   d) a polypeptide having at least 99% identity at the amino acid level to amino acids 1 to 424 of SEQ ID NO: 8;
   e) a polypeptide having at least 96% identity at the amino acid level to amino acids 1 to 424 of SEQ ID NO: 12; and
   f) a polypeptide having at least 85% identity at the amino acid level to amino acids 1 to 424 of SEQ ID NO: 19.

19. The transgenic plant cell of claim 15, wherein the plant prenyl protease has the amino acid sequence of SEQ ID NO: 4.

20. The transgenic plant cell of claim 15, wherein the plant cell is in a plant.

21. The transgenic plant cell of claim 15, wherein the plant cell is in a seed.

22. The transgenic plant cell of claim 15, wherein the plant cell is a monocot plant cell.

23. The transgenic plant cell of claim 15, wherein the plant cell is a dicot plant cell.

24. A transgenic plant which comprises an expression cassette which expresses a plant prenyl protease having an amino acid sequence comprising amino acids 1 to 424 of SEQ ID NO: 4 or a full-length homolog of the plant prenyl protease of SEQ ID NO: 4 wherein the homolog has prenyl protease activity and at least 80% identity at the amino acid level to amino acids 1 to 424 of SEQ ID NO: 4.

25. The transgenic plant of claim 24, wherein the homolog is selected from the group consisting of
   a) a polypeptide comprising amino acids 1 to 424 of SEQ ID NO: 6;
   b) a polypeptide encoded by a polynucleotide comprising nucleotides 1 to 1275 of SEQ ID NO: 3;
   c) a polypeptide encoded by a polynucleotide comprising nucleotides 1 to 1275 of SEQ ID NO: 5;
   d) a polypeptide having at least 95% identity at the amino acid level to amino acids 1 to 424 of SEQ ID NO: 4; and
   e) a polypeptide having at least 95% identity at the amino acid level to amino acids 1 to 424 of SEQ ID NO: 6.

26. The transgenic plant of claim 24, wherein the homolog is selected from the group consisting of
   a) a polypeptide comprising amino acids 1 to 424 of SEQ ID NO: 17;
   b) a polypeptide encoded by a polynucleotide comprising nucleotides 1 to 1405 of SEQ ID NO: 16; and
   c) a polypeptide having at least 95% identity at the amino acid level to amino acids 1 to 424 of SEQ ID NO: 17.

27. The transgenic plant of claim 24, wherein the homolog is selected from the group consisting of
   a) a polypeptide comprising amino acids 1 to 424 of SEQ ID NO: 8;
   b) a polypeptide comprising amino acids 1 to 424 of SEQ ID NO: 12;
   c) a polypeptide comprising amino acids 1 to 424 of SEQ ID NO: 19;
   d) a polypeptide encoded by a polynucleotide comprising nucleotides 1 to 1275 of SEQ ID NO: 7;
   e) a polypeptide encoded by a polynucleotide comprising nucleotides 1 to 1275 of SEQ ID NO: 11;
   f) a polypeptide encoded by a polynucleotide comprising nucleotides 1 to 1275 of SEQ ID NO: 18;
   g) a polypeptide having at least 99% identity at the amino acid level to amino acids 1 to 424 of SEQ ID NO: 8;
   h) a polypeptide having at least 96% identity at the amino acid level to amino acids 1 to 424 of SEQ ID NO: 12; and
   i) a polypeptide having at least 85% identity at the amino acid level to amino acids 1 to 424 of SEQ ID NO: 19.

28. The transgenic plant of claim 24, wherein the plant is a monocot.

29. The transgenic plant of claim 24, wherein the plant is a dicot.

30. The transgenic plant of claim 24, wherein the plant is selected from the group consisting of maize, wheat, rye, oat, triticale, rice, barley, soybean, peanut, cotton, rapeseed, canola, manihot, pepper, sunflower, tagetes, potato, tobacco, eggplant, tomato, *Vicia* species, pea, alfalfa, coffee, cacao, tea, *Salix* species, oil palm, coconut, perennial grass, and a forage crop.

31. The transgenic plant of claim 24, wherein the plant has an altered phenotype selected from the group consisting of increased tolerance to stress, delayed senescence, increased ABA sensitivity, increased yield, increased productivity, and increased biomass compared to a wild type plant.

32. The transgenic plant of claim 24, wherein the tolerance of the transgenic plant to drought is increased as compared to a wild type variety of the plant.

33. A plant seed produced by the plant of claim 24, wherein the seed comprises an isolated or recombinant nucleic acid which encodes the prenyl protease.

34. The plant seed of claim 33, wherein the seed is true breeding for an increased tolerance to an environmental stress selected from the group consisting of drought, high temperature, and low temperature as compared to a wild type variety of the seed.

35. A method of producing a transgenic plant comprising an isolated or recombinant nucleic acid encoding a prenyl protease wherein the plant has increased tolerance to an environmental stress as compared to a wild type variety of the plant, comprising transforming a plant cell with an expression vector comprising a polynucleotide sequence encoding a prenyl protease and generating from the plant cell the transgenic plant with increased tolerance to stress, wherein the polynucleotide encodes an amino acid sequence comprising amino acids 1 to 424 of SEQ ID NO: 4 or a full-length homolog of the plant prenyl protease of SEQ ID NO: 4 wherein the homolog has prenyl protease activity and at least 80% identity at the amino acid level to amino acids 1 to 424 of SEQ ID NO: 4.

36. The method of claim 35, wherein the environmental stress is selected from the group consisting of drought, high temperature, and low temperature.

37. The method of claim 35, wherein the polynucleotide sequence is selected from the group consisting of
   a) a polynucleotide comprising nucleotides 1 to 1275 of SEQ ID NO: 3;
   b) a polynucleotide comprising nucleotides 1 to 1275 of SEQ ID NO: 5;
   c) a polynucleotide encoding a polypeptide comprising amino acids 1 to 424 of SEQ ID NO: 6; and
   d) a polynucleotide encoding a polypeptide having at least 70% identity at the amino acid level to SEQ ID NO: 4 and 6.

38. The method of claim 35, wherein the polynucleotide sequence is selected from the group consisting of
   a) a polynucleotide comprising nucleotides 1 to 1275 of SEQ ID NO: 7;
   b) a polynucleotide comprising nucleotides 1 to 1275 of SEQ ID NO: 11;
   c) a polynucleotide comprising nucleotides 1 to 1275 of SEQ ID NO: 18;
   d) a polynucleotide encoding a polypeptide comprising amino acids 1 to 424 of SEQ ID NO: 8;
   e) a polynucleotide encoding a polypeptide comprising amino acids 1 to 424 of SEQ ID NO: 12;
   f) a polynucleotide encoding a polypeptide comprising amino acids 1 to 424 of SEQ ID NO: 19;
   g) a polynucleotide encoding a polypeptide having at least 99% identity at the amino acid level to amino acids 1 to 424 of SEQ ID NO: 8;
   h) a polynucleotide encoding a polypeptide having at least 96% identity at the amino acid level to amino acids 1 to 424 of SEQ ID NO: 12; and
   i) a polynucleotide encoding a polypeptide having at least 85% identity at the amino acid level to amino acids 1 to 424 of SEQ ID NO: 19.

39. The method of claim 35, wherein the polynucleotide sequence is selected from the group consisting of
  a) a polynucleotide comprising nucleotides 1 to 1405 of SEQ ID NO: 16;
  b) a polynucleotide encoding a polypeptide comprising amino acids 1 to 424 of SEQ ID NO: 17; and
  c) a polynucleotide encoding a polypeptide having at least 95% identity at the amino acid level to amino acids 1 to 424 of SEQ ID NO: 17.

40. The method of claim 35, wherein the plant is a monocot.

41. The method of claim 35, wherein the plant is a dicot.

42. The method of claim 35, wherein the plant is selected from the group consisting of maize, wheat, rye, oat, triticale, rice, barley, soybean, peanut, cotton, rapeseed, canola, manihot, pepper, sunflower, tagetes, potato, tobacco, eggplant, tomato, *Vicia* species, pea, alfalfa, coffee, cacao, tea, *Salix* species, oil palm, coconut, perennial grass, and a forage crop.

43. The method of claim 35, wherein the expression vector comprises a promoter that directs expression of the polynucleotide.

44. The method of claim 43, wherein the promoter is selected from the group consisting of a constitutive promoter, an ABA inducible promoter, a tissue-specific promoter, a guard cell-specific promoter, and a developmentally regulated promoter.

45. The method of claim 35, wherein the plant has an altered phenotype selected from the group consisting of increased tolerance to stress, delayed senescence, increased ABA sensitivity, increased yield, increased productivity, and increased biomass compared to a wild type plant.

46. The method of claim 35, wherein the plant's stress tolerance is increased by increasing expression of the polynucleotide in the plant.

47. A transgenic corn plant, plant cell, or seed which comprises a nucleic acid comprising nucleotides 1 to 1275 of SEQ ID NO: 3 or a nucleic acid encoding a plant prenyl protease having an amino acid sequence comprising amino acids 1 to 424 of SEQ ID NO: 4.

48. The transgenic plant of claim 24, wherein the plant prenyl protease has an amino acid sequence comprising amino acids 1 to 424 of SEQ ID NO: 4.

49. The transgenic plant of claim 25, wherein the homolog comprises a polypeptide comprising amino acids 1 to 424 of SEQ ID NO: 6.

50. The transgenic plant of claim 26, wherein the homolog comprises a polypeptide comprising amino acids 1 to 424 of SEQ ID NO: 17.

51. The transgenic plant of claim 27, wherein the homolog comprises a polypeptide comprising amino acids 1 to 424 of SEQ ID NO: 8.

52. The transgenic plant of claim 27, wherein the homolog comprises a polypeptide comprising amino acids 1 to 424 of SEQ ID NO: 12.

53. The transgenic plant of claim 27, wherein the homolog comprises a polypeptide comprising amino acids 1 to 424 of SEQ ID NO: 19.

54. The transgenic plant of claim 24, wherein the plant is a *Solanaceous* plant.

55. The method of claim 35, wherein the plant is a *Solanaceous* plant.

* * * * *

SEQUENCE LISTING

```
<160> NUMBER OF SEQ ID NOS: 91

<210> SEQ ID NO 1
<211> LENGTH: 1398
<212> TYPE: DNA
<213> ORGANISM: Physcomitrella patens
```

-continued

<400> SEQUENCE: 1

```
ggatccccg ggctgcagga attcggcacg agctcaagct gtccaatctg ccagcgcctc      60
tcaagggaat agttagtcaa gagaaatttg agaaagcgca ggcgtacagc ttagacaaga    120
gccgattcca ttttgtgcac gcggctgtga atatcgtgga ggaatcggca attcttctgc    180
tggggttgtt gccgtgggcg tgggataaga gtggatcgtt agtagggaag ctagggtttg    240
atgagaagag cgaaattttg cagacgcttt cttttcttgc ggtgaccacg ttgtggtcgc    300
agatacttga gcttccattc tcgctctact ccacgtttgt catcgaggcc cgccatggct    360
tcaacaagca aaccatatgg ttgtttttac gggatatgat catggggctg gctctcatga    420
tggtggttgg cccacccata gtgtcggcaa ttatctatat tgtgcagaac ggtgggccat    480
atcttgccct ctatctgtgg gcctttatgt tgctgttatc cctcgtgttg atggccctat    540
atcccgttct catcgcgcct cttttcaaca cattcacacc cttgccagaa gggcagcttc    600
gtgccaagat cgagaagctg gcatcctcct ggacttccc attgaagaaa ttgtttgtaa    660
ttgacggttc tactcggtca agccatagca acgcctacat gtatggattt tacaacagca    720
agcgcatcgt tctgtacgac actctaatat cgcaatgtaa gaatgaggaa gaagtagtgg    780
cagttatagc tcatgagctt ggccattgga agctgagcca cactatgtac tcgttcctgg    840
ccatgcaggt gcttacactg ttgcaattcg gaggctatac gcttgttcgg aactctagtg    900
gcctgttttt gagcttcggt ttctccacac agccagtgct tatcgggctg atcctattcc    960
agcacactat tatgcccttc catcatcttg taagctttgc tctcaacctg ttgagccgag   1020
ccttcgaatt tcaggcggat gcgttcgccc gctcattagg gtacagagag ccattgagag   1080
ctggcctgat caagctgcag gaggagaatc tgtctgccat gaacacggat ccgtggtatt   1140
cagcgtatca tcattcacac ccccgcttg ttgagcgatt gcaagctctt gatgaaacgt   1200
ccaagaaaac ggattagaac ttaccccctt cggaccgtag ttgagatttg taggaatata   1260
gcttcttcag gagaaagaaa caaaatgagc tatgtcctag cacatccact gtagaattca   1320
ctgatgaatg acgaatagta catgaacact cattctttaa aaaaaaaaaa aaaaaactcg   1380
agggggggcc cggtaccc                                                  1398
```

<210> SEQ ID NO 2
<211> LENGTH: 394
<212> TYPE: PRT
<213> ORGANISM: Physcomitrella patens

<400> SEQUENCE: 2

```
Leu Lys Leu Ser Asn Leu Pro Ala Pro Leu Lys Gly Ile Val Ser Gln
 1               5                  10                  15

Glu Lys Phe Glu Lys Ala Gln Ala Tyr Ser Leu Asp Lys Ser Arg Phe
             20                  25                  30

His Phe Val His Ala Ala Val Asn Ile Val Glu Glu Ser Ala Ile Leu
         35                  40                  45

Leu Leu Gly Leu Leu Pro Trp Ala Trp Asp Lys Ser Gly Ser Leu Val
     50                  55                  60

Gly Lys Leu Gly Phe Asp Glu Lys Ser Glu Ile Leu Gln Thr Leu Ser
 65                  70                  75                  80

Phe Leu Ala Val Thr Thr Leu Trp Ser Gln Ile Leu Glu Leu Pro Phe
                 85                  90                  95

Ser Leu Tyr Ser Thr Phe Val Ile Glu Ala Arg His Gly Phe Asn Lys
            100                 105                 110
```

```
Gln Thr Ile Trp Leu Phe Leu Arg Asp Met Ile Met Gly Leu Ala Leu
            115                 120                 125

Met Met Val Val Gly Pro Pro Ile Val Ser Ala Ile Ile Tyr Ile Val
130                 135                 140

Gln Asn Gly Gly Pro Tyr Leu Ala Leu Tyr Leu Trp Ala Phe Met Leu
145                 150                 155                 160

Leu Leu Ser Leu Val Leu Met Ala Leu Tyr Pro Val Leu Ile Ala Pro
                165                 170                 175

Leu Phe Asn Thr Phe Thr Pro Leu Pro Glu Gly Gln Leu Arg Ala Lys
            180                 185                 190

Ile Glu Lys Leu Ala Ser Ser Leu Asp Phe Pro Leu Lys Lys Leu Phe
        195                 200                 205

Val Ile Asp Gly Ser Thr Arg Ser Ser His Ser Asn Ala Tyr Met Tyr
    210                 215                 220

Gly Phe Tyr Asn Ser Lys Arg Ile Val Leu Tyr Asp Thr Leu Ile Ser
225                 230                 235                 240

Gln Cys Lys Asn Glu Glu Val Val Ala Val Ile Ala His Glu Leu
                245                 250                 255

Gly His Trp Lys Leu Ser His Thr Met Tyr Ser Phe Leu Ala Met Gln
            260                 265                 270

Val Leu Thr Leu Leu Gln Phe Gly Gly Tyr Thr Leu Val Arg Asn Ser
        275                 280                 285

Ser Gly Leu Phe Leu Ser Phe Gly Phe Ser Thr Gln Pro Val Leu Ile
    290                 295                 300

Gly Leu Ile Leu Phe Gln His Thr Ile Met Pro Phe His Leu Val
305                 310                 315                 320

Ser Phe Ala Leu Asn Leu Leu Ser Arg Ala Phe Glu Phe Gln Ala Asp
                325                 330                 335

Ala Phe Ala Arg Ser Leu Gly Tyr Arg Glu Pro Leu Arg Ala Gly Leu
            340                 345                 350

Ile Lys Leu Gln Glu Glu Asn Leu Ser Ala Met Asn Thr Asp Pro Trp
        355                 360                 365

Tyr Ser Ala Tyr His His Ser His Pro Pro Leu Val Glu Arg Leu Gln
    370                 375                 380

Ala Leu Asp Glu Thr Ser Lys Lys Thr Asp
385                 390

<210> SEQ ID NO 3
<211> LENGTH: 1275
<212> TYPE: DNA
<213> ORGANISM: Arabidopsis thaliana

<400> SEQUENCE: 3
atggcgattc ctttcatgga aaccgtcgtg ggttttatga tagtgatgta cattttgag       60 acgtatttgg atctgaggca actcactgct ctcaagcttc caactctccc gaaaaccttg     120
gttggtgtaa ttagccaaga gaagtttgag aaatcacgag catacagtct tgacaaaagc    180
tattttcact tgttcatga gtttgtaact atacttatgg actctgcaat tttgttcttt     240
gggatcttgc cttggttttg aagatgtct ggagctgttt taccgaggtt gggccttgat      300
ccagagaatg aaatactgca tactctttca ttcttggctg tgttatgac atggtcacag     360 atcactgatt tgccattttc tttgtactca actttcgtga tcgagtctcg gcatgggttc    420
aacaaacaaa caatatggat gttcattagg gacatgatca aaggaacatt cctctctgtc    480
atactaggcc cacccattgt tgccgcgata attttcatag tccagaaagg aggtccttat     540
```

-continued

```
cttgccatct atctgtgggc attcatgttt atcctgtctc tagtgatgat gactatatac    600
ccggtcttga tagcaccgct cttcaacaag ttcactcctc ttccagatgg agacctccgg    660
gagaagattg agaaacttgc ttcttctcta agtttccttt gaagaagct gtttgttgtc    720 gatggatcta caaggtcaag ccatagcaat gcttacatgt atggtttctt taagaacaaa    780
aggattgttc tttatgatac gttgattcag cagtgcaaga atgaggatga aattgtggcg    840
gttattgcac acgagcttgg acattggaaa ctgaatcaca ctacatactc gttcattgca    900
gttcaaatcc ttgccttctt acaatttgga ggatacactc ttgtcagaaa ctccactgat    960
ctcttcagga gtttcggatt tgatacacag cctgttctca ttggtttgat catatttcag   1020
cacactgtaa taccactgca acatccagta agctttggcc tcaaccttgt tagtcgagcg   1080
tttgagtttc aggctgatgc ttttgctgtg aagcttggct atgcaaaaga tcttcgtcct   1140
actctagtga aactacagga agagaactta tcagcaatga atactgatcc attgtactca   1200
gcttatcact actcacatcc tcctcttgtt gaaaggcttc gagccattga tggagaagac   1260
aagaagacag attaa                                                    1275
```

<210> SEQ ID NO 4
<211> LENGTH: 424
<212> TYPE: PRT
<213> ORGANISM: Arabidopsis thaliana

<400> SEQUENCE: 4

```
Met Ala Ile Pro Phe Met Glu Thr Val Val Gly Phe Met Ile Val Met
 1               5                  10                  15

Tyr Ile Phe Glu Thr Tyr Leu Asp Leu Arg Gln Leu Thr Ala Leu Lys
                20                  25                  30

Leu Pro Thr Leu Pro Lys Thr Leu Val Gly Val Ile Ser Gln Glu Lys
            35                  40                  45

Phe Glu Lys Ser Arg Ala Tyr Ser Leu Asp Lys Ser Tyr Phe His Phe
        50                  55                  60

Val His Glu Phe Val Thr Ile Leu Met Asp Ser Ala Ile Leu Phe Phe
    65                  70                  75                  80

Gly Ile Leu Pro Trp Phe Trp Lys Met Ser Gly Ala Val Leu Pro Arg
                85                  90                  95

Leu Gly Leu Asp Pro Glu Asn Glu Ile Leu His Thr Leu Ser Phe Leu
               100                 105                 110

Ala Gly Val Met Thr Trp Ser Gln Ile Thr Asp Leu Pro Phe Ser Leu
           115                 120                 125

Tyr Ser Thr Phe Val Ile Glu Ser Arg His Gly Phe Asn Lys Gln Thr
       130                 135                 140

Ile Trp Met Phe Ile Arg Asp Met Ile Lys Gly Thr Phe Leu Ser Val
145                 150                 155                 160

Ile Leu Gly Pro Pro Ile Val Ala Ala Ile Phe Ile Val Gln Lys
               165                 170                 175

Gly Gly Pro Tyr Leu Ala Ile Tyr Leu Trp Ala Phe Met Phe Ile Leu
           180                 185                 190

Ser Leu Val Met Met Thr Ile Tyr Pro Val Leu Ile Ala Pro Leu Phe
       195                 200                 205

Asn Lys Phe Thr Pro Leu Pro Asp Gly Asp Leu Arg Glu Lys Ile Glu
   210                 215                 220

Lys Leu Ala Ser Ser Leu Lys Phe Pro Leu Lys Lys Leu Phe Val Val
225                 230                 235                 240

Asp Gly Ser Thr Arg Ser Ser His Ser Asn Ala Tyr Met Tyr Gly Phe
```

```
                    245                 250                 255
Phe Lys Asn Lys Arg Ile Val Leu Tyr Asp Thr Leu Ile Gln Gln Cys
                260                 265                 270

Lys Asn Glu Asp Glu Ile Val Ala Val Ile Ala His Glu Leu Gly His
            275                 280                 285

Trp Lys Leu Asn His Thr Thr Tyr Ser Phe Ile Ala Val Gln Ile Leu
        290                 295                 300

Ala Phe Leu Gln Phe Gly Gly Tyr Thr Leu Val Arg Asn Ser Thr Asp
305                 310                 315                 320

Leu Phe Arg Ser Phe Gly Phe Asp Thr Gln Pro Val Leu Ile Gly Leu
                325                 330                 335

Ile Ile Phe Gln His Thr Val Ile Pro Leu Gln His Pro Val Ser Phe
                340                 345                 350

Gly Leu Asn Leu Val Ser Arg Ala Phe Glu Phe Gln Ala Asp Ala Phe
            355                 360                 365

Ala Val Lys Leu Gly Tyr Ala Lys Asp Leu Arg Pro Thr Leu Val Lys
        370                 375                 380

Leu Gln Glu Glu Asn Leu Ser Ala Met Asn Thr Asp Pro Leu Tyr Ser
385                 390                 395                 400

Ala Tyr His Tyr Ser His Pro Pro Leu Val Glu Arg Leu Arg Ala Ile
                405                 410                 415

Asp Gly Glu Asp Lys Lys Thr Asp
            420

<210> SEQ ID NO 5
<211> LENGTH: 1275
<212> TYPE: DNA
<213> ORGANISM: Arabidopsis thaliana

<400> SEQUENCE: 5
atggcgattc ctttcatgga aaccgtcgtg ggttttatga tagtgatgta cattttgag      60 acgtatttgg atctgaggca actcactgct ctcaagcttc aactctcccc gaaaaccttg    120
gttggtgtaa ttagccaaga aagtttgag aaatcacgag catacagtct tgacaaaagc    180
tattttcact ttgttcatga gtttgtaact atacttatgg actctgcaat tttgttcttt    240
gggatcttgc cttggttttg gaagatgtct ggagcagttt taccgaggtt gggccttgat    300
ccagagaatg aaatactgca tactctttca ttcttggctg gtgttatgac atggtcacag    360
atcactgatt tgccattttc tttgtactca actttcgtga tcgagtctcg gcatgggttc    420
aacaaacaaa caatatggat gttcattagg acatgatca aaggaacatt cctctctgtc      480
atactaggcc cacccattgt tgctgcgata atttttcatag tccagaaagg aggtccttat    540
cttgccatct atctgtgggc attcatgttt atcctgtctc tagtgatgat gactatatac    600
ccggtcttga tagcaccgct cttcaacaag ttcactcctc ttccagatgg agacctccgg    660
gagaagattg agaaacttgc ttcttctcta agtttccctt tgaagaagct gtttgttgtc    720
gatggatcta caaggtcaag ccatagcaat gcttacatgt atggtttctt taagaacaaa    780
aggattgttc tttatgatac gttgattcag cagtgcaaga tgaggatga attgtggcg      840 gttattgcac acgagcttgg acattggaaa ctgaatcaca ctacatactc gttcattgca    900
gttcaaatcc ttgccttctt acaatttgga ggatacactc ttgtcagaaa ctccactgat    960
ctcttcagga gttcggatt tgatacacag cctgttctca ttggttttgat catatttcag   1020 cacactgtaa taccactgca acatctagta agctttggcc tgaacctcgt tagtcgagcg   1080
tttgagtttc aggctgatgc ttttgctgtg aagcttggct atgcaaaaga tcttcgtcct   1140
```

```
gctctagtga aactacagga agagaactta tcagcaatga acactgatct attgtactca    1200
gcttatcact actcacatcc tcctcttgtt gaaaggcttc gagccattga tggagaagac    1260
aagaagacag attaa                                                     1275
```

<210> SEQ ID NO 6
<211> LENGTH: 424
<212> TYPE: PRT
<213> ORGANISM: Arabidopsis thaliana

<400> SEQUENCE: 6

```
Met Ala Ile Pro Phe Met Glu Thr Val Val Gly Phe Met Ile Val Met
 1               5                  10                  15

Tyr Ile Phe Glu Thr Tyr Leu Asp Leu Arg Gln Leu Thr Ala Leu Lys
                20                  25                  30

Leu Pro Thr Leu Pro Lys Thr Leu Val Gly Val Ile Ser Gln Glu Lys
            35                  40                  45

Phe Glu Lys Ser Arg Ala Tyr Ser Leu Asp Lys Ser Tyr Phe His Phe
        50                  55                  60

Val His Glu Phe Val Thr Ile Leu Met Asp Ser Ala Ile Leu Phe Phe
 65                  70                  75                  80

Gly Ile Leu Pro Trp Phe Trp Lys Met Ser Gly Ala Val Leu Pro Arg
                85                  90                  95

Leu Gly Leu Asp Pro Glu Asn Glu Ile Leu His Thr Leu Ser Phe Leu
            100                 105                 110

Ala Gly Val Met Thr Trp Ser Gln Ile Thr Asp Leu Pro Phe Ser Leu
        115                 120                 125

Tyr Ser Thr Phe Val Ile Glu Ser Arg His Gly Phe Asn Lys Gln Thr
    130                 135                 140

Ile Trp Met Phe Ile Arg Asp Met Ile Lys Gly Thr Phe Leu Ser Val
145                 150                 155                 160

Ile Leu Gly Pro Pro Ile Val Ala Ala Ile Phe Ile Val Gln Lys
                165                 170                 175

Gly Gly Pro Tyr Leu Ala Ile Tyr Leu Trp Ala Phe Met Phe Ile Leu
            180                 185                 190

Ser Leu Val Met Met Thr Ile Tyr Pro Val Leu Ile Ala Pro Leu Phe
        195                 200                 205

Asn Lys Phe Thr Pro Leu Pro Asp Gly Asp Leu Arg Glu Lys Ile Glu
    210                 215                 220

Lys Leu Ala Ser Ser Leu Lys Phe Pro Leu Lys Leu Phe Val Val
225                 230                 235                 240

Asp Gly Ser Thr Arg Ser Ser His Ser Asn Ala Tyr Met Tyr Gly Phe
                245                 250                 255

Phe Lys Asn Lys Arg Ile Val Leu Tyr Asp Thr Leu Ile Gln Gln Cys
            260                 265                 270

Lys Asn Glu Asp Glu Ile Val Ala Val Ile Ala His Glu Leu Gly His
        275                 280                 285

Trp Lys Leu Asn His Thr Thr Tyr Ser Phe Ile Ala Val Gln Ile Leu
    290                 295                 300

Ala Phe Leu Gln Phe Gly Gly Tyr Thr Leu Val Arg Asn Ser Thr Asp
305                 310                 315                 320

Leu Phe Arg Ser Phe Gly Phe Asp Thr Gln Pro Val Leu Ile Gly Leu
                325                 330                 335

Ile Ile Phe Gln His Thr Val Ile Pro Leu Gln His Leu Val Ser Phe
            340                 345                 350
```

Gly Leu Asn Leu Val Ser Arg Ala Phe Glu Phe Gln Ala Asp Ala Phe
         355                 360                 365

Ala Val Lys Leu Gly Tyr Ala Lys Asp Leu Arg Pro Ala Leu Val Lys
370                 375                 380

Leu Gln Glu Glu Asn Leu Ser Ala Met Asn Thr Asp Leu Leu Tyr Ser
385                 390                 395                 400

Ala Tyr His Tyr Ser His Pro Pro Leu Val Glu Arg Leu Arg Ala Ile
                405                 410                 415

Asp Gly Glu Asp Lys Lys Thr Asp
            420

<210> SEQ ID NO 7
<211> LENGTH: 1275
<212> TYPE: DNA
<213> ORGANISM: Arabidopsis thaliana

<400> SEQUENCE: 7

```
atggcgattc ctttcatgga aaccgtcgtg ggttttatga tagtgatgta cattttgag       60
acgtatttgg atctgaggca actcactgct ctcaagcttc caactctccc gaaaaccttg     120
gttggtgtaa ttagccaaga gaagtttgag aaatcacgag catacagtct tgacaaaagc    180
tattttcact tgttcatga gtttgtaact atacttatgg actctgcaat tttgttcttt     240
gggatcttgc cttggttttg aagatgtct ggagctgttt taccgaggtt gggccttgat     300
ccggagaatg aaatactgca tactctttca ttcttggctg tgttatgac atggtcacag     360
atcactgatt tgccatttc tttgtactca actttcgtga tcgagtctcg gcatgggttc     420
aacaaacaaa caatatggat gttcattagg gacatgatca aaggaacatt cctctctgtc    480
atactaggcc cacccattgt tgctgcgata attttcatag tccagaaagg aggtccttat    540
cttgccatct atctgtgggc attcatgttt atcctgtctc tagtgatgat gactatatac    600
ccggtcttga tagcaccgct cttcaacaaa ttcactcctc ttccagatgg agacctccgg    660
gagaagattg agaaacttgc ttcttcccta agtttccttt gaagaagct gtttgttgtc    720
gatggatcta caaggtcaag ccatagcaat gcttacatgt atggtttctt taagaacaaa    780
aggattgttc tttatgatac gttgattcag cagtgcaaga tgaggatga aattgtggcg     840
gttattgcac acgagcttgg acattggaaa ctgaatcaca ctacatactc gttcattgca    900
gttcaaatcc ttgccttctt acaatttgga ggatacactc ttctcagaaa ctccactgat    960
ctcttcagga gtttcggatt tgatacacag cctgttctca ttggtttgat catatttcag   1020
cacactgtaa taccactgca acatctagta agctttggcc tgaacctcgt tagtcgagcg   1080
tttgagtttc aggctgatgc ttttgctgtg aagcttgact atgcaaaaga tcttcgtcct   1140
gctctagtga aactacagga agagaactta tcaacaatga acactgatcc attgtactca   1200
gcttatcact actcacatcc tcctcttgtt gaaaggcttc gagccactga tggagaagac   1260
aagaagacag attaa                                                    1275
```

<210> SEQ ID NO 8
<211> LENGTH: 424
<212> TYPE: PRT
<213> ORGANISM: Arabidopsis thaliana

<400> SEQUENCE: 8

Met Ala Ile Pro Phe Met Glu Thr Val Val Gly Phe Met Ile Val Met
1               5                   10                  15

Tyr Ile Phe Glu Thr Tyr Leu Asp Leu Arg Gln Leu Thr Ala Leu Lys

```
                    20                  25                  30
Leu Pro Thr Leu Pro Lys Thr Leu Val Gly Val Ile Ser Gln Glu Lys
                35                  40                  45

Phe Glu Lys Ser Arg Ala Tyr Ser Leu Asp Lys Ser Tyr Phe His Phe
    50                  55                  60

Val His Glu Phe Val Thr Ile Leu Met Asp Ser Ala Ile Leu Phe Phe
65                  70                  75                  80

Gly Ile Leu Pro Trp Phe Trp Lys Met Ser Gly Ala Val Leu Pro Arg
                85                  90                  95

Leu Gly Leu Asp Pro Glu Asn Glu Ile Leu His Thr Leu Ser Phe Leu
                100                 105                 110

Ala Gly Val Met Thr Trp Ser Gln Ile Thr Asp Leu Pro Phe Ser Leu
                115                 120                 125

Tyr Ser Thr Phe Val Ile Glu Ser Arg His Gly Phe Asn Lys Gln Thr
    130                 135                 140

Ile Trp Met Phe Ile Arg Asp Met Ile Lys Gly Thr Phe Leu Ser Val
145                 150                 155                 160

Ile Leu Gly Pro Pro Ile Val Ala Ile Ile Phe Ile Val Gln Lys
                165                 170                 175

Gly Gly Pro Tyr Leu Ala Ile Tyr Leu Trp Ala Phe Met Phe Ile Leu
                180                 185                 190

Ser Leu Val Met Met Thr Ile Tyr Pro Val Leu Ile Ala Pro Leu Phe
                195                 200                 205

Asn Lys Phe Thr Pro Leu Pro Asp Gly Asp Leu Arg Glu Lys Ile Glu
    210                 215                 220

Lys Leu Ala Ser Ser Leu Lys Phe Pro Leu Lys Lys Leu Phe Val Val
225                 230                 235                 240

Asp Gly Ser Thr Arg Ser Ser His Ser Asn Ala Tyr Met Tyr Gly Phe
                245                 250                 255

Phe Lys Asn Lys Arg Ile Val Leu Tyr Asp Thr Leu Ile Gln Gln Cys
                260                 265                 270

Lys Asn Glu Asp Glu Ile Val Ala Val Ile Ala His Glu Leu Gly His
    275                 280                 285

Trp Lys Leu Asn His Thr Thr Tyr Ser Phe Ile Ala Val Gln Ile Leu
290                 295                 300

Ala Phe Leu Gln Phe Gly Gly Tyr Thr Leu Leu Arg Asn Ser Thr Asp
305                 310                 315                 320

Leu Phe Arg Ser Phe Gly Phe Asp Thr Gln Pro Val Leu Ile Gly Leu
                325                 330                 335

Ile Ile Phe Gln His Thr Val Ile Pro Leu Gln His Leu Val Ser Phe
                340                 345                 350

Gly Leu Asn Leu Val Ser Arg Ala Phe Glu Phe Gln Ala Asp Ala Phe
                355                 360                 365

Ala Val Lys Leu Asp Tyr Ala Lys Asp Leu Arg Pro Ala Leu Val Lys
                370                 375                 380

Leu Gln Glu Glu Asn Leu Ser Thr Met Asn Thr Asp Pro Leu Tyr Ser
385                 390                 395                 400

Ala Tyr His Tyr Ser His Pro Pro Leu Val Glu Arg Leu Arg Ala Thr
                405                 410                 415

Asp Gly Glu Asp Lys Lys Thr Asp
                420

<210> SEQ ID NO 9
<211> LENGTH: 1275
```

```
<212> TYPE: DNA
<213> ORGANISM: Artificial Sequence
<220> FEATURE:
<223> OTHER INFORMATION: Description of Artificial Sequence: sequence
      complementary to seq id no: 7

<400> SEQUENCE: 9
ttaatctgtc ttcttgtctt ctccatcagt ggctcgaagc ctttcaacaa gaggaggatg     60
tgagtagtga taagctgagt acaatggatc agtgttcatt gttgataagt tctcttcctg    120
tagtttcact agagcaggac gaagatcttt tgcatagtca agcttcacag caaaagcatc    180
agcctgaaac tcaaacgctc gactaacgag gttcaggcca aagcttacta gatgttgcag    240
tggtattaca gtgtgctgaa atatgatcaa accaatgaga acaggctgtg tatcaaatcc    300
gaaactcctg aagagatcag tggagtttct gagaagagtg tatcctccaa attgtaagaa    360
ggcaaggatt tgaactgcaa tgaacgagta tgtagtgtga ttcagtttcc aatgtccaag    420
ctcgtgtgca ataaccgcca caatttcatc ctcattcttg cactgctgaa tcaacgtatc    480
ataaagaaca atccttttgt tcttaaagaa accatacatg taagcattgc tatggcttga    540
ccttgtagat ccatcgacaa caaacagctt cttcaaagga aactttaggg aagaagcaag    600
tttctcaatc ttctcccgga ggtctccatc tggaagagga gtgaatttgt tgaagagcgg    660
tgctatcaag accgggtata tagtcatcat cactagagac aggataaaca tgaatgccca    720
cagatagatg gcaagataag gacctccttt ctggactatg aaaattatcg cagcaacaat    780
gggtgggcct agtatgacag agaggaatgt tcctttgatc atgtccctaa tgaacatcca    840
tattgtttgt ttgttgaacc catgccgaga ctcgatcacg aaagttgagt acaaagaaaa    900
tggcaaatca gtgatctgtg accatgtcat aacaccagcc aagaatgaaa gagtatgcag    960
tatttcattc tccggatcaa ggcccaacct cggtaaaaca gctccagaca tcttccaaaa   1020
ccaaggcaag atcccaaaga acaaaattgc agagtccata agtatagtta caaactcatg   1080
aacaaagtga aaatagcttt tgtcaagact gtatgctcgt gatttctcaa acttctcttg   1140
gctaattaca ccaaccaagg ttttcgggag agttggaagc ttgagagcag tgagttgcct   1200
cagatccaaa tacgtctcaa aaatgtacat cactatcata aaacccacga cggttttccat   1260
gaaaggaatc gccat                                                   1275

<210> SEQ ID NO 10
<211> LENGTH: 2047
<212> TYPE: DNA
<213> ORGANISM: Arabidopsis thaliana

<400> SEQUENCE: 10
ttgatgatga aaagagaag atcgaaacca agtcttacaa agaagagcga tttctctcaa     60
aggggaaggt aaaattgaca aatccacgcg ctagcttttc acgttcactc acgcgctaca    120
ttttgtataa tccacaaaac tttcaataaa ttacagaaaa accttgataa atttttacca    180
taacaacaag atccctgata ttattttcaa attgactcat aaagcattac aaaaggagat    240
ggttttctg aaacatgaaa tggttggtta cagaagacga tacatacaat aggcagctat    300
gttcatcatc tctttccttt tcctttagca tcaaagtgat gagactttag tttcttcttc    360
cgcactatcg cgcctgtgct gccaccacct ccttccctga aaggcattcc cattagagcc    420
aatagtttct gtccttcttg atcgctttta gccgttgtgc tgatgcatac atccattcct    480
ctcgtttttc caacggcatc aaacctgagt gtaataaac caaccaacca acatagagtt    540
tagttgctcg gttgtaaaca aagagtggga ctaaagagaa accatgcttg atcttgttga    600
```

```
accagcggat aacaagttag tagttttgat tttgagggta gatacaatag aactaacctg    660
atttcaggga atacaccttg gtctttcaca ccaatactgt agtttccgtt cccatcaaag    720
ctactgggac tcacaccttg gaaatctcga gttctcggaa gggctaagtt gataagacga    780
tccaagaagg agtacattac ctgtcacaac agtcaaaatc acaaaatgtt aatacataaa    840
taactcaaaa ggaaagtttg attagtcaag agaaatatag ctcacatctc ctctgagagt    900
gacagcaatc ccaagaggtt gatcttccct gatcttgaaa gtagcaatgg aagctctagc    960
tcgtgtctta ataggtttct gccctgtgat aagcgcgata tccttcatcg cagcctccaa   1020
acccttgtcg ttctgcgccg catctccaat accacaattc actacaatct tctgtacctt   1080
tggaacctgg tagagaagat gtccaagcag atatacaaca atgatgagat tgacaaattc   1140
acattcacat ttgtaaatgg cacatcccaa cagcacgatt ttatcaacac aacaatctta   1200
aatctaggct tcttcactac attttctaga agaaatcaat tcaaacttat cattaaaagc   1260
aaattaggtt taacattcgc tcaaaaaatt cgaattcact gagaattaga cttcaatcaa   1320
tcgcaacaga acaaaaacta ggtttgagct cagaggggaa ggatttgggg ttacctggtg   1380
aatattaacg tacttgaact cttctttgag cgcaggata atcctctcga ggtaagcggt   1440
tttgaggcgt tgagttttct cggcttcaga tttctcgacc agtacagttc cagacgccga   1500
gactttcacc acgtttctga gcggcggaga gagcattcgt gcggaggatg gagccgctaa   1560
tggtgagaaa cgtccgtgaa acgaagaagc ggaagactgc agaagcgaag gagacgccat   1620
tgtcgaagct ccaagtggat aaagtgtgaa gtgagagctc tcggcgttcg ttgttgatta   1680
aacccaatgg caccttcgta atttgttgac agtttgagga taaggagttt ccgtttagc    1740 ccctttaaaa cataatattt caactaaggc cccaatattt gataatatac tattatactt   1800
agagatttta gataaaatat aggggttgtt tcatatgggc ctaaatctca gcccgtttac   1860
tatttgggct tctaaggtat aacccgtacc cgtgtttttg ttgttttaca tatccacacc   1920
gacctgagaa gagtcaaaaa cgaaaaacct ctcttttgtc gttcctctgc tttcttcgat   1980
ttgcttctgc tttcttcgat ttgcttctgc tttcatcgcg gttcaggtca ctcttttctc   2040
agccatg                                                             2047

<210> SEQ ID NO 11
<211> LENGTH: 1275
<212> TYPE: DNA
<213> ORGANISM: Brassica napus

<400> SEQUENCE: 11
atggcgattc ctttcatgga aaccgtcgtt ggttttatga tagtgatgta cgttttttgag     60 acgtatttgg atctgaggca acatactgct ctcaagcttc ccactctccc aaagactttg    120
gttggagtca ttagccaaga gaagtttgag aaatctcgag cttacagtct tgacaaaagc    180
cattttcact ttgttcatga gtttgttact atacttatgg actctgcgat tctgttcttt    240
gggatcttgc cttggttttg gaagatatct ggcggctttc taccaatggt gggactcgat    300
ccagagaatg aaatcctgca cactctttca ttcttggctg tcttatgac atggtcacag     360 atcactgatt tgccattttc tttgtactca actttcgtga tcgagtctcg gcatgggttc    420
aacaaacaaa caatatggat gttcattagg gacatgatca aaggaatact cctctctgtc    480
atacctgccc ctcctatcgt tgccgcaatt attgttatag ttcagaaagg aggtccttac    540
ctcgccatct atctgtgggc attcatgttt atcctgtctc tagtgatgat gactatatac    600
cctgttttga ttgcacctct tttcaacaag ttcactcctc ttcctgatgg agacctccgg    660
```

```
gagaagattg agaaacttgc ttcttctcta aagtttcctc tgaagaagct gtttgttgtc    720
gatggatcta caaggtcaag ccatagtaat gcttacatgt atggtttctt caagaacaaa    780
aggattgttc tttatgacac attgattcag cagtgccaga atgagaatga aattgtggcg    840
gttattgcac acgagctggg acactggaag ctgaatcaca ctacatactc gttcattgct    900
gttcaaatcc ttgccttctt gcaatttgga ggatacactc ttgtcagaaa ctccactgat    960
ctcttcagga gttttggttt tgatacacaa ccagttctca ttggtttgat catatttcag   1020
cacactgtaa taccacttca acacctagta agctttgacc tcaaccttgt tagtcgagcg   1080
tttgagtttc aggctgatgc ttttgcagtg aatcttggtt atgcaaagga tctacgtcct   1140
gccctagtga agctacagga agagaactta tcagcgatga acacagaccc attgtactca   1200
gcttatcact actcacaccc tcctcttgta gagaggcttc gagccattga tggagaagac   1260
aagaagacag attaa                                                    1275
```

<210> SEQ ID NO 12
<211> LENGTH: 424
<212> TYPE: PRT
<213> ORGANISM: Brassica napus

<400> SEQUENCE: 12

```
Met Ala Ile Pro Phe Met Glu Thr Val Val Gly Phe Met Ile Val
 1               5                  10                  15

Tyr Val Phe Glu Thr Tyr Leu Asp Leu Arg Gln His Thr Ala Leu Lys
                20                  25                  30

Leu Pro Thr Leu Pro Lys Thr Leu Val Gly Val Ile Ser Gln Glu Lys
            35                  40                  45

Phe Glu Lys Ser Arg Ala Tyr Ser Leu Asp Lys Ser His Phe His Phe
        50                  55                  60

Val His Glu Phe Val Thr Ile Leu Met Asp Ser Ala Ile Leu Phe Phe
    65                  70                  75                  80

Gly Ile Leu Pro Trp Phe Trp Lys Ile Ser Gly Gly Phe Leu Pro Met
                85                  90                  95

Val Gly Leu Asp Pro Glu Asn Glu Ile Leu His Thr Leu Ser Phe Leu
            100                 105                 110

Ala Gly Leu Met Thr Trp Ser Gln Ile Thr Asp Leu Pro Phe Ser Leu
        115                 120                 125

Tyr Ser Thr Phe Val Ile Glu Ser Arg His Gly Phe Asn Lys Gln Thr
    130                 135                 140

Ile Trp Met Phe Ile Arg Asp Met Ile Lys Gly Ile Leu Leu Ser Val
145                 150                 155                 160

Ile Pro Ala Pro Pro Ile Val Ala Ala Ile Val Ile Val Gln Lys
                165                 170                 175

Gly Gly Pro Tyr Leu Ala Ile Tyr Leu Trp Ala Phe Met Phe Ile Leu
            180                 185                 190

Ser Leu Val Met Met Thr Ile Tyr Pro Val Leu Ile Ala Pro Leu Phe
        195                 200                 205

Asn Lys Phe Thr Pro Leu Pro Asp Gly Asp Leu Arg Glu Lys Ile Glu
    210                 215                 220

Lys Leu Ala Ser Ser Leu Lys Phe Pro Leu Lys Lys Leu Phe Val Val
225                 230                 235                 240

Asp Gly Ser Thr Arg Ser Ser His Ser Asn Ala Tyr Met Tyr Gly Phe
                245                 250                 255

Phe Lys Asn Lys Arg Ile Val Leu Tyr Asp Thr Leu Ile Gln Gln Cys
            260                 265                 270
```

```
Gln Asn Glu Asn Glu Ile Val Ala Val Ile Ala His Glu Leu Gly His
        275                 280                 285
Trp Lys Leu Asn His Thr Thr Tyr Ser Phe Ile Ala Val Gln Ile Leu
    290                 295                 300
Ala Phe Leu Gln Phe Gly Gly Tyr Thr Leu Val Arg Asn Ser Thr Asp
305                 310                 315                 320
Leu Phe Arg Ser Phe Gly Phe Asp Thr Gln Pro Val Leu Ile Gly Leu
            325                 330                 335
Ile Ile Phe Gln His Thr Val Ile Pro Leu Gln His Leu Val Ser Phe
            340                 345                 350
Asp Leu Asn Leu Val Ser Arg Ala Phe Glu Phe Gln Ala Asp Ala Phe
            355                 360                 365
Ala Val Asn Leu Gly Tyr Ala Lys Asp Leu Arg Pro Ala Leu Val Lys
        370                 375                 380
Leu Gln Glu Glu Asn Leu Ser Ala Met Asn Thr Asp Pro Leu Tyr Ser
385                 390                 395                 400
Ala Tyr His Tyr Ser His Pro Pro Leu Val Glu Arg Leu Arg Ala Ile
            405                 410                 415
Asp Gly Glu Asp Lys Lys Thr Asp
            420

<210> SEQ ID NO 13
<211> LENGTH: 1275
<212> TYPE: DNA
<213> ORGANISM: Artificial Sequence
<220> FEATURE:
<223> OTHER INFORMATION: Description of Artificial Sequence:
      complementary sequence to Seq id no: 11

<400> SEQUENCE: 13
ttaatctgtc ttcttgtctt ctccatcaat ggctcgaagc ctctctacaa gaggagggtg      60
tgagtagtga taagctgagt acaatgggtc tgtgttcatc gctgataagt tctcttcctg     120
tagcttcact agggcaggac gtagatcctt tgcataacca agattcactg caaaagcatc     180
agcctgaaac tcaaacgctc gactaacaag gttgaggtca agcttactag gtgttgaag     240
tggtattaca gtgtgctgaa atatgatcaa accaatgaga actggttgtg tatcaaaacc     300
aaaactcctg aagagatcag tggagtttct gacaagagtg tatcctccaa attgcaagaa     360
ggcaaggatt tgaacagcaa tgaacgagta tgtagtgtga ttcagcttcc agtgtcccag     420
ctcgtgtgca ataccgcca caatttcatt ctcattctgg cactgctgaa tcaatgtgtc     480
ataaagaaca atccttttgt tcttgaagaa accatacatg taagcattac tatggcttga     540
ccttgtagat ccatcgacaa caaacagctt cttcagagga aactttagag aagaagcaag     600
tttctcaatc ttctcccgga ggtctccatc aggaagagga gtgaacttgt tgaaaagagg     660
tgcaatcaaa acagggtata tagtcatcat cactagagac aggataaaca tgaatgccca     720
cagatagatg gcgaggtaag gacctccttt ctgaactata acaataattg cggcaacgat     780
aggagggca ggtatgacag agaggagtat tcctttgatc atgtccctaa tgaacatcca     840
tattgtttgt ttgttgaacc catgccgaga ctcgatcacg aaagttgagt acaaagaaaa     900
tggcaaatca gtgatctgtg accatgtcat aagaccagcc aagaatgaaa gagtgtgcag     960
gatttcattc tctggatcga gtcccaccat ggtagaaag ccgccagata tcttccaaaa    1020
ccaaggcaag atcccaaaga acagaatcgc agagtcccata agtatagtaa caaactcatg    1080
aacaaagtga aatggctttt tgtcaagact gtaagctcga gatttctcaa acttctcttg    1140
```

```
gctaatgact ccaaccaaag tctttgggag agtgggaagc ttgagagcag tatgttgcct      1200
cagatccaaa tacgtctcaa aaacgtacat cactatcata aaaccaacga cggttttccat     1260 gaaaggaatc gccat                                                        1275
```

<210> SEQ ID NO 14
<211> LENGTH: 1434
<212> TYPE: DNA
<213> ORGANISM: Glycine max

<400> SEQUENCE: 14

```
ctaatacgac tcactatagg gcaagcagtg gtaacaacgc agagtacgcg gggggagacg        60
catggttctg aactaattgt tataaataat acctaaaatt ttgagttgtc ctaaacattg       120
gggtttaaac aaatccaatc tctcaatata aaacccaatg atctcaccct cactccgttt      180
ctgatttctc actcttcgtt tctcgttcgg ttcatcagcg tgtgtctcag ccatggcgtt      240
tccctacatg gaagccgttg tcggatttat gatattaatg tacatttttg aaacttactt      300
ggatgtgcga caacataggg ccctcaaact tcctactctt ccaaagactt tagaaggtgt      360
tatcagccaa gagaaatttg agaaatctag agcctatagt cttgataaaa gccacttcca      420
ttttgttcac gagtttgtga caatagtgac agactctaca attttgtact ttgggggtatt     480 gccctggttt tggaagaaat caggagattt tatgacaata gctggtttca atgctgagaa      540
tgaaatactg catacccttg ccttcttagc agggctgatg atttggtcac agataacaga      600
tttgcccttt tctctgtact caacttttgt gattgaggcc cgtcatggtt ttaataagca      660
aacaccatgg ttattctttta gggacatgct taaaggaatt ttccttttccg taataattgg    720 tccacctatt gtggctgcaa tcattgtaat agtacagaaa ggaggtccat acttggccat      780
ctatctttgg gttttttacgt ttggtctttc tattgtgatg atgacccttt atccagtact     840
aatagctcca ctcttcaata agttcactcc acttccagat ggtcaactca gggagaaaat      900
cgagaaactt gcttcctccc tcaactatcc gttaaagaaa ctatttgttg tcgatggatc      960
cacaagatca agtcacagca atgcctatat gtatggattc ttcaagaaca agaggattgt     1020
cctttatgac acattaattc aacagtgcaa agacgatgag gaaattgttg ctgttattgc     1080
ccatgagttg ggacactgga agctcaacca tactgtgtac acatttgttg ctatgcagat     1140
tcttacactt ctacaatttg gaggatatac actagtgcga aattcagctg atctgtatcg     1200
aagctttggg tttgatacgc agccagtcct cattgggctc atcatatttc agcatactgt     1260
aatcccactt cagcaattgg tcagcttttgg tctgaaccta gtcagccgat catttgaatt     1320
tcaggctgat ggctttgcca agaagcttgg atatgcatct ggattacgcg gtggtcttgt     1380
gaaactacag gaggagaatc tgtcagctat gaatacagat ccttgctcgt gccg           1434
```

<210> SEQ ID NO 15
<211> LENGTH: 400
<212> TYPE: PRT
<213> ORGANISM: Glycine max

<400> SEQUENCE: 15

```
Met Ala Phe Pro Tyr Met Glu Ala Val Val Gly Phe Met Ile Leu Met
1               5                   10                  15

Tyr Ile Phe Glu Thr Tyr Leu Asp Val Arg Gln His Arg Ala Leu Lys
            20                  25                  30

Leu Pro Thr Leu Pro Lys Thr Leu Glu Gly Val Ile Ser Gln Glu Lys
        35                  40                  45

Phe Glu Lys Ser Arg Ala Tyr Ser Leu Asp Lys Ser His Phe His Phe
```

|  |  |  |  | 50 |  |  |  |  | 55 |  |  |  |  | 60 |  |

Val His Glu Phe Val Thr Ile Val Thr Asp Ser Thr Ile Leu Tyr Phe
 65                  70                  75                  80

Gly Val Leu Pro Trp Phe Trp Lys Lys Ser Gly Asp Phe Met Thr Ile
                 85                  90                  95

Ala Gly Phe Asn Ala Glu Asn Glu Ile Leu His Thr Leu Ala Phe Leu
            100                 105                 110

Ala Gly Leu Met Ile Trp Ser Gln Ile Thr Asp Leu Pro Phe Ser Leu
        115                 120                 125

Tyr Ser Thr Phe Val Ile Glu Ala Arg His Gly Phe Asn Lys Gln Thr
    130                 135                 140

Pro Trp Leu Phe Phe Arg Asp Met Leu Lys Gly Ile Phe Leu Ser Val
145                 150                 155                 160

Ile Ile Gly Pro Pro Ile Val Ala Ala Ile Ile Val Ile Val Gln Lys
                165                 170                 175

Gly Gly Pro Tyr Leu Ala Ile Tyr Leu Trp Val Phe Thr Phe Gly Leu
            180                 185                 190

Ser Ile Val Met Met Thr Leu Tyr Pro Val Leu Ile Ala Pro Leu Phe
        195                 200                 205

Asn Lys Phe Thr Pro Leu Pro Asp Gly Gln Leu Arg Glu Lys Ile Glu
    210                 215                 220

Lys Leu Ala Ser Ser Leu Asn Tyr Pro Leu Lys Leu Phe Val Val
225                 230                 235                 240

Asp Gly Ser Thr Arg Ser Ser His Ser Asn Ala Tyr Met Tyr Gly Phe
                245                 250                 255

Phe Lys Asn Lys Arg Ile Val Leu Tyr Asp Thr Leu Ile Gln Gln Cys
            260                 265                 270

Lys Asp Asp Glu Glu Ile Val Ala Val Ile Ala His Glu Leu Gly His
        275                 280                 285

Trp Lys Leu Asn His Thr Val Tyr Thr Phe Val Ala Met Gln Ile Leu
    290                 295                 300

Thr Leu Leu Gln Phe Gly Gly Tyr Thr Leu Val Arg Asn Ser Ala Asp
305                 310                 315                 320

Leu Tyr Arg Ser Phe Gly Phe Asp Thr Gln Pro Val Leu Ile Gly Leu
                325                 330                 335

Ile Ile Phe Gln His Thr Val Ile Pro Leu Gln Gln Leu Val Ser Phe
            340                 345                 350

Gly Leu Asn Leu Val Ser Arg Ser Phe Glu Phe Gln Ala Asp Gly Phe
        355                 360                 365

Ala Lys Lys Leu Gly Tyr Ala Ser Gly Leu Arg Gly Gly Leu Val Lys
    370                 375                 380

Leu Gln Glu Glu Asn Leu Ser Ala Met Asn Thr Asp Pro Cys Ser Cys
385                 390                 395                 400

<210> SEQ ID NO 16
<211> LENGTH: 1405
<212> TYPE: DNA
<213> ORGANISM: Glycine max

<400> SEQUENCE: 16
gcgagctctc gttcggttca tcagcgtgtg tctcagccat ggcgtttccc tacatggaag      60
ccgttgtcgg atttatgata ttaatgtaca tttttgaaac ttacttggat gtgcgacaac     120
atagggccct caaacttcct actcttccaa agactttaga aggtgttatc agccaagaga     180
aatttgagaa atctagagcc tatagtcttg ataaaagcca cttccatttt gttcacgagt     240

```
ttgtgacaat agtgacagac tctacaattt tgtactttgg ggtattgccc tggttttgga      300
agaaatcagg agattttatg acaatagctg gtttcaatgc tgagaatgaa atactgcata      360
cccttgcctt cttagcaggg ctgatgattt ggtcacagat aacagatttg ccctttttctc     420 tgtactcaac ttttgtgatt gaggcccgtc atggttttaa taagcaaaca ccatggttat      480
tctttaggga catgcttaaa ggaattttcc tttctgtaat aattggtcca cctattgtgg      540
ctgcaatcat tgtaatagta cagaaaggag gtccatactt ggccatctat ctttgggttt      600
ttacgtttgg tctttctatt gtgatgatga ccctttatcc agtactaata gctccactct      660
tcaataagtt cactccactt ccagatggtc aactcaggga gaaaatcgag aaacttgctt      720
cctccctcaa ctatccgtta agaaactat ttgttgtcga tggatccaca agatcaagtc       780
acagcaatgc ctatatgtat ggattcttca agaacaagag gattgtcctt tatgacacat      840
taattcaaca gtgcaaagac gatgaggaaa ttgttgctgt tattgcccat gagttgggac      900
actggaagct caaccatact gtgtacacat tgttgctat gcagattctt acacttctac        960
aatttggagg atatacacta gtgcgaaatt cagctgatct gtatcgaagc tttgggtttg      1020
atacgcagcc agtcctcatt gggctcatca tatttcagca tactgtaatc ccacttcagc      1080
aattggtcag ctttggtctg aacctagtca gccgatcatt tgaatttcag gctgatggct      1140
ttgccaagaa gcttggatat gcatctggat tacgcggtgg tcttgtgaaa ctacaggagg      1200
agaatctgtc agctatgaat acagatcctt ggtactctgc ttatcactat tctcatcctc      1260
cccttgttga aagattggct gtgctggacg aaccggataa gaaggaagac taagcaagta      1320
acttaaagat gaagagctgc aaaaattggc tatacccctaa cttgctatga tttagtgctg    1380
caatagctgt aatatctccc gggat                                            1405

<210> SEQ ID NO 17
<211> LENGTH: 424
<212> TYPE: PRT
<213> ORGANISM: Glycine max

<400> SEQUENCE: 17

Met Ala Phe Pro Tyr Met Glu Ala Val Val Gly Phe Met Ile Leu Met
 1               5                  10                  15

Tyr Ile Phe Glu Thr Tyr Leu Asp Val Arg Gln His Arg Ala Leu Lys
            20                  25                  30

Leu Pro Thr Leu Pro Lys Thr Leu Glu Gly Val Ile Ser Gln Glu Lys
        35                  40                  45

Phe Glu Lys Ser Arg Ala Tyr Ser Leu Asp Lys Ser His Phe His Phe
    50                  55                  60

Val His Glu Phe Val Thr Ile Val Thr Asp Ser Thr Ile Leu Tyr Phe
65                  70                  75                  80

Gly Val Leu Pro Trp Phe Trp Lys Lys Ser Gly Asp Phe Met Thr Ile
                85                  90                  95

Ala Gly Phe Asn Ala Glu Asn Glu Ile Leu His Thr Leu Ala Phe Leu
            100                 105                 110

Ala Gly Leu Met Ile Trp Ser Gln Ile Thr Asp Leu Pro Phe Ser Leu
        115                 120                 125

Tyr Ser Thr Phe Val Ile Glu Ala Arg His Gly Phe Asn Lys Gln Thr
    130                 135                 140

Pro Trp Leu Phe Phe Arg Asp Met Leu Lys Gly Ile Phe Leu Ser Val
145                 150                 155                 160

Ile Ile Gly Pro Pro Ile Val Ala Ala Ile Ile Val Ile Val Gln Lys
```

```
                    165                 170                 175
Gly Gly Pro Tyr Leu Ala Ile Tyr Leu Trp Val Phe Thr Phe Gly Leu
            180                 185                 190

Ser Ile Val Met Met Thr Leu Tyr Pro Val Leu Ile Ala Pro Leu Phe
            195                 200                 205

Asn Lys Phe Thr Pro Leu Pro Asp Gly Gln Leu Arg Glu Lys Ile Glu
            210                 215                 220

Lys Leu Ala Ser Ser Leu Asn Tyr Pro Leu Lys Lys Leu Phe Val Val
225                 230                 235                 240

Asp Gly Ser Thr Arg Ser Ser His Ser Asn Ala Tyr Met Tyr Gly Phe
            245                 250                 255

Phe Lys Asn Lys Arg Ile Val Leu Tyr Asp Thr Leu Ile Gln Gln Cys
            260                 265                 270

Lys Asp Asp Glu Glu Ile Val Ala Val Ile Ala His Glu Leu Gly His
            275                 280                 285

Trp Lys Leu Asn His Thr Val Tyr Thr Phe Val Ala Met Gln Ile Leu
            290                 295                 300

Thr Leu Leu Gln Phe Gly Gly Tyr Thr Leu Val Arg Asn Ser Ala Asp
305                 310                 315                 320

Leu Tyr Arg Ser Phe Gly Phe Asp Thr Gln Pro Val Leu Ile Gly Leu
            325                 330                 335

Ile Ile Phe Gln His Thr Val Ile Pro Leu Gln Gln Leu Val Ser Phe
            340                 345                 350

Gly Leu Asn Leu Val Ser Arg Ser Phe Glu Phe Gln Ala Asp Gly Phe
            355                 360                 365

Ala Lys Lys Leu Gly Tyr Ala Ser Gly Leu Arg Gly Gly Leu Val Lys
            370                 375                 380

Leu Gln Glu Glu Asn Leu Ser Ala Met Asn Thr Asp Pro Trp Tyr Ser
385                 390                 395                 400

Ala Tyr His Tyr Ser His Pro Pro Leu Val Arg Leu Ala Val Leu
            405                 410                 415

Asp Glu Pro Asp Lys Lys Glu Asp
            420

<210> SEQ ID NO 18
<211> LENGTH: 1275
<212> TYPE: DNA
<213> ORGANISM: Glycine max

<400> SEQUENCE: 18
atggcgtttc cctacatgga agccgttgtc ggatttatga tattaatgta cattttgaa    60 acttacttgg atgtgcgaca acatagggcc ctcaaacttc ctactcttcc aaagacttta   120
gagggtgtta tcagccaaga gaaatttgag aaatctagag cctatagtct tgataaaagc   180
cacttccatt tgttcacga gtttgtgaca atagtgacag actctacaat tttgtacttt   240
ggggtattgc cctggttttg aagaaatca ggagatttta tgacaatagc tggtttcaat    300
gctgagaatg aaatactgca taccettgcc ttcttagcag gctgatgat ttggtcacag    360 ataacagatt tgccctttc tctgtactca acttttgtga ttgaggcccg tcatggtttt   420
aataagcaaa caccatggtt attcttagg gacatgctta aaggaatttt cctttctgta    480
ataattggtc caccattgt ggctgcaatc attgtaatag tacagaaagg aggtccatac   540
ttggccatct atctttgggt ttttacgttt ggtctttcta ttgtgatgat gacccttat   600 ccagtactaa tagctccact cttcaataag ttcactccac ttccagatgg tcaactcagg   660
```

```
gagaaaatcg agaaacttgc ttcctccctc aactatccgt taaagaaact atttgttgtc    720
gatggatcca caagatcaag tcacagcaat gcctatatgt atggattctt caagaacaag    780
aggattgtcc cttatgacac attaattcaa cagtgcaaag acgatgagga aattgttgct    840
gttattgccc atgagttggg acactggaag ctcaaccata ctgtgtacac atttgttgct    900
atgcagattc ttacacttct acaatttgga ggatatacac tagtgcgaaa ttcagctgat    960
ctgtatcgaa gctttgggtt tgatacgcag ccagtcctca ttgggctcat catatttcag   1020
catactgtaa tcccacttca gcaattggtc agctttggtc tgaacctagt cagccgatca   1080
tttgaatttc aggctgatgg ctttgccaag aagcttggat atgcatctgg attacgcggt   1140
ggtcttgtga aactacagga ggagaatctg tcagctatga atacagatcc ttggtactct   1200
gcttatcact attctcatcc tccccttgtt gaaagattgg ccgcgctgga cgaaccggat   1260
aagaaggaag actaa                                                    1275
```

```
<210> SEQ ID NO 19
<211> LENGTH: 424
<212> TYPE: PRT
<213> ORGANISM: Glycine max

<400> SEQUENCE: 19
```

Met Ala Phe Pro Tyr Met Glu Ala Val Val Gly Phe Met Ile Leu Met
1               5                   10                  15

Tyr Ile Phe Glu Thr Tyr Leu Asp Val Arg Gln His Arg Ala Leu Lys
            20                  25                  30

Leu Pro Thr Leu Pro Lys Thr Leu Glu Gly Val Ile Ser Gln Glu Lys
        35                  40                  45

Phe Glu Lys Ser Arg Ala Tyr Ser Leu Asp Lys Ser His Phe His Phe
    50                  55                  60

Val His Glu Phe Val Thr Ile Val Thr Asp Ser Thr Ile Leu Tyr Phe
65                  70                  75                  80

Gly Val Leu Pro Trp Phe Trp Lys Lys Ser Gly Asp Phe Met Thr Ile
                85                  90                  95

Ala Gly Phe Asn Ala Glu Asn Glu Ile Leu His Thr Leu Ala Phe Leu
            100                 105                 110

Ala Gly Leu Met Ile Trp Ser Gln Ile Thr Asp Leu Pro Phe Ser Leu
        115                 120                 125

Tyr Ser Thr Phe Val Ile Glu Ala Arg His Gly Phe Asn Lys Gln Thr
    130                 135                 140

Pro Trp Leu Phe Phe Arg Asp Met Leu Lys Gly Ile Phe Leu Ser Val
145                 150                 155                 160

Ile Ile Gly Pro Pro Ile Val Ala Ala Ile Val Ile Val Gln Lys
                165                 170                 175

Gly Gly Pro Tyr Leu Ala Ile Tyr Leu Trp Val Phe Thr Phe Gly Leu
            180                 185                 190

Ser Ile Val Met Met Thr Leu Tyr Pro Val Leu Ile Ala Pro Leu Phe
        195                 200                 205

Asn Lys Phe Thr Pro Leu Pro Asp Gly Gln Leu Arg Glu Lys Ile Glu
    210                 215                 220

Lys Leu Ala Ser Ser Leu Asn Tyr Pro Leu Lys Lys Leu Phe Val Val
225                 230                 235                 240

Asp Gly Ser Thr Arg Ser Ser His Ser Asn Ala Tyr Met Tyr Gly Phe
                245                 250                 255

Phe Lys Asn Lys Arg Ile Val Pro Tyr Asp Thr Leu Ile Gln Gln Cys
            260                 265                 270

| | | | | | | | | | | | |
|---|---|---|---|---|---|---|---|---|---|---|---|
|Lys|Asp|Asp|Glu|Glu|Ile|Val|Ala|Val|Ile|Ala|His|Glu|Leu|Gly|His|
| |275| | | | |280| | | | |285| | | | |

Trp Lys Leu Asn His Thr Val Tyr Thr Phe Val Ala Met Gln Ile Leu
    290             295             300

Thr Leu Leu Gln Phe Gly Gly Tyr Thr Leu Arg Asn Ser Ala Asp
305             310             315                 320

Leu Tyr Arg Ser Phe Gly Phe Asp Thr Gln Pro Val Leu Ile Gly Leu
            325             330             335

Ile Ile Phe Gln His Thr Val Ile Pro Leu Gln Gln Leu Val Ser Phe
            340             345             350

Gly Leu Asn Leu Val Ser Arg Ser Phe Glu Phe Gln Ala Asp Gly Phe
            355             360             365

Ala Lys Lys Leu Gly Tyr Ala Ser Gly Leu Arg Gly Gly Leu Val Lys
            370             375             380

Leu Gln Glu Glu Asn Leu Ser Ala Met Asn Thr Asp Pro Trp Tyr Ser
385             390             395                 400

Ala Tyr His Tyr Ser His Pro Pro Leu Val Glu Arg Leu Ala Ala Leu
            405             410             415

Asp Glu Pro Asp Lys Lys Glu Asp
            420

```
<210> SEQ ID NO 20
<211> LENGTH: 1275
<212> TYPE: DNA
<213> ORGANISM: Artificial Sequence
<220> FEATURE:
<223> OTHER INFORMATION: Description of Artificial Sequence: complement
      to seq id no: 18

<400> SEQUENCE: 20
ttagtcttcc ttcttatccg gttcgtccag cgcggccaat ctttcaacaa ggggaggatg     60
agaatagtga taagcagagt accaaggatc tgtattcata gctgacagat tctcctcctg    120
tagtttcaca agaccaccgc gtaatccaga tgcatatcca agcttcttgg caaagccatc    180
agcctgaaat tcaaatgatc ggctgactag gttcagacca aagctgacca attgctgaag    240
tgggattaca gtatgctgaa atatgatgag cccaatgagg actggctgcg tatcaaaccc    300
aaagcttcga tacagatcag ctgaatttcg cactagtgta tatcctccaa attgtagaag    360
tgtaagaatc tgcatagcaa caaatgtgta cacagtatgg ttgagcttcc agtgtcccaa    420
ctcatgggca ataacagcaa caatttcctc atcgtctttg cactgttgaa ttaatgtgtc    480
ataagggaca atcctcttgt tcttgaagaa tccatacata taggcattgc tgtgacttga    540
tcttgtggat ccatcgacaa caaatagttt ctttaacgga tagttgaggg aggaagcaag    600
tttctcgatt ttctccctga gttgaccatc tggaagtgga gtgaacttat tgaagagtgg    660
agctattagt actggataaa gggtcatcat cacaatagaa agaccaaacg taaaaaccca    720
aagatagatg gccaagtatg gacctccttt ctgtactatt acaatgattg cagccacaat    780
aggtggacca attattacag aaaggaaaat tcctttaagc atgtccctaa agaataacca    840
tggtgtttgc ttattaaaac catgacgggc ctcaatcaca aaagttgagt acagagaaaa    900
gggcaaatct gttatctgtg accaaatcat cagccctgct aagaaggcaa gggtatgcag    960
tatttcattc tcagcattga aaccagctat tgtcataaaa tctcctgatt tcttccaaaa   1020
ccagggcaat accccaaagt acaaaattgt agagtctgtc actattgtca caactcgtg    1080 aacaaaatgg aagtggcttt tatcaagact ataggctcta gatttctcaa atttctcttg   1140
```

```
gctgataaca ccctctaaag tctttggaag agtaggaagt ttgagggccc tatgttgtcg   1200
cacatccaag taagtttcaa aaatgtacat taatatcata aatccgacaa cggcttccat   1260
gtagggaaac gccat                                                    1275
```

<210> SEQ ID NO 21
<211> LENGTH: 1301
<212> TYPE: DNA
<213> ORGANISM: Zea mays

<400> SEQUENCE: 21

```
acgaggctga gtgctgagaa tgagataata cacacccttg ctttcttagc tggttccatg     60
gtttggtcgc agattacaga cttgccgttc tctctctatt caacttttgt tatagaggct    120
cgacatggtt ttaacaagca aactatatgg ctcttcatta gggatatgat caaaggaatt    180
ttactatcca tgatattggg gccaccaatc gtggctgcta tcatctacat agtacagatt    240
ggaggacctt acctggctat atatctctgg ggttttatgt ttgtattagc tctactgatg    300
atgacaatat accccattgt gatagctcct ctgttcaaca agttcactcc tcttcctgaa    360
ggagtcctca gggaaaaaat agagaagctg gcagcttccc tcaagtttcc tttgaaaaag    420
cttttcgtgg tagatgggtc taccagatca agccacagta atgcctacat gtatggtttt    480
ttcaagaaca gcgcatagt actctatgac acattgattc agcagtgtag caatgaggat    540
gagatagttt ctgttatagc acatgaactt ggacactgga aactcaatca tactgtctat    600
tcctttgtag ctgtccagct gcttatgttt cttcaatttg gaggatatac tctagtaagg    660
agctccaaag atctatttgg aagttttggc ttcaaggacc agccagtaat aattggattg    720
atcattttcc cgcacaccat aatacccatc caacaccttc tgagctttcg cctgaacctt    780
gtcagcagag catttgaatt tcaggctgat gcctttgcca agaaccttgg atatgcccct    840
cagctccgag cagcccttgt taaactacag gaggagaact tgtctgcgat gaacaccgat    900
ccttggtatt cggcatatca ctactcccac ccaccactcg tcgagaggct gcaagctttg    960
gaagattcag acgacaaaaa agaagattag tcgatccttg tatgaggttt acatatggat   1020
ttttccctgc cacatgcaca ccgattcagt gcttggatgg tgagggtttt gacataggag   1080
tgttgtcaaa gctttagagt gcatctttcg gtcaggtgca acagcctttc ggtcattgag   1140
acatataagc gaattagcta ttaaaaaaaa cagaactgtt gcatcaaaaa aaaaaaaaa    1200 aaagaaacaa aaaaaaaaa aaaaaaaaa aagaaaaaa aaaaaaaaa aaaagtgctc       1260 tgcgttgtta ccactgcttg ccctatagtg atcgtatcag a                       1301
```

<210> SEQ ID NO 22
<211> LENGTH: 329
<212> TYPE: PRT
<213> ORGANISM: Zea mays

<400> SEQUENCE: 22

```
Thr Arg Leu Ser Ala Glu Asn Glu Ile Ile His Thr Leu Ala Phe Leu
  1               5                  10                  15

Ala Gly Ser Met Val Trp Ser Gln Ile Thr Asp Leu Pro Phe Ser Leu
             20                  25                  30

Tyr Ser Thr Phe Val Ile Glu Ala Arg His Gly Phe Asn Lys Gln Thr
         35                  40                  45

Ile Trp Leu Phe Ile Arg Asp Met Ile Lys Gly Ile Leu Leu Ser Met
     50                  55                  60

Ile Leu Gly Pro Pro Ile Val Ala Ala Ile Ile Tyr Ile Val Gln Ile
 65                  70                  75                  80
```

Gly Gly Pro Tyr Leu Ala Ile Tyr Leu Trp Gly Phe Met Phe Val Leu
            85                  90                  95

Ala Leu Leu Met Met Thr Ile Tyr Pro Ile Val Ile Ala Pro Leu Phe
        100                 105                 110

Asn Lys Phe Thr Pro Leu Pro Glu Gly Val Leu Arg Glu Lys Ile Glu
        115                 120                 125

Lys Leu Ala Ala Ser Leu Lys Phe Pro Leu Lys Lys Leu Phe Val Val
130                 135                 140

Asp Gly Ser Thr Arg Ser Ser His Ser Asn Ala Tyr Met Tyr Gly Phe
145                 150                 155                 160

Phe Lys Asn Lys Arg Ile Val Leu Tyr Asp Thr Leu Ile Gln Gln Cys
                165                 170                 175

Ser Asn Glu Asp Glu Ile Val Ser Val Ile Ala His Glu Leu Gly His
            180                 185                 190

Trp Lys Leu Asn His Thr Val Tyr Ser Phe Val Ala Val Gln Leu Leu
        195                 200                 205

Met Phe Leu Gln Phe Gly Gly Tyr Thr Leu Val Arg Ser Ser Lys Asp
    210                 215                 220

Leu Phe Gly Ser Phe Gly Phe Lys Asp Gln Pro Val Ile Ile Gly Leu
225                 230                 235                 240

Ile Ile Phe Pro His Thr Ile Pro Ile Gln His Leu Leu Ser Phe
                245                 250                 255

Arg Leu Asn Leu Val Ser Arg Ala Phe Glu Phe Gln Ala Asp Ala Phe
            260                 265                 270

Ala Lys Asn Leu Gly Tyr Ala Pro Gln Leu Arg Ala Ala Leu Val Lys
        275                 280                 285

Leu Gln Glu Glu Asn Leu Ser Ala Met Asn Thr Asp Pro Trp Tyr Ser
    290                 295                 300

Ala Tyr His Tyr Ser His Pro Pro Leu Val Glu Arg Leu Gln Ala Leu
305                 310                 315                 320

Glu Asp Ser Asp Asp Lys Lys Glu Asp
                325

<210> SEQ ID NO 23
<211> LENGTH: 1518
<212> TYPE: DNA
<213> ORGANISM: Zea mays

<400> SEQUENCE: 23
aaatccgagc tccggaatcg agcaaagcac ccgagcctgc gccgcgtcaa gccgtcaaag      60
ctcccccgct tcataccatt ccctcccccg atccctcgcc tcagccctca gctccgcccc     120
tcggtttccg aagcgccacc gccgacgtgg cctccctcgg ctccaatggc gttgccctac     180
ctggaggccg tgctttgctt tatgattttc atgtacatat ttgagacata tcttgacatc     240
cgtcagcata gagccctcaa gctgccaact ttgccaaaac ccctgctggg agtaattagt     300
gacgaaaagt ttgaacgctc tagagcttat agcctcgaca aaagctattt ccattttgtt     360
catgaggctg tgactatttt aatggatact acaatactat actatagagt tcttccctgg     420
ttttggaaga atctggagag ttagttacc agtgttgggc tgagtgctga gaatgagata      480
atacacaccc ttgctttctt agctggttcc atggtttggt cgcagattac agacttgccg     540
ttctctctct attcaacttt tgttatagag gctcgacatg gttttaacaa gcaaactata     600
tggctcttca ttagggatat gatcaaagga attttactat ccatgatatt ggggccacca     660
atcgtggctg ctatcatcta catagtacag attggaggac cttacctggc tatatatctc     720

```
tggggtttta tgtttgtatt agctctactg atgatgacaa tatacccat tgtgatagct    780 cctctgttca acaagttcac tcctcttcct gaaggagtcc tcaggaaaa aatagagaag    840 ctggcagctt ccctcaagtt tcctttgaaa aagcttttcg tggtagatgg gtctaccaga   900
tcaagccaca gtaatgccta catgtatggt tttttcaaga acaagcgcat agtactctat   960
gacacattga ttcagcagtg tagcaatgag gatgagatag tttctgttat agcacatgaa   1020
cttggacact ggaaactcaa tcatactgtc tattcctttg tagctgtcca gctgcttatg   1080
tttcttcaat ttggaggata tactctagta aggagctcca agatctatt tggaagtttt    1140 ggcttcaagg accagccagt aataattgga ttgatcattt tccagcacac cataataccc   1200
atccaacacc ttctgagctt ttgcctgaac cttgtcagca gagcatttga atttcaggct   1260
gatgcctttg ccaagaacct tggatatgcc cctcagctcc gagcagccct tgttaaacta   1320
caggaggaga acttgtctgc gatgaacacc gatccttggt attcggcata tcactactcc   1380
cacccaccac tcgtcgagag gctgcaagct cttgaagatt cagacagcaa aaagaagat    1440 tagtcgatcc ttgtatgagg tttacatatg gatttttccc tgccacatgc acaccgattc   1500
agtgcttgga tggtgagg                                                 1518

<210> SEQ ID NO 24
<211> LENGTH: 425
<212> TYPE: PRT
<213> ORGANISM: Zea mays

<400> SEQUENCE: 24

Met Ala Leu Pro Tyr Leu Glu Ala Val Leu Cys Phe Met Ile Phe Met
 1               5                  10                  15

Tyr Ile Phe Glu Thr Tyr Leu Asp Ile Arg Gln His Arg Ala Leu Lys
                20                  25                  30

Leu Pro Thr Leu Pro Lys Pro Leu Leu Gly Val Ile Ser Asp Glu Lys
            35                  40                  45

Phe Glu Arg Ser Arg Ala Tyr Ser Leu Asp Lys Ser Tyr Phe His Phe
        50                  55                  60

Val His Glu Ala Val Thr Ile Leu Met Asp Thr Thr Ile Leu Tyr Tyr
 65                 70                  75                  80

Arg Val Leu Pro Trp Phe Trp Lys Lys Ser Gly Glu Leu Val Thr Ser
                85                  90                  95

Val Gly Leu Ser Ala Glu Asn Glu Ile Ile His Thr Leu Ala Phe Leu
            100                 105                 110

Ala Gly Ser Met Val Trp Ser Gln Ile Thr Asp Leu Pro Phe Ser Leu
        115                 120                 125

Tyr Ser Thr Phe Val Ile Glu Ala Arg His Gly Phe Asn Lys Gln Thr
    130                 135                 140

Ile Trp Leu Phe Ile Arg Asp Met Ile Lys Gly Ile Leu Leu Ser Met
145                 150                 155                 160

Ile Leu Gly Pro Pro Ile Val Ala Ala Ile Tyr Ile Val Gln Ile
                165                 170                 175

Gly Gly Pro Tyr Leu Ala Ile Tyr Leu Trp Gly Phe Met Phe Val Leu
            180                 185                 190

Ala Leu Leu Met Met Thr Ile Tyr Pro Ile Val Ile Ala Pro Leu Phe
        195                 200                 205

Asn Lys Phe Thr Pro Leu Pro Glu Gly Val Leu Arg Glu Lys Ile Glu
    210                 215                 220

Lys Leu Ala Ala Ser Leu Lys Phe Pro Leu Lys Lys Leu Phe Val Val
```

```
                225                 230                 235                 240
Asp Gly Ser Thr Arg Ser Ser His Ser Asn Ala Tyr Met Tyr Gly Phe
                245                 250                 255

Phe Lys Asn Lys Arg Ile Val Leu Tyr Asp Thr Leu Ile Gln Gln Cys
            260                 265                 270

Ser Asn Glu Asp Glu Ile Val Ser Val Ile Ala His Glu Leu Gly His
            275                 280                 285

Trp Lys Leu Asn His Thr Val Tyr Ser Phe Val Ala Val Gln Leu Leu
            290                 295                 300

Met Phe Leu Gln Phe Gly Gly Tyr Thr Leu Val Arg Ser Ser Lys Asp
305                 310                 315                 320

Leu Phe Gly Ser Phe Gly Phe Lys Asp Gln Pro Val Ile Ile Gly Leu
                325                 330                 335

Ile Ile Phe Gln His Thr Ile Ile Pro Ile Gln His Leu Leu Ser Phe
                340                 345                 350

Cys Leu Asn Leu Val Ser Arg Ala Phe Glu Phe Gln Ala Asp Ala Phe
            355                 360                 365

Ala Lys Asn Leu Gly Tyr Ala Pro Gln Leu Arg Ala Ala Leu Val Lys
            370                 375                 380

Leu Gln Glu Glu Asn Leu Ser Ala Met Asn Thr Asp Pro Trp Tyr Ser
385                 390                 395                 400

Ala Tyr His Tyr Ser His Pro Pro Leu Val Glu Arg Leu Gln Ala Leu
                405                 410                 415

Glu Asp Ser Asp Ser Lys Lys Glu Asp
            420                 425

<210> SEQ ID NO 25
<211> LENGTH: 1275
<212> TYPE: DNA
<213> ORGANISM: Arabidopsis thaliana

<400> SEQUENCE: 25
atggcgattc ctttcatgga aaccgtcgtg ggttttatga tagtgatgta catttttgag      60
acgtatttgg atctgaggca actcactgct ctcaagcttc caactctccc gaaaaccttg     120
gttggtgtaa ttagccaaga aagtttgag  aaatcacgag catacagtct tgacaaaagc     180
tattttcact tgttcatga gtttgtaact atacttatgg actctgcaat tttgttcttt     240
gggatcttgc cttggttttg aagatgtct ggagctgttt taccgaggtt gggccttgat      300
ccagagaatg aaatactgca tactctttca ttcttggctg tgttatgac atggtcacag      360
atcactgatt tgccattttc tttgtactca actttcgtga tcgagtctcg gcatgggttc     420
aacaaacaaa caatatggat gttcattagg gacatgatca aggaacatt  cctctctgtc     480
atactaggcc cacccattgt tgctgcgata atttcatag  tccagaaagg aggtccttat     540
cttgccatct atctgtgggc attcatgttt atcctgtctc tagtgatgat gactatatac     600
ccggtcttga tagcaccgct cttcaacaag ttcactcctc ttccagatgg agacctccgg     660
gagaagattg agaaacttgc ttcttctcta aagtttcctt tgaagaagct gtttgttgtc     720
gatggatcta caaggtcaag ccatagcaat gcttacatgt atggtttctt taagaacaaa     780
aggattgttc tttatgatac gttgattcag cagtgcaaga tgaggatga  aattgtggcg     840
gttattgcac acgagcttgg acattggaaa ctgaatcaca ctacatactc gttcattgca     900
gttcaaatcc ttgccttctt acaatttgga ggatacactc ttgtcagaaa ctccactgat     960
ctcttcagga gttcggatt  tgatacacag cctgttctca ttggtttgat catatttcag    1020
```

-continued

```
cacactgtaa taccactgca acatctagta agctttggcc tgaacctcgt tagtcgagcg   1080
tttgagtttc aggctgatgc ttttgccgtg aagcttggct atgcaaaaga tcttcgtcct   1140
gctctagtga aactacagga agagaactta tcagcaatga acactgatcc attgcactca   1200
gcttatcact actcacatcc tcctcttgtt gaaaggcttc gagccattga tggagaagac   1260
aagaagacag attaa                                                    1275
```

<210> SEQ ID NO 26
<211> LENGTH: 424
<212> TYPE: PRT
<213> ORGANISM: Arabidopsis thaliana

<400> SEQUENCE: 26

```
Met Ala Ile Pro Phe Met Glu Thr Val Val Gly Phe Met Ile Val Met
1               5                   10                  15

Tyr Ile Phe Glu Thr Tyr Leu Asp Leu Arg Gln Leu Thr Ala Leu Lys
                20                  25                  30

Leu Pro Thr Leu Pro Lys Thr Leu Val Gly Val Ile Ser Gln Glu Lys
            35                  40                  45

Phe Glu Lys Ser Arg Ala Tyr Ser Leu Asp Lys Ser Tyr Phe His Phe
    50                  55                  60

Val His Glu Phe Val Thr Ile Leu Met Asp Ser Ala Ile Leu Phe Phe
65                  70                  75                  80

Gly Ile Leu Pro Trp Phe Trp Lys Met Ser Gly Ala Val Leu Pro Arg
                85                  90                  95

Leu Gly Leu Asp Pro Glu Asn Glu Ile Leu His Thr Leu Ser Phe Leu
            100                 105                 110

Ala Gly Val Met Thr Trp Ser Gln Ile Thr Asp Leu Pro Phe Ser Leu
        115                 120                 125

Tyr Ser Thr Phe Val Ile Glu Ser Arg His Gly Phe Asn Lys Gln Thr
    130                 135                 140

Ile Trp Met Phe Ile Arg Asp Met Ile Lys Gly Thr Phe Leu Ser Val
145                 150                 155                 160

Ile Leu Gly Pro Pro Ile Val Ala Ala Ile Ile Phe Ile Val Gln Lys
                165                 170                 175

Gly Gly Pro Tyr Leu Ala Ile Tyr Leu Trp Ala Phe Met Phe Ile Leu
            180                 185                 190

Ser Leu Val Met Met Thr Ile Tyr Pro Val Leu Ile Ala Pro Leu Phe
        195                 200                 205

Asn Lys Phe Thr Pro Leu Pro Asp Gly Asp Leu Arg Glu Lys Ile Glu
    210                 215                 220

Lys Leu Ala Ser Ser Leu Lys Phe Pro Leu Lys Lys Leu Phe Val Val
225                 230                 235                 240

Asp Gly Ser Thr Arg Ser Ser His Ser Asn Ala Tyr Met Tyr Gly Phe
                245                 250                 255

Phe Lys Asn Lys Arg Ile Val Leu Tyr Asp Thr Leu Ile Gln Gln Cys
            260                 265                 270

Lys Asn Glu Asp Glu Ile Val Ala Val Ile Ala His Glu Leu Gly His
        275                 280                 285

Trp Lys Leu Asn His Thr Thr Tyr Ser Phe Ile Ala Val Gln Ile Leu
    290                 295                 300

Ala Phe Leu Gln Phe Gly Gly Tyr Thr Leu Val Arg Asn Ser Thr Asp
305                 310                 315                 320

Leu Phe Arg Ser Phe Gly Phe Asp Thr Gln Pro Val Leu Ile Gly Leu
                325                 330                 335
```

Ile Ile Phe Gln His Thr Val Ile Pro Leu Gln His Leu Val Ser Phe
            340                 345                 350

Gly Leu Asn Leu Val Ser Arg Ala Phe Glu Phe Gln Ala Asp Ala Phe
            355                 360                 365

Ala Val Lys Leu Gly Tyr Ala Lys Asp Leu Arg Pro Ala Leu Val Lys
            370                 375                 380

Leu Gln Glu Glu Asn Leu Ser Ala Met Asn Thr Asp Pro Leu His Ser
385                 390                 395                 400

Ala Tyr His Tyr Ser His Pro Pro Leu Val Glu Arg Leu Arg Ala Ile
                405                 410                 415

Asp Gly Glu Asp Lys Lys Thr Asp
            420

<210> SEQ ID NO 27
<211> LENGTH: 1380
<212> TYPE: DNA
<213> ORGANISM: Arabidopsis thaliana

<400> SEQUENCE: 27
atggcgattc ctttcatgga aaccgtcgtg ggttttatga tagtgatgta cattttgag      60
acgtatttgg atctgaggca actcactgct ctcaagcttc aactctccc gaaaaccttg     120
gttggtgtaa ttagccaaga aagtttgag aaatcacgag catacaggga tatcatcact     180
gagaacttta atatatgcag ctattttcac tttgttcatg agtttgtaac tatacttatg     240
gactctgcaa ttttgttctt tgggatcttg ccttggtttt ggaagatgtc tggagctgtt     300
ttaccgaggt tgggccttga tccagagaat gaaatactgc atactctttc attcttggct     360
ggtgttatga catggtcaca gatcactgat ttgccatttt ctttgtactc aactttcgtg     420
atcgagtctc ggcatgggtt caacaaacaa acaatatgga tgttcattag ggacatgatc     480
aaaggaacat tcctctctgt catactaggc ccacccattt tgctgcgat aattttcata      540
gtccagaaag gaggtcctta tcttgccatc tatctgtggg cattcatgtt tatcctgtct     600
ctagtgatga tgactatata cccggtcttg atagcaccgc tcttcaacaa gttcactcct     660
cttccagatg gagacctccg ggagaagatt gagaaacttg cttcttctct aaagtttcct     720
ttgaagaagc tgtttgttgt cgatggatct acaaggtcaa gccatagcaa tgcttacatg     780
tatggtttct ttaagaacaa aaggattgtt ctttatgata cgttgattca gcagtgcaag     840
aatgaggatg aaattgtggc ggttattgca cacgagcttg acattggaa actgaatcac      900
actacatact cgttcattgc agttcaaatc cttgccttct tacaatttgg aggatacact     960
cttgtcagaa actccactga tctcttcagg agtttcggat tgatacaca gcctgttctc     1020
attggtttga tcatatttca gcacactgta ataccactgc aacatctagt aagctttggc     1080
ctgaacctcg ttagtcgagc gtttgagttt caggctgatg cttttgctgt gaagcttggc     1140
tatgcaaaag atcttcgtcc tgctctagtg aaactacagg tcagagaaga taacaacaga     1200
acacaaactg ttacctcaat tgtgtcaca cacttaaatg gatttttgt tgggattttg       1260
caggaagaga acttatcagc aatgaacact gatccattgt actcagctta tcactactca     1320
catcctcctc ttgttgaaag gcttcgagcc attgatggag aagacaagaa gacagattaa    1380

<210> SEQ ID NO 28
<211> LENGTH: 459
<212> TYPE: PRT
<213> ORGANISM: Arabidopsis thaliana

<400> SEQUENCE: 28

```
Met Ala Ile Pro Phe Met Glu Thr Val Gly Phe Met Ile Val Met
  1               5                  10                  15

Tyr Ile Phe Glu Thr Tyr Leu Asp Leu Arg Gln Leu Thr Ala Leu Lys
             20                  25                  30

Leu Pro Thr Leu Pro Lys Thr Leu Val Gly Val Ile Ser Gln Glu Lys
             35                  40                  45

Phe Glu Lys Ser Arg Ala Tyr Arg Asp Ile Ile Thr Glu Asn Phe Asn
 50                  55                  60

Ile Cys Ser Tyr Phe His Phe Val His Glu Phe Val Thr Ile Leu Met
 65                  70                  75                  80

Asp Ser Ala Ile Leu Phe Phe Gly Ile Leu Pro Trp Phe Trp Lys Met
                 85                  90                  95

Ser Gly Ala Val Leu Pro Arg Leu Gly Leu Asp Pro Glu Asn Glu Ile
                100                 105                 110

Leu His Thr Leu Ser Phe Leu Ala Gly Val Met Thr Trp Ser Gln Ile
             115                 120                 125

Thr Asp Leu Pro Phe Ser Leu Tyr Ser Thr Phe Val Ile Glu Ser Arg
130                 135                 140

His Gly Phe Asn Lys Gln Thr Ile Trp Met Phe Ile Arg Asp Met Ile
145                 150                 155                 160

Lys Gly Thr Phe Leu Ser Val Ile Leu Gly Pro Pro Ile Val Ala Ala
                165                 170                 175

Ile Ile Phe Ile Val Gln Lys Gly Pro Tyr Leu Ala Ile Tyr Leu
            180                 185                 190

Trp Ala Phe Met Phe Ile Leu Ser Leu Val Met Met Thr Ile Tyr Pro
            195                 200                 205

Val Leu Ile Ala Pro Leu Phe Asn Lys Phe Thr Pro Leu Pro Asp Gly
    210                 215                 220

Asp Leu Arg Glu Lys Ile Glu Lys Leu Ala Ser Ser Leu Lys Phe Pro
225                 230                 235                 240

Leu Lys Lys Leu Phe Val Val Asp Gly Ser Thr Arg Ser Ser His Ser
                245                 250                 255

Asn Ala Tyr Met Tyr Gly Phe Phe Lys Asn Lys Arg Ile Val Leu Tyr
                260                 265                 270

Asp Thr Leu Ile Gln Gln Cys Lys Asn Glu Asp Glu Ile Val Ala Val
                275                 280                 285

Ile Ala His Glu Leu Gly His Trp Lys Leu Asn His Thr Thr Tyr Ser
290                 295                 300

Phe Ile Ala Val Gln Ile Leu Ala Phe Leu Gln Phe Gly Gly Tyr Thr
305                 310                 315                 320

Leu Val Arg Asn Ser Thr Asp Leu Phe Arg Ser Phe Gly Phe Asp Thr
                325                 330                 335

Gln Pro Val Leu Ile Gly Leu Ile Ile Phe Gln His Thr Val Ile Pro
                340                 345                 350

Leu Gln His Leu Val Ser Phe Gly Leu Asn Leu Val Ser Arg Ala Phe
                355                 360                 365

Glu Phe Gln Ala Asp Ala Phe Ala Val Lys Leu Gly Tyr Ala Lys Asp
370                 375                 380

Leu Arg Pro Ala Leu Val Lys Leu Gln Val Arg Glu Asp Asn Asn Arg
385                 390                 395                 400

Thr Gln Thr Val Thr Ser Ile Cys Val Thr His Leu Asn Gly Phe Phe
                405                 410                 415

Val Gly Ile Leu Gln Glu Glu Asn Leu Ser Ala Met Asn Thr Asp Pro
```

|   |   |   | 420 |   |   | 425 |   |   | 430 |   |   |
|---|---|---|---|---|---|---|---|---|---|---|---|

Leu Tyr Ser Ala Tyr His Tyr Ser His Pro Pro Leu Val Glu Arg Leu
              435                 440                 445

Arg Ala Ile Asp Gly Glu Asp Lys Lys Thr Asp
    450                 455

<210> SEQ ID NO 29
<211> LENGTH: 3098
<212> TYPE: DNA
<213> ORGANISM: Arabidopsis thaliana

<400> SEQUENCE: 29

| | |
|---|---|
| atggcgattc ctttcatgga aaccgtcgtg ggtaagcttc aaaaccttt tctgagacat | 60 |
| tttactatcc tgtttcactc atcgtatttc gttttttgtt ttgggttttgct ttctgtgttg | 120 |
| tgtgtgttga gattccatga ctcgtttgtt tcatatacca tcgtctctgc ttctcgtttc | 180 |
| taaattttgt tcttttctaa tagtgcgtac cttgatctga ggttttatta ctcctactag | 240 |
| tttcttgtct tactcgtgcg tttgatttga tttgagctta tgtgatttca tcatctcttc | 300 |
| ctcggtttta gaatgtacgg agcttctctg ttaaccaaaa tctaggattt gggaagaaaa | 360 |
| gtcggagtct ttttttttcct cattcccgat tggaaattga gaatcttgaa attttctttt | 420 |
| gttcaagtca tacagcttga ggttttgggt tttcttgtca gggtattatt atgttcgtga | 480 |
| ctgcaactag agttttctgg agtttttgat aatgggtttt gtgttgtgga accgtatgtg | 540 |
| aatgttgcat caaaactctt tcagtgctcc aatgtttcca tcagtagtca gcacaagaga | 600 |
| tcttttttata tctggttgat caaaaaagta gatgatgtta ttgaattttc agtgatggag | 660 |
| tatctgttgt tgtggcattt agagtagatt cgtatttcat cttctgtttt attctttttc | 720 |
| ttacaggttt tatgatagtg atgtacattt ttgagacgta tttggatctg aggcaactca | 780 |
| ctgctctcaa gcttccaact ctcccgaaaa ccttggttgg tgtaattagc caagagaagt | 840 |
| tgagaaaatc acgagcatac agtcttgaca aaaggtttcg tcttgatcat atttatatca | 900 |
| ttttagttttt ttataattgc caggggatat catcactgag aactttaata tatgcagcta | 960 |
| ttttcacttt gttcatgagt ttgtaactat acttatggac tctgcaattt tgttcttttgg | 1020 |
| gatcttgcct tggttttgga aggtacatat ctggtttcgg tatacagtat ctcattttga | 1080 |
| atatagagtt gttacattac aattgtaaag ttttcatttt taccttagat gtctggagct | 1140 |
| gttttaccga ggttgggcct tgatccagag aatgaaatac tgcatactct tcattcttg | 1200 |
| gctggtgtta tgcatggtc acaggtgttc caaataaacc ccttcatata gtcctatacg | 1260 |
| tttagcatca aaatatctat ttcttaaga taataatatt tcttttatat tctgatgcag | 1320 |
| atcactgatt tgccatttc tttgtactca actttcgtga tcgagtctcg gcatgggttc | 1380 |
| aacaaagtat gtcgtatttc caacactacc ttgtgactta cgtttttta tcagagatgt | 1440 |
| ggattaaatt tgcttctaaa ttctgttgac agcaaacaat atggatgttc attagggaca | 1500 |
| tgatcaaagg aacattcctc tctgtcatac taggcccacc cattgttgct gcgataattt | 1560 |
| tcatagtcca ggtttgatga ttctggattc atcttatttc tgagttttttc acatggatga | 1620 |
| ctattctcca ttgagtgtga gcttcaaagt ttttagtttt cgtgttaaaa atttaaaatt | 1680 |
| tgcttctctg agcatgaagt ttctatcttt tccagaaaag gaggtcctta tcttgccatc | 1740 |
| tatctgtggg cattcatgtt tatcctgtct ctagtgatga tgactatata cccggtcttg | 1800 |
| atagcaccgc tcttcaacaa gttcactcct gtgtgtattt ctgtcatggc cattttacaa | 1860 |
| ttcactgctt gtttgcatat gttgttacca gacaatataa tctcccgctt ttttatggct | 1920 |

-continued

```
atagcttcca gatggagacc tccgggagaa gattgagaaa cttgcttctt ctctaaagtt    1980
tcctttgaag aagctgtttg ttgtcgatgg atctacaagg tcaagccata gcaatgtgag    2040
aagcttgaga tctcttccta cctactttac tctagtttac cattagaagc ttacgtatct    2100
tgttacatca tacaggctta catgtatggt ttctttaaga acaaaaggat tgttctttat    2160
gatacgttga ttcagcaggt actgtgactc ttgatgcttc aaacgagcta tactcacatt    2220 tctgttctg gttctgaaac ataacataat cttctattgt gcagtgcaag aatgaggatg    2280
aaattgtggc ggttattgca cacgagcttg acattggaa actgaatcac actacatact    2340
cgttcattgc agttcaagtg aggctcaacc gacagttcaa aaacttactc acatctacat    2400
ttcacttaag aaatcatgtc ttatgaccct ctctcaatgt tttgcttgca gatccttgcc    2460
ttcttacaat ttggaggata cactcttgtc agaaactcca ctgatctctt caggagtttc    2520
ggatttgata cacagcctgt tctcattggt ttgatcatat ttcaggtttg ttattttgc    2580 cttttgacac taatctaatg aatcaaggat ggattaagaa aaaaaaactc taaacctttg    2640
gttatatctc ctgtctgatt atcacagcac actgtaatac cactgcaaca tctagtaagc    2700
tttggcctga acctcgttag tcgagcgttt gagtttcagg taccatctta caatccctca    2760
agatccaacc atagtttctt tattgcaatg gcagcctcat ctactaatct gagttaacgt    2820
tccttttgca ggctgatgct tttgctgtga agcttggcta tgcaaaagat cttcgtcctg    2880
ctctagtgaa actacaggtc agagaagata acaacagaac acaaactgtt acctcaattt    2940
gtgtcacaca cttaaatgga ttttttgttg ggattttgca ggaagagaac ttatcagcaa    3000
tgaacactga tccattgtac tcagcttatc actactcaca tcctcctctt gttgaaaggc    3060
ttcgagccat tgatggagaa gacaagaaga cagattaa                           3098
```

<210> SEQ ID NO 30
<211> LENGTH: 316
<212> TYPE: PRT
<213> ORGANISM: Arabidopsis thaliana

<400> SEQUENCE: 30

```
Met Ala Ile Pro Phe Met Glu Thr Val Val Gly Phe Met Ile Val Met
  1               5                  10                  15

Tyr Ile Phe Glu Thr Tyr Leu Asp Leu Arg Gln Leu Thr Ala Leu Lys
             20                  25                  30

Leu Pro Thr Leu Pro Lys Thr Leu Ile Thr Asp Leu Pro Phe Ser Leu
         35                  40                  45

Tyr Ser Thr Phe Val Ile Glu Ser Arg His Gly Phe Asn Lys Gln Thr
     50                  55                  60

Ile Trp Met Phe Ile Arg Asp Met Ile Lys Gly Thr Phe Leu Ser Val
 65                  70                  75                  80

Ile Leu Gly Pro Pro Ile Val Ala Ala Ile Ile Phe Ile Val Gln Lys
                 85                  90                  95

Gly Gly Pro Tyr Leu Ala Ile Tyr Leu Trp Ala Phe Met Phe Ile Leu
            100                 105                 110

Ser Leu Val Met Met Thr Ile Tyr Pro Val Leu Ile Ala Pro Leu Phe
        115                 120                 125

Asn Lys Phe Thr Pro Leu Pro Asp Gly Asp Leu Arg Glu Lys Ile Glu
    130                 135                 140

Lys Leu Ala Ser Ser Leu Lys Phe Pro Leu Lys Lys Leu Phe Val Val
145                 150                 155                 160

Asp Gly Ser Thr Arg Ser Ser His Ser Asn Ala Tyr Met Tyr Gly Phe
                165                 170                 175
```

Phe Lys Asn Lys Arg Ile Val Leu Tyr Asp Thr Leu Ile Gln Gln Cys
            180                 185                 190

Lys Asn Glu Asp Glu Ile Val Ala Val Ile Ala His Glu Leu Gly His
        195                 200                 205

Trp Lys Leu Asn His Thr Thr Tyr Ser Phe Ile Ala Val Gln His Thr
    210                 215                 220

Val Ile Pro Leu Gln His Leu Val Ser Phe Gly Leu Asn Leu Val Ser
225                 230                 235                 240

Arg Ala Phe Glu Phe Gln Ala Asp Ala Phe Val Lys Leu Gly Tyr
                245                 250                 255

Ala Lys Asp Leu Arg Pro Ala Leu Val Lys Leu Gln Val Arg Glu Asp
            260                 265                 270

Asn Asn Arg Thr Gln Thr Glu Glu Asn Leu Ser Ala Met Asn Thr Asp
        275                 280                 285

Pro Leu Tyr Ser Ala Tyr His Tyr Ser His Pro Leu Val Glu Arg
                290                 295                 300

Leu Arg Ala Ile Asp Gly Glu Asp Lys Lys Thr Asp
305                 310                 315

<210> SEQ ID NO 31
<211> LENGTH: 453
<212> TYPE: PRT
<213> ORGANISM: Saccharomyces cerevisiae

<400> SEQUENCE: 31

Met Phe Asp Leu Lys Thr Ile Leu Asp His Pro Asn Ile Pro Trp Lys
  1               5                  10                  15

Leu Ile Ile Ser Gly Phe Ser Ile Ala Gln Phe Ser Phe Glu Ser Tyr
            20                  25                  30

Leu Thr Tyr Arg Gln Tyr Gln Lys Leu Ser Glu Thr Lys Leu Pro Pro
        35                  40                  45

Val Leu Glu Asp Glu Ile Asp Asp Glu Thr Phe His Lys Ser Arg Asn
    50                  55                  60

Tyr Ser Arg Ala Lys Ala Lys Phe Ser Ile Phe Gly Asp Val Tyr Asn
65                  70                  75                  80

Leu Ala Gln Lys Leu Val Phe Ile Lys Tyr Asp Leu Phe Pro Lys Ile
                85                  90                  95

Trp His Met Ala Val Ser Leu Leu Asn Ala Val Leu Pro Val Arg Phe
            100                 105                 110

His Met Val Ser Thr Val Ala Gln Ser Leu Cys Phe Leu Gly Leu Leu
        115                 120                 125

Ser Ser Leu Ser Thr Leu Val Asp Leu Pro Leu Ser Tyr Tyr Ser His
    130                 135                 140

Phe Val Leu Glu Glu Lys Phe Gly Phe Asn Lys Leu Thr Val Gln Leu
145                 150                 155                 160

Trp Ile Thr Asp Met Ile Lys Ser Leu Thr Leu Ala Tyr Ala Ile Gly
                165                 170                 175

Gly Pro Ile Leu Tyr Leu Phe Leu Lys Ile Phe Asp Lys Phe Pro Thr
            180                 185                 190

Asp Phe Leu Trp Tyr Ile Met Val Phe Leu Phe Val Val Gln Ile Leu
        195                 200                 205

Ala Met Thr Ile Ile Pro Val Phe Ile Met Pro Met Phe Asn Lys Phe
    210                 215                 220

Thr Pro Leu Glu Asp Gly Glu Leu Lys Lys Ser Ile Glu Ser Leu Ala
225                 230                 235                 240

```
Asp Arg Val Gly Phe Pro Leu Asp Lys Ile Phe Val Ile Asp Gly Ser
                245                 250                 255

Lys Arg Ser Ser His Ser Asn Ala Tyr Phe Thr Gly Leu Pro Phe Thr
            260                 265                 270

Ser Lys Arg Ile Val Leu Phe Asp Thr Leu Val Asn Ser Asn Ser Thr
        275                 280                 285

Asp Glu Ile Thr Ala Val Leu Ala His Glu Ile Gly His Trp Gln Lys
    290                 295                 300

Asn His Ile Val Asn Met Val Ile Phe Ser Gln Leu His Thr Phe Leu
305                 310                 315                 320

Ile Phe Ser Leu Phe Thr Ser Ile Tyr Arg Asn Thr Ser Phe Tyr Asn
                325                 330                 335

Thr Phe Gly Phe Phe Leu Glu Lys Ser Thr Gly Ser Phe Val Asp Pro
            340                 345                 350

Val Ile Thr Lys Glu Phe Pro Ile Ile Gly Phe Met Leu Phe Asn
        355                 360                 365

Asp Leu Leu Thr Pro Leu Glu Cys Ala Met Gln Phe Val Met Ser Leu
    370                 375                 380

Ile Ser Arg Thr His Glu Tyr Gln Ala Asp Ala Tyr Ala Lys Lys Leu
385                 390                 395                 400

Gly Tyr Lys Gln Asn Leu Cys Arg Ala Leu Ile Asp Leu Gln Ile Lys
                405                 410                 415

Asn Leu Ser Thr Met Asn Val Asp Pro Leu Tyr Ser Ser Tyr His Tyr
            420                 425                 430

Ser His Pro Thr Leu Ala Glu Arg Leu Thr Ala Leu Asp Tyr Val Ser
        435                 440                 445

Glu Lys Lys Lys Asn
    450

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 32
caggaaacag ctatgacc                                                 18

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 33
ctaaagggaa caaaagctg                                                19

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 34
tgtaaaacga cggccagt                                                 18
```

```
<210> SEQ ID NO 35
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 35
ccgttaacag ccatggcgat tcctttcatg gaa                                    33

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 36
gtcccgggac ttaatctgtc ttcttgtctt                                        30

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
agcagccacg attggtggcc ccaat                                             25

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gggccaccaa tcgtggctgc tatca                                             25

<210> SEQ ID NO 39
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
cgcagccagt cctcattggg ctcatc                                            26

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
cggatagttg agggaggaag caag                                              24

<210> SEQ ID NO 41
<211> LENGTH: 5544
<212> TYPE: DNA
<213> ORGANISM: Artificial Sequence
```

<220> FEATURE:
<223> OTHER INFORMATION: Description of Artificial Sequence:
      pBI121-AtCPP vector sequence

<400> SEQUENCE: 41

```
gtttacccgc caatatatcc tgtcaaacac tgatagttta aactgaaggc gggaaacgac    60
aatctgatca tgagcggaga attaagggag tcacgttatg accccgccg atgacgcggg    120
acaagccgtt ttacgtttgg aactgacaga accgcaacgt tgaaggagcc actcagccgc   180
gggtttctgg agtttaatga gctaagcaca tacgtcagaa accattattg cgcgttcaaa   240
agtcgcctaa ggtcactatc agctagcaaa tatttcttgt caaaaatgct ccactgacgt   300
tccataaatt cccctcggta tccaattaga gtctcatatt cactctcaat ccaaataatc   360
tgcaccggat ctggatcgtt tcgcatgatt gaacaagatg gattgcacgc aggttctccg   420
gccgcttggg tggagaggct attcggctat gactgggcac aacagacaat cggctgctct   480
gatgccgccg tgttccggct gtcagcgcag gggcgcccgg ttcttttgt caagaccgac    540
ctgtccggtg ccctgaatga actgcaggac gaggcagcgc ggctatcgtg gctggccacg   600
acgggcgttc cttgcgcagc tgtgctcgac gttgtcactg aagcgggaag gactggctg    660
ctattgggcg aagtgccggg gcaggatctc ctgtcatctc accttgctcc tgccgagaaa   720
gtatccatca tggctgatgc aatgcggcgg ctgcatacgc ttgatccggc tacctgccca   780
ttcgaccacc aagcgaaaca tcgcatcgag cgagcacgta ctcggatgga agccggtctt   840
gtcgatcagg atgatctgga cgaagagcat caggggctcg cgccagccga actgttcgcc   900
aggctcaagg cgcgcatgcc cgacggcgat gatctcgtcg tgacccatgg cgatgcctgc   960
ttgccgaata tcatggtgga aaatggccgc ttttctggat tcatcgactg tggccggctg  1020
ggtgtggcgg accgctatca ggacatagcg ttggctaccc gtgatattgc tgaagagctt  1080
ggcggcgaat gggctgaccg cttcctcgtg ctttacggta tcgccgctcc cgattcgcag  1140
cgcatcgcct tctatcgcct tcttgacgag ttcttctgag cgggactctg gggttcgaaa  1200
tgaccgacca gcgacgccc aacctgccat cacgagattt cgattccacc gccgccttct   1260
atgaaaggtt gggcttcgga atcgtttcc gggacgccgg ctggatgatc ctccagcgcg   1320
gggatctcat gctggagttc ttcgcccacg gatctctgc ggaacaggcg gtcgaaggtg    1380
ccgatatcat tacgacagca acggccgaca agcacaacgc cacgtcctg agcgacaata    1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg ttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt tgattatga aagatggca    1980
aacgctaata aggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
```

```
ttaccttccc tccctcaatc ggttgaatgt cgcccttttg tctttggccc aatacgcaaa    2280
ccgcctctcc ccgcgcgttg gccgattcat taatgcagct ggcacgacag gtttcccgac    2340
tggaaagcgg gcagtgagcg caacgcaatt aatgtgagtt agctcactca ttaggcaccc    2400
caggctttac actttatgct tccggctcgt atgttgtgtg gaattgtgag cggataacaa    2460
tttcacacag gaaacagcta tgaccatgat tacgccaagc ttgcatgcct gcagcccaca    2520
gatggttaga gaggcttacg cagcaggtct catcaagacg atctacccga gcaataatct    2580
ccaggaaatc aaataccttc caagaaggt taaagatgca gtcaaaagat tcaggactaa    2640
ctgcatcaag aacacagaga aagatatatt tctcaagatc agaagtacta ttccagtatg    2700
gacgattcaa ggcttgcttc acaaaccaag gcaagtaata gagattggag tctctaaaaa    2760
ggtagttccc actgaatcaa aggccatgga gtcaaagatt caaatagagg acctaacaga    2820
actcgccgta aagactggcg aacagttcat acagagtctc ttacgactca atgacaagaa    2880
gaaaatcttc gtcaacatgg tggagcacga cacacttgtc tactccaaaa atatcaaaga    2940
tacagtctca gaagaccaaa gggcaattga acttttcaa caagggtaa tatccggaaa    3000 cctcctcgga ttccattgcc cagctatctg tcactttatt gtgaagatag tggaaaagga    3060
aggtggctcc tacaaatgcc atcattgcga taaaggaaag gccatcgttg aagatgcctc    3120
tgccgacagt ggtcccaaag atggacccccc acccacgagg agcatcgtgg aaaaagaaga    3180
cgttccaacc acgtcttcaa agcaagtgga ttgatgtgat atctccactg acgtaaggga    3240
tgacgcacaa tcccactatc cttcgcaaga cccttcctct atataaggaa gttcatttca    3300
tttggagaga acacgggga ctctagagga tccatggcga ttcctttcat ggaaaccgtc    3360
gtgggtttta tgatagtgat gtacattttt gagacgtatt tggatctgag gcaactcact    3420
gctctcaagc ttccaactct cccgaaaacc ttggttggtg taattagcca agagaagttt    3480
gagaaatcac gagcatacag tcttgacaaa agctattttc actttgttca tgagtttgta    3540
actatactta tggactctgc aatttttgttc tttgggatct tgccttggtt ttggaagatg    3600
tctggagctg ttttaccgag gttgggcctt gatccggaga atgaaatact gcatactctt    3660
tcattcttgg ctggtgttat gacatggtca cagatcactg atttgccatt ttctttgtac    3720
tcaactttcg tgatcgagtc tcggcatggg ttcaacaaac aaacaatatg gatgttcatt    3780
agggacatga tcaaaggaac attcctctct gtcatactag gcccacccat tgttgctgcg    3840 ataatttttca tagtccagaa aggaggtcct tatcttgcca tctatctgtg ggcattcatg    3900
tttatcctgt ctctagtgat gatgactata tacccggtct tgatagcacc gctcttcaac    3960
aaattcactc ctcttccaga tggagacctc cgggagaaga ttgagaaact tgcttcttcc    4020
ctaaagtttc ctttgaagaa gctgtttgtt gtcgatggat ctacaaggtc aagccatagc    4080
aatgcttaca tgtatggttt cttaagaac aaaaggattg ttctttatga tacgttgatt    4140
cagcagtgca agaatgagga tgaaattgtg gcgttattg cacacgagct tggacattgg    4200
aaactgaatc acactacata ctcgttcatt gcagttcaaa tccttgcctt cttacaattt    4260
ggaggataca ctcttctcag aaactccact gatctcttca ggagtttcgg atttgataca    4320
cagcctgttc tcattggttt gatcatattt cagcacactg taataccact gcaacatcta    4380
gtaagctttg gcctgaacct cgttagtcga gcgtttgagt ttcaggctga tgcttttgct    4440
gtgaagcttg actatgcaaa agatcttcgt cctgctctag tgaaactaca ggaagagaac    4500
ttatcaacaa tgaacactga tccattgtac tcagcttatc actactcaca tcctcctctt    4560
gttgaaaggc ttcgagccac tgatggagaa gacaagaaga cagattaacc cctcgaattt    4620
```

-continued

```
ccccgatcgt tcaaacattt ggcaataaag tttcttaaga ttgaatcctg ttgccggtct      4680
tgcgatgatt atcatataat ttctgttgaa ttacgttaag catgtaataa ttaacatgta      4740
atgcatgacg ttatttatga gatgggtttt tatgattaga gtcccgcaat tatacattta     4800
atacgcgata gaaaacaaaa tatagcgcgc aaactaggat aaattatcgc gcgcggtgtc     4860
atctatgtta ctagatcggg aattcactgg ccgtcgtttt acaacgtcgt gactgggaaa     4920
accctggcgt tacccaactt aatcgccttg cagcacatcc cctttcgcc agctggcgta      4980 atagcgaaga ggcccgcacc gatcgccctt cccaacagtt gcgcagcctg aatggcgccc     5040
gctcctttcg ctttcttccc ttcctttctc gccacgttcg ccggctttcc ccgtcaagct     5100
ctaaatcggg ggctcccttt agggttccga tttagtgctt tacggcacct cgaccccaaa    5160
aaacttgatt tgggtgatgg ttcacgtagt gggccatcgc cctgatagac ggttttcgc     5220 cctttgacgt tggagtccac gttctttaat agtggactct tgttccaaac tggaacaaca    5280
ctcaacccta tctcgggcta ttcttttgat ttataaggga ttttgccgat ttcggaacca    5340
ccatcaaaca ggattttcgc ctgctggggc aaaccagcgt ggaccgcttg ctgcaactct    5400
ctcagggcca gcggtgaag gcaatcagc tgttgcccgt ctcactggtg aaaagaaaaa      5460
ccaccccagt acattaaaaa cgtccgcaat gtgttattaa gttgtctaag cgtcaattg     5520 tttacaccac aatatatcct gcca                                           5544
```

<210> SEQ ID NO 42
<211> LENGTH: 6484
<212> TYPE: DNA
<213> ORGANISM: Artificial Sequence
<220> FEATURE:
<223> OTHER INFORMATION: Description of Artificial Sequence:
    pBI121-HP-AtCPP vector sequence

<400> SEQUENCE: 42

```
gtttacccgc caatatatcc tgtcaaacac tgatagttta aactgaaggc gggaaacgac       60
aatctgatca tgagcggaga attaagggag tcacgttatg accccgccg atgacgcggg      120 acaagccgtt ttacgtttgg aactgacaga accgcaacgt tgaaggagcc actcagccgc     180
gggtttctgg agtttaatga gctaagcaca tacgtcagaa accattattg cgcgttcaaa    240
agtcgcctaa ggtcactatc agctagcaaa tatttcttgt caaaaatgct ccactgacgt    300
tccataaatt ccctcggta tccaattaga gtctcatatt cactctcaat ccaaataatc     360
tgcaccggat ctggatcgtt tcgcatgatt gaacaagatg gattgcacgc aggttctccg    420
gccgcttggg tggagaggct attcggctat gactgggcac aacagacaat cggctgctct    480
gatgccgccg tgttccggct gtcagcgcag gggcgcccgg ttctttttgt caagaccgac     540
ctgtccggtg ccctgaatga actgcaggac gaggcagcgc ggctatcgtg gctggccacg    600
acgggcgttc cttgcgcagc tgtgctcgac gttgtcactg aagcgggaag ggactggctg    660
ctattgggcg aagtgccggg gcaggatctc ctgtcatctc accttgctcc tgccgagaaa    720
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020 ggtgtggcg accgctatca ggacatagcg ttggctaccc gtgatattgc tgaagagctt    1080
ggcggcgaat gggctgaccg cttcctcgtg ctttacggta tcgccgctcc cgattcgcag   1140
```

```
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aagatggca   1980 aacgctaata ggggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagcccaca   2520
gatggttaga gaggcttacg cagcaggtct catcaagacg atctacccga gcaataatct   2580
ccaggaaatc aaataccttc ccaagaaggt taaagatgca gtcaaaagat tcaggactaa   2640
ctgcatcaag aacacagaga agatatatt tctcaagatc agaagtacta ttccagtatg   2700
gacgattcaa ggcttgcttc acaaaccaag gcaagtaata gagattggag tctctaaaaa   2760
ggtagttccc actgaatcaa aggccatgga gtcaaagatt caaatagagg acctaacaga   2820
actcgccgta aagactggcg aacagttcat acagagtctc ttacgactca atgacaagaa   2880
gaaaatcttc gtcaacatgg tggagcacga cacacttgtc tactccaaaa atatcaaaga   2940
tacagtctca gaagaccaaa gggcaattga acttttcaa caagggtaa tatccggaaa   3000 cctcctcgga ttccattgcc cagctatctg tcactttatt gtgaagatag tggaaaagga   3060
aggtggctcc tacaaatgcc atcattgcga taaaggaaag gccatcgttg aagatgcctc   3120
tgccgacagt ggtcccaaag atggaccccc acccacgagg agcatcgtgg aaaaagaaga   3180
cgttccaacc acgtcttcaa agcaagtgga ttgatgtgat atctccactg acgtaaggga   3240
tgacgcacaa tcccactatc cttcgcaaga cccttcctct atataaggaa gttcatttca   3300
tttggagaga acacggggga ctctagagga tcctcccaat gtccagctc gtgtgcaata   3360 accgccacca tttcatcctc attcttgcac tgctgaatca acgtatcata aagaacaatc   3420
cttttgttct taaagaaacc atacatgtaa gcattgctat ggcttgacct tgtagatcca   3480
tcgacaacaa acagcttctt caaaggaaac tttagggaag aagcaagttt ctcaatcttc   3540
```

```
tcccggaggt ctccatctgg aagaggagtg aatttgttga agagcggtgc tatcaagacc    3600
gggtatatag tcatcatcac tagagacagg ataaacatga atgcccacag atagatggca    3660
agataaggac ctcctttctg gactatgaaa attatcgcag caacaatggg tgggcctagt    3720
atgacagaga ggaatgttcc tttgatcatg tccctaatga acatccatat tgtttgtttg    3780
ttgaacccat gccgagactc gatcacgaaa gttgagtaca aagaaaatgg caaatcagtg    3840
atctgtgacc atgtcataac accagccaag aatgaaagag tatgcagtat ttcattctcc    3900
ggatcaaggc ccaacctcgg taaaagagga tccccatcta cccgcttcgc gtcggcatcc    3960
ggtcagtggc agtgaagggc aacagttcc  tgattaacca caaaccgttc tactttactg    4020
gctttggtcg tcatgaagat gcggacttgc gtggcaaagg attcgataac gtgctgatgg    4080
tgcacgacca cgcattaatg gactggattg gggccaactc ctaccgtacc tcgcattacc    4140
cttacgctga agagatgctc gactgggcag atgaacatgg catcgtggtg attgatgaaa    4200
ctgctgctgt cggcttttcg ctctctttag gcattggttt cgaagcgggc aacaagccga    4260
aagaactgta cagcgaagag gcagtcaacg ggaaactca  gcaagcgcac ttacaggcga    4320
ttaaagagct gatagcgcgt gacaaaaacc acccaagcgt ggtgatgtgg agtattgcca    4380
acgaaccgga tacccgtccg caaggtgcac gggaatattt cgcgccactg gcggaagcaa    4440
cgcgtaaact cgaccgacg  cgtccgatca cctgcgtcaa tgtaatgttc tgcgacgctc    4500
acaccgatac catcagcgat ctctttgatg tgctgtgcct gaaccgttat tacggatggt    4560
atgtccaaag cggcgatttg gaaacggcag agaaggtact ggaaaaagaa cttctggcct    4620
ggcaggagaa actgtacacc gacatgtgga gtgaagagta tcagtgtgca tggctggata    4680
tgtatcaccg cgtctttgat cgcgtcagcg ccgtcgtcgg tgaacaggta tggaatttcg    4740
ccgattttgc gacctcgcaa ggcatattgc gcgttggcgg taacaagaaa gggatcttca    4800
ctcgcgaccg caaaccgaag tcggcggctt ttctgctgca aaaacgctgg actggcatga    4860
acttcggtga aaaaccgcag cagggaggca aacaatgaat caacaactct cctggcgcac    4920
catcgtcggc tacagcctcg ggaattgcta ccgagctctt ttaccgaggt tgggccttga    4980
tccggagaat gaaatactgc atactctttc attcttggct ggtgttatga catggtcaca    5040
gatcactgat ttgccatttt ctttgtactc aactttcgtg atcgagtctc ggcatgggtt    5100
caacaaacaa acaatatgga tgttcattag ggacatgatc aaaggaacat tcctctctgt    5160
catactaggc ccacccattg ttgctgcgat aattttcata gtccagaaag gaggtcctta    5220
tcttgccatc tatctgtggg cattcatgtt tatcctgtct ctagtgatga tgactatata    5280
cccggtcttg atagcaccgc tcttcaacaa attcactcct cttccagatg gagacctccg    5340
ggagaagatt gagaaacttg cttcttccct aaagtttcct ttgaagaagc tgtttgttgt    5400
cgatggatct acaaggtcaa gccatagcaa tgcttacatg tatggtttct ttaagaacaa    5460
aaggattgtt ctttatgata cgttgattca gcagtgcaag aatgaggatg aaattgtggc    5520
ggttattgca cacgagcttg acattggga  gctcgaattt ccccgatcgt tcaaacattt    5580
ggcaataaag tttcttaaga ttgaatcctg ttgccggtct tgcgatgatt atcatataat    5640
ttctgttgaa ttacgttaag catgtaataa ttaacatgta atgcatgacg ttatttatga    5700
gatgggtttt tatgattaga gtcccgcaat tatacatttta atacgcgata gaaaacaaaa    5760
tatagcgcgc aaactaggat aaattatcgc gcgcggtgtc atctatgtta ctagatcggg    5820
aattcactgg ccgtcgtttt acaacgtcgt gactgggaaa accctggcgt tacccaactt    5880
aatcgccttg cagcacatcc ccctttcgcc agctggcgta atagcgaaga ggcccgcacc    5940
```

-continued

```
gatcgcccett  cccaacagtt  gcgcagcctg  aatggcgccc  gctcctttcg  ctttcttccc    6000
ttcctttctc  gccacgttcg  ccggctttcc  ccgtcaagct  ctaaatcggg  ggctcccttt    6060
agggttccga  tttagtgctt  tacggcacct  cgaccccaaa  aaacttgatt  tgggtgatgg    6120
ttcacgtagt  gggccatcgc  cctgatagac  ggttttttcgc  cctttgacgt  tggagtccac    6180
gttctttaat  agtggactct  tgttccaaac  tggaacaaca  ctcaacccta  tctcgggcta    6240
ttcttttgat  ttataaggga  ttttgccgat  ttcggaacca  ccatcaaaca  ggattttcgc    6300
ctgctggggc  aaaccagcgt  ggaccgcttg  ctgcaactct  ctcagggcca  ggcggtgaag    6360
ggcaatcagc  tgttgcccgt  ctcactggtg  aaaagaaaaa  ccaccccagt  acattaaaaa    6420
cgtccgcaat  gtgttattaa  gttgtctaag  cgtcaatttg  tttacaccac  aatatatcct    6480
gcca                                                                     6484

<210> SEQ ID NO 43
<211> LENGTH: 28
<212> TYPE: DNA
<213> ORGANISM: Artificial Sequence
<220> FEATURE:
<223> OTHER INFORMATION: Description of Artificial Sequence: PCR primer

<400> SEQUENCE: 43
aaaggatcca tggcgattcc tttcatgg                                            28

<210> SEQ ID NO 44
<211> LENGTH: 34
<212> TYPE: DNA
<213> ORGANISM: Artificial Sequence
<220> FEATURE:
<223> OTHER INFORMATION: Description of Artificial Sequence: PCR primer

<400> SEQUENCE: 44
aaacccgggt taatctgtct tcttgtcttc tcca                                     34

<210> SEQ ID NO 45
<211> LENGTH: 34
<212> TYPE: DNA
<213> ORGANISM: Artificial Sequence
<220> FEATURE:
<223> OTHER INFORMATION: Description of Artificial Sequence: PCR primer

<400> SEQUENCE: 45
ctggagctct tttaccgagg ttgggccttg atcc                                     34

<210> SEQ ID NO 46
<211> LENGTH: 34
<212> TYPE: DNA
<213> ORGANISM: Artificial Sequence
<220> FEATURE:
<223> OTHER INFORMATION: Description of Artificial Sequence: PCR primer

<400> SEQUENCE: 46
attgagctcc caatgtccaa gctcgtgtgc aata                                     34

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 47
gccgacagtg gtcccaaaga tgg                                                 23
```

<210> SEQ ID NO 48
<211> LENGTH: 28
<212> TYPE: DNA
<213> ORGANISM: Artificial Sequence
<220> FEATURE:
<223> OTHER INFORMATION: Description of Artificial Sequence: PCR primer

<400> SEQUENCE: 48
aaacccggga tggcgattcc tttcatgg                                28

<210> SEQ ID NO 49
<211> LENGTH: 34
<212> TYPE: DNA
<213> ORGANISM: Artificial Sequence
<220> FEATURE:
<223> OTHER INFORMATION: Description of Artificial Sequence: PCR primer

<400> SEQUENCE: 49
aaaggatcct taatctgtct tcttgtcttc tcca                          34

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: PCR primer

<400> SEQUENCE: 50
gcaagaccgg caacagga                                            18

<210> SEQ ID NO 51
<211> LENGTH: 5544
<212> TYPE: DNA
<213> ORGANISM: Artificial Sequence
<220> FEATURE:
<223> OTHER INFORMATION: Description of Artificial Sequence:
      pBI121-antisense-AtCPP vector sequence

<400> SEQUENCE: 51
gtttacccgc caatatatcc tgtcaaacac tgatagttta aactgaaggc gggaaacgac    60
aatctgatca tgagcggaga attaagggag tcacgttatg accccgccg atgacgcggg    120 acaagccgtt ttacgtttgg aactgacaga accgcaacgt tgaaggagcc actcagccgc   180
gggtttctgg agtttaatga gctaagcaca tacgtcagaa accattattg cgcgttcaaa   240
agtcgcctaa ggtcactatc agctagcaaa tatttcttgt caaaaatgct ccactgacgt   300
tccataaatt cccctcggta tccaattaga gtctcatatt cactctcaat ccaaataatc   360
tgcaccggat ctggatcgtt tcgcatgatt gaacaagatg gattgcacgc aggttctccg   420
gccgcttggg tggagaggct attcggctat gactgggcac aacagacaat cggctgctct   480
gatgccgccg tgttccggct gtcagcgcag gggcgcccgg ttcttttttgt caagaccgac   540 ctgtccggtg ccctgaatga actgcaggac gaggcagcgc ggctatcgtg gctggccacg   600
acgggcgttc cttgcgcagc tgtgctcgac gttgtcactg aagcgggaag gactggctg    660 ctattgggcg aagtgccggg gcaggatctc ctgtcatctc accttgctcc tgccgagaaa   720
gtatccatca tggctgatgc aatgcggcgg ctgcatacgc ttgatccggc tacctgccca   780
ttcgaccacc aagcgaaaca tcgcatcgag cgagcacgta ctcggatgga agccggtctt   840
gtcgatcagg atgatctgga cgaagagcat caggggctcg cgccagccga actgttcgcc   900
aggctcaagg cgcgcatgcc cgacggcgat gatctcgtcg tgacccatgg cgatgcctgc   960

```
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttccttctgag cgggactctg ggttcgaaa   1200 tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata gggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagcccaca   2520
gatggttaga gaggcttacg cagcaggtct catcaagacg atctacccga gcaataatct   2580
ccaggaaatc aaatacctcc ccagaaggt taaagatgca gtcaaaagat tcaggactaa   2640
ctgcatcaag aacacagaga agatatatt tctcaagatc agaagtacta ttccagtatg   2700
gacgattcaa ggcttgcttc acaaaccaag gcaagtaata gagattggag tctctaaaaa   2760
ggtagttccc actgaatcaa aggccatgga gtcaaagatt caaatagagg acctaacaga   2820
actcgccgta aagactggcg aacagttcat acagagtctc ttacgactca atgacaagaa   2880
gaaaatcttc gtcaacatgg tggagcacga cacacttgtc tactccaaaa atatcaaaga   2940
tacagtctca gaagaccaaa gggcaattga acttttcaa caagggtaa tatccggaaa   3000 cctcctcgga ttccattgcc cagctatctg tcactttatt gtgaagatag tggaaaagga   3060
aggtggctcc tacaaatgcc atcattgcga taaaggaaag gccatcgttg aagatgcctc   3120
tgccgacagt ggtcccaaag atggacccccc acccacgagg agcatcgtgg aaaaagaaga   3180
cgttccaacc acgtcttcaa agcaagtgga ttgatgtgat atctccactg acgtaaggga   3240
tgacgcacaa tcccactatc cttcgcaaga cccttcctct atataaggaa gttcatttca   3300
tttggagaga acacggggga ctctagagga tccttaatct gtcttcttgt cttctccatc   3360
```

```
agtggctcga agcctttcaa caagaggagg atgtgagtag tgataagctg agtacaatgg    3420
atcagtgttc attgttgata agttctcttc ctgtagtttc actagagcag gacgaagatc    3480
ttttgcatag tcaagcttca cagcaaaagc atcagcctga aactcaaacg ctcgactaac    3540
gaggttcagg ccaaagctta ctagatgttg cagtggtatt acagtgtgct gaaatatgat    3600
caaaccaatg agaacaggct gtgtatcaaa tccgaaactc ctgaagagat cagtggagtt    3660
tctgagaaga gtgtatcctc caaattgtaa gaaggcaagg atttgaactg caatgaacga    3720
gtatgtagtg tgattcagtt tccaatgtcc aagctcgtgt gcaataaccg ccacaatttc    3780
atcctcattc ttgcactgct gaatcaacgt atcataaaga acaatccttt tgttcttaaa    3840
gaaaccatac atgtaagcat tgctatggct tgaccttgta gatccatcga caacaaacag    3900
cttcttcaaa ggaaacttta gggaagaagc aagtttctca atcttctccc ggaggtctcc    3960
atctggaaga ggagtgaatt tgttgaagag cggtgctatc aagaccgggt atatagtcat    4020
catcactaga gacaggataa acatgaatgc ccacagatag atggcaagat aaggacctcc    4080
tttctggact atgaaaatta tcgcagcaac aatgggtggg cctagtatga cagagaggaa    4140
tgttcctttg atcatgtccc taatgaacat ccatattgtt tgtttgttga acccatgccg    4200
agactcgatc acgaaagttg agtacaaaga aaatggcaaa tcagtgatct gtgaccatgt    4260
cataacacca gccaagaatg aaagagtatg cagtatttca ttctccggat caaggcccaa    4320
cctcggtaaa acagctccag acatcttcca aaaccaaggc aagatcccaa agaacaaaat    4380
tgcagagtcc ataagtatag ttacaaactc atgaacaaag tgaaaatagc ttttgtcaag    4440
actgtatgct cgtgatttct caaacttctc ttggctaatt acaccaacca aggttttcgg    4500
gagagttgga agcttgagag cagtgagttg cctcagatcc aaatacgtct caaaaatgta    4560
catcactatc ataaaaccca cgacggtttc catgaaagga atcgccatcc cctcgaattt    4620
ccccgatcgt tcaaacattt ggcaataaag tttcttaaga ttgaatcctg ttgccggtct    4680
tgcgatgatt atcatataat ttctgttgaa ttacgttaag catgtaataa ttaacatgta    4740
atgcatgacg ttatttatga gatgggtttt tatgattaga gtcccgcaat tatacattta    4800
atacgcgata gaaaacaaaa tatagcgcgc aaactaggat aaaattatcg cgcgcggtgtc    4860
atctatgtta ctagatcggg aattcactgg ccgtcgtttt acaacgtcgt gactgggaaa    4920
accctggcgt tacccaactt aatcgccttg cagcacatcc cccttcgcc agctggcgta    4980
atagcgaaga ggcccgcacc gatcgccctt cccaacagtt gcgcagcctg aatggcgccc    5040
gctcctttcg ctttcttccc ttcctttctc gccacgttcg ccggctttcc ccgtcaagct    5100
ctaaatcggg ggctcccttt agggttccga tttagtgctt tacggcacct cgaccccaaa    5160
aaacttgatt tgggtgatgg ttcacgtagt gggccatcgc cctgatagac ggttttcgc    5220
cctttgacgt tggagtccac gttctttaat agtggactct tgttccaaac tggaacaaca    5280
ctcaaccctc tctcgggcta ttcttttgat ttataaggga ttttgccgat ttcggaacca    5340
ccatcaaaca ggattttcgc ctgctgggc aaaccagcgt ggaccgcttg ctgcaactct    5400
ctcagggcca gcggtgaag ggcaatcagc tgttgcccgt ctcactggtg aaaagaaaaa    5460
ccaccccagt acattaaaaa cgtccgcaat gtgttattaa gttgtctaag cgtcaatttg    5520
tttacaccac aatatatcct gcca                                           5544
```

<210> SEQ ID NO 52
<211> LENGTH: 5668
<212> TYPE: DNA
<213> ORGANISM: Artificial Sequence
<220> FEATURE:

<223> OTHER INFORMATION: Description of Artificial Sequence: vector sequence

<400> SEQUENCE: 52

```
gtttacccgc caatatatcc tgtcaaacac tgatagttta aactgaaggc gggaaacgac      60
aatctgatca tgagcggaga attaagggag tcacgttatg accccgccg atgacgcggg     120
acaagccgtt ttacgtttgg aactgacaga accgcaacgt tgaaggagcc actcagccgc    180
gggtttctgg agtttaatga gctaagcaca tacgtcagaa accattattg cgcgttcaaa    240
agtcgcctaa ggtcactatc agctagcaaa tatttcttgt caaaaatgct ccactgacgt    300
tccataaatt cccctcggta tccaattaga gtctcatatt cactctcaat ccaaataatc    360
tgcaccggat ctggatcgtt tcgcatgatt gaacaagatg gattgcacgc aggttctccg    420
gccgcttggg tggagaggct attcggctat gactgggcac aacagacaat cggctgctct    480
gatgccgccg tgttccggct gtcagcgcag gggcgcccgg ttcttttgt caagaccgac     540
ctgtccggtg ccctgaatga actgcaggac gaggcagcgc ggctatcgtg gctggccacg    600
acgggcgttc cttgcgcagc tgtgctcgac gttgtcactg aagcgggaag gactggctg     660
ctattgggcg aagtgccggg gcaggatctc ctgtcatctc accttgctcc tgccgagaaa    720
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg gatctctgc ggaacaggcg gtcgaaggtg    1380
ccgatatcat tacgacagca acggccgaca agcacaacgc cacgatcctg agcgacaata   1440
tgatcgggcc cggcgtccac atcaacgcg tcggcggcga ctgcccaggc aagaccgaga    1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt tgattatga  aaagatggca   1980
aacgctaata aggggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
```

```
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagggagcc   2520
atagatgcaa ttcaatcaaa ctgaaatttc tgcaagaatc tcaaacacgg agatctcaaa   2580
gtttgaaaga aaatttattt cttcgactca aaacaaactt acgaaattta ggtagaactt   2640
atatacatta tattgtaatt ttttgtaaca aaatgttttt attattatta tagaatttta   2700
ctggttaaat taaaaatgaa tagaaaaggt gaattaagag gagagaggag gtaaacattt   2760 tcttctatttt tttcatatttt tcaggataaa ttattgtaaa agtttacaag atttccattt   2820
gactagtgta aatgaggaat attctctagt aagatcatta tttcatctac ttcttttatc   2880
ttctaccagt agaggaataa acaatattta gctccttttgt aaatacaaat taattttcct   2940
tcttgacatc attcaatttt aattttacgt ataaaataaa agatcatacc tattagaacg   3000
attaaggaga aatacaattc gaatgagaag gatgtgccgt ttgttataat aaacagccac   3060
acgacgtaaa cgtaaaatga ccacatgatg ggccaataga catggaccga ctactaataa   3120
tagtaagtta catttttagga tggaataaat atcataccga catcagttttt gaaagaaaag   3180 ggaaaaaaag aaaaaataaa taaaagatat actaccgaca tgagttccaa aaagcaaaaa   3240
aaaagatcaa gccgacacag acacgcgtag agagcaaaat gactttgacg tcacaccacg   3300
aaaacagacg cttcatacgt gtcccttttat ctctctcagt ctctctataa acttagtgag   3360
accctcctct gttttactca caaatatgca aactagaaaa caatcatcag gaataaaggg   3420
tttgattact tctattggaa aggactctag aggatccatg gcgattcctt tcatggaaac   3480
cgtcgtgggt tttatgatag tgatgtacat tttttgagacg tatttggatc tgaggcaact   3540
cactgctctc aagcttccaa ctctcccgaa aaccttggtt ggtgtaatta gccaagagaa   3600
gtttgagaaa tcacgagcat acagtcttga caaaagctat tttcactttg ttcatgagtt   3660
tgtaactata cttatggact ctgcaatttt gttctttggg atcttgcctt ggttttggaa   3720
gatgtctgga gctgttttac cgaggttggg ccttgatccg gagaatgaaa tactgcatac   3780
tctttcattc ttggctggtg ttatgacatg gtcacagatc actgatttgc cattttcttt   3840
gtactcaact ttcgtgatcg agtctcggca tgggttcaac aaacaaacaa tatggatgtt   3900
cattagggac atgatcaaag gaacattcct ctctgtcata ctaggcccac ccattgttgc   3960
tgcgataatt ttcatagtcc agaaaggagg tccttatctt gccatctatc tgtgggcatt   4020 catgttttatc ctgtctctag tgatgatgac tatatacccg gtcttgatag caccgctctt   4080
caacaaattc actcctcttc cagatggaga cctccgggag aagattgaga aacttgcttc   4140
ttccctaaag tttcctttga agaagctgtt tgttgtcgat ggatctacaa ggtcaagcca   4200
tagcaatgct tacatgtatg gtttctttaa gaacaaaagg attgttctttt atgatacgtt   4260 gattcagcag tgcaagaatg aggatgaaat tgtggcggtt attgcacacg agcttggaca   4320
ttggaaactg aatcacacta catactcgtt cattgcagtt caaatccttg ccttcttaca   4380
atttggagga tacactcttc tcagaaactc cactgatctc ttcaggagtt tcggatttga   4440
tacacagcct gttctcattg gtttgatcat atttcagcac actgtaatac cactgcaaca   4500
tctagtaagc tttggcctga acctcgttag tcgagcgttt gagtttcagg ctgatgcttt   4560
tgctgtgaag cttgactatg caaaagatct tcgtcctgct ctagtgaaac tacaggaaga   4620
gaacttatca acaatgaaca ctgatccatt gtactcagct tatcactact cacatcctcc   4680
```

```
tcttgttgaa aggcttcgag ccactgatgg agaagacaag aagacagatt aaccccctcga   4740 atttccccga tcgttcaaac atttggcaat aaagtttctt aagattgaat cctgttgccg   4800
gtcttgcgat gattatcata taatttctgt tgaattacgt taagcatgta ataattaaca   4860
tgtaatgcat gacgttattt atgagatggg tttttatgat tagagtcccg caattataca   4920
tttaatacgc gatagaaaac aaaatatagc gcgcaaacta ggataaatta tcgcgcgcgg   4980
tgtcatctat gttactagat cgggaattca ctggccgtcg ttttacaacg tcgtgactgg   5040
gaaaaccctg gcgttaccca acttaatcgc cttgcagcac atccccctttt cgccagctgg   5100 cgtaatagcg aagaggcccg caccgatcgc ccttcccaac agttgcgcag cctgaatggc   5160
gcccgctcct ttcgctttct tcccttcctt tctcgccacg ttcgccggct ttccccgtca   5220
agctctaaat cggggggctcc ctttagggtt ccgatttagt gctttacggc acctcgaccc   5280
caaaaaactt gatttgggtg atggttcacg tagtgggcca tcgccctgat agacggtttt   5340
tcgccctttg acgttggagt ccacgttctt taatagtgga ctcttgttcc aaactggaac   5400
aacactcaac cctatctcgg gctattcttt tgatttataa gggattttgc cgatttcgga   5460
accaccatca aacaggattt tcgcctgctg gggcaaacca gcgtggaccg cttgctgcaa   5520
ctctctcagg gccaggcggt gaagggcaat cagctgttgc ccgtctcact ggtgaaaaga   5580
aaaaccaccc cagtacatta aaaacgtccg caatgtgtta ttaagttgtc taagcgtcaa   5640
tttgtttaca ccacaatata tcctgcca                                       5668

<210> SEQ ID NO 53
<211> LENGTH: 6608
<212> TYPE: DNA
<213> ORGANISM: Artificial Sequence
<220> FEATURE:
<223> OTHER INFORMATION: Description of Artificial Sequence:
      pRD29A-HP-AtCPP vector sequence

<400> SEQUENCE: 53
gtttacccgc caatatatcc tgtcaaacac tgatagttta aactgaaggc gggaaacgac     60
aatctgatca tgagcggaga attaagggag tcacgttatg accccgccg atgacgcggg    120 acaagccgtt ttacgtttgg aactgacaga accgcaacgt tgaaggagcc actcagccgc    180
gggtttctgg agtttaatga gctaagcaca tacgtcagaa accattattg cgcgttcaaa    240
agtcgcctaa ggtcactatc agctagcaaa tatttcttgt caaaaatgct ccactgacgt    300
tccataaatt cccctcggta tccaattaga gtctcatatt cactctcaat ccaaataatc    360
tgcaccggat ctggatcgtt tcgcatgatt gaacaagatg gattgcacgc aggttctccg    420
gccgcttggg tggagaggct attcggctat gactgggcac aacagacaat cggctgctct    480
gatgccgccg tgttccggct gtcagcgcag gggcgcccgg ttcttttttgt caagaccgac    540 ctgtccggtg ccctgaatga actgcaggac gaggcagcgc ggctatcgtg gctggccacg    600
acgggcgttc cttgcgcagc tgtgctcgac gttgtcactg aagcgggaag ggactggctg    660
ctattgggcg aagtgccggg gcaggatctc ctgtcatctc accttgctcc tgccgagaaa    720
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
```

```
ggtgtggcgg accgctatca ggacatagcg ttggctaccc gtgatattgc tgaagagctt      1080
ggcggcgaat gggctgaccg cttcctcgtg ctttacggta tcgccgctcc cgattcgcag      1140
cgcatcgcct tctatcgcct tcttgacgag ttcttctgag cgggactctg gggttcgaaa      1200
tgaccgacca agcgacgccc aacctgccat cacgagattt cgattccacc gccgccttct      1260
atgaaaggtt gggcttcgga atcgttttcc gggacgccgg ctggatgatc ctccagcgcg      1320
gggatctcat gctggagttc ttcgcccacg ggatctctgc ggaacaggcg gtcgaaggtg      1380
ccgatatcat tacgacagca acggccgaca agcacaacgc cacgatcctg agcgacaata      1440
tgatcgggcc cggcgtccac atcaacggcg tcggcggcga ctgcccaggc aagaccgaga      1500
tgcaccgcga tatcttgctg cgttcggata ttttcgtgga gttcccgcca cagacccgga      1560
tgatccccga tcgttcaaac atttggcaat aaagtttctt aagattgaat cctgttgccg      1620
gtcttgcgat gattatcata taatttctgt tgaattacgt taagcatgta ataattaaca      1680
tgtaatgcat gacgttattt atgagatggg ttttatgat tagagtcccg caattataca      1740
tttaatacgc gatagaaaac aaaatatagc gcgcaaacta ggataaatta tcgcgcgcgg      1800
tgtcatctat gttactagat cgggcctcct gtcaatgctg gcggcggctc tggtggtggt      1860
tctggtggcg gctctgaggg tggtggctct gagggtggcg gttctgaggg tggcggctct      1920
gagggaggcg gttccggtgg tggctctggt tccggtgatt ttgattatga aaagatggca      1980
aacgctaata agggggctat gaccgaaaat gccgatgaaa acgcgctaca gtctgacgct      2040
aaaggcaaac ttgattctgt cgctactgat tacggtgctg ctatcgatgg tttcattggt      2100
gacgtttccg gccttgctaa tggtaatggt gctactggtg attttgctgg ctctaattcc      2160
caaatggctc aagtcggtga cggtgataat tcacctttaa tgaataattt ccgtcaatat      2220
ttaccttccc tccctcaatc ggttgaatgt cgcccttttg tctttggccc aatacgcaaa      2280
ccgcctctcc ccgcgcgttg gccgattcat taatgcagct ggcacgacag gtttcccgac      2340
tggaaagcgg gcagtgagcg caacgcaatt aatgtgagtt agctcactca ttaggcaccc      2400
caggctttac actttatgct tccggctcgt atgttgtgtg gaattgtgag cggataacaa      2460
tttcacacag gaaacagcta tgaccatgat tacgccaagc ttgcatgcct gcagggagcc      2520
atagatgcaa ttcaatcaaa ctgaaatttc tgcaagaatc tcaaacacgg agatctcaaa      2580
gtttgaaaga aaatttattt cttcgactca aaacaaactt acgaaattta ggtagaactt      2640
atatacatta tattgtaatt ttttgtaaca aaatgttttt attattatta tagaatttta      2700
ctggttaaat taaaaatgaa tagaaaaggt gaattaagag gagagaggag gtaaacattt      2760 tcttctatt tttcatattt tcaggataaa ttattgtaaa agtttacaag atttccattt       2820
gactagtgta aatgaggaat attctctagt aagatcatta tttcatctac ttcttttatc      2880
ttctaccagt agaggaataa acaatattta gctcctttgt aaatacaaat taattttcct      2940
tcttgacatc attcaattt aattttacgt ataaaataaa agatcatacc tattagaacg       3000
attaaggaga aatacaattc gaatgagaag gatgtgccgt tgttataat aaacagccac       3060 acgacgtaaa cgtaaaatga ccacatgatg ggccaataga catggaccga ctactaataa      3120
tagtaagtta cattttagga tggaataaat atcataccga catcagtttt gaagaaaag       3180 ggaaaaaaag aaaaaataaa taaagatat actaccgaca tgagttccaa aaagcaaaaa       3240 aaagatcaa gccgacacag acacgcgtag agagcaaaat gactttgacg tcacaccacg       3300
aaaacagacg cttcatacgt gtcccttat ctctctcagt ctctctataa acttagtgag       3360
accctcctct gttttactca caaatatgca aactagaaaa caatcatcag gaataaaggg      3420
```

-continued

```
tttgattact tctattggaa aggactctag aggatcctcc caatgtccaa gctcgtgtgc    3480
aataaccgcc acaatttcat cctcattctt gcactgctga atcaacgtat cataaagaac    3540 aatcctttg  ttcttaaaga aaccatacat gtaagcattg ctatggcttg accttgtaga    3600
tccatcgaca acaaacagct tcttcaaagg aaactttagg gaagaagcaa gtttctcaat    3660
cttctcccgg aggtctccat ctggaagagg agtgaatttg ttgaagagcg gtgctatcaa    3720
gaccgggtat atagtcatca tcactagaga caggataaac atgaatgccc acagatagat    3780
ggcaagataa ggacctcctt tctggactat gaaaattatc gcagcaacaa tgggtgggcc    3840
tagtatgaca gagaggaatg ttcctttgat catgtcccta atgaacatcc atattgtttg    3900
tttgttgaac ccatgccgag actcgatcac gaaagttgag tacaaagaaa atggcaaatc    3960
agtgatctgt gaccatgtca taacaccagc caagaatgaa agagtatgca gtatttcatt    4020
ctccggatca aggcccaacc tcggtaaaag aggatcccca tctacccgct tcgcgtcggc    4080
atccggtcag tggcagtgaa gggcgaacag ttcctgatta accacaaacc gttctacttt    4140 actgctttg  gtcgtcatga agatgcggac ttgcgtggca aggattcga  taacgtgctg    4200 atggtgcacg accacgcatt aatggactgg attggggcca actcctaccg tacctcgcat    4260
tacccttacg ctgaagagat gctcgactgg gcagatgaac atggcatcgt ggtgattgat    4320
gaaactgctg ctgtcggctt ttcgctctct ttaggcattg gtttcgaagc gggcaacaag    4380
ccgaaagaac tgtacagcga agaggcagtc aacggggaaa ctcagcaagc gcacttacag    4440
gcgattaaag agctgatagc gcgtgacaaa aaccacccaa gcgtggtgat gtggagtatt    4500
gccaacgaac cggatacccg tccgcaaggt gcacgggaat atttcgcgcc actggcggaa    4560
gcaacgcgta aactcgaccc gacgcgtccg atcacctgcg tcaatgtaat gttctgcgac    4620
gctcacaccg ataccatcag cgatctcttt gatgtgctgt gcctgaaccg ttattacgga    4680
tggtatgtcc aaagcggcga tttgaaacg  gcagagaagg tactgaaaa  agaacttctg    4740 gcctggcagg agaaactgta caccgacatg tggagtgaag agtatcagtg tgcatggctg    4800
gatatgtatc accgcgtctt tgatcgcgtc agcgccgtcg tcggtgaaca ggtatggaat    4860
ttcgccgatt ttgcgacctc gcaaggcata ttgcgcgttg gcggtaacaa gaaagggatc    4920
ttcactcgcg accgcaaacc gaagtcggcg gcttttctgc tgcaaaaacg ctggactggc    4980
atgaacttcg gtgaaaaacc gcagcaggga ggcaaacaat gaatcaacaa ctctcctggc    5040
gcaccatcgt cggctacagc ctcgggaatt gctaccgagc tcttttaccg aggttgggcc    5100
ttgatccgga gaatgaaata ctgcatactc tttcattctt ggctggtgtt atgacatggt    5160
cacagatcac tgatttgcca ttttctttgt actcaacttt cgtgatcgag tctcggcatg    5220
ggttcaacaa acaaacaata tggatgttca ttagggacat gatcaaagga acattcctct    5280
ctgtcatact aggcccaccc attgttgctg cgataatttt catagtccag aaaggaggtc    5340
cttatcttgc catctatctg tgggcattca tgtttatcct gtctctagtg atgatgacta    5400
tatacccggt cttgatagca ccgctcttca acaaattcac tcctcttcca gatggagacc    5460
tccgggagaa gattgagaaa cttgcttctt ccctaaagtt tcctttgaag aagctgtttg    5520
ttgtcgatgg atctacaagg tcaagccata gcaatgctta catgtatggt ttctttaaga    5580
acaaaaggat tgttctttat gatacgttga ttcagcagtg caagaatgag gatgaaattg    5640
tggcggttat tgcacacgag cttggacatt gggagctcga atttccccga tcgttcaaac    5700
atttggcaat aaagtttctt aagattgaat cctgttgccg gtcttgcgat gattatcata    5760
taatttctgt tgaattacgt taagcatgta ataattaaca tgtaatgcat gacgttattt    5820
```

```
atgagatggg tttttatgat tagagtcccg caattataca tttaatacgc gatagaaaac   5880
aaaatatagc gcgcaaacta ggataaaatta tcgcgcgcgg tgtcatctat gttactagat   5940
cgggaattca ctggccgtcg ttttacaacg tcgtgactgg gaaaaccctg gcgttaccca   6000
acttaatcgc cttgcagcac atccccttt cgccagctgg cgtaatagcg aagaggcccg    6060
caccgatcgc ccttcccaac agttgcgcag cctgaatggc gcccgctcct ttcgctttct   6120
tcccttcctt tctcgccacg ttcgccggct ttccccgtca agctctaaat cggggggctcc  6180
ctttagggtt ccgatttagt gctttacggc acctcgaccc caaaaaactt gatttgggtg   6240
atggttcacg tagtgggcca tcgccctgat agacggtttt cgccctttg acgttggagt    6300
ccacgttctt taatagtgga ctcttgttcc aaactggaac aacactcaac cctatctcgg    6360
gctattcttt tgatttataa gggattttgc cgatttcgga accaccatca aacaggattt    6420
tcgcctgctg gggcaaacca gcgtggaccg cttgctgcaa ctctctcagg gccaggcggt    6480
gaagggcaat cagctgttgc ccgtctcact ggtgaaaaga aaaaccaccc cagtacatta    6540
aaaacgtccg caatgtgtta ttaagttgtc taagcgtcaa tttgtttaca ccacaatata    6600
tcctgcca                                                            6608

<210> SEQ ID NO 54
<211> LENGTH: 5668
<212> TYPE: DNA
<213> ORGANISM: Artificial Sequence
<220> FEATURE:
<223> OTHER INFORMATION: Description of Artificial Sequence:
      pRD29A-antisense-AtCPP vector sequence

<400> SEQUENCE: 54
gtttacccgc caatatatcc tgtcaaacac tgatagttta aactgaaggc gggaaacgac     60
aatctgatca tgagcggaga attaagggag tcacgttatg accccgccg atgacgcggg     120
acaagccgtt ttacgtttgg aactgacaga accgcaacgt tgaaggagcc actcagccgc    180
gggtttctgg agtttaatga gctaagcaca tacgtcagaa accattattg cgcgttcaaa    240
agtcgcctaa ggtcactatc agctagcaaa tatttcttgt caaaaatgct ccactgacgt    300
tccataaatt cccctcggta tccaattaga gtctcatatt cactctcaat ccaaataatc    360
tgcaccggat ctggatcgtt tcgcatgatt gaacaagatg gattgcacgc aggttctccg    420
gccgcttggg tggagaggct attcggctat gactgggcac aacagacaat cggctgctct    480
gatgccgccg tgttccggct gtcagcgcag gggcgcccgg ttcttttgt caagaccgac     540
ctgtccggtg ccctgaatga actgcaggac gaggcagcgc ggctatcgtg gctggccacg    600
acgggcgttc cttgcgcagc tgtgctcgac gttgtcactg aagcgggaag gactggctg    660
ctattgggcg aagtgccggg gcaggatctc ctgtcatctc accttgctcc tgccgagaaa    720
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg    1020
ggtgtggcgg accgctatca ggacatagcg ttggctaccc gtgatattgc tgaagagctt    1080
ggcggcgaat gggctgaccg cttcctcgtg ctttacggta tcgccgctcc cgattcgcag    1140
cgcatcgcct tctatcgcct tcttgacgag ttcttctgag cgggactctg gggttcgaaa    1200
tgaccgacca agcgacgccc aacctgccat cacgagattt cgattccacc gccgccttct    1260
```

```
atgaaaggtt gggcttcgga atcgttttcc gggacgccgg ctggatgatc ctccagcgcg    1320
gggatctcat gctggagttc ttcgcccacg ggatctctgc ggaacaggcg gtcgaaggtg    1380
ccgatatcat tacgcagca acggccgaca agcacaacgc cacgatcctg agcgacaata    1440
tgatcgggcc cggcgtccac atcaacggcg tcggcggcga ctgcccaggc aagaccgaga    1500
tgcaccgcga tatcttgctg cgttcggata ttttcgtgga gttcccgcca cagacccgga    1560
tgatccccga tcgttcaaac atttggcaat aaagtttctt aagattgaat cctgttgccg    1620
gtcttgcgat gattatcata taatttctgt tgaattacgt taagcatgta ataattaaca    1680
tgtaatgcat gacgttattt atgagatggg tttttatgat tagagtcccg caattataca    1740
tttaatacgc gatagaaaac aaaatatagc gcgcaaacta ggataaatta tcgcgcgcgg    1800
tgtcatctat gttactagat cgggcctcct gtcaatgctg gcggcggctc tggtggtggt    1860
tctggtggcg gctctgaggg tggtggctct gagggtggcg ttctgaggg tggcggctct    1920 gagggaggcg gttccggtgg tggctctggt tccggtgatt ttgattatga aaagatggca    1980
aacgctaata aggggggctat gaccgaaaat gccgatgaaa acgcgctaca gtctgacgct    2040
aaaggcaaac ttgattctgt cgctactgat tacggtgctg ctatcgatgg tttcattggt    2100
gacgtttccg gccttgctaa tggtaatggt gctactggtg attttgctgg ctctaattcc    2160
caaatggctc aagtcggtga cggtgataat tcacctttaa tgaataattt ccgtcaatat    2220
ttaccttccc tccctcaatc ggttgaatgt cgcccttttg tctttggccc aatacgcaaa    2280
ccgcctctcc ccgcgcgttg gccgattcat taatgcagct ggcacgacag gttttccgac    2340
tggaaagcgg gcagtgagcg caacgcaatt aatgtgagtt agctcactca ttaggcaccc    2400
caggctttac actttatgct tccggctcgt atgttgtgtg gaattgtgag cggataacaa    2460
tttcacacag gaaacagcta tgaccatgat tacgccaagc ttgcatgcct gcagggagcc    2520
atagatgcaa ttcaatcaaa ctgaaatttc tgcaagaatc tcaaacacgg agatctcaaa    2580
gtttgaaaga aaatttattt cttcgactca aaacaaactt acgaaattta ggtagaactt    2640
atatacatta tattgtaatt ttttgtaaca aaatgttttt attattatta tagaatttta    2700
ctggttaaat taaaaatgaa tagaaaaggt gaattaagag gagagaggag gtaaacattt    2760 tcttctatt tttcatattt tcaggataaa ttattgtaaa agtttacaag atttccattt    2820
gactagtgta aatgaggaat attctctagt aagatcatta tttcatctac ttcttttatc    2880
ttctaccagt agaggaataa acaatattta gctccttgt aaatacaaat taattttcct    2940
tcttgacatc attcaatttt aatttacgt ataaaataaa agatcatacc tattagaacg    3000
attaaggaga aatacaattc gaatgagaag gatgtgccgt tgttataat aaacagccac    3060 acgacgtaaa cgtaaaatga ccacatgatg ggccaataga catggaccga ctactaataa    3120
tagtaagtta cattttagga tggaataaat atcataccga catcagtttt gaagaaaaag    3180
ggaaaaaaag aaaaaataaa taaagatat actaccgaca tgagttccaa aaagcaaaaa    3240
aaaagatcaa gccgacacag acacgcgtag agagcaaaat gactttgacg tcacaccacg    3300
aaaacagacg cttcatacgt gtcccttat ctctctcagt ctctctataa acttagtgag    3360
accctcctct gttttactca caaatatgca aactagaaaa caatcatcag gaataaaggg    3420
tttgattact tctattggaa aggactctag aggatcctta atctgtcttc ttgtcttctc    3480
catcagtggc tcgaagcctt tcaacaagag gaggatgtga gtagtgataa gctgagtaca    3540
atggatcagt gttcattgtt gataagttct cttcctgtag tttcactaga gcaggacgaa    3600 gatctttgc atagtcaagc ttcacagcaa aagcatcagc ctgaaactca aacgctcgac    3660
```

```
taacgaggtt caggccaaag cttactagat gttgcagtgg tattacagtg tgctgaaata    3720
tgatcaaacc aatgagaaca ggctgtgtat caaatccgaa actcctgaag agatcagtgg    3780
agtttctgag aagagtgtat cctccaaatt gtaagaaggc aaggatttga actgcaatga    3840
acgagtatgt agtgtgattc agtttccaat gtccaagctc gtgtgcaata accgccacaa    3900
tttcatcctc attcttgcac tgctgaatca acgtatcata agaacaatc cttttgttct    3960 taaagaaacc atacatgtaa gcattgctat ggcttgacct tgtagatcca tcgacaacaa    4020
acagcttctt caaaggaaac tttagggaag aagcaagttt ctcaatcttc tcccggaggt    4080
ctccatctgg aagaggagtg aatttgttga agagcggtgc tatcaagacc gggtatatag    4140
tcatcatcac tagagacagg ataaacatga atgcccacag atagatggca agataaggac    4200
ctcctttctg gactatgaaa attatcgcag caacaatggg tgggcctagt atgacagaga    4260
ggaatgttcc tttgatcatg tccctaatga acatccatat tgtttgtttg ttgaacccat    4320
gccgagactc gatcacgaaa gttgagtaca agaaaatgg caaatcagtg atctgtgacc    4380
atgtcataac accagccaag aatgaaagag tatgcagtat ttcattctcc ggatcaaggc    4440
ccaacctcgg taaaacagct ccagacatct tccaaaacca aggcaagatc ccaaagaaca    4500
aaattgcaga gtccataagt atagttacaa actcatgaac aaagtgaaaa tagcttttgt    4560
caagactgta tgctcgtgat ttctcaaact tctcttggct aattcacca accaaggttt    4620 tcgggagagt tggaagcttg agagcagtga gttgcctcag atccaaatac gtctcaaaaa    4680
tgtacatcac tatcataaaa cccacgacgg tttccatgaa aggaatcgcc atcccctcga    4740
atttccccga tcgttcaaac atttggcaat aaagtttctt aagattgaat cctgttgccg    4800
gtcttgcgat gattatcata taatttctgt tgaattacgt taagcatgta ataattaaca    4860
tgtaatgcat gacgttattt atgagatggg tttttatgat tagagtcccg caattataca    4920
tttaatacgc gatagaaaac aaaatatagc gcgcaaacta ggataaatta tcgcgcgcgg    4980
tgtcatctat gttactagat cgggaattca ctggccgtcg ttttacaacg tcgtgactgg    5040
gaaaaccctg gcgttaccca acttaatcgc cttgcagcac atccccctttt cgccagctgg    5100 cgtaatagcg aagaggcccg caccgatcgc ccttcccaac agttgcgcag cctgaatggc    5160
gcccgctcct ttcgctttct tcccttcctt tctcgccacg ttcgccggct ttccccgtca    5220
agctctaaat cggggggctcc ctttagggtt ccgatttagt gctttacggc acctcgaccc    5280
caaaaaactt gatttgggtg atggttcacg tagtgggcca tcgccctgat agacggtttt    5340
tcgccctttg acgttggagt ccacgttctt taatagtgga ctcttgttcc aaactggaac    5400
aacactcaac cctatctcgg gctattcttt tgatttataa gggattttgc cgatttcgga    5460
accaccatca acaggatttt cgcctgctg gggcaaacca gcgtggaccg cttgctgcaa    5520
ctctctcagg gccaggcggt gaagggcaat cagctgttgc ccgtctcact ggtgaaaaga    5580
aaaaccaccc cagtacatta aaaacgtccg caatgtgtta ttaagttgtc taagcgtcaa    5640
tttgtttaca ccacaatata tcctgcca                                      5668
```

<210> SEQ ID NO 55
<211> LENGTH: 5074
<212> TYPE: DNA
<213> ORGANISM: Artificial Sequence
<220> FEATURE:
<223> OTHER INFORMATION: Description of Artificial Sequence: MuA-AtCPP vector sequence

<400> SEQUENCE: 55

```
gtttacccgc caatatatcc tgtcaaacac tgatagttta aactgaaggc gggaaacgac    60
aatctgatca tgagcggaga attaagggag tcacgttatg accccgccg atgacgcggg    120 acaagccgtt ttacgtttgg aactgacaga accgcaacgt tgaaggagcc actcagccgc   180
gggtttctgg agtttaatga gctaagcaca tacgtcagaa accattattg cgcgttcaaa   240
agtcgcctaa ggtcactatc agctagcaaa tatttcttgt caaaaatgct ccactgacgt   300
tccataaatt cccctcggta tccaattaga gtctcatatt cactctcaat ccaaataatc   360
tgcaccggat ctggatcgtt tcgcatgatt gaacaagatg gattgcacgc aggttctccg   420
gccgcttggg tggagaggct attcggctat gactgggcac aacagacaat cggctgctct   480
gatgccgccg tgttccggct gtcagcgcag gggcgcccgg ttcttttgt caagaccgac    540 ctgtccggtg ccctgaatga actgcaggac gaggcagcgc ggctatcgtg gctggccacg   600
acgggcgttc cttgcgcagc tgtgctcgac gttgtcactg aagcgggaag ggactggctg   660
ctattgggcg aagtgccggg gcaggatctc ctgtcatctc accttgctcc tgccgagaaa   720
gtatccatca tggctgatgc aatgcggcgg ctgcatacgc ttgatccggc tacctgccca   780
ttcgaccacc aagcgaaaca tcgcatcgag cgagcacgta ctcggatgga agccggtctt   840
gtcgatcagg atgatctgga cgaagagcat caggggctcg cgccagccga actgttcgcc   900
aggctcaagg cgcgcatgcc cgacggcgat gatctcgtcg tgacccatgg cgatgcctgc   960
ttgccgaata tcatggtgga aaatggccgc ttttctggat tcatcgactg tggccggctg  1020
ggtgtggcgg accgctatca ggacatagcg ttggctaccc gtgatattgc tgaagagctt  1080
ggcggcgaat gggctgaccg cttcctcgtg ctttacggta tcgccgctcc cgattcgcag  1140
cgcatcgcct tctatcgcct tcttgacgag ttcttctgag cgggactctg gggttcgaaa  1200
tgaccgacca agcgacgccc aacctgccat cacgagattt cgattccacc gccgccttct  1260
atgaaaggtt gggcttcgga atcgttttcc gggacgccgg ctggatgatc ctccagcgcg  1320
gggatctcat gctggagttc ttcgcccacg gatctctgc ggaacaggcg gtcgaaggtg    1380
ccgatatcat tacgacagca acggccgaca agcacaacgc cacgatcctg agcgacaata  1440
tgatcgggcc cggcgtccac atcaacggcg tcggcggcga ctgcccaggc aagaccgaga  1500
tgcaccgcga tatcttgctg cgttcggata ttttcgtgga gttcccgcca cagacccgga  1560
tgatccccga tcgttcaaac atttggcaat aaagtttctt aagattgaat cctgttgccg  1620
gtcttgcgat gattatcata taatttctgt tgaattacgt taagcatgta ataattaaca  1680
tgtaatgcat gacgttattt atgagatggg ttttttatgat tagagtcccg caattataca  1740
tttaatacgc gatagaaaac aaaatatagc gcgcaaacta ggataaatta tcgcgcgcgg  1800
tgtcatctat gttactagat cgggcctcct gtcaatgctg gcggcggctc tggtggtggt  1860
tctggtggcg gctctgaggg tggtggctct gagggtggcg gttctgaggg tggcggctct  1920
gagggaggcg gttccggtgg tggctctggt tccggtgatt tgattatga aaagatggca   1980 aacgctaata agggggctat gaccgaaaat gccgatgaaa acgcgctaca gtctgacgct  2040
aaaggcaaac ttgattctgt cgctactgat tacggtgctg ctatcgatgg tttcattggt  2100
gacgtttccg gccttgctaa tggtaatggt gctactggtg attttgctgg ctctaattcc  2160
caaatggctc aagtcggtga cggtgataat tcacctttaa tgaataattt ccgtcaatat  2220
ttaccttccc tccctcaatc ggttgaatgt cgcccttttg tctttggccc aatacgcaaa  2280
ccgcctctcc ccgcgcgttg gccgattcat taatgcagct ggcacgacag gtttcccgac  2340
tggaaagcgg gcagtgagcg caacgcaatt aatgtgagtt agctcactca ttaggcaccc  2400
```

```
caggctttac actttatgct tccggctcgt atgttgtgtg gaattgtgag cggataacaa    2460
tttcacacag gaaacagcta tgaccatgat tacgccaagc tgggaaattt ttcgccagtt    2520
ctaaatatcc ggaaacctct tgggatgcca ttgcccatct atctgtaatt tattgacgaa    2580
atagacgaaa aggaaggtgg ctcctataaa gcacatcatt gcgataacag aaaggccatt    2640
gttgaagata cctctgctga cattggtccc caagtggaag caccacccca tgaggagcac    2700
cgtggagtaa aagacgttc gagccacgtc gaaaaagcaa gtgtgttgat gtagtatctc    2760
cattgacgta agggatgacg cacaatccaa ctatccatcg caagaccatt gctctatata    2820
agaaagttaa tatcatttcg agtggccacg ctgagggga tccatggcga ttcctttcat    2880
ggaaaccgtc gtgggtttta tgatagtgat gtacatttt gagacgtatt tggatctgag    2940
gcaactcact gctctcaagc ttccaactct cccgaaaacc ttggttggtg taattagcca    3000
agagaagttt gagaaatcac gagcatacag tcttgacaaa agctattttc actttgttca    3060
tgagtttgta actatactta tggactctgc aatttttgttc tttgggatct tgccttggtt    3120
ttggaagatg tctggagctg ttttaccgag gttgggcctt gatccggaga atgaaatact    3180
gcatactctt tcattcttgg ctggtgttat gacatggtca cagatcactg atttgccatt    3240
ttctttgtac tcaactttcg tgatcgagtc tcggcatggg ttcaacaaac aaacaatatg    3300
gatgttcatt agggacatga tcaaaggaac attcctctct gtcatactag gcccacccat    3360
tgttgctgcg ataattttca tagtccagaa aggaggtcct tatcttgcca tctatctgtg    3420
ggcattcatg tttatcctgt ctctagtgat gatgactata tacccggtct tgatagcacc    3480
gctcttcaac aaattcactc ctcttccaga tggagacctc cgggagaaga ttgagaaact    3540
tgcttcttcc ctaaagtttc ctttgaagaa gctgtttgtt gtcgatggat ctacaaggtc    3600
aagccatagc aatgcttaca tgtatggttt ctttaagaac aaaaggattg ttctttatga    3660
tacgttgatt cagcagtgca agaatgagga tgaaattgtg gcggttattg cacacgagct    3720
tggacattgg aaactgaatc acactacata ctcgttcatt gcagttcaaa tccttgcctt    3780
cttacaattt ggaggataca ctcttctcag aaactccact gatctcttca ggagtttcgg    3840
atttgataca cagcctgttc tcattggttt gatcatattt cagcacactg taataccact    3900
gcaacatcta gtaagctttg gcctgaacct cgttagtcga gcgtttgagt tcaggctga    3960 tgcttttgct gtgaagcttg actatgcaaa agatcttcgt cctgctctag tgaaactaca    4020
ggaagagaac ttatcaacaa tgaacactga tccattgtac tcagcttatc actactcaca    4080
tcctcctctt gttgaaaggc ttcgagccac tgatggagaa gacaagaaga cagattaacc    4140
cctcgaattt ccccgatcgt tcaaacattt ggcaataaag tttcttaaga ttgaatcctg    4200
ttgccggtct tgcgatgatt atcatataat ttctgttgaa ttacgttaag catgtaataa    4260
ttaacatgta atgcatgacg ttatttatga gatgggtttt tatgattaga gtcccgcaat    4320
tatacattta atacgcgata gaaaacaaaa tatagcgcgc aaactaggat aaattatcgc    4380
gcgcggtgtc atctatgtta ctagatcggg aattcactgg ccgtcgtttt acaacgtcgt    4440
gactgggaaa accctggcgt tacccaactt aatcgccttg cagcacatcc cccttcgcc    4500 agctggcgta atagcgaaga ggcccgcacc gatcgccctt cccaacagtt gcgcagcctg    4560
aatgcgcccc gctcctttcg ctttcttccc ttcctttctc gccacgttcg ccggctttcc    4620
ccgtcaagct ctaaatcggg ggctcccttt agggttccga tttagtgctt tacggcacct    4680
cgaccccaaa aaacttgatt tgggtgatgg ttcacgtagt gggccatcgc cctgatagac    4740
ggtttttcgc cctttgacgt tggagtccac gttctttaat agtggactct tgttccaaac    4800
```

```
tggaacaaca ctcaaccta tctcgggcta ttcttttgat ttataaggga ttttgccgat    4860
ttcggaacca ccatcaaaca ggattttcgc ctgctgggc aaaccagcgt ggaccgcttg    4920
ctgcaactct ctcagggcca ggcggtgaag gcaatcagc tgttgcccgt ctcactggtg    4980
aaaagaaaaa ccaccccagt acattaaaaa cgtccgcaat gtgttattaa gttgtctaag    5040
cgtcaatttg tttacaccac aatatatcct gcca                                5074

<210> SEQ ID NO 56
<211> LENGTH: 5076
<212> TYPE: DNA
<213> ORGANISM: Artificial Sequence
<220> FEATURE:
<223> OTHER INFORMATION: Description of Artificial Sequence: MuA-GmCPP
      vector sequence

<400> SEQUENCE: 56
gtttacccgc caatatatcc tgtcaaacac tgatagttta aactgaaggc gggaaacgac      60
aatctgatca tgagcggaga attaagggag tcacgttatg acccccgccg atgacgcggg    120
acaagccgtt ttacgtttgg aactgacaga accgcaacgt tgaaggagcc actcagccgc    180
gggtttctgg agtttaatga gctaagcaca tacgtcagaa accattattg cgcgttcaaa    240
agtcgcctaa ggtcactatc agctagcaaa tatttcttgt caaaaatgct ccactgacgt    300
tccataaatt cccctcggta tccaattaga gtctcatatt cactctcaat ccaaataatc    360
tgcaccggat ctggatcgtt tcgcatgatt gaacaagatg gattgcacgc aggttctccg    420
gccgcttggg tggagaggct attcggctat gactgggcac aacagacaat cggctgctct    480
gatgccgccg tgttccggct gtcagcgcag gggcgcccgg ttcttttgt caagaccgac    540 ctgtccggtg ccctgaatga actgcaggac gaggcagcgc ggctatcgtg gctggccacg    600
acgggcgttc cttgcgcagc tgtgctcgac gttgtcactg aagcgggaag ggactggctg    660
ctattgggcg aagtgccggg gcaggatctc ctgtcatctc accttgctcc tgccgagaaa    720
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata tttcgtgga gttcccgcca cagacccgga   1560 tgatcccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg ttttttatgat tagagtcccg caattataca   1740
tttaatacgc gatagaaaac aaaatatagc gcgcaaacta ggataaatta tcgcgcgcgg   1800
```

```
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aagatggca    1980 aacgctaata aggggctat gaccgaaaat gccgatgaaa acgcgctaca gtctgacgct    2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat aatgcagct ggcacgacag gtttcccgac    2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc tgggaaattt ttcgccagtt   2520
ctaaatatcc ggaaacctct tgggatgcca ttgcccatct atctgtaatt tattgacgaa   2580
atagacgaaa aggaaggtgg ctcctataaa gcacatcatt gcgataacag aaaggccatt   2640
gttgaagata cctctgctga cattggtccc caagtggaag caccaccca tgaggagcac    2700 cgtggagtaa aagacgttc gagccacgtc gaaaaagcaa gtgtgttgat gtagtatctc    2760
cattgacgta agggatgacg cacaatccaa ctatccatcg caagaccatt gctctatata   2820
agaaagttaa tatcatttcg agtggccacg ctgaggggga tcgggatggc gtttccctac   2880
atggaagccg ttgtcggatt tatgatatta atgtacattt ttgaaactta cttggatgtg   2940
cgacaacata gggccctcaa acttcctact cttccaaaga cttagaggg tgttatcagc    3000 caagagaaat ttgagaaatc tagagcctat agtcttgata aaagccactt ccattttgtt   3060
cacgagtttg tgacaatagt gacagactct acaattttgt actttgggt attgccctgg    3120 ttttggaaga aatcaggaga ttttatgaca atagctggtt tcaatgctga gaatgaaata   3180
ctgcataccc ttgccttctt agcagggctg atgatttggt cacagataac agatttgccc   3240
ttttctctgt actcaacttt tgtgattgag gcccgtcatg gttttaataa gcaaacacca   3300
tggttattct ttagggacat gcttaaagga attttccttt ctgtaataat tggtccacct   3360
attgtggctg caatcattgt aatagtacag aaaggaggtc catacttggc catctatctt   3420
tgggttttta cgtttggtct ttctattgtg atgatgaccc tttatccagt actaatagct   3480
ccactcttca ataagttcac tccacttcca gatggtcaac tcagggagaa aatcgagaaa   3540
cttgcttcct ccctcaacta tccgttaaag aaactatttg ttgtcgatgg atccacaaga   3600
tcaagtcaca gcaatgccta tatgtatgga ttcttcaaga acaagaggat tgtcccttat   3660
gacacattaa ttcaacagtg caaagacgat gaggaaattg ttgctgttat tgcccatgag   3720
ttgggacact ggaagctcaa ccatactgtg tacacatttg ttgctatgca gattcttaca   3780
cttctacaat ttggaggata tacactagtg cgaaattcag ctgatctgta tcgaagcttt   3840
gggtttgata cgcagccagt cctcattggg ctcatcatat ttcagcatac tgtaatccca   3900
cttcagcaat tggtcagctt tggtctgaac ctagtcagcc gatcatttga atttcaggct   3960
gatggctttg ccaagaagct tggatatgca tctggattac gcggtggtct tgtgaaacta   4020
caggaggaga atctgtcagc tatgaataca gatccttggt actctgctta tcactattct   4080
catcctcccc ttgttgaaag attggccgcg ctggacgaac cggataagaa ggaagactaa   4140
gagctcgaat tccccgatc gttcaaacat ttggcaataa agtttcttaa gattgaatcc   4200
```

```
tgttgccggt cttgcgatga ttatcatata atttctgttg aattacgtta agcatgtaat    4260
aattaacatg taatgcatga cgttatttat gagatgggtt tttatgatta gagtcccgca    4320
attatacatt taatacgcga tagaaaacaa aatatagcgc gcaaactagg ataaattatc    4380
gcgcgcggtg tcatctatgt tactagatcg ggaattcact ggccgtcgtt ttacaacgtc    4440
gtgactggga aaaccctggc gttacccaac ttaatcgcct tgcagcacat ccccctttcg    4500
ccagctggcg taatagcgaa gaggcccgca ccgatcgccc ttcccaacag ttgcgcagcc    4560
tgaatggcgc ccgctccttt cgctttcttc ccttcctttc tcgccacgtt cgccggcttt    4620
ccccgtcaag ctctaaatcg ggggctccct ttagggttcc gatttagtgc tttacggcac    4680
ctcgacccca aaaaacttga tttgggtgat ggttcacgta gtgggccatc gccctgatag    4740
acggtttttc gccctttgac gttggagtcc acgttcttta atagtggact cttgttccaa    4800
actggaacaa cactcaaccc tatctcgggc tattcttttg atttataagg gattttgccg    4860
atttcggaac caccatcaaa caggattttc gcctgctggg gcaaaccagc gtggaccgct    4920
tgctgcaact ctctcagggc caggcggtga agggcaatca gctgttgccc gtctcactgg    4980
tgaaaagaaa aaccacccca gtacattaaa aacgtccgca atgtgttatt aagttgtcta    5040
agcgtcaatt tgtttacacc acaatatatc ctgcca                             5076

<210> SEQ ID NO 57
<211> LENGTH: 5549
<212> TYPE: DNA
<213> ORGANISM: Artificial Sequence
<220> FEATURE:
<223> OTHER INFORMATION: Description of Artificial Sequence:
      pBI121-GmCPP vector sequence

<400> SEQUENCE: 57
gtttacccgc caatatatcc tgtcaaacac tgatagttta aactgaaggc gggaaacgac      60
aatctgatca tgagcggaga attaagggag tcacgttatg accccgccg atgacgcggg     120 acaagccgtt ttacgtttgg aactgacaga accgcaacgt tgaaggagcc actcagccgc     180
gggtttctgg agtttaatga gctaagcaca tacgtcagaa accattattg cgcgttcaaa     240
agtcgcctaa ggtcactatc agctagcaaa tatttcttgt caaaaatgct ccactgacgt     300
tccataaatt ccccctcggta tccaattaga gtctcatatt cactctcaat ccaataatc     360 tgcaccggat ctggatcgtt tcgcatgatt gaacaagatg gattgcacgc aggttctccg     420
gccgcttggg tggagaggct attcggctat gactgggcac aacagacaat cggctgctct     480
gatgccgccg tgttccggct gtcagcgcag gggcgcccgg ttcttttttgt caagaccgac     540 ctgtccggtg ccctgaatga actgcaggac gaggcagcgc ggctatcgtg gctggccacg     600
acgggcgttc cttgcgcagc tgtgctcgac gttgtcactg aagcgggaag ggactggctg     660
ctattgggcg aagtgccggg gcaggatctc ctgtcatctc accttgctcc tgccgagaaa     720
gtatccatca tggctgatgc aatgcggcgg ctgcatacgc ttgatccggc tacctgccca     780
ttcgaccacc aagcgaaaca tcgcatcgag cgagcacgta ctcggatgga agccggtctt     840
gtcgatcagg atgatctgga cgaagagcat caggggctcg cgccagccga actgttcgcc     900
aggctcaagg cgcgcatgcc cgacggcgat gatctcgtcg tgacccatgg cgatgcctgc     960
ttgccgaata tcatggtgga aaatggccgc ttttctggat tcatcgactg tggccggctg    1020
ggtgtggcgg accgctatca ggacatagcg ttggctaccc gtgatattgc tgaagagctt    1080
ggcggcgaat gggctgaccg cttcctcgtg ctttacggta tcgccgctcc cgattcgcag    1140
```

```
cgcatcgcct tctatcgcct tcttgacgag ttcttctgag cgggactctg gggttcgaaa    1200
tgaccgacca agcgacgccc aacctgccat cacgagattt cgattccacc gccgccttct    1260
atgaaaggtt gggcttcgga atcgttttcc gggacgccgg ctggatgatc ctccagcgcg    1320
gggatctcat gctggagttc ttcgcccacg ggatctctgc ggaacaggcg gtcgaaggtg    1380
ccgatatcat tacgacagca acggccgaca agcacaacgc cacgatcctg agcgacaata    1440
tgatcgggcc cggcgtccac atcaacggcg tcggcggcga ctgcccaggc aagaccgaga    1500
tgcaccgcga tatcttgctg cgttcggata ttttcgtgga gttcccgcca cagacccgga    1560
tgatccccga tcgttcaaac atttggcaat aaagtttctt aagattgaat cctgttgccg    1620
gtcttgcgat gattatcata taatttctgt tgaattacgt taagcatgta ataattaaca    1680
tgtaatgcat gacgttattt atgagatggg tttttatgat tagagtcccg caattataca    1740
tttaatacgc gatagaaaac aaaatatagc gcgcaaacta ggataaatta tcgcgcgcgg    1800
tgtcatctat gttactagat cgggcctcct gtcaatgctg cggcggctc tggtggtggt     1860 tctggtggcg gctctgaggg tggtggctct gagggtggcg gttctgaggg tggcggctct    1920
gagggaggcg gttccggtgg tggctctggt tccggtgatt ttgattatga aaagatggca    1980
aacgctaata aggggggctat gaccgaaaat gccgatgaaa acgcgctaca gtctgacgct    2040
aaaggcaaac ttgattctgt cgctactgat tacggtgctg ctatcgatgg tttcattggt    2100
gacgtttccg gccttgctaa tggtaatggt gctactggtg attttgctgg ctctaattcc    2160
caaatggctc aagtcggtga cggtgataat tcacctttaa tgaataattt ccgtcaatat    2220
ttaccttccc tccctcaatc ggttgaatgt cgccctttg tctttggccc aatacgcaaa     2280
ccgcctctcc ccgcgcgttg gccgattcat taatgcagct ggcacgacag gtttcccgac    2340
tggaaagcgg gcagtgagcg caacgcaatt aatgtgagtt agctcactca ttaggcaccc    2400
caggctttac actttatgct tccggctcgt atgttgtgtg gaattgtgag cggataacaa    2460
tttcacacag gaaacagcta tgaccatgat tacgccaagc ttgcatgcct gcagcccaca    2520
gatggttaga gaggcttacg cagcaggtct catcaagacg atctacccga gcaataatct    2580
ccaggaaatc aaataccttc ccaagaaggt taaagatgca gtcaaaagat tcaggactaa    2640
ctgcatcaag aacacagaga aagatatatt tctcaagatc agaagtacta ttccagtatg    2700
gacgattcaa ggcttgcttc acaaaccaag gcaagtaata gagattggag tctctaaaaa    2760
ggtagttccc actgaatcaa aggccatgga gtcaaagatt caaatagagg acctaacaga    2820
actcgccgta aagactggcg aacagttcat acagagtctc ttacgactca atgacaagaa    2880
gaaaatcttc gtcaacatgg tggagcacga cacacttgtc tactccaaaa atatcaaaga    2940
tacagtctca gaagaccaaa gggcaattga acttttcaa caaagggtaa tatccggaaa     3000
cctcctcgga ttccattgcc cagctatctg tcactttatt gtgaagatag tggaaaagga    3060
aggtggctcc tacaaatgcc atcattgcga taaaggaaag gccatcgttg aagatgcctc    3120
tgccgacagt ggtcccaaag atggacccc acccacgagg agcatcgtgg aaaaagaaga    3180
cgttccaacc acgtcttcaa agcaagtgga ttgatgtgat atctccactg acgtaaggga    3240
tgacgcacaa tcccactatc cttcgcaaga ccctcctct atataaggaa gttcatttca    3300
tttggagaga acacggggga ctctagagga tccccgggta ggcgttccc tacatggaag   3360 ccgttgtcgg atttatgata ttaatgtaca ttttgaaac ttacttggat gtgcgacaac    3420
atagggccct caaacttcct actcttccaa agactttaga gggtgttatc agccaagaga    3480
aatttgagaa atctagagcc tatagtcttg ataaaagcca cttccatttt gttcacgagt    3540
```

```
ttgtgacaat agtgacagac tctacaattt tgtactttgg ggtattgccc tggttttgga    3600
agaaatcagg agattttatg acaatagctg gtttcaatgc tgagaatgaa atactgcata    3660
cccttgcctt cttagcaggg ctgatgattt ggtcacagat aacagatttg ccctttctc     3720
tgtactcaac ttttgtgatt gaggcccgtc atggttttaa taagcaaaca ccatggttat    3780
tctttaggga catgcttaaa ggaattttcc tttctgtaat aattggtcca cctattgtgg    3840
ctgcaatcat tgtaatagta cagaaaggag gtccatactt ggccatctat ctttgggttt    3900
ttacgtttgg tctttctatt gtgatgatga ccctttatcc agtactaata gctccactct    3960
tcaataagtt cactccactt ccagatggtc aactcaggga gaaaatcgag aaacttgctt    4020
cctccctcaa ctatccgtta aagaaactat tgttgtcga tggatccaca agatcaagtc     4080
acagcaatgc ctatatgtat ggattcttca agaacaagag gattgtccct tatgacacat    4140
taattcaaca gtgcaaagac gatgaggaaa ttgttgctgt tattgcccat gagttgggac    4200
actgaagct caaccatact gtgtacacat ttgttgctat gcagattctt acacttctac     4260
aatttggagg atatacacta gtgcgaaatt cagctgatct gtatcgaagc tttgggtttg    4320
atacgcagcc agtcctcatt gggctcatca tatttcagca tactgtaatc ccacttcagc    4380
aattggtcag ctttggtctg aacctagtca gccgatcatt tgaatttcag gctgatggct    4440
ttgccaagaa gcttggatat gcatctggat tacgcgtgg tcttgtgaaa ctacaggagg     4500
agaatctgtc agctatgaat acagatcctt ggtactctgc ttatcactat tctcatcctc    4560
cccttgttga agattggcc gcgctggacg aaccggataa gaaggaagac taagagctcg     4620
aatttccccg atcgttcaaa catttggcaa taaagtttct taagattgaa tcctgttgcc    4680
ggtcttgcga tgattatcat ataatttctg ttgaattacg ttaagcatgt aataattaac    4740
atgtaatgca tgacgttatt tatgagatgg gttttatga ttagagtccc gcaattatac     4800
atttaatacg cgatagaaaa caaaatatag cgcgcaaact aggataaatt atcgcgcgcg    4860
gtgtcatcta tgttactaga tcgggaattc actggccgtc gttttacaac gtcgtgactg    4920
ggaaaaccct ggcgttaccc aacttaatcg ccttgcagca catcccccctt cgccagctg     4980
gcgtaatagc gaagaggccc gcaccgatcg cccttcccaa cagttgcgca gcctgaatgg    5040
cgaccgctcc tttcgctttc ttcccttcct ttctcgccac gttcgccggc tttccccgtc    5100
aagctctaaa tcgggggctc cctttagggt tccgatttag tgctttacgg cacctcgacc    5160
ccaaaaaact tgatttgggt gatggttcac gtagtgggcc atcgccctga tagacggttt    5220
ttcgcccttt gacgttggag tccacgttct ttaatagtgg actcttgttc caaactggaa    5280
caacactcaa ccctatctcg ggctattctt ttgatttata agggattttg ccgatttcgg    5340
aaccaccatc aaacaggatt ttcgcctgct ggggcaaacc agcgtggacc gcttgctgca    5400
actctctcag ggccaggcgg tgaagggcaa tcagctgttg cccgtctcac tggtgaaaag    5460
aaaaaccacc ccagtacatt aaaaacgtcc gcaatgtgtt attaagttgt ctaagcgtca    5520
atttgtttac accacaatat atcctgcca                                      5549
```

<210> SEQ ID NO 58
<211> LENGTH: 6352
<212> TYPE: DNA
<213> ORGANISM: Artificial Sequence
<220> FEATURE:
<223> OTHER INFORMATION: Description of Artificial Sequence:
    pBI121-HP-GmCPP vector sequence

<400> SEQUENCE: 58

```
gtttacccgc caatatatcc tgtcaaacac tgatagttta aactgaaggc gggaaacgac     60
```

```
aatctgatca tgagcggaga attaagggag tcacgttatg accccgccg atgacgcggg      120 acaagccgtt ttacgtttgg aactgacaga accgcaacgt tgaaggagcc actcagccgc      180
gggtttctgg agtttaatga gctaagcaca tacgtcagaa accattattg cgcgttcaaa      240
agtcgcctaa ggtcactatc agctagcaaa tatttcttgt caaaaatgct ccactgacgt      300
tccataaatt cccctcggta tccaattaga gtctcatatt cactctcaat ccaaataatc      360
tgcaccggat ctggatcgtt tcgcatgatt gaacaagatg gattgcacgc aggttctccg      420
gccgcttggg tggagaggct attcggctat gactgggcac aacagacaat cggctgctct      480
gatgccgccg tgttccggct gtcagcgcag gggcgcccgg ttcttttgt caagaccgac      540 ctgtccggtg ccctgaatga actgcaggac gaggcagcgc ggctatcgtg gctggccacg      600
acgggcgttc cttgcgcagc tgtgctcgac gttgtcactg aagcgggaag gactggctg       660 ctattgggcg aagtgccggg gcaggatctc ctgtcatctc accttgctcc tgccgagaaa      720
gtatccatca tggctgatgc aatgcggcgg ctgcatacgc ttgatccggc tacctgccca      780
ttcgaccacc aagcgaaaca tcgcatcgag cgagcacgta ctcggatgga agccggtctt      840
gtcgatcagg atgatctgga cgaagagcat caggggctcg cgccagccga actgttcgcc      900
aggctcaagg cgcgcatgcc cgacggcgat gatctcgtcg tgacccatgg cgatgcctgc      960
ttgccgaata tcatggtgga aaatggccgc ttttctggat tcatcgactg tggccggctg     1020
ggtgtggcgg accgctatca ggacatagcg ttggctaccc gtgatattgc tgaagagctt     1080
ggcggcgaat gggctgaccg cttcctcgtg ctttacggta tcgccgctcc cgattcgcag     1140
cgcatcgcct tctatcgcct tcttgacgag ttcttctgag cgggactctg gggttcgaaa     1200
tgaccgacca agcgacgccc aacctgccat cacgagattt cgattccacc gccgccttct     1260
atgaaaggtt gggcttcgga atcgtttcc gggacgccgg ctggatgatc ctccagcgcg     1320
gggatctcat gctggagttc ttcgcccacg gatctctgc ggaacaggcg gtcgaaggtg     1380
ccgatatcat tacgacagca acggccgaca agcacaacgc cacgatcctg agcgacaata     1440
tgatcgggcc cggcgtccac atcaacgcg tcggcggcga ctgcccaggc aagaccgaga     1500
tgcaccgcga tatcttgctg cgttcggata tttcgtgga gttcccgcca cagacccgga     1560
tgatccccga tcgttcaaac attttggcaat aaagtttctt aagattgaat cctgttgccg     1620
gtcttgcgat gattatcata taatttctgt tgaattacgt taagcatgta ataattaaca     1680
tgtaatgcat gacgttattt atgagatggg tttttatgat tagagtcccg caattataca     1740
tttaatacgc gatagaaaac aaaatatagc gcgcaaacta ggataaatta tcgcgcgcgg     1800
tgtcatctat gttactagat cgggcctcct gtcaatgctg gcggcggctc tggtggtggt     1860
tctggtggcg gctctgaggg tggtggctct gagggtggcg gttctgaggg tggcggctct     1920
gagggaggcg gttccggtgg tggctctggt tccggtgatt ttgattatga aaagatggca     1980
aacgctaata agggggctat gaccgaaaat gccgatgaaa acgcgctaca gtctgacgct     2040
aaaggcaaac ttgattctgt cgctactgat tacggtgctg ctatcgatgg tttcattggt     2100
gacgtttccg gccttgctaa tggtaatggt gctactggtg attttgctgg ctctaattcc     2160
caaatggctc aagtcggtga cggtgataat tcacctttaa tgaataattt ccgtcaatat     2220
ttaccttccc tccctcaatc ggttgaatgt cgcccttttg tctttggccc aatacgcaaa     2280
ccgcctctcc ccgcgcgttg gccgattcat taatgcagct ggcacgacag gtttcccgac     2340
tggaaagcgg gcagtgagcg caacgcaatt aatgtgagtt agctcactca ttaggcaccc     2400
caggctttac actttatgct tccggctcgt atgttgtgtg gaattgtgag cggataacaa     2460
```

| | |
|---|---|
| tttcacacag gaaacagcta tgaccatgat tacgccaagc ttgcatgcct gcagcccaca | 2520 |
| gatggttaga gaggcttacg cagcaggtct catcaagacg atctacccga gcaataatct | 2580 |
| ccaggaaatc aaataccttc ccaagaaggt taaagatgca gtcaaaagat tcaggactaa | 2640 |
| ctgcatcaag aacacagaga agatatatt tctcaagatc agaagtacta ttccagtatg | 2700 |
| gacgattcaa ggcttgcttc acaaaccaag gcaagtaata gagattggag tctctaaaaa | 2760 |
| ggtagttccc actgaatcaa aggccatgga gtcaaagatt caaatagagg acctaacaga | 2820 |
| actcgccgta aagactggcg aacagttcat acagagtctc ttacgactca atgacaagaa | 2880 |
| gaaaatcttc gtcaacatgg tggagcacga cacacttgtc tactccaaaa atatcaaaga | 2940 |
| tacagtctca gaagaccaaa gggcaattga acttttcaa caagggtaa tatccggaaa | 3000 |
| cctcctcgga ttccattgcc cagctatctg tcactttatt gtgaagatag tggaaaagga | 3060 |
| aggtggctcc tacaaatgcc atcattgcga taaaggaaag gccatcgttg aagatgcctc | 3120 |
| tgccgacagt ggtcccaaag atggaccccc acccacgagg agcatcgtgg aaaaagaaga | 3180 |
| cgttccaacc acgtcttcaa agcaagtgga ttgatgtgat atctccactg acgtaaggga | 3240 |
| tgacgcacaa tcccactatc cttcgcaaga cccttcctct atataaggaa gttcatttca | 3300 |
| tttggagaga acacggggga ctctagaccg gttcgtccag cgcggccaat ctttcaacaa | 3360 |
| ggggaggatg agaatagtga taagcagagt accaaggatc tgtattcata gctgacagat | 3420 |
| tctcctcctg tagtttcaca agaccaccgc gtaatccaga tgcatatcca agcttcttgg | 3480 |
| caaagccatc agcctgaaat tcaaatgatc ggctgactag gttcagacca aagctgacca | 3540 |
| attgctgaag tgggattaca gtatgctgaa atatgatgag cccaatgagg actggctgcg | 3600 |
| tatcaaaccc aaagcttcga tacagatcag ctgaatttcg cactagtgta tatcctccaa | 3660 |
| attgtagaag tgtaagaatc tgcatagcaa caaatgtgta cacagtatgg ttgagcttcc | 3720 |
| agtgtcccaa ctcatgggca ataacagcaa caatttcctc atcgtctttg cactgttgaa | 3780 |
| ttaatgtgtc ataagggaca atcctcttgt tcttgaagaa tccatacata taggcattgc | 3840 |
| tgtgacttga tcttgtggat ccccatctac ccgcttcgcg tcggcatccg gtcagtggca | 3900 |
| gtgaagggcg aacagttcct gattaaccac aaaccgttct actttactgg ctttggtcgt | 3960 |
| catgaagatg cggacttgcg tggcaaagga ttcgataacg tgctgatggt gcacgaccac | 4020 |
| gcattaatgg actggattgg ggccaactcc taccgtacct cgcattaccc ttacgctgaa | 4080 |
| gagatgctcg actgggcaga tgaacatggc atcgtggtga ttgatgaaac tgctgctgtc | 4140 |
| ggcttttcgc tctctttagg cattggtttc gaagcgggca acaagccgaa agaactgtac | 4200 |
| agcgaagagg cagtcaacgg ggaaactcag caagcgcact tacaggcgat taaagagctg | 4260 |
| atagcgcgtg acaaaaacca cccaagcgtg gtgatgtgga gtattgccaa cgaaccggat | 4320 |
| acccgtccgc aaggtgcacg ggaatatttc gcgccactgg cggaagcaac gcgtaaactc | 4380 |
| gacccgacgc gtccgatcac ctgcgtcaat gtaatgttct gcgacgctca caccgatacc | 4440 |
| atcagcgatc tctttgatgt gctgtgcctg aaccgttatt acggatggta tgtccaaagc | 4500 |
| ggcgatttgg aaacggcaga aaggtactg gaaaagaac ttctggcctg gcaggagaaa | 4560 |
| ctgtacaccg acatgtggag tgaagagtat cagtgtgcat ggctggatat gtatcaccgc | 4620 |
| gtctttgatc gcgtcagcgc cgtcgtcggt gaacaggtat ggaatttcgc cgattttgcg | 4680 |
| acctcgcaag gcatattgcg cgttggcggt aacaagaaag ggatcttcac tcgcgaccgc | 4740 |
| aaaccgaagt cggcggcttt tctgctgcaa aaacgctgga ctggcatgaa cttcggtgaa | 4800 |
| aaaccgcagc agggaggcaa acaatgaatc aacaactctc ctggcgcacc atcgtcggct | 4860 |

| | |
|---|---|
| acagcctcgg gaattgctac cgagctcaca agatcaagtc acagcaatgc ctatatgtat | 4920 |
| ggattcttca agaacaagag gattgtccct tatgacacat taattcaaca gtgcaaagac | 4980 |
| gatgaggaaa ttgttgctgt tattgcccat gagttgggac actggaagct caaccatact | 5040 |
| gtgtacacat ttgttgctat gcagattctt acacttctac aatttggagg atatacacta | 5100 |
| gtgcgaaatt cagctgatct gtatcgaagc tttgggtttg atacgcagcc agtcctcatt | 5160 |
| gggctcatca tatttcagca tactgtaatc ccacttcagc aattggtcag ctttggtctg | 5220 |
| aacctagtca gccgatcatt tgaatttcag gctgatggct tgccaagaa gcttggatat | 5280 |
| gcatctggat tacgcggtgg tcttgtgaaa ctacaggagg agaatctgtc agctatgaat | 5340 |
| acagatcctt ggtactctgc ttatcactat tctcatcctc cccttgttga aagattggcc | 5400 |
| gcgctggacg aaccgggagc tcgaatttcc ccgatcgttc aaacatttgg caataaagtt | 5460 |
| tcttaagatt gaatcctgtt gccggtcttg cgatgattat catataattt ctgttgaatt | 5520 |
| acgttaagca tgtaataatt aacatgtaat gcatgacgtt atttatgaga tgggttttta | 5580 |
| tgattagagt cccgcaatta tacatttaat acgcgataga aaacaaaata tagcgcgcaa | 5640 |
| actaggataa attatcgcgc gcggtgtcat ctatgttact agatcgggaa ttcactggcc | 5700 |
| gtcgttttac aacgtcgtga ctgggaaaac cctggcgtta cccaacttaa tcgccttgca | 5760 |
| gcacatcccc ctttcgccag ctggcgtaat agcgaagagg cccgcaccga tcgcccttcc | 5820 |
| caacagttgc gcagcctgaa tggcgcccgc tcctttcgct ttcttccctt cctttctcgc | 5880 |
| cacgttcgcc ggctttcccc gtcaagctct aaatcggggg ctccctttag ggttccgatt | 5940 |
| tagtgcttta cggcacctcg accccaaaaa acttgatttg ggtgatggtt cacgtagtgg | 6000 |
| gccatcgccc tgatagacgg ttttttcgccc tttgacgttg gagtccacgt tctttaatag | 6060 |
| tggactcttg ttccaaactg gaacaacact caaccctatc tcgggctatt cttttgattt | 6120 |
| ataagggatt ttgccgattt cggaaccacc atcaaacagg attttcgcct gctgggcaa | 6180 |
| accagcgtgg accgcttgct gcaactctct cagggccagg cggtgaaggg caatcagctg | 6240 |
| ttgcccgtct cactggtgaa aagaaaaacc accccagtac attaaaaacg tccgcaatgt | 6300 |
| gttattaagt tgtctaagcg tcaatttgtt tacaccacaa tatatcctgc ca | 6352 |

<210> SEQ ID NO 59
<211> LENGTH: 5549
<212> TYPE: DNA
<213> ORGANISM: Artificial Sequence
<220> FEATURE:
<223> OTHER INFORMATION: Description of Artificial Sequence:
      pBI121-antisense-GmCPP vector sequence

<400> SEQUENCE: 59

| | |
|---|---|
| gtttacccgc caatatatcc tgtcaaacac tgatagttta aactgaaggc gggaaacgac | 60 |
| aatctgatca tgagcggaga attaagggag tcacgttatg accccgccg atgacgcggg | 120 |
| acaagccgtt ttacgtttgg aactgacaga accgcaacgt tgaaggagcc actcagccgc | 180 |
| gggtttctgg agtttaatga gctaagcaca tacgtcagaa accattattg cgcgttcaaa | 240 |
| agtcgcctaa ggtcactatc agctagcaaa tatttcttgt caaaaatgct ccactgacgt | 300 |
| tccataaatt cccctcggta tccaattaga gtctcatatt cactctcaat ccaaataatc | 360 |
| tgcaccggat ctggatcgtt tcgcatgatt gaacaagatg gattgcacgc aggttctccg | 420 |
| gccgcttggg tggagaggct attcggctat gactgggcac aacagacaat cggctgctct | 480 |
| gatgccgccg tgttccggct gtcagcgcag gggcgcccgg ttcttttgt caagaccgac | 540 |

```
ctgtccggtg ccctgaatga actgcaggac gaggcagcgc ggctatcgtg gctggccacg    600
acgggcgttc cttgcgcagc tgtgctcgac gttgtcactg aagcgggaag ggactggctg    660
ctattgggcg aagtgccggg gcaggatctc ctgtcatctc accttgctcc tgccgagaaa    720
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg ttttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata gggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagcccaca   2520
gatggttaga gaggcttacg cagcaggtct catcaagacg atctacccga gcaataatct   2580
ccaggaaatc aaataccttc caagaaggt taaagatgca gtcaaaagat tcaggactaa   2640
ctgcatcaag aacacagaga aagatatatt tctcaagatc agaagtacta ttccagtatg   2700
gacgattcaa ggcttgcttc acaaaccaag gcaagtaata gagattggag tctctaaaaa   2760
ggtagttccc actgaatcaa aggccatgga gtcaaagatt caaatagagg acctaacaga   2820
actcgccgta aagactggcg aacagttcat acagagtctc ttacgactca atgacaagaa   2880
gaaaatcttc gtcaacatgg tggagcacga cacacttgtc tactccaaaa atatcaaaga   2940
```

```
tacagtctca gaagaccaaa gggcaattga gacttttcaa caaagggtaa tatccggaaa   3000
cctcctcgga ttccattgcc cagctatctg tcacttattt gtgaagatag tggaaaagga   3060
aggtggctcc tacaaatgcc atcattgcga taaaggaaag gccatcgttg aagatgcctc   3120
tgccgacagt ggtcccaaag atggaccccc acccacgagg agcatcgtgg aaaaagaaga   3180
cgttccaacc acgtcttcaa agcaagtgga ttgatgtgat atctccactg acgtaaggga   3240
tgacgcacaa tcccactatc cttcgcaaga cccttcctct atataaggaa gttcatttca   3300
tttggagaga cacggggga ctctagagga tccccgggtt agtcttcctt cttatccggt   3360
tcgtccagcg cggccaatct ttcaacaagg ggaggatgag aatagtgata agcagagtac   3420
caaggatctg tattcatagc tgacagattc tcctcctgta gtttcacaag accaccgcgt   3480
aatccagatg catatccaag cttcttggca aagccatcag cctgaaattc aaatgatcgg   3540
ctgactaggt tcagaccaaa gctgaccaat tgctgaagtg ggattacagt atgctgaaat   3600
atgatgagcc caatgaggac tggctgcgta tcaaacccaa agcttcgata cagatcagct   3660
gaatttcgca ctagtgtata tcctccaaat tgtagaagtg taagaatctg catagcaaca   3720
aatgtgtaca cagtatggtt gagcttccag tgtcccaact catgggcaat aacagcaaca   3780
atttcctcat cgtctttgca ctgttgaatt aatgtgtcat aagggacaat cctcttgttc   3840
ttgaagaatc catacatata ggcattgctg tgacttgatc ttgtggatcc atcgacaaca   3900
aatagtttct ttaacggata gttgagggag gaagcaagtt tctcgatttt ctccctgagt   3960
tgaccatctg gaagtggagt gaacttattg aagagtggag ctattagtac tggataaagg   4020
gtcatcatca caatagaaag accaaacgta aaaacccaaa gatagatggc caagtatgga   4080
cctcctttct gtactattac aatgattgca gccacaatag gtggaccaat tattacagaa   4140
aggaaaattc ctttaagcat gtccctaaag aataaccatg gtgtttgctt attaaaacca   4200
tgacgggcct caatcacaaa agttgagtac agagaaaagg gcaaatctgt tatctgtgac   4260
caaatcatca gccctgctaa gaaggcaagg gtatgcagta tttcattctc agcattgaaa   4320
ccagctattg tcataaaatc tcctgatttc ttccaaaacc agggcaatac cccaaagtac   4380
aaaattgtag agtctgtcac tattgtcaca aactcgtgaa caaaatggaa gtggctttta   4440
tcaagactat aggctctaga tttctcaaat ttctcttggc tgataacacc ctctaaagtc   4500 tttgaagag taggaagttt gagggcccta tgttgtcgca catccaagta agtttcaaaa   4560
atgtacatta atatcataaa tccgacaacg gcttccatgt agggaaacgc catgagctcg   4620
aatttccccg atcgttcaaa catttggcaa taaagtttct taagattgaa tcctgttgcc   4680
ggtcttgcga tgattatcat ataatttctg ttgaattacg ttaagcatgt aataattaac   4740
atgtaatgca tgacgttatt tatgagatgg gttttatga ttagagtccc gcaattatac   4800
atttaatacg cgatagaaaa caaaatatag cgcgcaaact aggataaatt atcgcgcgcg   4860
gtgtcatcta tgttactaga tcgggaattc actggccgtc gttttacaac gtcgtgactg   4920
ggaaaaccct ggcgttaccc aacttaatcg ccttgcagca catcccccctt tcgccagctg   4980 gcgtaatagc gaagaggccc gcaccgatcg cccttcccaa cagttgcgca gcctgaatgg   5040
cgcccgctcc tttcgctttc ttcccttcct ttctcgccac gttcgccggc tttccccgtc   5100
aagctctaaa tcggggggctc cctttagggt tccgatttag tgctttacgg cacctcgacc   5160
ccaaaaaact tgatttgggt gatggttcac gtagtgggcc atcgccctga tagacggttt   5220
ttcgcccttt gacgttggag tccacgttct ttaatagtgg actcttgttc caaactggaa   5280
caacactcaa ccctatctcg ggctattctt ttgatttata agggattttg ccgatttcgg   5340
```

-continued

| | |
|---|---|
| aaccaccatc aaacaggatt ttcgcctgct ggggcaaacc agcgtggacc gcttgctgca | 5400 |
| actctctcag ggccaggcgg tgaagggcaa tcagctgttg cccgtctcac tggtgaaaag | 5460 |
| aaaaaccacc ccagtacatt aaaaacgtcc gcaatgtgtt attaagttgt ctaagcgtca | 5520 |
| atttgtttac accacaatat atcctgcca | 5549 |

<210> SEQ ID NO 60
<211> LENGTH: 5673
<212> TYPE: DNA
<213> ORGANISM: Artificial Sequence
<220> FEATURE:
<223> OTHER INFORMATION: Description of Artificial Sequence:
      pRD29A-GmCPP vector sequence

<400> SEQUENCE: 60

| | |
|---|---|
| gtttacccgc caatatatcc tgtcaaacac tgatagttta aactgaaggc gggaaacgac | 60 |
| aatctgatca tgagcggaga attaaggag tcacgttatg accccgccg atgacgcggg | 120 |
| acaagccgtt ttacgtttgg aactgacaga accgcaacgt tgaaggagcc actcagccgc | 180 |
| gggtttctgg agtttaatga gctaagcaca tacgtcagaa accattattg cgcgttcaaa | 240 |
| agtcgcctaa ggtcactatc agctagcaaa tatttcttgt caaaaatgct ccactgacgt | 300 |
| tccataaatt cccctcggta tccaattaga gtctcatatt cactctcaat ccaaataatc | 360 |
| tgcaccggat ctggatcgtt tcgcatgatt gaacaagatg gattgcacgc aggttctccg | 420 |
| gccgcttggg tggagaggct attcggctat gactgggcac aacagacaat cggctgctct | 480 |
| gatgccgccg tgttccggct gtcagcgcag gggcgcccgg ttcttttgt caagaccgac | 540 |
| ctgtccggtg ccctgaatga actgcaggac gaggcagcgc ggctatcgtg gctggccacg | 600 |
| acgggcgttc cttgcgcagc tgtgctcgac gttgtcactg aagcgggaag ggactggctg | 660 |
| ctattgggcg aagtgccggg gcaggatctc ctgtcatctc accttgctcc tgccgagaaa | 720 |
| gtatccatca tggctgatgc aatgcggcgg ctgcatacgc ttgatccggc tacctgccca | 780 |
| ttcgaccacc aagcgaaaca tcgcatcgag cgagcacgta ctcggatgga agccggtctt | 840 |
| gtcgatcagg atgatctgga cgaagagcat caggggctcg cgccagccga actgttcgcc | 900 |
| aggctcaagg cgcgcatgcc cgacggcgat gatctcgtcg tgacccatgg cgatgcctgc | 960 |
| ttgccgaata tcatggtgga aaatggccgc ttttctggat tcatcgactg tggccggctg | 1020 |
| ggtgtggcgg accgctatca ggacatagcg ttggctaccc gtgatattgc tgaagagctt | 1080 |
| ggcggcgaat gggctgaccg cttcctcgtg ctttacggta tcgccgctcc cgattcgcag | 1140 |
| cgcatcgcct tctatcgcct tcttgacgag ttcttctgag cgggactctg gggttcgaaa | 1200 |
| tgaccgacca agcgacgccc aacctgccat cacgagattt cgattccacc gccgccttct | 1260 |
| atgaaaggtt gggcttcgga atcgtttttcc gggacgccgg ctggatgatc ctccagcgcg | 1320 |
| gggatctcat gctggagttc ttcgcccacg gatctctgc ggaacaggcg gtcgaaggtg | 1380 |
| ccgatatcat tacgacagca acggccgaca agcacaacgc cacgatcctg agcgacaata | 1440 |
| tgatcgggcc cggcgtccac atcaacggcg tcggcggcga ctgccaggc aagaccgaga | 1500 |
| tgcaccgcga tatcttgctg cgttcggata ttttcgtgga gttcccgcca cagacccgga | 1560 |
| tgatccccga tcgttcaaac atttggcaat aaagtttctt aagattgaat cctgttgccg | 1620 |
| gtcttgcgat gattatcata taatttctgt tgaattacgt taagcatgta ataattaaca | 1680 |
| tgtaatgcat gacgttattt atgagatggg ttttatgat tagagtcccg caattataca | 1740 |
| tttaatacgc gatagaaaac aaaatatagc gcgcaaacta ggataaatta tcgcgcgcgg | 1800 |
| tgtcatctat gttactagat cgggcctcct gtcaatgctg gcggcggctc tggtggtggt | 1860 |

```
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata aggggctat gaccgaaaat gccgatgaaa acgcgctaca gtctgacgct    2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagggagcc   2520
atagatgcaa ttcaatcaaa ctgaaatttc tgcaagaatc tcaaacacgg agatctcaaa   2580
gtttgaaaga aaatttattt cttcgactca aacaaactt acgaaattta ggtagaactt    2640
atatacatta tattgtaatt ttttgtaaca aaatgttttt attattatta tagaatttta   2700
ctggttaaat taaaaatgaa tagaaaaggt gaattaagag gagagaggag gtaaacattt   2760 tcttctatt tttcatattt tcaggataaa ttattgtaaa agtttacaag atttccattt     2820
gactagtgta aatgaggaat attctctagt aagatcatta tttcatctac ttcttttatc   2880
ttctaccagt agaggaataa acaatattta gctcctttgt aaatacaaat taatttcct    2940 tcttgacatc attcaatttt aattttacgt ataaataaa agatcatacc tattagaacg    3000
attaaggaga aatacaattc gaatgagaag gatgtgccgt ttgttataat aaacagccac   3060
acgacgtaaa cgtaaaatga ccacatgatg ggccaataga catggaccga ctactaataa   3120
tagtaagtta catttagga tggaataaat atcataccga catcagtttt gaagaaaag    3180 ggaaaaaag aaaaaataaa taaaagatat actaccgaca tgagttccaa aaagcaaaaa   3240
aaaagatcaa gccgacacag acacgcgtag agagcaaaat gactttgacg tcacaccacg   3300
aaaacagacg cttcatacgt gtccctttat ctctctcagt ctctctataa acttagtgag   3360
accctcctct gttttactca caaatatgca aactagaaaa caatcatcag gaataaaggg   3420
tttgattact tctattggaa aggactctag aggatccccg ggatggcgtt tccctacatg   3480
gaagccgttg tcggatttat gatattaatg tacattttg aaacttactt ggatgtgcga    3540 caacatagg ccctcaaact tcctactctt ccaaagactt tagagggtgt tatcagccaa    3600
gagaaatttg agaaatctag agcctatagt cttgataaaa gccacttcca ttttgttcac   3660
gagtttgtga caatagtgac agactctaca attttgtact ttggggtatt gccctggttt   3720
tggaagaaat caggagattt tatgacaata gctggtttca atgctgagaa tgaaatactg   3780 cataccttg ccttcttagc agggctgatg atttggtcac agataacaga tttgccctt     3840 tctctgtact caacttttgt gattgaggcc cgtcatggtt ttaataagca aacaccatgg   3900
ttattcttta gggacatgct taaggaatt tccttctg taataattgg tccacctatt       3960
gtggctgcaa tcattgtaat agtacagaaa ggaggtccat acttggccat ctatctttgg   4020 gttttacgt ttggtctttc tattgtgatg atgacccttt atccagtact aatagctcca    4080
ctcttcaata agttcactcc acttccagat ggtcaactca gggagaaaat cgagaaactt   4140
gcttcctccc tcaactatcc gttaaagaaa ctatttgttg tcgatggatc cacaagatca   4200
agtcacagca atgcctatat gtatggattc ttcaagaaca agaggattgt cccttatgac   4260
```

```
acattaattc aacagtgcaa agacgatgag gaaattgttg ctgttattgc ccatgagttg    4320
ggacactgga agctcaacca tactgtgtac acatttgttg ctatgcagat tcttacactt    4380
ctacaatttg gaggatatac actagtgcga aattcagctg atctgtatcg aagctttggg    4440
tttgatacgc agccagtcct cattgggctc atcatatttc agcatactgt aatcccactt    4500
cagcaattgg tcagctttgg tctgaaccta gtcagccgat catttgaatt tcaggctgat    4560
ggctttgcca agaagcttgg atatgcatct ggattacgcg gtggtcttgt gaaactacag    4620
gaggagaatc tgtcagctat gaatacagat ccttggtact ctgcttatca ctattctcat    4680 cctcccttg ttgaaagatt ggccgcgctg gacgaaccgg ataagaagga agactaagag    4740
ctcgaatttc cccgatcgtt caaacatttg gcaataaagt ttcttaagat tgaatcctgt    4800
tgccggtctt gcgatgatta tcatataatt tctgttgaat tacgttaagc atgtaataat    4860
taacatgtaa tgcatgacgt tatttatgag atgggttttt atgattagag tcccgcaatt    4920
atacatttaa tacgcgatag aaaacaaaat atagcgcgca aactaggata aattatcgcg    4980
cgcggtgtca tctatgttac tagatcggga attcactggc cgtcgtttta caacgtcgtg    5040
actgggaaaa ccctggcgtt acccaactta atcgccttgc agcacatccc ctttcgcca    5100 gctggcgtaa tagcgaagag cccgcaccg atcgcccttc ccaacagttg cgcagcctga    5160
atggcgcccg ctcctttcgc tttcttccct cctttctcg ccacgttcgc cggctttccc    5220
cgtcaagctc taaatcgggg gctccctta gggttccgat ttagtgcttt acggcacctc    5280
gaccccaaaa aacttgattt gggtgatggt tcacgtagtg ggccatcgcc ctgatagacg    5340
gtttttcgcc ctttgacgtt ggagtccacg ttctttaata gtggactctt gttccaaact    5400
ggaacaacac tcaaccctat ctcgggctat tcttttgatt tataagggat tttgccgatt    5460
tcggaaccac catcaaacag gattttcgcc tgctgggca aaccagcgtg gaccgcttgc    5520
tgcaactctc tcagggccag gcggtgaagg gcaatcagct gttgcccgtc tcactggtga    5580
aaagaaaaac caccccagta cattaaaaac gtccgcaatg tgttattaag ttgtctaagc    5640
gtcaatttgt ttacaccaca atatatcctg cca                                 5673
```

<210> SEQ ID NO 61
<211> LENGTH: 6476
<212> TYPE: DNA
<213> ORGANISM: Artificial Sequence
<220> FEATURE:
<223> OTHER INFORMATION: Description of Artificial Sequence:
      pRD29A-HP-GmCPP vector sequence

<400> SEQUENCE: 61

```
gtttaccgc caatatatcc tgtcaaacac tgatagttta aactgaaggc gggaaacgac      60
aatctgatca tgagcggaga attaagggag tcacgttatg accccgccg atgacgcggg    120 acaagccgtt ttacgtttgg aactgacaga accgcaacgt tgaaggagcc actcagccgc    180
gggtttctgg agtttaatga gctaagcaca tacgtcagaa accattattg cgcgttcaaa    240
agtcgcctaa ggtcactatc agctagcaaa tatttcttgt caaaaatgct ccactgacgt    300
tccataaatt cccctcggta tccaattaga gtctcatatt cactctcaat ccaaataatc    360
tgcaccggat ctggatcgtt tcgcatgatt gaacaagatg gattgcacgc aggttctccg    420
gccgcttggg tggagaggct attcggctat gactgggcac aacagacaat cggctgctct    480
gatgccgccg tgttccggct gtcagcgcag gggcgcccgg ttcttttgt caagaccgac    540 ctgtccggtg ccctgaatga actgcaggac gaggcagcgc ggctatcgtg gctggccacg    600
```

```
acgggcgttc cttgcgcagc tgtgctcgac gttgtcactg aagcgggaag ggactggctg    660
ctattgggcg aagtgccggg gcaggatctc ctgtcatctc accttgctcc tgccgagaaa    720
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgtttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagcccggga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata aggggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgccctttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagggagcc   2520
atagatgcaa ttcaatcaaa ctgaaatttc tgcaagaatc tcaaacacgg agatctcaaa   2580
gtttgaaaga aaatttattt cttcgactca aaacaaactt acgaaattta ggtagaactt   2640
atatacatta tattgtaatt ttttgtaaca aaatgttttt attattatta tagaattta    2700 ctggttaaat taaaaatgaa tagaaaaggt gaattaagag gagagaggag gtaaacattt   2760 tcttctatt tttcatatt tcaggataaa ttattgtaaa agtttacaag atttccattt    2820
gactagtgta aatgaggaat attctctagt aagatcatta tttcatctac ttctttatc    2880 ttctaccagt agaggaataa acaatattta gctccttgt aaatacaaat taattttcct   2940
tcttgacatc attcaatttt aatttacgt ataaataaa agatcatacc tattagaacg    3000
```

```
attaaggaga aatacaattc gaatgagaag gatgtgccgt ttgttataat aaacagccac    3060
acgacgtaaa cgtaaaatga ccacatgatg ggccaataga catggaccga ctactaataa    3120
tagtaagtta cattttagga tggaataaat atcataccga catcagtttt gaaagaaaag    3180
ggaaaaaaag aaaaaataaa taaaagatat actaccgaca tgagttccaa aaagcaaaaa    3240
aaaagatcaa gccgacacag acacgcgtag agagcaaaat gactttgacg tcacaccacg    3300
aaaacagacc cttcatacgt gtcccttat ctctctcagt ctctctataa acttagtgag    3360
accctcctct gttttactca caaatatgca aactagaaaa caatcatcag gaataaaggg    3420
tttgattact tctattggaa aggactctag accggttcgt ccagcgcggc caatctttca    3480
acaaggggag gatgagaata gtgataagca gagtaccaag gatctgtatt catagctgac    3540
agattctcct cctgtagttt cacaagacca ccgcgtaatc cagatgcata tccaagcttc    3600
ttggcaaagc catcagcctg aaattcaaat gatcggctga ctaggttcag accaaagctg    3660
accaattgct gaagtgggat tacagtatgc tgaaatatga tgagcccaat gaggactggc    3720
tgcgtatcaa acccaaagct tcgatacaga tcagctgaat ttcgcactag tgtatatcct    3780
ccaaattgta gaagtgtaag aatctgcata gcaacaaatg tgtacacagt atggttgagc    3840
ttccagtgtc ccaactcatg ggcaataaca gcaacaattt cctcatcgtc tttgcactgt    3900
tgaattaatg tgtcataagg gacaatcctc ttgttcttga agaatccata catataggca    3960
ttgctgtgac ttgatcttgt ggatccccat ctacccgctt cgcgtcggca tccggtcagt    4020
ggcagtgaag ggcgaacagt tcctgattaa ccacaaaccg ttctacttta ctggctttgg    4080
tcgtcatgaa gatgcggact tgcgtggcaa aggattcgat aacgtgctga tggtgcacga    4140
ccacgcatta atggactgga ttggggccaa ctcctaccgt acctcgcatt ccccttacgc    4200
tgaagagatg ctcgactggg cagatgaaca tggcatcgtg gtgattgatg aaactgctgc    4260
tgtcggcttt tcgctctctt taggcattgg tttcgaagcg ggcaacaagc cgaaagaact    4320
gtacagcgaa gaggcagtca acggggaaac tcagcaagcg cacttacagg cgattaaaga    4380
gctgatagcg cgtgacaaaa accacccaag cgtggtgatg tggagtattg ccaacgaacc    4440 ggataccgt ccgcaaggtg cacgggaata tttcgcgcca ctggcggaag caacgcgtaa    4500
actcgacccg acgcgtccga tcacctgcgt caatgtaatg ttctgcgacg ctcacaccga    4560
taccatcagc gatctctttg atgtgctgtg cctgaaccgt tattacggat ggtatgtcca    4620
aagcggcgat ttggaaacgg cagagaaggt actggaaaaa gaacttctgg cctggcagga    4680
gaaactgtac accgacatgt ggagtgaaga gtatcagtgt gcatggctgg atatgtatca    4740
ccgcgtcttt gatcgcgtca gcgccgtcgt cggtgaacag gtatggaatt cgccgatttt    4800
tgcgacctcg caaggcatat tgcgcgttgg cggtaacaag aaagggatct tcactcgcga    4860
ccgcaaaccg aagtcggcgg cttttctgct gcaaaaacgc tggactggca tgaacttcgg    4920
tgaaaaaccg cagcagggag gcaaacaatg aatcaacaac tctcctggcg caccatcgtc    4980
ggctacagcc tcgggaattg ctaccgagct cacaagatca agtcacagca atgcctatat    5040
gtatggattc ttcaagaaca agaggattgt cccttatgac acattaattc aacagtgcaa    5100
agacgatgag gaaattgttg ctgttattgc ccatgagttg ggacactgga agctcaacca    5160
tactgtgtac acatttgttg ctatgcagat tcttacactt ctacaatttg gaggatatac    5220
actagtgcga aattcagctg atctgtatcg aagctttggg tttgatacgc agccagtcct    5280
cattgggctc atcatatttc agcatactgt aatcccactt cagcaattgg tcagctttgg    5340
tctgaaccta gtcagccgat catttgaatt tcaggctgat ggctttgcca agaagcttgg    5400
```

| | |
|---|---|
| atatgcatct ggattacgcg gtggtcttgt gaaactacag gaggagaatc tgtcagctat | 5460 |
| gaatacagat ccttggtact ctgcttatca ctattctcat cctcccttg ttgaaagatt | 5520 |
| ggccgcgctg gacgaaccgg gagctcgaat ttccccgatc gttcaaacat ttggcaataa | 5580 |
| agtttcttaa gattgaatcc tgttgccggt cttgcgatga ttatcatata atttctgttg | 5640 |
| aattacgtta agcatgtaat aattaacatg taatgcatga cgttatttat gagatgggtt | 5700 |
| tttatgatta gagtcccgca attatacatt taatacgcga tagaaaacaa aatatagcgc | 5760 |
| gcaaactagg ataaattatc gcgcgcggtg tcatctatgt tactagatcg ggaattcact | 5820 |
| ggccgtcgtt ttacaacgtc gtgactggga aaaccctggc gttacccaac ttaatcgcct | 5880 |
| tgcagcacat ccccctttcg ccagctggcg taatagcgaa gaggcccgca ccgatcgccc | 5940 |
| ttcccaacag ttgcgcagcc tgaatggcgc ccgctccttt cgctttcttc ccttcctttc | 6000 |
| tcgccacgtt cgccggcttt ccccgtcaag ctctaaatcg ggggctccct ttagggttcc | 6060 |
| gatttagtgc tttacggcac ctcgacccca aaaaacttga tttgggtgat ggttcacgta | 6120 |
| gtgggccatc gccctgatag acggtttttc gccctttgac gttggagtcc acgttcttta | 6180 |
| atagtggact cttgttccaa actggaacaa cactcaaccc tatctcgggc tattcttttg | 6240 |
| atttataagg gattttgccg atttcggaac caccatcaaa caggattttc gcctgctggg | 6300 |
| gcaaaccagc gtggaccgct tgctgcaact ctctcagggc caggcggtga agggcaatca | 6360 |
| gctgttgccc gtctcactgg tgaaaagaaa aaccaccca gtacattaaa aacgtccgca | 6420 |
| atgtgttatt aagttgtcta agcgtcaatt tgtttacacc acaatatatc ctgcca | 6476 |

<210> SEQ ID NO 62
<211> LENGTH: 5673
<212> TYPE: DNA
<213> ORGANISM: Artificial Sequence
<220> FEATURE:
<223> OTHER INFORMATION: Description of Artificial Sequence:
      pRD29A-antisense-GmCPP vector sequence

<400> SEQUENCE: 62

| | |
|---|---|
| gtttaccgc caatatatcc tgtcaaacac tgatagttta aactgaaggc gggaaacgac | 60 |
| aatctgatca tgagcggaga attaagggag tcacgttatg accccgccg atgacgcggg | 120 |
| acaagccgtt ttacgtttgg aactgacaga accgcaacgt tgaaggagcc actcagccgc | 180 |
| gggtttctgg agtttaatga gctaagcaca tacgtcagaa accattattg cgcgttcaaa | 240 |
| agtcgcctaa ggtcactatc agctagcaaa tatttcttgt caaaaatgct ccactgacgt | 300 |
| tccataaatt cccctcggta tccaattaga gtctcatatt cactctcaat ccaaataatc | 360 |
| tgcaccggat ctggatcgtt tcgcatgatt gaacaagatg gattgcacgc aggttctccg | 420 |
| gccgcttggg tggagaggct attcggctat gactgggcac aacagacaat cggctgctct | 480 |
| gatgccgccg tgttccggct gtcagcgcag gggcgcccgg ttcttttgt caagaccgac | 540 |
| ctgtccggtg ccctgaatga actgcaggac gaggcagcgc ggctatcgtg gctggccacg | 600 |
| acgggcgttc cttgcgcagc tgtgctcgac gttgtcactg aagcgggaag ggactggctg | 660 |
| ctattgggcg aagtgccggg gcaggatctc ctgtcatctc accttgctcc tgccgagaaa | 720 |
| gtatccatca tggctgatgc aatgcggcgg ctgcatacgc ttgatccggc tacctgccca | 780 |
| ttcgaccacc aagcgaaaca tcgcatcgag cgagcacgta ctcggatgga agccggtctt | 840 |
| gtcgatcagg atgatctgga cgaagagcat caggggctcg cgccagccga actgttcgcc | 900 |
| aggctcaagg cgcgcatgcc cgacggcgat gatctcgtcg tgacccatgg cgatgcctgc | 960 |
| ttgccgaata tcatggtgga aaatggccgc ttttctggat tcatcgactg tggccggctg | 1020 |

```
ggtgtggcgg accgctatca ggacatagcg ttggctaccc gtgatattgc tgaagagctt    1080
ggcggcgaat gggctgaccg cttcctcgtg ctttacggta tcgccgctcc cgattcgcag    1140
cgcatcgcct tctatcgcct tcttgacgag ttcttctgag cgggactctg ggttcgaaa     1200 tgaccgacca agcgacgccc aacctgccat cacgagattt cgattccacc gccgccttct    1260
atgaaaggtt gggcttcgga atcgttttcc gggacgccgg ctggatgatc ctccagcgcg    1320
gggatctcat gctggagttc ttcgcccacg ggatctctgc ggaacaggcg gtcgaaggtg    1380
ccgatatcat tacgacagca acggccgaca agcacaacgc cacgatcctg agcgacaata    1440
tgatcgggcc cggcgtccac atcaacggcg tcggcggcga ctgcccaggc aagaccgaga    1500
tgcaccgcga tatcttgctg cgttcggata ttttcgtgga gttcccgcca cagacccgga    1560
tgatccccga tcgttcaaac atttggcaat aaagtttctt aagattgaat cctgttgccg    1620
gtcttgcgat gattatcata taatttctgt tgaattacgt taagcatgta ataattaaca    1680
tgtaatgcat gacgttattt atgagatggg tttttatgat tagagtcccg caattataca    1740
tttaatacgc gatagaaaac aaaatatagc gcgcaaacta ggataaatta tcgcgcgcgg    1800
tgtcatctat gttactagat cgggcctcct gtcaatgctg gcggcggctc tggtggtggt    1860
tctggtggcg gctctgaggg tggtggctct gagggtggcg gttctgaggg tggcggctct    1920
gagggaggcg gttccggtgg tggctctggt tccggtgatt ttgattatga aaagatggca    1980
aacgctaata gggggctat gaccgaaaat gccgatgaaa acgcgctaca gtctgacgct    2040
aaaggcaaac ttgattctgt cgctactgat tacggtgctg ctatcgatgg tttcattggt    2100
gacgtttccg gccttgctaa tggtaatggt gctactggtg attttgctgg ctctaattcc    2160
caaatggctc aagtcggtga cggtgataat tcacctttaa tgaataattt ccgtcaatat    2220
ttaccttccc tccctcaatc ggttgaatgt cgcccttttg tctttggccc aatacgcaaa    2280
ccgcctctcc ccgcgcgttg gccgattcat taatgcagct ggcacgacag gtttcccgac    2340
tggaaagcgg gcagtgagcg caacgcaatt aatgtgagtt agctcactca ttaggcaccc    2400
caggctttac actttatgct tccggctcgt atgttgtgtg gaattgtgag cggataacaa    2460
tttcacacag gaaacagcta tgaccatgat tacgccaagc ttgcatgcct gcagggagcc    2520
atagatgcaa ttcaatcaaa ctgaaatttc tgcaagaatc tcaaacacgg agatctcaaa    2580
gtttgaaaga aaatttattt cttcgactca aaacaaactt acgaaattta ggtagaactt    2640
atatacatta tattgtaatt ttttgtaaca aaatgttttt attattatta tagaatttta    2700
ctggttaaat taaaaatgaa tagaaaaggt gaattaagag gagagaggag gtaaacattt    2760 tcttctatt tttcatattt tcaggataaa ttattgtaaa agtttacaag atttccattt     2820
gactagtgta aatgaggaat attctctagt aagatcatta tttcatctac ttcttttatc    2880
ttctaccagt agaggaataa acaatattta gctcctttgt aaatacaaat taattttcct    2940
tcttgacatc attcaatttt aattttacgt ataaaataaa agatcatacc tattagaacg    3000
attaaggaga aatacaattc gaatgagaag gatgtgccgt tgttataat aaacagccac     3060 acgacgtaaa cgtaaaatga ccacatgatg ggccaataga catggaccga ctactaataa    3120
tagtaagtta cattttagga tggaataaat atcataccga catcagtttt gaaagaaaag    3180 ggaaaaaag aaaaaataaa taaaagatat actaccgaca tgagttccaa aaagcaaaaa     3240
aaaagatcaa gccgacacag acacgcgtag agagcaaaat gactttgacg tcacaccacg    3300
aaaacagacg cttcatacgt gtccctttat ctctctcagt ctctctataa acttagtgag    3360
accctcctct gttttactca caaatatgca aactagaaaa caatcatcag gaataaaggg    3420
```

```
tttgattact tctattggaa aggactctag aggatccccg ggttagtctt ccttcttatc    3480
cggttcgtcc agcgcggcca atctttcaac aaggggagga tgagaatagt gataagcaga    3540
gtaccaagga tctgtattca tagctgacag attctcctcc tgtagtttca caagaccacc    3600
gcgtaatcca gatgcatatc caagcttctt ggcaaagcca tcagcctgaa attcaaatga    3660
tcggctgact aggttcagac caaagctgac caattgctga agtgggatta cagtatgctg    3720
aaatatgatg agcccaatga ggactggctg cgtatcaaac ccaaagcttc gatacagatc    3780
agctgaattt cgcactagtg tatatcctcc aaattgtaga agtgtaagaa tctgcatagc    3840
aacaaatgtg tacacagtat ggttgagctt ccagtgtccc aactcatggg caataacagc    3900
aacaatttcc tcatcgtctt tgcactgttg aattaatgtg tcataaggga caatcctctt    3960
gttcttgaag aatccataca tataggcatt gctgtgactt gatcttgtgg atccatcgac    4020
aacaaatagt ttctttaacg gatagttgag ggaggaagca agtttctcga ttttctccct    4080
gagttgacca tctggaagtg gagtgaactt attgaagagt ggagctatta gtactggata    4140
aagggtcatc atcacaatag aaagaccaaa cgtaaaaacc caaagataga tggccaagta    4200
tggacctcct ttctgtacta ttacaatgat tgcagccaca ataggtggac caattattac    4260
agaaaggaaa attcctttaa gcatgtccct aaagaataac catggtgttt gcttattaaa    4320
accatgacgg gcctcaatca caaagttga gtacagagaa aagggcaaat ctgttatctg    4380
tgaccaaatc atcagccctg ctaagaaggc aagggtatgc agtatttcat tctcagcatt    4440
gaaaccagct attgtcataa aatctcctga tttcttccaa aaccagggca ataccccaaa    4500
gtacaaaatt gtagagtctg tcactattgt cacaaactcg tgaacaaaat ggaagtggct    4560
tttatcaaga ctataggctc tagatttctc aaatttctct tggctgataa caccctctaa    4620
agtctttgga agagtaggaa gtttgagggc cctatgttgt cgcacatcca gtaagtttc    4680
aaaaatgtac attaatatca taaatccgac aacggcttcc atgtagggaa acgccatgag    4740
ctcgaatttc cccgatcgtt caaacatttg gcaataaagt ttcttaagat tgaatcctgt    4800
tgccggtctt gcgatgatta tcatataatt tctgttgaat tacgttaagc atgtaataat    4860
taacatgtaa tgcatgacgt tatttatgag atgggttttt atgattagag tcccgcaatt    4920
atacatttaa tacgcgatag aaaacaaaat atagcgcgca aactaggata aattatcgcg    4980
cgcggtgtca tctatgttac tagatcggga attcactggc cgtcgtttta caacgtcgtg    5040
actgggaaaa ccctggcgtt acccaactta atcgccttgc agcacatccc ctttcgcca    5100
gctggcgtaa tagcgaagag gcccgcaccg atcgcccttc ccaacagttg cgcagcctga    5160
atggcgcccg ctcctttcgc tttcttccct tcctttctcg ccacgttcgc cggctttccc    5220
cgtcaagctc taaatcgggg gctcccttta gggttccgat ttagtgcttt acggcacctc    5280
gaccccaaaa aacttgattt gggtgatggt tcacgtagtg ggccatcgcc ctgatagacg    5340
gtttttcgcc ctttgacgtt ggagtccacg ttctttaata gtggactctt gttccaaact    5400
ggaacaacac tcaaccctat ctcgggctat tctttgatt tataagggat tttgccgatt    5460
tcggaaccac catcaaacag gattttcgcc tgctggggca aaccagcgtg gaccgcttgc    5520
tgcaactctc tcagggccag gcggtgaagg gcaatcagct gttgcccgtc tcactggtga    5580
aaagaaaaac cacccccagta cattaaaaac gtccgcaatg tgttattaag ttgtctaagc    5640
gtcaatttgt ttacaccaca atatatcctg cca                                 5673

<210> SEQ ID NO 63
<211> LENGTH: 5544
```

```
<212> TYPE: DNA
<213> ORGANISM: Artificial Sequence
<220> FEATURE:
<223> OTHER INFORMATION: Description of Artificial Sequence:
      pBI121-BnCPP vector sequence

<400> SEQUENCE: 63
gtttacccgc caatatatcc tgtcaaacac tgatagttta aactgaaggc gggaaacgac      60
aatctgatca tgagcggaga attaagggag tcacgttatg accccgccg atgacgcggg     120 acaagccgtt ttacgtttgg aactgacaga accgcaacgt tgaaggagcc actcagccgc    180
gggtttctgg agtttaatga gctaagcaca tacgtcagaa accattattg cgcgttcaaa    240
agtcgcctaa ggtcactatc agctagcaaa tatttcttgt caaaaatgct ccactgacgt    300
tccataaatt cccctcggta tccaattaga gtctcatatt cactctcaat ccaaataatc    360
tgcaccggat ctggatcgtt tcgcatgatt gaacaagatg gattgcacgc aggttctccg    420
gccgcttggg tggagaggct attcggctat gactgggcac aacagacaat cggctgctct    480
gatgccgccg tgttccggct gtcagcgcag gggcgcccgg ttcttttgt caagaccgac     540 ctgtccggtg ccctgaatga actgcaggac gaggcagcgc ggctatcgtg gctggccacg    600
acgggcgttc cttgcgcagc tgtgctcgac gttgtcactg aagcgggaag ggactggctg    660
ctattgggcg aagtgccggg gcaggatctc ctgtcatctc accttgctcc tgccgagaaa    720
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg gatctctgc ggaacaggcg gtcgaaggtg     1380
ccgatatcat tacgacagca acggccgaca agcacaacgc cacgatcctg agcgacaata   1440
tgatcgggcc cggcgtccac atcaacgcg tcggcggcga ctgccaggc aagaccgaga     1500 tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata aatttctgt tgaattacgt taagcatgta ataattaaca    1680
tgtaatgcat gacgttattt atgagatggg ttttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
```

-continued

```
caaatggctc aagtcggtga cggtgataat tcacctttaa tgaataattt ccgtcaatat      2220
ttaccttccc tccctcaatc ggttgaatgt cgcccttttg tctttggccc aatacgcaaa      2280
ccgcctctcc ccgcgcgttg gccgattcat taatgcagct ggcacgacag gtttcccgac      2340
tggaaagcgg gcagtgagcg caacgcaatt aatgtgagtt agctcactca ttaggcaccc      2400
caggctttac actttatgct tccggctcgt atgttgtgtg gaattgtgag cggataacaa      2460
tttcacacag gaaacagcta tgaccatgat tacgccaagc ttgcatgcct gcagcccaca      2520
gatggttaga gaggcttacg cagcaggtct catcaagacg atctacccga gcaataatct      2580
ccaggaaatc aaataccttc caagaaggt taaagatgca gtcaaagat tcaggactaa        2640 ctgcatcaag aacacagaga aagatatatt tctcaagatc agaagtacta ttccagtatg      2700
gacgattcaa ggcttgcttc acaaaccaag gcaagtaata gagattggag tctctaaaaa      2760
ggtagttccc actgaatcaa aggccatgga gtcaaagatt caaatagagg acctaacaga      2820
actcgccgta aagactggcg aacagttcat acagagtctc ttacgactca atgacaagaa      2880
gaaaatcttc gtcaacatgg tggagcacga cacacttgtc tactccaaaa atatcaaaga      2940
tacagtctca gaagaccaaa gggcaattga acttttcaa caagggtaa tatccggaaa        3000 cctcctcgga ttccattgcc cagctatctg tcactttatt gtgaagatag tggaaaagga     3060
aggtggctcc tacaaatgcc atcattgcga taaaggaaag gccatcgttg aagatgcctc      3120
tgccgacagt ggtcccaaag atggaccccc acccacgagg agcatcgtgg aaaaagaaga     3180
cgttccaacc acgtcttcaa agcaagtgga ttgatgtgat atctccactg acgtaaggga     3240
tgacgcacaa tcccactatc cttcgcaaga cccttcctct atataaggaa gttcatttca     3300
tttggagaga acacggggga ctctagagga tccatggcga ttcctttcat ggaaaccgtc     3360
gttggtttta tgatagtgat gtacgttttt gagacgtatt tggatctgag gcaacatact     3420
gctctcaagc ttcccactct cccaaagact tggttggag tcattagcca agagaagttt      3480
gagaaatctc gagcttacag tcttgacaaa agccattttc actttgttca tgagtttgtt      3540
actatactta tggactctgc gattctgttc tttgggatct tgccttggtt ttggaagata     3600
tctggcggct ttctaccaat ggtgggactc gatccagaga atgaaatcct gcacactctt     3660
tcattcttgg ctggtcttat gacatggtca cagatcactg atttgccatt ttctttgtac     3720
tcaactttcg tgatcgagtc tcggcatggg ttcaacaaac aaacaatatg gatgttcatt     3780
agggacatga tcaaaggaat actcctctct gtcataccg cccctcctat cgttgccgca     3840
attattgtta tagttcagaa aggaggtcct tacctcgcca tctatctgtg ggcattcatg     3900
tttatcctgt ctctagtgat gatgactata taccctgttt tgattgcacc tcttttcaac     3960
aagttcactc ctcttcctga tggagacctc cgggagaaga ttgagaaact tgcttcttct    4020
ctaaagtttc tctgaagaa gctgtttgtt gtcgatggat ctacaaggtc aagccatagt     4080
aatgcttaca tgtatggttt cttcaagaac aaaaggatt ttctttatga cacattgatt     4140
cagcagtgcc agaatgagaa tgaaattgtg gcggttattg cacacgagct gggacactgg    4200
aagctgaatc acactacata ctcgttcatt gctgttcaaa tccttgcctt cttgcaattt    4260
ggaggataca ctcttgtcag aaactccact gatctcttca ggagttttgg ttttgataca    4320
caaccagttc tcattggttt gatcatattt cagcacactg taataccact tcaacaccta   4380
gtaagctttg acctcaacct tgttagtcga gcgtttgagt ttcaggctga tgcttttgca   4440
gtgaatcttg gttatgcaaa ggatctacgt cctgccctag tgaagctaca ggaagagaac  4500
ttatcagcga tgaacacaga cccattgtac tcagcttatc actactcaca ccctcctctt  4560
```

| | |
|---|---|
| gtagagaggc ttcgagccat tgatggagaa gacaagaaga cagattaacc cctcgaattt | 4620 |
| ccccgatcgt tcaaacattt ggcaataaag tttcttaaga ttgaatcctg ttgccggtct | 4680 |
| tgcgatgatt atcatataat ttctgttgaa ttacgttaag catgtaataa ttaacatgta | 4740 |
| atgcatgacg ttatttatga gatgggtttt tatgattaga gtcccgcaat tatacattta | 4800 |
| atacgcgata gaaaacaaaa tatagcgcgc aaactaggat aaattatcgc gcgcggtgtc | 4860 |
| atctatgtta ctagatcggg aattcactgg ccgtcgtttt acaacgtcgt gactgggaaa | 4920 |
| accctggcgt tacccaactt aatcgccttg cagcacatcc ccctttcgcc agctggcgta | 4980 |
| atagcgaaga ggcccgcacc gatcgccctt cccaacagtt gcgcagcctg aatggcgccc | 5040 |
| gctcctttcg ctttcttccc ttcctttctc gccacgttcg ccggctttcc ccgtcaagct | 5100 |
| ctaaatcggg ggctcccttt agggttccga tttagtgctt tacggcacct cgaccccaaa | 5160 |
| aaacttgatt tgggtgatgg ttcacgtagt gggccatcgc cctgatagac ggttttcgc | 5220 |
| cctttgacgt tggagtccac gttctttaat agtggactct tgttccaaac tggaacaaca | 5280 |
| ctcaaccta tctcgggcta ttcttttgat ttataaggga ttttgccgat ttcggaacca | 5340 |
| ccatcaaaca ggattttcgc ctgctggggc aaaccagcgt ggaccgcttg ctgcaactct | 5400 |
| ctcagggcca ggcggtgaag ggcaatcagc tgttgcccgt ctcactggtg aaaagaaaaa | 5460 |
| ccaccccagt acattaaaaa cgtccgcaat gtgttattaa gttgtctaag cgtcaatttg | 5520 |
| tttacaccac aatatatcct gcca | 5544 |

<210> SEQ ID NO 64
<211> LENGTH: 6474
<212> TYPE: DNA
<213> ORGANISM: Artificial Sequence
<220> FEATURE:
<223> OTHER INFORMATION: Description of Artificial Sequence:
      pBI121-HP-BnCPP   vector sequence

<400> SEQUENCE: 64

| | |
|---|---|
| gtttacccgc caatatatcc tgtcaaacac tgatagttta aactgaaggc gggaaacgac | 60 |
| aatctgatca tgagcggaga attaagggag tcacgttatg accccgccg atgacgcggg | 120 |
| acaagccgtt ttacgtttgg aactgacaga accgcaacgt tgaaggagcc actcagccgc | 180 |
| gggtttctgg agtttaatga gctaagcaca tacgtcagaa accattattg cgcgttcaaa | 240 |
| agtcgcctaa ggtcactatc agctagcaaa tatttcttgt caaaaatgct ccactgacgt | 300 |
| tccataaatt cccctcggta tccaattaga gtctcatatt cactctcaat ccaaataatc | 360 |
| tgcaccggat ctggatcgtt tcgcatgatt gaacaagatg gattgcacgc aggttctccg | 420 |
| gccgcttggg tggagaggct attcggctat gactgggcac aacagacaat cggctgctct | 480 |
| gatgccgccg tgttccggct gtcagcgcag gggcgcccgg ttcttttgt caagaccgac | 540 |
| ctgtccggtg ccctgaatga actgcaggac gaggcagcgc ggctatcgtg gctggccacg | 600 |
| acgggcgttc cttgcgcagc tgtgctcgac gttgtcactg aagcgggaag gactggctgc | 660 |
| ctattgggcg aagtgccggg gcaggatctc ctgtcatctc accttgctcc tgccgagaaa | 720 |
| gtatccatca tggctgatgc aatgcggcgg ctgcatacgc ttgatccggc tacctgccca | 780 |
| ttcgaccacc aagcgaaaca tcgcatcgag cgagcacgta ctcggatgga agccggtctt | 840 |
| gtcgatcagg atgatctgga cgaagagcat caggggctcg cgccagccga actgttcgcc | 900 |
| aggctcaagg cgcgcatgcc cgacggcgat gatctcgtcg tgacccatgg cgatgcctgc | 960 |
| ttgccgaata tcatggtgga aaatggccgc ttttctggat tcatcgactg tggccggctg | 1020 |
| ggtgtggcgg accgctatca ggacatagcg ttggctaccc gtgatattgc tgaagagctt | 1080 |

```
ggcggcgaat gggctgaccg cttcctcgtg ctttacggta tcgccgctcc cgattcgcag    1140
cgcatcgcct tctatcgcct tcttgacgag ttcttctgag cgggactctg gggttcgaaa    1200
tgaccgacca agcgacgccc aacctgccat cacgagattt cgattccacc gccgccttct    1260
atgaaaggtt gggcttcgga atcgttttcc gggacgccgg ctggatgatc ctccagcgcg    1320
gggatctcat gctggagttc ttcgcccacg ggatctctgc ggaacaggcg gtcgaaggtg    1380
ccgatatcat tacgacagca acggccgaca agcacaacgc cacgatcctg agcgacaata    1440
tgatcgggcc cggcgtccac atcaacggcg tcggcggcga ctgcccaggc aagaccgaga    1500
tgcaccgcga tatcttgctg cgttcggata ttttcgtgga gttcccgcca cagacccgga    1560
tgatccccga tcgttcaaac atttggcaat aaagtttctt aagattgaat cctgttgccg    1620
gtcttgcgat gattatcata taatttctgt tgaattacgt taagcatgta ataattaaca    1680
tgtaatgcat gacgttattt atgagatggg tttttatgat tagagtcccg caattataca    1740
tttaatacgc gatagaaaac aaaatatagc gcgcaaacta ggataaatta tcgcgcgcgg    1800
tgtcatctat gttactagat cgggcctcct gtcaatgctg gcggcggctc tggtggtggt    1860
tctggtggcg gctctgaggg tggtggctct gagggtggcg gttctgaggg tggcggctct    1920
gagggaggcg gttccggtgg tggctctggt tccggtgatt ttgattatga aaagatggca    1980
aacgctaata agggggctat gaccgaaaat gccgatgaaa acgcgctaca gtctgacgct    2040
aaaggcaaac ttgattctgt cgctactgat tacggtgctg ctatcgatgg tttcattggt    2100
gacgtttccg gccttgctaa tggtaatggt gctactggtg attttgctgg ctctaattcc    2160
caaatggctc aagtcggtga cggtgataat tcacctttaa tgaataattt ccgtcaatat    2220
ttaccttccc tccctcaatc ggttgaatgt cgcccttttg tctttggccc aatacgcaaa    2280
ccgcctctcc ccgcgcgttg gccgattcat taatgcagct ggcacgacag gtttcccgac    2340
tggaaagcgg gcagtgagcg caacgcaatt aatgtgagtt agctcactca ttaggcaccc    2400
caggctttac actttatgct tccggctcgt atgttgtgtg gaattgtgag cggataacaa    2460
tttcacacag gaaacagcta tgaccatgat tacgccaagc ttgcatgcct gcagcccaca    2520
gatggttaga gaggcttacg cagcaggtct catcaagacg atctacccga gcaataatct    2580
ccaggaaatc aaataccttc ccaagaaggt taaagatgca gtcaaagatt caggactaa    2640 ctgcatcaag aacacagaga aagatatatt tctcaagatc agaagtacta ttccagtatg    2700
gacgattcaa ggcttgcttc acaaaccaag gcaagtaata gagattggag tctctaaaaa    2760
ggtagttccc actgaatcaa aggccatgga gtcaaagatt caaatagagg acctaacaga    2820
actcgccgta aagactggcg aacagttcat acagagtctc ttacgactca atgacaagaa    2880
gaaaatcttc gtcaacatgg tggagcacga cacacttgtc tactccaaaa atatcaaaga    2940
tacagtctca gaagaccaaa gggcaattga acttttcaa caaagggtaa tatcggaaa     3000 cctcctcgga ttccattgcc cagctatctg tcactttatt gtgaagatag tggaaaagga    3060
aggtggctcc tacaaatgcc atcattgcga taaaggaaag gccatcgttg aagatgcctc    3120
tgccgacagt ggtcccaaag atggaccccc acccacgagg agcatcgtgg aaaaagaaga    3180
cgttccaacc acgtcttcaa agcaagtgga ttgatgtgat atctccactg acgtaaggga    3240
tgacgcacaa tcccactatc cttcgcaaga ccctcctct atataaggaa gttcatttca    3300
tttggagaga acacggggga ctctagacca gtgtcccagc tcgtgtgcaa taaccgccac    3360
aatttcattc tcattctggc actgctgaat caatgtgtca taaagaacaa tccttttgtt    3420
cttgaagaaa ccatacatgt aagcattact atggcttgac cttgtagatc catcgacaac    3480
```

```
aaacagcttc ttcagaggaa actttagaga agaagcaagt ttctcaatct tctcccggag   3540
gtctccatca ggaagaggag tgaacttgtt gaaaagaggt gcaatcaaaa cagggtatat   3600
agtcatcatc actagagaca ggataaacat gaatgcccac agatagatgg cgaggtaagg   3660
acctcctttc tgaactataa caataattgc ggcaacgata ggaggggcag gtatgacaga   3720
gaggagtatt cctttgatca tgtccctaat gaacatccat attgtttgtt tgttgaaccc   3780
atgccgagac tcgatcacga aagttgagta caaagaaaat ggcaaatcag tgatctgtga   3840
ccatgtcata agaccagcca agaatgaaag agtgtgcagg atttcattct ctggatcgag   3900
tcccaccatt ggtagaagga tccccatcta cccgcttcgc gtcggcatcc ggtcagtggc   3960
agtgaagggc gaacagttcc tgattaacca caaaccgttc tactttactg gctttggtcg   4020
tcatgaagat gcggacttgc gtggcaaagg attcgataac gtgctgatgg tgcacgacca   4080
cgcattaatg gactggattg gggccaactc ctaccgtacc tcgcattacc cttacgctga   4140
agagatgctc gactgggcag atgaacatgg catcgtggtg attgatgaaa ctgctgctgt   4200
cggcttttcg ctctctttag gcattggttt cgaagcgggc aacaagccga agaactgta    4260
cagcgaagag gcagtcaacg gggaaactca gcaagcgcac ttacaggcga ttaaagagct   4320
gatagcgcgt gacaaaaacc acccaagcgt ggtgatgtgg agtattgcca acgaaccgga   4380
tacccgtccg caaggtgcac gggaatattt cgcgccactg gcggaagcaa cgcgtaaact   4440
cgacccgacg cgtccgatca cctgcgtcaa tgtaatgttc tgcgacgctc acaccgatac   4500
catcagcgat ctctttgatg tgctgtgcct gaaccgttat tacggatggt atgtccaaag   4560
cggcgatttg gaaacggcag agaaggtact ggaaaaagaa cttctggcct ggcaggagaa   4620
actgtacacc gacatgtgga gtgaagagta tcagtgtgca tggctggata tgtatcaccg   4680
cgtctttgat cgcgtcagcg ccgtcgtcgg tgaacaggta tggaatttcg ccgattttgc   4740
gacctcgcaa ggcatattgc gcgttggcgg taacaagaaa gggatcttca ctcgcgaccg   4800
caaaccgaag tcggcggctt ttctgctgca aaaacgctgg actggcatga acttcggtga   4860
aaaaccgcag cagggaggca acaatgaat caacaactct cctggcgcac catcgtcggc   4920
tacagcctcg ggaattgcta ccgagctctt ctaccaatgg tgggactcga tccagagaat   4980
gaaatcctgc acactctttc attcttggct ggtcttatga catggtcaca gatcactgat   5040
ttgccatttt ctttgtactc aactttcgtg atcgagtctc ggcatgggtt caacaaacaa   5100
acaatatgga tgttcattag gacatgatc aaaggaatac tcctctctgt catacctgcc    5160
cctcctatcg ttgccgcaat tattgttata gttcagaaag gaggtcctta cctcgccatc   5220
tatctgtggg cattcatgtt tatcctgtct ctagtgatga tgactatata ccctgttttg   5280
attgcacctc ttttcaacaa gttcactcct cttcctgatg gagacctccg ggagaagatt   5340
gagaaacttg cttcttctct aaagtttcct ctgaagaagc tgtttgttgt cgatggatct   5400
acaaggtcaa gccatagtaa tgcttacatg tatggtttct tcaagaacaa aaggattgtt   5460
ctttatgaca cattgattca gcagtgccag aatgagaatg aaattgtggc ggttattgca   5520
cacgagctgg gacactggga gctcgaattt ccccgatcgt tcaaacattt ggcaataaag   5580
tttcttaaga ttgaatcctg ttgccggtct tgcgatgatt atcatataat ttctgttgaa   5640
ttacgttaag catgtaataa ttaacatgta atgcatgacg ttatttatga gatgggtttt   5700
tatgattaga gtcccgcaat tatacattta atacgcgata gaaaacaaaa tatagcgcgc   5760
aaactaggat aaattatcgc gcgcggtgtc atctatgtta ctagatcggg aattcactgg   5820
ccgtcgtttt acaacgtcgt gactgggaaa accctggcgt tacccaactt aatcgccttg   5880
```

-continued

| | |
|---|---|
| cagcacatcc cccttctcgcc agctggcgta atagcgaaga ggcccgcacc gatcgccctt | 5940 |
| cccaacagtt gcgcagcctg aatggcgccc gctcctttcg ctttcttccc ttcctttctc | 6000 |
| gccacgttcg ccggctttcc ccgtcaagct ctaaatcggg gctccctt agggttccga | 6060 |
| tttagtgctt tacggcacct cgaccccaaa aaacttgatt tgggtgatgg ttcacgtagt | 6120 |
| gggccatcgc cctgatagac ggtttttcgc cctttgacgt tggagtccac gttctttaat | 6180 |
| agtggactct tgttccaaac tggaacaaca ctcaacccta tctcgggcta ttcttttgat | 6240 |
| ttataaggga ttttgccgat ttcggaacca ccatcaaaca ggattttcgc ctgctggggc | 6300 |
| aaaccagcgt ggaccgcttg ctgcaactct ctcagggcca ggcggtgaag gcaatcagc | 6360 |
| tgttgcccgt ctcactggtg aaaagaaaaa ccaccccagt acattaaaaa cgtccgcaat | 6420 |
| gtgttattaa gttgtctaag cgtcaatttg tttacaccac aatatatcct gcca | 6474 |

<210> SEQ ID NO 65
<211> LENGTH: 5544
<212> TYPE: DNA
<213> ORGANISM: Artificial Sequence
<220> FEATURE:
<223> OTHER INFORMATION: Description of Artificial Sequence:
    pBI121-antisense-BnCPP vector sequence

<400> SEQUENCE: 65

| | |
|---|---|
| gtttacccgc caatatatcc tgtcaaacac tgatagttta aactgaaggc gggaaacgac | 60 |
| aatctgatca tgagcggaga attaagggag tcacgttatg accccgccg atgacgcggg | 120 |
| acaagccgtt ttacgtttgg aactgacaga accgcaacgt tgaaggagcc actcagccgc | 180 |
| gggtttctgg agtttaatga gctaagcaca tacgtcagaa accattattg cgcgttcaaa | 240 |
| agtcgcctaa ggtcactatc agctagcaaa tatttcttgt caaaaatgct ccactgacgt | 300 |
| tccataaatt ccccctcggta tccaattaga gtctcatatt cactctcaat ccaaataatc | 360 |
| tgcaccggat ctggatcgtt tcgcatgatt gaacaagatg gattgcacgc aggttctccg | 420 |
| gccgcttggg tggagaggct attcggctat gactgggcac aacagacaat cggctgctct | 480 |
| gatgccgccg tgttccggct gtcagcgcag gggcgcccgg ttcttttgt caagaccgac | 540 |
| ctgtccggtg ccctgaatga actgcaggac gaggcagcgc ggctatcgtg gctggccacg | 600 |
| acgggcgttc cttgcgcagc tgtgctcgac gttgtcactg aagcgggaag ggactggctg | 660 |
| ctattgggcg aagtgccggg gcaggatctc ctgtcatctc accttgctcc tgccgagaaa | 720 |
| gtatccatca tggctgatgc aatgcggcgg ctgcatacgc ttgatccggc tacctgccca | 780 |
| ttcgaccacc aagcgaaaca tcgcatcgag cgagcacgta ctcggatgga gccggtctt | 840 |
| gtcgatcagg atgatctgga cgaagagcat caggggctcg cgccagccga actgttcgcc | 900 |
| aggctcaagg cgcgcatgcc cgacggcgat gatctcgtcg tgacccatgg cgatgcctgc | 960 |
| ttgccgaata tcatggtgga aaatggccgc ttttctggat tcatcgactg tggccggctg | 1020 |
| ggtgtggcgg accgctatca ggacatagcg ttggctaccc gtgatattgc tgaagagctt | 1080 |
| ggcggcgaat gggctgaccg cttcctcgtg ctttacggta tcgccgctcc cgattcgcag | 1140 |
| cgcatcgcct tctatcgcct tcttgacgag ttcttctgag cgggactctg gggttcgaaa | 1200 |
| tgaccgacca agcgacgccc aacctgccat cacgagattt cgattccacc gccgccttct | 1260 |
| atgaaaggtt gggcttcgga atcgttttcc gggacgccgg ctggatgatc ctccagcgcg | 1320 |
| gggatctcat gctggagttc ttcgcccacg gatctctgc ggaacaggcg gtcgaaggtg | 1380 |
| ccgatatcat tacgacagca acggccgaca agcacaacgc cacgatcctg agcgacaata | 1440 |

```
tgatcgggcc cggcgtccac atcaacggcg tcggcggcga ctgcccaggc aagaccgaga    1500
tgcaccgcga tatcttgctg cgttcggata ttttcgtgga gttcccgcca cagacccgga    1560
tgatccccga tcgttcaaac atttggcaat aaagtttctt aagattgaat cctgttgccg    1620
gtcttgcgat gattatcata taatttctgt tgaattacgt taagcatgta ataattaaca    1680
tgtaatgcat gacgttattt atgagatggg tttttatgat tagagtcccg caattataca    1740
tttaatacgc gatagaaaac aaaatatagc gcgcaaacta ggataaatta tcgcgcgcgg    1800
tgtcatctat gttactagat cgggcctcct gtcaatgctg gcggcggctc tggtggtggt    1860
tctggtggcg ctctgaggg tggtggctct gagggtggcg ttctgagggt ggcggctct     1920
gagggaggcg gttccggtgg tggctctggt tccggtgatt ttgattatga aagatggca    1980
aacgctaata aggggctat gaccgaaaat gccgatgaaa acgcgctaca gtctgacgct    2040
aaaggcaaac ttgattctgt cgctactgat tacggtgctg ctatcgatgg tttcattggt    2100
gacgtttccg gccttgctaa tggtaatggt gctactggtg attttgctgg ctctaattcc    2160
caaatggctc aagtcggtga cggtgataat tcaccttaa tgaataattt ccgtcaatat     2220
ttaccttccc tccctcaatc ggttgaatgt cgccctttg tctttggccc aatacgcaaa     2280
ccgcctctcc ccgcgcgttg gccgattcat taatgcagct ggcacgacag gtttcccgac    2340
tggaaagcgg gcagtgagcg caacgcaatt aatgtgagtt agctcactca ttaggcaccc    2400
caggctttac actttatgct tccggctcgt atgttgtgtg gaattgtgag cggataacaa    2460
tttcacacag gaaacagcta tgaccatgat tacgccaagc ttgcatgcct gcagcccaca    2520
gatggttaga gaggcttacg cagcaggtct catcaagacg atctacccga gcaataatct    2580
ccaggaaatc aaataccttc caagaaggt taaagatgca gtcaaaagat tcaggactaa    2640
ctgcatcaag aacacagaga aagatatatt tctcaagatc agaagtacta ttccagtatg    2700
gacgattcaa ggcttgcttc acaaaccaag gcaagtaata gagattggag tctctaaaaa    2760
ggtagttccc actgaatcaa aggccatgga gtcaaagatt caaatagagg acctaacaga    2820
actcgccgta aagactggcg aacagttcat acagagtctc ttacgactca atgacaagaa    2880
gaaaatcttc gtcaacatgg tggagcacga cacacttgtc tactccaaaa atatcaaaga    2940
tacagtctca gaagaccaaa gggcaattga acttttcaa caagggtaa tatccggaaa     3000
cctcctcgga ttccattgcc cagctatctg tcactttatt gtgaagatag tggaaaagga    3060
aggtggctcc tacaaatgcc atcattgcga taaaggaaag gccatcgttg aagatgcctc    3120
tgccgacagt ggtcccaaag atggaccccc acccacgagg agcatcgtgg aaaaagaaga    3180
cgttccaacc acgtcttcaa agcaagtgga ttgatgtgat atctccactg acgtaaggga    3240
tgacgcacaa tccactatc cttcgcaaga cccttcctct atataaggaa gttcatttca     3300
tttggagaga acacggggga ctctagagga tccttaatct gtcttcttgt cttctccatc    3360
aatggctcga agcctctcta caagaggagg gtgtgagtag tgataagctg agtacaatgg    3420
gtctgtgttc atcgctgata agttctcttc ctgtagcttc actagggcag gacgtagatc    3480
ctttgcataa ccaagattca ctgcaaaagc atcagcctga aactcaaacg ctcgactaac    3540
aaggttgagg tcaaagctta ctaggtgttg aagtggtatt acagtgtgct gaaatatgat    3600
caaaccaatg agaactggtt gtgtatcaaa accaaaactc ctgaagagat cagtggagtt    3660
tctgacaaga gtgtatcctc caaattgcaa gaaggcaagg atttgaacag caatgaacga    3720
gtatgtagtg tgattcagct tccagtgtcc cagctcgtgt gcaataaccg ccacaatttc    3780
attctcattc tggcactgct gaatcaatgt gtcataaaga acaatccttt tgttcttgaa    3840
```

```
gaaaccatac atgtaagcat tactatggct tgaccttgta gatccatcga caacaaacag    3900
cttcttcaga ggaaacttta gagaagaagc aagtttctca atcttctccc ggaggtctcc    3960
atcaggaaga ggagtgaact tgttgaaaag aggtgcaatc aaaacagggt atatagtcat    4020
catcactaga gacaggataa acatgaatgc ccacagatag atggcgaggt aaggacctcc    4080
tttctgaact ataacaataa ttgcggcaac gataggaggg gcaggtatga cagagaggag    4140
tattcctttg atcatgtccc taatgaacat ccatattgtt tgtttgttga acccatgccg    4200
agactcgatc acgaaagttg agtacaaaga aaatggcaaa tcagtgatct gtgaccatgt    4260
cataagacca gccaagaatg aaagagtgtg caggatttca ttctctggat cgagtcccac    4320
cattggtaga aagccgccag atatcttcca aaaccaaggc aagatcccaa agaacagaat    4380
cgcagagtcc ataagtatag taacaaactc atgaacaaag tgaaaatggc ttttgtcaag    4440
actgtaagct cgagatttct caaacttctc ttggctaatg actccaacca aagtctttgg    4500
gagagtggga agcttgagag cagtatgttg cctcagatcc aaatacgtct caaaaacgta    4560
catcactatc ataaaaccaa cgacggtttc catgaaagga atcgccatcc cctcgaattt    4620
ccccgatcgt tcaaacattt ggcaataaag tttcttaaga ttgaatcctg ttgccggtct    4680
tgcgatgatt atcatataat ttctgttgaa ttacgttaag catgtaataa ttaacatgta    4740
atgcatgacg ttatttatga gatgggtttt tatgattaga gtcccgcaat tatacattta    4800
atacgcgata gaaaacaaaa tatagcgcgc aaactaggat aaattatcgc gcgcggtgtc    4860
atctatgtta ctagatcggg aattcactgg ccgtcgtttt acaacgtcgt gactgggaaa    4920
accctggcgt tacccaactt aatcgccttg cagcacatcc cctttcgcc agctggcgta    4980 atagcgaaga ggcccgcacc gatcgccctt cccaacagtt gcgcagcctg aatggcgccc    5040
gctcctttcg ctttcttccc ttcctttctc gccacgttcg ccggctttcc ccgtcaagct    5100
ctaaatcggg ggctcccttt agggttccga tttagtgctt tacggcacct cgaccccaaa    5160
aaacttgatt tgggtgatgg ttcacgtagt gggccatcgc cctgatagac ggttttcgc    5220 cctttgacgt tggagtccac gttctttaat agtggactct tgttccaaac tggaacaaca    5280
ctcaacccta tctcgggcta ttcttttgat ttataaggga ttttgccgat ttcggaacca    5340
ccatcaaaca ggattttcgc ctgctggggc aaaccagcgt ggaccgcttg ctgcaactct    5400
ctcagggcca ggcggtgaag gcaatcagc tgttgcccgt ctcactggtg aaaagaaaaa    5460
ccaccccagt acattaaaaa cgtccgcaat gtgttattaa gttgtctaag cgtcaatttg    5520
tttacaccac aatatatcct gcca                                           5544
```

<210> SEQ ID NO 66
<211> LENGTH: 5668
<212> TYPE: DNA
<213> ORGANISM: Artificial Sequence
<220> FEATURE:
<223> OTHER INFORMATION: Description of Artificial Sequence:
      pRD29A-BnCPP vector sequence

<400> SEQUENCE: 66

```
gtttacccgc caatatatcc tgtcaaacac tgatagttta aactgaaggc gggaaacgac     60
aatctgatca tgagcggaga attaagggag tcacgttatg accccgccg atgacgcggg    120 acaagccgtt ttacgtttgg aactgacaga accgcaacgt tgaaggagcc actcagccgc    180
gggtttctgg agtttaatga gctaagcaca tacgtcagaa accattattg cgcgttcaaa    240
agtcgcctaa ggtcactatc agctagcaaa tatttcttgt caaaaatgct ccactgacgt    300
tccataaatt cccctcggta tccaattaga gtctcatatt cactctcaat ccaaataatc    360
```

```
tgcaccggat ctggatcgtt tcgcatgatt gaacaagatg gattgcacgc aggttctccg    420
gccgcttggg tggagaggct attcggctat gactgggcac aacagacaat cggctgctct    480
gatgccgccg tgttccggct gtcagcgcag gggcgcccgg ttcttttgt caagaccgac     540 ctgtccggtg ccctgaatga actgcaggac gaggcagcgc ggctatcgtg gctggccacg    600
acgggcgttc cttgcgcagc tgtgctcgac gttgtcactg aagcgggaag ggactggctg    660
ctattgggcg aagtgccggg gcaggatctc ctgtcatctc accttgctcc tgccgagaaa    720
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg ggttcgaaa    1200 tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg gatctctgc ggaacaggcg gtcgaaggtg    1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcaccttaa tgaataattt ccgtcaatat    2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagggagcc   2520
atagatgcaa ttcaatcaaa ctgaaatttc tgcaagaatc tcaaacacgg agatctcaaa   2580
gtttgaaaga aaatttattt cttcgactca aaacaaactt acgaaattta ggtagaactt   2640
atatacatta tattgtaatt ttttgtaaca aaatgttttt attattatta tagaatttta   2700
ctggttaaat taaaaatgaa tagaaaaggt gaattaagag gagagaggag gtaaacattt   2760
```

```
tcttctattt tttcatattt tcaggataaa ttattgtaaa agtttacaag atttccattt    2820
gactagtgta aatgaggaat attctctagt aagatcatta tttcatctac ttcttttatc    2880
ttctaccagt agaggaataa acaatattta gctcctttgt aaatacaaat taattttcct    2940
tcttgacatc attcaatttt aattttacgt ataaaataaa agatcatacc tattagaacg    3000
attaaggaga aatacaattc gaatgagaag gatgtgccgt ttgttataat aaacagccac    3060
acgacgtaaa cgtaaaatga ccacatgatg ggccaataga catggaccga ctactaataa    3120
tagtaagtta cattttagga tggaataaat atcataccga catcagtttt gaaagaaaag    3180
ggaaaaaaag aaaaaataaa taaaagatat actaccgaca tgagttccaa aaagcaaaaa    3240
aaaagatcaa gccgacacag acacgcgtag agagcaaaat gactttgacg tcacaccacg    3300
aaaacagacg cttcatacgt gtccctttat ctctctcagt ctctctataa acttagtgag    3360
accctcctct gttttactca caaatatgca aactagaaaa caatcatcag gaataaaggg    3420
tttgattact tctattggaa aggactctag aggatccatg gcgattcctt tcatggaaac    3480
cgtcgttggt tttatgatag tgatgtacgt ttttgagacg tatttggatc tgaggcaaca    3540
tactgctctc aagcttccca ctctcccaaa gactttggtt ggagtcatta gccaagagaa    3600
gtttgagaaa tctcgagctt acagtcttga caaaagccat tttcactttg ttcatgagtt    3660
tgttactata cttatggact ctgcgattct gttcttggg atcttgcctt ggttttggaa    3720
gatatctggc ggcttttctac caatggtggg actcgatcca gagaatgaaa tcctgcacac    3780
tctttcattc ttggctggtc ttatgacatg gtcacagatc actgatttgc cattttcttt    3840
gtactcaact ttcgtgatcg agtctcggca tgggttcaac aaacaaacaa tatggatgtt    3900
cattagggac atgatcaaag gaatactcct ctctgtcata cctgcccctc ctatcgttgc    3960
cgcaattatt gttatagttc agaaaggagg tccttacctc gccatctatc tgtgggcatt    4020
catgtttatc ctgtctctag tgatgatgac tatatacct gttttgattg cacctctttt    4080
caacaagttc actcctcttc ctgatggaga cctccgggag aagattgaga aacttgcttc    4140
ttctctaaag tttcctctga agaagctgtt tgttgtcgat ggatctacaa ggtcaagcca    4200
tagtaatgct tacatgtatg gtttcttcaa gaacaaaagg attgttcttt atgacacatt    4260
gattcagcag tgccagaatg agaatgaaat tgtggcggtt attgcacacg agctgggaca    4320
ctggaagctg aatcacacta catactcgtt cattgctgtt caaatccttg ccttcttgca    4380
atttggagga tacactcttg tcagaaactc cactgatctc ttcaggagtt ttggttttga    4440
tacacaacca gttctcattg gtttgatcat atttcagcac actgtaatac cacttcaaca    4500
cctagtaagc tttgacctca accttgttag tcgagcgttt gagtttcagg ctgatgcttt    4560
tgcagtgaat cttggttatg caaaggatct acgtcctgcc ctagtgaagc tacaggaaga    4620
gaacttatca gcgatgaaca cagacccatt gtactcagct tatcactact cacaccctcc    4680
tcttgtagag aggcttcgag ccattgatgg agaagacaag aagacagatt aacccctcga    4740
atttccccga tcgttcaaac atttggcaat aaagtttctt aagattgaat cctgttgccg    4800
gtcttgcgat gattatcata taatttctgt tgaattacgt taagcatgta ataattaaca    4860
tgtaatgcat gacgttattt atgagatggg ttttatgat tagagtcccg caattataca    4920
tttaatacgc gatagaaaac aaaatatagc gcgcaaacta ggataaatta tcgcgcgcgg    4980
tgtcatctat gttactagat cgggaattca ctggccgtcg ttttacaacg tcgtgactgg    5040
gaaaaccctg gcgttaccca acttaatcgc cttgcagcac atcccccttt cgccagctgg    5100
cgtaatagcg aagaggcccg caccgatcgc ccttcccaac agttgcgcag cctgaatggc    5160
```

```
gcccgctcct ttcgctttct tcccttcctt tctcgccacg ttcgccggct ttccccgtca    5220
agctctaaat cggggctcc ctttagggtt ccgatttagt gctttacggc acctcgaccc     5280
caaaaaactt gatttgggtg atggttcacg tagtgggcca tcgccctgat agacggtttt    5340 tcgcccttg  acgttggagt ccacgttctt taatagtgga ctcttgttcc aaactggaac    5400
aacactcaac cctatctcgg gctattcttt tgatttataa gggattttgc cgatttcgga    5460
accaccatca aacaggattt tcgcctgctg gggcaaacca gcgtggaccg cttgctgcaa    5520
ctctctcagg gccaggcggt gaagggcaat cagctgttgc ccgtctcact ggtgaaaaga    5580
aaaaccaccc cagtacatta aaaacgtccg caatgtgtta ttaagttgtc taagcgtcaa    5640
tttgtttaca ccacaatata tcctgcca                                      5668

<210> SEQ ID NO 67
<211> LENGTH: 6598
<212> TYPE: DNA
<213> ORGANISM: Artificial Sequence
<220> FEATURE:
<223> OTHER INFORMATION: Description of Artificial Sequence:
      pRD29A-HP-BnCPP vector sequence

<400> SEQUENCE: 67
gtttacccgc caatatatcc tgtcaaacac tgatagttta aactgaaggc gggaaacgac      60
aatctgatca tgagcggaga attaagggag tcacgttatg accccgccg atgacgcggg     120 acaagccgtt ttacgtttgg aactgacaga accgcaacgt tgaaggagcc actcagccgc    180
gggtttctgg agtttaatga gctaagcaca tacgtcagaa accattattg cgcgttcaaa    240
agtcgcctaa ggtcactatc agctagcaaa tatttcttgt caaaaatgct ccactgacgt    300
tccataaatt cccctcggta tccaattaga gtctcatatt cactctcaat ccaaataatc    360
tgcaccggat ctggatcgtt tcgcatgatt gaacaagatg gattgcacgc aggttctccg    420
gccgcttggg tggagaggct attcggctat gactgggcac aacagacaat cggctgctct    480
gatgccgccg tgttccggct gtcagcgcag gggcgcccgg ttcttttgt caagaccgac    540 ctgtccggtg ccctgaatga actgcaggac gaggcagcgc ggctatcgtg gctggccacg    600
acgggcgttc cttgcgcagc tgtgctcgac gttgtcactg aagcgggaag ggactggctg    660
ctattgggcg aagtgccggg gcaggatctc ctgtcatctc accttgctcc tgccgagaaa    720
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg    1020
ggtgtggcgg accgctatca ggacatagcg ttggctaccc gtgatattgc tgaagagctt    1080
ggcggcgaat gggctgaccg cttcctcgtg ctttacggta tcgccgctcc cgattcgcag    1140
cgcatcgcct tctatcgcct tcttgacgag ttcttctgag cgggactctg gggttcgaaa    1200
tgaccgacca agcgacgccc aacctgccat cacgagattt cgattccacc gccgccttct    1260
atgaaaggtt gggcttcgga atcgttttcc gggacgccgg ctggatgatc ctccagcgcg    1320
gggatctcat gctggagttc ttcgcccacg gatctctgc ggaacaggcg gtcgaaggtg     1380
ccgatatcat tacgcagca acggccgaca agcacaacgc cacgatcctg agcgacaata    1440
tgatcgggcc cggcgtccac atcaacggcg tcggcggcga ctgcccaggc aagaccgaga    1500
```

```
tgcaccgcga tatcttgctg cgttcggata ttttcgtgga gttcccgcca cagacccgga    1560
tgatccccga tcgttcaaac atttggcaat aaagtttctt aagattgaat cctgttgccg    1620
gtcttgcgat gattatcata taatttctgt tgaattacgt taagcatgta ataattaaca    1680
tgtaatgcat gacgttattt atgagatggg ttttatgat tagagtcccg caattataca    1740
tttaatacgc gatagaaaac aaaatatagc gcgcaaacta ggataaatta tcgcgcgcgg    1800
tgtcatctat gttactagat cgggcctcct gtcaatgctg gcggcggctc tggtggtggt    1860
tctggtggcg gctctgaggg tggtggctct gagggtggcg gttctgaggg tggcggctct    1920
gagggaggcg gttccggtgg tggctctggt tccggtgatt ttgattatga aaagatggca    1980
aacgctaata agggggctat gaccgaaaat gccgatgaaa acgcgctaca gtctgacgct    2040
aaaggcaaac ttgattctgt cgctactgat tacggtgctg ctatcgatgg tttcattggt    2100
gacgtttccg gccttgctaa tggtaatggt gctactggtg attttgctgg ctctaattcc    2160
caaatggctc aagtcggtga cggtgataat tcacctttaa tgaataattt ccgtcaatat    2220
ttaccttccc tccctcaatc ggttgaatgt cgcccttttg tctttggccc aatacgcaaa    2280
ccgcctctcc ccgcgcgttg gccgattcat taatgcagct ggcacgacag gtttcccgac    2340
tggaaagcgg gcagtgagcg caacgcaatt aatgtgagtt agctcactca ttaggcaccc    2400
caggctttac actttatgct tccggctcgt atgttgtgtg gaattgtgag cggataacaa    2460
tttcacacag gaaacagcta tgaccatgat tacgccaagc ttgcatgcct gcagggagcc    2520
atagatgcaa ttcaatcaaa ctgaaatttc tgcaagaatc tcaaacacgg agatctcaaa    2580
gtttgaaaga aaatttattt cttcgactca aaacaaactt acgaaattta ggtagaactt    2640
atatacatta tattgtaatt ttttgtaaca aaatgttttt attattatta tagaatttta    2700
ctggttaaat taaaaatgaa tagaaaaggt gaattaagag gagagaggag gtaaacattt    2760
tcttctattt tttcatattt tcaggataaa ttattgtaaa agtttacaag atttccattt    2820
gactagtgta aatgaggaat attctctagt aagatcatta tttcatctac ttctttttatc   2880 ttctaccagt agaggaataa acaatattta gctcctttgt aaatacaaat taattttcct    2940
tcttgacatc attcaatttt aattttacgt ataaaataaa agatcatacc tattagaacg    3000
attaaggaga aatacaattc gaatgagaag gatgtgccgt tgttataat aaacagccac     3060 acgacgtaaa cgtaaaatga ccacatgatg ggccaataga catggaccga ctactaataa    3120
tagtaagtta cattttagga tggaataaat atcataccga catcagtttt gaaagaaaag    3180
ggaaaaaaag aaaaaataaa taaaagatat actaccgaca tgagttccaa aaagcaaaaa    3240
aaaagatcaa gccgacacag acacgcgtag agagcaaaat gactttgacg tcacaccacg    3300
aaaacagacg cttcatacgt gtcccttat ctctctcagt ctctctataa acttagtgag    3360
accctcctct gttttactca caaatatgca aactagaaaa caatcatcag gaataaaggg    3420
tttgattact tctattggaa aggactctag accagtgtcc cagctcgtgt gcaataaccg    3480
ccacaatttc attctcattc tggcactgct gaatcaatgt gtcataaaga acaatccttt    3540
tgttcttgaa gaaccatac atgtaagcat tactatggct tgaccttgta gatccatcga    3600
caacaaacag cttcttcaga ggaaacttta gagaagaagc aagtttctca atcttctccc    3660
ggaggtctcc atcaggaaga ggagtgaact tgttgaaaag aggtgcaatc aaaacagggt    3720
atatagtcat catcactaga gacaggataa acatgaatgc ccacagatag atggcgaggt    3780
aaggacctcc tttctgaact ataacaataa ttgcggcaac gataggaggg gcaggtatga    3840
cagagaggag tattccttg atcatgtccc taatgaacat ccatattgtt tgtttgttga    3900
```

```
acccatgccg agactcgatc acgaaagttg agtacaaaga aaatggcaaa tcagtgatct    3960
gtgaccatgt cataagacca gccaagaatg aaagagtgtg caggatttca ttctctggat    4020
cgagtcccac cattggtaga aggatcccca tctacccgct tcgcgtcggc atccggtcag    4080
tggcagtgaa gggcgaacag ttcctgatta accacaaacc gttctacttt actggctttg    4140
gtcgtcatga agatgcggac ttgcgtggca aaggattcga taacgtgctg atggtgcacg    4200
accacgcatt aatggactgg attggggcca actcctaccg tacctcgcat tacccttacg    4260
ctgaagagat gctcgactgg gcagatgaac atggcatcgt ggtgattgat gaaactgctg    4320
ctgtcggctt ttcgctctct ttaggcattg gtttcgaagc gggcaacaag ccgaaagaac    4380
tgtacagcga agaggcagtc aacggggaaa ctcagcaagc gcacttacag gcgattaaag    4440
agctgatagc gcgtgacaaa aaccacccaa gcgtggtgat gtggagtatt gccaacgaac    4500
cggatacccg tccgcaaggt gcacgggaat atttcgcgcc actggcggaa gcaacgcgta    4560
aactcgaccc gacgcgtccg atcacctgcg tcaatgtaat gttctgcgac gctcacaccg    4620
ataccatcag cgatctcttt gatgtgctgt gcctgaaccg ttattacgga tggtatgtcc    4680
aaagcggcga tttggaaacg gcagagaagg tactggaaaa agaacttctg gcctggcagg    4740
agaaactgta caccgacatg tggagtgaag agtatcagtg tgcatggctg gatatgtatc    4800
accgcgtctt tgatcgcgtc agcgccgtcg tcggtgaaca ggtatggaat ttcgccgatt    4860
ttgcgacctc gcaaggcata ttgcgcgttg gcggtaacaa gaaagggatc ttcactcgcg    4920
accgcaaacc gaagtcggcg gcttttctgc tgcaaaaacg ctggactggc atgaacttcg    4980
gtgaaaaacc gcagcaggga ggcaaacaat gaatcaacaa ctctcctggc gcaccatcgt    5040
cggctacagc ctcgggaatt gctaccgagc tcttctacca atggtgggac tcgatccaga    5100
gaatgaaatc ctgcacactc tttcattctt ggctggtctt atgacatggt cacagatcac    5160
tgatttgcca ttttctttgt actcaacttt cgtgatcgag tctcggcatg ggttcaacaa    5220
acaaacaata tggatgttca ttagggacat gatcaaagga atactcctct ctgtcatacc    5280 tgccctcct atcgttgccg caattattgt tatagttcag aaaggaggtc cttacctcgc    5340
catctatctg tgggcattca tgtttatcct gtctctagtg atgatgacta tatacctgt    5400 tttgattgca cctcttttca acaagttcac tcctcttcct gatggagacc tccgggagaa    5460
gattgagaaa cttgcttctt ctctaaagtt tcctctgaag aagctgtttg ttgtcgatgg    5520
atctacaagg tcaagccata gtaatgctta catgtatggt ttcttcaaga acaaaaggat    5580
tgttctttat gacacattga ttcagcagtg ccagaatgag aatgaaattg tggcggttat    5640
tgcacacgag ctgggacact gggagctcga atttccccga tcgttcaaac atttggcaat    5700
aaagtttctt aagattgaat cctgttgccg gtcttgcgat gattatcata taatttctgt    5760
tgaattacgt taagcatgta ataattaaca tgtaatgcat gacgttattt atgagatggg    5820
tttttatgat tagagtcccg caattataca tttaatacgc gatagaaaac aaaatatagc    5880
gcgcaaacta ggataaatta tcgcgcgcgg tgtcatctat gttactagat cgggaattca    5940
ctggccgtcg ttttacaacg tcgtgactgg gaaaaccctg gcgttaccca acttaatcgc    6000
cttgcagcac atccccccttt cgccagctgg cgtaatagcg aagaggcccg caccgatcgc    6060
ccttcccaac agttgcgcag cctgaatggc gcccgctcct ttcgctttct tcccttcctt    6120
tctcgccacg ttcgccggct ttccccgtca agctctaaat cggggctcc ctttagggtt    6180 ccgatttagt gctttacggc acctcgaccc caaaaaactt gatttgggtg atggttcacg    6240
tagtgggcca tcgccctgat agacggtttt tcgccctttg acgttggagt ccacgttctt    6300
```

```
taatagtgga ctcttgttcc aaactggaac aacactcaac cctatctcgg gctattcttt   6360
tgatttataa gggattttgc cgatttcgga accaccatca aacaggattt tcgcctgctg   6420
gggcaaacca gcgtggaccg cttgctgcaa ctctctcagg gccaggcggt gaagggcaat   6480
cagctgttgc ccgtctcact ggtgaaaaga aaaaccaccc cagtacatta aaaacgtccg   6540
caatgtgtta ttaagttgtc taagcgtcaa tttgtttaca ccacaatata tcctgcca    6598
```

<210> SEQ ID NO 68
<211> LENGTH: 5668
<212> TYPE: DNA
<213> ORGANISM: Artificial Sequence
<220> FEATURE:
<223> OTHER INFORMATION: Description of Artificial Sequence:
      pRD29A-antisense-BnCPP vector sequence

<400> SEQUENCE: 68

```
gtttacccgc caatatatcc tgtcaaacac tgatagttta aactgaaggc gggaaacgac     60
aatctgatca tgagcggaga attaagggag tcacgttatg acccccgccg atgacgcggg    120
acaagccgtt ttacgtttgg aactgacaga accgcaacgt tgaaggagcc actcagccgc    180
gggtttctgg agtttaatga gctaagcaca tacgtcagaa accattattg cgcgttcaaa    240
agtcgcctaa ggtcactatc agctagcaaa tatttcttgt caaaaatgct ccactgacgt    300
tccataaatt cccctcggta tccaattaga gtctcatatt cactctcaat ccaataatc    360 tgcaccggat ctggatcgtt tcgcatgatt gaacaagatg gattgcacgc aggttctccg    420
gccgcttggg tggagaggct attcggctat gactgggcac aacagacaat cggctgctct    480
gatgccgccg tgttccggct gtcagcgcag gggcgcccgg ttcttttttgt caagaccgac    540 ctgtccggtg ccctgaatga actgcaggac gaggcagcgc ggctatcgtg gctggccacg    600
acgggcgttc cttgcgcagc tgtgctcgac gttgtcactg aagcgggaag ggactggctg    660
ctattgggcg aagtgccggg gcaggatctc ctgtcatctc accttgctcc tgccgagaaa    720
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg gatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560 tgatcccccga tcgttcaaac attttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg ttttttatgat tagagtcccg caattataca   1740
tttaatacgc gatagaaaac aaaatatagc gcgcaaacta ggataaatta tcgcgcgcgg   1800
```

```
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata aggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagggagcc   2520
atagatgcaa ttcaatcaaa ctgaaatttc tgcaagaatc tcaaacacgg agatctcaaa   2580
gtttgaaaga aaatttatt cttcgactca aaacaaactt acgaaattta ggtagaactt   2640
atatacatta tattgtaatt ttttgtaaca aaatgttttt attattatta tagaatttta   2700
ctggttaaat taaaaatgaa tagaaaaggt gaattaagag gagagaggag gtaaacattt   2760
tcttctattt tttcatattt tcaggataaa ttattgtaaa agtttacaag atttccattt   2820
gactagtgta aatgaggaat attctctagt aagatcatta tttcatctac ttcttttatc   2880
ttctaccagt agaggaataa acaatattta gctcctttgt aaatacaaat taattttcct   2940
tcttgacatc attcaatttt aatttacgt ataaatttaa agatcatacc tattagaacg   3000
attaaggaga aatacaattc gaatgagaag gatgtgccgt ttgttataat aaacagccac   3060
acgacgtaaa cgtaaaatga ccacatgatg ggccaataga catggaccga ctactaataa   3120
tagtaagtta cattttagga tggaataaat atcataccga catcagtttt gaaagaaaag   3180 ggaaaaaag aaaaaataaa taaaagatat actaccgaca tgagttccaa aaagcaaaaa   3240
aaaagatcaa gccgacacag acacgcgtag agagcaaaat gactttgacg tcacaccacg   3300
aaaacagacg cttcatacgt gtcccttat ctctctcagt ctctctataa acttagtgag   3360
accctcctct gttttactca caaatatgca aactagaaaa caatcatcag gaataaaggg   3420
tttgattact tctattggaa aggactctag aggatcctta atctgtcttc ttgtcttctc   3480
catcaatggc tcgaagcctc tctacaagag gagggtgtga gtagtgataa gctgagtaca   3540
atgggtctgt gttcatcgct gataagttct cttcctgtag cttcactagg gcaggacgta   3600
gatcctttgc ataaccaaga ttcactgcaa aagcatcagc ctgaaactca aacgctcgac   3660
taacaaggtt gaggtcaaag cttactaggt gttgaagtgg tattacagtg tgctgaaata   3720
tgatcaaacc aatgagaact ggttgtgtat caaaaccaaa actcctgaag gatcagtgg   3780 agtttctgac aagagtgtat cctccaaatt gcaagaaggc aaggatttga acagcaatga   3840
acgagtatgt agtgtgattc agcttccagt gtcccagctc gtgtgcaata accgccacaa   3900
tttcattctc attctggcac tgctgaatca atgtgtcata aagaacaatc cttttgttct   3960
tgaagaaacc atacatgtaa gcattactat ggcttgacct tgtagatcca tcgacaacaa   4020
acagcttctt cagaggaaac tttagagaag aagcaagttt ctcaatcttc tcccggaggt   4080
ctccatcagg aagaggagtg aacttgttga aagaggtgc aatcaaaaca gggtatatag   4140
tcatcatcac tagagacagg ataaacatga atgcccacag atagatggcg aggtaaggac   4200
```

```
ctcctttctg aactataaca ataattgcgg caacgatagg aggggcaggt atgacagaga    4260
ggagtattcc tttgatcatg tccctaatga acatccatat tgtttgtttg ttgaacccat    4320
gccgagactc gatcacgaaa gttgagtaca aagaaaatgg caaatcagtg atctgtgacc    4380
atgtcataag accagccaag aatgaaagag tgtgcaggat ttcattctct ggatcgagtc    4440
ccaccattgg tagaaagccg ccagatatct tccaaaacca aggcaagatc caaagaaca    4500
gaatcgcaga gtccataagt atagtaacaa actcatgaac aaagtgaaaa tggcttttgt    4560
caagactgta agctcgagat ttctcaaact tctcttggct aatgactcca accaaagtct    4620
ttgggagagt gggaagcttg agagcagtat gttgcctcag atccaaatac gtctcaaaaa    4680
cgtacatcac tatcataaaa ccaacgacgg tttccatgaa aggaatcgcc atccctcga    4740
atttccccga tcgttcaaac atttggcaat aaagtttctt aagattgaat cctgttgccg    4800
gtcttgcgat gattatcata taatttctgt tgaattacgt taagcatgta ataattaaca    4860
tgtaatgcat gacgttattt atgagatggg tttttatgat tagagtcccg caattataca    4920
tttaatacgc gatagaaaac aaaatatagc gcgcaaacta ggataaatta tcgcgcgcgg    4980
tgtcatctat gttactagat cgggaattca ctggccgtcg ttttacaacg tcgtgactgg    5040
gaaaaccctg gcgttaccca acttaatcgc cttgcagcac atccccctttt cgccagctgg    5100
cgtaatagcg aagaggcccg caccgatcgc ccttcccaac agttgcgcag cctgaatggc    5160
gcccgctcct ttcgctttct tcccttcctt tctcgccacg ttcgccggct tccccgtca    5220
agctctaaat cggggctcc ctttaggtt ccgatttagt gctttacggc acctcgaccc    5280
caaaaaactt gatttgggtg atggttcacg tagtgggcca tcgccctgat agacggtttt    5340
tcgccctttg acgttggagt ccacgttctt aatagtgga ctcttgttcc aaactggaac    5400
aacactcaac cctatctcgg gctattcttt tgatttataa gggattttgc cgatttcgga    5460
accaccatca acaggatttt cgcctgctg gggcaaacca gcgtggaccg cttgctgcaa    5520
ctctctcagg gccaggcggt gaagggcaat cagctgttgc ccgtctcact ggtgaaaaga    5580
aaaaccaccc cagtacatta aaaacgtccg caatgtgtta ttaagttgtc taagcgtcaa    5640
tttgtttaca ccacaatata tcctgcca                                        5668
```

<210> SEQ ID NO 69
<211> LENGTH: 5074
<212> TYPE: DNA
<213> ORGANISM: Artificial Sequence
<220> FEATURE:
<223> OTHER INFORMATION: Description of Artificial Sequence: MuA-BnCPP
    vector sequence

<400> SEQUENCE: 69

```
gtttacccgc caatatatcc tgtcaaacac tgatagttta aactgaaggc gggaaacgac     60
aatctgatca tgagcggaga attaagggag tcacgttatg acccccgccg atgacgcggg    120
acaagccgtt ttacgtttgg aactgacaga accgcaacgt tgaaggagcc actcagccgc    180
gggtttctgg agtttaatga gctaagcaca tacgtcagaa accattattg cgcgttcaaa    240
agtcgcctaa ggtcactatc agctagcaaa tatttcttgt caaaaatgct ccactgacgt    300
tccataaatt cccctcggta tccaattaga gtctcatatt cactctcaat ccaataatc    360
tgcaccggat ctggatcgtt tcgcatgatt gaacaagatg gattgcacgc aggttctccg    420
gccgcttggg tggagaggct attcggctat gactgggcac aacagacaat cggctgctct    480
gatgccgccg tgttccggct gtcagcgcag gggcgcccgg ttcttttttgt caagaccgac    540
```

```
ctgtccggtg ccctgaatga actgcaggac gaggcagcgc ggctatcgtg gctggccacg    600
acgggcgttc cttgcgcagc tgtgctcgac gttgtcactg aagcgggaag ggactggctg    660
ctattgggcg aagtgccggg gcaggatctc ctgtcatctc accttgctcc tgccgagaaa    720
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc tgggaaattt ttcgccagtt   2520
ctaaatatcc ggaaacctct tgggatgcca ttgcccatct atctgtaatt tattgacgaa   2580
atagacgaaa aggaaggtgg ctcctataaa gcacatcatt gcgataacag aaaggccatt   2640
gttgaagata cctctgctga cattggtccc caagtggaag caccacccca tgaggagcac   2700
cgtggagtaa aagacgttc gagccacgtc gaaaaagcaa gtgtgttgat gtagtatctc   2760
cattgacgta agggatgacg cacaatccaa ctatccatcg caagaccatt gctctatata   2820
agaaagttaa tatcatttcg agtggccacg ctgaggggga tccatggcga ttcctttcat   2880
ggaaaccgtc gttggtttta tgatagtgat gtacgttttt gagacgtatt tggatctgag   2940
```

```
gcaacatact gctctcaagc ttcccactct cccaaagact ttggttggag tcattagcca    3000
agagaagttt gagaaatctc gagcttacag tcttgacaaa agccatttc actttgttca    3060
tgagtttgtt actatactta tggactctgc gattctgttc tttgggatct tgccttggtt    3120
ttggaagata tctggcggct ttctaccaat ggtgggactc gatccagaga atgaaatcct    3180
gcacactctt tcattcttgg ctggtcttat gacatggtca cagatcactg atttgccatt    3240
ttctttgtac tcaactttcg tgatcgagtc tcggcatggg ttcaacaaac aaacaatatg    3300
gatgttcatt agggacatga tcaaaggaat actcctctct gtcatacctg cccctcctat    3360
cgttgccgca attattgtta tagttcagaa aggaggtcct tacctcgcca tctatctgtg    3420
ggcattcatg tttatcctgt ctctagtgat gatgactata taccctgttt tgattgcacc    3480
tcttttcaac aagttcactc ctcttcctga tggagacctc cgggagaaga ttgagaaact    3540
tgcttcttct ctaaagtttc ctctgaagaa gctgtttgtt gtcgatggat ctacaaggtc    3600
aagccatagt aatgcttaca tgtatggttt cttcaagaac aaaaggattg ttctttatga    3660
cacattgatt cagcagtgcc agaatgagaa tgaaattgtg gcggttattg cacacgagct    3720
gggacactgg aagctgaatc acactacata ctcgttcatt gctgttcaaa tccttgcctt    3780
cttgcaattt ggaggataca ctcttgtcag aaactccact gatctcttca ggagttttgg    3840
ttttgataca caaccagttc tcattggttt gatcatattt cagcacactg taataccact    3900
tcaacaccta gtaagctttg acctcaacct tgttagtcga gcgtttgagt ttcaggctga    3960
tgcttttgca gtgaatcttg gttatgcaaa ggatctacgt cctgccctag tgaagctaca    4020
ggaagagaac ttatcagcga tgaacacaga cccattgtac tcagcttatc actactcaca    4080
ccctcctctt gtagagaggc ttcgagccat tgatggagaa gacaagaaga cagattaacc    4140
cctcgaattt ccccgatcgt tcaaacattt ggcaataaag tttcttaaga ttgaatcctg    4200
ttgccggtct tgcgatgatt atcatataat ttctgttgaa ttcgttaag catgtaataa    4260
ttaacatgta atgcatgacg ttatttatga gatgggtttt tatgattaga gtcccgcaat    4320
tatacattta atacgcgata gaaaacaaaa tatagcgcgc aaactaggat aaattatcgc    4380
gcgcggtgtc atctatgtta ctagatcggg aattcactgg ccgtcgtttt acaacgtcgt    4440
gactgggaaa accctggcgt tacccaactt aatcgccttg cagcacatcc cctttcgcc     4500
agctggcgta atagcgaaga ggcccgcacc gatcgccctt cccaacagtt gcgcagcctg    4560
aatggcgccc gctcctttcg ctttcttccc ttccttctc gccacgttcg ccggctttcc    4620
ccgtcaagct ctaaatcggg ggctcccttt agggttccga tttagtgctt tacggcacct    4680
cgaccccaaa aaacttgatt tgggtgatgg ttcacgtagt gggccatcgc cctgatagac    4740
ggttttcgc cctttgacgt tggagtccac gttctttaat agtggactct tgttccaaac     4800
tggaacaaca ctcaacccta tctcgggcta ttcttttgat ttataaggga ttttgccgat    4860
ttcggaacca ccatcaaaca ggattttcgc ctgctgggc aaaccagcgt ggaccgcttg     4920
ctgcaactct ctcagggcca ggcggtgaag ggcaatcagc tgttgcccgt ctcactggtg    4980
aaaagaaaaa ccaccccagt acattaaaaa cgtccgcaat gtgttattaa gttgtctaag    5040
cgtcaatttg tttacaccac aatatatcct gcca                               5074
```

<210> SEQ ID NO 70
<211> LENGTH: 33
<212> TYPE: DNA
<213> ORGANISM: Artificial Sequence
<220> FEATURE:
<223> OTHER INFORMATION: Description of Artificial Sequence: PCR Primer
    sequence

```
<400> SEQUENCE: 70
aaacccggga tggcgtttcc ctacatggaa gcc                                    33

<210> SEQ ID NO 71
<211> LENGTH: 34
<212> TYPE: DNA
<213> ORGANISM: Artificial Sequence
<220> FEATURE:
<223> OTHER INFORMATION: Description of Artificial Sequence: PCR Primer
      sequence

<400> SEQUENCE: 71
aaagagctct tagtcttcct tcttatccgg ttcg                                   34

<210> SEQ ID NO 72
<211> LENGTH: 28
<212> TYPE: DNA
<213> ORGANISM: Artificial Sequence
<220> FEATURE:
<223> OTHER INFORMATION: Description of Artificial Sequence: PCR Primer
      sequence

<400> SEQUENCE: 72
aaacccggga tggcgattcc tttcatgg                                          28

<210> SEQ ID NO 73
<211> LENGTH: 33
<212> TYPE: DNA
<213> ORGANISM: Artificial Sequence
<220> FEATURE:
<223> OTHER INFORMATION: Description of Artificial Sequence: PCR Primer
      sequence

<400> SEQUENCE: 73
aaaggatcct taatctgtct tcttgtcttc tcc                                    33

<210> SEQ ID NO 74
<211> LENGTH: 30
<212> TYPE: DNA
<213> ORGANISM: Artificial Sequence
<220> FEATURE:
<223> OTHER INFORMATION: Description of Artificial Sequence: PCR Primer
      sequence

<400> SEQUENCE: 74
aaagagctct tctaccaatg gtgggactcg                                        30

<210> SEQ ID NO 75
<211> LENGTH: 29
<212> TYPE: DNA
<213> ORGANISM: Artificial Sequence
<220> FEATURE:
<223> OTHER INFORMATION: Description of Artificial Sequence: PCR Primer
      sequence

<400> SEQUENCE: 75
aaagagctcc cagtgtccca gctcgtgtg                                         29

<210> SEQ ID NO 76
<211> LENGTH: 30
<212> TYPE: DNA
<213> ORGANISM: Artificial Sequence
<220> FEATURE:
<223> OTHER INFORMATION: Description of Artificial Sequence: PCR Primer
      sequence

<400> SEQUENCE: 76
```
aaaggatcct tctaccaatg gtgggactcg                                    30

<210> SEQ ID NO 77
<211> LENGTH: 29
<212> TYPE: DNA
<213> ORGANISM: Artificial Sequence
<220> FEATURE:
<223> OTHER INFORMATION: Description of Artificial Sequence: PCR Primer
      sequence

<400> SEQUENCE: 77
aaatctagac cagtgtccca gctcgtgtg                                     29

<210> SEQ ID NO 78
<211> LENGTH: 34
<212> TYPE: DNA
<213> ORGANISM: Artificial Sequence
<220> FEATURE:
<223> OTHER INFORMATION: Description of Artificial Sequence: PCR Primer
      sequence

<400> SEQUENCE: 78
gatgagctca caagatcaag tcacagcaat gcct                               34

<210> SEQ ID NO 79
<211> LENGTH: 29
<212> TYPE: DNA
<213> ORGANISM: Artificial Sequence
<220> FEATURE:
<223> OTHER INFORMATION: Description of Artificial Sequence: PCR Primer
      sequence

<400> SEQUENCE: 79
aaagagctcc cggttcgtcc agcgcggcc                                     29

<210> SEQ ID NO 80
<211> LENGTH: 34
<212> TYPE: DNA
<213> ORGANISM: Artificial Sequence
<220> FEATURE:
<223> OTHER INFORMATION: Description of Artificial Sequence: PCR Primer
      sequence

<400> SEQUENCE: 80
gatggatcca caagatcaag tcacagcaat gcct                               34

<210> SEQ ID NO 81
<211> LENGTH: 29
<212> TYPE: DNA
<213> ORGANISM: Artificial Sequence
<220> FEATURE:
<223> OTHER INFORMATION: Description of Artificial Sequence: PCR Primer
      sequence

<400> SEQUENCE: 81
ccttctagac cggttcgtcc agcgcggcc                                     29

<210> SEQ ID NO 82
<211> LENGTH: 30
<212> TYPE: DNA
<213> ORGANISM: Artificial Sequence
<220> FEATURE:
<223> OTHER INFORMATION: Description of Artificial Sequence: PCR Primer
      sequence

<400> SEQUENCE: 82
tttaagcttg gagccataga tgcaattcaa                                    30

-continued

```
<210> SEQ ID NO 83
<211> LENGTH: 18
<212> TYPE: DNA
<213> ORGANISM: Artificial Sequence
<220> FEATURE:
<223> OTHER INFORMATION: Description of Artificial Sequence: PCR Primer
      sequence

<400> SEQUENCE: 83
gcaagaccgg caacagga                                                    18

<210> SEQ ID NO 84
<211> LENGTH: 1217
<212> TYPE: DNA
<213> ORGANISM: Artificial sequence
<220> FEATURE:
<223> OTHER INFORMATION: Description of Artificial Sequence: Consensus
      sequence
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (5)..(9)
<223> OTHER INFORMATION: n is a, c, g, or t
<220> FEATURE:
<221> NAME/KEY: misc_feature
<222> LOCATION: (11)..(13)
<223> OTHER INFORMATION: n is a, c, g, or t
<220> FEATURE:
<221> NAME/KEY: misc_feature
<222> LOCATION: (15)..(19)
<223> OTHER INFORMATION: n is a, c, g, or t
<220> FEATURE:
<221> NAME/KEY: misc_feature
<222> LOCATION: (21)..(28)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (50)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
```

```
<222> LOCATION: (59)..(62)
<223> OTHER INFORMATION: n is a, c, g, or t
<220> FEATURE:
<221> NAME/KEY: misc_feature
<222> LOCATION: (65)..(66)
<223> OTHER INFORMATION: n is a, c, g, or t
<220> FEATURE:
<221> NAME/KEY: misc_feature
<222> LOCATION: (68)..(69)
<223> OTHER INFORMATION: n is a, c, g, or t
<220> FEATURE:
<221> NAME/KEY: misc_feature
<222> LOCATION: (71)..(71)
<223> OTHER INFORMATION: n is a, c, g, or t
<220> FEATURE:
<221> NAME/KEY: misc_feature
<222> LOCATION: (74)..(75)
<223> OTHER INFORMATION: n is a, c, g, or t
<220> FEATURE:
<221> NAME/KEY: misc_feature
<222> LOCATION: (77)..(77)
<223> OTHER INFORMATION: n is a, c, g, or t
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (83)..(83)
<223> OTHER INFORMATION: n is a, c, g, or t
<220> FEATURE:
<221> NAME/KEY: misc_feature
<222> LOCATION: (89)..(93)
<223> OTHER INFORMATION: n is a, c, g, or t
<220> FEATURE:
<221> NAME/KEY: misc_feature
<222> LOCATION: (95)..(98)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (104)..(104)
<223> OTHER INFORMATION: n is a, c, g, or t
<220> FEATURE:
<221> NAME/KEY: misc_feature
<222> LOCATION: (107)..(108)
<223> OTHER INFORMATION: n is a, c, g, or t
<220> FEATURE:
<221> NAME/KEY: misc_feature
<222> LOCATION: (110)..(111)
<223> OTHER INFORMATION: n is a, c, g, or t
<220> FEATURE:
<221> NAME/KEY: misc_feature
<222> LOCATION: (113)..(113)
<223> OTHER INFORMATION: n is a, c, g, or t
<220> FEATURE:
<221> NAME/KEY: misc_feature
<222> LOCATION: (115)..(119)
<223> OTHER INFORMATION: n is a, c, g, or t
<220> FEATURE:
<221> NAME/KEY: misc_feature
<222> LOCATION: (123)..(125)
<223> OTHER INFORMATION: n is a, c, g, or t
<220> FEATURE:
<221> NAME/KEY: misc_feature
<222> LOCATION: (128)..(128)
<223> OTHER INFORMATION: n is a, c, g, or t
<220> FEATURE:
<221> NAME/KEY: misc_feature
<222> LOCATION: (131)..(131)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
```

-continued

```
<222> LOCATION: (140)..(140)
<223> OTHER INFORMATION: n is a, c, g, or t
<220> FEATURE:
<221> NAME/KEY: misc_feature
<222> LOCATION: (142)..(142)
<223> OTHER INFORMATION: n is a, c, g, or t
<220> FEATURE:
<221> NAME/KEY: misc_feature
<222> LOCATION: (144)..(145)
<223> OTHER INFORMATION: n is a, c, g, or t
<220> FEATURE:
<221> NAME/KEY: misc_feature
<222> LOCATION: (149)..(149)
<223> OTHER INFORMATION: n is a, c, g, or t
<220> FEATURE:
<221> NAME/KEY: misc_feature
<222> LOCATION: (151)..(152)
<223> OTHER INFORMATION: n is a, c, g, or t
<220> FEATURE:
<221> NAME/KEY: misc_feature
<222> LOCATION: (155)..(156)
<223> OTHER INFORMATION: n is a, c, g, or t
<220> FEATURE:
<221> NAME/KEY: misc_feature
<222> LOCATION: (158)..(161)
<223> OTHER INFORMATION: n is a, c, g, or t
<220> FEATURE:
<221> NAME/KEY: misc_feature
<222> LOCATION: (164)..(165)
<223> OTHER INFORMATION: n is a, c, g, or t
<220> FEATURE:
<221> NAME/KEY: misc_feature
<222> LOCATION: (167)..(168)
<223> OTHER INFORMATION: n is a, c, g, or t
<220> FEATURE:
<221> NAME/KEY: misc_feature
<222> LOCATION: (170)..(170)
<223> OTHER INFORMATION: n is a, c, g, or t
<220> FEATURE:
<221> NAME/KEY: misc_feature
<222> LOCATION: (173)..(174)
<223> OTHER INFORMATION: n is a, c, g, or t
<220> FEATURE:
<221> NAME/KEY: misc_feature
<222> LOCATION: (176)..(183)
<223> OTHER INFORMATION: n is a, c, g, or t
<220> FEATURE:
<221> NAME/KEY: misc_feature
<222> LOCATION: (185)..(186)
<223> OTHER INFORMATION: n is a, c, g, or t
<220> FEATURE:
<221> NAME/KEY: misc_feature
<222> LOCATION: (188)..(189)
<223> OTHER INFORMATION: n is a, c, g, or t
<220> FEATURE:
<221> NAME/KEY: misc_feature
<222> LOCATION: (191)..(191)
<223> OTHER INFORMATION: n is a, c, g, or t
<220> FEATURE:
<221> NAME/KEY: misc_feature
<222> LOCATION: (194)..(194)
<223> OTHER INFORMATION: n is a, c, g, or t
<220> FEATURE:
<221> NAME/KEY: misc_feature
<222> LOCATION: (198)..(200)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
<222> LOCATION: (206)..(206)
<223> OTHER INFORMATION: n is a, c, g, or t
<220> FEATURE:
<221> NAME/KEY: misc_feature
<222> LOCATION: (208)..(212)
<223> OTHER INFORMATION: n is a, c, g, or t
<220> FEATURE:
<221> NAME/KEY: misc_feature
```

```
<222> LOCATION: (215)..(219)
<223> OTHER INFORMATION: n is a, c, g, or t
<220> FEATURE:
<221> NAME/KEY: misc_feature
<222> LOCATION: (221)..(222)
<223> OTHER INFORMATION: n is a, c, g, or t
<220> FEATURE:
<221> NAME/KEY: misc_feature
<222> LOCATION: (224)..(227)
<223> OTHER INFORMATION: n is a, c, g, or t
<220> FEATURE:
<221> NAME/KEY: misc_feature
<222> LOCATION: (229)..(233)
<223> OTHER INFORMATION: n is a, c, g, or t
<220> FEATURE:
<221> NAME/KEY: misc_feature
<222> LOCATION: (236)..(237)
<223> OTHER INFORMATION: n is a, c, g, or t
<220> FEATURE:
<221> NAME/KEY: misc_feature
<222> LOCATION: (239)..(241)
<223> OTHER INFORMATION: n is a, c, g, or t
<220> FEATURE:
<221> NAME/KEY: misc_feature
<222> LOCATION: (243)..(246)
<223> OTHER INFORMATION: n is a, c, g, or t
<220> FEATURE:
<221> NAME/KEY: misc_feature
<222> LOCATION: (250)..(251)
<223> OTHER INFORMATION: n is a, c, g, or t
<220> FEATURE:
<221> NAME/KEY: misc_feature
<222> LOCATION: (254)..(254)
<223> OTHER INFORMATION: n is a, c, g, or t
<220> FEATURE:
<221> NAME/KEY: misc_feature
<222> LOCATION: (257)..(258)
<223> OTHER INFORMATION: n is a, c, g, or t
<220> FEATURE:
<221> NAME/KEY: misc_feature
<222> LOCATION: (260)..(260)
<223> OTHER INFORMATION: n is a, c, g, or t
<220> FEATURE:
<221> NAME/KEY: misc_feature
<222> LOCATION: (263)..(263)
<223> OTHER INFORMATION: n is a, c, g, or t
<220> FEATURE:
<221> NAME/KEY: misc_feature
<222> LOCATION: (266)..(266)
<223> OTHER INFORMATION: n is a, c, g, or t
<220> FEATURE:
<221> NAME/KEY: misc_feature
<222> LOCATION: (270)..(270)
<223> OTHER INFORMATION: n is a, c, g, or t
<220> FEATURE:
<221> NAME/KEY: misc_feature
<222> LOCATION: (272)..(272)
<223> OTHER INFORMATION: n is a, c, g, or t
<220> FEATURE:
<221> NAME/KEY: misc_feature
<222> LOCATION: (275)..(276)
<223> OTHER INFORMATION: n is a, c, g, or t
<220> FEATURE:
<221> NAME/KEY: misc_feature
<222> LOCATION: (278)..(278)
<223> OTHER INFORMATION: n is a, c, g, or t
<220> FEATURE:
<221> NAME/KEY: misc_feature
<222> LOCATION: (281)..(281)
<223> OTHER INFORMATION: n is a, c, g, or t
<220> FEATURE:
<221> NAME/KEY: misc_feature
<222> LOCATION: (283)..(287)
<223> OTHER INFORMATION: n is a, c, g, or t
<220> FEATURE:
<221> NAME/KEY: misc_feature
<222> LOCATION: (289)..(289)
<223> OTHER INFORMATION: n is a, c, g, or t
<220> FEATURE:
<221> NAME/KEY: misc_feature
```

```
<222> LOCATION: (291)..(293)
<223> OTHER INFORMATION: n is a, c, g, or t
<220> FEATURE:
<221> NAME/KEY: misc_feature
<222> LOCATION: (299)..(299)
<223> OTHER INFORMATION: n is a, c, g, or t
<220> FEATURE:
<221> NAME/KEY: misc_feature
<222> LOCATION: (305)..(308)
<223> OTHER INFORMATION: n is a, c, g, or t
<220> FEATURE:
<221> NAME/KEY: misc_feature
<222> LOCATION: (311)..(312)
<223> OTHER INFORMATION: n is a, c, g, or t
<220> FEATURE:
<221> NAME/KEY: misc_feature
<222> LOCATION: (314)..(314)
<223> OTHER INFORMATION: n is a, c, g, or t
<220> FEATURE:
<221> NAME/KEY: misc_feature
<222> LOCATION: (317)..(317)
<223> OTHER INFORMATION: n is a, c, g, or t
<220> FEATURE:
<221> NAME/KEY: misc_feature
<222> LOCATION: (320)..(320)
<223> OTHER INFORMATION: n is a, c, g, or t
<220> FEATURE:
<221> NAME/KEY: misc_feature
<222> LOCATION: (323)..(324)
<223> OTHER INFORMATION: n is a, c, g, or t
<220> FEATURE:
<221> NAME/KEY: misc_feature
<222> LOCATION: (326)..(326)
<223> OTHER INFORMATION: n is a, c, g, or t
<220> FEATURE:
<221> NAME/KEY: misc_feature
<222> LOCATION: (329)..(329)
<223> OTHER INFORMATION: n is a, c, g, or t
<220> FEATURE:
<221> NAME/KEY: misc_feature
<222> LOCATION: (332)..(332)
<223> OTHER INFORMATION: n is a, c, g, or t
<220> FEATURE:
<221> NAME/KEY: misc_feature
<222> LOCATION: (335)..(335)
<223> OTHER INFORMATION: n is a, c, g, or t
<220> FEATURE:
<221> NAME/KEY: misc_feature
<222> LOCATION: (338)..(338)
<223> OTHER INFORMATION: n is a, c, g, or t
<220> FEATURE:
<221> NAME/KEY: misc_feature
<222> LOCATION: (341)..(341)
<223> OTHER INFORMATION: n is a, c, g, or t
<220> FEATURE:
<221> NAME/KEY: misc_feature
<222> LOCATION: (344)..(344)
<223> OTHER INFORMATION: n is a, c, g, or t
<220> FEATURE:
<221> NAME/KEY: misc_feature
<222> LOCATION: (348)..(348)
<223> OTHER INFORMATION: n is a, c, g, or t
<220> FEATURE:
<221> NAME/KEY: misc_feature
<222> LOCATION: (350)..(350)
<223> OTHER INFORMATION: n is a, c, g, or t
<220> FEATURE:
<221> NAME/KEY: misc_feature
<222> LOCATION: (353)..(353)
<223> OTHER INFORMATION: n is a, c, g, or t
<220> FEATURE:
<221> NAME/KEY: misc_feature
<222> LOCATION: (359)..(359)
<223> OTHER INFORMATION: n is a, c, g, or t
<220> FEATURE:
<221> NAME/KEY: misc_feature
<222> LOCATION: (362)..(362)
<223> OTHER INFORMATION: n is a, c, g, or t
<220> FEATURE:
<221> NAME/KEY: misc_feature
```

```
<222> LOCATION: (365)..(365)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t
<220> FEATURE:
<221> NAME/KEY: misc_feature
<222> LOCATION: (374)..(376)
<223> OTHER INFORMATION: n is a, c, g, or t
<220> FEATURE:
<221> NAME/KEY: misc_feature
<222> LOCATION: (381)..(381)
<223> OTHER INFORMATION: n is a, c, g, or t
<220> FEATURE:
<221> NAME/KEY: misc_feature
<222> LOCATION: (383)..(383)
<223> OTHER INFORMATION: n is a, c, g, or t
<220> FEATURE:
<221> NAME/KEY: misc_feature
<222> LOCATION: (386)..(387)
<223> OTHER INFORMATION: n is a, c, g, or t
<220> FEATURE:
<221> NAME/KEY: misc_feature
<222> LOCATION: (389)..(390)
<223> OTHER INFORMATION: n is a, c, g, or t
<220> FEATURE:
<221> NAME/KEY: misc_feature
<222> LOCATION: (395)..(395)
<223> OTHER INFORMATION: n is a, c, g, or t
<220> FEATURE:
<221> NAME/KEY: misc_feature
<222> LOCATION: (399)..(399)
<223> OTHER INFORMATION: n is a, c, g, or t
<220> FEATURE:
<221> NAME/KEY: misc_feature
<222> LOCATION: (401)..(401)
<223> OTHER INFORMATION: n is a, c, g, or t
<220> FEATURE:
<221> NAME/KEY: misc_feature
<222> LOCATION: (403)..(404)
<223> OTHER INFORMATION: n is a, c, g, or t
<220> FEATURE:
<221> NAME/KEY: misc_feature
<222> LOCATION: (407)..(413)
<223> OTHER INFORMATION: n is a, c, g, or t
<220> FEATURE:
<221> NAME/KEY: misc_feature
<222> LOCATION: (416)..(420)
<223> OTHER INFORMATION: n is a, c, g, or t
<220> FEATURE:
<221> NAME/KEY: misc_feature
<222> LOCATION: (422)..(423)
<223> OTHER INFORMATION: n is a, c, g, or t
<220> FEATURE:
<221> NAME/KEY: misc_feature
<222> LOCATION: (425)..(428)
<223> OTHER INFORMATION: n is a, c, g, or t
<220> FEATURE:
<221> NAME/KEY: misc_feature
<222> LOCATION: (430)..(431)
<223> OTHER INFORMATION: n is a, c, g, or t
<220> FEATURE:
<221> NAME/KEY: misc_feature
<222> LOCATION: (434)..(434)
<223> OTHER INFORMATION: n is a, c, g, or t
<220> FEATURE:
<221> NAME/KEY: misc_feature
<222> LOCATION: (437)..(437)
<223> OTHER INFORMATION: n is a, c, g, or t
<220> FEATURE:
<221> NAME/KEY: misc_feature
<222> LOCATION: (440)..(440)
<223> OTHER INFORMATION: n is a, c, g, or t
<220> FEATURE:
<221> NAME/KEY: misc_feature
<222> LOCATION: (443)..(444)
<223> OTHER INFORMATION: n is a, c, g, or t
<220> FEATURE:
<221> NAME/KEY: misc_feature
```

```
<222> LOCATION: (446)..(446)
<223> OTHER INFORMATION: n is a, c, g, or t
<220> FEATURE:
<221> NAME/KEY: misc_feature
<222> LOCATION: (449)..(449)
<223> OTHER INFORMATION: n is a, c, g, or t
<220> FEATURE:
<221> NAME/KEY: misc_feature
<222> LOCATION: (452)..(452)
<223> OTHER INFORMATION: n is a, c, g, or t
<220> FEATURE:
<221> NAME/KEY: misc_feature
<222> LOCATION: (455)..(458)
<223> OTHER INFORMATION: n is a, c, g, or t
<220> FEATURE:
<221> NAME/KEY: misc_feature
<222> LOCATION: (461)..(461)
<223> OTHER INFORMATION: n is a, c, g, or t
<220> FEATURE:
<221> NAME/KEY: misc_feature
<222> LOCATION: (464)..(464)
<223> OTHER INFORMATION: n is a, c, g, or t
<220> FEATURE:
<221> NAME/KEY: misc_feature
<222> LOCATION: (469)..(470)
<223> OTHER INFORMATION: n is a, c, g, or t
<220> FEATURE:
<221> NAME/KEY: misc_feature
<222> LOCATION: (473)..(473)
<223> OTHER INFORMATION: n is a, c, g, or t
<220> FEATURE:
<221> NAME/KEY: misc_feature
<222> LOCATION: (476)..(476)
<223> OTHER INFORMATION: n is a, c, g, or t
<220> FEATURE:
<221> NAME/KEY: misc_feature
<222> LOCATION: (479)..(479)
<223> OTHER INFORMATION: n is a, c, g, or t
<220> FEATURE:
<221> NAME/KEY: misc_feature
<222> LOCATION: (482)..(483)
<223> OTHER INFORMATION: n is a, c, g, or t
<220> FEATURE:
<221> NAME/KEY: misc_feature
<222> LOCATION: (485)..(485)
<223> OTHER INFORMATION: n is a, c, g, or t
<220> FEATURE:
<221> NAME/KEY: misc_feature
<222> LOCATION: (488)..(489)
<223> OTHER INFORMATION: n is a, c, g, or t
<220> FEATURE:
<221> NAME/KEY: misc_feature
<222> LOCATION: (491)..(491)
<223> OTHER INFORMATION: n is a, c, g, or t
<220> FEATURE:
<221> NAME/KEY: misc_feature
<222> LOCATION: (497)..(497)
<223> OTHER INFORMATION: n is a, c, g, or t
<220> FEATURE:
<221> NAME/KEY: misc_feature
<222> LOCATION: (502)..(503)
<223> OTHER INFORMATION: n is a, c, g, or t
<220> FEATURE:
<221> NAME/KEY: misc_feature
<222> LOCATION: (506)..(506)
<223> OTHER INFORMATION: n is a, c, g, or t
<220> FEATURE:
<221> NAME/KEY: misc_feature
<222> LOCATION: (508)..(508)
<223> OTHER INFORMATION: n is a, c, g, or t
<220> FEATURE:
<221> NAME/KEY: misc_feature
<222> LOCATION: (512)..(516)
<223> OTHER INFORMATION: n is a, c, g, or t
<220> FEATURE:
<221> NAME/KEY: misc_feature
<222> LOCATION: (518)..(519)
<223> OTHER INFORMATION: n is a, c, g, or t
<220> FEATURE:
<221> NAME/KEY: misc_feature
```

-continued

```
<222> LOCATION: (521)..(522)
<223> OTHER INFORMATION: n is a, c, g, or t
<220> FEATURE:
<221> NAME/KEY: misc_feature
<222> LOCATION: (524)..(525)
<223> OTHER INFORMATION: n is a, c, g, or t
<220> FEATURE:
<221> NAME/KEY: misc_feature
<222> LOCATION: (528)..(528)
<223> OTHER INFORMATION: n is a, c, g, or t
<220> FEATURE:
<221> NAME/KEY: misc_feature
<222> LOCATION: (534)..(534)
<223> OTHER INFORMATION: n is a, c, g, or t
<220> FEATURE:
<221> NAME/KEY: misc_feature
<222> LOCATION: (536)..(537)
<223> OTHER INFORMATION: n is a, c, g, or t
<220> FEATURE:
<221> NAME/KEY: misc_feature
<222> LOCATION: (539)..(539)
<223> OTHER INFORMATION: n is a, c, g, or t
<220> FEATURE:
<221> NAME/KEY: misc_feature
<222> LOCATION: (542)..(542)
<223> OTHER INFORMATION: n is a, c, g, or t
<220> FEATURE:
<221> NAME/KEY: misc_feature
<222> LOCATION: (545)..(546)
<223> OTHER INFORMATION: n is a, c, g, or t
<220> FEATURE:
<221> NAME/KEY: misc_feature
<222> LOCATION: (548)..(549)
<223> OTHER INFORMATION: n is a, c, g, or t
<220> FEATURE:
<221> NAME/KEY: misc_feature
<222> LOCATION: (551)..(551)
<223> OTHER INFORMATION: n is a, c, g, or t
<220> FEATURE:
<221> NAME/KEY: misc_feature
<222> LOCATION: (554)..(554)
<223> OTHER INFORMATION: n is a, c, g, or t
<220> FEATURE:
<221> NAME/KEY: misc_feature
<222> LOCATION: (557)..(557)
<223> OTHER INFORMATION: n is a, c, g, or t
<220> FEATURE:
<221> NAME/KEY: misc_feature
<222> LOCATION: (560)..(560)
<223> OTHER INFORMATION: n is a, c, g, or t
<220> FEATURE:
<221> NAME/KEY: misc_feature
<222> LOCATION: (563)..(563)
<223> OTHER INFORMATION: n is a, c, g, or t
<220> FEATURE:
<221> NAME/KEY: misc_feature
<222> LOCATION: (569)..(569)
<223> OTHER INFORMATION: n is a, c, g, or t
<220> FEATURE:
<221> NAME/KEY: misc_feature
<222> LOCATION: (571)..(572)
<223> OTHER INFORMATION: n is a, c, g, or t
<220> FEATURE:
<221> NAME/KEY: misc_feature
<222> LOCATION: (578)..(578)
<223> OTHER INFORMATION: n is a, c, g, or t
<220> FEATURE:
<221> NAME/KEY: misc_feature
<222> LOCATION: (581)..(582)
<223> OTHER INFORMATION: n is a, c, g, or t
<220> FEATURE:
<221> NAME/KEY: misc_feature
<222> LOCATION: (584)..(584)
<223> OTHER INFORMATION: n is a, c, g, or t
<220> FEATURE:
<221> NAME/KEY: misc_feature
<222> LOCATION: (587)..(587)
<223> OTHER INFORMATION: n is a, c, g, or t
<220> FEATURE:
<221> NAME/KEY: misc_feature
```

```
<222> LOCATION: (590)..(590)
<223> OTHER INFORMATION: n is a, c, g, or t
<220> FEATURE:
<221> NAME/KEY: misc_feature
<222> LOCATION: (593)..(596)
<223> OTHER INFORMATION: n is a, c, g, or t
<220> FEATURE:
<221> NAME/KEY: misc_feature
<222> LOCATION: (599)..(600)
<223> OTHER INFORMATION: n is a, c, g, or t
<220> FEATURE:
<221> NAME/KEY: misc_feature
<222> LOCATION: (602)..(602)
<223> OTHER INFORMATION: n is a, c, g, or t
<220> FEATURE:
<221> NAME/KEY: misc_feature
<222> LOCATION: (604)..(605)
<223> OTHER INFORMATION: n is a, c, g, or t
<220> FEATURE:
<221> NAME/KEY: misc_feature
<222> LOCATION: (608)..(608)
<223> OTHER INFORMATION: n is a, c, g, or t
<220> FEATURE:
<221> NAME/KEY: misc_feature
<222> LOCATION: (611)..(611)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (620)..(620)
<223> OTHER INFORMATION: n is a, c, g, or t
<220> FEATURE:
<221> NAME/KEY: misc_feature
<222> LOCATION: (623)..(624)
<223> OTHER INFORMATION: n is a, c, g, or t
<220> FEATURE:
<221> NAME/KEY: misc_feature
<222> LOCATION: (626)..(626)
<223> OTHER INFORMATION: n is a, c, g, or t
<220> FEATURE:
<221> NAME/KEY: misc_feature
<222> LOCATION: (629)..(630)
<223> OTHER INFORMATION: n is a, c, g, or t
<220> FEATURE:
<221> NAME/KEY: misc_feature
<222> LOCATION: (632)..(633)
<223> OTHER INFORMATION: n is a, c, g, or t
<220> FEATURE:
<221> NAME/KEY: misc_feature
<222> LOCATION: (635)..(635)
<223> OTHER INFORMATION: n is a, c, g, or t
<220> FEATURE:
<221> NAME/KEY: misc_feature
<222> LOCATION: (637)..(638)
<223> OTHER INFORMATION: n is a, c, g, or t
<220> FEATURE:
<221> NAME/KEY: misc_feature
<222> LOCATION: (641)..(642)
<223> OTHER INFORMATION: n is a, c, g, or t
<220> FEATURE:
<221> NAME/KEY: misc_feature
<222> LOCATION: (644)..(644)
<223> OTHER INFORMATION: n is a, c, g, or t
<220> FEATURE:
<221> NAME/KEY: misc_feature
<222> LOCATION: (647)..(647)
<223> OTHER INFORMATION: n is a, c, g, or t
<220> FEATURE:
<221> NAME/KEY: misc_feature
<222> LOCATION: (650)..(651)
<223> OTHER INFORMATION: n is a, c, g, or t
<220> FEATURE:
<221> NAME/KEY: misc_feature
<222> LOCATION: (653)..(653)
<223> OTHER INFORMATION: n is a, c, g, or t
<220> FEATURE:
<221> NAME/KEY: misc_feature
```

```
<222> LOCATION: (656)..(656)
<223> OTHER INFORMATION: n is a, c, g, or t
<220> FEATURE:
<221> NAME/KEY: misc_feature
<222> LOCATION: (659)..(660)
<223> OTHER INFORMATION: n is a, c, g, or t
<220> FEATURE:
<221> NAME/KEY: misc_feature
<222> LOCATION: (662)..(662)
<223> OTHER INFORMATION: n is a, c, g, or t
<220> FEATURE:
<221> NAME/KEY: misc_feature
<222> LOCATION: (665)..(665)
<223> OTHER INFORMATION: n is a, c, g, or t
<220> FEATURE:
<221> NAME/KEY: misc_feature
<222> LOCATION: (668)..(668)
<223> OTHER INFORMATION: n is a, c, g, or t
<220> FEATURE:
<221> NAME/KEY: misc_feature
<222> LOCATION: (671)..(671)
<223> OTHER INFORMATION: n is a, c, g, or t
<220> FEATURE:
<221> NAME/KEY: misc_feature
<222> LOCATION: (674)..(675)
<223> OTHER INFORMATION: n is a, c, g, or t
<220> FEATURE:
<221> NAME/KEY: misc_feature
<222> LOCATION: (677)..(677)
<223> OTHER INFORMATION: n is a, c, g, or t
<220> FEATURE:
<221> NAME/KEY: misc_feature
<222> LOCATION: (683)..(683)
<223> OTHER INFORMATION: n is a, c, g, or t
<220> FEATURE:
<221> NAME/KEY: misc_feature
<222> LOCATION: (686)..(686)
<223> OTHER INFORMATION: n is a, c, g, or t
<220> FEATURE:
<221> NAME/KEY: misc_feature
<222> LOCATION: (689)..(689)
<223> OTHER INFORMATION: n is a, c, g, or t
<220> FEATURE:
<221> NAME/KEY: misc_feature
<222> LOCATION: (692)..(692)
<223> OTHER INFORMATION: n is a, c, g, or t
<220> FEATURE:
<221> NAME/KEY: misc_feature
<222> LOCATION: (695)..(695)
<223> OTHER INFORMATION: n is a, c, g, or t
<220> FEATURE:
<221> NAME/KEY: misc_feature
<222> LOCATION: (698)..(698)
<223> OTHER INFORMATION: n is a, c, g, or t
<220> FEATURE:
<221> NAME/KEY: misc_feature
<222> LOCATION: (707)..(707)
<223> OTHER INFORMATION: n is a, c, g, or t
<220> FEATURE:
<221> NAME/KEY: misc_feature
<222> LOCATION: (710)..(710)
<223> OTHER INFORMATION: n is a, c, g, or t
<220> FEATURE:
<221> NAME/KEY: misc_feature
<222> LOCATION: (712)..(713)
<223> OTHER INFORMATION: n is a, c, g, or t
<220> FEATURE:
<221> NAME/KEY: misc_feature
<222> LOCATION: (716)..(716)
<223> OTHER INFORMATION: n is a, c, g, or t
<220> FEATURE:
<221> NAME/KEY: misc_feature
<222> LOCATION: (718)..(718)
<223> OTHER INFORMATION: n is a, c, g, or t
<220> FEATURE:
<221> NAME/KEY: misc_feature
<222> LOCATION: (722)..(723)
<223> OTHER INFORMATION: n is a, c, g, or t
<220> FEATURE:
<221> NAME/KEY: misc_feature
```

```
<222> LOCATION: (725)..(725)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (731)..(731)
<223> OTHER INFORMATION: n is a, c, g, or t
<220> FEATURE:
<221> NAME/KEY: misc_feature
<222> LOCATION: (733)..(734)
<223> OTHER INFORMATION: n is a, c, g, or t
<220> FEATURE:
<221> NAME/KEY: misc_feature
<222> LOCATION: (737)..(737)
<223> OTHER INFORMATION: n is a, c, g, or t
<220> FEATURE:
<221> NAME/KEY: misc_feature
<222> LOCATION: (740)..(740)
<223> OTHER INFORMATION: n is a, c, g, or t
<220> FEATURE:
<221> NAME/KEY: misc_feature
<222> LOCATION: (743)..(744)
<223> OTHER INFORMATION: n is a, c, g, or t
<220> FEATURE:
<221> NAME/KEY: misc_feature
<222> LOCATION: (746)..(746)
<223> OTHER INFORMATION: n is a, c, g, or t
<220> FEATURE:
<221> NAME/KEY: misc_feature
<222> LOCATION: (749)..(752)
<223> OTHER INFORMATION: n is a, c, g, or t
<220> FEATURE:
<221> NAME/KEY: misc_feature
<222> LOCATION: (755)..(755)
<223> OTHER INFORMATION: n is a, c, g, or t
<220> FEATURE:
<221> NAME/KEY: misc_feature
<222> LOCATION: (758)..(762)
<223> OTHER INFORMATION: n is a, c, g, or t
<220> FEATURE:
<221> NAME/KEY: misc_feature
<222> LOCATION: (764)..(764)
<223> OTHER INFORMATION: n is a, c, g, or t
<220> FEATURE:
<221> NAME/KEY: misc_feature
<222> LOCATION: (767)..(768)
<223> OTHER INFORMATION: n is a, c, g, or t
<220> FEATURE:
<221> NAME/KEY: misc_feature
<222> LOCATION: (770)..(770)
<223> OTHER INFORMATION: n is a, c, g, or t
<220> FEATURE:
<221> NAME/KEY: misc_feature
<222> LOCATION: (773)..(774)
<223> OTHER INFORMATION: n is a, c, g, or t
<220> FEATURE:
<221> NAME/KEY: misc_feature
<222> LOCATION: (776)..(776)
<223> OTHER INFORMATION: n is a, c, g, or t
<220> FEATURE:
<221> NAME/KEY: misc_feature
<222> LOCATION: (779)..(780)
<223> OTHER INFORMATION: n is a, c, g, or t
<220> FEATURE:
<221> NAME/KEY: misc_feature
<222> LOCATION: (782)..(782)
<223> OTHER INFORMATION: n is a, c, g, or t
<220> FEATURE:
<221> NAME/KEY: misc_feature
<222> LOCATION: (788)..(788)
<223> OTHER INFORMATION: n is a, c, g, or t
<220> FEATURE:
<221> NAME/KEY: misc_feature
<222> LOCATION: (791)..(791)
<223> OTHER INFORMATION: n is a, c, g, or t
<220> FEATURE:
<221> NAME/KEY: misc_feature
```

```
<222> LOCATION: (794)..(794)
<223> OTHER INFORMATION: n is a, c, g, or t
<220> FEATURE:
<221> NAME/KEY: misc_feature
<222> LOCATION: (797)..(798)
<223> OTHER INFORMATION: n is a, c, g, or t
<220> FEATURE:
<221> NAME/KEY: misc_feature
<222> LOCATION: (800)..(800)
<223> OTHER INFORMATION: n is a, c, g, or t
<220> FEATURE:
<221> NAME/KEY: misc_feature
<222> LOCATION: (803)..(803)
<223> OTHER INFORMATION: n is a, c, g, or t
<220> FEATURE:
<221> NAME/KEY: misc_feature
<222> LOCATION: (806)..(806)
<223> OTHER INFORMATION: n is a, c, g, or t
<220> FEATURE:
<221> NAME/KEY: misc_feature
<222> LOCATION: (812)..(812)
<223> OTHER INFORMATION: n is a, c, g, or t
<220> FEATURE:
<221> NAME/KEY: misc_feature
<222> LOCATION: (815)..(815)
<223> OTHER INFORMATION: n is a, c, g, or t
<220> FEATURE:
<221> NAME/KEY: misc_feature
<222> LOCATION: (817)..(818)
<223> OTHER INFORMATION: n is a, c, g, or t
<220> FEATURE:
<221> NAME/KEY: misc_feature
<222> LOCATION: (821)..(821)
<223> OTHER INFORMATION: n is a, c, g, or t
<220> FEATURE:
<221> NAME/KEY: misc_feature
<222> LOCATION: (825)..(827)
<223> OTHER INFORMATION: n is a, c, g, or t
<220> FEATURE:
<221> NAME/KEY: misc_feature
<222> LOCATION: (830)..(831)
<223> OTHER INFORMATION: n is a, c, g, or t
<220> FEATURE:
<221> NAME/KEY: misc_feature
<222> LOCATION: (833)..(833)
<223> OTHER INFORMATION: n is a, c, g, or t
<220> FEATURE:
<221> NAME/KEY: misc_feature
<222> LOCATION: (836)..(837)
<223> OTHER INFORMATION: n is a, c, g, or t
<220> FEATURE:
<221> NAME/KEY: misc_feature
<222> LOCATION: (839)..(839)
<223> OTHER INFORMATION: n is a, c, g, or t
<220> FEATURE:
<221> NAME/KEY: misc_feature
<222> LOCATION: (842)..(843)
<223> OTHER INFORMATION: n is a, c, g, or t
<220> FEATURE:
<221> NAME/KEY: misc_feature
<222> LOCATION: (845)..(845)
<223> OTHER INFORMATION: n is a, c, g, or t
<220> FEATURE:
<221> NAME/KEY: misc_feature
<222> LOCATION: (848)..(849)
<223> OTHER INFORMATION: n is a, c, g, or t
<220> FEATURE:
<221> NAME/KEY: misc_feature
<222> LOCATION: (851)..(851)
<223> OTHER INFORMATION: n is a, c, g, or t
<220> FEATURE:
<221> NAME/KEY: misc_feature
<222> LOCATION: (855)..(858)
<223> OTHER INFORMATION: n is a, c, g, or t
<220> FEATURE:
<221> NAME/KEY: misc_feature
<222> LOCATION: (860)..(861)
<223> OTHER INFORMATION: n is a, c, g, or t
<220> FEATURE:
<221> NAME/KEY: misc_feature
```

```
<222> LOCATION: (863)..(863)
<223> OTHER INFORMATION: n is a, c, g, or t
<220> FEATURE:
<221> NAME/KEY: misc_feature
<222> LOCATION: (869)..(869)
<223> OTHER INFORMATION: n is a, c, g, or t
<220> FEATURE:
<221> NAME/KEY: misc_feature
<222> LOCATION: (875)..(875)
<223> OTHER INFORMATION: n is a, c, g, or t
<220> FEATURE:
<221> NAME/KEY: misc_feature
<222> LOCATION: (878)..(878)
<223> OTHER INFORMATION: n is a, c, g, or t
<220> FEATURE:
<221> NAME/KEY: misc_feature
<222> LOCATION: (881)..(881)
<223> OTHER INFORMATION: n is a, c, g, or t
<220> FEATURE:
<221> NAME/KEY: misc_feature
<222> LOCATION: (884)..(885)
<223> OTHER INFORMATION: n is a, c, g, or t
<220> FEATURE:
<221> NAME/KEY: misc_feature
<222> LOCATION: (887)..(888)
<223> OTHER INFORMATION: n is a, c, g, or t
<220> FEATURE:
<221> NAME/KEY: misc_feature
<222> LOCATION: (890)..(890)
<223> OTHER INFORMATION: n is a, c, g, or t
<220> FEATURE:
<221> NAME/KEY: misc_feature
<222> LOCATION: (892)..(893)
<223> OTHER INFORMATION: n is a, c, g, or t
<220> FEATURE:
<221> NAME/KEY: misc_feature
<222> LOCATION: (896)..(899)
<223> OTHER INFORMATION: n is a, c, g, or t
<220> FEATURE:
<221> NAME/KEY: misc_feature
<222> LOCATION: (901)..(902)
<223> OTHER INFORMATION: n is a, c, g, or t
<220> FEATURE:
<221> NAME/KEY: misc_feature
<222> LOCATION: (905)..(905)
<223> OTHER INFORMATION: n is a, c, g, or t
<220> FEATURE:
<221> NAME/KEY: misc_feature
<222> LOCATION: (907)..(911)
<223> OTHER INFORMATION: n is a, c, g, or t
<220> FEATURE:
<221> NAME/KEY: misc_feature
<222> LOCATION: (914)..(914)
<223> OTHER INFORMATION: n is a, c, g, or t
<220> FEATURE:
<221> NAME/KEY: misc_feature
<222> LOCATION: (917)..(917)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t
<220> FEATURE:
<221> NAME/KEY: misc_feature
<222> LOCATION: (923)..(929)
<223> OTHER INFORMATION: n is a, c, g, or t
<220> FEATURE:
<221> NAME/KEY: misc_feature
<222> LOCATION: (932)..(932)
<223> OTHER INFORMATION: n is a, c, g, or t
<220> FEATURE:
<221> NAME/KEY: misc_feature
<222> LOCATION: (935)..(935)
<223> OTHER INFORMATION: n is a, c, g, or t
<220> FEATURE:
<221> NAME/KEY: misc_feature
<222> LOCATION: (938)..(939)
<223> OTHER INFORMATION: n is a, c, g, or t
<220> FEATURE:
<221> NAME/KEY: misc_feature
```

```
<222> LOCATION: (941)..(941)
<223> OTHER INFORMATION: n is a, c, g, or t
<220> FEATURE:
<221> NAME/KEY: misc_feature
<222> LOCATION: (944)..(944)
<223> OTHER INFORMATION: n is a, c, g, or t
<220> FEATURE:
<221> NAME/KEY: misc_feature
<222> LOCATION: (947)..(948)
<223> OTHER INFORMATION: n is a, c, g, or t
<220> FEATURE:
<221> NAME/KEY: misc_feature
<222> LOCATION: (950)..(950)
<223> OTHER INFORMATION: n is a, c, g, or t
<220> FEATURE:
<221> NAME/KEY: misc_feature
<222> LOCATION: (954)..(954)
<223> OTHER INFORMATION: n is a, c, g, or t
<220> FEATURE:
<221> NAME/KEY: misc_feature
<222> LOCATION: (956)..(956)
<223> OTHER INFORMATION: n is a, c, g, or t
<220> FEATURE:
<221> NAME/KEY: misc_feature
<222> LOCATION: (959)..(959)
<223> OTHER INFORMATION: n is a, c, g, or t
<220> FEATURE:
<221> NAME/KEY: misc_feature
<222> LOCATION: (965)..(965)
<223> OTHER INFORMATION: n is a, c, g, or t
<220> FEATURE:
<221> NAME/KEY: misc_feature
<222> LOCATION: (968)..(969)
<223> OTHER INFORMATION: n is a, c, g, or t
<220> FEATURE:
<221> NAME/KEY: misc_feature
<222> LOCATION: (971)..(971)
<223> OTHER INFORMATION: n is a, c, g, or t
<220> FEATURE:
<221> NAME/KEY: misc_feature
<222> LOCATION: (974)..(974)
<223> OTHER INFORMATION: n is a, c, g, or t
<220> FEATURE:
<221> NAME/KEY: misc_feature
<222> LOCATION: (977)..(978)
<223> OTHER INFORMATION: n is a, c, g, or t
<220> FEATURE:
<221> NAME/KEY: misc_feature
<222> LOCATION: (980)..(980)
<223> OTHER INFORMATION: n is a, c, g, or t
<220> FEATURE:
<221> NAME/KEY: misc_feature
<222> LOCATION: (983)..(983)
<223> OTHER INFORMATION: n is a, c, g, or t
<220> FEATURE:
<221> NAME/KEY: misc_feature
<222> LOCATION: (986)..(990)
<223> OTHER INFORMATION: n is a, c, g, or t
<220> FEATURE:
<221> NAME/KEY: misc_feature
<222> LOCATION: (992)..(992)
<223> OTHER INFORMATION: n is a, c, g, or t
<220> FEATURE:
<221> NAME/KEY: misc_feature
<222> LOCATION: (999)..(1001)
<223> OTHER INFORMATION: n is a, c, g, or t
<220> FEATURE:
<221> NAME/KEY: misc_feature
<222> LOCATION: (1004)..(1004)
<223> OTHER INFORMATION: n is a, c, g, or t
<220> FEATURE:
<221> NAME/KEY: misc_feature
<222> LOCATION: (1010)..(1011)
<223> OTHER INFORMATION: n is a, c, g, or t
<220> FEATURE:
<221> NAME/KEY: misc_feature
<222> LOCATION: (1013)..(1013)
<223> OTHER INFORMATION: n is a, c, g, or t
<220> FEATURE:
<221> NAME/KEY: misc_feature
```

```
<222> LOCATION: (1016)..(1017)
<223> OTHER INFORMATION: n is a, c, g, or t
<220> FEATURE:
<221> NAME/KEY: misc_feature
<222> LOCATION: (1020)..(1020)
<223> OTHER INFORMATION: n is a, c, g, or t
<220> FEATURE:
<221> NAME/KEY: misc_feature
<222> LOCATION: (1022)..(1022)
<223> OTHER INFORMATION: n is a, c, g, or t
<220> FEATURE:
<221> NAME/KEY: misc_feature
<222> LOCATION: (1025)..(1025)
<223> OTHER INFORMATION: n is a, c, g, or t
<220> FEATURE:
<221> NAME/KEY: misc_feature
<222> LOCATION: (1028)..(1028)
<223> OTHER INFORMATION: n is a, c, g, or t
<220> FEATURE:
<221> NAME/KEY: misc_feature
<222> LOCATION: (1037)..(1037)
<223> OTHER INFORMATION: n is a, c, g, or t
<220> FEATURE:
<221> NAME/KEY: misc_feature
<222> LOCATION: (1042)..(1043)
<223> OTHER INFORMATION: n is a, c, g, or t
<220> FEATURE:
<221> NAME/KEY: misc_feature
<222> LOCATION: (1046)..(1046)
<223> OTHER INFORMATION: n is a, c, g, or t
<220> FEATURE:
<221> NAME/KEY: misc_feature
<222> LOCATION: (1049)..(1056)
<223> OTHER INFORMATION: n is a, c, g, or t
<220> FEATURE:
<221> NAME/KEY: misc_feature
<222> LOCATION: (1058)..(1058)
<223> OTHER INFORMATION: n is a, c, g, or t
<220> FEATURE:
<221> NAME/KEY: misc_feature
<222> LOCATION: (1060)..(1061)
<223> OTHER INFORMATION: n is a, c, g, or t
<220> FEATURE:
<221> NAME/KEY: misc_feature
<222> LOCATION: (1064)..(1074)
<223> OTHER INFORMATION: n is a, c, g, or t
<220> FEATURE:
<221> NAME/KEY: misc_feature
<222> LOCATION: (1076)..(1077)
<223> OTHER INFORMATION: n is a, c, g, or t
<220> FEATURE:
<221> NAME/KEY: misc_feature
<222> LOCATION: (1079)..(1085)
<223> OTHER INFORMATION: n is a, c, g, or t
<220> FEATURE:
<221> NAME/KEY: misc_feature
<222> LOCATION: (1088)..(1089)
<223> OTHER INFORMATION: n is a, c, g, or t
<220> FEATURE:
<221> NAME/KEY: misc_feature
<222> LOCATION: (1091)..(1091)
<223> OTHER INFORMATION: n is a, c, g, or t
<220> FEATURE:
<221> NAME/KEY: misc_feature
<222> LOCATION: (1094)..(1094)
<223> OTHER INFORMATION: n is a, c, g, or t
<220> FEATURE:
<221> NAME/KEY: misc_feature
<222> LOCATION: (1097)..(1097)
<223> OTHER INFORMATION: n is a, c, g, or t
<220> FEATURE:
<221> NAME/KEY: misc_feature
<222> LOCATION: (1103)..(1103)
<223> OTHER INFORMATION: n is a, c, g, or t
<220> FEATURE:
<221> NAME/KEY: misc_feature
<222> LOCATION: (1109)..(1110)
<223> OTHER INFORMATION: n is a, c, g, or t
<220> FEATURE:
<221> NAME/KEY: misc_feature
```

```
<222> LOCATION: (1112)..(1112)
<223> OTHER INFORMATION: n is a, c, g, or t
<220> FEATURE:
<221> NAME/KEY: misc_feature
<222> LOCATION: (1115)..(1116)
<223> OTHER INFORMATION: n is a, c, g, or t
<220> FEATURE:
<221> NAME/KEY: misc_feature
<222> LOCATION: (1118)..(1118)
<223> OTHER INFORMATION: n is a, c, g, or t
<220> FEATURE:
<221> NAME/KEY: misc_feature
<222> LOCATION: (1124)..(1124)
<223> OTHER INFORMATION: n is a, c, g, or t
<220> FEATURE:
<221> NAME/KEY: misc_feature
<222> LOCATION: (1127)..(1127)
<223> OTHER INFORMATION: n is a, c, g, or t
<220> FEATURE:
<221> NAME/KEY: misc_feature
<222> LOCATION: (1130)..(1130)
<223> OTHER INFORMATION: n is a, c, g, or t
<220> FEATURE:
<221> NAME/KEY: misc_feature
<222> LOCATION: (1132)..(1133)
<223> OTHER INFORMATION: n is a, c, g, or t
<220> FEATURE:
<221> NAME/KEY: misc_feature
<222> LOCATION: (1135)..(1135)
<223> OTHER INFORMATION: n is a, c, g, or t
<220> FEATURE:
<221> NAME/KEY: misc_feature
<222> LOCATION: (1137)..(1137)
<223> OTHER INFORMATION: n is a, c, g, or t
<220> FEATURE:
<221> NAME/KEY: misc_feature
<222> LOCATION: (1139)..(1139)
<223> OTHER INFORMATION: n is a, c, g, or t
<220> FEATURE:
<221> NAME/KEY: misc_feature
<222> LOCATION: (1142)..(1142)
<223> OTHER INFORMATION: n is a, c, g, or t
<220> FEATURE:
<221> NAME/KEY: misc_feature
<222> LOCATION: (1145)..(1145)
<223> OTHER INFORMATION: n is a, c, g, or t
<220> FEATURE:
<221> NAME/KEY: misc_feature
<222> LOCATION: (1151)..(1152)
<223> OTHER INFORMATION: n is a, c, g, or t
<220> FEATURE:
<221> NAME/KEY: misc_feature
<222> LOCATION: (1154)..(1154)
<223> OTHER INFORMATION: n is a, c, g, or t
<220> FEATURE:
<221> NAME/KEY: misc_feature
<222> LOCATION: (1157)..(1157)
<223> OTHER INFORMATION: n is a, c, g, or t
<220> FEATURE:
<221> NAME/KEY: misc_feature
<222> LOCATION: (1160)..(1160)
<223> OTHER INFORMATION: n is a, c, g, or t
<220> FEATURE:
<221> NAME/KEY: misc_feature
<222> LOCATION: (1163)..(1163)
<223> OTHER INFORMATION: n is a, c, g, or t
<220> FEATURE:
<221> NAME/KEY: misc_feature
<222> LOCATION: (1166)..(1166)
<223> OTHER INFORMATION: n is a, c, g, or t
<220> FEATURE:
<221> NAME/KEY: misc_feature
<222> LOCATION: (1169)..(1169)
<223> OTHER INFORMATION: n is a, c, g, or t
<220> FEATURE:
<221> NAME/KEY: misc_feature
<222> LOCATION: (1172)..(1172)
<223> OTHER INFORMATION: n is a, c, g, or t
<220> FEATURE:
<221> NAME/KEY: misc_feature
```

```
<222> LOCATION: (1175)..(1176)
<223> OTHER INFORMATION: n is a, c, g, or t
<220> FEATURE:
<221> NAME/KEY: misc_feature
<222> LOCATION: (1178)..(1179)
<223> OTHER INFORMATION: n is a, c, g, or t
<220> FEATURE:
<221> NAME/KEY: misc_feature
<222> LOCATION: (1181)..(1184)
<223> OTHER INFORMATION: n is a, c, g, or t
<220> FEATURE:
<221> NAME/KEY: misc_feature
<222> LOCATION: (1186)..(1190)
<223> OTHER INFORMATION: n is a, c, g, or t
<220> FEATURE:
<221> NAME/KEY: misc_feature
<222> LOCATION: (1193)..(1193)
<223> OTHER INFORMATION: n is a, c, g, or t
<220> FEATURE:
<221> NAME/KEY: misc_feature
<222> LOCATION: (1195)..(1202)
<223> OTHER INFORMATION: n is a, c, g, or t
<220> FEATURE:
<221> NAME/KEY: misc_feature
<222> LOCATION: (1204)..(1205)
<223> OTHER INFORMATION: n is a, c, g, or t
<220> FEATURE:
<221> NAME/KEY: misc_feature
<222> LOCATION: (1208)..(1211)
<223> OTHER INFORMATION: n is a, c, g, or t
<220> FEATURE:
<221> NAME/KEY: misc_feature
<222> LOCATION: (1214)..(1215)
<223> OTHER INFORMATION: n is a, c, g, or t
<220> FEATURE:
<221> NAME/KEY: misc_feature
<222> LOCATION: (1217)..(1217)
<223> OTHER INFORMATION: n is a, c, g, or t

<400> SEQUENCE: 84 nnntnnnng nnntnnnnna nnnnnnncn tcaanctnnc nantntnccn nnnncnntnn      60
nnggnntnnt nagnnangan aantttgann nnncnnnngc ntanagnntn nanannnnna    120
gcnnnttnca ntttgtncan gngnntgtna nnatnntnnn nganncnncn atnntnnnnn    180
nnngnntnnt nccntggnnn tggnanannn nnggnnnnnt nntnnnnann nnnggnntnn    240
ntnnnnagan nganatnntn canacncttn cnttnntngc ngnnnnnang nnntggtcnc    300
agatnnnnga nntnccnttn tcnntntant cnacnttngt natngagncn cgncatggnt    360
tnaanaanca aacnnnatgg ntnttnntnn ggganatgnt nanngnnnnn nnnctnnnnn    420
tnntnnnngn nccnccnatn gtnncngcna tnatnnnnat ngtncagann ggnggnccnt    480
anntngcnnt ntatctntgg gnnttnangt tnnnnntnnc nntnntgntg atgncnntnt    540
anccnntnnt natngcnccn ctnttcaana nnttcacncc nntnccngan ggnnnnctnn    600
gngnnaanat ngagaanctn gcnncntcnn tnnantnncc nntnaanaan ntnttngtnn    660 tngangntc nacnngntca agncanagna angcntanat gtatggnttn tnnaananca    720
anngnatngt ncnntangan acnntnatnn nncantgnnn nnangannan gannntngtnn   780 cngttatngc ncangannt ggncantgga anctnannca nactnnntan ncnttnntng    840
cnntncannt ncttnnnntn ntncaattng gaggntanac nctnnntnngn anntcnnnng   900 nnctntnnnn nagnttnggn ttnnnnnnnc anccngtnnt natnggnntn atcntnttnc   960
agcanacnnt natnccnntn cancannnnn tnagctttnn nctnaacctn ntnagnngan  1020
cnttngantt tcaggcngat gnntngcnn nnnnnntngn ntannnnnnn nnntngnn     1080 nnnnnctnnt naanctncag gangagaann tntcnncnat gaanacngan cnntngnant  1140
cngcntatca nnantcncan ccnccnctg tngangnnt nnnngnnnnn gangnnnnnn    1200
```
nnannaannn ngannan                                              1217

<210> SEQ ID NO 85
<211> LENGTH: 268
<212> TYPE: PRT
<213> ORGANISM: Artificial sequence
<220> FEATURE:
<223> OTHER INFORMATION: Description of Artificial Sequence: Consensus
      sequence
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (11)..(13)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(28)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (35)..(40)
<223> OTHER INFORMATION: Xaa can be any naturally occurring amino acid
<220> FEATURE:
<221> NAME/KEY: misc_feature
<222> LOCATION: (43)..(47)
<223> OTHER INFORMATION: Xaa can be any naturally occurring amino acid
<220> FEATURE:
<221> NAME/KEY: misc_feature
<222> LOCATION: (49)..(54)
<223> OTHER INFORMATION: Xaa can be any naturally occurring amino acid
<220> FEATURE:
<221> NAME/KEY: misc_feature
<222> LOCATION: (57)..(62)
<223> OTHER INFORMATION: Xaa can be any naturally occurring amino acid
<220> FEATURE:
<221> NAME/KEY: misc_feature
<222> LOCATION: (64)..(73)
<223> OTHER INFORMATION: Xaa can be any naturally occurring amino acid
<220> FEATURE:
<221> NAME/KEY: misc_feature
<222> LOCATION: (75)..(77)
<223> OTHER INFORMATION: Xaa can be any naturally occurring amino acid
<220> FEATURE:
<221> NAME/KEY: misc_feature
<222> LOCATION: (79)..(86)
<223> OTHER INFORMATION: Xaa can be any naturally occurring amino acid
<220> FEATURE:
<221> NAME/KEY: misc_feature
<222> LOCATION: (88)..(90)
<223> OTHER INFORMATION: Xaa can be any naturally occurring amino acid
<220> FEATURE:

```
<221> NAME/KEY: misc_feature
<222> LOCATION: (92)..(93)
<223> OTHER INFORMATION: Xaa can be any naturally occurring amino acid
<220> FEATURE:
<221> NAME/KEY: misc_feature
<222> LOCATION: (95)..(95)
<223> OTHER INFORMATION: Xaa can be any naturally occurring amino acid
<220> FEATURE:
<221> NAME/KEY: misc_feature
<222> LOCATION: (97)..(97)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid
<220> FEATURE:
<221> NAME/KEY: misc_feature
<222> LOCATION: (105)..(106)
<223> OTHER INFORMATION: Xaa can be any naturally occurring amino acid
<220> FEATURE:
<221> NAME/KEY: misc_feature
<222> LOCATION: (108)..(108)
<223> OTHER INFORMATION: Xaa can be any naturally occurring amino acid
<220> FEATURE:
<221> NAME/KEY: misc_feature
<222> LOCATION: (110)..(112)
<223> OTHER INFORMATION: Xaa can be any naturally occurring amino acid
<220> FEATURE:
<221> NAME/KEY: misc_feature
<222> LOCATION: (115)..(115)
<223> OTHER INFORMATION: Xaa can be any naturally occurring amino acid
<220> FEATURE:
<221> NAME/KEY: misc_feature
<222> LOCATION: (118)..(122)
<223> OTHER INFORMATION: Xaa can be any naturally occurring amino acid
<220> FEATURE:
<221> NAME/KEY: misc_feature
<222> LOCATION: (125)..(125)
<223> OTHER INFORMATION: Xaa can be any naturally occurring amino acid
<220> FEATURE:
<221> NAME/KEY: misc_feature
<222> LOCATION: (127)..(127)
<223> OTHER INFORMATION: Xaa can be any naturally occurring amino acid
<220> FEATURE:
<221> NAME/KEY: misc_feature
<222> LOCATION: (130)..(130)
<223> OTHER INFORMATION: Xaa can be any naturally occurring amino acid
<220> FEATURE:
<221> NAME/KEY: misc_feature
<222> LOCATION: (134)..(134)
<223> OTHER INFORMATION: Xaa can be any naturally occurring amino acid
<220> FEATURE:
<221> NAME/KEY: misc_feature
<222> LOCATION: (143)..(144)
<223> OTHER INFORMATION: Xaa can be any naturally occurring amino acid
<220> FEATURE:
<221> NAME/KEY: misc_feature
<222> LOCATION: (146)..(166)
<223> OTHER INFORMATION: Xaa can be any naturally occurring amino acid
<220> FEATURE:
<221> NAME/KEY: misc_feature
<222> LOCATION: (168)..(170)
<223> OTHER INFORMATION: Xaa can be any naturally occurring amino acid
<220> FEATURE:
<221> NAME/KEY: misc_feature
<222> LOCATION: (172)..(172)
<223> OTHER INFORMATION: Xaa can be any naturally occurring amino acid
<220> FEATURE:
<221> NAME/KEY: misc_feature
<222> LOCATION: (176)..(176)
<223> OTHER INFORMATION: Xaa can be any naturally occurring amino acid
<220> FEATURE:
<221> NAME/KEY: misc_feature
<222> LOCATION: (180)..(182)
<223> OTHER INFORMATION: Xaa can be any naturally occurring amino acid
<220> FEATURE:
<221> NAME/KEY: misc_feature
<222> LOCATION: (184)..(196)
<223> OTHER INFORMATION: Xaa can be any naturally occurring amino acid
<220> FEATURE:
```

```
<221> NAME/KEY: misc_feature
<222> LOCATION: (198)..(203)
<223> OTHER INFORMATION: Xaa can be any naturally occurring amino acid
<220> FEATURE:
<221> NAME/KEY: misc_feature
<222> LOCATION: (205)..(207)
<223> OTHER INFORMATION: Xaa can be any naturally occurring amino acid
<220> FEATURE:
<221> NAME/KEY: misc_feature
<222> LOCATION: (209)..(209)
<223> OTHER INFORMATION: Xaa can be any naturally occurring amino acid
<220> FEATURE:
<221> NAME/KEY: misc_feature
<222> LOCATION: (212)..(213)
<223> OTHER INFORMATION: Xaa can be any naturally occurring amino acid
<220> FEATURE:
<221> NAME/KEY: misc_feature
<222> LOCATION: (215)..(215)
<223> OTHER INFORMATION: Xaa can be any naturally occurring amino acid
<220> FEATURE:
<221> NAME/KEY: misc_feature
<222> LOCATION: (219)..(220)
<223> OTHER INFORMATION: Xaa can be any naturally occurring amino acid
<220> FEATURE:
<221> NAME/KEY: misc_feature
<222> LOCATION: (222)..(223)
<223> OTHER INFORMATION: Xaa can be any naturally occurring amino acid
<220> FEATURE:
<221> NAME/KEY: misc_feature
<222> LOCATION: (225)..(225)
<223> OTHER INFORMATION: Xaa can be any naturally occurring amino acid
<220> FEATURE:
<221> NAME/KEY: misc_feature
<222> LOCATION: (227)..(229)
<223> OTHER INFORMATION: Xaa can be any naturally occurring amino acid
<220> FEATURE:
<221> NAME/KEY: misc_feature
<222> LOCATION: (231)..(232)
<223> OTHER INFORMATION: Xaa can be any naturally occurring amino acid
<220> FEATURE:
<221> NAME/KEY: misc_feature
<222> LOCATION: (236)..(236)
<223> OTHER INFORMATION: Xaa can be any naturally occurring amino acid
<220> FEATURE:
<221> NAME/KEY: misc_feature
<222> LOCATION: (239)..(239)
<223> OTHER INFORMATION: Xaa can be any naturally occurring amino acid
<220> FEATURE:
<221> NAME/KEY: misc_feature
<222> LOCATION: (241)..(243)
<223> OTHER INFORMATION: Xaa can be any naturally occurring amino acid
<220> FEATURE:
<221> NAME/KEY: misc_feature
<222> LOCATION: (245)..(245)
<223> OTHER INFORMATION: Xaa can be any naturally occurring amino acid
<220> FEATURE:
<221> NAME/KEY: misc_feature
<222> LOCATION: (248)..(248)
<223> OTHER INFORMATION: Xaa can be any naturally occurring amino acid
<220> FEATURE:
<221> NAME/KEY: misc_feature
<222> LOCATION: (252)..(252)
<223> OTHER INFORMATION: Xaa can be any naturally occurring amino acid
<220> FEATURE:
<221> NAME/KEY: misc_feature
<222> LOCATION: (254)..(254)
<223> OTHER INFORMATION: Xaa can be any naturally occurring amino acid
<220> FEATURE:
<221> NAME/KEY: misc_feature
<222> LOCATION: (258)..(265)
<223> OTHER INFORMATION: Xaa can be any naturally occurring amino acid
<220> FEATURE:
<221> NAME/KEY: misc_feature
<222> LOCATION: (267)..(268)
<223> OTHER INFORMATION: Xaa can be any naturally occurring amino acid

<400> SEQUENCE: 85

Leu Xaa Xaa Xaa Xaa Leu Pro Xaa Xaa Leu Xaa Xaa Xaa Leu Pro Xaa
 1               5                  10                  15
```

Ser Xaa Tyr Ser Xaa Phe Val Xaa Glu Xaa Xaa Xaa Gly Phe Asn Lys
            20                  25                  30

Xaa Thr Xaa Xaa Xaa Xaa Xaa Asp Met Xaa Xaa Xaa Xaa Xaa Xaa Leu
        35                  40                  45

Xaa Xaa Xaa Xaa Xaa Xaa Pro Ile Xaa Xaa Xaa Xaa Xaa Ile Xaa
    50                  55                  60

Xaa Xaa Xaa Xaa Xaa Xaa Xaa Xaa Tyr Xaa Xaa Xaa Phe Xaa Xaa
65                  70                  75                  80

Xaa Xaa Xaa Xaa Xaa Xaa Met Xaa Xaa Xaa Pro Xaa Xaa Ile Xaa Pro
                85                  90                  95

Xaa Phe Asn Xaa Phe Thr Pro Leu Xaa Xaa Gly Xaa Leu Xaa Xaa Xaa
            100                 105                 110

Ile Glu Xaa Leu Ala Xaa Xaa Xaa Xaa Pro Leu Xaa Lys Xaa Phe
            115                 120                 125

Val Xaa Asp Gly Ser Xaa Arg Ser Ser His Ser Asn Ala Tyr Xaa Xaa
    130                 135                 140

Gly Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Glu Xaa Xaa Xaa Val Xaa Ala His Glu Xaa
                165                 170                 175

Gly His Trp Xaa Xaa Xaa His Xaa Xaa Xaa Xaa Xaa Xaa Xaa Xaa
            180                 185                 190

Xaa Xaa Xaa Xaa Pro Xaa Xaa Xaa Xaa Xaa Phe Xaa Xaa Xaa Leu
        195                 200                 205

Xaa Ser Arg Xaa Xaa Glu Xaa Gln Ala Asp Xaa Xaa Ala Xaa Xaa Leu
        210                 215                 220

Xaa Tyr Xaa Xaa Xaa Leu Xaa Xaa Asn Leu Ser Xaa Met Asn Xaa Asp
225                 230                 235                 240

Xaa Xaa Xaa Ser Xaa Tyr His Xaa Ser His Pro Xaa Leu Xaa Glu Arg
            245                 250                 255

Leu Xaa Xaa Xaa Xaa Xaa Xaa Xaa Xaa Lys Xaa Xaa
            260                 265

<210> SEQ ID NO 86
<211> LENGTH: 1275
<212> TYPE: DNA
<213> ORGANISM: Artificial Sequence
<220> FEATURE:
<223> OTHER INFORMATION: Description of Artificial Sequence: Consensus
      sequence
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (6)..(8)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (14)..(15)
<223> OTHER INFORMATION: n is a, c, g, or t
<220> FEATURE:
<221> NAME/KEY: misc_feature
<222> LOCATION: (18)..(25)

-continued

```
<223> OTHER INFORMATION: n is a, c, g, or t
<220> FEATURE:
<221> NAME/KEY: misc_feature
<222> LOCATION: (27)..(30)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (83)..(84)
<223> OTHER INFORMATION: n is a, c, g, or t
<220> FEATURE:
<221> NAME/KEY: misc_feature
<222> LOCATION: (86)..(87)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t
<220> FEATURE:
<221> NAME/KEY: misc_feature
<222> LOCATION: (111)..(111)
<223> OTHER INFORMATION: n is a, c, g, or t
<220> FEATURE:
<221> NAME/KEY: misc_feature
<222> LOCATION: (114)..(114)
<223> OTHER INFORMATION: n is a, c, g, or t
<220> FEATURE:
<221> NAME/KEY: misc_feature
<222> LOCATION: (117)..(117)
```

```
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (122)..(123)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (129)..(129)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (156)..(157)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (168)..(169)
<223> OTHER INFORMATION: n is a, c, g, or t
<220> FEATURE:
<221> NAME/KEY: misc_feature
<222> LOCATION: (172)..(172)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (176)..(176)
<223> OTHER INFORMATION: n is a, c, g, or t
<220> FEATURE:
<221> NAME/KEY: misc_feature
<222> LOCATION: (181)..(181)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (186)..(186)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (207)..(207)
<223> OTHER INFORMATION: n is a, c, g, or t
<220> FEATURE:
<221> NAME/KEY: misc_feature
<222> LOCATION: (210)..(210)
```

```
<223> OTHER INFORMATION: n is a, c, g, or t
<220> FEATURE:
<221> NAME/KEY: misc_feature
<222> LOCATION: (214)..(214)
<223> OTHER INFORMATION: n is a, c, g, or t
<220> FEATURE:
<221> NAME/KEY: misc_feature
<222> LOCATION: (216)..(216)
<223> OTHER INFORMATION: n is a, c, g, or t
<220> FEATURE:
<221> NAME/KEY: misc_feature
<222> LOCATION: (218)..(219)
<223> OTHER INFORMATION: n is a, c, g, or t
<220> FEATURE:
<221> NAME/KEY: misc_feature
<222> LOCATION: (226)..(226)
<223> OTHER INFORMATION: n is a, c, g, or t
<220> FEATURE:
<221> NAME/KEY: misc_feature
<222> LOCATION: (228)..(228)
<223> OTHER INFORMATION: n is a, c, g, or t
<220> FEATURE:
<221> NAME/KEY: misc_feature
<222> LOCATION: (232)..(232)
<223> OTHER INFORMATION: n is a, c, g, or t
<220> FEATURE:
<221> NAME/KEY: misc_feature
<222> LOCATION: (236)..(236)
<223> OTHER INFORMATION: n is a, c, g, or t
<220> FEATURE:
<221> NAME/KEY: misc_feature
<222> LOCATION: (244)..(244)
<223> OTHER INFORMATION: n is a, c, g, or t
<220> FEATURE:
<221> NAME/KEY: misc_feature
<222> LOCATION: (246)..(246)
<223> OTHER INFORMATION: n is a, c, g, or t
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (266)..(267)
<223> OTHER INFORMATION: n is a, c, g, or t
<220> FEATURE:
<221> NAME/KEY: misc_feature
<222> LOCATION: (270)..(270)
<223> OTHER INFORMATION: n is a, c, g, or t
<220> FEATURE:
<221> NAME/KEY: misc_feature
<222> LOCATION: (273)..(273)
<223> OTHER INFORMATION: n is a, c, g, or t
<220> FEATURE:
<221> NAME/KEY: misc_feature
<222> LOCATION: (275)..(277)
<223> OTHER INFORMATION: n is a, c, g, or t
<220> FEATURE:
<221> NAME/KEY: misc_feature
<222> LOCATION: (280)..(280)
<223> OTHER INFORMATION: n is a, c, g, or t
<220> FEATURE:
<221> NAME/KEY: misc_feature
<222> LOCATION: (282)..(283)
<223> OTHER INFORMATION: n is a, c, g, or t
<220> FEATURE:
<221> NAME/KEY: misc_feature
<222> LOCATION: (285)..(285)
<223> OTHER INFORMATION: n is a, c, g, or t
<220> FEATURE:
<221> NAME/KEY: misc_feature
<222> LOCATION: (287)..(291)
<223> OTHER INFORMATION: n is a, c, g, or t
<220> FEATURE:
<221> NAME/KEY: misc_feature
<222> LOCATION: (294)..(295)
<223> OTHER INFORMATION: n is a, c, g, or t
<220> FEATURE:
<221> NAME/KEY: misc_feature
<222> LOCATION: (297)..(298)
```

-continued

```
<223> OTHER INFORMATION: n is a, c, g, or t
<220> FEATURE:
<221> NAME/KEY: misc_feature
<222> LOCATION: (301)..(301)
<223> OTHER INFORMATION: n is a, c, g, or t
<220> FEATURE:
<221> NAME/KEY: misc_feature
<222> LOCATION: (303)..(303)
<223> OTHER INFORMATION: n is a, c, g, or t
<220> FEATURE:
<221> NAME/KEY: misc_feature
<222> LOCATION: (315)..(315)
<223> OTHER INFORMATION: n is a, c, g, or t
<220> FEATURE:
<221> NAME/KEY: misc_feature
<222> LOCATION: (321)..(321)
<223> OTHER INFORMATION: n is a, c, g, or t
<220> FEATURE:
<221> NAME/KEY: misc_feature
<222> LOCATION: (324)..(324)
<223> OTHER INFORMATION: n is a, c, g, or t
<220> FEATURE:
<221> NAME/KEY: misc_feature
<222> LOCATION: (328)..(328)
<223> OTHER INFORMATION: n is a, c, g, or t
<220> FEATURE:
<221> NAME/KEY: misc_feature
<222> LOCATION: (330)..(330)
<223> OTHER INFORMATION: n is a, c, g, or t
<220> FEATURE:
<221> NAME/KEY: misc_feature
<222> LOCATION: (336)..(336)
<223> OTHER INFORMATION: n is a, c, g, or t
<220> FEATURE:
<221> NAME/KEY: misc_feature
<222> LOCATION: (339)..(339)
<223> OTHER INFORMATION: n is a, c, g, or t
<220> FEATURE:
<221> NAME/KEY: misc_feature
<222> LOCATION: (342)..(343)
<223> OTHER INFORMATION: n is a, c, g, or t
<220> FEATURE:
<221> NAME/KEY: misc_feature
<222> LOCATION: (345)..(345)
<223> OTHER INFORMATION: n is a, c, g, or t
<220> FEATURE:
<221> NAME/KEY: misc_feature
<222> LOCATION: (350)..(351)
<223> OTHER INFORMATION: n is a, c, g, or t
<220> FEATURE:
<221> NAME/KEY: misc_feature
<222> LOCATION: (363)..(363)
<223> OTHER INFORMATION: n is a, c, g, or t
<220> FEATURE:
<221> NAME/KEY: misc_feature
<222> LOCATION: (366)..(366)
<223> OTHER INFORMATION: n is a, c, g, or t
<220> FEATURE:
<221> NAME/KEY: misc_feature
<222> LOCATION: (375)..(375)
<223> OTHER INFORMATION: n is a, c, g, or t
<220> FEATURE:
<221> NAME/KEY: misc_feature
<222> LOCATION: (382)..(382)
<223> OTHER INFORMATION: n is a, c, g, or t
<220> FEATURE:
<221> NAME/KEY: misc_feature
<222> LOCATION: (396)..(396)
<223> OTHER INFORMATION: n is a, c, g, or t
<220> FEATURE:
<221> NAME/KEY: misc_feature
<222> LOCATION: (402)..(402)
<223> OTHER INFORMATION: n is a, c, g, or t
<220> FEATURE:
<221> NAME/KEY: misc_feature
<222> LOCATION: (406)..(406)
<223> OTHER INFORMATION: n is a, c, g, or t
<220> FEATURE:
<221> NAME/KEY: misc_feature
<222> LOCATION: (408)..(408)
```

-continued

```
<223> OTHER INFORMATION: n is a, c, g, or t
<220> FEATURE:
<221> NAME/KEY: misc_feature
<222> LOCATION: (411)..(411)
<223> OTHER INFORMATION: n is a, c, g, or t
<220> FEATURE:
<221> NAME/KEY: misc_feature
<222> LOCATION: (417)..(417)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (423)..(423)
<223> OTHER INFORMATION: n is a, c, g, or t
<220> FEATURE:
<221> NAME/KEY: misc_feature
<222> LOCATION: (426)..(426)
<223> OTHER INFORMATION: n is a, c, g, or t
<220> FEATURE:
<221> NAME/KEY: misc_feature
<222> LOCATION: (433)..(434)
<223> OTHER INFORMATION: n is a, c, g, or t
<220> FEATURE:
<221> NAME/KEY: misc_feature
<222> LOCATION: (439)..(439)
<223> OTHER INFORMATION: n is a, c, g, or t
<220> FEATURE:
<221> NAME/KEY: misc_feature
<222> LOCATION: (441)..(441)
<223> OTHER INFORMATION: n is a, c, g, or t
<220> FEATURE:
<221> NAME/KEY: misc_feature
<222> LOCATION: (445)..(445)
<223> OTHER INFORMATION: n is a, c, g, or t
<220> FEATURE:
<221> NAME/KEY: misc_feature
<222> LOCATION: (457)..(457)
<223> OTHER INFORMATION: n is a, c, g, or t
<220> FEATURE:
<221> NAME/KEY: misc_feature
<222> LOCATION: (459)..(459)
<223> OTHER INFORMATION: n is a, c, g, or t
<220> FEATURE:
<221> NAME/KEY: misc_feature
<222> LOCATION: (467)..(469)
<223> OTHER INFORMATION: n is a, c, g, or t
<220> FEATURE:
<221> NAME/KEY: misc_feature
<222> LOCATION: (474)..(474)
<223> OTHER INFORMATION: n is a, c, g, or t
<220> FEATURE:
<221> NAME/KEY: misc_feature
<222> LOCATION: (480)..(480)
<223> OTHER INFORMATION: n is a, c, g, or t
<220> FEATURE:
<221> NAME/KEY: misc_feature
<222> LOCATION: (484)..(486)
<223> OTHER INFORMATION: n is a, c, g, or t
<220> FEATURE:
<221> NAME/KEY: misc_feature
<222> LOCATION: (488)..(489)
<223> OTHER INFORMATION: n is a, c, g, or t
<220> FEATURE:
<221> NAME/KEY: misc_feature
<222> LOCATION: (492)..(492)
<223> OTHER INFORMATION: n is a, c, g, or t
<220> FEATURE:
<221> NAME/KEY: misc_feature
<222> LOCATION: (495)..(495)
<223> OTHER INFORMATION: n is a, c, g, or t
<220> FEATURE:
<221> NAME/KEY: misc_feature
<222> LOCATION: (498)..(498)
<223> OTHER INFORMATION: n is a, c, g, or t
<220> FEATURE:
<221> NAME/KEY: misc_feature
<222> LOCATION: (501)..(501)
```

```
<223> OTHER INFORMATION: n is a, c, g, or t
<220> FEATURE:
<221> NAME/KEY: misc_feature
<222> LOCATION: (504)..(504)
<223> OTHER INFORMATION: n is a, c, g, or t
<220> FEATURE:
<221> NAME/KEY: misc_feature
<222> LOCATION: (507)..(507)
<223> OTHER INFORMATION: n is a, c, g, or t
<220> FEATURE:
<221> NAME/KEY: misc_feature
<222> LOCATION: (510)..(510)
<223> OTHER INFORMATION: n is a, c, g, or t
<220> FEATURE:
<221> NAME/KEY: misc_feature
<222> LOCATION: (514)..(514)
<223> OTHER INFORMATION: n is a, c, g, or t
<220> FEATURE:
<221> NAME/KEY: misc_feature
<222> LOCATION: (516)..(516)
<223> OTHER INFORMATION: n is a, c, g, or t
<220> FEATURE:
<221> NAME/KEY: misc_feature
<222> LOCATION: (522)..(522)
<223> OTHER INFORMATION: n is a, c, g, or t
<220> FEATURE:
<221> NAME/KEY: misc_feature
<222> LOCATION: (537)..(537)
<223> OTHER INFORMATION: n is a, c, g, or t
<220> FEATURE:
<221> NAME/KEY: misc_feature
<222> LOCATION: (540)..(541)
<223> OTHER INFORMATION: n is a, c, g, or t
<220> FEATURE:
<221> NAME/KEY: misc_feature
<222> LOCATION: (543)..(543)
<223> OTHER INFORMATION: n is a, c, g, or t
<220> FEATURE:
<221> NAME/KEY: misc_feature
<222> LOCATION: (555)..(555)
<223> OTHER INFORMATION: n is a, c, g, or t
<220> FEATURE:
<221> NAME/KEY: misc_feature
<222> LOCATION: (560)..(561)
<223> OTHER INFORMATION: n is a, c, g, or t
<220> FEATURE:
<221> NAME/KEY: misc_feature
<222> LOCATION: (564)..(564)
<223> OTHER INFORMATION: n is a, c, g, or t
<220> FEATURE:
<221> NAME/KEY: misc_feature
<222> LOCATION: (566)..(566)
<223> OTHER INFORMATION: n is a, c, g, or t
<220> FEATURE:
<221> NAME/KEY: misc_feature
<222> LOCATION: (571)..(573)
<223> OTHER INFORMATION: n is a, c, g, or t
<220> FEATURE:
<221> NAME/KEY: misc_feature
<222> LOCATION: (576)..(576)
<223> OTHER INFORMATION: n is a, c, g, or t
<220> FEATURE:
<221> NAME/KEY: misc_feature
<222> LOCATION: (580)..(580)
<223> OTHER INFORMATION: n is a, c, g, or t
<220> FEATURE:
<221> NAME/KEY: misc_feature
<222> LOCATION: (582)..(582)
<223> OTHER INFORMATION: n is a, c, g, or t
<220> FEATURE:
<221> NAME/KEY: misc_feature
<222> LOCATION: (594)..(595)
<223> OTHER INFORMATION: n is a, c, g, or t
<220> FEATURE:
<221> NAME/KEY: misc_feature
<222> LOCATION: (597)..(597)
<223> OTHER INFORMATION: n is a, c, g, or t
<220> FEATURE:
<221> NAME/KEY: misc_feature
<222> LOCATION: (600)..(600)
```

```
<223> OTHER INFORMATION: n is a, c, g, or t
<220> FEATURE:
<221> NAME/KEY: misc_feature
<222> LOCATION: (603)..(603)
<223> OTHER INFORMATION: n is a, c, g, or t
<220> FEATURE:
<221> NAME/KEY: misc_feature
<222> LOCATION: (606)..(607)
<223> OTHER INFORMATION: n is a, c, g, or t
<220> FEATURE:
<221> NAME/KEY: misc_feature
<222> LOCATION: (609)..(609)
<223> OTHER INFORMATION: n is a, c, g, or t
<220> FEATURE:
<221> NAME/KEY: misc_feature
<222> LOCATION: (612)..(612)
<223> OTHER INFORMATION: n is a, c, g, or t
<220> FEATURE:
<221> NAME/KEY: misc_feature
<222> LOCATION: (615)..(615)
<223> OTHER INFORMATION: n is a, c, g, or t
<220> FEATURE:
<221> NAME/KEY: misc_feature
<222> LOCATION: (618)..(618)
<223> OTHER INFORMATION: n is a, c, g, or t
<220> FEATURE:
<221> NAME/KEY: misc_feature
<222> LOCATION: (621)..(621)
<223> OTHER INFORMATION: n is a, c, g, or t
<220> FEATURE:
<221> NAME/KEY: misc_feature
<222> LOCATION: (627)..(627)
<223> OTHER INFORMATION: n is a, c, g, or t
<220> FEATURE:
<221> NAME/KEY: misc_feature
<222> LOCATION: (630)..(630)
<223> OTHER INFORMATION: n is a, c, g, or t
<220> FEATURE:
<221> NAME/KEY: misc_feature
<222> LOCATION: (639)..(639)
<223> OTHER INFORMATION: n is a, c, g, or t
<220> FEATURE:
<221> NAME/KEY: misc_feature
<222> LOCATION: (645)..(645)
<223> OTHER INFORMATION: n is a, c, g, or t
<220> FEATURE:
<221> NAME/KEY: misc_feature
<222> LOCATION: (651)..(652)
<223> OTHER INFORMATION: n is a, c, g, or t
<220> FEATURE:
<221> NAME/KEY: misc_feature
<222> LOCATION: (654)..(654)
<223> OTHER INFORMATION: n is a, c, g, or t
<220> FEATURE:
<221> NAME/KEY: misc_feature
<222> LOCATION: (658)..(658)
<223> OTHER INFORMATION: n is a, c, g, or t
<220> FEATURE:
<221> NAME/KEY: misc_feature
<222> LOCATION: (666)..(666)
<223> OTHER INFORMATION: n is a, c, g, or t
<220> FEATURE:
<221> NAME/KEY: misc_feature
<222> LOCATION: (669)..(669)
<223> OTHER INFORMATION: n is a, c, g, or t
<220> FEATURE:
<221> NAME/KEY: misc_feature
<222> LOCATION: (684)..(684)
<223> OTHER INFORMATION: n is a, c, g, or t
<220> FEATURE:
<221> NAME/KEY: misc_feature
<222> LOCATION: (687)..(687)
<223> OTHER INFORMATION: n is a, c, g, or t
<220> FEATURE:
<221> NAME/KEY: misc_feature
<222> LOCATION: (690)..(690)
<223> OTHER INFORMATION: n is a, c, g, or t
<220> FEATURE:
<221> NAME/KEY: misc_feature
<222> LOCATION: (693)..(693)
```

```
<223> OTHER INFORMATION: n is a, c, g, or t
<220> FEATURE:
<221> NAME/KEY: misc_feature
<222> LOCATION: (695)..(695)
<223> OTHER INFORMATION: n is a, c, g, or t
<220> FEATURE:
<221> NAME/KEY: misc_feature
<222> LOCATION: (699)..(700)
<223> OTHER INFORMATION: n is a, c, g, or t
<220> FEATURE:
<221> NAME/KEY: misc_feature
<222> LOCATION: (702)..(702)
<223> OTHER INFORMATION: n is a, c, g, or t
<220> FEATURE:
<221> NAME/KEY: misc_feature
<222> LOCATION: (708)..(708)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t
<220> FEATURE:
<221> NAME/KEY: misc_feature
<222> LOCATION: (729)..(729)
<223> OTHER INFORMATION: n is a, c, g, or t
<220> FEATURE:
<221> NAME/KEY: misc_feature
<222> LOCATION: (735)..(735)
<223> OTHER INFORMATION: n is a, c, g, or t
<220> FEATURE:
<221> NAME/KEY: misc_feature
<222> LOCATION: (741)..(741)
<223> OTHER INFORMATION: n is a, c, g, or t
<220> FEATURE:
<221> NAME/KEY: misc_feature
<222> LOCATION: (744)..(744)
<223> OTHER INFORMATION: n is a, c, g, or t
<220> FEATURE:
<221> NAME/KEY: misc_feature
<222> LOCATION: (747)..(747)
<223> OTHER INFORMATION: n is a, c, g, or t
<220> FEATURE:
<221> NAME/KEY: misc_feature
<222> LOCATION: (753)..(753)
<223> OTHER INFORMATION: n is a, c, g, or t
<220> FEATURE:
<221> NAME/KEY: misc_feature
<222> LOCATION: (756)..(756)
<223> OTHER INFORMATION: n is a, c, g, or t
<220> FEATURE:
<221> NAME/KEY: misc_feature
<222> LOCATION: (765)..(765)
<223> OTHER INFORMATION: n is a, c, g, or t
<220> FEATURE:
<221> NAME/KEY: misc_feature
<222> LOCATION: (771)..(771)
<223> OTHER INFORMATION: n is a, c, g, or t
<220> FEATURE:
<221> NAME/KEY: misc_feature
<222> LOCATION: (780)..(780)
<223> OTHER INFORMATION: n is a, c, g, or t
<220> FEATURE:
<221> NAME/KEY: misc_feature
<222> LOCATION: (789)..(789)
<223> OTHER INFORMATION: n is a, c, g, or t
<220> FEATURE:
<221> NAME/KEY: misc_feature
<222> LOCATION: (791)..(791)
<223> OTHER INFORMATION: n is a, c, g, or t
<220> FEATURE:
<221> NAME/KEY: misc_feature
<222> LOCATION: (798)..(798)
<223> OTHER INFORMATION: n is a, c, g, or t
<220> FEATURE:
<221> NAME/KEY: misc_feature
<222> LOCATION: (801)..(801)
<223> OTHER INFORMATION: n is a, c, g, or t
<220> FEATURE:
<221> NAME/KEY: misc_feature
<222> LOCATION: (804)..(804)
```

-continued

```
<223> OTHER INFORMATION: n is a, c, g, or t
<220> FEATURE:
<221> NAME/KEY: misc_feature
<222> LOCATION: (810)..(810)
<223> OTHER INFORMATION: n is a, c, g, or t
<220> FEATURE:
<221> NAME/KEY: misc_feature
<222> LOCATION: (817)..(817)
<223> OTHER INFORMATION: n is a, c, g, or t
<220> FEATURE:
<221> NAME/KEY: misc_feature
<222> LOCATION: (819)..(820)
<223> OTHER INFORMATION: n is a, c, g, or t
<220> FEATURE:
<221> NAME/KEY: misc_feature
<222> LOCATION: (822)..(822)
<223> OTHER INFORMATION: n is a, c, g, or t
<220> FEATURE:
<221> NAME/KEY: misc_feature
<222> LOCATION: (825)..(826)
<223> OTHER INFORMATION: n is a, c, g, or t
<220> FEATURE:
<221> NAME/KEY: misc_feature
<222> LOCATION: (828)..(828)
<223> OTHER INFORMATION: n is a, c, g, or t
<220> FEATURE:
<221> NAME/KEY: misc_feature
<222> LOCATION: (837)..(837)
<223> OTHER INFORMATION: n is a, c, g, or t
<220> FEATURE:
<221> NAME/KEY: misc_feature
<222> LOCATION: (840)..(840)
<223> OTHER INFORMATION: n is a, c, g, or t
<220> FEATURE:
<221> NAME/KEY: misc_feature
<222> LOCATION: (849)..(849)
<223> OTHER INFORMATION: n is a, c, g, or t
<220> FEATURE:
<221> NAME/KEY: misc_feature
<222> LOCATION: (852)..(852)
<223> OTHER INFORMATION: n is a, c, g, or t
<220> FEATURE:
<221> NAME/KEY: misc_feature
<222> LOCATION: (856)..(856)
<223> OTHER INFORMATION: n is a, c, g, or t
<220> FEATURE:
<221> NAME/KEY: misc_feature
<222> LOCATION: (858)..(858)
<223> OTHER INFORMATION: n is a, c, g, or t
<220> FEATURE:
<221> NAME/KEY: misc_feature
<222> LOCATION: (864)..(864)
<223> OTHER INFORMATION: n is a, c, g, or t
<220> FEATURE:
<221> NAME/KEY: misc_feature
<222> LOCATION: (870)..(870)
<223> OTHER INFORMATION: n is a, c, g, or t
<220> FEATURE:
<221> NAME/KEY: misc_feature
<222> LOCATION: (873)..(873)
<223> OTHER INFORMATION: n is a, c, g, or t
<220> FEATURE:
<221> NAME/KEY: misc_feature
<222> LOCATION: (876)..(876)
<223> OTHER INFORMATION: n is a, c, g, or t
<220> FEATURE:
<221> NAME/KEY: misc_feature
<222> LOCATION: (879)..(879)
<223> OTHER INFORMATION: n is a, c, g, or t
<220> FEATURE:
<221> NAME/KEY: misc_feature
<222> LOCATION: (883)..(885)
<223> OTHER INFORMATION: n is a, c, g, or t
<220> FEATURE:
<221> NAME/KEY: misc_feature
<222> LOCATION: (889)..(889)
<223> OTHER INFORMATION: n is a, c, g, or t
<220> FEATURE:
<221> NAME/KEY: misc_feature
<222> LOCATION: (891)..(891)
```

-continued

```
<223> OTHER INFORMATION: n is a, c, g, or t
<220> FEATURE:
<221> NAME/KEY: misc_feature
<222> LOCATION: (894)..(895)
<223> OTHER INFORMATION: n is a, c, g, or t
<220> FEATURE:
<221> NAME/KEY: misc_feature
<222> LOCATION: (900)..(901)
<223> OTHER INFORMATION: n is a, c, g, or t
<220> FEATURE:
<221> NAME/KEY: misc_feature
<222> LOCATION: (903)..(903)
<223> OTHER INFORMATION: n is a, c, g, or t
<220> FEATURE:
<221> NAME/KEY: misc_feature
<222> LOCATION: (906)..(906)
<223> OTHER INFORMATION: n is a, c, g, or t
<220> FEATURE:
<221> NAME/KEY: misc_feature
<222> LOCATION: (909)..(909)
<223> OTHER INFORMATION: n is a, c, g, or t
<220> FEATURE:
<221> NAME/KEY: misc_feature
<222> LOCATION: (913)..(913)
<223> OTHER INFORMATION: n is a, c, g, or t
<220> FEATURE:
<221> NAME/KEY: misc_feature
<222> LOCATION: (915)..(916)
<223> OTHER INFORMATION: n is a, c, g, or t
<220> FEATURE:
<221> NAME/KEY: misc_feature
<222> LOCATION: (918)..(919)
<223> OTHER INFORMATION: n is a, c, g, or t
<220> FEATURE:
<221> NAME/KEY: misc_feature
<222> LOCATION: (921)..(921)
<223> OTHER INFORMATION: n is a, c, g, or t
<220> FEATURE:
<221> NAME/KEY: misc_feature
<222> LOCATION: (936)..(936)
<223> OTHER INFORMATION: n is a, c, g, or t
<220> FEATURE:
<221> NAME/KEY: misc_feature
<222> LOCATION: (939)..(939)
<223> OTHER INFORMATION: n is a, c, g, or t
<220> FEATURE:
<221> NAME/KEY: misc_feature
<222> LOCATION: (942)..(943)
<223> OTHER INFORMATION: n is a, c, g, or t
<220> FEATURE:
<221> NAME/KEY: misc_feature
<222> LOCATION: (945)..(946)
<223> OTHER INFORMATION: n is a, c, g, or t
<220> FEATURE:
<221> NAME/KEY: misc_feature
<222> LOCATION: (951)..(951)
<223> OTHER INFORMATION: n is a, c, g, or t
<220> FEATURE:
<221> NAME/KEY: misc_feature
<222> LOCATION: (954)..(955)
<223> OTHER INFORMATION: n is a, c, g, or t
<220> FEATURE:
<221> NAME/KEY: misc_feature
<222> LOCATION: (963)..(963)
<223> OTHER INFORMATION: n is a, c, g, or t
<220> FEATURE:
<221> NAME/KEY: misc_feature
<222> LOCATION: (965)..(967)
<223> OTHER INFORMATION: n is a, c, g, or t
<220> FEATURE:
<221> NAME/KEY: misc_feature
<222> LOCATION: (969)..(969)
<223> OTHER INFORMATION: n is a, c, g, or t
<220> FEATURE:
<221> NAME/KEY: misc_feature
<222> LOCATION: (972)..(972)
<223> OTHER INFORMATION: n is a, c, g, or t
<220> FEATURE:
<221> NAME/KEY: misc_feature
<222> LOCATION: (975)..(975)
```

```
<223> OTHER INFORMATION: n is a, c, g, or t
<220> FEATURE:
<221> NAME/KEY: misc_feature
<222> LOCATION: (978)..(978)
<223> OTHER INFORMATION: n is a, c, g, or t
<220> FEATURE:
<221> NAME/KEY: misc_feature
<222> LOCATION: (987)..(987)
<223> OTHER INFORMATION: n is a, c, g, or t
<220> FEATURE:
<221> NAME/KEY: misc_feature
<222> LOCATION: (990)..(990)
<223> OTHER INFORMATION: n is a, c, g, or t
<220> FEATURE:
<221> NAME/KEY: misc_feature
<222> LOCATION: (993)..(993)
<223> OTHER INFORMATION: n is a, c, g, or t
<220> FEATURE:
<221> NAME/KEY: misc_feature
<222> LOCATION: (996)..(996)
<223> OTHER INFORMATION: n is a, c, g, or t
<220> FEATURE:
<221> NAME/KEY: misc_feature
<222> LOCATION: (1005)..(1006)
<223> OTHER INFORMATION: n is a, c, g, or t
<220> FEATURE:
<221> NAME/KEY: misc_feature
<222> LOCATION: (1008)..(1008)
<223> OTHER INFORMATION: n is a, c, g, or t
<220> FEATURE:
<221> NAME/KEY: misc_feature
<222> LOCATION: (1023)..(1023)
<223> OTHER INFORMATION: n is a, c, g, or t
<220> FEATURE:
<221> NAME/KEY: misc_feature
<222> LOCATION: (1032)..(1032)
<223> OTHER INFORMATION: n is a, c, g, or t
<220> FEATURE:
<221> NAME/KEY: misc_feature
<222> LOCATION: (1038)..(1038)
<223> OTHER INFORMATION: n is a, c, g, or t
<220> FEATURE:
<221> NAME/KEY: misc_feature
<222> LOCATION: (1041)..(1041)
<223> OTHER INFORMATION: n is a, c, g, or t
<220> FEATURE:
<221> NAME/KEY: misc_feature
<222> LOCATION: (1044)..(1047)
<223> OTHER INFORMATION: n is a, c, g, or t
<220> FEATURE:
<221> NAME/KEY: misc_feature
<222> LOCATION: (1050)..(1050)
<223> OTHER INFORMATION: n is a, c, g, or t
<220> FEATURE:
<221> NAME/KEY: misc_feature
<222> LOCATION: (1058)..(1059)
<223> OTHER INFORMATION: n is a, c, g, or t
<220> FEATURE:
<221> NAME/KEY: misc_feature
<222> LOCATION: (1062)..(1062)
<223> OTHER INFORMATION: n is a, c, g, or t
<220> FEATURE:
<221> NAME/KEY: misc_feature
<222> LOCATION: (1068)..(1068)
<223> OTHER INFORMATION: n is a, c, g, or t
<220> FEATURE:
<221> NAME/KEY: misc_feature
<222> LOCATION: (1071)..(1071)
<223> OTHER INFORMATION: n is a, c, g, or t
<220> FEATURE:
<221> NAME/KEY: misc_feature
<222> LOCATION: (1074)..(1074)
<223> OTHER INFORMATION: n is a, c, g, or t
<220> FEATURE:
<221> NAME/KEY: misc_feature
<222> LOCATION: (1078)..(1078)
<223> OTHER INFORMATION: n is a, c, g, or t
<220> FEATURE:
<221> NAME/KEY: misc_feature
<222> LOCATION: (1080)..(1080)
```

-continued

```
<223> OTHER INFORMATION: n is a, c, g, or t
<220> FEATURE:
<221> NAME/KEY: misc_feature
<222> LOCATION: (1086)..(1086)
<223> OTHER INFORMATION: n is a, c, g, or t
<220> FEATURE:
<221> NAME/KEY: misc_feature
<222> LOCATION: (1100)..(1101)
<223> OTHER INFORMATION: n is a, c, g, or t
<220> FEATURE:
<221> NAME/KEY: misc_feature
<222> LOCATION: (1107)..(1109)
<223> OTHER INFORMATION: n is a, c, g, or t
<220> FEATURE:
<221> NAME/KEY: misc_feature
<222> LOCATION: (1113)..(1113)
<223> OTHER INFORMATION: n is a, c, g, or t
<220> FEATURE:
<221> NAME/KEY: misc_feature
<222> LOCATION: (1118)..(1119)
<223> OTHER INFORMATION: n is a, c, g, or t
<220> FEATURE:
<221> NAME/KEY: misc_feature
<222> LOCATION: (1126)..(1128)
<223> OTHER INFORMATION: n is a, c, g, or t
<220> FEATURE:
<221> NAME/KEY: misc_feature
<222> LOCATION: (1130)..(1132)
<223> OTHER INFORMATION: n is a, c, g, or t
<220> FEATURE:
<221> NAME/KEY: misc_feature
<222> LOCATION: (1134)..(1134)
<223> OTHER INFORMATION: n is a, c, g, or t
<220> FEATURE:
<221> NAME/KEY: misc_feature
<222> LOCATION: (1137)..(1139)
<223> OTHER INFORMATION: n is a, c, g, or t
<220> FEATURE:
<221> NAME/KEY: misc_feature
<222> LOCATION: (1141)..(1143)
<223> OTHER INFORMATION: n is a, c, g, or t
<220> FEATURE:
<221> NAME/KEY: misc_feature
<222> LOCATION: (1146)..(1146)
<223> OTHER INFORMATION: n is a, c, g, or t
<220> FEATURE:
<221> NAME/KEY: misc_feature
<222> LOCATION: (1152)..(1152)
<223> OTHER INFORMATION: n is a, c, g, or t
<220> FEATURE:
<221> NAME/KEY: misc_feature
<222> LOCATION: (1161)..(1161)
<223> OTHER INFORMATION: n is a, c, g, or t
<220> FEATURE:
<221> NAME/KEY: misc_feature
<222> LOCATION: (1167)..(1168)
<223> OTHER INFORMATION: n is a, c, g, or t
<220> FEATURE:
<221> NAME/KEY: misc_feature
<222> LOCATION: (1170)..(1170)
<223> OTHER INFORMATION: n is a, c, g, or t
<220> FEATURE:
<221> NAME/KEY: misc_feature
<222> LOCATION: (1174)..(1174)
<223> OTHER INFORMATION: n is a, c, g, or t
<220> FEATURE:
<221> NAME/KEY: misc_feature
<222> LOCATION: (1176)..(1176)
<223> OTHER INFORMATION: n is a, c, g, or t
<220> FEATURE:
<221> NAME/KEY: misc_feature
<222> LOCATION: (1182)..(1182)
<223> OTHER INFORMATION: n is a, c, g, or t
<220> FEATURE:
<221> NAME/KEY: misc_feature
<222> LOCATION: (1185)..(1185)
<223> OTHER INFORMATION: n is a, c, g, or t
<220> FEATURE:
<221> NAME/KEY: misc_feature
<222> LOCATION: (1188)..(1188)
```

```
<223> OTHER INFORMATION: n is a, c, g, or t
<220> FEATURE:
<221> NAME/KEY: misc_feature
<222> LOCATION: (1190)..(1191)
<223> OTHER INFORMATION: n is a, c, g, or t
<220> FEATURE:
<221> NAME/KEY: misc_feature
<222> LOCATION: (1193)..(1193)
<223> OTHER INFORMATION: n is a, c, g, or t
<220> FEATURE:
<221> NAME/KEY: misc_feature
<222> LOCATION: (1195)..(1195)
<223> OTHER INFORMATION: n is a, c, g, or t
<220> FEATURE:
<221> NAME/KEY: misc_feature
<222> LOCATION: (1200)..(1200)
<223> OTHER INFORMATION: n is a, c, g, or t
<220> FEATURE:
<221> NAME/KEY: misc_feature
<222> LOCATION: (1212)..(1212)
<223> OTHER INFORMATION: n is a, c, g, or t
<220> FEATURE:
<221> NAME/KEY: misc_feature
<222> LOCATION: (1215)..(1215)
<223> OTHER INFORMATION: n is a, c, g, or t
<220> FEATURE:
<221> NAME/KEY: misc_feature
<222> LOCATION: (1218)..(1218)
<223> OTHER INFORMATION: n is a, c, g, or t
<220> FEATURE:
<221> NAME/KEY: misc_feature
<222> LOCATION: (1224)..(1224)
<223> OTHER INFORMATION: n is a, c, g, or t
<220> FEATURE:
<221> NAME/KEY: misc_feature
<222> LOCATION: (1230)..(1230)
<223> OTHER INFORMATION: n is a, c, g, or t
<220> FEATURE:
<221> NAME/KEY: misc_feature
<222> LOCATION: (1233)..(1233)
<223> OTHER INFORMATION: n is a, c, g, or t
<220> FEATURE:
<221> NAME/KEY: misc_feature
<222> LOCATION: (1236)..(1237)
<223> OTHER INFORMATION: n is a, c, g, or t
<220> FEATURE:
<221> NAME/KEY: misc_feature
<222> LOCATION: (1239)..(1242)
<223> OTHER INFORMATION: n is a, c, g, or t
<220> FEATURE:
<221> NAME/KEY: misc_feature
<222> LOCATION: (1244)..(1248)
<223> OTHER INFORMATION: n is a, c, g, or t
<220> FEATURE:
<221> NAME/KEY: misc_feature
<222> LOCATION: (1251)..(1251)
<223> OTHER INFORMATION: n is a, c, g, or t
<220> FEATURE:
<221> NAME/KEY: misc_feature
<222> LOCATION: (1253)..(1253)
<223> OTHER INFORMATION: n is a, c, g, or t
<220> FEATURE:
<221> NAME/KEY: misc_feature
<222> LOCATION: (1255)..(1257)
<223> OTHER INFORMATION: n is a, c, g, or t
<220> FEATURE:
<221> NAME/KEY: misc_feature
<222> LOCATION: (1260)..(1260)
<223> OTHER INFORMATION: n is a, c, g, or t
<220> FEATURE:
<221> NAME/KEY: misc_feature
<222> LOCATION: (1267)..(1268)
<223> OTHER INFORMATION: n is a, c, g, or t
<220> FEATURE:
<221> NAME/KEY: misc_feature
<222> LOCATION: (1272)..(1272)
<223> OTHER INFORMATION: n is a, c, g, or t

<400> SEQUENCE: 86
```

-continued

```
atnncnnntn cntnnatnnn nnnnntnnnn ggnttttatga tantnatgta cnttttttgan       60 acntanttgg atntgngnca acnnanngcn ctcaancttc cnactctncc naanacnttn        120
gnnggngtna tnagccaaga gaantttgag aaatcnngag cntanagnnt tnananaagc        180
nanttncant ttgttcanga gtttgtnacn atantnanng actctncnat tntgtncttt        240
gggntnttgc cntggttttg gaagannntcn ggngnnnttn tnncnannnn nggnntnnat       300
ncngagaatg aaatnctgca nacncttncn ttcttngcng gnntnatgan ntggtcacag        360
atnacngatt tgccnttttc tntgtactca actttngtga tngagncncg ncatggnttn       420
aanaancaaa cannatggnt nttcnttagg gacatgntna aaggaannnt cctntctgtn        480
atannngnnc cnccnatngt ngcngcnatn attntnatag tncagaaagg aggtccntan        540
ntngccatct atcntgggn nttnangttt nnnctntctn tngtgatgat gacnntntan         600
ccngtnntna tngcnccnct nttcaanaan ttcactccnc ttccngatgg nnanctcngg        660
gagaanatng agaaacttgc ttcntcnctn aantntccnn tnaagaanct ntttgttgtc        720
gatggatcna caagntcaag ncanagnaat gcntanatgt atggnttctt naagaacaan       780
aggattgtnc nttatganac nttnattcan cagtgcnann angannanga aattgtngcn       840
gttattgcnc angagntngg acantggaan ctnaancana ctnnntacnc nttnnttgcn       900
ntncanatnc ttncnntnnt ncaatttgga ggatanacnc tnntnngaaa ntcnnctgat       960
ctntnnngna gnttnggntt tgatacncan ccngtnctca ttggnntnat catatttcag     1020
canactgtaa tnccactnca ncannnngtn agctttgnnc tnaacctngt nagncgancn      1080 tttganttc aggctgatgn ntttgcnnng aancttgnnt atgcannngn nntncgnnnt       1140
nnnctngtga anctacagga ngagaanntn tcancnatga anacngancn ntngnactcn     1200
gcttatcact antcncancc tccncttgtn ganagnntnn nngnnnnnga ngnannngan      1260
aagaagnnag antaa                                                       1275
```

<210> SEQ ID NO 87
<211> LENGTH: 298
<212> TYPE: PRT
<213> ORGANISM: Artificial Sequence
<220> FEATURE:
<223> OTHER INFORMATION: Description of Artificial Sequence: Consensus
      sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (28)..(29)
<223> OTHER INFORMATION: Xaa can be any naturally occurring amino acid -continued

```
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (76)..(77)
<223> OTHER INFORMATION: Xaa can be any naturally occurring amino acid
<220> FEATURE:
<221> NAME/KEY: misc_feature
<222> LOCATION: (82)..(83)
<223> OTHER INFORMATION: Xaa can be any naturally occurring amino acid
<220> FEATURE:
<221> NAME/KEY: misc_feature
<222> LOCATION: (92)..(92)
<223> OTHER INFORMATION: Xaa can be any naturally occurring amino acid
<220> FEATURE:
<221> NAME/KEY: misc_feature
<222> LOCATION: (107)..(107)
<223> OTHER INFORMATION: Xaa can be any naturally occurring amino acid
<220> FEATURE:
<221> NAME/KEY: misc_feature
<222> LOCATION: (109)..(109)
<223> OTHER INFORMATION: Xaa can be any naturally occurring amino acid
<220> FEATURE:
<221> NAME/KEY: misc_feature
<222> LOCATION: (111)..(111)
<223> OTHER INFORMATION: Xaa can be any naturally occurring amino acid
<220> FEATURE:
<221> NAME/KEY: misc_feature
<222> LOCATION: (114)..(114)
<223> OTHER INFORMATION: Xaa can be any naturally occurring amino acid
<220> FEATURE:
<221> NAME/KEY: misc_feature
<222> LOCATION: (119)..(119)
<223> OTHER INFORMATION: Xaa can be any naturally occurring amino acid
<220> FEATURE:
<221> NAME/KEY: misc_feature
<222> LOCATION: (138)..(138)
<223> OTHER INFORMATION: Xaa can be any naturally occurring amino acid
<220> FEATURE:
<221> NAME/KEY: misc_feature
<222> LOCATION: (151)..(152)
<223> OTHER INFORMATION: Xaa can be any naturally occurring amino acid
<220> FEATURE:
<221> NAME/KEY: misc_feature
<222> LOCATION: (184)..(184)
<223> OTHER INFORMATION: Xaa can be any naturally occurring amino acid
<220> FEATURE:
<221> NAME/KEY: misc_feature
<222> LOCATION: (193)..(196)
<223> OTHER INFORMATION: Xaa can be any naturally occurring amino acid
<220> FEATURE:
<221> NAME/KEY: misc_feature
<222> LOCATION: (215)..(215)
<223> OTHER INFORMATION: Xaa can be any naturally occurring amino acid
<220> FEATURE:
<221> NAME/KEY: misc_feature
<222> LOCATION: (217)..(217)
<223> OTHER INFORMATION: Xaa can be any naturally occurring amino acid
```

```
<220> FEATURE:
<221> NAME/KEY: misc_feature
<222> LOCATION: (219)..(219)
<223> OTHER INFORMATION: Xaa can be any naturally occurring amino acid
<220> FEATURE:
<221> NAME/KEY: misc_feature
<222> LOCATION: (221)..(221)
<223> OTHER INFORMATION: Xaa can be any naturally occurring amino acid
<220> FEATURE:
<221> NAME/KEY: misc_feature
<222> LOCATION: (230)..(231)
<223> OTHER INFORMATION: Xaa can be any naturally occurring amino acid
<220> FEATURE:
<221> NAME/KEY: misc_feature
<222> LOCATION: (235)..(235)
<223> OTHER INFORMATION: Xaa can be any naturally occurring amino acid
<220> FEATURE:
<221> NAME/KEY: misc_feature
<222> LOCATION: (242)..(242)
<223> OTHER INFORMATION: Xaa can be any naturally occurring amino acid
<220> FEATURE:
<221> NAME/KEY: misc_feature
<222> LOCATION: (249)..(249)
<223> OTHER INFORMATION: Xaa can be any naturally occurring amino acid
<220> FEATURE:
<221> NAME/KEY: misc_feature
<222> LOCATION: (252)..(253)
<223> OTHER INFORMATION: Xaa can be any naturally occurring amino acid
<220> FEATURE:
<221> NAME/KEY: misc_feature
<222> LOCATION: (255)..(255)
<223> OTHER INFORMATION: Xaa can be any naturally occurring amino acid
<220> FEATURE:
<221> NAME/KEY: misc_feature
<222> LOCATION: (258)..(259)
<223> OTHER INFORMATION: Xaa can be any naturally occurring amino acid
<220> FEATURE:
<221> NAME/KEY: misc_feature
<222> LOCATION: (266)..(266)
<223> OTHER INFORMATION: Xaa can be any naturally occurring amino acid
<220> FEATURE:
<221> NAME/KEY: misc_feature
<222> LOCATION: (271)..(273)
<223> OTHER INFORMATION: Xaa can be any naturally occurring amino acid
<220> FEATURE:
<221> NAME/KEY: misc_feature
<222> LOCATION: (288)..(290)
<223> OTHER INFORMATION: Xaa can be any naturally occurring amino acid
<220> FEATURE:
<221> NAME/KEY: misc_feature
<222> LOCATION: (292)..(293)
<223> OTHER INFORMATION: Xaa can be any naturally occurring amino acid
<220> FEATURE:
<221> NAME/KEY: misc_feature
<222> LOCATION: (297)..(297)
<223> OTHER INFORMATION: Xaa can be any naturally occurring amino acid

<400> SEQUENCE: 87

Met Ala Xaa Pro Xaa Met Glu Xaa Val Val Gly Phe Met Ile Xaa Met
  1               5                  10                  15

Tyr Xaa Phe Glu Thr Tyr Leu Asp Xaa Arg Gln Xaa Xaa Ala Leu Lys
                 20                  25                  30

Leu Pro Thr Leu Pro Lys Thr Leu Xaa Thr Asp Leu Pro Phe Ser Leu
             35                  40                  45

Tyr Ser Thr Phe Val Ile Glu Xaa Arg His Gly Phe Asn Lys Gln Thr
         50                  55                  60

Xaa Trp Xaa Phe Xaa Arg Asp Met Xaa Lys Gly Xaa Xaa Leu Ser Val
 65                  70                  75                  80

Ile Xaa Xaa Pro Pro Ile Val Ala Ala Ile Xaa Ile Val Gln Lys
                 85                  90                  95

Gly Gly Pro Tyr Leu Ala Ile Tyr Leu Trp Xaa Phe Xaa Phe Xaa Leu
                100                 105                 110
```

```
Ser Xaa Val Met Met Thr Xaa Tyr Pro Val Leu Ile Ala Pro Leu Phe
    115                 120                 125

Asn Lys Phe Thr Pro Leu Pro Asp Gly Xaa Leu Arg Glu Lys Ile Glu
130                 135                 140

Lys Leu Ala Ser Ser Leu Xaa Xaa Pro Leu Lys Lys Leu Phe Val Val
145                 150                 155                 160

Asp Gly Ser Thr Arg Ser Ser His Ser Asn Ala Tyr Met Tyr Gly Phe
                165                 170                 175

Phe Lys Asn Lys Arg Ile Val Xaa Tyr Asp Thr Leu Ile Gln Gln Cys
                180                 185                 190

Xaa Xaa Xaa Xaa Glu Ile Val Ala Val Ile Ala His Glu Leu Gly His
            195                 200                 205

Trp Lys Leu Asn His Thr Xaa Tyr Xaa Phe Xaa Ala Xaa Gln His Thr
210                 215                 220

Val Ile Pro Leu Gln Xaa Xaa Val Ser Phe Xaa Leu Asn Leu Val Ser
225                 230                 235                 240

Arg Xaa Phe Glu Phe Gln Ala Asp Xaa Phe Ala Xaa Xaa Leu Xaa Tyr
                245                 250                 255

Ala Xaa Xaa Leu Arg Glu Asn Leu Ser Xaa Met Asn Thr Asp Xaa Xaa
            260                 265                 270

Xaa Ser Ala Tyr His Tyr Ser His Pro Pro Leu Val Glu Arg Leu Xaa
        275                 280                 285

Xaa Xaa Asp Xaa Xaa Asp Lys Lys Xaa Asp
290                 295

<210> SEQ ID NO 88
<211> LENGTH: 1275
<212> TYPE: DNA
<213> ORGANISM: Artificial sequence
<220> FEATURE:
<223> OTHER INFORMATION: Description of Artificial Sequence: Consensus
      sequence
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (6)..(8)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(25)
<223> OTHER INFORMATION: n is a, c, g, or t
<220> FEATURE:
<221> NAME/KEY: misc_feature
<222> LOCATION: (27)..(30)
<223> OTHER INFORMATION: n is a, c, g, or t
<220> FEATURE:
<221> NAME/KEY: misc_feature
<222> LOCATION: (168)..(169)
<223> OTHER INFORMATION: n is a, c, g, or t
<220> FEATURE:
<221> NAME/KEY: misc_feature
<222> LOCATION: (172)..(172)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
```

```
<220> FEATURE:
<221> NAME/KEY: misc_feature
<222> LOCATION: (176)..(176)
<223> OTHER INFORMATION: n is a, c, g, or t
<220> FEATURE:
<221> NAME/KEY: misc_feature
<222> LOCATION: (276)..(276)
<223> OTHER INFORMATION: n is a, c, g, or t
<220> FEATURE:
<221> NAME/KEY: misc_feature
<222> LOCATION: (303)..(303)
<223> OTHER INFORMATION: n is a, c, g, or t
<220> FEATURE:
<221> NAME/KEY: misc_feature
<222> LOCATION: (504)..(504)
<223> OTHER INFORMATION: n is a, c, g, or t
<220> FEATURE:
<221> NAME/KEY: misc_feature
<222> LOCATION: (630)..(630)
<223> OTHER INFORMATION: n is a, c, g, or t
<220> FEATURE:
<221> NAME/KEY: misc_feature
<222> LOCATION: (687)..(687)
<223> OTHER INFORMATION: n is a, c, g, or t
<220> FEATURE:
<221> NAME/KEY: misc_feature
<222> LOCATION: (943)..(943)
<223> OTHER INFORMATION: n is a, c, g, or t
<220> FEATURE:
<221> NAME/KEY: misc_feature
<222> LOCATION: (1046)..(1046)
<223> OTHER INFORMATION: n is a, c, g, or t
<220> FEATURE:
<221> NAME/KEY: misc_feature
<222> LOCATION: (1062)..(1062)
<223> OTHER INFORMATION: n is a, c, g, or t
<220> FEATURE:
<221> NAME/KEY: misc_feature
<222> LOCATION: (1068)..(1068)
<223> OTHER INFORMATION: n is a, c, g, or t
<220> FEATURE:
<221> NAME/KEY: misc_feature
<222> LOCATION: (1107)..(1107)
<223> OTHER INFORMATION: n is a, c, g, or t
<220> FEATURE:
<221> NAME/KEY: misc_feature
<222> LOCATION: (1118)..(1118)
<223> OTHER INFORMATION: n is a, c, g, or t
<220> FEATURE:
<221> NAME/KEY: misc_feature
<222> LOCATION: (1141)..(1141)
<223> OTHER INFORMATION: n is a, c, g, or t
<220> FEATURE:
<221> NAME/KEY: misc_feature
<222> LOCATION: (1174)..(1174)
<223> OTHER INFORMATION: n is a, c, g, or t
<220> FEATURE:
<221> NAME/KEY: misc_feature
<222> LOCATION: (1182)..(1182)
<223> OTHER INFORMATION: n is a, c, g, or t
<220> FEATURE:
<221> NAME/KEY: misc_feature
<222> LOCATION: (1190)..(1190)
<223> OTHER INFORMATION: n is a, c, g, or t
<220> FEATURE:
<221> NAME/KEY: misc_feature
<222> LOCATION: (1195)..(1195)
<223> OTHER INFORMATION: n is a, c, g, or t
<220> FEATURE:
<221> NAME/KEY: misc_feature
<222> LOCATION: (1247)..(1247)
<223> OTHER INFORMATION: n is a, c, g, or t

<400> SEQUENCE: 88
atnncnnntn cttttatnnn nnnnntnnnn ggttttatga tagtgatgta cattttgag      60 acgtatttgg atctgaggca actcactgct ctcaagcttc caactctccc gaaaaccttg    120
gttggtgtaa ttagccaaga gaagtttgag aaatcacgag catacagnnt tnananaagc   180
```

```
tattttcact tgttcatga gtttgtaact atacttatgg actctgcaat tttgttcttt    240
gggatcttgc cttggttttg gaagatgtct ggagcngttt taccgaggtt gggccttgat    300
ccngagaatg aaatactgca tactctttca ttcttggctg gtgttatgac atggtcacag    360
atcactgatt tgccattttc tttgtactca actttcgtga tcgagtctcg gcatgggttc    420
aacaaacaaa caatatggat gttcattagg gacatgatca aaggaacatt cctctctgtc    480
atactaggcc cacccattgt tgcngcgata attttcatag tccagaaagg aggtccttat    540
cttgccatct atctgtgggc attcatgttt atcctgtctc tagtgatgat gactatatac    600
ccggtcttga tagcaccgct cttcaacaan ttcactcctc ttccagatgg agacctccgg    660
gagaagattg agaaacttgc ttcttcncta aagtttcctt tgaagaagct gtttgttgtc    720
gatggatcta caaggtcaag ccatagcaat gcttacatgt atggtttctt taagaacaaa    780
aggattgttc tttatgatac gttgattcag cagtgcaaga atgaggatga aattgtggcg    840
gttattgcac acgagcttgg acattggaaa ctgaatcaca ctacatactc gttcattgca    900
gttcaaatcc ttgccttctt acaatttgga ggatacactc ttntcagaaa ctccactgat    960
ctcttcagga gtttcggatt tgatacacag cctgttctca ttggtttgat catatttcag   1020
cacactgtaa taccactgca acatcnagta agctttggcc tnaacctngt tagtcgagcg   1080
tttgagtttc aggctgatgc ttttgcngtg aagcttgnct atgcaaaaga tcttcgtcct   1140
nctctagtga aactacagga agagaactta tcancaatga anactgatcn attgnactca   1200
gcttatcact actcacatcc tcctcttgtt gaaaggcttc gagccantga tggagaagac   1260
aagaagacag attaa                                                    1275
```

<210> SEQ ID NO 89
<211> LENGTH: 306
<212> TYPE: PRT
<213> ORGANISM: Artificial sequence
<220> FEATURE:
<223> OTHER INFORMATION: Description of Artificial Sequence: Consensus
      sequence
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (231)..(231)
<223> OTHER INFORMATION: Xaa can be any naturally occurring amino acid
<220> FEATURE:
<221> NAME/KEY: misc_feature
<222> LOCATION: (255)..(255)
<223> OTHER INFORMATION: Xaa can be any naturally occurring amino acid
<220> FEATURE:
<221> NAME/KEY: misc_feature
<222> LOCATION: (263)..(263)
<223> OTHER INFORMATION: Xaa can be any naturally occurring amino acid
<220> FEATURE:
<221> NAME/KEY: misc_feature
<222> LOCATION: (269)..(269)
<223> OTHER INFORMATION: Xaa can be any naturally occurring amino acid
<220> FEATURE:
<221> NAME/KEY: misc_feature
<222> LOCATION: (274)..(274)
<223> OTHER INFORMATION: Xaa can be any naturally occurring amino acid
<220> FEATURE:
<221> NAME/KEY: misc_feature
<222> LOCATION: (279)..(279)
<223> OTHER INFORMATION: Xaa can be any naturally occurring amino acid
<220> FEATURE:
<221> NAME/KEY: misc_feature
<222> LOCATION: (281)..(281)
<223> OTHER INFORMATION: Xaa can be any naturally occurring amino acid
<220> FEATURE:

<221> NAME/KEY: misc_feature
<222> LOCATION: (298)..(298)
<223> OTHER INFORMATION: Xaa can be any naturally occurring amino acid

<400> SEQUENCE: 89

Met Ala Ile Pro Phe Met Glu Thr Val Val Gly Phe Met Ile Val Met
1               5                   10                  15

Tyr Ile Phe Glu Thr Tyr Leu Asp Leu Arg Gln Leu Thr Ala Leu Lys
            20                  25                  30

Leu Pro Thr Leu Pro Lys Thr Leu Xaa Thr Asp Leu Pro Phe Ser Leu
        35                  40                  45

Tyr Ser Thr Phe Val Ile Glu Ser Arg His Gly Phe Asn Lys Gln Thr
    50                  55                  60

Ile Trp Met Phe Ile Arg Asp Met Ile Lys Gly Thr Phe Leu Ser Val
65                  70                  75                  80

Ile Leu Gly Pro Pro Ile Val Ala Ala Ile Phe Ile Val Gln Lys
                85                  90                  95

Gly Gly Pro Tyr Leu Ala Ile Tyr Leu Trp Ala Phe Met Phe Ile Leu
            100                 105                 110

Ser Leu Val Met Met Thr Ile Tyr Pro Val Leu Ile Ala Pro Leu Phe
            115                 120                 125

Asn Lys Phe Thr Pro Leu Pro Asp Gly Asp Leu Arg Glu Lys Ile Glu
            130                 135                 140

Lys Leu Ala Ser Ser Leu Lys Phe Pro Leu Lys Lys Leu Phe Val Val
145                 150                 155                 160

Asp Gly Ser Thr Arg Ser Ser His Ser Asn Ala Tyr Met Tyr Gly Phe
                165                 170                 175

Phe Lys Asn Lys Arg Ile Val Leu Tyr Asp Thr Leu Ile Gln Gln Cys
            180                 185                 190

Lys Asn Glu Asp Glu Ile Val Ala Val Ile Ala His Glu Leu Gly His
            195                 200                 205

Trp Lys Leu Asn His Thr Thr Tyr Ser Phe Ile Ala Val Gln His Thr
210                 215                 220

Val Ile Pro Leu Gln His Xaa Val Ser Phe Gly Leu Asn Leu Val Ser
225                 230                 235                 240

Arg Ala Phe Glu Phe Gln Ala Asp Ala Phe Ala Val Lys Leu Xaa Tyr
            245                 250                 255

Ala Lys Asp Leu Arg Pro Xaa Leu Val Lys Leu Gln Xaa Glu Asn Leu
            260                 265                 270

Ser Xaa Met Asn Thr Asp Xaa Leu Xaa Ser Ala Tyr His Tyr Ser His
            275                 280                 285

Pro Pro Leu Val Glu Arg Leu Arg Ala Xaa Asp Gly Glu Asp Lys Lys
            290                 295                 300

Thr Asp
305

<210> SEQ ID NO 90
<211> LENGTH: 1275
<212> TYPE: DNA
<213> ORGANISM: Artificial sequence
<220> FEATURE:
<223> OTHER INFORMATION: Description of Artificial Sequence: Consensus
      sequence
<220> FEATURE:
<221> NAME/KEY: misc_feature
<222> LOCATION: (123)..(123)
<223> OTHER INFORMATION: n is a, c, g, or t
<220> FEATURE:
<221> NAME/KEY: misc_feature

```
<222> LOCATION: (791)..(791)
<223> OTHER INFORMATION: n is a, c, g, or t
<220> FEATURE:
<221> NAME/KEY: misc_feature
<222> LOCATION: (1242)..(1242)
<223> OTHER INFORMATION: n is a, c, g, or t
<220> FEATURE:
<221> NAME/KEY: misc_feature
<222> LOCATION: (1244)..(1244)
<223> OTHER INFORMATION: n is a, c, g, or t

<400> SEQUENCE: 90
atggcgtttc cctacatgga agccgttgtc ggatttatga tattaatgta catttttgaa      60
acttacttgg atgtgcgaca catagggcc ctcaaacttc ctactcttcc aaagacttta     120
ganggtgtta tcagccaaga gaaatttgag aaatctagag cctatagtct tgataaaagc    180
cacttccatt ttgttcacga gtttgtgaca atagtgacaa actctacaat tttgtacttt    240
ggggtattgc cctggttttg gaagaaatca ggagatttta tgacaatagc tggtttcaat    300
gctgagaatg aaatactgca tacccttgcc ttcttagcag ggctgatgat ttggtcacag    360
ataacagatt tgcccttttc tctgtactca acttttgtga ttgaggcccg tcatggtttt    420
aataagcaaa caccatggtt attctttagg gacatgctta aaggaatttt cctttctgta    480
ataattggtc cacctattgt ggctgcaatc attgtaatag tacagaaagg aggtccatac    540
ttggccatct atctttgggt tttacgtttt ggtctttcta ttgtgatgat gaccctttat    600
ccagtactaa tagctccact cttcaataag ttcactccac ttccagatgg tcaactcagg    660
gagaaaatcg agaaacttgc ttcctccctc aactatccgt taaagaaact atttgttgtc    720
gatggatcca aagatcaag tcacagcaat gcctatatgt atggattctt caagaacaag    780
aggattgtcc nttatgacac attaattcaa cagtgcaaag acgatgagga aattgttgct    840
gttattgccc atgagttggg acactggaag ctcaaccata ctgtgtacac atttgttgct    900
atgcagattc ttacacttct acaatttgga ggatatacac tagtgcgaaa ttcagctgat    960
ctgtatcgaa gctttgggtt tgatacgcag ccagtcctca ttgggctcat catatttcag   1020
catactgtaa tcccacttca gcaattggtc agctttggtc tgaacctagt cagccgatca   1080
tttgaatttc aggctgatgg ctttgccaag aagcttggat atgcatctgg attacgcggt   1140
ggtcttgtga aactacagga ggagaatctg tcagctatga atacagatcc ttggtactct   1200
gcttatcact attctcatcc tccccttgtt gaaagattgg cngngctgga cgaaccggat   1260
aagaaggaag actaa                                                    1275

<210> SEQ ID NO 91
<211> LENGTH: 424
<212> TYPE: PRT
<213> ORGANISM: Artificial sequence
<220> FEATURE:
<223> OTHER INFORMATION: Description of Artificial Sequence: Consensus
      sequence
<220> FEATURE:
<221> NAME/KEY: misc_feature
<222> LOCATION: (264)..(264)
<223> OTHER INFORMATION: Xaa can be any naturally occurring amino acid
<220> FEATURE:
<221> NAME/KEY: misc_feature
<222> LOCATION: (415)..(415)
<223> OTHER INFORMATION: Xaa can be any naturally occurring amino acid

<400> SEQUENCE: 91

Met Ala Phe Pro Tyr Met Glu Ala Val Val Gly Phe Met Ile Leu Met
 1               5                  10                  15

Tyr Ile Phe Glu Thr Tyr Leu Asp Val Arg Gln His Arg Ala Leu Lys
```

-continued

```
              20                  25                  30
Leu Pro Thr Leu Pro Lys Thr Leu Glu Gly Val Ile Ser Gln Glu Lys
             35                  40                  45

Phe Glu Lys Ser Arg Ala Tyr Ser Leu Asp Lys Ser His Phe His Phe
         50                  55                  60

Val His Glu Phe Val Thr Ile Val Thr Asp Ser Thr Ile Leu Tyr Phe
 65                  70                  75                  80

Gly Val Leu Pro Trp Phe Trp Lys Lys Ser Gly Asp Phe Met Thr Ile
                 85                  90                  95

Ala Gly Phe Asn Ala Glu Asn Glu Ile Leu His Thr Leu Ala Phe Leu
            100                 105                 110

Ala Gly Leu Met Ile Trp Ser Gln Ile Thr Asp Leu Pro Phe Ser Leu
            115                 120                 125

Tyr Ser Thr Phe Val Ile Glu Ala Arg His Gly Phe Asn Lys Gln Thr
            130                 135                 140

Pro Trp Leu Phe Phe Arg Asp Met Leu Lys Gly Ile Phe Leu Ser Val
145                 150                 155                 160

Ile Ile Gly Pro Pro Ile Val Ala Ala Ile Val Ile Val Gln Lys
                165                 170                 175

Gly Gly Pro Tyr Leu Ala Ile Tyr Leu Trp Val Phe Thr Phe Gly Leu
            180                 185                 190

Ser Ile Val Met Met Thr Leu Tyr Pro Val Leu Ile Ala Pro Leu Phe
            195                 200                 205

Asn Lys Phe Thr Pro Leu Pro Asp Gly Gln Leu Arg Glu Lys Ile Glu
            210                 215                 220

Lys Leu Ala Ser Ser Leu Asn Tyr Pro Leu Lys Lys Leu Phe Val Val
225                 230                 235                 240

Asp Gly Ser Thr Arg Ser Ser His Ser Asn Ala Tyr Met Tyr Gly Phe
                245                 250                 255

Phe Lys Asn Lys Arg Ile Val Xaa Tyr Asp Thr Leu Ile Gln Gln Cys
            260                 265                 270

Lys Asp Asp Glu Glu Ile Val Ala Val Ile Ala His Glu Leu Gly His
            275                 280                 285

Trp Lys Leu Asn His Thr Val Tyr Thr Phe Val Ala Met Gln Ile Leu
            290                 295                 300

Thr Leu Leu Gln Phe Gly Gly Tyr Thr Leu Val Arg Asn Ser Ala Asp
305                 310                 315                 320

Leu Tyr Arg Ser Phe Gly Phe Asp Thr Gln Pro Val Leu Ile Gly Leu
                325                 330                 335

Ile Ile Phe Gln His Thr Val Ile Pro Leu Gln Gln Leu Val Ser Phe
            340                 345                 350

Gly Leu Asn Leu Val Ser Arg Ser Phe Glu Phe Gln Ala Asp Gly Phe
            355                 360                 365

Ala Lys Lys Leu Gly Tyr Ala Ser Gly Leu Arg Gly Gly Leu Val Lys
            370                 375                 380

Leu Gln Glu Glu Asn Leu Ser Ala Met Asn Thr Asp Pro Trp Tyr Ser
385                 390                 395                 400

Ala Tyr His Tyr Ser His Pro Pro Leu Val Glu Arg Leu Ala Xaa Leu
                405                 410                 415

Asp Glu Pro Asp Lys Lys Glu Asp
            420
```